United States Patent
Baker et al.

(10) Patent No.: US 10,125,100 B2
(45) Date of Patent: *Nov. 13, 2018

(54) KINASE INHIBITORS

(71) Applicants: Respivert Limited, High Wycombe, Buckinghamshire (GB); Topivert Pharma Limited, London (GB)

(72) Inventors: Thomas Matthew Baker, Nottingham (GB); Matthew Colin Thor Fyfe, London (GB); Geraint Jones, Nottingham (GB); Stephen Malcolm Thom, Nottingham (GB)

(73) Assignees: Respivert Limited, Topivert Pharma Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/604,258

(22) Filed: May 24, 2017

(65) Prior Publication Data

US 2017/0253563 A1 Sep. 7, 2017

Related U.S. Application Data

(62) Division of application No. 14/872,527, filed on Oct. 1, 2015, now Pat. No. 9,751,837.

(30) Foreign Application Priority Data

Oct. 1, 2014 (GB) .................................. 1417344.7
Jun. 18, 2015 (GB) .................................. 1510694.1

(51) Int. Cl.
C07D 213/74 (2006.01)
C07D 213/80 (2006.01)
(Continued)

(52) U.S. Cl.
CPC ........ *C07D 213/74* (2013.01); *A61K 31/4375* (2013.01); *A61K 31/44* (2013.01);
(Continued)

(58) Field of Classification Search
CPC .............. A61K 31/4412; A61K 31/505; A61K 31/444; A61K 31/541; A61K 31/551;
(Continued)

(56) References Cited

U.S. PATENT DOCUMENTS 6,319,921 B1 11/2001 Cirillo et al.
6,492,393 B1 12/2002 Breitfelder et al.
(Continued)

FOREIGN PATENT DOCUMENTS

EP 1 777 218 A1 4/2007
WO WO 99/23091 5/1999
(Continued)

OTHER PUBLICATIONS

Traore et al., New aminopyridine derivatives as inhibitors of the TAM family; European Journal of Medicinal Chemistry, (2013), 70, 789-801.*

(Continued)

*Primary Examiner* — Alexander R Pagano
*Assistant Examiner* — Ebenezer O Sackey
(74) *Attorney, Agent, or Firm* — McCarter & English, LLP; Steven G. Davis

(57) ABSTRACT

There are provided compounds of formulas III and VIIa:

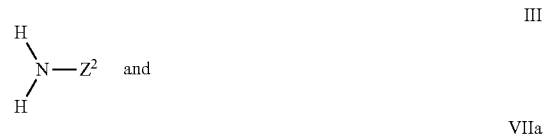

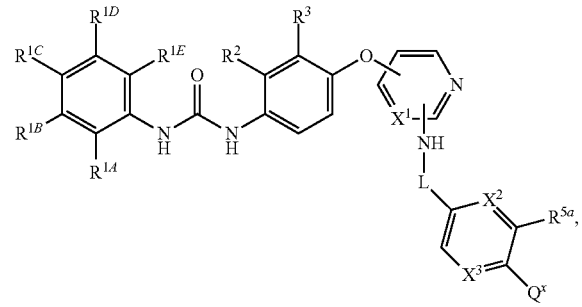

or a salt or protected derivative thereof, wherein $Z^2$ represents a structural fragment of formula V,

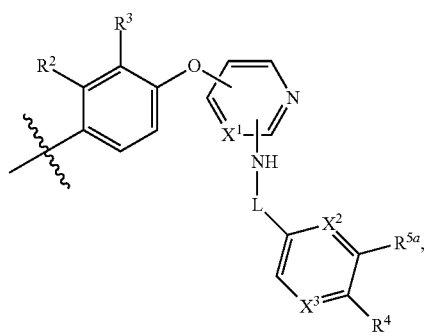

wherein $R^{1A}$ to $R^{1E}$, $R^2$ to $R^4$, $R^{5a}$, L and $X^1$ to $X^3$ have meanings given in the description, which compounds have antiinflammatory activity, for example through inhibition of one or more of members of: the family of p38 mitogen-activated protein kinase enzymes; Syk kinase; and members of the Src family of tyrosine kinases) and have use in therapy, including in pharmaceutical combinations, especially in the treatment of inflammatory diseases, including inflammatory diseases of the lung, eye and intestines.

4 Claims, No Drawings

(51) Int. Cl.
| | |
|---|---|
| C07D 401/12 | (2006.01) |
| C07D 239/47 | (2006.01) |
| C07D 413/12 | (2006.01) |
| C07H 13/08 | (2006.01) |
| C07H 15/26 | (2006.01) |
| C07F 9/58 | (2006.01) |
| C07F 9/6512 | (2006.01) |
| C07F 9/6558 | (2006.01) |
| C07H 19/048 | (2006.01) |
| A61K 31/4412 | (2006.01) |
| A61K 31/44 | (2006.01) |
| A61K 31/506 | (2006.01) |
| A61K 31/675 | (2006.01) |
| A61K 31/7052 | (2006.01) |
| C07D 453/02 | (2006.01) |
| A61K 31/4375 | (2006.01) |
| A61K 31/4439 | (2006.01) |
| A61K 31/4545 | (2006.01) |
| A61K 31/496 | (2006.01) |
| A61K 31/5377 | (2006.01) |
| A61K 31/541 | (2006.01) |
| A61K 31/551 | (2006.01) |
| A61K 31/553 | (2006.01) |
| A61K 31/635 | (2006.01) |
| A61K 31/706 | (2006.01) |
| C07D 405/12 | (2006.01) |
| A61K 45/06 | (2006.01) |
| A61K 31/444 | (2006.01) |
| A61K 31/505 | (2006.01) |

(52) U.S. Cl.
CPC ........ *A61K 31/444* (2013.01); *A61K 31/4412* (2013.01); *A61K 31/4439* (2013.01); *A61K 31/4545* (2013.01); *A61K 31/496* (2013.01); *A61K 31/505* (2013.01); *A61K 31/506* (2013.01); *A61K 31/5377* (2013.01); *A61K 31/541* (2013.01); *A61K 31/551* (2013.01); *A61K 31/553* (2013.01); *A61K 31/635* (2013.01); *A61K 31/675* (2013.01); *A61K 31/706* (2013.01); *A61K 31/7052* (2013.01); *A61K 45/06* (2013.01); *C07D 213/80* (2013.01); *C07D 239/47* (2013.01); *C07D 401/12* (2013.01); *C07D 405/12* (2013.01); *C07D 413/12* (2013.01); *C07D 453/02* (2013.01); *C07F 9/587* (2013.01); *C07F 9/588* (2013.01); *C07F 9/65127* (2013.01); *C07F 9/65583* (2013.01); *C07H 13/08* (2013.01); *C07H 15/26* (2013.01); *C07H 19/048* (2013.01)

(58) Field of Classification Search
CPC .. A61K 31/553; A61K 31/635; A61K 31/706; A61K 31/4375; A61K 31/4439; A61K 31/4545; A61K 31/496; A61K 31/5377; A61K 31/44; A61K 31/506; A61K 31/675; A61K 31/7052; A61K 45/06; C07D 213/74; C07D 453/02; C07D 405/02; C07H 19/048; C07H 15/26; C07F 9/587; C07F 9/65583; C07F 9/65127; C07F 9/588

See application file for complete search history.

(56) References Cited

U.S. PATENT DOCUMENTS

| | | | |
|---|---|---|---|
| 6,492,529 B1 | 12/2002 | Kapadia et al. | |
| 6,525,046 B1 | 2/2003 | Cirillo et al. | |
| 6,852,717 B2 | 2/2005 | Cirillo et al. | |
| 6,872,726 B2 | 3/2005 | Cirillo et al. | |
| 6,894,173 B2 | 5/2005 | Zhang et al. | |
| 6,916,814 B2 | 7/2005 | Moss et al. | |
| 7,241,758 B2 | 7/2007 | Hoa et al. | |
| 7,279,475 B2 | 10/2007 | Cirillo et al. | |
| 7,790,756 B2* | 9/2010 | Flynn | C07D 401/12 514/341 |
| 7,838,541 B2 | 11/2010 | Dumas et al. | |
| 8,293,748 B2 | 10/2012 | Ito et al. | |
| 8,293,771 B2 | 10/2012 | Ito et al. | |
| 8,299,073 B2 | 10/2012 | Ito et al. | |
| 8,299,074 B2 | 10/2012 | Ito et al. | |
| 8,618,140 B2 | 12/2013 | Ito et al. | |
| 8,642,773 B2 | 2/2014 | Ito et al. | |
| 8,927,563 B2 | 1/2015 | Fyfe | |
| 8,933,228 B2 | 1/2015 | Murray et al. | |
| 8,975,285 B2 | 3/2015 | Ito et al. | |
| 9,024,041 B2 | 5/2015 | King-Underwood | |
| 9,079,893 B2 | 7/2015 | Cass | |
| 9,108,950 B2 | 8/2015 | Ito et al. | |
| 9,249,125 B2 | 2/2016 | Duffy et al. | |
| 9,447,076 B2 | 9/2016 | Longshaw et al. | |
| 9,481,648 B2 | 11/2016 | Baker et al. | |
| 9,499,486 B2* | 11/2016 | Fyfe | A61K 31/4412 |
| 9,624,196 B2 | 4/2017 | Longshaw et al. | |
| 9,751,837 B2* | 9/2017 | Baker | A61K 31/4412 |
| 9,790,174 B2* | 10/2017 | Thom | C07C 317/48 |
| 9,822,076 B2* | 11/2017 | Fyfe | C07D 213/74 |
| 9,890,185 B2 | 2/2018 | Fyfe et al. | |
| 2001/0011135 A1 | 8/2001 | Riedl et al. | |
| 2003/0083333 A1 | 5/2003 | Cirillo et al. | |
| 2003/0125354 A1 | 7/2003 | Hao et al. | |
| 2003/0130309 A1 | 7/2003 | Moss et al. | |
| 2004/0053908 A1 | 3/2004 | Funahashi et al. | |
| 2004/0077647 A1 | 4/2004 | Cirillo et al. | |
| 2004/0152725 A1 | 8/2004 | Moss et al. | |
| 2005/0032797 A1 | 2/2005 | Cirillo et al. | |
| 2006/0128734 A1 | 6/2006 | Floersheimer et al. | |
| 2006/0160832 A1 | 7/2006 | Funahashi et al. | |
| 2006/0247259 A1 | 11/2006 | Funahashi et al. | |
| 2008/0312192 A1 | 12/2008 | Bold et al. | |
| 2010/0197911 A1 | 8/2010 | Funahashi et al. | |
| 2011/0118470 A1 | 5/2011 | Funahashi et al. | |
| 2012/0244120 A1 | 9/2012 | Charron et al. | |
| 2013/0029990 A1 | 1/2013 | King-Underwood et al. | |
| 2013/0040962 A1 | 2/2013 | King-Underwood et al. | |
| 2013/0040995 A1 | 2/2013 | King-Underwood et al. | |
| 2013/0102607 A1 | 4/2013 | Cass et al. | |
| 2013/0123260 A1 | 5/2013 | Charron et al. | |
| 2013/0150343 A1 | 6/2013 | Van Niel et al. | |
| 2013/0156826 A1 | 6/2013 | Murray et al. | |
| 2014/0057915 A1 | 2/2014 | Cariou et al. | |
| 2014/0114064 A1 | 4/2014 | Ito et al. | |
| 2014/0228410 A1 | 8/2014 | Ito et al. | |
| 2014/0249169 A1 | 9/2014 | Ito et al. | |
| 2014/0296208 A1 | 10/2014 | Baker et al. | |
| 2014/0296271 A1 | 10/2014 | Fyfe | |
| 2015/0166483 A1 | 6/2015 | Fyfe | |
| 2015/0203475 A1 | 7/2015 | Duffy et al. | |
| 2015/0210722 A1 | 7/2015 | Fyfe et al. | |
| 2015/0218137 A1 | 8/2015 | Cariou et al. | |
| 2015/0225373 A1 | 8/2015 | Fyfe et al. | |
| 2015/0225427 A1 | 8/2015 | Fyfe et al. | |
| 2015/0232450 A1 | 8/2015 | Longshaw et al. | |
| 2015/0252024 A1 | 9/2015 | Ito et al. | |
| 2015/0329523 A1 | 11/2015 | Frickel et al. | |
| 2016/0009695 A1 | 1/2016 | Ito et al. | |
| 2016/0016934 A1 | 1/2016 | Fyfe | |
| 2016/0039797 A1 | 2/2016 | Fyfe | |
| 2016/0045482 A1 | 2/2016 | Charron | |
| 2016/0045512 A1 | 2/2016 | Charron | |
| 2016/0096805 A1 | 4/2016 | Fyfe | |
| 2016/0115152 A1 | 4/2016 | King-Underwood | |
| 2016/0318909 A1 | 11/2016 | Fyfe | |
| 2016/0318958 A1 | 11/2016 | Fyfe | |
| 2016/0340343 A1 | 11/2016 | Fyfe et al. | |
| 2016/0340375 A1 | 11/2016 | Fyfe et al. | |
| 2016/0368896 A1 | 12/2016 | Longshaw et al. | |

(56) References Cited

U.S. PATENT DOCUMENTS

| | | |
|---|---|---|
| 2016/0376232 A1 | 12/2016 | Thom |
| 2017/0029378 A1 | 2/2017 | Fyfe |
| 2017/0057945 A1 | 3/2017 | Longshaw et al. |
| 2017/0209445 A1 | 7/2017 | Fyfe |
| 2018/0044288 A1 | 2/2018 | Baker et al. |
| 2018/0118719 A1 | 5/2018 | Longshaw et al. |

FOREIGN PATENT DOCUMENTS

| | | |
|---|---|---|
| WO | WO 00/041698 | 7/2000 |
| WO | WO 00/043384 | 7/2000 |
| WO | WO 00/055139 | 9/2000 |
| WO | WO 01/04115 | 1/2001 |
| WO | WO 01/36403 | 5/2001 |
| WO | WO 02/083628 | 10/2002 |
| WO | WO 02/083642 | 10/2002 |
| WO | WO 02/092576 | 11/2002 |
| WO | WO 02/096876 | 12/2002 |
| WO | WO 2003/005999 | 1/2003 |
| WO | WO 2003/068223 | 8/2003 |
| WO | WO 2003/068228 | 8/2003 |
| WO | WO 2003/072569 | 9/2003 |
| WO | WO 2003/099771 | 12/2003 |
| WO | WO 2004/014870 | 2/2004 |
| WO | WO 2005/023761 | 3/2004 |
| WO | WO 2004/113352 | 12/2004 |
| WO | WO 2005/005396 | 1/2005 |
| WO | WO 2005/018624 | 3/2005 |
| WO | WO 2005/044825 | 5/2005 |
| WO | WO 2005/051366 | 6/2005 |
| WO | WO 2006/015775 | 2/2006 |
| WO | WO 2006/043090 | 4/2006 |
| WO | WO 2007/004749 | 1/2007 |
| WO | WO 2007/053394 | 5/2007 |
| WO | WO 2010/038085 | 4/2010 |
| WO | WO 2010/038086 | 4/2010 |
| WO | WO 2010/067130 | 6/2010 |
| WO | WO 2010/067131 | 6/2010 |
| WO | WO 2010/112936 | 10/2010 |
| WO | WO 2011/070368 | 6/2011 |
| WO | WO 2011/070369 | 6/2011 |
| WO | WO 2011/121366 | 10/2011 |
| WO | WO 2011/124923 | 10/2011 |
| WO | WO 2011/124930 | 10/2011 |
| WO | WO 2011/158039 | 12/2011 |
| WO | WO 2011/158042 | 12/2011 |
| WO | WO 2011/158044 | 12/2011 |
| WO | WO 2013/050756 | 4/2013 |
| WO | WO 2013/050757 | 4/2013 |
| WO | WO 2013/083604 A1 | 6/2013 |
| WO | WO 2014/027209 | 2/2014 |
| WO | WO 2014/033446 | 3/2014 |
| WO | WO 2014/033447 | 3/2014 |
| WO | WO 2014/033448 | 3/2014 |
| WO | WO 2014/033449 | 3/2014 |
| WO | WO 2014/076484 | 5/2014 |
| WO | WO 201/140582 | 9/2014 |
| WO | WO 2014/162121 | 10/2014 |
| WO | WO 2014/162122 | 10/2014 |
| WO | WO 2014/162126 | 10/2014 |
| WO | WO 2015/092423 | 6/2015 |
| WO | WO 2015/121444 | 8/2015 |
| WO | WO 2015/121660 | 8/2015 |

OTHER PUBLICATIONS

U.S. Appl. No. 14/561,290, filed Dec. 5, 2014, Murray.
U.S. Appl. No. 15/457,810, filed Mar. 13, 2017, Longshaw et al.
U.S. Appl. No. 15/515,079, filed Mar. 28, 2017, Fyfe.
Badrinarayan, et al. 2011 "Sequence, structure, and active site analyses of p38 MAP kinase: Exploiting DFG-out conformation as a strategy to design new type II leads" *Journal of Chemical Information and Modeling* 51; 115-129.
Barnes, et al. 2007 "Trimethylsilylpyrazoles as novel inhibitors of p38 MAP kinase: A new use of silicon bioisosteres in medicinal chemistry" *Bioorganic & Medicinal Chemistry* 17; 354-357.
Boehm, et al. 2000 "New inhibitors of p38 kinase" *Expert Opinion on Therapeutic Patents* 10(1): 25-37.
Brinkmann, et al. 2010 "Fingolimod (FTY720): discovery and development of an oral drug to treat multiple sclerosis" *Nature Reviews Drug Discovery* 9: 883-897.
CAS Registry No. 1379462-42-6, 2012 American Chemical Society.
CAS Registry No. 1379401-24-7, 2012 American Chemical Society.
CAS Registry No. 1379397-83-7, 2012 American Chemical Society.
CAS Registry No. 1379457-84-7, 2012 American Chemical Society.
CAS Registry No. 1384608-34-7, 2012 American Chemical Society.
CAS Registry No. 1379462-36-8, 2012 American Chemical Society.
CAS Registry No. 1384595-05-4, 2012 American Chemical Society.
CAS Registry No. 1384611-77-1, 2012 American Chemical Society.
CAS Registry No. 1384610-90-5, 2012 American Chemical Society.
Cirillo, et al. 2009 "Discovery and characterization of the N-phenyl-N'-naphthylurea class of p38 kinase inhibitors" *Bioorganic & Medicinal Chemistry* 19; 2386-2391.
Cogan, et al. 2008 "Structure-based design and subsequent optimization of 2-tolyl-(1,2,3-triazol-1-yl-4-carboxamide) inhibitors of p38 MAP kinase" *Bioorganic & Medicinal Chemistry* 18; 3251-3255.
Coughlin, et al. 2010 "Approaches and limitations of phosphatidylinositol-3-kinase pathway activation status as a predictive biomarker in the clinical development of targeted therapy" *Breast Cancer Res Treat* 124: 1-11.
Dietrich, et al. 2010 "The design, synthesis, and evaluation of 8 hybrid DFG-out allosteric kinase inhibitors: A structural analysis of the binding interactions of Gleevec®, Nexavar®, and BIRB-796" *Bioorganic & Medicinal Chemistry* 18; 5738-5748.
Dodeller, et al. 2006 "The p38 mitogen-activated protein kinase signaling cascade in CD4 T cells" *Arthritis Research & Therapy* 8(2): 1-11.
Dumas, et al. 2004 "Recent developments in the discovery of protein kinase inhibitors from the urea class" *Current Opinion in Drug Discovery & Development* 7(5); 600-616.
Goldberg, et al. 2007 "Discovery and Optimization of p38 Inhibitors via Computer-Assisted Drug Decision" *Journal of Medicinal Chemistry* 50; 4016-4026.
Jope, et al. 2007 "Glycogen synthase kinase-3 (GSK3): Inflammation, diseases, and therapeutics" *Neurochem Res* 32: 577-595.
Judge, et al. 2006 "Potassium channel blockers in multiple sclerosis: Neuronal $K_v$ channels and effects of symptomatic treatment" *Pharmacology & Therapeutics* 111: 224-259.
Kim, et al. 2009 "Src family kinases as mediators of endothelial permeability: effects on inflammation and metastasis" *Cell Tissue Res* 335: 249-259.
Kuster "Kinase inhibitors, Methods and Protocols" *Methods in Molecular Biology* 795 Chapters 1 and 2 (in 46 pages).
Lima, et al. 2011 "Anti-inflammatory effects of LASSBio-998, a new drug candidate designed to be a p38 MAPK inhibitor, in an experimental model of acute lung inflammation" *Pharmacological Reports* 63: 1029-1039.
Liu, et al. 2011 "Src phosphorylation of endothelial cell surface intercellular adhesion molecule-1 mediates neutrophil adhesion and contributes to the mechanism of lung inflammation" *Arterioscler Thromb Vasc Biol* 31: 1342-1350.
Masuda, et al. 2008 "Syk inhibitors as treatment for allergic rhinitis" *Pulmonary Pharmacology & Therapeutics* 21: 461-467.
McDermott, et al. 2009 "Personalized cancer therapy with selective kinase inhibitors: An emerging paradigm in medical oncology" *Journal of Clinical Oncology* 27(33): 5650-5659.

(56) References Cited

OTHER PUBLICATIONS

Menard, et al. 2009 "Novel potent BRAF inhibitors: Toward 1 nM compounds through optimization of the Central Phenyl Ring" *Journal of Medicinal Chemistry* 52; 3881-3891.

Montalban, et al. 2010 "KR-003048, a potent, orally active inhibitors of p38 mitogen-activated protein kinase" *European Journal of Pharmacology* 632; 93-102.

Montalban, et al. 2010 "Optimization of α-ketoamide based p38 inhibitors through modifications to the region that binds to the allosteric site" *Bioorganic & Medicinal Chemistry* 20; 4819-4824.

Pettus, et al. 2008 "Small Molecule p38 MAP Kinase Inhibitors for the Treatment of Inflammatory Diseases: Novel Structures and Developments During 2006-2008" *Current Topics in Medicinal Chemistry* 8; 1452-1467.

Sawyers 2008 "The cancer biomarker problem" *Nature* 452: 548-552.

Singh, et al. 2007 "Spleen tyrosine kinase (Syk) biology, inhibitors and therapeutic applications" *Annual Reports in Medicinal Chemistry* 42: 379-391.

Singh, et al. 2010 "A randomized, placebo-controlled study of the effects of the p38 MAPK inhibitor SB-681323 on blood biomarkers of inflammation in COPD patients" *J Clin Pharmacol* 50: 94-100.

Sutherland, et al. 2004 "Management of chronic obstructive pulmonary disease" *The New England Journal of Medicine* 350: 2689-2697.

To, et al. 2015 "Potent anti-inflammatory effects of the narrow spectrum kinase inhibitor RV1088 on rheumatoid arthritis synovial membrane cells" *British Journal of Pharmacology* 172: 3805-3816.

Weinblatt, et al. 2010 "An oral spleen tyrosine kinase (Syk) inhibitor for rheumatoid arthritis" The New England Journal of Medicine 363(14): 1303-1312.

Written Opinion and International Search Report for PCT/GB2015/052876 completed Nov. 19, 2015 in 14 pages.

Written Opinion for PCT/GB2015/052877 dated 2015 (in 6 pages).

Yamamoto, et al. 2003 "The orally available spleen tyrosine kinase inhibitor 2-[7-(3,4-Dimethoxyphenyl)-imidazo[1,2-c]pyrimidin-5-ylamino]-nicotinamide dihydrochloride (BAY 61-3606) blocks antigen-induced airway inflammation in rodents" *The Journal of Pharmacology and Experimental Therapeutics* 306(3): 1174-1181.

Zambon, et al. 2010 "Novel hinge binder improves activity and pharmacokinetic properties of BRAF inhibitors" *Journal of Medicinal Chemistry* 53; 5639-5655.

U.S. Appl. No. 16/035,502, Baker T.M.
U.S. Appl. No. 16/032,858, Longshaw, A.

\* cited by examiner

KINASE INHIBITORS

FIELD OF THE INVENTION

This invention relates, inter alia, to compounds which are antiinflammatory agents (e.g. through inhibition of one or more of members of: the family of p38 mitogen-activated protein kinase enzymes (referred to herein as p38 MAP kinase inhibitors), for example the alpha kinase sub-type thereof; Syk kinase; and the Src family of tyrosine kinases). The invention also relates to the use of such compounds in therapy, including in mono- and combination therapies, especially in the treatment of inflammatory diseases, including inflammatory diseases of the lung (such as asthma and chronic obstructive pulmonary disease (COPD)), eye (such as uveitis or keratoconjunctivitis sicca (dry eye disease, also known as xerophthalmia)) and gastrointestinal tract (such as Crohn's disease and ulcerative colitis).

BACKGROUND OF THE INVENTION

The listing or discussion of an apparently prior-published document in this specification should not necessarily be taken as an acknowledgement that the document is part of the state of the art or is common general knowledge.

Four p38 MAPK isoforms (alpha, beta, gamma and delta respectively) have been identified, each displaying different patterns of tissue expression. The p38 MAPK alpha and beta isoforms are found ubiquitously throughout the body, are present in many different cell types and are inhibited by a number of previously described small molecular weight compounds. Early classes of inhibitors were highly toxic due to the broad tissue distribution of these isoforms which resulted in off-target effects of the compounds. Some of the more recently identified inhibitors show improved selectivity for p38 MAPK alpha and beta isoforms and have wider safety margins.

p38 MAP kinase is believed to play a pivotal role in many of the signalling pathways that are involved in initiating and maintaining chronic, persistent inflammation in human disease, for example, in severe asthma, COPD and inflammatory bowel disease (IBD). There is now an abundant literature which demonstrates that p38 MAP kinase is activated by a range of pro-inflammatory cytokines and that its activation results in the recruitment and release of further pro-inflammatory cytokines. Indeed, data from some clinical studies demonstrate beneficial changes in disease activity in patients during treatment with p38 MAP kinase inhibitors. For instance, Smith describes the inhibitory effect of p38 MAP kinase inhibitors on TNFα (but not IL-8) release from human PBMCs (Smith, S. J., *Br. J. Pharmacol.*, 2006, 149:393-404).

The use of inhibitors of p38 MAP kinase in the treatment of COPD and IBD has also been proposed. Small molecule inhibitors targeted to p38 MAPKα/β have proved to be effective in reducing various parameters of inflammation in:
- cells and tissues obtained from patients with COPD, who are generally corticosteroid insensitive (Smith, S. J., *Br. J. Pharmacol.*, 2006, 149:393-404);
- biopsies from IBD patients (Docena, G. et al., *J. Trans. Immunol.*, 2010, 162:108-115); and
- in vivo animal models (Underwood, D. C. et al., *Am. J. Physiol.*, 2000, 279:L895-902; Nath, P. et al., *Eur. J. Pharmacol.*, 2006, 544:160-167).

Irusen and colleagues also suggested the possibility of involvement of p38 MAPKα/β on corticosteroid insensitivity via the reduction of binding affinity of the glucocorticoid receptor (GR) in nuclei (Irusen, E. et al., *J. Allergy Clin. Immunol.*, 2002, 109:649-657). Clinical investigations in inflammatory diseases with a range of p38 MAP kinase inhibitors, including AMG548, BIRB 796, VX702, SCIO469 and SCIO323, have been described (Lee, M. R. and Dominguez, C., *Current Med. Chem.*, 2005, 12:2979-2994.). However, the major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specifically mentioned above.

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. The recent publication of Mercado et al. (2007; *American Thoracic Society Abstract A*56) demonstrates that silencing p38 MAPK γ has the potential to restore sensitivity to corticosteroids. Thus, there may be a dual benefit for patients in the use of a p38 MAP kinase inhibitor for the treatment of COPD.

Many patients diagnosed with asthma or with COPD continue to suffer from uncontrolled symptoms and from exacerbations of their medical condition that can result in hospitalisation. This occurs despite the use of the most advanced, currently available treatment regimens, comprising of combination products of an inhaled corticosteroid and a long acting β-agonist. Data accumulated over the last decade indicates that a failure to manage effectively the underlying inflammatory component of the disease in the lung is the most likely reason that exacerbations occur. Given the established efficacy of corticosteroids as anti-inflammatory agents and, in particular, of inhaled corticosteroids in the treatment of asthma, these findings have provoked intense investigation. Resulting studies have identified that some environmental insults invoke corticosteroid-insensitive inflammatory changes in patients' lungs. An example is the response arising from virally-mediated upper respiratory tract infections (URTI), which have particular significance in increasing morbidity associated with asthma and COPD.

It has been disclosed previously that compounds that inhibit the activity of both the c-Src and Syk kinases are effective agents against rhinovirus replication (Charron, C. E. et al., WO 2011/158042) and that compounds that inhibit p59-HCK are effective against influenza virus replication (Charron, C. E. et al., WO 2011/070369). Taken together with inhibition of p38 MAPK, these are particularly attractive properties for compounds to possess that are intended to treat patients with chronic respiratory diseases.

Certain p38 MAPK inhibitors have also been described as inhibitors of replication of respiratory syncytial virus (Cass L. et al., WO 2011/158039).

The precise etiology of IBD is uncertain, but is believed to be governed by genetic and environmental factors that interact to promote an excessive and poorly controlled mucosal inflammatory response directed against components of the luminal microflora. This response is mediated through infiltration of inflammatory neutrophils, dendritic cells and T-cells from the periphery. p38 has become an obvious target for investigation in IBD models as a consequence of its ubiquitous expression in inflammatory cells.

Studies investigating the efficacy of p38 inhibitors in animal models of IBD and human biopsies from IBD patients indicated that p38 could be a target for the treatment of IBD (Hove, T. ten et al., *Gut,* 2002, 50:507-512, Docena, G. et al., *J. Trans. Immunol,* 2010, 162:108-115). However, these findings are not completely consistent with other groups reporting no effect with p38 inhibitors (Malamut G. et al., *Dig. Dis. Sci,* 2006, 51:1443-1453). A clinical study in Crohn's patients using the p38 alpha inhibitor BIRB796 demonstrated potential clinical benefit with an improvement in C-reactive protein levels. However this improvement was transient, returning to baseline by week 8 (Schreiber, S. et al., *Clin. Gastro. Hepatology,* 2006, 4:325-334). A small clinical study investigating the efficacy of CNI-1493, a p38 and Jnk inhibitor, in patients with severe Crohn's disease showed significant improvement in clinical score over 8 weeks (Hommes, D. et al. *Gastroenterology.* 2002 122:7-14).

T cells are known to play a key role in mediating inflammation of the gastrointestinal tract. Pioneering work by Powrie and colleagues demonstrated that transfer of naive CD4+ cells into severely compromised immunodeficient (SCID) animals results in the development of colitis which is dependent on the presence of commensal bacteria (Powrie F. et al. *Int Immunol.* 1993 5:1461-71). Furthermore, investigation of mucosal membranes from IBD patients showed an upregulation of CD4+ cells which were either Th1 (IFNg/IL-2) or Th2 (IL5/TGFb) biased depending on whether the patient had Crohn's disease or ulcerative colitis (Fuss I J. et al. *J Immunol.* 1996 157:1261-70.). Similarly, T cells are known to play a key role in inflammatory disorders of the eye with several studies reporting increased levels of T cell associated cytokines (IL-17 and IL-23) in sera of Beçhets patients (Chi W. et al. *Invest Ophthalmol Vis Sci.* 2008 49:3058-64). In support of these observations, Direskeneli and colleagues demonstrated that Beçhets patients have increased Th17 cells and decreased Treg cells in their peripheral blood (Direskeneli H. et al. J Allergy Clin Immunol. 2011 128:665-6).

One approach to inhibit T cell activation is to target kinases which are involved in activation of the T cell receptor signalling complex. Syk and Src family kinases are known to play a key role in this pathway, where Src family kinases, Fyn and Lck, are the first signalling molecules to be activated downstream of the T cell receptor (Barber E K. et al. *PNAS* 1989, 86:3277-81). They initiate the tyrosine phosphorylation of the T cell receptor leading to the recruitment of the Syk family kinase, ZAP-70. Animal studies have shown that ZAP-70 knockout results in a SCID phenotype (Chan A C. et al. *Science.* 1994, 10; 264(5165):1599-601).

A clinical trial in rheumatoid arthritis patients with the Syk inhibitor Fostamatinib demonstrated the potential of Syk as an anti-inflammatory target with patients showing improved clinical outcome and reduced serum levels of IL-6 and MMP-3 (Weinblatt M E. et al. *Arthritis Rheum.* 2008 58:3309-18). Syk kinase is widely expressed in cells of the hematopoietic system, most notably in B cells and mature T cells. Through interaction with immunoreceptor tyrosine-based activation motifs (ITAM), it plays an important role in regulating T cell and B cell expansion as well as mediating immune-receptor signalling in inflammatory cells. Syk activation leads to IL-6 and MMP release—inflammatory mediators commonly found upregulated in inflammatory disorders including IBD and rheumatoid arthritis (Wang Y D. et al *World J Gastroenterol* 2007; 13: 5926-5932, Litinsky I et al. *Cytokine.* 2006 January 33:106-10).

In addition to playing key roles in cell signalling events which control the activity of pro-inflammatory pathways, kinase enzymes are now also recognised to regulate the activity of a range of cellular functions, including the maintenance of DNA integrity (Shilo, Y. *Nature Reviews Cancer,* 2003, 3: 155-168) and co-ordination of the complex processes of cell division. Indeed, certain kinase inhibitors (the so-called "Olaharski kinases") have been found to alter the frequency of micronucleus formation in vitro (Olaharski, A. J. et al., *PLoS Comput. Biol.,* 2009, 5(7), e1000446; doi: 10.1371/journal.pcbi.1000446). Micronucleus formation is implicated in, or associated with, disruption of mitotic processes and is therefore undesirable. Inhibition of glycogen synthase kinase 3α (GSK3α) was found to be a particularly significant factor that increases the likelihood of a kinase inhibitor promoting micronucleus formation. Also, inhibition of the kinase GSK3β with RNAi has been reported to promote micronucleus formation (Tighe, A. et al., *BMC Cell Biology,* 2007, 8:34).

Whilst it may be possible to attenuate the adverse effects of inhibition of Olaharski kinases such as GSK3α by optimisation of the dose and/or by changing the route of administration of a molecule, it would be advantageous to identify further therapeutically useful molecules with low or negligible inhibition of Olaharski kinases, such as GSK 3α and/or have low or negligible disruption of mitotic processes (e.g. as measured in a mitosis assay).

Various compounds, including urea derivatives, are disclosed as inhibiting one or more kinases. Examples of such compounds may be found in WO 99/23091, WO 00/041698, WO 00/043384, WO 00/055139, WO 01/36403, WO 01/4115, WO 02/083628, WO 02/083642, WO 02/092576, WO 02/096876, WO 2003/005999, WO 2003/068223, WO 2003/068228, WO 2003/072569, WO 2004/014870, WO 2004/113352, WO 2005/005396, WO 2005/018624, WO 2005/023761, WO 2005/044825, WO 2006/015775, WO 2006/043090, WO 2007/004749, WO 2007/053394, WO 2013/050756, WO 2013/050757, WO 2014/027209, WO 2014/033446, WO 2014/033447, WO 2014/033448, WO 2014/033449, WO 2014/076484, WO 2014/140582 WO 2014/162121, WO 2014/162122, WO 2014/162126 and WO 2015/092423. Further examples may be found in articles published in:

*Curr. Opin. Drug Devel.* (2004, 7(5), 600-616);
*J. Med. Chem.* (2007, 50, 4016-4026; 2009, 52, 3881-3891; and 2010, 53, 5639-5655);
*Bioorg. Med. Chem. Lett.* (2007, 17, 354-357; 2008, 18, 3251-3255; 2009, 19, 2386-2391; and 2010, 20, 4819-4824);
*Curr. Top. Med. Chem.* (2008, 8, 1452-1467);
*Bioorg. Med. Chem.* (2010, 18, 5738-5748);
*Eur. J. Pharmacol.* (2010, 632, 93-102);
*J. Chem. Inf. Model.* (2011, 51, 115-129); and
*Br. J. Pharmacol.* (2015, 172, 3805-3816).

Nevertheless, there remains a need to identify and develop new kinase inhibitors, specifically alternative p38 MAP kinase inhibitors that are suitable for the treatment of inflammation. There is particularly a need for such inhibitors that have improved therapeutic potential over currently available treatments or, in particular, that exhibit a superior therapeutic index (e.g. inhibitors that are at least equally efficacious and, in one or more respects, are less toxic at the relevant therapeutic dose than previous agents).

SUMMARY OF THE INVENTION

We have now discovered, surprisingly, that certain aniline-substituted diarylureas inhibit one or more of p38 MAP kinase, Syk and Src family kinases and therefore possess good anti-inflammatory properties.

Thus, according to a first aspect of the invention, there is provided a compound of formula I,

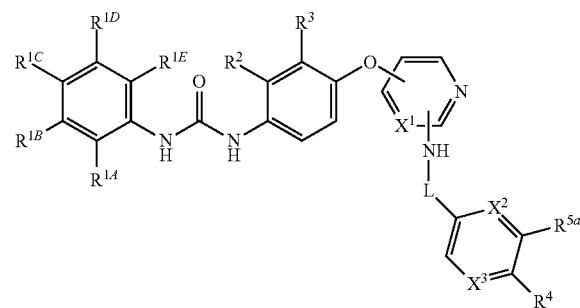

wherein:
R$^{1A}$ represents
C$_{1-6}$ alkoxy, C$_{1-6}$ alkyl, C$_{2-6}$ alkenyl, C$_{2-6}$ alkynyl, which latter four groups are optionally substituted by one or more substituents selected from C$_{1-2}$ alkyl, halo, hydroxy, —OP(O)(OH)$_2$ and C$_{1-2}$ alkoxy,
H, halo, cyano,
phenyl or Het$^1$, which latter two groups are optionally substituted with one or more substituents selected from C$_{1-2}$ alkyl and C$_{1-2}$ alkoxy,
or R$^{1A}$ and R$^{1B}$ together represent a structural fragment selected from the following

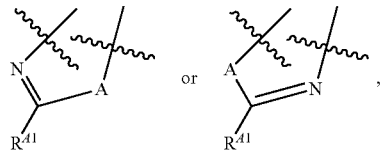

wherein the wavy lines represent the points of attachment to the phenyl ring;
A represents O, S or N(R$^{A2}$);
R$^{A1}$ represents H, C$_{1-4}$ alkyl or hydroxy;
R$^{A2}$ represents H or C$_{1-4}$ alkyl;
R$^{1B}$ represents —NR$^X$S(O)$_2$R$^{Y1}$, —C(O)NR$^X$R$^Y$, H, halo, cyano, —C$_{1-4}$ alkylene-CN, —C$_{1-4}$ alkylene-OH, —NR$^X$R$^{X1}$, —C(O)OR$^X$, —S(O)$_2$NR$^X$R$^Y$, —NR$^X$C(O)R$^Y$, —NR$^{X2}$S(O)$_2$NR$^X$R$^Y$, —NR$^X$P(O)R$^{Y1}$R$^{Y2}$, —NR$^X$C(O)OR$^{Y1}$ or Het$^1$ optionally substituted with one or more substituents selected from halo, hydroxy, C$_{1-2}$ alkyl and C$_{1-2}$ alkoxy;
R$^X$ and R$^{X1}$ independently represent H or C$_{1-6}$ alkyl optionally substituted by one or more substituents selected from halo, hydroxy, —OP(O)(OH)$_2$ and C$_{1-2}$ alkoxy, or R$^X$ and R$^{X1}$ together represent C$_{3-6}$ n-alkylene or C$_{4-5}$ n-alkylene interrupted between C2 and C3 by —O— or —N(R$^{X2}$)—, or R$^{X1}$ represents Het$^1$ optionally substituted with one or more substituents selected from halo, hydroxy, C$_{1-2}$ alkyl and C$_{1-2}$ alkoxy;
R$^Y$, R$^{Y1}$ and R$^{Y2}$ independently represent C$_{1-6}$ alkyl, C$_{3-7}$ cycloalkyl, phenyl, benzyl, Het$^1$ or Het$^2$, which latter six groups are optionally substituted by one or more substituents selected from C$_{1-2}$ alkyl, halo, hydroxy, —OP(O)(OH)$_2$, C$_{1-2}$ alkoxy, C(O)OH, C(O)O—(C$_{1-4}$ alkyl) and —N(R$^a$)(R$^b$), and/or which Het$^2$ group is substituted with one or more oxo groups,
or R$^Y$ represents H,
or R$^X$ and R$^Y$ together represent C$_{3-6}$ n-alkylene or C$_{4-5}$ n-alkylene interrupted between C2 and C3 by —O—, —S(O)$_n$— or —N(R$^{X2}$)—;
R$^a$ and R$^b$ independently represent H, methyl or —C(R$^c$)(R$^d$)—C$_{1-3}$ alkyl, the C$_{1-3}$ alkyl portion of which latter group is optionally substituted by one or more hydroxy substituents,
or R$^a$ and R$^b$ together represent C$_{3-6}$ n-alkylene or C$_{4-5}$ n-alkylene interrupted between C2 and C3 by —O—, —S(O)$_m$— or —N(R$^{X2}$)—;
R$^c$ and R$^d$ independently represent H or methyl;
each R$^{X2}$ independently represents H or C$_{1-4}$ alkyl;
R$^{1C}$ and R$^{1E}$ independently represent H, halo, cyano or methyl;
provided that at least one of R$^{1A}$, R$^{1B}$, R$^{1C}$ and R$^{1E}$ is other than H;
R$^{1D}$ represents trimethylsilyl, C$_{2-7}$ alkyl, C$_{2-7}$ alkenyl, C$_{2-7}$ alkynyl, C$_{3-7}$ cycloalkyl, phenyl, Het$^1$ or Het$^2$, which latter seven groups are optionally substituted by one or more substituents selected from C$_{1-2}$ alkyl, halo, cyano, hydroxy, —OP(O)(OH)$_2$ and C$_{1-2}$ alkoxy;
R$^2$ and R$^3$, together with the C-atoms to which they are attached, form a fused phenyl or pyridyl ring, which latter two rings are optionally substituted by one or more substituents selected from C$_{1-3}$ alkyl, C$_{1-3}$ haloalkyl, cyano and halo,
or one of R$^2$ and R$^3$ represents H, halo, cyano, C$_{1-3}$ alkyl or C$_{1-3}$ haloalkyl and the other independently represents halo, cyano, C$_{1-3}$ alkyl or C$_{1-3}$ haloalkyl,
or R$^2$ and R$^3$ together combine to form C$_{3-5}$ alkylene or C$_{3-5}$ alkenylene, which latter two groups are optionally substituted by one or more substituents selected from C$_{1-3}$ alkyl, C$_{1-3}$ haloalkyl, cyano and halo;
X$^1$ represents N or CH;
L represents a direct bond or C$_{1-2}$ alkylene;
X$^2$ represents CR$^Z$ or N;
X$^3$ represents CR$^{5b}$ or N;
R$^Z$ represents H, halo, cyano, hydroxy, C$_{1-3}$ alkyl or C$_{1-3}$ alkoxy, which latter two groups are optionally substituted by one or more halo atoms;
R$^4$ represents
-Q$^1$-[C(R$^{6c}$)(R$^{6d}$)—(CH$_2$)$_{0-1}$CH$_2$—Z]$_{1-12}$—CH$_2$(CH$_2$)$_{0-1}$CH$_2$—R$^{6a}$,
-Q$^2$-C(R$^{6c}$)(R$^{6d}$)—[C$_{1-5}$ alkylene]-R$^{6a}$, which C$_{1-5}$ alkylene group is optionally substituted by oxo and/or by one or more R$^{6e}$,
-Q$^3$-[C$_{1-4}$ alkylene]$_{0-1}$-Het$^{x1}$, which C$_{1-4}$ alkylene group is optionally substituted by oxo and/or by one or more R$^{6e}$ and which Het$^{x1}$ group is optionally substituted by one or more substituents selected from halo, hydroxy, oxo, C$_{3-6}$ cycloalkyl, C$_{1-3}$ alkoxy and —[C(O)]$_{0-1}$—C$_{1-4}$ alkyl, the C$_{1-4}$ alkyl part of which latter group is optionally substituted by one or more R$^{6e}$,
-Q$^{22}$-[C$_{1-4}$ alkylene]$_{0-1}$-phenyl, which C$_{1-4}$ alkylene group is optionally substituted by oxo and/or by one or more R$^{6e}$, and which phenyl group is substituted by —[C(O)]$_{0-1}$—C$_{1-4}$ alkyl, the C$_{1-4}$ alkyl part of which latter group is optionally substituted by one or more R$^{6e}$, and which phenyl group is optionally further substituted by one or more substituents selected from halo, hydroxy, oxo, C$_{3-6}$ cycloalkyl and C$_{1-3}$ alkoxy, —S(O)$_p$R$^{6b}$,
—[C$_{1-4}$ alkylene]$_{0-1}$-CO$_2$H, Het$^{x2}$ which Het$^{x2}$ group is optionally substituted by one or more substituents selected from halo, hydroxy, oxo, $C_{1-3}$ alkyl and $C_{1-3}$ alkoxy,
—COR$^{6b}$,
—CH$_2$OH,
—CH$_2$OP(O)(OH)$_2$ or
-Q$^4$-P(O)(OR$^9$)(R$^7$);
Z represents, independently upon each occurrence, O, C(O)N(R$^8$) or N(R$^8$)C(O);
R$^{5a}$ and R$^{5b}$ independently represent $C_{1-3}$ alkoxy or $C_{1-3}$ alkyl, which latter two groups are optionally substituted by one or more halo atoms, or R$^{5a}$ and R$^{5b}$ independently represent —N(R$^e$)(R$^f$), $C_{2-3}$ alkynyl, H, cyano, —C(O)NH$_2$, hydroxy, halo or —S(O)$_{0-2}$—$C_{1-3}$ alkyl;
R$^{6a}$ represents OR$^{7a}$, —S(O)$_{0-2}$R$^{7aa}$, N(R$^{7b}$)R$^{7c}$ or CO$_2$H;
R$^{6b}$ represents $C_{1-8}$ alkyl, $C_{3-8}$ cycloalkyl, phenyl, Het$^1$ or Het$^2$, which latter five groups are optionally substituted by one or more substituents selected from halo, hydroxy, —OP(O)(OH)$_2$, $C_{1-3}$ alkyl, $C_{1-3}$ alkoxy, —$C_{1-3}$ alkylene-R$^{6e}$ and CO$_2$H,
or R$^{6b}$ represents —$C_{1-4}$ alkylene-Het$^3$, which Het$^3$ group is optionally substituted by one or more substituents selected from halo, hydroxy, oxo, $C_{3-6}$ cycloalkyl, $C_{1-3}$ alkoxy and —[C(O)]$_{0-1}$—$C_{1-3}$ alkyl, which $C_{1-3}$ alkyl group is optionally substituted by one or more R$^{6e}$,
or, when p is 1 or 2, R$^{6b}$ may alternatively represent OH,
or, when p is 2, R$^{6b}$ may alternatively represent —N(R$^{7b}$)R$^{7c}$ or —N(R$^{7b}$)—C(O)—R$^{7c}$;
R$^{6e}$ represents, independently upon each occurrence, halo, hydroxy, —OP(O)(OH)$_2$, $C_{1-3}$ alkoxy, —N(R$^g$)(R$^h$) or —CO$_2$H;
R$^{7a}$ to R$^{7c}$ independently represent H or $C_{1-4}$ alkyl optionally substituted by one or more halo atoms or by —CO$_2$H,
or R$^{7a}$ represents P(O)(OH)$_2$ or Het$^3$, which latter group is optionally substituted by one or more substituents selected from halo, hydroxy, oxo, $C_{3-6}$ cycloalkyl, $C_{1-3}$ alkoxy and —[C(O)]$_{0-1}$—$C_{1-3}$ alkyl, which $C_{1-3}$ alkyl group is optionally substituted by one or more R$^{6e}$,
or R$^{7b}$ and/or R$^{7c}$ represents —[$C_a$ alkylene]-[$C_b$ alkylene]-OR$^{7d}$,
or R$^{7b}$ and R$^{7c}$ together with the N-atom to which they are attached, form a 4- to 7-membered heterocyclic group that is fully saturated, partially unsaturated or fully aromatic and which heterocyclic group contains one N atom (the atom to which R$^{7b}$ and R$^{7c}$ are attached) and, optionally, one or more further heteroatoms selected from O, S and N, and which heterocyclic group is optionally substituted by one or more substituents selected from halo, hydroxy, oxo, $C_{1-4}$ alkyl, $C_{1-4}$ alkoxy and $C_{1-4}$ hydroxyalkyl;
a and b independently represent an integer selected from 1, 2 and 3, wherein the sum of a and b is 2, 3 or 4;
R$^{7d}$ represents H or $C_{1-4}$ alkyl optionally substituted by one or more halo atoms;
R$^{7aa}$ represents —C(R$^{7d}$)(R$^{7e}$)—$C_{1-3}$ alkylene-OH or $C_{1-4}$ alkyl optionally substituted by one or more halo atoms or by —CO$_2$H;
Q$^1$, Q$^2$, Q$^{22}$ and Q$^3$ independently represent —C(O)N(R$^8$)—, —O— or —S(O)$_2$N(R$^8$)—, or Q$^1$, Q$^2$ and Q$^{22}$ independently represent S(O)$_q$;
Q$^4$ represents a direct bond or $C_{1-3}$ alkylene;
n, m, p and q independently represent 0, 1 or 2;
R$^{6c}$, R$^{6d}$, R$^e$, R$^f$, R$^g$, R$^h$ and R$^8$ independently represent H or methyl,
or R$^{6c}$ and R$^{6d}$ independently represent hydroxymethyl;
R$^7$ represents H, hydroxy, $C_{1-4}$ alkyl, $C_{1-4}$ alkoxy, $C_{3-7}$ cycloalkyl or phenyl, which latter four groups are optionally substituted by one or more substituents selected from halo, OH, $C_{1-3}$ alkyl and $C_{1-3}$ alkoxy;
R$^9$ represents H or $C_{1-4}$ alkyl, which latter group is optionally substituted by one or more halo atoms or by phenyl, which phenyl group is optionally substituted by one or more substituents selected from halo, OH, $C_{1-3}$ alkyl and $C_{1-3}$ alkoxy;
Het$^{x1}$ and Het$^{x2}$ independently represent Het$^{1a}$ or Het$^3$;
Het$^1$ and Het$^{1a}$ represent, independently upon each occurrence, a 5- or 6-membered heterocyclic group that is fully aromatic, which group contains one or more heteroatoms selected from N, O and S; and
Het$^2$ and Het$^3$ represent, independently upon each occurrence, a 4- to 9-membered heterocyclic group that is fully saturated or partially unsaturated, and is monocyclic or is fused or bridged bicyclic, which group contains one or more heteroatoms selected from N, O and S;
or a pharmaceutically acceptable salt thereof,
which compounds may be referred to hereinafter as "the compounds of the invention".

DETAILED DESCRIPTION OF CERTAIN EMBODIMENTS

Pharmaceutically acceptable salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I in the form of a salt with another counter-ion, for example using a suitable ion exchange resin.

Examples of pharmaceutically acceptable salts include acid addition salts derived from mineral acids and organic acids, and salts derived from metals.

For the avoidance of doubt, compounds of formula I may contain the stated atoms in any of their natural or non-natural isotopic forms. In this respect, embodiments of the invention that may be mentioned include those in which:
(a) the compound of formula I is not isotopically enriched or labelled with respect to any atoms of the compound; and
(b) the compound of formula I is isotopically enriched or labelled with respect to one or more atoms of the compound.

References herein to an "isotopic derivative" relate to the second of these two embodiments. In particular embodiments of the invention, the compound of formula I is isotopically enriched or labelled (with respect to one or more atoms of the compound) with one or more stable isotopes. Thus, the compounds of the invention that may be mentioned include, for example, compounds of formula I that are isotopically enriched or labelled with one or more atoms such as deuterium or the like.

Compounds of formula I may exhibit tautomerism. All tautomeric forms and mixtures thereof are included within the scope of the invention.

Unless otherwise specified, alkyl groups and alkoxy groups as defined herein may be straight-chain or, when there is a sufficient number (i.e. a minimum of three) of carbon atoms, be branched. Particular alkyl groups that may be mentioned include, for example, methyl, ethyl, n-propyl, iso-propyl, butyl, n-butyl and tert-butyl. Particular alkoxy groups that may be mentioned include, for example, methoxy, ethoxy, propoxy, and butoxy.

Unless otherwise specified, cycloalkyl groups as defined herein may, when there is a sufficient number (i.e. a minimum of four) of carbon atoms, be part cyclic/acyclic.

Unless otherwise specified, alkylene groups as defined herein may be straight-chain or, when there is a sufficient number (i.e. a minimum of two) of carbon atoms, be branched. In particular embodiments of the invention, alkylene refers to straight-chain alkylene.

Unless otherwise stated, the point of attachment of aryl groups may be via any atom of the ring system. However, when aryl groups are bicyclic or tricyclic, they are linked to the rest of the molecule via an aromatic ring. $C_{6-14}$ aryl groups include phenyl, naphthyl and the like. Embodiments of the invention that may be mentioned include those in which aryl is phenyl.

For the avoidance of doubt, oxo substituents that may be present on heterocyclic groups represented by $Het^2$, $Het^3$ or $N(R^{7b})R^{7c}$ may be attached to any appropriate atoms in the heterocyclic ring including, where valencies allow, to C—, N— and/or S— atoms within the ring (thereby forming keto, N-oxide, S(O) and/or $S(O)_2$ groups).

Values of $Het^{1a}$ that may be mentioned include imidazolyl (e.g. imidazol-4-yl) and tetrazolyl (e.g. tetrazol-5-yl).

Values of $Het^2$ that may be mentioned include piperazinyl (e.g. piperazin-1-yl), piperidinyl (e.g. piperidin-1-yl) and pyrrolidinyl (e.g. pyrrolidin-1-yl).

Values of $Het^3$ that may be mentioned include dihydropyridinyl (e.g. 1,2-dihydropyridin-1-yl), homomorpholinyl (e.g. homomorpholin-4-yl), morpholinyl (e.g. morpholin-4-yl), homopiperazinyl (e.g. homopiperazin-1-yl), piperazinyl (e.g. piperazin-1-yl), piperidinyl (e.g. piperidin-1-yl or piperidin-4-yl), pyranyl (e.g. pyran-2-yl or pyran-3-yl), pyridinyl (e.g. pyridin-3-yl or pyridin-4-yl), pyrrolidinyl (e.g. pyrrolidin-1-yl), thiomorpholinyl (e.g. thiomorpholin-4-yl) and quinuclidinyl (e.g. quinuclidin-4-yl).

Unless otherwise specified, the term "halo" includes references to fluoro, chloro, bromo or iodo, in particular to fluoro, chloro or bromo, especially fluoro or chloro.

Embodiments of the invention that may be mentioned include those in which:
(a) $R^{1A}$ represents
$C_{1-6}$ alkoxy, $C_{1-6}$ alkyl, $C_{2-6}$ alkenyl, $C_{2-6}$ alkynyl, which latter four groups are optionally substituted by one or more substituents selected from $C_{1-2}$ alkyl, halo, hydroxy, and $C_{1-2}$ alkoxy,
H, halo, cyano,
phenyl or $Het^1$, which latter two groups are optionally substituted with one or more substituents selected from $C_{1-2}$ alkyl and $C_{1-2}$ alkoxy,
or $R^{1A}$ and $R^{1B}$ together represent a structural fragment selected from the following

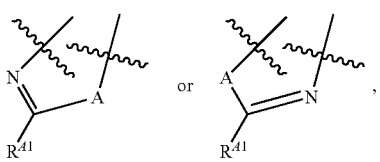

wherein the wavy lines represent the points of attachment to the phenyl ring;
(b) $R^X$ and $R^{X1}$ independently represent H or $C_{1-6}$ alkyl, or $R^X$ and $R^{X1}$ together represent $C_{3-6}$ n-alkylene or $C_{4-5}$ n-alkylene interrupted between C2 and C3 by —O— or —$N(R^{X2})$—, or $R^{X1}$ represents $Het^1$ optionally substituted with one or more substituents selected from halo, hydroxy, $C_{1-2}$ alkyl and $C_{1-2}$ alkoxy;
(c) $R^Y$, $R^{Y1}$ and $R^{Y2}$ independently represent $C_{1-6}$ alkyl, $C_{3-7}$ cycloalkyl, phenyl, benzyl, $Het^1$ or $Het^2$, which latter six groups are optionally substituted by one or more substituents selected from $C_{1-2}$ alkyl, halo, hydroxy, $C_{1-2}$ alkoxy, C(O)OH, C(O)O—($C_{1-4}$ alkyl) and —$N(R^a)(R^b)$, and/or which $Het^2$ group is substituted with one or more oxo groups,
or $R^Y$ represents H,
or $R^X$ and $R^Y$ together represent $C_{3-6}$ n-alkylene or $C_{4-5}$ n-alkylene interrupted between C2 and C3 by —O—, —$S(O)_n$— or —$N(R^{X2})$—;
(d) $R^{1D}$ represents trimethylsilyl, $C_{2-7}$ alkyl, $C_{2-7}$ alkenyl, $C_{2-7}$ alkynyl, $C_{3-7}$ cycloalkyl, phenyl, $Het^1$ or $Het^2$, which latter seven groups are optionally substituted by one or more substituents selected from $C_{1-2}$ alkyl, halo, cyano, hydroxy and $C_{1-2}$ alkoxy;
(e) $X^3$ represents $CR^{5b}$;
(f) $R^4$ represents
-$Q^1$-[$C(R^{6c})(R^{6d})$—$(CH_2)_{0-1}$—$CH_2$—$O]_{1-12}$—$CH_2$$(CH_2)_{0-1}CH_2$—$R^{6a}$,
-$Q^2$-$C(R^{6c})(R^{6d})$—[$C_{1-5}$ alkylene]-$R^{6a}$, which $C_{1-5}$ alkylene group is optionally substituted by oxo,
-$Q^3$-[$C_{1-4}$ alkylene]$_{0-1}$-$Het^3$, which $Het^3$ group is optionally substituted by one or more substituents selected from halo, hydroxy, oxo, $C_{1-3}$ alkyl, $C_{1-3}$ alkoxy and $C_{1-3}$ hydroxyalkyl,
—$S(O)_pR^{6b}$,
—$CO_2H$,
$Het^{1a}$,
—$COR^{6b}$ or
—$CH_2OH$;
(g) $R^{6a}$ represents $OR^{7a}$, $N(R^{7b})R^{7c}$ or $CO_2H$;
(h) $R^{6b}$ represents $C_{1-8}$ alkyl, $C_{3-8}$ cycloalkyl, phenyl, $Het^1$ or $Het^2$, which latter five groups are optionally substituted by one or more substituents selected from halo, hydroxyl, $C_{1-3}$ alkyl and $C_{1-3}$ alkoxy;
(i) $R^{7a}$ to $R^{7c}$ independently represent H or $C_{1-4}$ alkyl optionally substituted by one or more halo atoms,
or $R^{7a}$ represents $P(O)(OH)_2$,
or $R^{7b}$ and/or $R^{7c}$ represents —[$C_a$ alkylene]-[$C_b$ alkylene]-$OR^{7d}$,
or $R^{7b}$ and $R^{7c}$ together with the N-atom to which they are attached, form a 4- to 7-membered heterocyclic group that is fully saturated, partially unsaturated or fully aromatic and which heterocyclic group contains one N atom (the atom to which $R^{7b}$ and $R^{7c}$ are attached) and, optionally, one or more further heteroatoms selected from O, S and N, and which heterocyclic group is optionally substituted by one or more substituents selected from halo, hydroxy, oxo, $C_{1-4}$ alkyl, $C_{1-4}$ alkoxy and $C_{1-4}$ hydroxyalkyl;
(j) $R^{6c}$ and $R^{6d}$ independently represent H or methyl; and
(k) $R^{5a}$ and $R^{5b}$ independently represent $C_{1-3}$ alkoxy or $C_{1-3}$ alkyl, which latter two groups are optionally substituted by one or more halo atoms, or $R^{5a}$ and $R^{5b}$ independently represent —$N(R^e)(R^f)$, $C_{2-3}$ alkynyl, H, cyano, —$C(O)NH_2$, hydroxy or halo.

Embodiments of the invention that may be mentioned include those in which one or more of the following definitions apply to the compounds of formula I:
(a1) $R^{1A}$ represents $C_{1-6}$ alkoxy, $C_{1-6}$ alkyl, $C_{2-6}$ alkenyl, $C_{2-6}$ alkynyl, which latter four groups are substituted by —OP$(O)(OH)_2$ and are optionally further substituted by one or more substituents selected from $C_{1-2}$ alkyl, halo, hydroxy, —OP(O)(OH)$_2$ and $C_{1-2}$ alkoxy;

(b1) $R^X$ or $R^{X1}$ represents $C_{1-6}$ alkyl substituted by one or more substituents selected from halo, hydroxy, —OP(O)(OH)$_2$ and $C_{1-2}$ alkoxy;

(c1) $R^Y$, $R^{Y1}$ and $R^{Y2}$ independently represent $C_{1-6}$ alkyl, $C_{3-7}$ cycloalkyl, phenyl, benzyl, Het$^1$ or Het$^2$, which latter six groups are substituted by —OP(O)(OH)$_2$ and are optionally further substituted by one or more substituents selected from $C_{1-2}$ alkyl, halo, hydroxy, —OP(O)(OH)$_2$, $C_{1-2}$ alkoxy, C(O)OH, C(O)O—($C_{1-4}$ alkyl) and —N($R^a$)($R^b$), and which Het$^2$ group is optionally further substituted with one or more oxo groups;

(d1) $R^{1D}$ represents $C_{2-7}$ alkyl, $C_{2-7}$ alkenyl, $C_{2-7}$ alkynyl, $C_{3-7}$ cycloalkyl, phenyl, Het$^1$ or Het$^2$, which latter seven groups are substituted by —OP(O)(OH)$_2$ and are optionally further substituted by one or more substituents selected from $C_{1-2}$ alkyl, halo, cyano, hydroxy, —OP(O)(OH)$_2$ and $C_{1-2}$ alkoxy;

(e1) $X^3$ represents N;

(f1) $R^4$ represents
- $-Q^1-[C(R^{6c})(R^{6d})-(CH_2)_{0-1}CH_2-Z]_{1-12}-CH_2(CH_2)_{0-1}CH_2-R^{6a}$ in which at least one occurrence of Z represents C(O)NH or NHC(O);
- $-Q^2-C(R^{6c})(R^{6d})-[C_{1-5}$ alkylene]$-R^{6a}$, which $C_{1-5}$ alkylene group is substituted by $R^{6e}$ and is optionally further substituted by oxo and/or by one or more $R^{6e}$,
- $-Q^3-[C_{1-4}$ alkylene]$_{0-1}$-Het$^{1a}$, which $C_{1-4}$ alkylene group is optionally substituted by oxo and/or by one or more $R^{6e}$ and which Het$^{1a}$ group is optionally substituted by one or more substituents selected from halo, hydroxy, oxo, $C_{3-6}$ cycloalkyl, $C_{1-3}$ alkoxy and —[C(O)]$_{0-1}$—$C_{1-3}$ alkyl, the $C_{1-3}$ alkyl part of which latter group is optionally substituted by one or more $R^{6e}$;
- $-Q^3-[C_{1-4}$ alkylene]$_{0-1}$-Het$^3$, which $C_{1-4}$ alkylene group is substituted by oxo and/or by one or more $R^{6e}$ and which Het$^3$ group is optionally substituted by one or more substituents selected from halo, hydroxy, oxo, $C_{3-6}$ cycloalkyl, $C_{1-3}$ alkoxy and —[C(O)]$_{0-1}$—$C_{1-3}$ alkyl, the $C_{1-3}$ alkyl part of which latter group is optionally substituted by one or more $R^{6e}$;
- $-Q^3-[C_{1-4}$ alkylene]$_{0-1}$-Het$^3$, which Het$^3$ group is substituted by
  $C_{3-6}$ cycloalkyl,
  $C_{1-3}$ alkyl substituted by halo, $C_{1-3}$ alkoxy, —N($R^g$)($R^h$) or —CO$_2$H and optionally further substituted by one or more $R^e$ or
  —C(O)—$C_{1-3}$ alkyl, the $C_{1-3}$ alkyl part of which latter group is optionally substituted by one or more $R^{6e}$,
  and which Het$^3$ group is optionally further substituted by one or more substituents selected from halo, hydroxy, oxo, $C_{3-6}$ cycloalkyl, $C_{1-3}$ alkoxy and —[C(O)]$_{0-1}$—$C_{1-3}$ alkyl, the $C_{1-3}$ alkyl part of which latter group is optionally substituted by one or more $R^{6e}$,
  Het$^{1a}$ substituted by one or more substituents selected from halo, hydroxy, oxo, $C_{1-3}$ alkyl and $C_{1-3}$ alkoxy,
  Het$^3$ optionally substituted by one or more substituents selected from halo, hydroxy, oxo, $C_{1-3}$ alkyl and $C_{1-3}$ alkoxy,
  —CH$_2$OP(O)(OH)$_2$ or
  $-Q^4-P(O)(OR^9)(R^7)$ (e.g. —P(O)(OR$^9$)(R$^7$));

(g1) $R^4$ represents
- $-Q^3-[C_{1-4}$ alkylene]$_{0-1}$-Het$^{x1}$, which $C_{1-4}$ alkylene group is optionally substituted by oxo and/or by one or more $R^{6e}$ and which Het$^{x1}$ group is substituted by —[C(O)]$_{0-1}$—$C_4$ alkyl, the $C_4$ alkyl part of which latter group is optionally substituted by one or more $R^{6e}$, and which Het$^{x1}$ group is optionally further substituted by one or more substituents selected from halo, hydroxy, oxo, $C_{3-6}$ cycloalkyl, $C_{1-3}$ alkoxy and —[C(O)]$_{0-1}$—$C_{1-4}$ alkyl, the $C_{1-4}$ alkyl part of which latter group is optionally substituted by one or more $R^{6e}$,
- $-Q^{22}-[C_{1-4}$ alkylene]$_{0-1}$-phenyl, which $C_{1-4}$ alkylene group is optionally substituted by oxo and/or by one or more $R^{6e}$, and which phenyl group is substituted by —[C(O)]$_{0-1}$—$C_{1-4}$ alkyl, the $C_{1-4}$ alkyl part of which latter group is optionally substituted by one or more $R^{6e}$, and which phenyl group is optionally further substituted by one or more substituents selected from halo, hydroxy, oxo, $C_{3-6}$ cycloalkyl and $C_{1-3}$ alkoxy, —$C_{1-4}$ alkylene-CO$_2$H, (h1) $R^{6a}$ represents —S(O)$_{0-2}R^{7aa}$;

(i1) $R^{6b}$ represents
$C_{1-8}$ alkyl, $C_{3-8}$ cycloalkyl, phenyl, Het$^1$ or Het$^2$, which latter five groups are substituted by —OP(O)(OH)$_2$, —$C_{1-3}$ alkylene-$R^{6e}$ or CO$_2$H and are optionally further substituted by one or more substituents selected from halo, hydroxy, —OP(O)(OH)$_2$, $C_{1-3}$ alkyl, $C_{1-3}$ alkoxy, —$C_{1-3}$ alkylene-$R^{6e}$ and CO$_2$H or
—$C_{1-4}$ alkylene-Het$^3$, which Het$^3$ group is optionally substituted by one or more substituents selected from halo, hydroxy, oxo, $C_{3-6}$ cycloalkyl, $C_{1-3}$ alkoxy and —[C(O)]$_{0-1}$—$C_{1-3}$ alkyl, which $C_{1-3}$ alkyl group is optionally substituted by one or more $R^{6e}$,
or, when p is 1 or 2, $R^{6b}$ may alternatively represent OH
or, when p is 2, $R^{6b}$ may alternatively represent —N($R^{7b}$)$R^{7c}$ or —N($R^{7b}$)—C(O)—$R^{7c}$, (j1) $R^{7a}$ represents Het$^3$, which latter group is optionally substituted by one or more substituents selected from halo, hydroxy, oxo, $C_{3-6}$ cycloalkyl, $C_{1-3}$ alkoxy and —[C(O)]$_{0-1}$—$C_{1-3}$ alkyl, which $C_{1-3}$ alkyl group is optionally substituted by one or more $R^{6e}$, (k1) $R^{7a}$, $R^{7aa}$, $R^{7b}$ and/or $R^{7c}$ represents $C_{1-4}$ alkyl substituted by —CO$_2$H;

(l1) $R^{6c}$ and/or $R^{6d}$ represents hydroxymethyl;

(m1) $R^{5a}$ and/or $R^{5b}$ represents —S(O)$_{0-2}$—$C_{1-3}$ alkyl.

In particular, embodiments of the invention that may be mentioned include those in which any one or more of (e1), (g1), (k1) and (m1) above apply.

Other embodiments of the invention that may be mentioned include those in which:

(1) $X^3$ represents $CR^{5b}$;

(2) $R^4$ represents
- $-Q^1-[C(R^{6c})(R^{6d})-(CH_2)_{0-1}CH_2-Z]_{1-12}-CH_2(CH_2)_{0-1}CH_2-R^{6a}$,
- $-Q^2-C(R^{6c})(R^{6d})-[C_{1-5}$ alkylene]$-R^{6a}$, which $C_{1-5}$ alkylene group is optionally substituted by oxo and/or by one or more $R^{6e}$,
- $-Q^3-[C_{1-4}$ alkylene]$_{0-1}$-Het$^{x1}$, which $C_{1-4}$ alkylene group is optionally substituted by oxo and/or by one or more $R^{6e}$ and which Het$^{x1}$ group is optionally substituted by one or more substituents selected from halo, hydroxy, oxo, $C_{3-6}$ cycloalkyl, $C_{1-3}$ alkoxy and —[C(O)]$_{0-1}$—$C_{1-3}$ alkyl, the $C_{1-3}$ alkyl part of which latter group is optionally substituted by one or more $R^{6e}$,
  —S(O)$_p$R$^{6b}$,
  —CO$_2$H,
  Het$^{x2}$ which Het$^{x2}$ group is optionally substituted by one or more substituents selected from halo, hydroxy, oxo, $C_{1-3}$ alkyl and $C_{1-3}$ alkoxy,
  —COR$^{6b}$,
  —CH$_2$OH,
  —CH$_2$OP(O)(OH)$_2$ or
  $-Q^4-P(O)(OR^9)(R^7)$;

(3) $R^{7a}$ to $R^{7c}$ independently represent H or $C_{1-4}$ alkyl optionally substituted by one or more halo atoms,
or $R^{7a}$ represents $P(O)(OH)_2$ or $Het^3$, which latter group is optionally substituted by one or more substituents selected from halo, hydroxy, oxo, $C_{3-6}$ cycloalkyl, $C_{1-3}$ alkoxy and
$-[C(O)]_{0-1}-C_{1-3}$ alkyl, which $C_{1-3}$ alkyl group is optionally substituted by one or more $R^{6e}$,
or $R^{7b}$ and/or $R^{7c}$ represents $-[C_a$ alkylene]-$[C_b$ alkylene]-$OR^{7d}$,
or $R^{7b}$ and $R^{7c}$ together with the N-atom to which they are attached, form a 4- to 7-membered heterocyclic group that is fully saturated, partially unsaturated or fully aromatic and which heterocyclic group contains one N atom (the atom to which $R^{7b}$ and $R^{7c}$ are attached) and, optionally, one or more further heteroatoms selected from O, S and N, and which heterocyclic group is optionally substituted by one or more substituents selected from halo, hydroxy, oxo, $C_{1-4}$ alkyl, $C_{1-4}$ alkoxy and $C_{1-4}$ hydroxyalkyl;
(4) $R^{7aa}$ represents $-C(R^{7d})(R^{7e})-C_{1-3}$ alkylene-OH or $C_{1-4}$ alkyl optionally substituted by one or more halo atoms; and
(5) $R^{5a}$ and $R^{5b}$ independently represent $C_{1-3}$ alkoxy or $C_{1-3}$ alkyl, which latter two groups are optionally substituted by one or more halo atoms, or $R^{5a}$ and $R^{5b}$ independently represent $-N(R^e)(R^f)$, $C_{2-3}$ alkynyl, H, cyano, $-C(O)NH_2$, hydroxy or halo.

In particular, such other embodiments of the invention that may be mentioned include those in which (1) to (5) above all apply and any one or more of (a1) to (d1), (f1), (h1) to (j1) and (l1) apply.

Particular embodiments of the invention that may be mentioned include those in which, in the compound of formula I, $R^4$ represents -$Q^1$-$[C(R^{6c})(R^{6d})-(CH_2)_{0-1}CH_2-Z]_{1-12}-CH_2(CH_2)_{0-1}CH_2-R^{6a}$, -$Q^2$-$C(R^{6c})(R^{6d})-[C_{1-5}$ alkylene]-$R^{6a}$, which $C_{1-5}$ alkylene group is optionally substituted by oxo and/or by one or more $R^{6e}$, -$Q^3$-$[C_{1-4}$ alkylene]$_{0-1}$-$Het^{x1}$, which $C_{1-4}$ alkylene group is optionally substituted by oxo and/or by one or more $R^{6e}$ and which $Het^{x1}$ group is optionally substituted by one or more substituents selected from halo, hydroxy, oxo, $C_{3-6}$ cycloalkyl, $C_{1-3}$ alkoxy and $-[C(O)]_{0-1}-C_{1-4}$ alkyl (e.g. $-[C(O)]_{0-1}-C_{1-3}$ alkyl), the $C_{1-4}$ alkyl part of which latter group is optionally substituted by one or more $R^{6e}$,

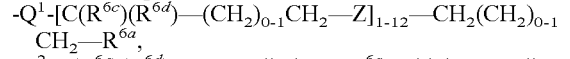-$[C_{1-4}$ alkylene]$_{0-1}$-phenyl, which $C_{1-4}$ alkylene group is optionally substituted by oxo and/or by one or more $R^{6e}$, and which phenyl group is substituted by $-[C(O)]_{0-1}-C_{1-4}$ alkyl, the $C_{1-4}$ alkyl part of which latter group is optionally substituted by one or more $R^{6e}$, and which phenyl group is optionally further substituted by one or more substituents selected from halo, hydroxy, oxo, $C_{3-6}$ cycloalkyl and $C_{1-3}$ alkoxy,
$-S(O)_pR^{6b}$,
$-C_{1-4}$ alkylene-$CO_2H$ (e.g. $-CO_2H$),
$Het^{x2}$ which $Het^{x2}$ group is optionally substituted by one or more substituents selected from halo, hydroxy, oxo, $C_{1-3}$ alkyl and $C_{1-3}$ alkoxy,
$-COR^{6b}$,
$-CH_2OH$,
$-CH_2OP(O)(OH)_2$ or
$-P(O)(OR^9)(R^7)$.

Other embodiments of the invention that may be mentioned include those in which, in the compound of formula I, $R^4$ represents $-C_{1-3}$ alkylene-$P(O)(OR^9)(R^7)$.

Embodiments of the invention that may be mentioned include those in which one or more of the following definitions apply to the compounds of formula I:
(a) $R^{1A}$ represents $C_{1-4}$ alkoxy, $C_{1-4}$ alkyl, $C_{2-4}$ alkenyl or $C_{2-4}$ alkynyl, which latter four groups are optionally substituted by one or more halo substituents, or $R^{1A}$ represents H, halo or cyano;
(b) $R^{1B}$ represents $-NR^XS(O)_2R^{Y1}$, $-C(O)NR^XR^Y$, H, halo, cyano, $-C_{1-2}$ alkylene-CN, $-C_{1-2}$ alkylene-OH, $-S(O)_2NR^XR^Y$, $-NR^XC(O)R^Y$, $-NR^{X2}S(O)_2NR^XR^Y$ or $Het^1$, which latter group is optionally substituted with one or more substituents selected from halo, hydroxy, methyl and methoxy;
(c) $R^X$ represents H or $C_{1-3}$ alkyl optionally substituted by hydroxy or $-OP(O)(OH)_2$ (e.g. $R^X$ represents H or $C_{1-3}$ alkyl);
(d) $R^Y$ and $R^{Y1}$ independently represent $C_{1-4}$ alkyl, $C_{4-6}$ cycloalkyl, phenyl, benzyl, $Het^1$ or $Het^2$, which latter six groups are optionally substituted by one or more substituents selected from methyl, halo, hydroxy, $-OP(O)(OH)_2$, methoxy, $NH_2$, $N(H)CH_3$, $N(CH_3)_2$, $C(O)OH$ and $C(O)OCH_3$ (e.g. by one or more substituents selected from methyl, halo, hydroxy, methoxy, $NH_2$, $N(H)CH_3$, $N(CH_3)_2$, $C(O)OH$ and $C(O)OCH_3$),
or $R^Y$ represents H,
or $R^X$ and $R^Y$ together represent $C_{4-5}$ n-alkylene optionally interrupted between C2 and C3 by $-O-$ or $-N(R^{X2})-$;
(e) each $R^{X2}$ independently represents H or methyl;
(f) $R^{1C}$ and $R^{1E}$ independently represent H or halo;
(g) $R^{1D}$ represents trimethylsilyl, $C_{2-5}$ alkyl, $C_{2-5}$ alkenyl, $C_{2-5}$ alkynyl, $C_{3-6}$ cycloalkyl, phenyl, $Het^1$ or $Het^2$, which latter seven groups are optionally substituted by one or more substituents selected from methyl, halo, cyano, hydroxy and methoxy;
(h) $R^2$ and $R^3$, together with the C-atoms to which they are attached, form a fused phenyl ring, which ring is optionally substituted by one or more halo groups,
or one of $R^2$ and $R^3$ represents H, halo, cyano, methyl or halomethyl and the other independently represents halo, cyano, methyl or halomethyl,
or $R^2$ and $R^3$ together combine to form $C_{3-4}$ alkylene or $C_{3-4}$ alkenylene, which latter two groups are optionally substituted by one or more substituents selected from methyl, halomethyl, cyano and halo;
(i) $X^1$ represents N or CH;
(j) L represents $CH_2$ or, particularly, a direct bond;
(k) $X^2$ represents N or, particularly, $CR^Z$;
(l) $R^Z$ represents halo, cyano, methyl or methoxy, which latter two groups are optionally substituted by one or more halo atoms, or, particularly, $R^Z$ represents H;
(m) $X^3$ represents $CR^{5b}$;
(n) $R^4$ represents
-$Q^1$-$[C(R^{6c})(R^{6d})-(CH_2)_{0-1}-CH_2-Z]_{1-6}-CH_2CH_2-R^{6a}$ -$Q^2$-$C(R^{6c})(R^{6d})-[C_{1-4}$ alkylene]-$R^{6a}$, which $C_{1-4}$ alkylene group is optionally substituted by oxo and/or by one or more $R^{6e}$ (e.g. by one or more substituents selected from halo, hydroxy and $-N(R^g)(R^h)$),

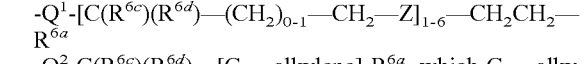-$[C_{1-4}$ alkylene]$_{0-1}$-$Het^{x1}$, which $C_{1-4}$ alkylene group is optionally substituted by oxo and/or by one or more $R^{6e}$ (e.g. by one or more substituents selected from halo, hydroxy, $-N(R^g)(R^h)$ and $-CO_2H$) and which $Het^{x1}$ group is optionally substituted by one or more substituents selected from halo, hydroxy, oxo, $C_{1-3}$ alkyl, $C_{1-3}$ alkoxy, $C_{1-3}$ hydroxyalkyl, $C_{3-5}$ cycloalkyl and $-C(O)-C_{1-3}$ alkyl, the $C_{1-3}$ alkyl part of which latter group is optionally substituted by one or more $R^{6e}$ (e.g. by one or more substituents selected from halo, hydroxy, —N($R^g$)($R^h$) and —$CO_2$H)
—S(O)$_{0-2}$$R^{6b}$,
$CO_2$H,
$Het^{1a}$ optionally substituted by one or more substituents selected from halo, hydroxy, methyl and methoxy,
$Het^3$ optionally substituted by one or more substituents selected from oxo, hydroxy and methyl,
—$COR^{6b}$ or
-$Q^4$-P(O)(O$R^9$)($R^7$) (e.g. —P(O)(O$R^9$)($R^7$))
(e.g. $R^4$ represents
-$Q^1$-[C($R^{6c}$)($R^{6d}$)—$CH_2$—O]$_{1-6}$$CH_2$$CH_2$—$R^{6a}$,
-$Q^2$-C($R^{6c}$)($R^{6d}$)—[$C_{1-4}$ alkylene]-$R^{6a}$, which $C_{1-4}$ alkylene group is optionally substituted by oxo,
-$Q^3$-[$C_{1-4}$ alkylene]$_{0-1}$-$Het^3$, which $Het^3$ group is optionally substituted by one or more substituents selected from halo, hydroxy, oxo, methyl, methoxy and $C_{1-2}$ hydroxyalkyl, —S(O)$_{0-2}$$R^{6b}$,
$Het^{1a}$, or
$CO_2$H);
(o) $R^{5a}$ and $R^{5b}$ independently represent $C_{1-2}$ alkoxy or $C_{1-2}$ alkyl, which latter two groups are optionally substituted by one or more halo atoms, or $R^{5a}$ and $R^{5b}$ independently represent —N(CH$_3$)$_2$, $C_{2-3}$ alkynyl, H, cyano or halo;
(p) $R^{6a}$ represents $CO_2$H or, particularly, O$R^{7a}$ or N($R^{7b}$)$R^{7c}$;
(q) $R^{6b}$ represents
$Het^2$ optionally substituted by one or more substituents selected from halo, hydroxy, methyl, methoxy, $CO_2$H and —$C_{1-3}$ alkylene-$R^{6e}$ (wherein $R^{6e}$ is as hereinbefore defined or, particularly, represents hydroxy or —N($R^g$)($R^h$))
$C_{1-4}$ alkyl or $C_{4-6}$ cycloalkyl, which latter two groups are optionally substituted by one or more substituents selected from halo, methyl and methoxy
or, when p is 1 or 2, $R^{6b}$ may alternatively represent OH
or, when p is 2, $R^{6b}$ may alternatively represent —N(H)$R^{7c}$ or —N(H)—C(O)—$R^{7c}$(e.g. $R^{6b}$ represents $C_{1-4}$ alkyl or $C_{4-6}$ cycloalkyl, which latter two groups are optionally substituted by one or more substituents selected from halo, methyl and methoxy);
(r) $R^7$ represents H, hydroxy, $C_{1-3}$ alkyl or phenyl;
(s) $R^9$ represents H or $C_{1-3}$ alkyl (e.g. ethyl);
(t) $R^{7a}$ represents
$Het^3$ optionally substituted by one or more substituents selected from halo, hydroxy, oxo, $C_{1-3}$ alkyl and $C_{1-3}$ hydroxyalkyl or, particularly,
H
$C_{1-3}$ alkyl optionally substituted by one or more halo atoms, or
P(O)(OH)$_2$;
(u) $R^{7b}$ and $R^{7c}$ independently represent H or $C_{1-3}$ alkyl (e.g. ethyl or, particularly, methyl) optionally substituted by one or more halo atoms,
or $R^{7b}$ represents H or methyl and $R^{7c}$ represents —[$C_{1-3}$ alkylene]-$CH_2$—O$R^{7d}$,
or $R^{7b}$ and $R^{7c}$, together with the N-atom to which they are attached, form a 5- to 7-membered heterocyclic group that is fully saturated, partially unsaturated or fully aromatic and which heterocyclic group contains one N atom (the atom to which $R^{7b}$ and $R^{7c}$ are attached) and, optionally, one or more further heteroatoms selected from O, S and N, and which heterocyclic group is optionally substituted by one or more substituents selected from halo, hydroxy, oxo, methyl, methoxy and $C_{1-3}$ hydroxyalkyl;

(v) $R^{7d}$ represents H or $C_{1-2}$ alkyl optionally substituted by one or more fluoro atoms;
(w) $Q^1$, $Q^2$ and $Q^3$ independently represent C(O)N$R^8$, S(O)$_{1-2}$, S(O)$_2$N$R^8$ or O (e.g. $Q^1$, $Q^2$ and $Q^3$ independently represent O, C(O)N$R^8$ or S(O)$_2$N$R^8$ or $Q^1$ and $Q^2$ independently represent S(O)$_2$ or S(O));
(x) $Q^4$ represents $CH_2$ or, particularly, a direct bond;
(z) $R^{6c}$, $R^{6d}$ and $R^8$ independently represent H or methyl, or $R^{6c}$ and $R^{6d}$ independently represent hydroxymethyl;
(z) $Het^1$ and $Het^{1a}$ represent, independently upon each occurrence, a 5- or 6-membered heterocyclic group that is fully aromatic, which group contains one or more heteroatoms selected from N, O and S;
(aa) $Het^2$ and $Het^3$ represent, independently upon each occurrence, a 5- to 8-membered (e.g. a 5- or 6-membered) heterocyclic group that is fully saturated or partially unsaturated, which group is monocyclic or is fused or bridged bicyclic and which group contains one or more heteroatoms selected from N, O and S.

Other embodiments of the invention that may be mentioned include those in which when $R^4$ represents —C(O)N($R^8$)—C($R^{6c}$)($R^{6d}$)—[$C_{1-5}$ alkylene]-N($R^{7b}$)$R^{7c}$, which $C_{1-5}$ alkylene group is optionally substituted by oxo and/or by one or more $R^{6e}$, then:
$R^{7b}$ and $R^{7c}$ both represent H or, particularly,
$R^{7b}$ and/or $R^{7c}$ represents —[$C_a$ alkylene]-[$C_b$ alkylene]-O$R^{7d}$,
or $R^{7b}$ and $R^{7c}$ together with the N-atom to which they are attached, form a 4- to 7-membered heterocyclic group that is fully saturated, partially unsaturated or fully aromatic and which heterocyclic group contains one N atom (the atom to which $R^{7b}$ and $R^{7c}$ are attached) and, optionally, one or more further heteroatoms selected from O, S and N, and which heterocyclic group is optionally substituted by one or more substituents selected from halo, hydroxy, oxo, $C_{1-4}$ alkyl, $C_{1-4}$ alkoxy and $C_{1-4}$ hydroxyalkyl
or, when $R^{1B}$ represents —C(O)N$R^X R^Y$, H, halo, cyano, —$C_{1-4}$ alkylene-CN, —$C_{1-4}$ alkylene-OH, —N$R^X R^{X1}$, —C(O)O$R^X$, —S(O)$_2$N$R^X R^Y$, —N$R^X$C(O)$R^Y$, —N$R^X$P(O)$R^{Y1} R^{Y2}$, or $Het^1$ optionally substituted with one or more substituents selected from halo, hydroxy, $C_{1-2}$ alkyl and $C_{1-2}$ alkoxy, $R^{7b}$ and/or $R^{7c}$ may alternatively represent H or $C_{1-4}$ alkyl optionally substituted by one or more halo atoms
(e.g. when $R^4$ represents —C(O)N($R^8$)—C($R^{6c}$)($R^{6d}$)—[$C_{1-5}$ alkylene]-N($R^{7b}$)$R^{7c}$, which $C_{1-5}$ alkylene group is optionally substituted by oxo and/or by one or more $R^{6e}$, then $R^{7b}$ and/or $R^{7c}$ represents —[$C_a$ alkylene]-[$C_b$ alkylene]-O$R^{7d}$, or $R^{7b}$ and $R^{7c}$ together with the N-atom to which they are attached, form a 4- to 7-membered heterocyclic group that is fully saturated, partially unsaturated or fully aromatic and which heterocyclic group contains one N atom (the atom to which $R^{7b}$ and $R^{7c}$ are attached) and, optionally, one or more further heteroatoms selected from O, S and N, and which heterocyclic group is optionally substituted by one or more substituents selected from halo, hydroxy, oxo, $C_{1-4}$ alkyl, $C_{1-4}$ alkoxy and $C_{1-4}$ hydroxyalkyl).

Embodiments of the invention that may be mentioned include those in which the compound of formula I is a compound of formula Ia,

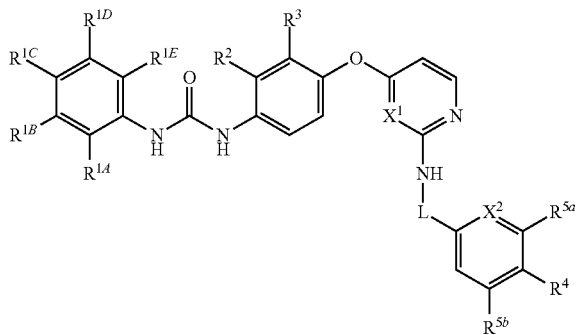

Ia wherein $R^{1A}$ to $R^{1E}$, $R^2$ to $R^4$, $R^{5a}$, $R^{5b}$, L, $X^1$ and $X^2$ are as hereinbefore defined.

Embodiments of the invention that may be mentioned include those in which one or more of the following definitions apply to the compounds of formula I and Ia:
(a) $R^{1A}$ represents $C_{1-2}$ alkoxy (e.g. methoxy) optionally substituted by one or more halo substituents, or $R^{1A}$ represents H;
(b) $R^{1B}$ represents —N($R^{XX}$)S(O)$_2$$R^{Y1}$, —C(O)N($R^{XX}$)$R^Y$, —N(H)C(O)$R^{YY}$ or, particularly, —N(H)S(O)$_2$$R^{Y1}$, —C(O)N(H)$R^Y$, —S(O)$_2$N(H)$R^Y$, —N(H)C(O)$R^Y$ or —N(H)S(O)$_2$NR$^X$$R^Y$;
(c) $R^{XX}$ represents —CH$_2$CH$_2$—OP(O)(OH)$_2$ or, particularly, —CH$_2$CH$_2$—OH;
(d) $R^X$ represents H or methyl;
(e) $R^Y$ and $R^{Y1}$ independently represent $C_{1-2}$ alkyl (e.g. methyl), or $R^Y$ represents H, or $R^X$ and $R^Y$ together represent $C_{4-5}$ n-alkylene optionally interrupted between C2 and C3 by —O— or —N($R^{X2}$)—;
(f) $R^{YY}$ represents $C_{1-3}$ alkyl substituted by hydroxy or —OP(O)(OH)$_2$ (e.g. methyl substituted by hydroxy or, particularly, —OP(O)(OH)$_2$);
(g) $R^{X2}$ represents H or methyl;
(h) $R^{1C}$ and $R^{1E}$ both represent H;
(i) $R^{1D}$ represents trimethylsilyl, $C_{3-5}$ alkyl (e.g. C$_4$ alkyl, such as tert-butyl), $C_{3-5}$ alkynyl or Het$^2$, which latter three groups are optionally substituted by cyano, hydroxy or methoxy, and/or which Het$^2$ group is optionally substituted by one or more substituents selected from methyl and halo;
(j) $R^2$ and $R^3$, together with the C-atoms to which they are attached, form a fused phenyl ring, or $R^2$ and $R^3$ both represent chloro;
(k) $X^1$ represents N or, particularly, CH;
(l) L represents a direct bond;
(m) $X^2$ represents $CR^Z$;
(n) $R^Z$ represents H;
(o) $R^4$ represents
-Q$^1$-[C($R^{6c}$)($R^{6d}$)—(CH$_2$)$_{0-1}$—CH$_2$—Z]$_{1-3}$—CH$_2$CH$_2$—$R^{6a}$,
-Q$^2$-C($R^{6c}$)($R^{6d}$)—[C$_{1-4}$ alkylene]-$R^{6a}$, which C$_{1-4}$ alkylene group is optionally substituted by oxo and/or by one or more substituents selected from hydroxy and —N($R^g$)($R^h$),
-Q$^3$-[C$_{1-4}$ alkylene]$_{0-1}$-Het$^{v1}$, which C$_{1-4}$ alkylene group is optionally substituted by oxo and/or by one or more substituents selected from hydroxy, —N($R^g$)($R^h$) and —CO$_2$H, and which Het$^{v1}$ group is optionally substituted by one or more substituents selected from halo, hydroxy, oxo, $C_{1-3}$ alkyl, $C_{1-3}$ alkoxy, $C_{1-3}$ hydroxyalkyl, $C_{3-5}$ cycloalkyl and —C(O)—$C_{1-3}$ alkyl, the $C_{1-3}$ alkyl part of which latter group is optionally substituted by one or more substituents selected from hydroxy, —N($R^g$)($R^h$) and —CO$_2$H and —S(O)$_{1-2}$$R^{6b}$,
Het$^{1a}$ optionally substituted by methyl or hydroxy,
Het$^3$ optionally substituted by oxo,
CO$_2$H,
—COR$^{6b}$ or
—P(O)(OR$^9$)(R$^7$);
(e.g. $R^4$ represents
-Q$^1$[C($R^{6c}$)($R^{6d}$)—CH$_2$—O]$_{1-3}$—CH$_2$CH$_2$—$R^{6a}$,
-Q$^2$-C($R^{6c}$)($R^{6d}$)—[C$_{1-3}$ alkylene]-$R^{6a}$, which C$_{1-3}$ alkylene group is optionally substituted by oxo,
—C(O)NR$^8$—[C$_{1-4}$ alkylene]$_{0-1}$-Het$^3$, which Het$^3$ group is optionally substituted by one or more substituents selected from hydroxy, oxo, methyl, methoxy and $C_{1-2}$ hydroxyalkyl, —S(O)$_{1-2}$$R^{6b}$,
tetrazolyl, or
CO$_2$H);
(p) $R^{5a}$ and $R^{5b}$ independently represent H or $C_{1-2}$ alkoxy (e.g. methoxy), or $R^{5a}$ represents OH, halo, $C_{1-2}$ alkyl or, particularly, —N(CH$_3$)$_2$, ethynyl or cyano;
(q) Z represents, independently upon each occurrence, C(O)NH, NHC(O) or, particularly, O (e.g. all occurrences of Z represent C(O)NH, NHC(O) or, particularly, O);
(r) $R^{6a}$ represents CO$_2$H or, particularly, OR$^{7a}$ or N($R^{7b}$)$R^{7c}$;
(s) $R^{6b}$ represents
Het$^2$ optionally substituted by one or more substituents selected from hydroxy, CO$_2$H, hydroxymethyl and —CH$_2$CH$_2$—N($R^g$)($R^h$),
$C_{1-3}$ alkyl (e.g. methyl)
or, when p is 1, $R^{6b}$ may alternatively represent OH
or, when p is 2, $R^{6b}$ may alternatively represent —NH$_2$ or —N(H)—C(O)—$C_{1-2}$ alkyl (e.g. $R^{6b}$ represents $C_{1-3}$ alkyl (e.g. methyl);
(t) $R^{6c}$ and $R^{6d}$ independently represent H, methyl or hydroxymethyl (e.g. $R^{6c}$ represents H, methyl or hydroxymethyl and $R^{6d}$ represents H, or $R^{6c}$ and $R^{6d}$ both represent hydroxymethyl)
or, particularly, $R^{6c}$ and $R^{6d}$ independently represent methyl or, particularly, H (e.g. $R^{6c}$ and $R^{6d}$ both represent H or $R^{6c}$ represents methyl and $R^{6d}$ represents H);
(u) $R^7$ represents H, hydroxy, ethyl, phenyl or, particularly, methyl;
(v) $R^9$ represents H or ethyl;
(w) $R^{7a}$ represents
Het$^3$ optionally substituted by one or more substituents selected from hydroxy, methyl and hydroxymethyl or, particularly,
H, methyl, or P(O)(OH)$_2$;
(x) $R^{7b}$ and $R^{7c}$ independently represent H or methyl,
or $R^{7b}$ represents H or methyl and $R^{7x}$ represents —[C$_{1-2}$ alkylene]-CH$_2$—OR$^{7d}$,
or $R^{7b}$ and $R^{7c}$, together with the N-atom to which they are attached, form a 5- to 7-membered heterocyclic group that is fully saturated or partially unsaturated and which heterocyclic group contains one N atom (the atom to which $R^{7b}$ and $R^{7c}$ are attached) and, optionally, one further heteroatom selected from O, S and N, and which heterocyclic group is optionally substituted by one or more substituents selected from fluoro, hydroxy, oxo, methyl and $C_{1-2}$ hydroxyalkyl;
(y) $R^{7d}$ represents H or $C_{1-2}$ alkyl;
(z) Q$^1$, Q$^2$ and Q$^3$ independently represent C(O)NR$^8$, S(O)$_2$, S(O), S(O)$_2$NR$^8$ or O;

(aa) $R^8$ represents H or methyl;
(ab) $R^g$ and $R^h$ independently represent H or methyl (e.g. $R^g$ and $R^h$ both represent either H or methyl);
(ac) $Het^{1a}$ represents a 5- or 6-membered heterocyclic group that is fully aromatic, which group contains an N-atom and optionally contains one to three further heteroatoms selected from N, O and S (e.g. $Het^{1a}$ represents imidazolyl or tetrazolyl);
(ad) $Het^2$ and $Het^3$ represent, independently upon each occurrence, a 5- to 8-membered (e.g. a 5- or 6-membered monocyclic group, or an 8-membered bridged bicyclic group) heterocyclic group that is fully saturated or partially unsaturated, which group is monocyclic or is bridged bicyclic and which group contains one or two heteroatoms selected from N, O and S.

Further embodiments of the invention that may be mentioned include those in which the compound of formula I or Ia is a compound of formula Ib,

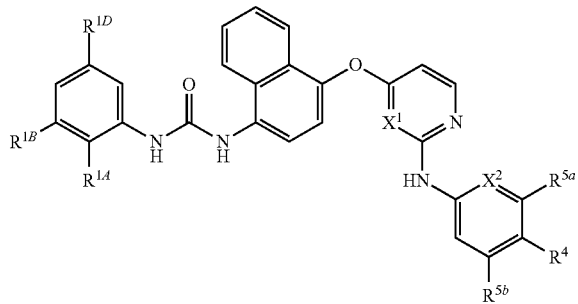

Ib or a pharmaceutically acceptable salt thereof, wherein $R^{1A}$, $R^{1B}$, $R^{1D}$, $R^4$, $R^{5a}$, $R^{5b}$, $X^1$ and $X^2$ are as hereinbefore defined.

Embodiments of the invention that may be mentioned include those in which one or more of the following definitions apply to the compounds of formula I, Ia and Ib:
(a) $R^{1A}$ represents H or, particularly, methoxy;
(b) $R^{1B}$ represents —N(CH$_2$CH$_2$OH)S(O)$_2$CH$_3$, —N[CH$_2$CH$_2$OP(O)(OH)$_2$]S(O)$_2$CH$_3$—C(O)N(H)—CH$_2$CH$_2$—OH, —N(H)C(O)CH$_2$OH, —N(H)C(O)CH$_2$OP(O)(OH)$_2$ or, particularly, —N(H)S(O)$_2$CH$_3$ or —C(O)NH$_2$;
(c) $R^{1D}$ represents $C_4$ alkyl, such as tert-butyl;
(d) $X^1$ represents N or, particularly, CH;
(e) $X^2$ represents $CR^Z$;
(f) $R^Z$ represents H;
(g) $R^4$ represents
-Q$^1$-[C(H)(R$^{6c}$)—CH$_2$—Z]$_{1-3}$—CH$_2$CH$_2$—R$^{6a}$,
—C(O)NH—[CH$_2$CH$_2$CH$_2$—O]—[CH$_2$(CH$_2$)$_{0-1}$CH$_2$—O]$_{0-1}$—CH$_2$CH$_2$—R$^{6a}$,
-Q$^2$-C(R$^{6c}$)(R$^{6d}$)—[C$_{1-4}$ alkylene]-R$^{6a}$, which C$_{1-3}$ alkylene group is optionally substituted by oxo and/or by one or more hydroxy groups,
Q$^3$-[C$_{1-4}$ alkylene]$_{0-1}$-Het$^3$, which Het$^3$ group is optionally substituted by one or more substituents selected from halo, hydroxy, oxo, C$_{1-3}$ alkyl (e.g. methyl, ethyl or isopropyl), methoxy, C$_{3-4}$ cycloalkyl (e.g. cyclopropyl), C$_{1-2}$ hydroxyalkyl and —C(O)—C$_{1-3}$ alkyl, the C$_{1-3}$ alkyl part of which latter group is substituted by hydroxy, —N(R$^g$)(R$^h$) or —CO$_2$H,
—C(O)NH—C$_{1-4}$ alkylene-Het$^{1a}$, which C$_{1-4}$ alkylene group is optionally substituted by CO$_2$H,
—S(O)$_{1-2}$CH$_3$,
—S(O)OH,
—S(O)$_2$NH$_2$,
—S(O)$_2$NH—C(O)—C$_{1-2}$ alkyl,
Het$^{1a}$,
Het$^3$ optionally substituted by oxo,
CO$_2$H,
—C(O)—Het$^3$, which Het$^3$ group is optionally substituted by one or more substituents selected from hydroxy, CO$_2$H, hydroxymethyl and —CH$_2$CH$_2$—N(R$^g$)(R$^h$),
—P(O)(O—CH$_2$CH$_3$)(R$^7$) or
—P(O)(OH)(R$^7$);
(e.g. $R^4$ represents
-Q$^1$-[C(H)(R$^{6c}$)—CH$_2$—O]$_{1-3}$—CH$_2$CH$_2$—R$^{6a}$ (e.g. -Q$^1$-[C(H)(R$^{6c}$)—CH$_2$—O]$_{1-2}$—CH$_2$CH$_2$—R$^{6a}$),
-Q$^2$-C(H)(R$^{6c}$)—[C$_{1-3}$ alkylene]-R$^{6a}$, which C$_{1-3}$ alkylene group is optionally substituted by oxo,
—C(O)NH—[C$_{1-4}$ alkylene]$_{0-1}$-Het$^3$, which Het$^3$ group is optionally substituted by one or more substituents selected from oxo, methyl and methoxy,
—S(O)$_{1-2}$CH$_3$, or
CO$_2$H);
(h) $R^{5a}$ and $R^{5b}$ independently represent H, methyl, methoxy, hydroxy, ethynyl, cyano, halo or —N(CH$_3$)$_2$ or, particularly, $R^{5a}$ and $R^{5b}$ independently represent H or methoxy, or $R^{5a}$ represents ethynyl or cyano (e.g. $R^{5a}$ and $R^{5b}$ both represent H, both represent methoxy or, particularly, $R^{5a}$ represents cyano or methoxy and $R^{5b}$ represents H);
(i) $R^{6a}$ represents CO$_2$H or, particularly, OR$^{7a}$ or N(R$^{7b}$)R$^{7c}$;
(j) $R^{6c}$ represents H, methyl or hydroxymethyl and $R^{6d}$ represents H, or $R^{6c}$ and $R^{6d}$ both represent hydroxymethyl (e.g. $R^{6d}$ represents H and $R^{6c}$ represents methyl or, particularly, H);
(k) $R^{7a}$ represents
Het$^3$ optionally substituted by one or more substituents selected from hydroxy and hydroxymethyl or, particularly,
H, methyl, or P(O)(OH)$_2$
(e.g. $R^{7a}$ represents H or, particularly, methyl);
(l) $R^{7b}$ and $R^{7c}$ independently represent H or methyl,
or $R^{7b}$ represents H or methyl and $R^{7x}$ represents —CH$_2$CH$_2$—OR$^{7d}$,
or, particularly, $R^{7b}$ and $R^{7c}$, together with the N-atom to which they are attached, form
a 5- to 7-membered heterocyclic group that is fully saturated and which heterocyclic group contains one N atom (the atom to which $R^{7b}$ and $R^{7c}$ are attached) and, optionally, one further heteroatom selected from O, S and N, and which heterocyclic group is optionally substituted by one or more substituents selected from hydroxy, oxo, methyl and C$_{1-2}$ hydroxyalkyl;
(m) $R^{7d}$ represents H or methyl;
(n) $R^7$ represents ethyl or, particularly, methyl;
(o) $Q^1$, $Q^2$ and $Q^3$ independently represent S(O)$_2$, S(O), S(O)$_2$NR$^8$, O, C(O)N(CH$_3$) or, particularly, C(O)NH;
(p) $R^8$ represents H or, particularly, methyl;
(q) Het$^3$ represents a 5- to 7-membered (e.g. a 5- or, particularly, a 6-membered) heterocyclic group that is fully saturated, which group contains one or two heteroatoms selected from N, O and S.

Certain embodiments of the invention relate to compounds of formula I, Ia or Ib in which $R^{5b}$ is H and $R^{5a}$ is other than H (e.g. methyl, methoxy, hydroxy, ethynyl, cyano, halo, or —N(CH$_3$)$_2$).

Certain other embodiments of the invention relate to compounds of formula I, Ia or Ib in which $R^{5a}$ and $R^{5b}$ are both other than H (e.g. $R^{5a}$ and $R^{5b}$ are independently selected from methyl, methoxy, hydroxy, ethynyl, cyano, halo and —N(CH$_3$)$_2$ or, particularly, $R^{5a}$ and $R^{5b}$ are both methoxy).

Particular embodiments of the invention that may be mentioned include those in which one or more of the following definitions apply to the compounds of formula I, Ia and Ib:
(a) $R^{1A}$ represents methoxy;
(b) $R^{1B}$ represents —N(H)S(O)$_2$CH$_3$;
(c) $R^{1D}$ represents tert-butyl;
(d) $X^1$ represents CH;
(e) $X^2$ represents CH;
(f) $R^4$ represents
—C(O)NH—[CH$_2$CH$_2$—O]$_{1-2}$—CH$_2$CH$_2$—OR$^{7a}$ or
—P(O)(OH)(R$^7$);
(g) $R^{7a}$ represents H or P(O)(OH)$_2$;
(h) $R^7$ represents methyl;
(i) $R^{5a}$ represents methoxy;
(j) $R^{5b}$ represents H or methoxy.

Particular embodiments of the invention that may be mentioned include those in which, in the compounds of formula I, Ia and Ib, $R^4$ represents —P(O)(OR$^9$)(R$^7$) and $R^{1A}$ to $R^{1E}$, $R^2$, $R^3$, $X^1$, L, $X^2$, $R^{5a}$, $R^{5b}$, $R^7$ and $R^9$ are as defined above (e.g. $R^{1A}$ to $R^{1E}$, $R^2$, $R^3$, $X^1$, L, $X^2$, $R^{5a}$ and $R^{5b}$ are as defined in any of the embodiments above and $R^7$ represents C$_{1-4}$ alkyl, such as methyl, and/or $R^9$ represents C$_{1-4}$ alkyl (such as ethyl) or, particularly, H).

Other compounds of formula I, Ia or Ib that may be mentioned include the compounds of the examples described hereinafter. Thus, embodiments of the invention that may be mentioned include those in which the compound of formula I, Ia or Ib is a compound selected from the list:
4-((4-((4-(3-(5-(tert-butyl)-2-methoxy-3-(methylsulfonamido)phenyl)ureido)naphthalen-1-yl)oxy)pyridin-2-yl)amino)-2-methoxybenzoic acid;
4-((4-((4-(3-(5-(tert-butyl)-2-methoxy-3-(methylsulfonamido)phenyl)ureido)naphthalen-1-yl)oxy)pyridin-2-yl)amino)-2-methoxy-N-(2-morpholinoethyl)benzamide;
4-((4-((4-(3-(5-(tert-butyl)-3-carbamoyl-2-methoxyphenyl)ureido)naphthalen-1-yl)oxy)pyridin-2-yl)amino)-2-methoxybenzoic acid;
4-((4-((4-(3-(5-(tert-butyl)-3-carbamoyl-2-methoxyphenyl)ureido)naphthalen-1-yl)oxy)pyridin-2-yl)amino)-2-methoxy-N-(2-morpholinoethyl)benzamide;
4-((4-((4-(3-(5-(tert-butyl)-2-methoxy-3-(methylsulfonamido)phenyl)ureido)naphthalen-1-yl)oxy)pyridin-2-yl)amino)-2-methoxy-N-(2-(2-(2-methoxyethoxy)ethoxy)ethyl)benzamide;
4-((4-((4-(3-(5-(tert-butyl)-3-carbamoyl-2-methoxyphenyl)ureido)naphthalen-1-yl)oxy)pyridin-2-yl)amino)-2-methoxy-N-(2-(2-(2-methoxyethoxy)ethoxy)ethyl)benzamide;
4-((4-((4-(3-(5-(tert-butyl)-2-methoxy-3-(methylsulfonamido)phenyl)ureido)naphthalen-1-yl)oxy)pyridin-2-yl)amino)-2-methoxy-N-(2-(1-oxidothiomorpholino)ethyl)benzamide;
1-[5-tert-butyl-3-(methanesulfonamido)-2-methoxy-phenyl]-3-[4-[[2-[3-cyano-4-[2-[2-(2-methoxyethoxy)ethoxy]ethoxy]anilino]-4-pyridyl]oxy]-1-naphthyl]urea;
1-[5-tert-butyl-3-(methanesulfonamido)-2-methoxy-phenyl]-3-[4-[[2-[3-cyano-4-(2-morpholinoethoxy)anilino]-4-pyridyl]oxy]-1-naphthyl]urea;
1-[5-tert-butyl-3-(methanesulfonamido)-2-methoxy-phenyl]-3-[4-[[2-[3-cyano-4-(3-morpholinopropoxy)anilino]-4-pyridyl]oxy]-1-naphthyl]urea;
1-[5-tert-butyl-3-(methanesulfonamido)-2-methoxy-phenyl]-3-[4-[[2-[3-methoxy-4-[2-[2-(2-methoxyethoxy)ethoxy]ethylsulfinyl]anilino]-4-pyridyl]oxy]-1-naphthyl]urea;
1-[5-tert-butyl-3-(methanesulfonamido)-2-methoxy-phenyl]-3-[4-[[2-[3-methoxy-4-[2-[2-(2-methoxyethoxy)ethoxy]ethylsulfonyl]anilino]-4-pyridyl]oxy]-1-naphthyl]urea;
1-[5-tert-butyl-3-(methanesulfonamido)-2-methoxy-phenyl]-3-[4-[[2-[3-methoxy-4-[methyl(3-morpholinopropyl)sulfamoyl]anilino]-4-pyridyl]oxy]-1-naphthyl]urea;
4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[2-(1-methyl-4-piperidyl)ethyl]benzamide;
4-[[4-[[4-[[5-tert-butyl-3-(methanesulfonamido)-2-methoxy-phenyl]carbamoylamino]-1-naphthyl]oxy]-2-pyridyl]amino]-2-ethynyl-N-(2-morpholinoethyl)benzamide;
4-[[4-[[4-[[5-tert-butyl-3-(methanesulfonamido)-2-methoxy-phenyl]carbamoylamino]-1-naphthyl]oxy]-2-pyridyl]amino]-N-[2-[2-(2-hydroxyethoxy)ethoxy]ethyl]-2-methoxy-benzamide;
4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[2-(4-methylpiperazin-1-yl)ethyl]benzamide;
4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(3-morpholinopropyl)benzamide;
4-[[4-[[4-[[5-tert-butyl-3-(methanesulfonamido)-2-methoxy-phenyl]carbamoylamino]-1-naphthyl]oxy]-2-pyridyl]amino]-N-[2-[(2S,6R)-2,6-dimethylmorpholin-4-yl]ethyl]-2-methoxy-benzamide;
4-[[4-[[4-[[5-tert-butyl-3-(methanesulfonamido)-2-methoxy-phenyl]carbamoylamino]-1-naphthyl]oxy]-2-pyridyl]amino]-N-[2-(2,2-dimethylmorpholin-4-yl)ethyl]-2-methoxy-benzamide;
4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(2-morpholino-2-oxoethyl)benzamide;
4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[2-(4-methyl-1,4-diazepan-1-yl)ethyl]benzamide;
4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[(1R)-2-[2-(2-methoxyethoxy)ethoxy]-1-methyl-ethyl]benzamide;
4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[(1S)-2-[2-(2-methoxyethoxy)ethoxy]-1-methyl-ethyl]benzamide;
4-[[4-[[4-[[5-tert-butyl-3-(methanesulfonamido)-2-methoxy-phenyl]carbamoylamino]-1-naphthyl]oxy]pyrimidin-2-yl]amino]-2-methoxy-N-(2-morpholinoethyl)benzamide;
4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(1-methyl-4-piperidyl)benzamide;
4-[[4-[[4-[[5-tert-butyl-3-(methanesulfonamido)-2-methoxy-phenyl]carbamoylamino]-1-naphthyl]oxy]-2-pyridyl]amino]-N-[2-(3,3-dimethylmorpholin-4-yl)ethyl]-2-methoxy-benzamide;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(2-thiomorpholinoethyl)benzamide;

4-[[4-[[4-[[5-tert-butyl-3-(methanesulfonamido)-2-methoxy-phenyl]carbamoylamino]-1-naphthyl]oxy]-2-pyridyl]amino]-N-[2-(4-hydroxy-1-piperidyl)ethyl]-2-methoxy-benzamide;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(2-methyl-2-morpholino-propyl)benzamide;

1-[5-tert-butyl-3-(methanesulfonamido)-2-methoxy-phenyl]-3-[4-[[2-[3-methoxy-4-[methyl(2-morpholinoethyl)sulfamoyl]anilino]-4-pyridyl]oxy]-1-naphthyl]urea;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[2-(1-piperidyl)ethyl]benzamide;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(2-pyrrolidin-1-ylethyl)benzamide;

4-[[4-[[4-[[5-tert-butyl-3-(methanesulfonamido)-2-methoxy-phenyl]carbamoylamino]-1-naphthyl]oxy]-2-pyridyl]amino]-N-[2-(1,1-dioxo-1,4-thiazinan-4-yl)ethyl]-2-methoxy-benzamide;

5-[[4-[[4-[[4-[[5-tert-butyl-3-(methanesulfonamido)-2-methoxy-phenyl]carbamoylamino]-1-naphthyl]oxy]-2-pyridyl]amino]-2-methoxy-benzoyl]amino]pentanoic acid;

4-[[4-[[4-[[5-tert-butyl-3-(methanesulfonamido)-2-methoxy-phenyl]carbamoylamino]-1-naphthyl]oxy]-2-pyridyl]amino]benzoic acid;

4-[[4-[[4-[[5-tert-butyl-3-(methanesulfonamido)-2-methoxy-phenyl]carbamoylamino]-1-naphthyl]oxy]-2-pyridyl]amino]-N-(2-morpholinoethyl)benzamide;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[(1S)-1-methyl-2-morpholino-ethyl]benzamide;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(2-piperazin-1-ylethyl)benzamide;

3-[2-[2-[[4-[[4-[[5-tert-butyl-3-(methanesulfonamido)-2-methoxy-phenyl]carbamoylamino]-1-naphthyl]oxy]-2-pyridyl]amino]-2-methoxy-benzoyl]amino]ethoxy]ethoxy]propanoic acid;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(4-morpholinobutyl)benzamide;

4-[[4-[[4-[[5-tert-butyl-3-(methanesulfonamido)-2-methoxy-phenyl]carbamoylamino]-1-naphthyl]oxy]-2-pyridyl]amino]-N-[2-[4-(2-hydroxyethyl)piperazin-1-yl]ethyl]-2-methoxy-benzamide;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[3-(4-methylpiperazin-1-yl)propyl]benzamide;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-methyl-N-(2-morpholinoethyl)benzamide;

4-[[4-[[4-[[5-tert-butyl-3-(methanesulfonamido)-2-methoxy-phenyl]carbamoylamino]-1-naphthyl]oxy]-2-pyridyl]amino]-N-[2-[2-hydroxyethyl(methyl)amino]ethyl]-2-methoxy-benzamide;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[2-[2-methoxyethyl(methyl)amino]ethyl]-benzamide;

4-[[4-[[4-[[5-tert-butyl-3-(methanesulfonamido)-2-methoxy-phenyl]carbamoylamino]-1-naphthyl]oxy]-2-pyridyl]amino]-2,6-dimethoxy-N-(2-morpholinoethyl)benzamide;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-methyl-N-(3-morpholinopropyl)benzamide;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[3-(1-oxo-1,4-thiazinan-4-yl)propyl]benzamide;

4-[[4-[[4-[[5-tert-butyl-3-(methanesulfonamido)-2-methoxy-phenyl]carbamoylamino]-1-naphthyl]oxy]-2-pyridyl]amino]-N-[3-(1,1-dioxo-1,4-thiazinan-4-yl)propyl]-2-methoxy-benzamide;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[2-(1,4-oxazepan-4-yl)ethyl]benzamide;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[3-(1,4-oxazepan-4-yl)propyl]benzamide;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[(1-methyl-4-piperidyl)methyl]benzamide;

4-[[4-[[4-[[5-tert-butyl-3-(methanesulfonamido)-2-methoxy-phenyl]carbamoylamino]-1-naphthyl]oxy]-2-pyridyl]amino]-N-[2-(4,4-difluoro-1-piperidyl)ethyl]-2-methoxy-benzamide;

2-[2-[2-[[4-[[4-[[5-tert-butyl-3-(methanesulfonamido)-2-methoxyphenyl]carbamoylamino]-1-naphthyl]oxy]-2-pyridyl]amino]-2-methoxybenzoyl]amino]ethoxy]ethoxy]ethyl dihydrogen phosphate;

4-[[4-[[4-[[5-tert-butyl-3-(methanesulfonamido)-2-methoxy-phenyl]carbamoylamino]-1-naphthyl]oxy]-2-pyridyl]amino]-2-(dimethylamino)benzoic acid;

4-((4-((4-(3-(5-(tert-butyl)-2-methoxy-3-(methylsulfonamido)phenyl)ureido)naphthalen-1-yl)oxy)pyrimidin-2-yl)amino)-2-methoxy-N-(2-(1-methylpiperidin-4-yl)ethyl)benzamide;

4-((4-((4-(3-(5-(tert-butyl)-2-methoxy-3-(methylsulfonamido)phenyl)ureido)naphthalen-1-yl)oxy)pyrimidin-2-yl)amino)-2-methoxy-N-(3-morpholinopropyl)benzamide;

4-((4-((4-(3-(5-(tert-butyl)-2-methoxy-3-(methylsulfonamido)phenyl)ureido)naphthalen-1-yl)oxy)pyrimidin-2-yl)amino)-2-methoxy-N-(3-(4-methylpiperazin-1-yl)propyl)benzamide;

4-((4-((4-(3-(5-(tert-butyl)-2-methoxy-3-(methylsulfonamido)phenyl)ureido)naphthalen-1-yl)oxy)pyrimidin-2-yl)amino)-2-methoxy-N-(2-(4-methylpiperazin-1-yl)ethyl)benzamide;

2-(4-((4-((4-(3-(5-(tert-butyl)-2-methoxy-3-(methylsulfonamido)phenyl)ureido)naphthalen-1-yl)oxy)pyridin-2-yl)amino)-2-methoxybenzamido)acetic acid;

4-(4-((4-((4-(3-(5-(tert-butyl)-2-methoxy-3-(methylsulfonamido)phenyl)ureido)-naphthalen-1-yl)oxy)pyridin-2-yl)amino)-2-methoxybenzamido)butanoic acid;

4-((4-((4-(3-(5-(tert-butyl)-2-methoxy-3-(methylsulfonamido)phenyl)ureido)naphthalen-1-yl)oxy)pyridin-2-yl)amino)-2,6-dimethoxy-N-(2-(1-methylpiperidin-4-yl)ethyl)benzamide;

4-((4-((4-(3-(5-(tert-butyl)-2-methoxy-3-(methylsulfonamido)phenyl)ureido)naphthalen-1-yl)oxy)pyridin-2-yl)amino)-2,6-dimethoxy-N-(3-(4-methylpiperazin-1-yl)propyl)benzamide;

(S)-2-(4-((4-((4-(3-(5-(tert-butyl)-2-methoxy-3-(methylsulfonamido)phenyl)ureido)-naphthalen-1-yl)oxy)pyridin-2-yl)amino)-2-methoxybenzamido)-3-(1H-imidazol-4-yl)propanoic acid;

(S)-1-(4-((4-((4-(3-(5-(tert-butyl)-2-methoxy-3-(methylsulfonamido)phenyl)ureido)-naphthalen-1-yl)oxy)pyridin-2-yl)amino)-2-methoxybenzoyl)pyrrolidine-2-carboxylic acid;

4-((4-((4-(3-(5-(tert-butyl)-2-methoxy-3-(methylsulfonamido)phenyl)ureido)naphthalen-1-yl)oxy)pyrimidin-2-yl)amino)-2-methoxybenzoic acid;

3-(4-((4-((4-(3-(5-(tert-butyl)-2-methoxy-3-(methylsulfonamido)phenyl)ureido)-naphthalen-1-yl)oxy)pyridin-2-yl)amino)-2-methoxybenzamido)propanoic acid;

4-((4-((4-(3-(5-(tert-butyl)-2-methoxy-3-(methylsulfonamido)phenyl)ureido)naphthalen-1-yl)oxy)pyrimidin-2-yl)amino)-2,6-dimethoxy-N-(2-(4-methylpiperazin-1-yl)ethyl)benzamide;

4-((4-((4-(3-(5-(tert-butyl)-2-methoxy-3-(methylsulfonamido)phenyl)ureido)naphthalen-1-yl)oxy)pyridin-2-yl)amino)-2-methoxy-N-methyl-N-(2-(1-methylpiperidin-4-yl)ethyl) benzenesulfonamide;

4-((4-((4-(3-(5-(tert-butyl)-2-methoxy-3-(methylsulfonamido)phenyl)ureido)naphthalen-1-yl)oxy)pyridin-2-yl)amino)-2-methoxy-N-methyl-N-(2-(4-methylpiperazin-1-yl)ethyl)benzene sulfonamide;

4-((4-((4-(3-(5-(tert-butyl)-2-methoxy-3-(methylsulfonamido)phenyl)ureido)naphthalen-1-yl)oxy)pyrimidin-2-yl)amino)-2-(dimethylamino)benzoic acid;

4-((4-((4-(3-(5-(tert-butyl)-2-methoxy-3-(methylsulfonamido)phenyl)ureido)naphthalen-1-yl)oxy)pyridin-2-yl)amino)-N-(5-(dimethylamino)pentyl)-2-methoxybenzamide;

4-((4-((4-(3-(5-(tert-butyl)-2-methoxy-3-(methylsulfonamido)phenyl)ureido)naphthalen-1-yl)oxy)pyridin-2-yl)amino)-N-(2-(4-ethylpiperazin-1-yl)ethyl)-2-methoxybenzamide;

4-((4-((4-(3-(5-(tert-butyl)-2-methoxy-3-(methylsulfonamido)phenyl)ureido)naphthalen-1-yl)oxy)pyridin-2-yl)amino)-N-(2-(4-isopropylpiperazin-1-yl)ethyl)-2-methoxybenzamide;

4-((4-((4-(3-(5-(tert-butyl)-2-methoxy-3-(methylsulfonamido)phenyl)ureido)naphthalen-1-yl)oxy)pyridin-2-yl)amino)-N-(2-(4-hydroxy-1-methylpiperidin-4-yl)ethyl)-2-methoxy benzamide;

4-((4-((4-(3-(5-(tert-butyl)-2-methoxy-3-(methylsulfonamido)phenyl)ureido)naphthalen-1-yl)oxy)pyridin-2-yl)amino)-2-methoxy-N-methyl-N-(2-(4-methylpiperazin-1-yl)ethyl)benzamide;

4-((4-((4-(3-(5-(tert-butyl)-2-methoxy-3-(methylsulfonamido)phenyl)ureido)naphthalen-1-yl)oxy)pyridin-2-yl)amino)-2-methoxy-N-(2-(2,2,4-trimethylpiperazin-1-yl)ethyl)benzamide;

(S)-2-(4-((4-((4-(3-(5-(tert-butyl)-2-methoxy-3-(methylsulfonamido)phenyl)ureido)-naphthalen-1-yl)oxy)pyridin-2-yl)amino)-2-methoxybenzamido)-3-hydroxypropanoic acid;

N-((4-((4-((4-(3-(5-(tert-butyl)-2-methoxy-3-(methylsulfonamido)phenyl)ureido)-naphthalen-1-yl)oxy)pyrimidin-2-yl)amino)-2-methoxyphenyl)sulfonyl)propionamide;

4-((4-((4-(3-(5-(tert-butyl)-2-methoxy-3-(methylsulfonamido)phenyl)ureido)naphthalen-1-yl)oxy)pyridin-2-yl)amino)-2-methoxy-N-(1-(4-methylpiperazin-1-yl)propan-2-yl)benzamide;

4-((4-((4-(3-(5-(tert-butyl)-2-methoxy-3-(methylsulfonamido)phenyl)ureido)naphthalen-1-yl)oxy)pyridin-2-yl)amino)-N-(2-(2-hydroxyethoxy)ethyl)-2-methoxybenzamide;

4-((4-((4-(3-(5-(tert-butyl)-2-methoxy-3-(methylsulfonamido)phenyl)ureido)naphthalen-1-yl)oxy)pyridin-2-yl)amino)-N-(2-hydroxyethyl)-2-methoxybenzamide;

4-((4-((4-(3-(3-(tert-butyl)-5-(methylsulfonamido)phenyl)ureido)naphthalen-1-yl)oxy)pyridin-2-yl)amino)-2-methoxy-N-(2-(4-methylpiperazin-1-yl)ethyl)benzamide;

4-((4-((4-(3-(3-(tert-butyl)-5-(methylsulfonamido)phenyl)ureido)naphthalen-1-yl)oxy)pyridin-2-yl)amino)-2-methoxy-N-(3-(4-methylpiperazin-1-yl)propyl)benzamide;

4-((4-((4-(3-(5-(tert-butyl)-2-methoxy-3-(methylsulfonamido)phenyl)ureido)naphthalen-1-yl)oxy)pyridin-2-yl)amino)-2-(dimethylamino)-N-(2-(4-methylpiperazin-1-yl)ethyl)benzamide;

4-((4-((4-(3-(5-(tert-butyl)-2-methoxy-3-(methylsulfonamido)phenyl)ureido)naphthalen-1-yl)oxy)pyridin-2-yl)amino)-2-methoxy-N-((3R,4R,5S,6R)-2,4,5-trihydroxy-6-(hydroxymethyl)tetrahydro-2H-pyran-3-yl)benzamide;

4-((4-((4-(3-(3-(tert-butyl)-5-(methylsulfonamido)phenyl)ureido)naphthalen-1-yl)oxy)pyridin-2-yl)amino)-2-methoxy-N-(2-(1-methylpiperidin-4-yl)ethyl)benzamide;

4-((4-((4-(3-(5-(tert-butyl)-2-methoxy-3-(methylsulfonamido)phenyl)ureido)naphthalen-1-yl)oxy)pyridin-2-yl)amino)-2-(dimethylamino)-N-(2-(2-(2-hydroxyethoxy)ethoxy)ethyl) benzamide;

(S)-2-amino-6-(4-((4-((4-(3-(5-(tert-butyl)-2-methoxy-3-(methylsulfonamido)phenyl)-ureido)naphthalen-1-yl)oxy)pyridin-2-yl)amino)-2-methoxybenzamido)hexanoic acid;

4-((4-((4-(3-(5-(tert-butyl)-2-methoxy-3-(methylsulfonamido)phenyl)ureido)naphthalen-1-yl)oxy)pyridin-2-yl)amino)-2-methoxy-N-(2-(2-(2-(((3R,4S,5R,6R)-3,4,5-trihydroxy-6-(hydroxymethyl)tetrahydro-2H-pyran-2-yl)oxy)ethoxy)ethoxy)ethyl)benzamide;

4-((4-((4-(3-(5-(tert-butyl)-2-methoxy-3-(methylsulfonamido)phenyl)ureido)naphthalen-1-yl)oxy)pyridin-2-yl)amino)-2-methoxy-N-((2S,3R,4R,5R)-2,3,4,5,6-pentahydroxyhexyl) benzamide;

6-(4-((4-((4-(3-(5-(tert-butyl)-2-methoxy-3-(methylsulfonamido)phenyl)ureido)-naphthalen-1-yl)oxy)pyridin-2-yl)amino)-2-methoxybenzamido)hexanoic acid;

4-((4-((4-(3-(5-(tert-butyl)-2-methoxy-3-(methylsulfonamido)phenyl)ureido)naphthalen-1-yl)oxy)pyrimidin-2-yl)amino)-N-(2-(2-(2-hydroxyethoxy)ethoxy)ethyl)-2-methoxybenzamide;

4-((4-((4-(3-(5-(tert-butyl)-2-methoxy-3-(methylsulfonamido)phenyl)ureido)naphthalen-1-yl)oxy)pyridin-2-yl)amino)-2,6-dimethoxy-N-(1-methylpiperidin-4-yl)benzamide;

4-((4-((4-(3-(5-(tert-butyl)-2-methoxy-3-(methylsulfonamido)phenyl)ureido)naphthalen-1-yl)oxy)pyridin-2-yl)amino)-2,6-dimethoxy-N-((1-methylpiperidin-4-yl)methyl)benzamide;

3-(3-(4-((4-((4-(3-(5-(tert-butyl)-2-methoxy-3-(methylsulfonamido)phenyl)ureido)-naphthalen-1-yl)oxy)pyridin-2-yl)amino)-2-methoxybenzamido)propoxy)propanoic acid;

2-(2-(4-((4-((4-(3-(5-(tert-butyl)-2-methoxy-3-(methylsulfonamido)phenyl)ureido)-naphthalen-1-yl)oxy)pyridin-2-yl)amino)-2-methoxybenzamido)ethoxy)ethyl dihydrogen phosphate;

4-((2-(4-((4-((4-(3-(5-(tert-butyl)-2-methoxy-3-(methylsulfonamido)phenyl)ureido)-naphthalen-1-yl)oxy)pyridin-2-yl)amino)-2-methoxybenzamido)ethyl)amino)-4-oxobutanoic acid;

3-(3-(4-((4-((4-(3-(5-(tert-butyl)-2-methoxy-3-(methylsulfonamido)phenyl)ureido)-naphthalen-1-yl)oxy)pyridin-2-yl)amino)-2-methoxybenzamido)propanamido)propanoic acid;

4-((4-((4-(3-(5-(tert-butyl)-2-methoxy-3-(methylsulfonamido)phenyl)ureido)naphthalen-1-yl)oxy)pyridin-2-yl)amino)-2-methoxy-N-(3-oxo-3-((2R,3R,4R,5S)-3,4,5-trihydroxy-2-(hydroxymethyl)piperidin-1-yl)propyl)benzamide;

N-(5-(tert-butyl)-3-(3-(4-((2-((4-(4-(2-(dimethylamino)ethyl)piperazine-1-carbonyl)-3,5-dimethoxyphenyl)amino)pyridin-4-yl)oxy)naphthalen-1-yl)ureido)-2-methoxyphenyl)methane sulfonamide;

N-(5-(tert-butyl)-2-methoxy-3-(3-(4-((2-((3-methoxy-4-((3-(4-methylpiperazin-1-yl)propyl) sulfonyl)phenyl)amino)pyridin-4-yl)oxy)naphthalen-1-yl)ureido)phenyl)methanesulfonamide;

N-(5-(tert-butyl)-2-methoxy-3-(3-(4-((2-((3-methoxy-4-((2R,3R,4R,5S)-3,4,5-trihydroxy-2-(hydroxymethyl)piperidine-1-carbonyl)phenyl)amino)pyridin-4-yl)oxy)naphthalen-1-yl)ureido)phenyl)methanesulfonamide;

4-((4-((4-(3-(5-(tert-butyl)-2-methoxy-3-(methylsulfonamido)phenyl)ureido)naphthalen-1-yl)oxy)pyridin-2-yl)amino)-N-(2-(4-(2-(dimethylamino)acetyl)piperazin-1-yl)ethyl)-2-methoxybenzamide;

4-(4-(2-(4-((4-((4-(3-(5-(tert-butyl)-2-methoxy-3-(methylsulfonamido)phenyl)ureido)-naphthalen-1-yl)oxy)pyridin-2-yl)amino)-2-methoxybenzamido)ethyl)piperazin-1-yl)-4-oxobutanoic acid;

(S)-2-amino-5-(4-(2-(4-((4-((4-(3-(5-(tert-butyl)-2-methoxy-3-(methylsulfonamido)-phenyl)ureido)naphthalen-1-yl)oxy)pyridin-2-yl)amino)-2-methoxybenzamido)ethyl)piperazin-1-yl)-5-oxopentanoic acid;

4-((4-((4-(3-(5-(tert-butyl)-2-methoxy-3-(methylsulfonamido)phenyl)ureido)naphthalen-1-yl)oxy)pyridin-2-yl)amino)-N-(1,3-dihydroxy-2-(hydroxymethyl)propan-2-yl)-2-methoxybenzamide;

4-((4-((4-(3-(5-(tert-butyl)-2-methoxy-3-(methylsulfonamido)phenyl)ureido)naphthalen-1-yl)oxy)pyridin-2-yl)amino)-N-(3-hydroxy-2,2-bis(hydroxymethyl)propyl)-2,6-dimethoxybenzamide;

4-((4-((4-(3-(5-(tert-butyl)-2-methoxy-3-(methylsulfonamido)phenyl)ureido)naphthalen-1-yl)oxy)pyridin-2-yl)amino)-2-methoxy-N-(((2S,3R,4R,5S,6R)-3,4,5-trihydroxy-6-(hydroxymethyl)tetrahydro-2H-pyran-2-yl)methyl)benzamide;

2-((5-(tert-butyl)-2-methoxy-3-(3-(4-((2-((3-methoxy-4-((2-(1-oxidothiomorpholino)-ethyl)carbamoyl)phenyl)amino)pyridin-4-yl)oxy)naphthalen-1-yl)ureido)phenyl)amino)-2-oxoethyl dihydrogen phosphate;

(R)-4-((4-((4-(3-(5-(tert-butyl)-2-methoxy-3-(methylsulfonamido)phenyl)ureido)-naphthalen-1-yl)oxy)pyridin-2-yl)amino)-2-methoxy-N-(1-methylpyrrolidin-3-yl)benzamide;

(R)-4-((4-((4-(3-(5-(tert-butyl)-2-methoxy-3-(methylsulfonamido)phenyl)ureido)-naphthalen-1-yl)oxy)pyridin-2-yl)amino)-N-(2-(3-hydroxypyrrolidin-1-yl)ethyl)-2-methoxybenzamide;

4-[[4-[[4-[[5-tert-butyl-3-(methanesulfonamido)-2-methoxy-phenyl]carbamoylamino]-1-naphthyl]oxy]-2-pyridyl]amino]-2-chloro-benzoic acid;

4-[[4-[[4-[[5-tert-butyl-3-(methanesulfonamido)-2-methoxy-phenyl]carbamoylamino]-1-naphthyl]oxy]-2-pyridyl]amino]-2-ethyl-benzoic acid;

4-[[4-[[4-[[5-tert-butyl-3-(methanesulfonamido)-2-methoxy-phenyl]carbamoylamino]-1-naphthyl]oxy]-2-pyridyl]amino]-2-(difluoromethoxy)benzoic acid;

6-[[4-[[4-[[5-tert-butyl-3-(methanesulfonamido)-2-methoxy-phenyl]carbamoylamino]-1-naphthyl]oxy]-2-pyridyl]amino]-4-methoxy-pyridine-3-carboxylic acid;

4-[[4-[[4-[[5-tert-butyl-3-(methanesulfonamido)-2-methoxy-phenyl]carbamoylamino]-1-naphthyl]oxy]-2-pyridyl]amino]-2-hydroxy-benzoic acid;

4-[[4-[[4-[[5-tert-butyl-3-(methanesulfonamido)-2-methoxy-phenyl]carbamoylamino]-1-naphthyl]oxy]-2-pyridyl]amino]-2-fluoro-benzoic acid;

(2S)-2-amino-3-[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]phenyl]-propanoic acid;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[(1R)-1-methyl-2-morpholino-ethyl]benzamide;

4-[[4-[[4-[[5-tert-butyl-3-(methanesulfonamido)-2-methoxy-phenyl]carbamoylamino]-1-naphthyl]oxy]-2-pyridyl]amino]-2-hydroxy-N-(2-morpholinoethyl)benzamide;

4-[[4-[[4-[[5-tert-butyl-3-(methanesulfonamido)-2-methoxy-phenyl]carbamoylamino]-1-naphthyl]oxy]-2-pyridyl]amino]-N-[2-[2-(2-methoxyethoxy)ethoxy]ethyl]benzamide;

4-[[4-[[4-[[5-tert-butyl-3-(methanesulfonamido)-2-methoxy-phenyl]carbamoylamino]-1-naphthyl]oxy]-2-pyridyl]amino]-N-[2-(4-fluoro-1-piperidyl)ethyl]-2-methoxy-benzamide;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-quinuclidin-4-yl-benzamide;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(quinuclidin-4-ylmethyl)benzamide;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(2-quinuclidin-4-ylethyl)benzamide;

1-[5-tert-butyl-3-(methanesulfonamido)-2-methoxy-phenyl]-3-[4-[[2-(3-methoxy-4-methylsulfonyl-anilino)-4-pyridyl]oxy]-1-naphthyl]urea;

1-[5-tert-butyl-3-(methanesulfonamido)-2-methoxy-phenyl]-3-[4-[[2-(3-methoxy-4-methylsulfinyl-anilino)-4-pyridyl]oxy]-1-naphthyl]urea;

1-[5-tert-butyl-3-(methanesulfonamido)-2-methoxy-phenyl]-3-[4-[[2-[3-methoxy-4-(2-morpholinoethylsulfonyl)anilino]-4-pyridyl]oxy]-1-naphthyl]urea;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[3-(1-methyl-4-piperidyl)propyl]benzamide;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[2-(4-piperidyl)ethyl]benzamide;

4-[[4-[[4-[[5-tert-butyl-3-(methanesulfonamido)-2-methoxy-phenyl]carbamoylamino]-1-naphthyl]oxy]-2-pyridyl]amino]-2,6-dimethoxy-N-(4-morpholinobutyl)benzamide;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[(1R)-1-methyl-3-morpholino-propyl]benzamide;

4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[(1S)-1-methyl-3-morpholino-propyl]benzamide;

2-[5-tert-butyl-2-methoxy-3-[[4-[[2-[3-methoxy-4-[2-(1-oxo-1,4-thiazinan-4-yl)ethylcarbamoyl]anilino]-4-pyridyl]oxy]-1-naphthyl]carbamoylamino]-N-methylsulfonyl-anilino]ethyl dihydrogen phosphate;

[4-[[4-[[4-[[5-tert-butyl-3-(methanesulfonamido)-2-methoxy-phenyl]carbamoylamino]-1-naphthyl]oxy]-2-pyridyl]amino]-2-methoxy-phenyl]phosphinic acid;

30   [4-[[4-[[4-[[5-tert-butyl-3-(methanesulfonamido)-2-methoxy-phenyl]carbamoylamino]-1-naphthyl]oxy]-2-pyridyl]amino]-2-methoxy-phenyl]phosphonic acid;

[4-[[4-[[4-[[5-tert-butyl-3-(methanesulfonamido)-2-methoxy-phenyl]carbamoylamino]-1-naphthyl]oxy]-2-pyridyl]amino]-2,6-dimethoxy-phenyl]-methyl-phosphinic acid;

4-[[4-[[4-[[5-tert-butyl-3-(methanesulfonamido)-2-methoxy-phenyl]carbamoylamino]-1-naphthyl]oxy]-2-pyridyl]amino]-2-methoxy-benzenesulfinic acid;

4-[[4-[[4-[[5-tert-butyl-3-(methanesulfonamido)-2-methoxy-phenyl]carbamoylamino]-1-naphthyl]oxy]-2-pyridyl]amino]-2-(trifluoromethoxy)benzoic acid;

6-[[4-[[4-[[5-tert-butyl-3-(methanesulfonamido)-2-methoxy-phenyl]carbamoylamino]-1-naphthyl]oxy]-2-pyridyl]amino]-2-methoxy-pyridine-3-carboxylic acid;

4-[[4-[[4-[[5-tert-butyl-3-(methanesulfonamido)-2-methoxy-phenyl]carbamoylamino]-1-naphthyl]oxy]-2-pyridyl]amino]-2,6-dimethyl-benzoic acid;

N-(5-(tert-butyl)-2-methoxy-3-(3-(4-((2-((3-methoxy-4-((3-morpholinopropyl)sulfonyl)phenyl)-amino)pyridin-4-yl)oxy)naphthalen-1-yl)ureido)phenyl)methanesulfonamide;

4-((4-((4-(3-(5-(tert-butyl)-2-methoxy-3-(methylsulfonamido)phenyl)ureido)naphthalen-1-yl)oxy)pyridin-2-yl)amino)-2-(dimethylamino)-N-(2-morpholinoethyl)benzamide;

4-((4-((4-(3-(5-(tert-butyl)-2-methoxy-3-(methylsulfonamido)phenyl)ureido)naphthalen-1-yl)oxy)pyridin-2-yl)amino)-2,6-dimethoxy-N-(2-(4-methylpiperazin-1-yl)ethyl)benzamide;

4-((4-((4-(3-(5-(tert-butyl)-2-methoxy-3-(methylsulfonamido)phenyl)ureido)naphthalen-1-yl)oxy)pyridin-2-yl)amino)-2,6-dimethoxy-N-(3-morpholinopropyl)benzamide;

N-(5-(tert-butyl)-2-methoxy-3-(3-(4-((2-((3-methoxy-4-(2H-tetrazol-5-yl)phenyl)amino)pyridin-4-yl)oxy)naphthalen-1-yl)ureido)phenyl)methanesulfonamide;

4-((4-((4-(3-(5-(tert-butyl)-2-methoxy-3-(methylsulfonamido)phenyl)ureido)naphthalen-1-yl)oxy)pyridin-2-yl)amino)-2-methoxy-N-methyl-N-(3-(4-methylpiperazin-1-yl)propyl)benzenesulfonamide;

4-((4-((4-(3-(5-(tert-butyl)-2-methoxy-3-(methylsulfonamido)phenyl)ureido)naphthalen-1-yl)oxy)pyridin-2-yl)amino)-N-(2-(4-cyclopropylpiperazin-1-yl)ethyl)-2-methoxybenzamide;

4-((4-((4-(3-(5-(tert-butyl)-2-methoxy-3-(methylsulfonamido)phenyl)ureido)naphthalen-1-yl)oxy)pyridin-2-yl)amino)-2-methoxy-N-(2-(piperidin-4-yl)ethyl)benzamide;

4-((4-((4-(3-(5-(tert-butyl)-2-methoxy-3-(methylsulfonamido)phenyl)ureido)naphthalen-1-yl)oxy)pyrimidin-2-yl)amino)-2-methoxybenzenesulfonamide;

4-((4-((4-(3-(5-(tert-butyl)-2-methoxy-3-(methylsulfonamido)phenyl)ureido)naphthalen-1-yl)oxy)pyridin-2-yl)amino)-2-hydroxy-N-(3-morpholinopropyl)benzamide;

4-((4-((4-(3-(3-(tert-butyl)-5-(methylsulfonamido)phenyl)ureido)naphthalen-1-yl)oxy)pyridin-2-yl)amino)-2-methoxybenzoic acid;

N-(5-(tert-butyl)-2-methoxy-3-(3-(4-((2-((3-methoxy-4-(2-oxopyridin-1 (2H)-yl)phenyl)amino)-pyridin-4-yl)oxy)naphthalen-1-yl)ureido)phenyl)methanesulfonamide;

5-(tert-butyl)-N-(2-hydroxyethyl)-2-methoxy-3-(3-(4-((2-((3-methoxy-4-((2-(1-oxidothiomorpholino)ethyl)carbamoyl)phenyl)amino)pyridin-4-yl)oxy)naphthalen-1-yl)ureido)benzamide;

4-(2-(4-((4-((4-(3-(5-(tert-butyl)-2-methoxy-3-(methylsulfonamido)phenyl)ureido)naphthalen-1-yl)oxy)pyridin-2-yl)amino)-2-methoxybenzamido)ethyl)morpholine 4-oxide;

7-(4-((4-((4-(3-(5-(tert-butyl)-2-methoxy-3-(methylsulfonamido)phenyl)ureido)naphthalen-1-yl)oxy)pyridin-2-yl)amino)-2-methoxybenzamido)heptanoic acid;

2-(4-((4-((4-(3-(5-(tert-butyl)-2-methoxy-3-(methylsulfonamido)phenyl)ureido)naphthalen-1-yl)oxy)pyridin-2-yl)amino)-2-methoxybenzamido)ethyl dihydrogen phosphate;

4-((4-((4-(3-(5-(tert-butyl)-2-methoxy-3-(methylsulfonamido)phenyl)ureido)naphthalen-1-yl)oxy)pyridin-2-yl)amino)-N-(2-(2-(2-hydroxyethoxy)ethoxy)ethyl)-2,6-dimethoxybenzamide;

4-((4-((4-(3-(5-(tert-butyl)-2-methoxy-3-(methylsulfonamido)phenyl)ureido)naphthalen-1-yl)oxy)pyridin-2-yl)amino)-N-(2-(4-(2-hydroxyethyl)piperazin-1-yl)ethyl)-2,6-dimethoxybenzamide;

4-((4-((4-(3-(5-(tert-butyl)-2-methoxy-3-(methylsulfonamido)phenyl)ureido)naphthalen-1-yl)oxy)pyridin-2-yl)amino)-N-(3-hydroxy-2,2-bis(hydroxymethyl)propyl)-2-methoxybenzamide;

4-((4-((4-(3-(5-(tert-butyl)-2-methoxy-3-(methylsulfonamido)phenyl)ureido)naphthalen-1-yl)oxy)pyridin-2-yl)amino)-N-(2-(dimethylamino)ethyl)-2,6-dimethoxybenzamide;

N-(5-(tert-butyl)-3-(3-(4-((2-((4-((2-(2-(2-hydroxyethoxy)ethoxy)ethyl)sulfonyl)-3-methoxyphenyl)amino)pyridin-4-yl)oxy)naphthalen-1-yl)ureido)-2-methoxyphenyl)-methanesulfonamide;

4-((4-((4-(3-(5-(tert-butyl)-3-(2-hydroxyacetamido)-2-methoxyphenyl)ureido)naphthalen-1-yl)oxy)pyridin-2-yl)amino)-2-methoxy-N-(2-(1-oxidothiomorpholino)ethyl)benzamide;

4-((4-((4-(3-(5-(tert-butyl)-2-methoxy-3-(methylsulfonamido)phenyl)ureido)naphthalen-1-yl)oxy)pyridin-2-yl)amino)-2-methoxy-N-((2S,3S,4R)-2,3,4,5-tetrahydroxypentyl)benzamide;

ethyl (4-((4-((4-(3-(5-(tert-butyl)-2-methoxy-3-(methylsulfonamido)phenyl)ureido)naphthalen-1-yl)oxy)pyridin-2-yl)amino)-2-methoxyphenyl)(methyl)phosphinate;

(4-((4-((4-(3-(5-(tert-butyl)-2-methoxy-3-(methylsulfonamido)phenyl)ureido)naphthalen-1-yl)oxy)pyridin-2-yl)amino)-2-methoxyphenyl)(methyl)phosphinic acid;

(5-(tert-butyl)-3-(3-(4-((2-((4-((3-hydroxy-2,2-bis(hydroxymethyl)propyl)sulfonyl)-3-methoxyphenyl)amino)pyridin-4-yl)oxy)naphthalen-1-yl)ureido)-2-methoxyphenyl)-methanesulfonamide;

4-[[4-[[4-[[5-tert-butyl-3-(methanesulfonamido)-2-methoxyphenyl]carbamoylamino]-1-naphthyl]oxy]-2-pyridyl]amino]-2,6-dimethoxybenzoic acid;

2-(2-(2-(4-((4-((4-(3-(5-(tert-butyl)-2-methoxy-3-(methylsulfonamido)phenyl)ureido)-naphthalen-1-yl)oxy)pyridin-2-yl)amino)-2,6-dimethoxybenzamido)ethoxy)ethoxy)ethyl dihydrogen phosphate;

4-((4-((4-(3-(5-(tert-butyl)-3-(N-(2-hydroxyethyl)methylsulfonamido)-2-methoxyphenyl)ureido) naphthalen-1-yl)oxy)pyridin-2-yl)amino)-2-methoxy-N-(2-(1-oxidothiomorpholino)ethyl)benzamide;

5-(tert-butyl)-2-methoxy-3-(3-(4-((2-((3-methoxy-4-((2-(1-oxidothiomorpholino)ethyl)-carbamoyl)phenyl)amino)pyridin-4-yl)oxy)naphthalen-1-yl)ureido)benzoic acid;

diethyl (4-((4-((4-(3-(5-(tert-butyl)-2-methoxy-3-(methylsulfonamido)phenyl)ureido)-naphthalen-1-yl)oxy)pyridin-2-yl)amino)-2-methoxyphenyl)phosphonate;

[4-[[4-[[4-[[5-tert-butyl-3-(methanesulfonamido)-2-methoxy-phenyl]carbamoylamino]-1-naphthyl]oxy]-2-pyridyl]amino]-2-methoxy-phenyl]-ethoxy-phosphinic acid;

ethyl (4-((4-((4-(3-(5-(tert-butyl)-2-methoxy-3-(methylsulfonamido)phenyl)ureido)naphthalen-1-yl)oxy)pyridin-2-yl)amino)-2-methoxyphenyl)(ethyl)phosphinate;

[4-[[4-[[4-[[5-tert-butyl-3-(methanesulfonamido)-2-methoxy-phenyl]carbamoylamino]-1-naphthyl]oxy]-2-pyridyl]amino]-2-methoxy-phenyl]-ethyl-phosphinic acid;

ethyl (4-((4-((4-(3-(5-(tert-butyl)-2-methoxy-3-(methylsulfonamido)phenyl)ureido)-naphthalen-1-yl)oxy)pyridin-2-yl)amino)-2-methoxyphenyl)(phenyl)phosphinate;

[4-[[4-[[4-[[5-tert-butyl-3-(methanesulfonamido)-2-methoxy-phenyl]carbamoylamino]-1-naphthyl]oxy]-2-pyridyl]amino]-2-methoxy-phenyl]-phenyl-phosphinic acid;

ethyl (4-((4-((4-(3-(5-(tert-butyl)-2-methoxy-3-(N-methyl-methylsulfonamido)phenyl)-ureido)naphthalen-1-yl)oxy)pyridin-2-yl)amino)-2-methoxyphenyl)(methyl)phosphinate;

[4-[[4-[[4-[[5-tert-butyl-2-methoxy-3-[methyl(methylsulfonyl)amino]phenyl]carbamoyl-amino]-1-naphthyl]oxy]-2-pyridyl]amino]-2-methoxy-phenyl]-methyl-phosphinic acid;

ethyl (4-((4-((4-(3-(5-(tert-butyl)-2-methoxy-3-(methylcarbamoyl)phenyl)ureido)-naphthalen-1-yl)oxy)pyridin-2-yl)amino)-2-methoxyphenyl)(methyl)phosphinate;

40 [4-[[4-[[4-[[5-tert-butyl-2-methoxy-3-(methylcarbamoyl)phenyl]carbamoylamino]-1-naphthyl]oxy]-2-pyridyl]amino]-2-methoxy-phenyl]-methyl-phosphinic acid;

ethyl (4-((4-((4-(3-(5-(tert-butyl)-2-methoxy-3-(methylsulfonamido)phenyl)ureido)naphthalen-1-yl)oxy)pyridin-2-yl)amino)-2-methylphenyl)(methyl)phosphinate;

[4-[[4-[[4-[[5-tert-butyl-3-(methanesulfonamido)-2-methoxy-phenyl]carbamoylamino]-1-naphthyl]oxy]-2-pyridyl]amino]-2-methyl-phenyl]-methyl-phosphinic acid;

ethyl (4-((4-((4-(3-(5-(tert-butyl)-2-methoxy-3-(methylsulfonamido)phenyl) ureido)-naphthalen-1-yl)oxy)pyridin-2-yl)amino)-2-ethoxyphenyl)(methyl)-phosphinate;

[4-[[4-[[4-[[5-tert-butyl-3-(methanesulfonamido)-2-methoxy-phenyl]carbamoylamino]-1-naphthyl]oxy]-2-pyridyl]amino]-2-ethoxy-phenyl]-methyl-phosphinic acid;

ethyl (4-((4-((4-(3-(5-(tert-butyl)-2-methoxy-3-(methylsulfonamido)phenyl) ureido)-naphthalen-1-yl)oxy)pyrimidin-2-yl)amino)-2-methoxyphenyl)(methyl)phosphinate;

[4-[[4-[[4-[[5-tert-butyl-3-(methanesulfonamido)-2-methoxy-phenyl]carbamoylamino]-1-naphthyl]oxy]pyrimidin-2-yl]amino]-2-methoxy-phenyl]-methyl-phosphinic acid;

ethyl (4-((4-((4-(3-(5-(tert-butyl)-2-methoxy-3-(methylsulfonamido)phenyl) ureido)-naphthalen-1-yl)oxy)pyridin-2-yl)amino)-2-chlorophenyl)(methyl)phosphinate;

[4-[[4-[[4-[[5-tert-butyl-3-(methanesulfonamido)-2-methoxy-phenyl]carbamoylamino]-1-naphthyl]oxy]-2-pyridyl]amino]-2-chloro-phenyl]-methyl-phosphinic acid;

ethyl (4-((4-((4-(3-(5-(tert-butyl)-2-methoxy-3-(methylsulfonamido)phenyl) ureido)-naphthalen-1-yl)oxy)pyridin-2-yl)amino)-2-(dimethylamino)phenyl)(methyl)phosphinate;

[4-[[4-[[4-[[5-tert-butyl-3-(methanesulfonamido)-2-methoxy-phenyl]carbamoylamino]-1-naphthyl]oxy]-2-pyridyl]amino]-2-(dimethylamino)phenyl]-methyl-phosphinic acid;

ethyl 4-((4-((4-(3-(5-(tert-butyl)-2-methoxy-3-(methylsulfonamido)phenyl)ureido)-naphthalen-1-yl)oxy)pyridin-2-yl)amino)-2-methoxybenzyl(methyl)phosphinate;

(4-((4-((4-(3-(5-(tert-butyl)-2-methoxy-3-(methylsulfonamido)phenyl) ureido)naphthalen-1-yl)oxy)pyridin-2-yl)amino)-2-methoxybenzyl)(methyl)phosphinic acid;

ethyl (4-((4-((4-(3-(3-(tert-butyl)-5-(methylsulfonamido)phenyl)ureido)naphthalen-1-yl)oxy)pyridin-2-yl)amino)-2-methoxyphenyl)(methyl)phosphinate;

[4-[[4-[[4-[[3-tert-butyl-5-(methanesulfonamido)phenyl]carbamoylamino]-1-naphthyl]oxy]-2-pyridyl]amino]-2-methoxy-phenyl]-methyl-phosphinic acid;

4-[[4-[[4-[[5-tert-butyl-3-(methanesulfonamido)-2-methoxy-phenyl]carbamoylamino]-1-naphthyl]oxy]-2-pyridyl]amino]-2-(trifluoromethyl)benzoic acid;

(2R)-2-amino-3-[[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino] propanoic acid;

(2S)-2-amino-3-[[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino] propanoic acid;

(2R)-2-amino-4-[[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino] butanoic acid;

(2S)-2-amino-4-[[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino] butanoic acid;

(2R)-2-amino-5-[[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino] pentanoic acid;

(2S)-2-amino-5-[[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino] pentanoic acid;

(2R)-2-amino-6-[[4-[[4-[[4-[[5-tert-butyl-3-(methanesulfo-
   namido)-2-methoxy-phenyl]-carbamoylamino]-1-naph-
   thyl]oxy]-2-pyridyl]amino]-2-methoxy-benzoyl]amino]
   hexanoic acid;
(2R)-2-amino-7-[[4-[[4-[[4-[[5-tert-butyl-3-(methanesulfo-
   namido)-2-methoxy-phenyl]-carbamoylamino]-1-naph-
   thyl]oxy]-2-pyridyl]amino]-2-methoxy-benzoyl]amino]
   heptanoic acid;
(2S)-2-amino-7-[[4-[[4-[[4-[[5-tert-butyl-3-(methanesulfo-
   namido)-2-methoxy-phenyl]-carbamoylamino]-1-naph-
   thyl]oxy]-2-pyridyl]amino]-2-methoxy-benzoyl]amino]
   heptanoic acid;
(2S)-6-[[4-[[4-[[4-[[5-tert-butyl-3-(methanesulfonamido)-2-
   methoxy-phenyl]carbamoylamino]-1-naphthyl]oxy]-2-
   pyridyl]amino]-2-methoxy-benzoyl]amino]-2-(methyl-
   amino)hexanoic acid;
(2S)-6-[[4-[[4-[[4-[[5-tert-butyl-3-(methanesulfonamido)-2-
   methoxy-phenyl]carbamoylamino]-1-naphthyl]oxy]-2-
   pyridyl]amino]-2-methoxy-benzoyl]amino]-2-(dimethyl-
   amino)hexanoic acid;
(2R)-2-amino-5-[4-[2-[[4-[[4-[[4-[[5-tert-butyl-3-(methane-
   sulfonamido)-2-methoxy-phenyl]-carbamoylamino]-1-
   naphthyl]oxy]-2-pyridyl]amino]-2-methoxy-benzoyl]
   amino]ethyl]piperazin-1-yl]-5-oxo-pentanoic acid;
(2S)-2-amino-4-[4-[2-[[4-[[4-[[4-[[5-tert-butyl-3-(methane-
   sulfonamido)-2-methoxy-phenyl]-carbamoylamino]-1-
   naphthyl]oxy]-2-pyridyl]amino]-2-methoxy-benzoyl]
   amino]ethyl]piperazin-1-yl]-4-oxo-butanoic acid;
(2R)-2-amino-4-[4-[2-[[4-[[4-[[4-[[5-tert-butyl-3-(methane-
   sulfonamido)-2-methoxy-phenyl]-carbamoylamino]-1-
   naphthyl]oxy]-2-pyridyl]amino]-2-methoxy-benzoyl]
   amino]ethyl]piperazin-1-yl]-4-oxo-butanoic acid;
5-[[4-[[4-[[5-tert-butyl-3-(methanesulfonamido)-2-
   methoxy-phenyl]carbamoylamino]-1-naphthyl]oxy]-2-
   pyridyl]amino]-3-methoxy-pyridine-2-carboxylic acid;
4-[[4-[[4-[[5-tert-butyl-3-(methanesulfonamido)-2-
   methoxy-phenyl]carbamoylamino]-1-naphthyl]oxy]-2-
   pyridyl]amino]-2-methylsulfanyl-benzoic acid;
4-[[4-[[4-[[5-tert-butyl-3-(methanesulfonamido)-2-
   methoxy-phenyl]carbamoylamino]-1-naphthyl]oxy]-2-
   pyridyl]amino]-2-methylsulfinyl-benzoic acid;
4-[[4-[[4-[[5-tert-butyl-3-(methanesulfonamido)-2-
   methoxy-phenyl]carbamoylamino]-1-naphthyl]oxy]-2-
   pyridyl]amino]-2-methylsulfonyl-benzoic acid;
2-[4-[[4-[[4-[[5-tert-butyl-3-(methanesulfonamido)-2-
   methoxy-phenyl]carbamoylamino]-1-naphthyl]oxy]-2-
   pyridyl]amino]-2-methoxy-phenyl]acetic acid;
2-[4-[[4-[[4-[[5-tert-butyl-3-(methanesulfonamido)-2-
   methoxy-phenyl]carbamoylamino]-1-naphthyl]oxy]-2-
   pyridyl]amino]-2-methoxy-benzoyl]amino]butoxy]acetic
   acid;
2-[4-[[4-[[4-[[5-tert-butyl-3-(methanesulfonamido)-2-
   methoxy-phenyl]carbamoylamino]-1-naphthyl]oxy]-2-
   pyridyl]amino]-2-methoxy-benzoyl]amino]butylamino]
   acetic acid;
3-[3-[[4-[[4-[[5-tert-butyl-3-(methanesulfonamido)-2-
   methoxy-phenyl]carbamoylamino]-1-naphthyl]oxy]-2-
   pyridyl]amino]-2-methoxy-benzoyl]amino]propylamino]
   propanoic acid;
4-[2-[[4-[[4-[[4-[[5-tert-butyl-3-(methanesulfonamido)-2-
   methoxy-phenyl]carbamoylamino]-1-naphthyl]oxy]-2-
   pyridyl]amino]-2-methoxy-benzoyl]amino]ethylamino]
   butanoic acid;
(2S)-2-amino-3-[4-[[[4-[[4-[[4-[[5-tert-butyl-3-(methane-
   sulfonamido)-2-methoxy-phenyl]-carbamoylamino]-1-
   naphthyl]oxy]-2-pyridyl]amino]-2-methoxy-benzoyl]
   amino]methyl]-phenyl]propanoic acid;
(2R)-2-amino-3-[4-[[[4-[[4-[[4-[[5-tert-butyl-3-(methane-
   sulfonamido)-2-methoxy-phenyl]-carbamoylamino]-1-
   naphthyl]oxy]-2-pyridyl]amino]-2-methoxy-benzoyl]
   amino]methyl]-phenyl]propanoic acid;
(2R)-2-amino-3-[4-[[4-[[4-[[4-[[5-tert-butyl-3-(methanesul-
   fonamido)-2-methoxy-phenyl]-carbamoylamino]-1-
   naphthyl]oxy]-2-pyridyl]amino]-2-methoxy-benzoyl]
   amino]phenyl]-propanoic acid;
(4S)-4-amino-5-[4-[2-[[4-[[4-[[4-[[5-tert-butyl-3-(methane-
   sulfonamido)-2-methoxy-phenyl]-carbamoylamino]-1-
   naphthyl]oxy]-2-pyridyl]amino]-2-methoxy-benzoyl]
   amino]ethyl]piperazin-1-yl]-5-oxo-pentanoic acid;
(3S)-3-amino-4-[4-[2-[[4-[[4-[[4-[[5-tert-butyl-3-(methane-
   sulfonamido)-2-methoxy-phenyl]-carbamoylamino]-1-
   naphthyl]oxy]-2-pyridyl]amino]-2-methoxy-benzoyl]
   amino]ethyl]piperazin-1-yl]-4-oxo-butanoic acid;
(2S)-2-amino-6-[4-[2-[[4-[[4-[[4-[[5-tert-butyl-3-(methane-
   sulfonamido)-2-methoxy-phenyl]-carbamoylamino]-1-
   naphthyl]oxy]-2-pyridyl]amino]-2-methoxy-benzoyl]
   amino]ethyl]piperazin-1-yl]-6-oxo-hexanoic acid;
(2R)-2-amino-6-[4-[2-[[4-[[4-[[4-[[5-tert-butyl-3-(methane-
   sulfonamido)-2-methoxy-phenyl]-carbamoylamino]-1-
   naphthyl]oxy]-2-pyridyl]amino]-2-methoxy-benzoyl]
   amino]ethyl]piperazin-1-yl]-6-oxo-hexanoic acid;
(2S)-5-[4-[2-[[4-[[4-[[4-[[5-tert-butyl-3-(methanesulfona-
   mido)-2-methoxy-phenyl]carbamoyl-amino]-1-naphthyl]
   oxy]-2-pyridyl]amino]-2-methoxy-benzoyl]amino]ethyl]
   piperazin-1-yl]-2-(methylamino)-5-oxo-pentanoic acid;
   and
(2S)-5-[4-[2-[[4-[[4-[[4-[[5-tert-butyl-3-(methanesulfona-
   mido)-2-methoxy-phenyl]carbamoyl-amino]-1-naphthyl]
   oxy]-2-pyridyl]amino]-2-methoxy-benzoyl]amino]ethyl]
   piperazin-1-yl]-2-(dimethylamino)-5-oxo-pentanoic acid,
or a pharmaceutically acceptable salt thereof.

Alternative embodiments of the invention that may be mentioned include those in which the compound of formula I, Ia or Ib is as hereinbefore defined, provided that it is not: (i) one compound selected from the above list, or a pharmaceutically acceptable salt thereof; or (ii) any two or more compounds selected from the above list, or pharmaceutically acceptable salts thereof.

Examples of salts of compounds of formula I, Ia or Ib include all pharmaceutically acceptable salts, such as, without limitation, acid addition salts of strong mineral acids such as HCl, $H_2SO_4$ and HBr salts (e.g. HCl or HBr salts) and addition salts of strong organic acids such as methanesulfonic acid.

Particular salts of compounds of formula I, Ia or Ib that may be mentioned include hydrochloric acid salts and, for those compounds containing one or more acidic functional groups (e.g. functional groups comprising OH attached directly to a C(O), $S(O)_{1-2}$ or P(O) moiety), sodium, ammonium, calcium, magnesium, N-methylglucamine ((2R,3R,4R,5S)-6-(methylamino)-hexane-1,2,3,4,5-pentol) or benethamine (N-benzyl-2-phenethylamine) salts (e.g. sodium or ammonium salts).

Particular hydrochloride salts that may be mentioned include hydrochloride salts of the following compounds:
4-((4-((4-(3-(5-(tert-butyl)-2-methoxy-3-(methylsulfona-
   mido)phenyl)ureido)naphthalen-1-yl)oxy)pyridin-2-yl)
   amino)-2-methoxybenzoic acid;
5-[[4-[[4-[[5-tert-butyl-3-(methanesulfonamido)-2-
   methoxyphenyl]carbamoylamino]-1-naphthyl]oxy]-2-
   pyridyl]amino]-2-methoxybenzoyl]amino]pentanoic
   acid;

2-(4-((4-((4-(3-(5-(tert-butyl)-2-methoxy-3-(methylsulfonamido)phenyl)ureido)naphthalen-1-yl)oxy)pyridin-2-yl)amino)-2-methoxybenzamido)acetic acid;

4-(4-((4-((4-(3-(5-(tert-butyl)-2-methoxy-3-(methylsulfonamido)phenyl)ureido)-naphthalen-1-yl)oxy)pyridin-2-yl)amino)-2-methoxybenzamido)butanoic acid;

(S)-1-(4-((4-((4-(3-(5-(tert-butyl)-2-methoxy-3-(methylsulfonamido)phenyl)ureido)naphthalen-1-yl)oxy)pyridin-2-yl)amino)-2-methoxybenzoyl)pyrrolidine-2-carboxylic acid;

3-(4-((4-((4-(3-(5-(tert-butyl)-2-methoxy-3-(methylsulfonamido)phenyl)ureido)naphthalen-1-yl)oxy)pyridin-2-yl)amino)-2-methoxybenzamido)propanoic acid;

6-(4-((4-((4-(3-(5-(tert-butyl)-2-methoxy-3-(methylsulfonamido)phenyl)ureido)naphthalen-1-yl)oxy)pyridin-2-yl)amino)-2-methoxybenzamido)hexanoic acid;

4-((2-(4-((4-((4-(3-(5-(tert-butyl)-2-methoxy-3-(methylsulfonamido)phenyl)ureido)naphthalen-1-yl)oxy)pyridin-2-yl)amino)-2-methoxybenzamido)ethyl)amino)-4-oxobutanoic acid;

4-((4-((4-(3-(3-(tert-butyl)-5-(methylsulfonamido)phenyl)ureido)naphthalen-1-yl)oxy)pyridin-2-yl)amino)-2-methoxybenzoic acid;

7-(4-((4-((4-(3-(5-(tert-butyl)-2-methoxy-3-(methylsulfonamido)phenyl)ureido)naphthalen-1-yl)oxy)pyridin-2-yl)amino)-2-methoxybenzamido)heptanoic acid; and 4-[[4-[[4-[[5-tert-butyl-3-(methanesulfonamido)-2-methoxy-phenyl]carbamoylamino]-1-naphthyl]oxy]-2-pyridyl]amino]-2-fluoro-benzoic acid.

Particular dihydrochloride salts that may be mentioned include dihydrochloride salts of the following compounds:

(S)-2-(4-((4-((4-(3-(5-(tert-butyl)-2-methoxy-3-(methylsulfonamido)phenyl)ureido)naphthalen-1-yl)oxy)pyridin-2-yl)amino)-2-methoxybenzamido)-3-(1H-imidazol-4-yl)propanoic acid;

(S)-2-amino-6-(4-((4-((4-(3-(5-(tert-butyl)-2-methoxy-3-(methylsulfonamido)phenyl)ureido)-naphthalen-1-yl)oxy)pyridin-2-yl)amino)-2-methoxybenzamido)hexanoic acid; and (2S)-2-amino-3-[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]phenyl]-propanoic acid.

Particular sodium and ammonium salts that may be mentioned include sodium or ammonium (e.g. sodium, disodium, ammonium or diammonium) salts of the following compounds:

4-((4-((4-(3-(5-(tert-butyl)-2-methoxy-3-(methylsulfonamido)phenyl)ureido)naphthalen-1-yl)oxy)pyridin-2-yl)amino)-2-methoxybenzoic acid;

4-((4-((4-(3-(5-(tert-butyl)-2-methoxy-3-(methylsulfonamido)phenyl)ureido)naphthalen-1-yl)oxy)pyrimidin-2-yl)amino)-2-methoxybenzoic acid;

(S)-2-(4-((4-((4-(3-(5-(tert-butyl)-2-methoxy-3-(methylsulfonamido)phenyl)ureido)-naphthalen-1-yl)oxy)pyridin-2-yl)amino)-2-methoxybenzamido)-3-hydroxypropanoic acid;

N-((4-((4-((4-(3-(5-(tert-butyl)-2-methoxy-3-(methylsulfonamido)phenyl)ureido)-naphthalen-1-yl)oxy)pyrimidin-2-yl)amino)-2-methoxyphenyl)sulfonyl)propionamide;

2-(2-(4-((4-((4-(3-(5-(tert-butyl)-2-methoxy-3-(methylsulfonamido)phenyl)ureido)naphthalen-1-yl)oxy)pyridin-2-yl)amino)-2-methoxybenzamido)ethoxy)ethyl dihydrogen phosphate;

2-(2-(2-(4-((4-((4-(3-(5-(tert-butyl)-2-methoxy-3-(methylsulfonamido)phenyl)ureido)-naphthalen-1-yl)oxy)pyridin-2-yl)amino)-2-methoxybenzamido)ethoxy)ethoxy)ethyl dihydrogen phosphate;

2-((5-(tert-butyl)-2-methoxy-3-(3-(4-((2-((3-methoxy-4-((2-(1-oxidothiomorpholino)-ethyl)carbamoyl)phenyl)amino)pyridin-4-yl)oxy)naphthalen-1-yl)ureido)phenyl)amino)-2-oxoethyl dihydrogen phosphate;

(4-((4-((4-(3-(5-(tert-butyl)-2-methoxy-3-(methylsulfonamido)phenyl)ureido)naphthalen-1-yl)oxy)pyridin-2-yl)amino)-2-methoxyphenyl)(methyl)phosphinic acid;

2-(2-(2-(4-((4-((4-(3-(5-(tert-butyl)-2-methoxy-3-(methylsulfonamido)phenyl)ureido)-naphthalen-1-yl)oxy)pyridin-2-yl)amino)-2,6-dimethoxybenzamido)ethoxy)ethoxy)ethyl dihydrogen phosphate;

2-(4-((4-((4-(3-(5-(tert-butyl)-2-methoxy-3-(methylsulfonamido)phenyl)ureido)naphthalen-1-yl)oxy)pyridin-2-yl)amino)-2-methoxybenzamido)ethyl dihydrogen phosphate;

[4-[[4-[[4-[[5-tert-butyl-3-(methanesulfonamido)-2-methoxy-phenyl]carbamoylamino]-1-naphthyl]oxy]-2-pyridyl]amino]-2-(dimethylamino)phenyl]-methyl-phosphinic acid; and (4-((4-((4-(3-(5-(tert-butyl)-2-methoxy-3-(methylsulfonamido)phenyl)ureido)naphthalen-1-yl)oxy)pyridin-2-yl)amino)-2-methoxybenzyl)(methyl)phosphinic acid.

Specific embodiments of the above-described compounds of formula I, Ia or Ib that may be mentioned include those in which $R^4$:

(a) represents -$Q^4$-P(O)(O$R^9$)($R^7$) (e.g. —P(O)(O$R^9$)($R^7$)); or (b) does not represent -$Q^4$-P(O)(O$R^9$)($R^7$).

Thus, further embodiments of the invention that may be mentioned include those in which either (i) the compound of formula I, Ia or Ib represents, or (ii) the compound of formula I, Ia or Ib is as hereinbefore defined, provided that is does not represent a compound selected from the list comprising:

[4-[[4-[[4-[[5-tert-butyl-3-(methanesulfonamido)-2-methoxy-phenyl]carbamoylamino]-1-naphthyl]oxy]-2-pyridyl]amino]-2-methoxy-phenyl]phosphinic acid;

[4-[[4-[[4-[[5-tert-butyl-3-(methanesulfonamido)-2-methoxy-phenyl]carbamoylamino]-1-naphthyl]oxy]-2-pyridyl]amino]-2-methoxy-phenyl]phosphonic acid;

[4-[[4-[[4-[[5-tert-butyl-3-(methanesulfonamido)-2-methoxy-phenyl]carbamoylamino]-1-naphthyl]oxy]-2-pyridyl]amino]-2,6-dimethoxy-phenyl]-methyl-phosphinic acid;

ethyl (4-((4-((4-(3-(5-(tert-butyl)-2-methoxy-3-(methylsulfonamido)phenyl)ureido)naphthalen-1-yl)oxy)pyridin-2-yl)amino)-2-methoxyphenyl)(methyl)phosphinate;

(4-((4-((4-(3-(5-(tert-butyl)-2-methoxy-3-(methylsulfonamido)phenyl)ureido)naphthalen-1-yl)oxy)pyridin-2-yl)amino)-2-methoxyphenyl)(methyl)phosphinic acid;

diethyl (4-((4-((4-(3-(5-(tert-butyl)-2-methoxy-3-(methylsulfonamido)phenyl)ureido)-naphthalen-1-yl)oxy)pyridin-2-yl)amino)-2-methoxyphenyl)phosphonate;

[4-[[4-[[4-[[5-tert-butyl-3-(methanesulfonamido)-2-methoxy-phenyl]carbamoylamino]-1-naphthyl]oxy]-2-pyridyl]amino]-2-methoxy-phenyl]-ethoxy-phosphinic acid;

ethyl (4-((4-((4-(3-(5-(tert-butyl)-2-methoxy-3-(methylsulfonamido)phenyl)ureido)naphthalen-1-yl)oxy)pyridin-2-yl)amino)-2-methoxyphenyl)(ethyl)phosphinate;

[4-[[4-[[4-[[5-tert-butyl-3-(methanesulfonamido)-2-methoxy-phenyl]carbamoylamino]-1-naphthyl]oxy]-2-pyridyl]amino]-2-methoxy-phenyl]-ethyl-phosphinic acid;

ethyl (4-((4-((4-(3-(5-(tert-butyl)-2-methoxy-3-(methylsulfonamido)phenyl)ureido)-naphthalen-1-yl)oxy)pyridin-2-yl)amino)-2-methoxyphenyl)(phenyl)phosphinate;
[4-[[4-[[4-[[5-tert-butyl-3-(methanesulfonamido)-2-methoxy-phenyl]carbamoylamino]-1-naphthyl]oxy]-2-pyridyl]amino]-2-methoxy-phenyl]-phenyl-phosphinic acid;
ethyl (4-((4-((4-(3-(5-(tert-butyl)-2-methoxy-3-(N-methylmethylsulfonamido)phenyl)-ureido)naphthalen-1-yl)oxy)pyridin-2-yl)amino)-2-methoxyphenyl)(methyl)phosphinate;
[4-[[4-[[4-[[5-tert-butyl-2-methoxy-3-[methyl(methylsulfonyl)amino]phenyl]carbamoyl-amino]-1-naphthyl]oxy]-2-pyridyl]amino]-2-methoxy-phenyl]-methyl-phosphinic acid;
ethyl (4-((4-((4-(3-(5-(tert-butyl)-2-methoxy-3-(methylcarbamoyl)phenyl)ureido)-naphthalen-1-yl)oxy)pyridin-2-yl)amino)-2-methoxyphenyl)(methyl)phosphinate;
[4-[[4-[[4-[[5-tert-butyl-2-methoxy-3-(methylcarbamoyl)phenyl]carbamoylamino]-1-naphthyl]oxy]-2-pyridyl]amino]-2-methoxy-phenyl]-methyl-phosphinic acid;
ethyl (4-((4-((4-(3-(5-(tert-butyl)-2-methoxy-3-(methylsulfonamido)phenyl)ureido)naphthalen-1-yl)oxy)pyridin-2-yl)amino)-2-methylphenyl)(methyl)phosphinate;
[4-[[4-[[4-[[5-tert-butyl-3-(methanesulfonamido)-2-methoxy-phenyl]carbamoylamino]-1-naphthyl]oxy]-2-pyridyl]amino]-2-methyl-phenyl]-methyl-phosphinic acid;
ethyl (4-((4-((4-(3-(5-(tert-butyl)-2-methoxy-3-(methylsulfonamido)phenyl)ureido)-naphthalen-1-yl)oxy)pyridin-2-yl)amino)-2-ethoxyphenyl)(methyl)-phosphinate;
[4-[[4-[[4-[[5-tert-butyl-3-(methanesulfonamido)-2-methoxy-phenyl]carbamoylamino]-1-naphthyl]oxy]-2-pyridyl]amino]-2-ethoxy-phenyl]-methyl-phosphinic acid;
ethyl (4-((4-((4-(3-(5-(tert-butyl)-2-methoxy-3-(methylsulfonamido)phenyl)ureido)-naphthalen-1-yl)oxy)pyrimidin-2-yl)amino)-2-methoxyphenyl)(methyl)phosphinate;
[4-[[4-[[4-[[5-tert-butyl-3-(methanesulfonamido)-2-methoxy-phenyl]carbamoylamino]-1-naphthyl]oxy]pyrimidin-2-yl]amino]-2-methoxy-phenyl]-methyl-phosphinic acid;
ethyl (4-((4-((4-(3-(5-(tert-butyl)-2-methoxy-3-(methylsulfonamido)phenyl)ureido)-naphthalen-1-yl)oxy)pyridin-2-yl)amino)-2-chlorophenyl)(methyl)phosphinate;
[[4-[[4-[[4-[[5-tert-butyl-3-(methanesulfonamido)-2-methoxy-phenyl]carbamoylamino]-1-naphthyl]oxy]-2-pyridyl]amino]-2-chloro-phenyl]-methyl-phosphinic acid;
ethyl (4-((4-((4-(3-(5-(tert-butyl)-2-methoxy-3-(methylsulfonamido)phenyl)ureido)-naphthalen-1-yl)oxy)pyridin-2-yl)amino)-2-(dimethylamino)phenyl)(methyl)phosphinate;
[4-[[4-[[4-[[5-tert-butyl-3-(methanesulfonamido)-2-methoxy-phenyl]carbamoylamino]-1-naphthyl]oxy]-2-pyridyl]amino]-2-(dimethylamino)phenyl]-methyl-phosphinic acid;
ethyl 4-((4-((4-(3-(5-(tert-butyl)-2-methoxy-3-(methylsulfonamido)phenyl)ureido)-naphthalen-1-yl)oxy)pyridin-2-yl)amino)-2-methoxybenzyl(methyl)phosphinate;
(4-((4-((4-(3-(5-(tert-butyl)-2-methoxy-3-(methylsulfonamido)phenyl)ureido)naphthalen-1-yl)oxy)pyridin-2-yl)amino)-2-methoxybenzyl)(methyl)phosphinic acid; and
ethyl (4-((4-((4-(3-(3-(tert-butyl)-5-(methylsulfonamido)phenyl)ureido)naphthalen-1-yl)oxy)pyridin-2-yl)amino)-2-methoxyphenyl)(methyl)phosphinate;
[4-[[4-[[4-[[3-tert-butyl-5-(methanesulfonamido)phenyl]carbamoylamino]-1-naphthyl]oxy]-2-pyridyl]amino]-2-methoxy-phenyl]-methyl-phosphinic acid,
or a pharmaceutically acceptable salt thereof.

In particular, further embodiments of the invention that may be mentioned include those in which the salt of the compound of formula I, Ia or Ib either (i) represents; or (ii) does not represent a sodium or ammonium salt of (4-((4-((4-(3-(5-(tert-butyl)-2-methoxy-3-(methylsulfonamido)phenyl)ureido)naphthalen-1-yl)oxy)pyridin-2-yl)amino)-2-methoxyphenyl)(methyl)phosphinic acid.

Still further embodiments of the invention that may be mentioned include those in which either
(i) the compound of formula I, Ia or Ib represents, or
(ii) the compound of formula I, Ia or Ib is as hereinbefore defined, provided that is does not represent
4-((4-((4-(3-(5-(tert-butyl)-2-methoxy-3-(methylsulfonamido)phenyl)ureido)naphthalen-1-yl)oxy)pyridin-2-yl)amino)-2-methoxybenzoic acid,
or a pharmaceutically acceptable salt thereof (e.g. a hydrochloride, sodium, calcium, magnesium or ammonium salt thereof).

The compound 4-((4-((4-(3-(5-(tert-butyl)-2-methoxy-3-(methylsulfonamido)phenyl)ureido)-naphthalen-1-yl)oxy)pyridin-2-yl)amino)-2-methoxybenzoic acid may also be known by the chemical name 4-[[4-[[4-[[5-tert-butyl-3-(methanesulfonamido)-2-methoxyphenyl]-carbamoylamino]-1-naphthyl]oxy]-2-pyridyl]amino]-2-methoxy-benzoic acid.

References herein to a compound of the invention (a compound of formula I, Ia or Ib) are intended to include references to the compound and to all pharmaceutically acceptable salts, solvates, isotopic derivatives and/or tautomers of said compound, unless the context specifically indicates otherwise. In this respect, solvates that may be mentioned include hydrates.

The compounds of the invention (compounds of formula I, Ia or Ib) are p38 MAP kinase inhibitors (especially of the alpha subtype) and are therefore useful in medicine, in particular for the treatment of inflammatory diseases. Further aspects of the invention that may be mentioned therefore include the following.

(a) A pharmaceutical formulation comprising a compound of formula I, Ia or Ib, as hereinbefore defined, or pharmaceutically acceptable salt thereof, in admixture with a pharmaceutically acceptable adjuvant, diluent or carrier.

(b) A combination product comprising
(A) a compound of formula I, Ia or Ib, as hereinbefore defined, or pharmaceutically acceptable salt thereof, and
(B) another therapeutic agent,
wherein each of components (A) and (B) is formulated in admixture with a pharmaceutically-acceptable adjuvant, diluent or carrier.

In this aspect of the invention, the combination product may be either a single (combination) pharmaceutical formulation or a kit-of-parts.

Thus, this aspect of the invention encompasses a pharmaceutical formulation including a compound of formula I, Ia or Ib, as hereinbefore defined, or pharmaceutically acceptable salt thereof, and another therapeutic agent, in admixture with a pharmaceutically acceptable adjuvant, diluent or carrier (which formulation is hereinafter referred to as a "combined preparation").

It also encompasses a kit of parts comprising components:
(i) a pharmaceutical formulation including a compound of formula I, Ia or Ib, as hereinbefore defined, or pharmaceutically acceptable salt thereof, in admixture with a pharmaceutically acceptable adjuvant, diluent or carrier; and (ii) a pharmaceutical formulation including another therapeutic agent, in admixture with a pharmaceutically-acceptable adjuvant, diluent or carrier, which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier.

(c) A process for preparing the pharmaceutical formulation of aspect (a) above, said process comprising the step of admixing the compound of formula I, Ia or Ib, as hereinbefore defined, or pharmaceutically acceptable salt thereof, with a pharmaceutically acceptable adjuvant, diluent or carrier.

Embodiments of this aspect of the invention that may be mentioned include those in which the pharmaceutically acceptable adjuvant, diluent or carrier is a topically acceptable adjuvant, diluent or carrier (and/or wherein the process is for preparing a topical pharmaceutical formulation, i.e. a pharmaceutical formulation that is adapted for topical administration).

(d) A compound of formula I, Ia or Ib, as hereinbefore defined, or pharmaceutically acceptable salt thereof, for use in medicine (or for use as a medicament or as a pharmaceutical).

(e) A compound of formula I, Ia or Ib, as hereinbefore defined, or pharmaceutically acceptable salt thereof, or a pharmaceutical formulation or combination product as defined in connection with aspect (a) or (b) of the invention, for use in the treatment or prevention of an inflammatory disease.

(f) The use of
a compound of formula I, Ia or Ib, as hereinbefore defined, or pharmaceutically acceptable salt thereof, or
a pharmaceutical formulation or combination product as defined in connection with aspect (a) or (b) of the invention, for the preparation of a medicament for the treatment or prevention of an inflammatory disease.

(g) A method of treating or preventing an inflammatory disease, said method comprising administering to a subject an effective amount of
a compound of formula I, Ia or Ib, as hereinbefore defined, or pharmaceutically acceptable salt thereof, or
a pharmaceutical formulation or combination product as defined in connection with aspect (a) or (b) of the invention.

(h) A method of sensitizing a subject to the anti-inflammatory effects of a corticosteroid, said method comprising administering to the subject an effective amount of
a compound of formula I, Ia or Ib, as hereinbefore defined, or pharmaceutically acceptable salt thereof, or
a pharmaceutical formulation or combination product as defined in connection with aspect (a) or (b) of the invention.

Embodiments of this aspect of the invention that may be mentioned include those in which the subject is one who has become refractory to the anti-inflammatory effects of a corticosteroid.

References herein to "preventing an inflammatory disease" include references to preventing (or reducing the likelihood of) the recurrence of an inflammatory disease in a subject who has previously suffered from such a disease (e.g. a subject who has previously received treatment for that disease, for example treatment according to the method described in (g) above).

Thus, still further aspects of the invention that may be mentioned include the following.

(i) A compound of formula I, Ia or Ib, as hereinbefore defined, or pharmaceutically acceptable salt thereof, or a pharmaceutical formulation or combination product as defined in connection with aspect (a) or (b) of the invention, for use in reducing the likelihood of the recurrence of an inflammatory disease in a subject who has previously received treatment for that disease (e.g. treatment with a compound of formula I, Ia or Ib, as hereinbefore defined, or pharmaceutically acceptable salt thereof, or a pharmaceutical formulation or combination product as defined in connection with aspect (a) or (b) of the invention).

(j) The use of
a compound of formula I, Ia or Ib, as hereinbefore defined, or pharmaceutically acceptable salt thereof, or
a pharmaceutical formulation or combination product as defined in connection with aspect (a) or (b) of the invention,
for the preparation of a medicament for reducing the likelihood of the recurrence of an inflammatory disease in a subject who has previously received treatment for that disease (e.g. treatment with a compound of formula I, Ia or Ib, as hereinbefore defined, or pharmaceutically acceptable salt thereof, or a pharmaceutical formulation or combination product as defined in connection with aspect (a) or (b) of the invention).

(k) A method of reducing the likelihood of the recurrence of an inflammatory disease in a subject who has previously received treatment for that disease (e.g. treatment with a compound of formula I, Ia or Ib, as hereinbefore defined, or pharmaceutically acceptable salt thereof, or a pharmaceutical formulation or combination product as defined in connection with aspect (a) or (b) of the invention), said method comprising administering to said subject an effective amount of
a compound of formula I, Ia or Ib, as hereinbefore defined, or pharmaceutically acceptable salt thereof, or
a pharmaceutical formulation or combination product as defined in connection with aspect (a) or (b) of the invention.

Formulations

In relation to aspects (a) and (b) above, diluents and carriers that may be mentioned include those suitable for parenteral, oral, topical, mucosal and rectal administration.

The pharmaceutical formulations and combination products of aspects (a) and (b) above may be prepared e.g. for parenteral, subcutaneous, intramuscular, intravenous, intra-articular, intravitreous, periocular, retrobulbar, subconjunctival, sub-Tenon, topical ocular or peri-articular administration, particularly in the form of liquid solutions, emulsions or suspensions; for oral administration, particularly in the form of tablets or capsules, and especially involving technologies aimed at furnishing colon-targeted drug release (Patel, M. M. *Expert Opin. Drug Deliv.* 2011, 8 (10), 1247-1258); for topical e.g. pulmonary or intranasal administration, particularly in the form of powders, nasal drops or aerosols and transdermal administration; for topical ocular administration, particularly in the form of solutions, emulsions, suspensions, ointments, implants/inserts, gels, jellies or liposomal microparticle formulations (Ghate, D.; Edelhauser, H. F. Expert *Opin. Drug Deliv.* 2006, 3 (2), 275-287);

for ocular administration, particularly in the form of biodegradable and non-biodegradable implants, liposomes and nanoparticles (Thrimawithana, T. R. et al. *Drug Discov. Today* 2011, 16 (5/6), 270-277); for mucosal administration e.g. to buccal, sublingual or vaginal mucosa, and for rectal administration e.g. in the form of a suppository or enema.

The pharmaceutical formulations and combination products of aspects (a) and (b) above may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered sprays. For buccal administration, typical excipients include sugars, calcium stearate, magnesium stearate, pregelatinised starch, and the like.

Pharmaceutical formulations and combination products suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrrolidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules. Such two-piece hard shell capsules may be made from, for example, gelatin or hydroxylpropyl methylcellulose (HPMC).

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

A compound of the invention may be administered topically (e.g. to the lung, eye or intestines). Thus, embodiments of aspects (a) and (b) above that may be mentioned include pharmaceutical formulations and combination products that are adapted for topical administration. Such formulations include those in which the excipients (including any adjuvant, diluent and/or carrier) are topically acceptable.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoroethane (propellant 114), and dichlorodifluoromethane (propellant 12).

Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a non-pressurised formulation such as an aqueous solution or suspension. This may be administered by means of a nebuliser e.g. one that can be hand-held and portable or for home or hospital use (i.e. non-portable). The formulation may comprise excipients such as water, buffers, tonicity adjusting agents, pH adjusting agents, surfactants and co-solvents. Suspension liquid and aerosol formulations (whether pressurised or unpressurised) will typically contain the compound of the invention in finely divided form, for example with a $D_{50}$ of 0.5-10 μm e.g. around 1-5 μm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

Topical administration to the lung may also be achieved by use of a dry-powder formulation. A dry powder formulation will contain the compound of the disclosure in finely divided form, typically with a mass mean aerodynamic diameter (MMAD) of 1-10 μm or a $D_{50}$ of 0.5-10 μm e.g. around 1-5 μm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of large particle size e.g. an MMAD of 50 μm or more, e.g. 100 μm or more or a $D_{50}$ of 40-150 μm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac® 70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients such as sodium stearate, calcium stearate or magnesium stearate.

A dry powder formulation is typically delivered using a dry powder inhaler (DPI) device. Examples of dry powder delivery systems include SPINHALER, DISKHALER, TURBOHALER, DISKUS and CLICKHALER. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

In one embodiment a compound of the present invention is provided in a micronized dry powder formulation, for example further comprising lactose of a suitable grade optionally together with magnesium stearate, filled into a single dose device such as AEROLISER or filled into a multi dose device such as DISKUS.

The compounds of the present invention may also be administered rectally, for example in the form of suppositories or enemas, which include aqueous or oily solutions as well as suspensions and emulsions. Such compositions are prepared following standard procedures, well known by those skilled in the art. For example, suppositories can be prepared by mixing the active ingredient with a conventional suppository base such as cocoa butter or other glycerides, e.g. Suppocire. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the inhibitor will be about 0.0001 to less than 4.0% (w/w).

Preferably, for topical ocular administration, the compositions administered according to the present invention will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

The compositions administered according to the present invention may also include various other ingredients, including, but not limited to, tonicity agents, buffers, surfactants, stabilizing polymer, preservatives, co-solvents and viscosity building agents. Preferred pharmaceutical compositions of the present invention include the inhibitor with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars, such as dextrose, fructose, galactose, and/or simply polyols, such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will present in the range of 2 to 5% w/w (e.g. 2 to 4% w/w). Preferred tonicity agents of the invention include the simple sugars or the sugar alcohols, such as D-mannitol.

An appropriate buffer system (e.g. sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7, or a target pH of 6.5 to 7.6.

Surfactants may optionally be employed to deliver higher concentrations of inhibitor. The surfactants function to solubilise the inhibitor and stabilise colloid dispersion, such as micellar solution, microemulsion, emulsion and suspension. Examples of surfactants which may optionally be used include polysorbate, poloxamer, polyoxyl 40 stearate, polyoxyl castor oil, tyloxapol, triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

For example, a formulation of 4-((4-((4-(3-(5-(tert-butyl)-2-methoxy-3-(methylsulfonamido)-phenyl)ureido)naphthalen-1-yl)oxy)pyridin-2-yl)amino)-2-methoxybenzoic acid, or pharmaceutically acceptable salt thereof, for topical ocular administration may comprise:
(a) water;
(b) a surfactant (e.g. polyoxyl 40 stearate);
(c) a tonicity agent (e.g. mannitol); and
(d) an appropriate buffer system (e.g. a phosphate buffer containing a mixture of monobasic dihydrogen phosphate and dibasic monohydrogen phosphate) chosen to maintain a target pH within the range from 6.5 to 8.

In such topical ocular formulations, one or more (e.g. all) of the following may apply:
(i) 4-((4-((4-(3-(5-(tert-butyl)-2-methoxy-3-(methylsulfonamido)-phenyl)ureido)-naphthalen-1-yl)oxy)pyridin-2-yl)amino)-2-methoxybenzoic acid is present at a concentration in the range from 0.001 to 20 mg/mL (e.g. from 0.01 to 10 mg/mL, 0.1 to 2 mg/mL or, particularly, 1 mg/mL);
(ii) the surfactant (e.g. polyoxyl 40 stearate) is present at from 1 to 10% w/w (e.g. from 2 to 5% w/w, such as from 2.5 to 4% w/w or, particularly, 3% w/w);
(iii) the tonicity agent (e.g. mannitol) is present at from 1 to 15% w/w (e.g. from 2 to 10% w/w, such as from 3 to 6% w/w or, particularly, 4.5% w/w);

(iv) the buffer system used as a component of the formulation is an aqueous phosphate buffer (e.g. a 10 mM aqueous phosphate buffer) chosen to maintain a target pH within the range from 6.5 to 8.0 (e.g. within the range from 7.0 to 7.8 or, particularly, from 7.2 to 7.6).

Additional agents that may be added to the ophthalmic compositions of the present invention are demulcents which function as a stabilising polymer. The stabilizing polymer should be an ionic/charged example with precedence for topical ocular use, more specifically, a polymer that carries negative charge on its surface that can exhibit a zeta-potential of (−) 10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers, polycarbophil and Pemulen®, specifically Carbomer 974p (polyacrylic acid), at 0.1-0.5% w/w.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family, vinyl polymers and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The medical practitioner, or other skilled person, will be able to determine a suitable dosage for the compounds of the invention, and hence the amount of the compound of the invention that should be included in any particular pharmaceutical formulation (whether in unit dosage form or otherwise).

Embodiments of the invention that may be mentioned in connection with the combination products described at (b) above include those in which the other therapeutic agent is one or more therapeutic agents that are known by those skilled in the art to be suitable for treating inflammatory diseases (e.g. the specific diseases mentioned below).

For example, for the treatment of respiratory disorders (such as COPD or asthma), the other therapeutic agent is one or more agents selected from the list comprising:
  steroids (e.g. budesonide, beclomethasone dipropionate, fluticasone propionate, mometasone furoate, fluticasone furoate; a further example is ciclesonide);
  beta agonists, particularly beta2 agonists (e.g. terbutaline, salbutamol, salmeterol, formoterol; further examples are vilanterol, olodaterol, reproterol and fenoterol); and
  xanthines (e.g. theophylline).

For example, for the treatment of respiratory disorders (such as COPD or asthma), the other therapeutic agent is one or more agents selected from the list comprising:
  muscarinic antagonists (e.g. tiotropium, umeclidinium, glycopyrronium, aclidinium and daratropium, any of these for example as the bromide salt); and
  phosphodiesterase inhibitors.

Further, for the treatment of gastrointestinal disorders (such as Crohn's disease or ulcerative colitis), the other therapeutic agent may be, for example, one or more agents selected from the list comprising:
  5-aminosalicylic acid, or a prodrug thereof (such as sulfasalazine, olsalazine or balsalazide);
  corticosteroids (e.g. prednisolone, methylprednisolone, or budesonide);
  immunosuppressants (e.g. cyclosporin, tacrolimus, methotrexate, azathioprine or 6-mercaptopurine);
  anti-TNFα antibodies (e.g. infliximab, adalimumab, certolizumab pegol or golimumab); anti-IL12/IL23 antibodies (e.g. ustekinumab) or small molecule IL12/IL23 inhibitors (e.g. apilimod);
  anti-α4β7 antibodies (e.g. vedolizumab);
  toll-like receptor (TLR) blockers (e.g. BL-7040; Avecia (Cambridge, UK));
  MAdCAM-1 blockers (e.g. PF-00547659);
  antibodies against the cell adhesion molecule a4-integrin (e.g. natalizumab);
  antibodies against the IL2 receptor a subunit (e.g. daclizumab or basiliximab); anti-Smad7 antibodies (e.g. mongersen (GED0301; all-P-ambo-2'-deoxy-P-thioguanylyl-(3'→5')-P-thiothymidylyl-(3'→5')-2'-deoxy-5-methyl-P-thiocytidylyl-(3'→5')-2'-deoxy-P-thioguanylyl-(3'→5')-2'-deoxy-P-thiocytidylyl-(3'→5')-2'-deoxy-P-thiocytidylyl-(3'→5')-2'-deoxy-P-thiocytidylyl-(3'→5')-2'-deoxy-P-thiocytidylyl-(3'→5')-P-thiothymidylyl-(3'→5')-P-thiothymidylyl-(3'→5')-2'-deoxy-Pthiocytidylyl-(3'→5')-P-thiothymidylyl-(3'→5')-2'-deoxy-P-thiocytidylyl-(3'→5')-2'-deoxy-P-thiocytidylyl-(3'→5')-2'-deoxy-P-thiocytidylyl-(3'→5')-2'-deoxy-5-methyl-P-thiocytidylyl-(3'→5')-2'-deoxy-Pthioguanylyl-(3'→5')-2'-deoxy-P-thiocytidylyl-(3'→5')-2'-deoxy-Pthioadenylyl-(3'→5')-2'-deoxy-P-thioguanylyl-(3'→5')-2'-deoxycytidine));
  sphingosine 1-phosphate receptor 1 (S1P1) modulators (e.g. ozanimod ((S)-5-(3-(1-((2-hydroxyethyl)amino)-2,3-dihydro-1H-inden-4-yl)-1,2,4-oxadiazol-5-yl)-2-isopropoxybenzonitrile), amiselimod (MT1303; 2-amino-2-{2-[4-(heptyloxy)-3-(trifluoromethyl)phenyl]ethyl}propane-1,3-diol) or APD334 (2-[7-[4-cyclopentyl-3-(trifluoromethyl)benzyloxy]-1,2,3,4-tetrahydrocyclopenta[b]indol-3(R)-yl]acetic acid));
  JAK inhibitors (e.g. tofacitinib, baricitinib (1-(ethylsulfonyl)-3-[4-(7H-pyrrolo[2,3-d]pyrimidin-4-yl)-1H-pyrazol-1-yl]-3-azetidineacetonitrile), filgotinib (N-[5-[4-[(1,1-dioxo-1,4-thiazinan-4-yl)methyl]phenyl]-[1,2,4]triazolo[1,5-a]pyridin-2-yl]cyclopropanecarboxamide), peficitinib (4-(((1R,2r,3S,5s,7s)-5-hydroxyadamantan-2-yl)amino)-1H-pyrrolo[2,3-b]pyridine-5-carboxamide) or R348 (see, for example, US 2014/0206708));
  STAT3 inhibitors (e.g. TAK-114; (3E)-1-methyl-3-(2-oxo-1H-indol-3-ylidene)indol-2-one);
  receptor-interacting protein-1 (RIP1) kinase inhibitors (e.g. GSK2982772);
  Syk inhibitors and prodrugs thereof (e.g. fostamatinib and R-406);
  Phosphodiesterase-4 inhibitors (e.g. tetomilast);
  HMPL-004;
  probiotics;
  microbiome modulators (e.g. SGM1019);
  Dersalazine;
  semapimod/CPSI-2364; and
  protein kinase C inhibitors (e.g. AEB-071)

(e.g. for the treatment of gastrointestinal disorders (such as Crohn's disease or ulcerative colitis), the other therapeutic agent may be, for example, one or more agents selected from the list comprising:

- 5-aminosalicylic acid, or a prodrug thereof (such as sulfasalazine, olsalazine or balsalazide);
- corticosteroids (e.g. prednisolone, methylprednisolone, or budesonide);
- immunosuppressants (e.g. cyclosporin, tacrolimus, methotrexate, azathioprine or 6-mercaptopurine);
- anti-TNFα antibodies (e.g. infliximab, adalimumab, certolizumab pegol or golimumab);
- anti-IL12/IL23 antibodies (e.g. ustekinumab) or small molecule IL12/IL23 inhibitors (e.g. apilimod);
- anti-α4β7 antibodies (e.g. vedolizumab);
- MAdCAM-1 blockers (e.g. PF-00547659);
- antibodies against the cell adhesion molecule a4-integrin (e.g. natalizumab);
- antibodies against the IL2 receptor a subunit (e.g. daclizumab or basiliximab);
- JAK3 inhibitors (e.g. tofacitinib or R348);
- Syk inhibitors and prodrugs thereof (e.g. fostamatinib and R-406);
- Phosphodiesterase-4 inhibitors (e.g. tetomilast);
- HMPL-004;
- probiotics;
- Dersalazine;
- semapimod/CPSI-2364; and
- protein kinase C inhibitors (e.g. AEB-071)).

For the treatment of eye disorders (such as uveitis and keratoconjunctivitis sicca (dry eye)), the other therapeutic agent may be, for example, one or more agents selected from the list comprising:

- corticosteroids (e.g. dexamethasone, prednisolone, triamcinolone acetonide, difluprednate or fluocinolone acetonide);
- glucocorticoid agonists (e.g. mapracorat);
- immunosuppressants (e.g. cyclosporin, voclosporin, azathioprine, methotrexate, mycophenolate mofetil or tacrolimus);
- anti-TNFα antibodies (e.g. infliximab, adalimumab, certolizumab pegol, ESBA-105 or golimumab);
- anti-IL-17A antibodies (e.g. secukinumab);
- mTOR inhibitors (e.g. sirolimus);
- VGX-1027;
- adenosine A3 receptor agonists (e.g. CF-101);
- lifitegrast;
- IL1 blockers (e.g. EBI-005; Hou et al. *PNAS* 2013, 110(10), 3913-3918); RGN-259 (Thymosin β4);
- SI-614;
- OTX-101;
- JNK inhibitors (e.g. XG-104);
- MAP kinase signalling inhibitors (e.g. DA-6034; {[2-(3,4-dimethoxyphenyl)-5-methoxy-4-oxochromen-7-yl]oxy}acetic acid);
- mucin stimulators (e.g. rebamipide; 2-[(4-chlorobenzoyl)amino]-3-(2-oxo-1H-quinolin-4-yl)propanoic acid);
- MIM-D3 (Tavilermide; see, for example, US 2013/0345395);
- JAK inhibitors (e.g. tofacitinib, baricitinib (1-(ethylsulfonyl)-3-[4-(7H-pyrrolo[2,3-d]pyrimidin-4-yl)-1H-pyrazol-1-yl]-3-azetidineacetonitrile), filgotinib (N-[5-[4-[(1,1-dioxo-1,4-thiazinan-4-yl)methyl]phenyl]-[1,2,4]triazolo[1,5-a]pyridin-2-yl]cyclopropanecarboxamide), peficitinib (4-(((1R,2r,3S,5s,7s)-5-hydroxyadamantan-2-yl)amino)-1H-pyrrolo[2,3-b]pyridine-5-carboxamide) or R348 (see, for example, US 2014/0206708)); and
- protein kinase C inhibitors (e.g. AEB-071).

(e.g. for the treatment of eye disorders (such as uveitis and keratoconjunctivitis sicca (dry eye)), the other therapeutic agent may be, for example, one or more agents selected from the list comprising:

- corticosteroids (e.g. dexamethasone, prednisolone, triamcinolone acetonide, difluprednate or fluocinolone acetonide);
- glucocorticoid agonists (e.g. mapracorat);
- immunosuppressants (e.g. cyclosporin, voclosporin, azathioprine, methotrexate, mycophenolate mofetil or tacrolimus);
- anti-TNFα antibodies (e.g. infliximab, adalimumab, certolizumab pegol, ESBA-105 or golimumab);
- anti-IL-17A antibodies (e.g. secukinumab);
- mTOR inhibitors (e.g. sirolimus);
- VGX-1027;
- adenosine A3 receptor agonists (e.g. CF-101);
- lifitegrast;
- JAK3 inhibitors (e.g. tofacitinib or R348); and
- protein kinase C inhibitors (e.g. AEB-071)).

In particular embodiments, for the treatment of eye disorders (such as uveitis and keratoconjunctivitis sicca (dry eye)), the other therapeutic agent may be, for example, one or more agents selected from the list comprising:

- corticosteroids (e.g. dexamethasone, prednisolone, triamcinolone acetonide, difluprednate or fluocinolone acetonide);
- immunosuppressants (e.g. cyclosporin, voclosporin, azathioprine, methotrexate, mycophenolate mofetil or tacrolimus);
- anti-TNFα antibodies (e.g. infliximab, adalimumab, certolizumab pegol, ESBA-105 or golimumab);
- anti-IL-17A antibodies (e.g. secukinumab);
- mTOR inhibitors (e.g. sirolimus);
- VGX-1027;
- JAK inhibitors (e.g. tofacitinib, baricitinib, filgotinib, peficitinib or R348) (e.g. JAK3 inhibitors such as tofacitinib or R348); and
- protein kinase C inhibitors (e.g. AEB-071).

Medical Uses

The compounds of the invention may be used as monotherapies for inflammatory diseases, or in combination therapies for such diseases.

Thus, embodiments of aspects (e) to (g) above that may be mentioned include those in which the compound of formula I, Ia or Ib (or pharmaceutically acceptable salt thereof) is the sole pharmacologically active ingredient utilised in the treatment.

However, in other embodiments of aspects (e) to (g) above, the compound of formula I, Ia or Ib (or pharmaceutically acceptable salt thereof) is administered to a subject who is also administered one or more other therapeutic agents (e.g. wherein the one or more other therapeutic agents are as defined above in connection with combination products).

When used herein, the term "inflammatory disease" specifically includes references to any one or more of the following:

(i) lung diseases or disorders having an inflammatory component, such as cystic fibrosis, pulmonary hypertension, lung sarcoidosis, idiopathic pulmonary fibrosis or, particularly, COPD (including chronic bronchitis and emphysema), asthma or pediatric asthma;

(ii) skin diseases or disorders having an inflammatory component, such as atopic dermatitis, allergic dermatitis, contact dermatitis or psoriasis;

(iii) nasal diseases or disorders having an inflammatory component, such as allergic rhinitis, rhinitis or sinusitis;

(iv) eye diseases or disorders having an inflammatory component, such as conjunctivitis, allergic conjunctivitis, glaucoma, diabetic retinopathy, macular oedema (including diabetic macular oedema), central retinal vein occlusion (CRVO), dry and/or wet age related macular degeneration (AMD), post-operative cataract inflammation, or, particularly, keratoconjunctivitis sicca (dry eye, also known as xerophthalmia), uveitis (including posterior, anterior and pan uveitis), corneal graft and limbal cell transplant rejection; and (v) gastrointestinal diseases or disorders having an inflammatory component, such as gluten sensitive enteropathy (coeliac disease), eosinophilic esophagitis, intestinal graft versus host disease or, particularly, Crohn's disease or ulcerative colitis.

References herein to diseases having an inflammatory component include references to diseases that involve inflammation, whether or not there are other (non-inflammatory) symptoms or consequences of the disease.

According to a further aspect of the invention there is provided a process for the preparation of a compound of formula I (e.g. a compound of formula Ib in which $R^{1A}$ and $R^{5a}$ both represent methoxy, $R^{1B}$ represents —NHS(O)$_2$CH$_3$, $R^{1D}$ represents tert-butyl, $X^1$ and $X^2$ both represent CH, $R^{5b}$ represents H and $R^4$ represents —CO$_2$H) which process comprises:

(a) reaction of a compound of formula II

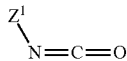

II with a compound of formula III,

III wherein one of $Z^1$ and $Z^2$ is a structural fragment of formula IV

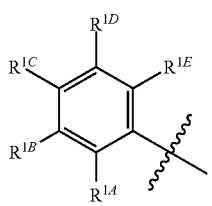

IV and the other of $Z^1$ and $Z^2$ is a structural fragment of formula V

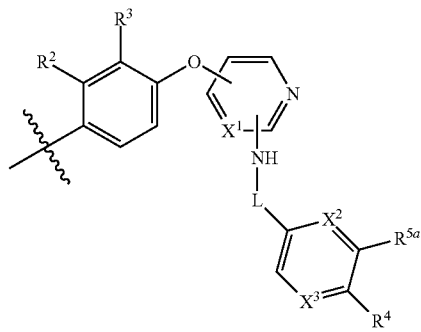

V where $R^{1A}$ to $R^{1E}$, $R^2$ to $R^4$, $R^{5a}$, L and $X^1$ to $X^3$ are as hereinbefore defined (e.g. $X^3$ represents $CR^{5b}$ and $R^{1A}$ to $R^{1E}$, $R^2$ to $R^4$, $R^{5a}$, $R^{5b}$, L and $X^2$ are as hereinbefore defined), for example under conditions known to those skilled in the art, for example at a temperature from ambient (e.g. 15 to 30° C.) to about 110° C. in the presence of a suitable organic solvent (e.g. a polar aprotic solvent such as DMF, THF, 1,4-dioxane, or mixtures thereof);

(b) reaction of a compound of formula IIa,

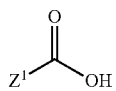

IIa wherein $Z^1$ is as defined above, with a suitable azide-forming agent (i.e. a suitable source of a leaving group and activated azide ion, such as diphenyl phosphorazidate; see, for example, *Tetrahedron* 1974, 30, 2151-2157) under conditions known to those skilled in the art, such as at sub-ambient to ambient temperature (e.g. from an initial temperature of about −5 to 5° C. to ambient temperature post-reaction) in the presence of an amine base (e.g. triethylamine or a sterically hindered base such as N,N-diisopropylethylamine) and a suitable organic solvent (e.g. a polar aprotic solvent such as DMF, THF, 1,4-dioxane, or mixtures thereof), which reaction is followed, without isolation, by thermal rearrangement (e.g. under heating) of the intermediate acyl azide (of formula $Z^1$—C(O)—N$_3$) e.g. at ambient temperature (such as from 15 to 30° C.) to provide, in situ, a compound of formula II, which compound is then reacted with a compound of formula III, as defined above, to provide the compound of formula I;

(c) reaction of a compound of formula IIb,

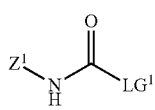

IIb wherein LG$^1$ represents a suitable leaving group (e.g. imidazolyl, chloro, or aryloxy, such as phenoxy) and $Z^1$ is as defined above, with a compound of formula III, as defined above, for example under conditions known to those skilled in the art, such as at ambient temperature (e.g. from ambient to 80° C.), optionally in the presence of an amine base (e.g. triethylamine or a sterically hindered base like N,N-diisopropylethylamine) and a suitable organic solvent (e.g. an aprotic solvent, such as dichloromethane or an ester such as isopropyl acetate);

(d) reaction of a compound of formula VI,

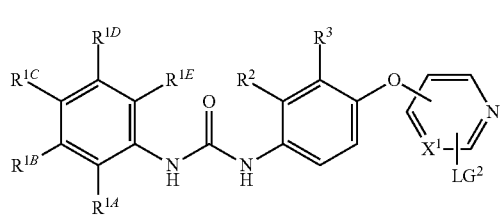

VI wherein LG$^2$ represents a suitable leaving group (e.g. a halo group such as chloro or bromo) and R$^{1A}$ to R$^{1E}$, R$^2$, R$^3$ and X$^1$ are as hereinbefore defined with a compound of formula VII,

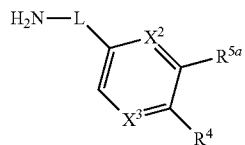

VII wherein R$^4$, R$^{5a}$, L, X$^2$ and X$^3$ are as hereinbefore defined (e.g. X$^3$ represents CR$^{5b}$ and R$^4$, R$^{5a}$, R$^{5b}$, L and X$^2$ are as hereinbefore defined), for example under conditions known to those skilled in the art (e.g. as described in *J. Am. Chem. Soc.* 2011, 133, 15686-15696), such as at elevated temperature (e.g. from 50 to 110° C.) in the presence of a suitable organic solvent (e.g. a polar aprotic solvent such as DMF, THF, 1,4-dioxane, or mixtures thereof) and, optionally, an acidic catalyst (e.g. a sulfonic acid such as para-toluenesulfonic acid);

(e) for compounds of formula I in which R$^4$ represents
—S(O)$_{1-2}$—[C(R$^{6c}$)(R$^{6d}$)—(CH$_2$)$_{0-1}$CH$_2$—Z]$_{1-12}$—CH$_2$(CH$_2$)$_{0-1}$CH$_2$—R$^{6a}$,
—S(O)$_{1-2}$—C(R$^{6c}$)(R$^{6d}$)—[C$_{1-5}$ alkylene]-R$^{6a}$,
—S(O)$_{1-2}$R$^{6b}$,
which C$_{1-5}$ alkylene group is optionally substituted as described above,
oxidation of a corresponding compound of formula I in which, respectively, R$^4$ represents
—S—[C(R$^{6c}$)(R$^{6d}$)—(CH$_2$)$_{0-1}$CH$_2$—Z]$_{1-12}$—CH$_2$(CH$_2$)$_{0-1}$CH$_2$—R$^{6a}$,
—S—C(R$^{6c}$)(R$^{6d}$)—[C$_{1-5}$ alkylene]-R$^{6a}$,
—S—R$^{6b}$,
which C$_{1-5}$ alkylene group is optionally substituted as described above,
wherein R$^{6a}$ to R$^{6d}$ are as hereinbefore defined, for example under conditions known to those skilled in the art (e.g. at 0 to 25° C. in the presence of a suitable solvent (such as dichloromethane, methanol or a mixture thereof) and a peracid, such as meta-chloroperbenzoic acid);

(f) for compounds of formula I in which R$^4$ represents
-Q$^{1a}$-NR$^8$—[C(R$^{6c}$)(R$^{6d}$)—(CH$_2$)$_{0-1}$CH$_2$—Z]$_{1-12}$—CH$_2$(CH$_2$)$_{0-1}$CH$_2$—R$^{6a}$,
-Q$^{2a}$-NR$^8$—C(R$^{6c}$)(R$^{6d}$)—[C$_{1-5}$ alkylene]-R$^{6a}$ or
-Q$^{3a}$-NR$^8$—[C$_{1-4}$ alkylene]$_{0-1}$-Het$^3$, which C$_{1-5}$ alkylene and Het$^3$ groups are optionally substituted as described above, and wherein Q$^{1a}$, Q$^{2a}$ and Q$^{3a}$ represent C(O) or S(O)$_2$, reaction of a compound of formula VIIa,

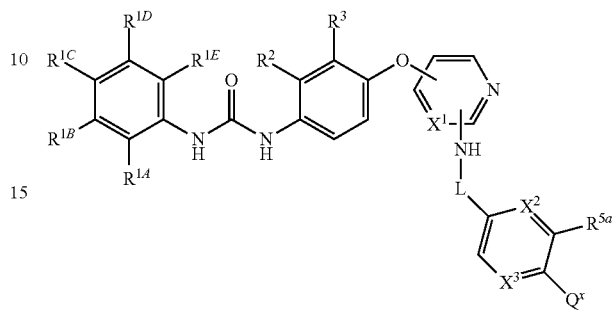

VIIa wherein Q$^x$ represents —[C$_{1-4}$ alkylene]$_{0-1}$C(O)OR$^{4'}$ or —S(O)$_2$-LG$^2$ (e.g. Q$^x$ represents —C(O)OR$^{4'}$ or —S(O)$_2$-LG$^2$), R$^{4'}$ represents H or a C$_{1-4}$ alkyl group (e.g. a C$_4$ alkyl group or a C$_{1-3}$ alkyl group, such as methyl) and R$^{1A}$ to R$^{1E}$, R$^2$, R$^3$, R$^{5a}$, L, X$^1$ to X$^3$ and LG$^2$ are as hereinbefore defined (e.g. X$^3$ represents CR$^{5b}$ and R$^{1A}$ to R$^{1E}$, R$^2$, R$^3$, R$^{5a}$, R$^{5b}$, L, X$^1$, X$^2$ and LG$^2$ are as hereinbefore defined), with a compound of formula VIIb, VIIc or VIId, HNR$^8$—[C(R$^{6c}$)(R$^{6d}$)—(CH$_2$)$_{0-1}$CH$_2$—Z]$_{1-12}$—CH$_2$(CH$_2$)$_{0-1}$CH$_2$—R$^{6a}$  VIIb HNR$^8$—C(R$^{6c}$)(R$^{6d}$)—[C$_{1-5}$alkylene]-R$^{6a1}$ or  VIIc HNR$^8$—[C$_{1-4}$alkylene]$_{0-1}$-Het$^3$  VIId which C$_{1-5}$ alkylene and Het$^3$ groups are optionally substituted as described above, wherein R$^{6c}$, R$^{6d}$, R$^8$ and Het$^3$ are as hereinbefore defined, and R$^{6a1}$ takes the same definition as R$^{6a}$ above, except that CO$_2$H is only present in protected form (e.g. as C(O)O—C$_{1-4}$ alkyl), for example under conditions known to those skilled in the art, such as (i) when R$^{4'}$ represents a C$_{1-3}$ alkyl group, reaction at ambient temperature in the presence of a suitable Lewis acidic catalyst (e.g. a trialkyl aluminium reagent such as trimethylaluminium) and an aprotic organic solvent (e.g. THF) or (ii) when R$^{4'}$ represents H, reaction in the presence of a tertiary amine base (e.g. a trialkylamine such as triethylamine or diisopropylethylamine or a cyclic amine such as N-methylpyrrolidine or N-methylmorpholine), an amide (peptide) coupling reagent (e.g. T3P, HATU, CDI, BOP, PyBOP, HOAt, HOBt or a carbodiimide such as DCC or diisopropylcarbodiimide) and an aprotic organic solvent (e.g. a chlorinated solvent such as DCM, an ester such as ethyl acetate, an amide of dimethylamine such as DMF, or a mixture of any such solvents), followed, if necessary, by deprotection of R$^{6a1}$ when that group represents C(O)O—C$_{1-4}$ alkyl;

(g) for compounds of formula I in which R$^4$ represents —S(O)$_2$—N(R$^{7b}$)R$^{7c}$, reaction of a compound of formula VIIa, as defined above, in which Q$^x$ represents —S(O)$_2$-LG$^2$ with a compound of formula HN(R$^{7b}$)R$^{7c}$, wherein R$^{7b}$ and R$^{7c}$ are as defined above, for example under conditions known to those skilled in the art (e.g. conditions as described at (f) above];

(h) for compounds of formula I in which R$^{1B}$ represents —C(O)NR$^X$R$^Y$, reaction of a compound of formula VIIe,

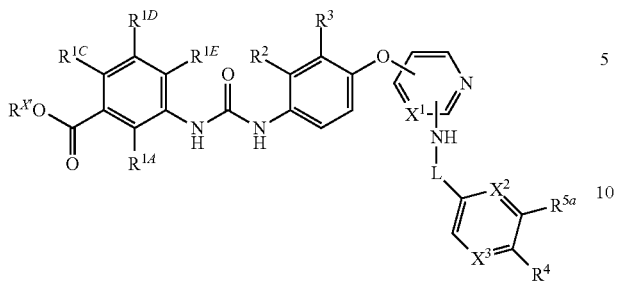

wherein $R^{1A}$, $R^{X1}$, $R^{1D}$, $R^{1E}$, $R^2$ to $R^4$, $R^{5a}$, L and $X^1$ to $X^3$ are as hereinbefore defined (e.g. $X^3$ represents $CR^{5b}$ and $R^{1A}$, $R^{1C}$, $R^{1D}$, $R^{1E}$, $R^2$ to $R^4$, $R^{5a}$, $R^{5b}$, L, $X^1$ and $X^2$ are as hereinbefore defined) and $R^{X'}$ represents H or $C_{1-4}$ alkyl, with a compound of formula VIIf,

wherein $R^X$ and $R^Y$ are as hereinbefore defined, under conditions known to those skilled in the art, for example
  when $R^{X'}$ represents H, reaction in the presence of a suitable solvent, a base (e.g. triethylamine or N,N-diisopropylethylamine) and an amide (peptide) coupling reagent, such as HATU, CDI, N,N'-dicyclohexylcarbodiimide, N,N'-diisopropylcarbodiimide BOP or PyBOP, optionally in combination with an activated ester-forming agent such as HOBt or 1-hydroxy-7-azabenzotriazole,
  when $R^{X'}$ represents H, conversion of the carboxylic acid to an acid halide (e.g. by reaction with a halogenating agent such as thionyl chloride), followed by reaction with the compound of formula (XI) in the presence of a suitable solvent and a base (e.g. triethylamine or N,N-diisopropylethylamine), or
  when $R^{X'}$ represents $C_{1-4}$ alkyl (e.g. methyl), reaction in the presence of a trialkylaluminum (e.g. trimethylaluminium) and an aprotic solvent (e.g. THF);
(i) for compounds of formula I in which
  $R^{1A}$ represents $C_{1-6}$ alkoxy, $C_{1-6}$ alkyl, $C_{2-6}$ alkenyl, $C_{2-6}$ alkynyl, which latter four groups are substituted by —OP(O)(OH)$_2$ and are optionally further substituted by one or more substituents selected from $C_{1-2}$ alkyl, halo, hydroxy, and $C_{1-2}$ alkoxy,
  $R^X$ and/or $R^{X1}$ represents $C_{1-6}$ alkyl substituted by —OP(O)(OH)$_2$ and optionally further substituted by one or more substituents selected from halo, hydroxy and $C_{1-2}$ alkoxy,
  $R^Y$, $R^{Y1}$ and/or $R^{Y2}$ independently represent $C_{1-6}$ alkyl, $C_{3-7}$ cycloalkyl, phenyl, benzyl, Het$^1$ or Het$^2$, which latter six groups are substituted by —OP(O)(OH)$_2$ and are optionally further substituted by one or more substituents selected from $C_{1-2}$ alkyl, halo, hydroxy, $C_{1-2}$ alkoxy, C(O)OH, C(O)O—($C_{1-4}$ alkyl) and —N($R^a$)($R^b$), and which Het$^2$ group is optionally further substituted with one or more oxo groups,
  $R^{1D}$ represents $C_{2-7}$ alkyl, $C_{2-7}$ alkenyl, $C_{2-7}$ alkynyl, $C_{3-7}$ cycloalkyl, phenyl, Het$^1$ or Het$^2$, which latter seven groups are substituted by —OP(O)(OH)$_2$ and are optionally further substituted by one or more substituents selected from $C_{1-2}$ alkyl, halo, cyano, hydroxy and $C_{1-2}$ alkoxy;
  $R^4$ represents —CH$_2$OP(O)(OH)$_2$,
  $R^{6b}$ represents $C_{1-8}$ alkyl, $C_{3-8}$ cycloalkyl, phenyl, Het$^1$ or Het$^2$, which latter five groups are substituted by —OP(O)(OH)$_2$ and are optionally further substituted by one or more substituents selected from halo, hydroxy, $C_{1-3}$ alkyl, $C_{1-3}$ alkoxy, —$C_{1-3}$ alkylene-$R^{6e}$ and CO$_2$H,
  $R^{6e}$ represents —OP(O)(OH)$_2$ or
  $R^{7a}$ represents P(O)(OH)$_2$,
reaction of a hydroxy group on a corresponding compound of formula I in which, respectively,
  $R^{1A}$ represents $C_{1-6}$ alkoxy, $C_{1-6}$ alkyl, $C_{2-6}$ alkenyl, $C_{2-6}$ alkynyl, which latter four groups are substituted by hydroxy and are optionally further substituted by one or more substituents selected from $C_{1-2}$ alkyl, halo, hydroxy, and $C_{1-2}$ alkoxy,
  $R^X$ and/or $R^{X1}$ represents $C_{1-6}$ alkyl substituted by hydroxy and optionally further substituted by one or more substituents selected from halo, hydroxy and $C_{1-2}$ alkoxy,
  $R^Y$, $R^{Y1}$ and/or $R^{Y2}$ independently represent $C_{1-6}$ alkyl, $C_{3-7}$ cycloalkyl, phenyl, benzyl, Het$^1$ or Het$^2$, which latter six groups are substituted by hydroxy and are optionally further substituted by one or more substituents selected from $C_{1-2}$ alkyl, halo, hydroxy, $C_{1-2}$ alkoxy, C(O)OH, C(O)O—($C_{1-4}$ alkyl) and —N($R^a$)($R^b$), and which Het$^2$ group is optionally further substituted with one or more oxo groups,
  $R^{1D}$ represents $C_{2-7}$ alkyl, $C_{2-7}$ alkenyl, $C_{2-7}$ alkynyl, $C_{3-7}$ cycloalkyl, phenyl, Het$^1$ or Het$^2$, which latter seven groups are substituted by hydroxy and are optionally further substituted by one or more substituents selected from $C_{1-2}$ alkyl, halo, cyano, hydroxy and $C_{1-2}$ alkoxy;
  $R^4$ represents —CH$_2$OH,
  $R^{6b}$ represents $C_{1-8}$ alkyl, $C_{3-8}$ cycloalkyl, phenyl, Het$^1$ or Het$^2$, which latter five groups are substituted by hydroxy and are optionally further substituted by one or more substituents selected from halo, hydroxy, $C_{1-3}$ alkyl, $C_{1-3}$ alkoxy, —$C_{1-3}$ alkylene-$R^{6e}$ and CO$_2$H,
  $R^{6e}$ represents hydroxy or
  $R^{7a}$ represents H,
with a di-tert-butyl or dibenzyl di($C_{1-4}$ alkyl)phosphoramidite (e.g. di-tert-butyl diethylphosphoramidite (Dunn, D., et al., *J. Biol. Chem.* 1996, 271, 168-173) or dibenzyl-N,N-diisopropylphosphoramidite (Locher, C. P., et al., WO 2014/014845, 23 Jan. 2014)), under conditions known to those skilled in the art, for example in the presence of an activator (e.g. tetrazole or 5-methyl-1H-tetrazole) and an aprotic organic solvent (e.g. THF or DMF), followed by reaction with an oxidant (e.g. hydrogen peroxide or mCPBA) and then removal of the tert-butyl or benzyl protecting groups (e.g. for the tert-butyl protecting groups, by acid-catalysed hydrolysis, such as by reaction with trifluoroacetic acid or, for the benzyl protecting groups, by hydrogenation in the presence of a suitable catalyst (e.g. a palladium catalyst, such as Pd/C), optionally in the presence of a base (e.g. sodium hydroxide, sodium bicarbonate or sodium carbonate));
(j) deprotection of an protected derivative of a compound of formula I, under conditions known to those skilled in the art, wherein the protected derivative bears a protecting group on an O- or N-atom of the compound of formula I (and, for the avoidance of doubt, a protected derivative of one compound of formula I may or may not represent another compound of formula I).

Examples of protected derivatives of compounds of formula I include those where:
- an O-atom is protected with a benzyl group, which benzyl group may be removed by hydrogenation, for example in the presence of a palladium catalyst (such as Pd/C);
- an O-atom of an acid (e.g. a carboxylic, sulfonic, phosphonic or phosphinic acid) is protected with an alkyl group (such as methyl, ethyl or tert-butyl), which alkyl group may be removed by either basic hydrolysis (e.g. for methyl or ethyl groups, by a hydrolysis reaction using an alkali metal hydroxide such as sodium hydroxide) or acid hydrolysis (e.g. for a tert-butyl group, by a hydrolysis reaction using an acid such as trifluoroacetic acid);
- an N-atom of an amine is protected with a carbamate group, such as a benzyl or tert-butyl carbamate, which groups may be removed under similar conditions to those used to remove benzyl or tert-butyl groups from O-atoms.

Protected derivatives of compounds of formula I in which $R^4$ represents —[$C_{1-4}$ alkylene]$_{0-1}$—$CO_2H$ also include compounds of formula VIIa, as hereinbefore defined, in which $Q^x$ represents —[$C_{1-4}$ alkylene]$_{0-1}$-C(O)$OR^{4'}$ (e.g. $Q^x$ represents —C(O)$OR^{4'}$) and $R^{4'}$ represents a $C_{1-4}$ alkyl group (e.g. a $C_4$ alkyl group or a $C_{1-3}$ alkyl group, such as methyl).

Thus, the process described at (j) above encompasses, for example, a process for the preparation of a compound of formula I in which $R^4$ represents -$Q^4$-P(O)(O$R^9$)($R^7$) and $R^9$ represents H, which process comprises hydrolysing a corresponding compound of formula I in which $R^4$ represents -$Q^4$-P(O)(O$R^9$)($R^7$) and $R^9$ represents $C_{1-4}$ alkyl, which latter group is optionally substituted by one or more halo atoms or by phenyl, which phenyl group is optionally substituted by one or more substituents selected from halo, OH, $C_{1-3}$ alkyl and $C_{1-3}$ alkoxy (e.g. a corresponding compound of formula I in which $R^4$ represents -$Q^4$-P(O)(O$R^9$)($R^7$) and $R^9$ represents methyl or ethyl). The hydrolysis may be basic hydrolysis (e.g. for methyl or ethyl groups, by a hydrolysis reaction using an alkali metal hydroxide such as sodium hydroxide), for example conducted at elevated temperature (such as from 30 to 70° C. or, particularly, from 40 to 50° C.) in the presence of an aqueous solvent mixture (e.g. a solvent comprising water and one or more polar organic solvents such as one or more water-miscible, polar organic solvents (e.g. an aprotic solvent such as dioxane and/or a protic solvent such as ethanol)).

Compounds of formula II may be prepared according to or by analogy with methods known to those skilled in the art, for example by reaction of a compound of formula IIa, as defined above, with an azide-forming agent, followed by rearrangement of the intermediate acyl azide (as described at (b) above; see, for example, *Tetrahedron* 1974, 30, 2151-2157).

Compounds of formula IIb may be prepared reaction of a compound of formula VIII,

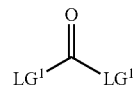

wherein $LG^1$ is as hereinbefore defined, with a compound of formula IX,

wherein $Z^1$ is as hereinbefore defined, for example under conditions known to those skilled in the art.

Amines of formula IX may be prepared from carboxylic acids of formula IIa through the route described in (b) above, where the intermediate isocyanate II is hydrolysed with water to give a carbamic acid that loses carbon dioxide to furnish IX. By the same token, the intermediate isocyanate II can be reacted with an alcohol, such as t-butanol, to generate a protected version of IX.

Certain compounds of formula III in which $Z^2$ represents a structural fragment of formula V, or compounds of formula IX in which $Z^1$ represents a structural fragment of formula V, may be synthesised employing the route outlined in Scheme 1 (see, for example: WO 2003/072569; and WO 2008/046216), wherein $R^2$ to $R^4$, $R^{5a}$ and $X^1$ to $X^3$ are as hereinbefore defined (e.g. $X^3$ represents $CR^{5b}$ and $R^2$ to $R^4$, $R^{5a}$, $R^{5b}$, $X^1$ and $X^2$ are as hereinbefore defined), $LG^3$ and $LG^4$ represent leaving groups, e.g. halogen or methanesulfonyl, and FG represents a real or latent $NH_2$ group, i.e., a group that is readily transformed into an $NH_2$ group, such as nitro or a protected variant NH-$PG^2$, where $PG^2$ is a typical protecting group (see, for example: Greene, T. W.; Wuts, P. G. M. Protective Groups in Organic Synthesis; Wiley, 4th revised edition, 2006; ISBN-10: 0471697540), e.g. a carbamate ester or carboxamide. The sequence starts with the base-mediated $S_NAr$ displacement of $LG^3$ in XI by the aroxides formed when X is treated with base to generate ethers XII. The remaining halogen or methanesulfonyl substituent ($LG^4$) of the ether XII is then displaced (i) by an amine of formula VII in a second $S_NAr$ reaction or (ii) via a Buchwald coupling (see, for example, WO 2009/017838) with an amine of formula VII to furnish the desired compound (when FG is $NH_2$), or XIII (when FG is nitro or NH-$PG^2$). When FG is nitro in XIII, the $NH_2$ group may be revealed by a reduction reaction, typically done through hydrogenation employing a suitable catalyst, e.g. palladium on carbon, or employing dissolving metal conditions, such as with iron in glacial acetic acid. Alternatively, when FG is a protecting group, the $NH_2$ group may be revealed by a deprotection reaction. Although only depicted as taking place in the final step of the sequence, it should be noted that the unmasking of the latent $NH_2$ group represented by FG can take place at any stage in the synthetic route shown in Scheme 1.

Scheme 1

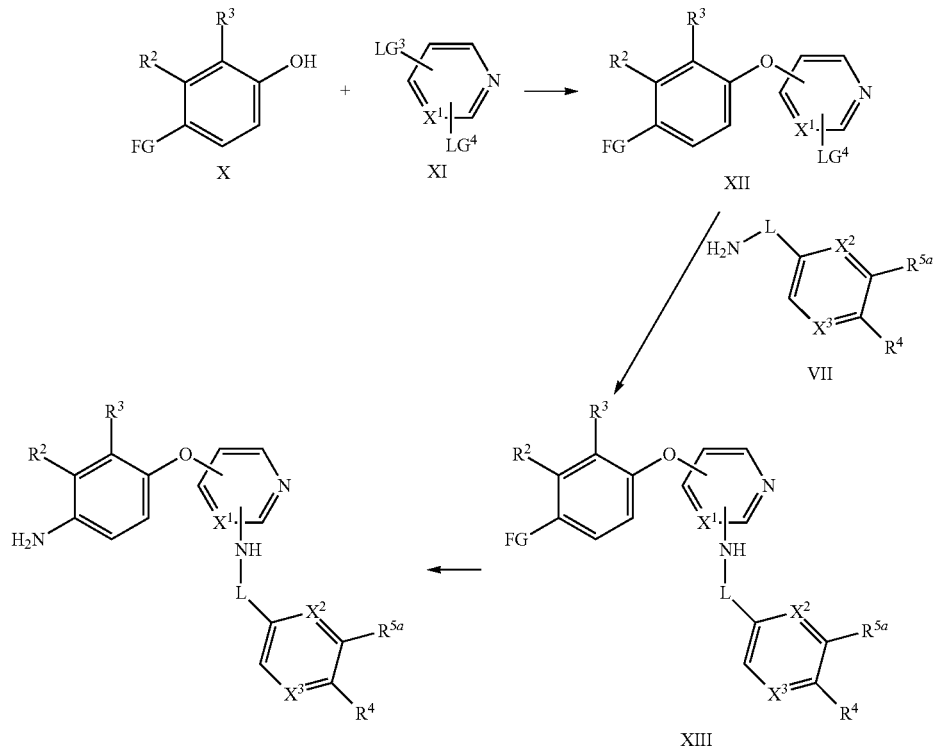

In a similar manner, amines of formula IX in which $Z^1$ represents a structural fragment of formula IV may be synthesised by conversion of a latent to a real $NH_2$ group in a compound of formula XIIIa,

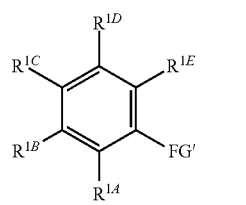

XIIIa wherein FG' is as defined for FG above, except that it does not represent $NH_2$, and $R^{1A}$ to $R^{1E}$ are as hereinbefore defined.

Compounds of formula III in which $Z^2$ represents a structural fragment of formula V, or compounds of formula IX in which $Z^1$ represents a structural fragment of formula V, wherein, in the structural fragment of formula V, $R^4$ represents -$Q^{1a}$-$NR^8$—[C($R^{6c}$)($R^{6d}$)—($CH_2$)$_{0-1}CH_2$—O]$_{1-12}$—$CH_2$ ($CH_2$)$_{0-1}CH_2$—$R^{6a}$, -$Q^{2a}$-$NR^8$—C($R^{6c}$)($R^{6d}$)—[$C_{1-5}$ alkylene]-$R^{6a}$ or -$Q^{3a}$-$NR^8$—[$C_{1-4}$ alkylene]$_{0-1}$-$Het^3$, which $C_{1-5}$ alkylene and $Het^3$ groups are optionally substituted as described above, may be prepared by analogy with processes described herein for preparing compounds of formula I (see process (f) above) and other compounds of formula III (see, for example, Scheme 1 above), for example by reaction of a compound of XIIIb XIIIb

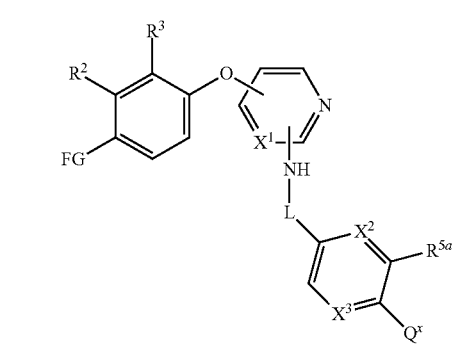

wherein FG, $R^2$, $R^3$, $R^{5a}$, L, $X^1$ to $X^3$ and $Q^x$ are as hereinbefore defined (e.g. $X^3$ represents $CR^{5b}$ and FG, $R^2$, $R^3$, $R^{5a}$, $R^{5b}$, L, $X^1$, $X^2$ and $Q^x$ are as hereinbefore defined), with a compound of formula VIIb, VIIc or VIId, as hereinbefore defined, under conditions known to those skilled in the art (for example the peptide coupling conditions described in respect of process (f) above), followed by conversion (if necessary) of FG to $NH_2$, for example as described above in connection with Scheme 1.

Compounds of formula VI may be synthesised by analogy with the compounds of formula I (see, for example, alternative processes (a) to (c) above). For example, compounds of formula VI can be prepared by reaction of a compound of formula IIx with a compound of formula IIIx, wherein the compounds of formulae IIx and IIIx take the same definitions as the compounds of formulae II and III, with the exception that one of $Z^1$ and $Z^2$ represents a structural fragment of formula IV, as hereinbefore defined, and the other of $Z^1$ and $Z^2$ represents a structural fragment of formula Va,

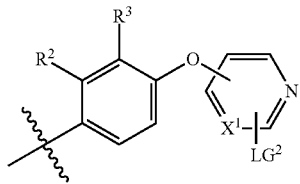

Va

Compounds of formula VII in which L represents a direct bond may be prepared according to or by analogy with procedures known to those skilled in the art, for example as described below.

(i) For compounds of formula VII in which $R^4$ represents
—O—[C($R^{6c}$)($R^{6d}$)—(CH$_2$)$_{0-1}$CH$_2$—Z]$_{1-12}$—CH$_2$(CH$_2$)$_{0-1}$CH$_2$—$R^{6a}$ or
—O—C($R^{6c}$)($R^{6d}$)—[C$_{1-5}$ alkylene]-$R^{6a}$,
which C$_{1-5}$ alkylene groups is optionally substituted as described above, reaction of a compound of formula XIV,

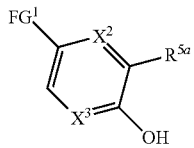

XIV wherein $FG^1$ either represents FG or C(O)O—(C$_{1-6}$ alkyl), and FG, $R^{5a}$, $X^2$ and $X^3$ are as hereinbefore defined (e.g. $X^3$ represents CR$^{5b}$ and FG, $R^{5a}$, $R^{5b}$ and $X^2$ are as hereinbefore defined), with a compound of formula XVa or XVb LG$^5$-[C($R^{6c}$)($R^{6d}$)—(CH$_2$)$_{0-1}$CH$_2$—Z]$_{1-12}$—CH$_2$(CH$_2$)$_{0-1}$CH$_2$—$R^{6a1}$   XVa LG$^5$-C($R^{6c}$)($R^{6d}$)—[C$_{1-5}$alkylene]-$R^{6a1}$   XVb which C$_{1-5}$ alkylene groups is optionally substituted as described above, wherein LG$^5$ represents a suitable leaving group such as halo, (perfluoro)alkane-sulfonate or arylsulfonate (e.g. methanesulfonate or p-toluenesulfonate) and $R^{6a1}$, $R^{6c}$ and $R^{6d}$ are as hereinbefore defined, under conditions known to those skilled in the art (e.g. in the presence of an organic solvent and either a suitable base, followed by
when $FG^1$ represents NH-PG$^2$, removal of the PG$^2$ protecting group,
when $FG^1$ represents NO$_2$, reduction of NO$_2$ to NH$_2$ or
when $FG^1$ represents C(O)O—(C$_{1-6}$ alkyl), saponification to provide the corresponding carboxylic acid and then reaction with a suitable azide-forming agent and thermal rearrangement of the resulting acyl azide (see, for example, process (b) above) and/or by deprotection of $R^{6a1}$ when that group represents C(O)O—C$_{1-4}$ alkyl.

(ii) For compounds of formula VII in which $R^4$ represents
—O—[C($R^{6c}$)($R^{6d}$)—(CH$_2$)$_{0-1}$CH$_2$—Z]$_{1-12}$—CH$_2$(CH$_2$)$_{0-1}$CH$_2$—$R^{6a}$ or
—O—C($R^{6c}$)($R^{6d}$)—[C$_{1-5}$ alkylene]-$R^{6a}$ which C$_{1-5}$ alkylene groups is optionally substituted as described above, reaction of a compound of formula XIV, as hereinbefore defined, with a compound of formula XVIa or XVIb HO—[C($R^{6c}$)($R^{6d}$)—(CH$_2$)$_{0-1}$CH$_2$—Z]$_{1-12}$—CH$_2$(CH$_2$)$_{0-1}$CH$_2$—$R^{6a}$   XVIa HO—C($R^{6c}$)($R^{6d}$)—[C$_{1-5}$alkylene]-NR$^{6a}$   XVIb which C$_{1-5}$ alkylene groups is optionally substituted as described above, wherein $R^{6a1}$, $R^{6c}$ and $R^{6d}$ are as hereinbefore defined, under conditions known to those skilled in the art (e.g. under Mitsunobu conditions, i.e. in the presence of using triphenylphosphine and an azodicarboxylate, such as diethyl azodicarboxylate or diisopropyl azodicarboxylate), followed by
when $FG^1$ represents NH-PG$^2$, removal of the PG$^2$ protecting group,
when $FG^1$ represents NO$_2$, reduction of NO$_2$ to NH$_2$ or
when $FG^1$ represents C(O)O—(C$_{1-6}$ alkyl), saponification to provide the corresponding carboxylic acid and then reaction with a suitable azide-forming agent and thermal rearrangement of the resulting acyl azide (see, for example, process (b) above) and/or by deprotection of $R^{6a1}$ when that group represents C(O)O—C$_{1-4}$ alkyl.

(iii) For compounds of formula VII in which $R^4$ represents
—S—[C($R^{6c}$)($R^{6d}$)—(CH$_2$)$_{0-1}$CH$_2$—Z]$_{1-12}$—CH$_2$(CH$_2$)$_{0-1}$CH$_2$—$R^{6a}$,
—S—C($R^{6c}$)($R^{6d}$)—[C$_{1-5}$ alkylene]-$R^{6a}$ or
—S—$R^{6b}$,
which C$_{1-5}$ alkylene groups is optionally substituted as described above, reaction of a compound of formula XVII,

XVII wherein $FG^1$, $R^{5a}$, $X^2$ and $X^3$ are as hereinbefore defined (e.g. $X^3$ represents CR$^{5b}$ and $FG^1$, $R^{5a}$, $R^{5b}$ and $X^2$ are as hereinbefore defined), with a compound of formula XVa or XVb, as hereinbefore defined, or a compound of formula XVIII LG$^5$-$R^{6b}$   XVIII wherein LG$^5$ and $R^{6b}$ are as hereinbefore defined, under conditions known to those skilled in the art (e.g. in the presence of a suitable base and an organic solvent), followed by
when $FG^1$ represents NH-PG$^2$, removal of the PG$^2$ protecting group,
when $FG^1$ represents NO$_2$, reduction of NO$_2$ to NH$_2$ or
when $FG^1$ represents C(O)O—(C$_{1-6}$ alkyl), saponification to provide the corresponding carboxylic acid and then reaction with a suitable azide-forming agent and thermal rearrangement of the resulting acyl azide (see, for example, process (b) above).

(iv) For compounds of formula VII in which $X^2$ represents CR$^Z$ and $R^4$ represents
—S(O)$_{1-2}$—[C($R^{6c}$)($R^{6d}$)—(CH$_2$)$_{0-1}$CH$_2$—Z]$_{1-12}$—CH$_2$(CH$_2$)$_{0-1}$CH$_2$—$R^{6a}$,
—S(O)$_{1-2}$—C($R^{6c}$)($R^{6d}$)—[C$_{1-5}$ alkylene]-$R^{6a}$ or
—S(O)$_{1-2}$—$R^{6b}$, which $C_{1-5}$ alkylene groups is optionally substituted as described above, oxidation of a compound of formula XIX,

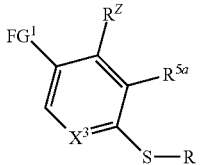

XIX wherein R represents
—[C($R^{6c}$)($R^{6d}$)—(CH$_2$)$_{0-1}$CH$_2$—Z]$_{1-12}$—CH$_2$(CH$_2$)$_{0-1}$CH$_2$—$R^{6a}$,
—C($R^{6c}$)($R^{6d}$)—[C$_{1-5}$ alkylene]-$R^{6a}$ or
—$R^{6b}$,
which $C_{1-5}$ alkylene groups is optionally substituted as described above, and wherein $FG^1$, $R^{5a}$, $X^3$ and $R^Z$ are as hereinbefore defined (e.g. $X^3$ represents $CR^{5b}$ and $FG^1$, $R^{5a}$, $R^{5b}$ and $R^Z$ are as hereinbefore defined), under conditions known to those skilled in the art (e.g. in the presence of a peracid, such as meta-chloroperbenzoic acid), followed by
when $FG^1$ represents NH-$PG^2$, removal of the $PG^2$ protecting group,
when $FG^1$ represents $NO_2$, reduction of $NO_2$ to $NH_2$ or
when $FG^1$ represents C(O)O—(C$_{1-6}$ alkyl), saponification to provide the corresponding carboxylic acid and then reaction with a suitable azide-forming agent and thermal rearrangement of the resulting acyl azide (see, for example, process (b) above).

(v) For compounds of formula VII in which $R^4$ represents —S—$R^{6b}$, coupling of a compound of formula XX

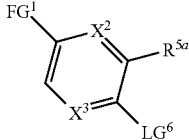

XX wherein $LG^6$ represents a suitable leaving group such as halo or trifluoromethanesulfonate, $FG^1$, $R^{5a}$, $X^2$ and $X^3$ are as hereinbefore defined (e.g. $X^3$ represents $CR^{5b}$ and $FG^1$, $R^{5a}$, $R^{5b}$ and $X^2$ are as hereinbefore defined), with a compound of formula XXI,

 H—S—$R^{6b}$   XXI wherein $R^{6b}$ is as hereinbefore defined, under conditions known to those skilled in the art (e.g. in the presence of a Pd(0) catalyst, Cu(I) iodide and a suitable base), followed by
when $FG^1$ represents NH-$PG^2$, removal of the $PG^2$ protecting group,
when $FG^1$ represents $NO_2$, reduction of $NO_2$ to $NH_2$ or
when $FG^1$ represents C(O)O—(C$_{1-6}$ alkyl), saponification to provide the corresponding carboxylic acid and then reaction with a suitable azide-forming agent and thermal rearrangement of the resulting acyl azide (see, for example, process (b) above).

(vi) For compounds of formula VII in which $R^4$ represents -$Q^1$-[C($R^{6c}$)($R^{6d}$)—(CH$_2$)$_{0-1}$CH$_2$—O]$_{1-12}$—CH$_2$(CH$_2$)$_{0-1}$CH$_2$—$R^{6a}$ wherein $Q^1$ and $R^{6a}$ are as hereinbefore defined, reaction of a compound of formula XXII

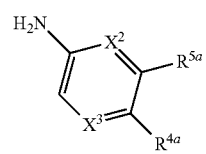

XXII in which $R^{4a}$ represents
-$Q^1$-[C($R^{6c}$)($R^{6d}$)—(CH$_2$)$_{0-1}$CH$_2$—O]$_x$—CH$_2$(CH$_2$)$_{0-1}$CH$_2$—OH
and $R^{5a}$, $X^2$ and $X^3$ are as hereinbefore defined (e.g. $X^3$ represents $CR^{5b}$ and $R^{5a}$, $R^{5b}$ and $X^2$ are as hereinbefore defined),
with a compound of formula XXIII,

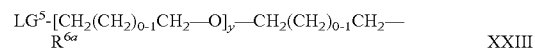

XXIII wherein x and y are integers from 0 to 11, the sum of x and y being from 0 to 11, and $Q^1$, $LG^5$ and $R^{6a}$ are as hereinbefore defined, under conditions known to those skilled in the art (e.g. at ambient temperature in the presence of a base such as sodium hydride and a polar organic solvent such as DMF).

(vii) For compounds of formula VII in which $X^2$ represents $CR^Z$ and $R^4$ represents
—S—C($R^{6c}$)($R^{6d}$)—[C$_{1-5}$ alkylene]-N($R^{7b}$)$R^{7c}$
which $C_{1-5}$ alkylene groups is optionally substituted as described above, reaction of a compound of formula XXIV,

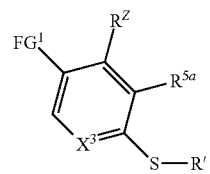

XXIV wherein R' represents
—C($R^{6c}$)($R^{6d}$)—[C$_{1-5}$ alkylene]-$LG^6$
which $C_{1-5}$ alkylene groups is optionally substituted as described above, with a compound of formula HN($R^{7b}$)$R^{7c}$, wherein $FG^1$, $R^{5a}$, $R^{6c}$, $R^{6d}$, $R^{7b}$, $R^{7c}$, $R^Z$, $X^3$ and $LG^6$ are as hereinbefore defined (e.g. $X^3$ represents $CR^{5b}$ and $FG^1$, $R^{5a}$, $R^{5b}$, $R^{6c}$, $R^{6d}$, $R^{7b}$, $R^{7c}$, $R^Z$ and $LG^6$ are as hereinbefore defined), under conditions known to those skilled in the art (for example in the presence of a suitable organic solvent (e.g. acetone) and, optionally, catalyst for nucleophilic displacement, such as an iodide sale (e.g. sodium iodide)), followed by
when $FG^1$ represents NH-$PG^2$, removal of the $PG^2$ protecting group,
when $FG^1$ represents $NO_2$, reduction of $NO_2$ to $NH_2$ or
when $FG^1$ represents C(O)O—(C$_{1-6}$ alkyl), saponification to provide the corresponding carboxylic acid and then reaction with a suitable azide-forming agent and thermal rearrangement of the resulting acyl azide (see, for example, process (b) above).

(viii) For compounds of formula VII in which $R^4$ represents -$Q^{1a}$-N$R^8$—[CH$_2$(CH$_2$)$_{0-1}$CH$_2$—O]$_{1-12}$—CH$_2$(CH$_2$)$_{0-1}$CH$_2$—$R^{6a}$, -Q$^{2a}$-NR$^8$—C(R$^{6c}$)(R$^{6d}$)—[C$_{1-5}$ alkylene]-R$^{6a}$ or
-Q$^{3a}$-NR$^8$—[C$_{1-4}$ alkylene]$_{0-1}$-Het$^3$,
which C$_{1-5}$ alkylene group is optionally substituted as described above, reaction of a compound of formula XXV,

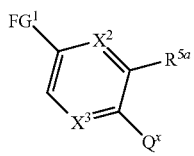

wherein FG$^1$, R$^{5a}$, R$^{6a}$, R$^{6c}$, R$^{6d}$, X$^2$, X$^3$ and Q$^x$ are as hereinbefore defined (e.g. X$^3$ represents CR$^{5b}$ and FG$^1$, R$^{5a}$, R$^{5b}$, R$^{6a}$, R$^{6c}$, R$^{6d}$, X$^2$ and Q$^x$ are as hereinbefore defined), with a compound of formula VIIb, VIIc or VIId, as hereinbefore defined, under conditions known to those skilled in the art (for example the peptide coupling conditions described in respect of process (f) above), followed by
when FG$^1$ represents NH-PG$^2$, removal of the PG$^2$ protecting group,
when FG$^1$ represents NO$_2$, reduction of NO$_2$ to NH$_2$ or
when FG$^1$ represents C(O)O—(C$_{1-6}$ alkyl), saponification to provide the corresponding carboxylic acid and then reaction with a suitable azide-forming agent and thermal rearrangement of the resulting acyl azide (see, for example, process (b) above).

(ix) For compounds of formula VII in which R$^4$ represents —S(O)$_2$—R$^{6b}$, coupling of a compound of formula XX, as hereinbefore defined, with a compound of formula XXVI,

(M$^{s+}$)($^-$O—S(O)—R$^{6b}$)$_s$       XXVI wherein M$^{s+}$ is a metal cation, s is 1 or 2 (e.g. s is 1 and M is an alkali metal such as potassium or, particularly, sodium) and R$^{6b}$ is as hereinbefore defined, under conditions known to those skilled in the art (e.g. at elevated temperature (e.g. 80 to 100° C.) in the presence of: a suitable transition metal catalyst, such as Cu(I) iodide; an aprotic organic solvent, such as DMSO; a suitable base, such as an alkali metal hydroxide (e.g. NaOH); and, optionally, an organic ligand for Cu(I), such as L-proline), followed by
when FG$^1$ represents NH-PG$^2$, removal of the PG$^2$ protecting group,
when FG$^1$ represents NO$_2$, reduction of NO$_2$ to NH$_2$ or
when FG$^1$ represents C(O)O—(C$_{1-6}$ alkyl), saponification to provide the corresponding carboxylic acid and then reaction with a suitable azide-forming agent and thermal rearrangement of the resulting acyl azide (see, for example, process (b) above).

(x) For compounds of formula VII in which R$^4$ represents —P(O)(OR$^9$)(R$^7$), reaction of a compound of formula XX, as hereinbefore defined, with a compound of formula XXVIa,

HP(O)(OR$^{99}$)(R$^7$)       XXVIa wherein R$^{99}$ represents a C$_{1-4}$ alkyl group optionally substituted by one or more halo atoms or phenyl (e.g. R$^{99}$ represents ethyl), and R$^7$ is as hereinbefore defined, under conditions known to those skilled in the art (e.g. at elevated temperature (e.g. 80 to 100° C.) in the presence of a suitable catalyst (such as Xantphos G3 palladacycle precatalyst (i.e. [(4,5-bis(diphenylphosphino)-9,9-dimethyxanthene)-2-(2'-amino-1,1'-biphenyl)]palladium(II) methanesulfonate) or Pd(Ph$_3$P)$_4$), a base (e.g. diisopropylethylamine or triethylamine) and an aprotic organic solvent, such as toluene, followed by
when FG$^1$ represents NH-PG$^2$, removal of the PG$^2$ protecting group,
when FG$^1$ represents NO$_2$, reduction of NO$_2$ to NH$_2$ or
when FG$^1$ represents C(O)O—(C$_{1-6}$ alkyl), saponification to provide the corresponding carboxylic acid and then reaction with a suitable azide-forming agent and thermal rearrangement of the resulting acyl azide (see, for example, process (b) above).

(xa) For compounds of formula VII in which R$^4$ represents —CH$_2$—P(O)(OR$^9$)(R$^7$), reaction of a compound of formula XXa

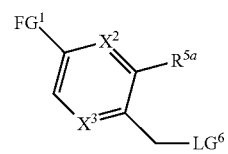

wherein LG$^6$ is as hereinbefore defined (e.g. bromo) and R$^{5a}$, X$^2$, X$^3$ and FG$^1$ are as hereinbefore defined (e.g. X$^3$ represents CR$^{5b}$ and R$^{5a}$, R$^{5b}$, X$^2$, FG$^1$ and LG$^6$ are as hereinbefore defined), with a compound of formula XXVIaa,

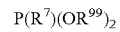
P(R$^7$)(OR$^{99}$)$_2$       XXVIaa wherein R$^7$ and R$^{99}$ are as hereinbefore defined, followed by
when FG$^1$ represents NH-PG$^2$, removal of the PG$^2$ protecting group,
when FG$^1$ represents NO$_2$, reduction of NO$_2$ to NH$_2$ or
when FG$^1$ represents C(O)O—(C$_{1-6}$ alkyl), saponification to provide the corresponding carboxylic acid and then reaction with a suitable azide-forming agent and thermal rearrangement of the resulting acyl azide (see, for example, process (b) above).

(xb) For compounds of formula VII in which R$^4$ represents —[C$_{0-3}$ alkylene]-CH$_2$C(O)OR$^{4'}$, coupling of a compound of formula XXb

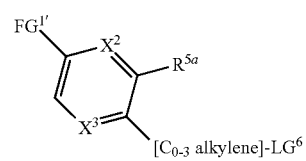

wherein LG$^6$ represents a suitable leaving group such as halo or trifluoromethanesulfonate, FG$^{1'}$ represents NH-PG$^2$ or NO$_2$, and R$^{5a}$, X$^2$ and X$^3$ are as hereinbefore defined (e.g. X$^3$ represents CR$^{5b}$ and R$^{5a}$, R$^{5b}$ and X$^2$ are as hereinbefore defined), with a malonate ester of formula XXc

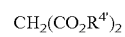
CH$_2$(CO$_2$R$^{4'}$)$_2$       XXc for example under conditions known to those skilled in the art (e.g. in the presence of Cu(I) bromide and a suitable base, e.g., sodium hydride), followed by hydrolysis, decarboxylation and re-esterification with $R^{4'}OH$, then when $FG^1$ represents $NH-PG^2$, removal of the $PG^2$ protecting group or when $FG^1$ represents $NO_2$, reduction of $NO_2$ to $NH_2$.

(xi) For compounds of formula VII in which $R^4$ represents $Het^{x2}$ and $Het^{x2}$ is an N-linked heterocyclic group that is optionally substituted as described above, reaction of a compound of formula XX, as hereinbefore defined, in which $FG^1$ represents $NO_2$, with a compound of formula XXVIb, $$Het^{x3}\text{-}H \qquad \text{XXVIb}$$

wherein $Het^{x3}$ is a heterocycle as defined for $Het^{x2}$ above, which heterocycle contains an N-atom that (at least in one tautomeric form) is linked to the hydrogen atom depicted, for example in the presence of a base (e.g. $Cs_2CO_3$) followed by reduction of $NO_2$ ($FG^1$) to $NH_2$.

(xii) For compounds of formula VII in which $R^4$ represents tetrazol-5-yl, reaction of a compound of formula XXVIc,

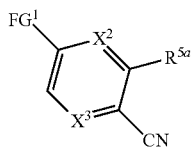

XXVIc wherein $R^{5a}$, $X^2$, $X^3$ and $FG^1$ are as hereinbefore defined (e.g. $X^3$ represents $CR^{5b}$ and $R^{5a}$, $R^{5b}$, $X^2$ and $FG^1$ are as hereinbefore defined), with azidotributylstannane, for example at elevated temperature in the presence of a polar, aprotic organic solvent (e.g. dimethoxyethane), followed by when $FG^1$ represents $NH-PG^2$, removal of the $PG^2$ protecting group, when $FG^1$ represents $NO_2$, reduction of $NO_2$ to $NH_2$ or when $FG^1$ represents $C(O)O-(C_{1-6}$ alkyl), saponification to provide the corresponding carboxylic acid and then reaction with a suitable azide-forming agent and thermal rearrangement of the resulting acyl azide (see, for example, process (b) above).

Compounds of formula VII in which L represents $C_{1-2}$ alkylene may be prepared by analogous procedures.

Compounds of formula VIIa in which in which $Q^x$ represents $-[C_{1-4}$ alkylene$]_{0-1}$—$C(O)OR^{4'}$ and $R^{4'}$ represents a $C_{1-4}$ alkyl group (e.g. a $C_4$ alkyl group or a $C_{1-3}$ alkyl group, such as methyl) may be prepared by analogy with the procedures described herein for preparation of compounds of formula I (see, for example, processes (a) to (d) and Scheme 1 above), or of formula Ib in which $R^{1A}$ and $R^{5a}$ both represent methoxy, $R^{1B}$ represents —NHS(O)$_2$CH$_3$, $R^{1D}$ represents tert-butyl, $X^1$ and $X^2$ both represent CH, $R^{5b}$ represents H and $R^4$ represents —CO$_2$H.

For example, $R^4$ may be replaced by $-[C_{1-4}$ alkylene$]_{0-1}$-$C(O)OR^{4'}$ (e.g. —$C(O)OR^{4'}$) in:

the structural fragment of formula V (to give a structural fragment of formula Vp, and corresponding compounds of formulae IIp, IIap, IIbp and IIIp, in which $Z^1$ and $Z^2$ are replaced by $Z^{1p}$ and $Z^{2p}$, respectively, wherein one of $Z^{1'}$ and $Z^{2p}$ is a structural fragment of formula IV, as defined above, and the other of $Z^{1'}$ and $Z^{2p}$ is a structural fragment of formula Vp); or the compound of formula VII (to give a compound of formula VIIp).

Alternatively, compounds of formula VIIa in which $Q^x$ represents $-[C_{1-4}$ alkylene$]_{0-1}$-$C(O)OR^{4'}$ (e.g. —$C(O)OR^{4'}$) and $R^{4'}$ represents a $C_{1-4}$ alkyl group (e.g. a $C_4$ alkyl group or a $C_{1-3}$ alkyl group, such as methyl) may be prepared by converting, in a compound of formula XIIIb

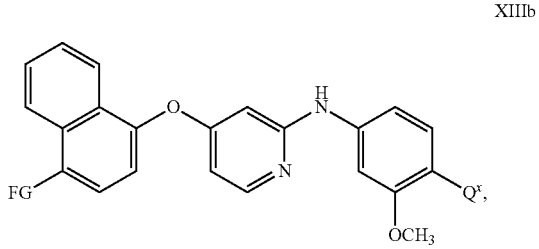

XIIIb the group FG to $NH_2$, wherein $Q^x$ represents $-[C_{1-4}$ alkylene$]_{0-1}$-$C(O)OR^{4'}$ (e.g. —$C(O)OR^{4'}$) and $R^{4'}$ represents a $C_{1-4}$ alkyl group (e.g. a $C_4$ alkyl group or a $C_{1-3}$ alkyl group, such as methyl) and FG is as hereinbefore defined (e.g. by converting FG to $NH_2$ as described above in connection with Scheme 1), followed by reaction with, for example, a compound of formula IIb where $Z^1$ represents a structural fragment of formula IV.

Compounds of formula VIIb and VIIc in which $R^{6a1}$ represents $OR^{7a}$ in which $R^{7a}$ represents $P(O)(OH)_2$ (or a di-O-tert-butyl or di-O-benzyl protected derivative thereof) may be prepared by reaction of a corresponding compound of formula VIIb and VIIc, in which $R^{6a1}$ represents $OR^{7a}$ where $R^{7a}$ represents H, with di-tert-butyl diethylphosphoramidite or dibenzyl-N,N-diisopropylphosphoramidite, for example in the presence of an activator (e.g. tetrazole or 5-methyl-1H-tetrazole) and an aprotic organic solvent (e.g. THF or DMF), followed by reaction with an oxidant (e.g. hydrogen peroxide or mCPBA) and then optionally followed by removal of the tert-butyl or benzyl protecting groups by hydrolysis using an acid (such as trifluoroacetic acid) or by hydrogenation in the presence of a suitable catalyst (e.g. a palladium catalyst, such as Pd/C), respectively, which deprotection step can alternatively be performed upon a compound formed using a compound of formula VIIb or VIIc (e.g. a compound of formula I).

Similar interconversions of functional groups may also be employed to prepare compounds of formula XIIIa. For example, compounds of formula XIIIa in which $R^{1B}$ represents —CH$_2$CN may be prepared by reaction of a compound of formula XXVII,

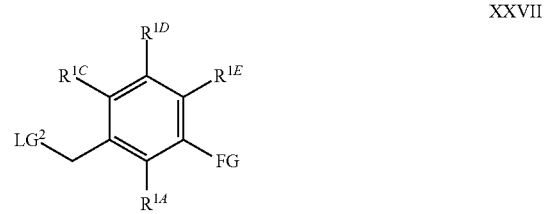

XXVII wherein FG, $LG^2$, $R^{1A}$ and $R^{1C}$ to $R^{1E}$ are as hereinbefore defined, with a source of cyanide ion (e.g. NaCN), for example under conditions known to those skilled in the art, such as in the presence of a polar, aprotic organic solvent (e.g. DMSO).

Also, compounds of formula XIIIa in which $R^{1B}$ represents —$NR^XS(O)_2R^{Y1}$ in which $R^X$ represents —$CH_2$—$C_{1-5}$ alkyl optionally substituted by one hydroxy (or a O-protected derivative thereof) may be prepared by reaction of a compound of formula XIIIa in which $R^{1B}$ represents —N(H)S(O)$_2R^{Y1}$ with a compound of formula XXVIIa,

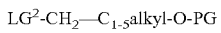-$CH_2$—$C_{1-5}$alkyl-O-PG            XXVIIa wherein PG represents a protecting group such as benzyl and $LG^2$ is as hereinbefore defined, for example in the presence of a base (e.g. $K_2CO_3$) and a polar organic solvent (e.g. DMF), optionally followed by removal of the PG protecting group (e.g. in the case of benzyl, by hydrogenation in the presence of a palladium catalyst), which deprotection step can alternatively be performed upon a compound formed using the compound of formula XIIIa (e.g. a compound of formula I or IIb).

Compounds of formula XXIV in which $LG^6$ represents halo can be prepared according to or by analogy with procedures known to those skilled in the art, for example by reaction of a compound of formula XXVIII,

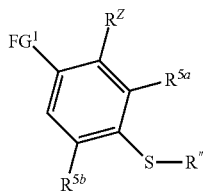                                                XXVIII wherein R" represents —$CH_2$—[$C_{1-5}$ alkylene]-OH, with a halogenating agent (e.g. a mixture of 2,4,6-trichloro,1,3,5-triazine and dimethylformamide).

Compounds of formula XXVII may be prepared according to (or by analogy with) procedures know to those skilled in the art. For example, compounds of formula XXVII in which $LG^2$ represents Cl may be prepared by chlorination of a corresponding compound of formula XXIX,

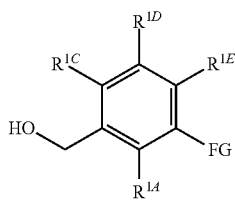                                                XXIX wherein FG, $R^{1A}$ and $R^{1C}$ to $R^{1E}$ are as hereinbefore defined, for example under conditions known to those skilled in the art, such as by reaction with thionyl chloride.

Compounds of formula XXIX may, for example, be prepared by reduction of corresponding compounds of formula XXX,

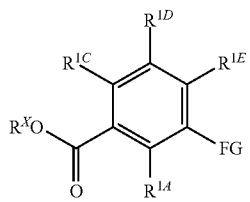                                                XXX wherein FG, $R^X$, $R^{1A}$ and $R^{1C}$ to $R^{1E}$ are as hereinbefore defined, for example under conditions known to those skilled in the art, such as by reaction with borohydride or aluminium hydride-based reducing agent (e.g. an alkali metal borohydride or aluminium hydride, such as lithium borohydride or lithium aluminium hydride) in the presence of a reaction-inert organic solvent.

It will be understood by persons skilled in the art that compounds represented by formulae II, IIx and IIb are generally reactive intermediates. These intermediates may be formed in situ and reacted directly, without isolation, with compounds of formula III to provide compounds of formula I. Furthermore, it will be understood by those skilled in the art that the use of appropriate protective groups may be required during the processes described above for any of the groups $Z^1$ and $Z^2$ which possess chemically-sensitive functional groups, for example, a hydroxyl group or an amino function.

Many of the compounds illustrated in the Schemes are either commercially available, or can be obtained using the cited procedures, or can be readily prepared by conventional methods by those skilled in the art. See for example Regan, J. et al.; *J. Med. Chem.* 2003, 46, 4676-4686, WO 2000/043384, WO 2007/053346, WO 2007/087448, WO 2007/089512, WO 2009/117080 and WO 2014/027209.

Novel intermediates as described herein form an aspect of the invention. In this respect, further aspects of the invention relate to:

(i) a compound of formula II, IIa or IIb as hereinbefore defined, wherein $Z^1$ represents a structural fragment of formula V, or a salt or protected derivative thereof;

(ii) a compound of formula III as hereinbefore defined, wherein $Z^2$ represents a structural fragment of formula V, or a salt or protected derivative thereof;

(iii) a compound of formula VII as hereinbefore defined, wherein $R^4$ represents -$Q^4$-P(O)(O$R^9$)($R^7$), or a salt or protected derivative thereof;

(iv) a compound of formula VIIa as hereinbefore defined (e.g. a compound of formula VIIa in which $Q^x$ represents —[$C_{1-4}$ alkylene]$_{0-1}$-C(O)O—$C_{1-4}$ alkyl (e.g. —C(O)O—$C_4$ alkyl or, particularly, —C(O)O—$C_{1-3}$ alkyl) or —S(O)$_2$-$LG^2$), or a salt or protected derivative thereof; and (v) a compound of formula XIII or XIIIb as hereinbefore defined, or a salt or protected derivative thereof.

In these aspects of the invention, embodiments of the compounds of formulae II, IIa, IIb, III, VII, VIIa, XIII and XIIIb that may be mentioned include those in which one or more (e.g. all) of the following apply:

(a) $X^1$ represents N or, particularly, CH;
(b) $X^2$ represents N or, particularly, CH;
(c) $X^3$ represents C$R^{5b}$;
(d) L represents a direct bond;
(e) one of $R^{5a}$ and $R^{5b}$ (e.g. $R^{5b}$) represents H, halo (e.g. chloro), methyl, ethyl, —N(CH$_3$)$_2$, hydroxy, difluoromethoxy, trifluoromethoxy or, particularly, methoxy and the other of $R^{5a}$ and $R^{5b}$ (e.g. $R^{5a}$) represents methyl, methoxy or, particularly, H.

Other embodiments of the compounds of formulae II, IIa, IIb, III, VII and XIII that may be mentioned include those in which one or more (e.g. all) of (a) to (e) above apply and/or:

(f) $R^4$ represents —P(O)(OH)(CH$_3$) or —P(O)(OCH$_2$CH$_3$)(CH$_3$) or, for compounds of formulae II, IIa, IIb, III and XIII only, $R^4$ represents —CO$_2$H.

Other embodiments of the compounds of formulae II, IIa, IIb, III, VIIa, XIII and XIIIb that may be mentioned include those in which one or more (e.g. all) of (a) to (f) above apply and/or:

(g) $R^2$ and $R^3$, together with the C-atoms to which they are attached, form a fused phenyl ring.

Particular compounds of formulae II, IIa, IIb, III, VIIa, XIII and XIIIb, or salts or protected derivatives thereof, that may be mentioned include those in which one or more (e.g. all) of the following apply:

$R^2$ and $R^3$, together with the C-atoms to which they are attached, form a fused phenyl ring;
$X^1$, $X^2$ and $X^3$ all represent CH;
L represents a direct bond;
$R^{5a}$ represents methoxy; and
$R^4$ represents —CO$_2$H, or a protected form thereof.

Protected derivatives of the compounds of formulae III, VII, XIII and XIIIb include those in which the essential NH$_2$ group (or NH$_2$ group represented by FG) is protected. In this respect, such protected derivatives include amides or, particularly, carbamates of those compounds. For example, those protected derivatives include compounds in which a H-atom of the NH$_2$ group is replaced by:

R'—C(O)—, wherein R' is H, C$_{1-8}$ alkyl, phenyl or benzyl, which latter two groups are optionally substituted by one or more groups selected from halo, hydroxy, methyl and methoxy; or R"—O—C(O)—, wherein R" is tert-butyl, phenyl, benzyl or fluorenyl, which latter three groups are optionally substituted by one or more groups selected from halo, hydroxy, methyl and methoxy.

Protected derivatives of the compounds of formulae II, IIa, IIb, III, VII and XIII in which $R^4$ represents —CO$_2$H additionally (or alternatively) include those in which the carboxyl moiety is protected. In this respect, such protected derivatives also include esters (e.g. C$_{1-8}$ alkyl esters, such as ethyl or, particularly, methyl esters) of such compounds.

Those skilled in the art will appreciate that compounds of formula III in which $Z^2$ represents a structural fragment of formula V may be protected at the essential NH$_2$ group and/or, when $R^4$ represents —CO$_2$H, at the carboxyl moiety. In this respect, for example, particular protected derivatives of compounds of formula III in which $Z^2$ represents a structural fragment of formula V that may be mentioned include:

methyl 4-((4-((4-aminonaphthalen-1-yl)oxy)pyridin-2-yl)amino)-2-methoxybenzoate;
methyl 4-((4-((4-((tert-butoxycarbonyl)amino)naphthalen-1-yl)oxy)pyridin-2-yl)amino)-2-methoxybenzoate; and
tert-butyl (4-((2-((4-(ethoxy(methyl)phosphoryl)-3-methoxyphenyl)amino)pyridin-4-yl)oxy)naphthalen-1-yl)carbamate.

A particular compound of formula III that may be mentioned is ethyl (4-((4-((4-aminonaphthalen-1-yl)oxy)pyridin-2-yl)amino)-2-methoxyphenyl)(methyl)phosphinate.

Alternative embodiments of the invention relate to a compound that is either:

(i) a protected derivative of compound of formula III in which $Z^2$ represents a structural fragment of formula V; or (ii) a compound of formula XIIIb, or a protected derivative thereof, provided that said compound is not:
methyl 4-((4-((4-aminonaphthalen-1-yl)oxy)pyridin-2-yl)amino)-2-methoxybenzoate; or
methyl 4-((4-((4-((tert-butoxycarbonyl)amino)naphthalen-1-yl)oxy)pyridin-2-yl)amino)-2-methoxybenzoate.

Still further embodiments of the invention relate to a compound of formula VIIa as hereinbefore defined, provided that said compound either:

(a) is; or
(b) is not methyl 4-((4-((4-(3-(5-(tert-butyl)-2-methoxy-3-(methylsulfonamido)phenyl)ureido)naphthalen-1-yl)oxy)pyridin-2-yl)amino)-2-methoxybenzoate.

The aspects of the invention described herein (e.g. the above-mentioned compounds, combinations, methods and uses) may have the advantage that, in the treatment of the conditions described herein, they may be more convenient for the physician and/or patient than, be more efficacious than, be less toxic than, have better selectivity over, have a broader range of activity than, be more potent than, produce fewer side effects than, have a better pharmacokinetic and/or pharmacodynamic profile than, have more suitable solid state morphology than, have better long term stability than, or may have other useful pharmacological properties over, similar compounds, combinations, methods (treatments) or uses known in the prior art for use in the treatment of those conditions or otherwise.

The compounds of the invention may additionally (or alternatively):

exhibit a long duration of action and/or persistence of action (e.g. in comparison to other previously disclosed p38 MAP kinase inhibitors such as, for example, BIRB796);

exhibit potent inhibition of Syk (e.g. they may have an IC$_{50}$ against Syk of 500 nM or less, such as 350 nM or less);

not strongly inhibit GSK 3α (e.g. they may have an IC$_{50}$ against GSK 3α of 1,000 nM or greater; such as 1,500, 2,000, 3,000, 4,000, 5,000, 6,000, 7,000, 8,000, 9,000 or 10,000 nM or greater);

target a smaller portion of the kinome, i.e., with improved selectivity, as illustrated by lowered KinomeScan Selectivity Scores;

maintain a relatively high local drug concentration between doses (e.g. a high local concentration relative to other previously disclosed p38 MAP kinase inhibitors such as, for example, BIRB796);

exhibit properties that are particularly suited to topical/local administration (e.g. following topical/local administration, the generation of high target tissue concentrations but low plasma concentrations of the compounds of formula (I) and/or rapid clearance of the compounds of formula (I) from plasma, for example as a result of high renal or hepatic extraction);

exhibit little or no β-catenin induction and/or inhibition of mitosis in cells;

display reduced cytotoxicities;

not produce increases in binucleated cells containing micronuclei in the human lymphocyte in vitro micronucleus test;

exhibit little or no time-dependent inhibition of members of the cytochrome P450 superfamily;

show improved chemical stability in the presence of water (e.g. stability to hydrolysis in aqueous mixtures at elevated temperatures) compared to previously disclosed p38 MAP kinase inhibitors such as, for example, BIRB796;

following administration to a patient, give rise to metabolites associated with little or no safety (e.g. toxicity) concerns;

display reduced ocular irritancy or toxicity in both preclinical species and humans following topical administration;

exhibit good aqueous solubility and/or cellular permeability (e.g. exhibit good aqueous solubility and potent inhibition of the release of certain cytokines, such as IL-8 and/or IFNγ, in cells);

be more readily formulated in aqueous solution in the pH range 7-8 with lower quantities of solubilising excipients;

have a high degree of crystallinity; and/or exhibit little or no hygroscopicity in the solid state.

EXPERIMENTAL METHODS

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated or under a balloon of hydrogen. Microwave reactions were performed in a CEM Discover and Smithcreator microwave reactor, heating to a constant temperature using variable power microwave irradiation.

Normal phase column chromatography was routinely carried out on an automated flash chromatography system such as CombiFlash Companion or CombiFlash RF system using pre-packed silica (230-400 mesh, 40-63 μm) cartridges. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% $NH_3$ in MeOH.

Analytical Methods

Analytical HPLC was carried out using a Waters Xselect CSH C18, 2.5 μm, 4.6×30 mm column eluting with a gradient of 0.1% Formic Acid in MeCN in 0.1% aqueous Formic Acid or a Waters Xbridge BEH C18, 2.5 μm, 4.6×30 mm column eluting with a gradient of MeCN in aqueous 10 mM Ammonium Bicarbonate. UV spectra of the eluted peaks were measured using either a diode array or variable wavelength detector on an Agilent 1100 system.

Analytical LCMS was carried out using a Waters Xselect CSH C18, 2.5 μm, 4.6×30 mm column eluting with a gradient of 0.1% Formic Acid in MeCN in 0.1% aqueous Formic Acid or a Waters Xbridge BEH C18, 2.5 μm, 4.6×30 mm column eluting with a gradient of MeCN in aqueous 10 mM Ammonium Bicarbonate. UV and mass spectra of the eluted peaks were measured using a variable wavelength detector on either an Agilent 1200 or an Agilent Infinity 1260 LCMS with 6120 single quadrupole mass spectrometer with positive and negative ion electrospray.

Preparative HPLC was carried out using a Waters Xselect CSH C18, 5 μm, 19×50 mm column using either a gradient of either 0.1% Formic Acid in MeCN in 0.1% aqueous Formic Acid or a gradient of MeCN in aqueous 10 mM Ammonium Bicarbonate or employing a Waters Xbridge BEH O18, 5 μm, 19×50 mm column using a gradient of MeCN in aqueous 10 mM Ammonium Bicarbonate. Fractions were collected following detection by UV at a single wavelength measured by a variable wavelength detector on a Gilson 215 preparative HPLC or Varian PrepStar preparative HPLC or by mass and UV at a single wavelength measured by a ZQ single quadrupole mass spectrometer, with positive and negative ion electrospray, and a dual wavelength detector on a Waters FractionLynx LCMS.

$^1$H NMR Spectroscopy: $^1$H NMR spectra were acquired on a Bruker Avance III spectrometer at 400 MHz. Either the central peaks of chloroform-d, dimethylsulfoxide-$d_6$ or an internal standard of tetramethylsilane were used as references.

Preparation of Compounds of the Invention

Example 1

4-((4-((4-(3-(5-(tert-Butyl)-2-methoxy-3-(methylsulfonamido)phenyl)ureido)naphthalen-1-yl)oxy)pyridin-2-yl)amino)-2-methoxybenzoic acid

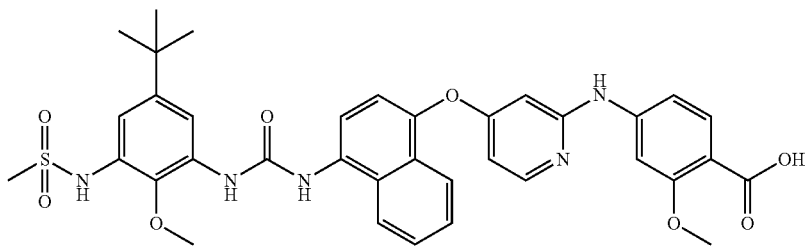

(i) tert-Butyl (4-((2-chloropyridin-4-yl)oxy)naphthalen-1-yl)carbamate

Method 1

A mixture of 4-((2-chloropyridin-4-yl)oxy)naphthalen-1-amine (see, for example, Ito, K. et al., WO 2010/112936, 7 Oct. 2010; 1000 mg, 3.69 mmol) and di-tert-butyl dicarbonate (750 mg, 3.44 mmol) in t-BuOH (10 mL) was stirred at reflux for 18 h. The mixture was diluted with water (15 mL) and the solid collected by filtration. The solid was triturated in diethyl ether to yield the sub-title compound (1002 mg) as a pale grey solid.

$^1$H NMR (DMSO-d6) 400 MHz, δ: 9.37 (s, 1H), 8.28 (d, 1H), 8.16 (d, 1H), 8.82 (dd, 1H), 7.66 (d, 1H), 7.66-7.54 (m, 2H), 7.40 (d, 1H), 7.03 (d, 1H), 6.91 (dd, 1H), 1.52 (s, 9H).

LCMS m/z 371 (M+H)$^+$ (ES$^+$); 369 (M−H)$^-$ (ES$^-$)

Method 2

2-Chloro-4-fluoropyridine (33 mL, 365 mmol) was added to a mixture of tert-butyl (4-hydroxynaphthalen-1-yl)carbamate (85 g, 328 mmol) and $Cs_2CO_3$ (139 g, 426 mmol) in DMSO (600 mL) and stirred at rt for 24 h. Water (1 L) was added, the mixture stirred for 1 h, then the precipitate filtered off. The reaction was repeated on a further 85 g scale of naphthol. The combined precipitates were washed with water (2 L), ether (4×400 mL) and dried under vacuum at 70° C. for 72 h to afford the sub-title compound (201.6 g) as a light grey solid.

$^1$H NMR (400 MHz, DMSO-d6) δ 9.38 (s, 1H), 8.28 (d, 1H), 8.16 (d, 1H), 7.82 (d, 1H), 7.67-7.56 (m, 3H), 7.40 (d, 1H), 7.03 (d, 1H), 6.92 (dd, 1H), 1.52 (s, 9H).

LCMS m/z 371 (M+H)$^+$ (ES$^+$); 369 (M−H)$^−$ (ES$^−$)

(ii) Methyl 4-((4-((4-((tert-butoxycarbonyl)amino) naphthalen-1-yl)oxy)pyridin-2-yl)amino)-2-methoxybenzoate Method 1

A suspension of the product from step (i) above (2.0 g, 5.39 mmol), methyl 4-amino-2-methoxybenzoate (1.0 g, 5.52 mmol), BINAP (300 mg, 0.482 mmol) and cesium carbonate (3.5 g, 10.74 mmol) in 1,4-dioxane (30 mL) was degassed with nitrogen for 10 min. $Pd_2dba_3$ (200 mg, 0.218 mmol) was added and the mixture was heated to 90° C. overnight. The mixture was diluted with diethyl ether (60 mL) and filtered. The filtrate was then washed with water (2×100 mL), and saturated brine (50 mL). The organic phase was dried (MgSO$_4$), filtered and concentrated under reduced pressure to yield the crude product as a red foam. The crude product was purified by chromatography on the Companion (80 g column, 20-50% EtOAc in hexane) to afford the sub-title compound (2.34 g) as a yellow foam.

$^1$H NMR (400 MHz, DMSO-d6) δ: 9.38 (s, 1H), 9.36 (s, 1H), 8.18 (d, 1H), 8.14 (d, 1H), 7.83 (d, 1H), 7.54-7.66 (m, 5H), 7.37 (d, 1H), 7.22 (dd, 1H), 6.69 (dd, 1H), 6.15 (d, 1H), 3.74 (s, 3H), 3.71 (s, 3H), 1.53 (s, 9H).

LCMS m/z 516 (M+H)$^+$ (ES$^+$)

Method 2

A mixture of methyl 4-amino-2-methoxybenzoate (10.8 g, 59.6 mmol), the product from step (i) above (20.09 g, 54.2 mmol) and potassium carbonate (15 g, 109 mmol) in DMF (300 mL) was degassed with $N_2$ for 10 min. BrettPhos G3 precatalyst (1 g, 1.103 mmol) was added and the mixture heated at 85° C. for 3 h. The mixture was cooled then partitioned between DCM (500 mL) and water (800 mL). The organic layer was washed with water (500 mL), dried (MgSO$_4$), filtered and evaporated under reduced pressure. The residue was triturated with ether, filtered and dried to afford the sub-title compound (21.7 g) as a grey solid.

$^1$H NMR (400 MHz, DMSO-d6) δ 9.38 (s, 1H), 9.36 (s, 1H), 8.18 (d, 1H), 8.14 (d, 1H), 7.83 (d, 1H), 7.54-7.66 (m, 5H), 7.38 (d, 1H), 7.22 (dd, 1H), 6.69 (dd, 1H), 6.14 (d, 1H), 3.74 (s, 3H), 3.71 (s, 3H), 1.53 (s, 9H).

LCMS m/z 516 (M+H)$^+$ (ES$^+$)

(iii) Methyl 4-((4-((4-aminonaphthalen-1-yl)oxy) pyridin-2-yl)amino)-2-methoxybenzoate TFA (7 mL, 91 mmol) was added to a solution of the product from step (ii) above (2.34 g, 4.08 mmol) in DCM (50 mL) and the reaction stirred for 2 h. The solvents were evaporated and the residue partitioned between sat NaHCO$_3$ soln. (100 mL) and DCM (60 mL). The organics were separated, dried (MgSO$_4$), filtered and the solvent evaporated to afford the sub-title compound (1.5 g) as a pale brown foam.

LCMS m/z 416 (M+H)$^+$ (ES$^+$)

(iv) Phenyl (5-(tert-butyl)-2-methoxy-3-(methylsulfonamido)phenyl)carbamate

Phenyl chloroformate (0.750 mL, 5.98 mmol) was added to a stirred solution of N-(3-amino-5-(tert-butyl)-2-methoxyphenyl)methanesulfonamide (see, for example, Cirillo, P. F. et al., WO 2002/083628, 24 Oct. 2002; 1.5 g, 5.51 mmol) and NaHCO$_3$ (1.0 g, 11.90 mmol) in THF (15 mL) and DCM (15 mL) and the mixture was stirred for 2 h. The mixture was washed with water (20 mL) and the organic layer separated, dried (MgSO$_4$), filtered and evaporated to a brown foam which was stirred in cyclohexane (20 mL) to afford the sub-title compound (2.05 g) as a colourless solid.

LCMS m/z 393 (M+H)$^+$ (ES$^+$); 391 (M−H)$^−$ (ES$^−$)

(v) Methyl 4-((4-((4-(3-(5-(tert-butyl)-2-methoxy-3-(methylsulfonamido)phenyl)ureido)-naphthalen-1-yl)oxy)pyridin-2-yl)amino)-2-methoxybenzoate Method 1

Triethylamine (20 μL, 0.143 mmol) was added to a solution of the product from step (iv) above (300 mg, 0.764 mmol) and the product from step (ii) above (300 mg, 0.722 mmol) in iPrOAc (15 mL) at 65° C. (block temperature) and the mixture stirred overnight. The reaction was cooled to rt and concentrated in vacuo affording a pale brown foam. The foam was slurried in Et$_2$O (10 mL) for 2 h and the resulting solid collected by filtration, washing with further portions of Et$_2$O, affording the sub-title compound (433 mg) as a pale pink solid.

LCMS m/z 358 (M+2H)$^{2+}$ (ES$^+$)

Method 2

Triethylamine (600 μL, 4.30 mmol) was added to a solution of the product from step (iv) above (9.0 g, 22.93 mmol) and the product from step (iii) above (9.0 g, 21.66 mmol) in iPrOAc (300 mL) at 65° C. (block temperature) and the mixture stirred for 24 h. The reaction was cooled to room temperature and concentrated in vacuo affording a brown foam. The crude product was purified by chromatography on the Companion (330 g column, 1-5% MeOH in DCM) to afford the sub-title compound (13.2 g) as a pale pink solid.

$^1$H NMR (400 MHz, DMSO-d6) δ: 9.40 (s, 1H), 9.35 (s, 1H), 916 (s, 1H), 8.93 (s, 1H), 8.31 (d, 1H), 8.17-8.20 (m, 2H), 8.13 (d, 1H), 7.87 (d, 1H), 7.69-7.73 (m, 1H), 7.60-7.63 (m, 2H), 7.53 (d, 1H), 7.41 (d, 1H), 7.24 (dd, 1H), 7.03 (d, 1H), 6.69 (dd, 1H), 6.17 (d, 1H), 3.81 (s, 3H), 3.74 (s, 3H), 3.71 (s, 3H), 3.10 (s, 3H), 1.27 (s, 9H).

LCMS m/z 714 (M+H)$^+$ (ES$^+$)

(vi) 4-((4-((4-(3-(5-(tert-Butyl)-2-methoxy-3-(methylsulfonamido)phenyl)ureido)naphthalen-1-yl)oxy) pyridin-2-yl)amino)-2-methoxybenzoic acid Method 1

An aqueous solution of lithium hydroxide monohydrate (25 mg, 0.596 mmol) in water (3 mL) was added to a solution of the product from step (v) above (433 mg, 0.540 mmol) in THF (2 mL) and methanol (1 mL) and the mixture was stirred at rt overnight. Lithium hydroxide monohydrate (25 mg, 0.596 mmol) was added and stirring was continued for a further 3 days. The mixture was concentrated under reduced pressure to remove THF and methanol then diluted with water (25 mL). A solution of citric acid monohydrate (250 mg, 1.190 mmol) in water (5 mL) was added and the resulting precipitate was collected by filtration to yield the title compound (360 mg) as a pale pink solid.

$^1$H NMR (400 MHz, DMSO-d6) δ 11.96 (br s, 1H), 9.39 (s, 1H), 9.31 (s, 1H), 9.14 (s, 1H), 8.91 (s, 1H), 8.30 (d, 1H), 8.19 (d, 1H), 8.18 (d, 1H), 8.12 (d, 1H), 7.87 (d, 1H), 7.71 (ddd, 1H), 7.63 (d, 1H), 7.61 (ddd, 1H), 7.51 (d, 1H), 7.40 (d, 1H), 7.22 (dd, 1H), 7.02 (d, 1H), 6.68 (dd, 1H), 6.16 (d, 1H), 3.81 (s, 3H), 3.75 (s, 3H), 3.10 (s, 3H), 1.27 (s, 9H). 90% purity LCMS m/z 700 (M+H)$^+$ (ES$^+$)

Method 2

To a stirred solution of the product from step (v) above (33.4 g, 45.9 mmol) in THF (300 mL) was added NaOH (6M aq.) (85.0 mL, 510 mmol). MeOH (60 mL) was added and stirring continued for 28 h. The reaction was concentrated in vacuo affording a yellow solid. The material was suspended in water (200 mL) and acidified with 6M HCl (100 mL) causing a white solid to precipitate. The solid was collected by filtration, washing with water. The resulting solid was dried on the frit for 1 h then further dried at 40° C. under vacuum affording the title compound as the hydrochloride salt as a white solid.

$^1$H NMR (of hydrochloride salt; 400 MHz, DMSO-d6) δ: 9.80 (s, 1H), 9.59 (s, 1H), 9.15 (s, 1H), 9.02 (s, 1H), 8.37 (d, 1H), 8.13-8.18 (m, 3H), 7.86 (d, 1H), 7.70-7.74 (m, 1H), 7.62-7.66 (m, 2H), 7.44 (d, 1H), 7.35 (s, 1H), 7.10 (d, 1H), 7.03 (d, 1H), 6.78 (d, 1H), 6.26 (d, 1H), 3.81 (s, 3H), 3.75 (s, 3H), 3.10 (s, 3H), 1.27 (s, 9H).

LCMS m/z 700 (M+H)$^+$ (ES$^+$)

The hydrochloride salt was loaded in 2.0 g batches, dissolved in THF, onto a pre-conditioned cartridge of SCX resin (20 g of resin, conditioned in MeCN). The resin was washed with MeCN then the product released in 1% NH$_3$ in MeOH. The NH$_3$ fractions were combined and concentrated in vacuo, affording the title compound (30 g) as the free acid as a pale pink solid.

$^1$H NMR (of free acid; 400 MHz, DMSO-d6) δ: 9.56 (s, 1H), 9.28 (s, 1H), 9.00 (s, 1H), 8.34 (d, 1H), 8.16-8.17 (m, 2H), 8.11 (d, 1H), 7.86 (d, 1H), 7.69-7.71 (m, 1H), 7.57-7.63 (m, 2H), 7.48 (d, 1H), 7.40 (d, 1H), 7.21 (dd, 1H), 7.03 (d, 1H), 6.66 (dd, 1H), 6.16 (d, 1H), 3.81 (s, 3H), 3.73 (s, 3H), 3.09 (s, 3H), 1.27 (s, 9H).

LCMS m/z 700 (M+H)$^+$ (ES$^+$)

The free acid (1.0 g, 1.386 mmol) was suspended in an aqueous solution of NaOH (0.057 g, 1.414 mmol) in water (25 mL). MeOH (5 mL) was added and the mixture stirred until homogeneity was achieved. The resulting solution was diluted with MeOH (20 mL) and concentrated in vacuo, affording a pale grey solid. The material was suspended in MeCN (5 mL), to which water (0.5 mL) was added and the suspension stirred over the weekend. The suspension was filtered and the resulting solid washed with MeCN (2×3 mL) and dried under vacuum at 50° C., affording the title compound as the sodium salt (940 mg) as a white solid.

$^1$H NMR (of sodium salt; 400 MHz, DMSO-d6) δ: 9.68 (s, 1H), 9.07 (s, 1H), 9.02 (s, 1H), 8.35 (d, 1H), 8.08-8.13 (m, 2H), 8.02 (d, 1H), 7.85 (d, 1H), 7.64-7.68 (m, 1H), 7.57-7.61 (m, 1H), 7.37-7.43 (m, 2H), 7.30 (s, 1H), 7.11 (dd, 1H), 7.03 (d, 1H), 6.61 (dd, 1H), 6.12 (d, 1H), 3.80 (s, 3H), 3.65 (s, 3H), 2.96 (s, 3H), 1.25 (s, 9H).

LCMS m/z 700 (M+H)$^+$ (ES$^+$)

Example 2

4-((4-((4-(3-(5-(tert-Butyl)-2-methoxy-3-(methylsulfonamido)phenyl)ureido)naphthalen-1-yl)oxy)pyridin-2-yl)amino)-2-methoxy-N-(2-morpholinoethyl) benzamide

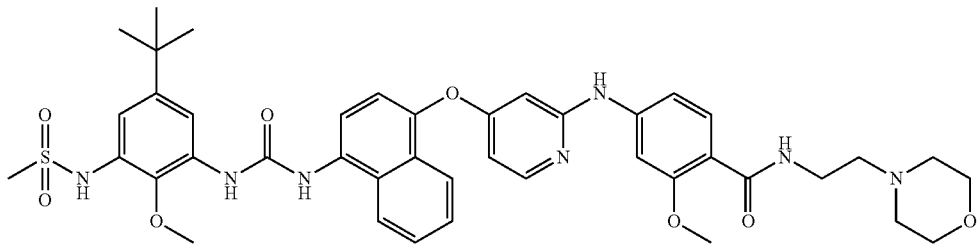 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCOCC1]

HATU (50 mg, 0.131 mmol) was added to a stirred solution of Example 1 above (80 mg, 0.102 mmol), 2-morpholinoethanamine (30 mg, 0.230 mmol) and Hünig's Base (50 μL, 0.286 mmol) in DMF (2 mL) and stirred at rt overnight. The mixture was diluted with water (10 mL) and extracted with ethyl acetate (10 mL). The organic phase was washed with saturated brine (10 mL), dried (MgSO$_4$) and filtered. The solvent was removed under reduced pressure and the crude product was purified by preparative HPLC (Gilson, Acidic (0.1% Formic acid), Acidic, Waters X-Select Prep-C18, 5 μm, 19×50 mm column, 20-50% MeCN in Water) to afford a colourless foam. The foam was dissolved in ethyl acetate (10 mL) then washed with saturated NaHCO$_3$ solution (10 mL), saturated brine (10 mL), dried (MgSO$_4$), filtered and evaporated under reduced pressure to afford the title compound (27 mg) as a white solid.

$^1$H NMR (400 MHz, DMSO-d6) δ 9.40 (s, 1H), 9.26 (s, 1H), 9.14 (s, 1H), 8.92 (s, 1H), 8.30 (d, 1H), 8.21 (t, 1H), 8.19 (d, 1H), 8.17 (d, 1H), 8.12 (d, 1H), 7.87 (d, 1H), 7.77 (d, 1H), 7.71 (ddd, 1H), 7.62 (ddd, 1H), 7.58 (d, 1H), 7.40 (d, 1H), 7.23 (dd, 1H), 7.03 (d, 1H), 6.65 (dd, 1H), 6.16 (d, 1H), 3.87 (s, 3H), 3.81 (s, 3H), 3.66-3.55 (m, 4H), 3.43-3.33 (m, 2H), 3.10 (s, 3H), 2.46 (t, 2H), 2.46-2.36 (m, 4H), 1.27 (s, 9H).

LCMS m/z 812 (M+H)$^+$ (ES$^+$)

Example 3

4-((4-((4-(3-(5-(tert-Butyl)-3-carbamoyl-2-methoxyphenyl)ureido)naphthalen-1-yl)oxy)pyridin-2-yl)amino)-2-methoxybenzoic acid

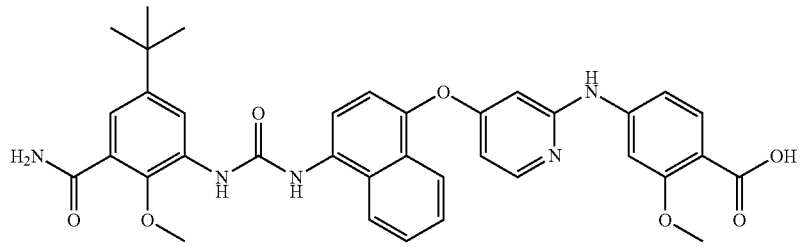 [SMILES: COc1cc(Nc2cc(Oc3ccc(NC(=O)Nc4cc(C(C)(C)C)cc(C(N)=O)c4OC)c4ccccc34)ccn2)ccc1C(=O)O]

(i) Phenyl (5-(tert-butyl)-3-carbamoyl-2-methoxyphenyl)carbamate

Phenyl chloroformate (1.0 mL, 7.97 mmol) was added to a stirred solution of 3-amino-5-(tert-butyl)-2-methoxybenzamide (1.32 g, 5.94 mmol) and NaHCO$_3$ (1.5 g, 17.86 mmol) in THF (25 mL) and DCM (50 mL) and the mixture stirred overnight. The reaction was diluted with DCM (30 mL) and water (50 mL) and the organic phase dried via hydrophobic frit then concentrated in vacuo affording a waxy white solid. The solid was slurried in cyclohexane (40 mL) for 3 h then isolated by filtration to afford the sub-title compound (1.9 g) as a fluffy, white solid.

LCMS m/z 343 (M+H)$^+$ (ES$^+$)

(ii) Methyl 4-((4-((4-(3-(5-(tert-butyl)-3-carbamoyl-2-methoxyphenyl)ureido)naphthalen-1-yl)oxy)pyridin-2-yl)amino)-2-methoxybenzoate Triethylamine (20 µL, 0.143 mmol) was added to a solution of the product from step (i) above (250 mg, 0.730 mmol) and methyl 4-((4-((4-aminonaphthalen-1-yl)oxy)pyridin-2-yl)amino)-2-methoxybenzoate (see Example 1(iii) above; 300 mg, 0.722 mmol) in iPrOAc (15 mL) at 65° C. (block temperature) and the mixture stirred overnight. The reaction was cooled to rt causing a solid to precipitate. The solid was collected by filtration to afford the sub-title compound (150 mg) as a dark pink solid. The filtrate was concentrated in vacuo affording a yellow oil. The oil was slurried in Et$_2$O for 2 h after which time the resulting solid was recovered by filtration washing with more Et$_2$O to afford a 2$^{nd}$ crop of the product (246 mg) as a pale pink solid.

LCMS m/z 333 (M+2H)$^{2+}$ (ES$^+$), 90% purity

(iii) 4-((4-((4-(3-(5-(tert-Butyl)-3-carbamoyl-2-methoxyphenyl)ureido)naphthalen-1-yl)oxy)pyridin-2-yl)amino)-2-methoxybenzoic acid An aqueous solution of lithium hydroxide monohydrate (25 mg, 0.596 mmol) in water (3 mL) was added to a solution of the product from step (ii) above (396 mg, 0.537 mmol) in THF (2 mL) and methanol (1 mL) and the mixture was stirred at rt overnight. Lithium hydroxide monohydrate (25 mg, 0.596 mmol) was added and stirring was continued for a further 3 days. The mixture was concentrated under reduced pressure to remove THF and methanol then diluted with water (25 mL). A solution of citric acid (250 mg, 1.190 mmol) in water (5 mL) was added and the resulting precipitate was collected by filtration to afford the title compound (300 mg) as a pale pink solid.

$^1$H NMR (400 MHz, DMSO-d6) δ 11.93 (br s, 1H), 9.47 (s, 1H), 9.31 (s, 1H), 8.92 (s, 1H), 8.46 (d, 1H), 8.31 (d, 1H), 8.18 (d, 1H), 8.11 (d, 1H), 7.87 (d, 1H), 7.73-7.66 (m, 1H), 7.71 (ddd, 1H), 7.63 (d, 1H), 7.61 (ddd, 1H), 7.56 (br s, 1H), 7.51 (d, 1H), 7.41 (dd, 1H), 7.22 (d, 1H), 7.22 (dd, 1H), 6.67 (dd, 1H), 6.17 (d, 1H), 3.83 (s, 3H), 3.75 (s, 3H), 1.29 (s, 9H).

LCMS m/z 650 (M+H)$^+$ (ES$^+$)

Example 4

4-((4-((4-(3-(5-(tert-Butyl)-3-carbamoyl-2-methoxyphenyl)ureido)naphthalen-1-yl)oxy)pyridin-2-yl)amino)-2-methoxy-N-(2-morpholinoethyl)benzamide

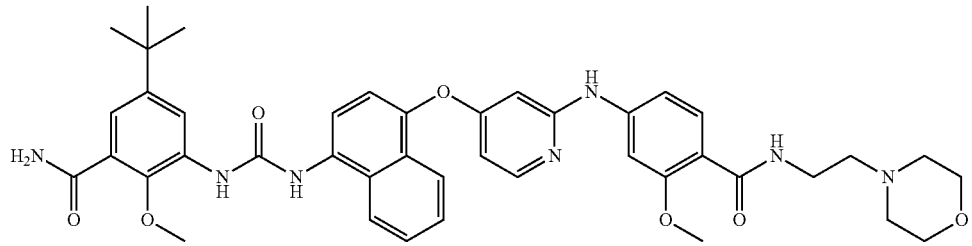 [SMILES: COc1cc(Nc2cc(Oc3ccc(NC(=O)Nc4cc(C(C)(C)C)cc(C(N)=O)c4OC)c4ccccc34)ccn2)ccc1C(=O)NCCN1CCOCC1]

HATU (50 mg, 0.131 mmol) was added to a stirred solution of Example 3 above (80 mg, 0.123 mmol), 2-morpholinoethanamine (30 mg, 0.230 mmol) and Hünig's Base (50 µL, 0.286 mmol) in DMF (2 mL) and stirred at rt overnight. The mixture was diluted with water (10 mL) and extracted with ethyl acetate (10 mL). The organic phase was washed with saturated brine (10 mL), dried (MgSO$_4$) and filtered. The solvent was removed under reduced pressure and the crude product was purified by preparative HPLC (Gilson, Acidic (0.1% Formic acid), Acidic, Waters X-Select Prep-C18, 5 µm, 19×50 mm column, 20-50% MeCN in Water) to afford a colourless foam. The foam was dissolved in ethyl acetate (10 mL) then washed with saturated NaHCO₃ solution (10 mL), saturated brine (10 mL), dried (MgSO₄), filtered and evaporated under reduced pressure to afford the title compound (14 mg) as a white solid.

¹H NMR (400 MHz, DMSO-d6) δ 9.49 (s, 1H), 9.27 (s, 1H), 8.93 (s, 1H), 8.46 (d, 1H), 8.31 (t, 1H), 8.21 (t, 1H), 8.17 (d, 1H), 8.11 (d, 1H), 7.87 (d, 1H), 7.77 (d, 1H), 7.74-7.67 (m, 2H), 7.62 (ddd, 1H), 7.60-7.53 (m, 2H), 7.40 (d, 1H), 7.23 (dd, 1H), 7.22 (d, 1H), 6.65 (dd, 1H), 6.16 (d, 1H), 3.88 (s, 3H), 3.83 (s, 3H), 3.65-3.56 (m, 4H), 3.46-3.35 (m, 2H), 2.46 (t, 2H), 2.46-2.36 (m, 4H), 1.29 (s, 9H).

LCMS m/z 762 (M+H)⁺ (ES⁺)

Example 5

4-((4-((4-(3-(5-(tert-Butyl)-2-methoxy-3-(methylsulfonamido)phenyl)ureido)naphthalen-1-yl)oxy)pyridin-2-yl)amino)-2-methoxy-N-(2-(2-(2-methoxyethoxy)ethoxy)ethyl)benzamide

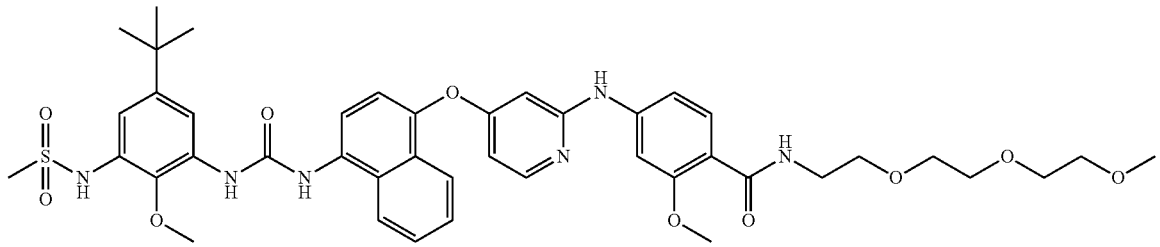

HATU (50 mg, 0.131 mmol) was added to a stirred solution of 4-((4-((4-(3-(5-(tert-butyl)-2-methoxy-3-(methylsulfonamido)phenyl)ureido)naphthalen-1-yl)oxy)pyridin-2-yl)amino)-2-methoxybenzoic acid (see Example 1 above; 80 mg, 0.102 mmol), 2-(2-(2-methoxyethoxy)-ethoxy)ethanamine (30 mg, 0.184 mmol) and Hünig's base (50 µL, 0.286 mmol) in DMF (2 mL) and stirred at rt overnight. The mixture was diluted with water (10 mL) and extracted with ethyl acetate (10 mL). The organic phase was washed with saturated brine (10 mL), dried (MgSO₄) and filtered. The solvent was removed under reduced pressure and the crude product was purified by preparative HPLC (Gilson, Acidic (0.1% Formic acid), Acidic, Waters X-Select Prep-C18, 5 µm, 19×50 mm column, 20-50% MeCN in Water) to afford a colourless foam. The foam was dissolved in ethyl acetate (10 mL) then washed with saturated NaHCO₃ solution (10 mL), saturated brine (10 mL), dried (MgSO₄) and filtered. The solvent was removed under reduced pressure and the residue was purified by chromatography on the Companion (4 g column, 2-5% MeOH/DCM) to afford the title compound (19 mg) as a cream solid.

¹H NMR (400 MHz, DMSO-d6) δ 9.40 (s, 1H), 9.28 (s, 1H), 9.16 (s, 1H), 8.93 (s, 1H), 8.31 (d, 1H), 8.19 (d, 1H), 8.17 (d, 1H), 8.13 (d, 1H), 8.10 (t, 1H), 7.87 (d, 1H), 7.76 (d, 1H), 7.71 (ddd, 1H), 7.62 (ddd, 1H), 7.59 (d, 1H), 7.40 (d, 1H), 7.23 (dd, 1H), 7.02 (d, 1H), 6.66 (dd, 1H), 6.15 (d, 1H), 3.85 (s, 3H), 3.81 (s, 3H), 3.58-3.43 (m, 8H), 3.47-3.36 (m, 4H), 3.22 (s, 3H), 3.10 (s, 3H), 1.27 (s, 9H).

LCMS m/z 845 (M+H)⁺ (ES⁺); 843 (M−H)⁻ (ES⁻)

Example 6

4-((4-((4-(3-(5-(tert-Butyl)-3-carbamoyl-2-methoxyphenyl)ureido)naphthalen-1-yl)oxy)pyridin-2-yl)amino)-2-methoxy-N-(2-(2-(2-methoxyethoxy)ethoxy)ethyl)benzamide

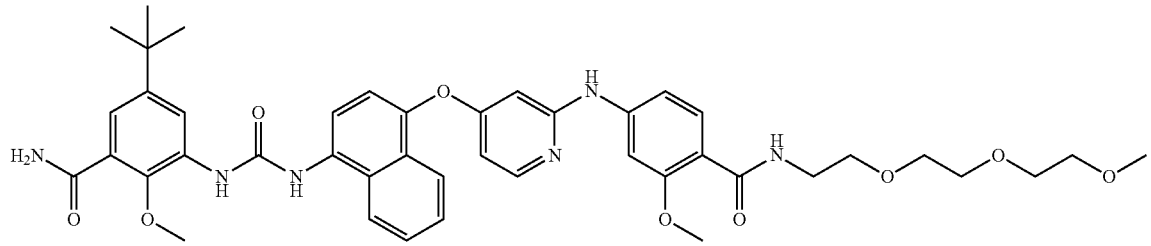 [SMILES: COCCOCCOCCNC(=O)c1ccc(Nc2cc(Oc3ccc(NC(=O)Nc4cc(C(C)(C)C)cc(C(N)=O)c4OC)c4ccccc34)ccn2)cc1OC]

HATU (50 mg, 0.131 mmol) was added to a stirred solution of 4-((4-((4-(3-(5-(tert-butyl)-3-carbamoyl-2-methoxyphenyl)ureido)naphthalen-1-yl)oxy)pyridin-2-yl)amino)-2-methoxybenzoic acid (see Example 3 above; 80 mg, 0.123 mmol), 2-(2-(2-methoxyethoxy)ethoxy)ethanamine (30 mg, 0.184 mmol) and Hünig's Base (50 µL, 0.286 mmol) in DMF (2 mL) and stirred at rt overnight. The mixture was diluted with water (10 mL) and extracted with ethyl acetate (10 mL). The organic phase was washed with saturated brine (10 mL), dried (MgSO$_4$) and filtered. The solvent was removed under reduced pressure and the crude product was purified by preparative HPLC (Gilson, Acidic (0.1% Formic acid), Acidic, Waters X-Select Prep-C18, 5 µm, 19×50 mm column, 20-50% MeCN in Water) to afford a colourless foam. The foam was dissolved in ethyl acetate (10 mL) then washed with saturated NaHCO$_3$ solution (10 mL), saturated brine (10 mL), dried (MgSO$_4$) and filtered. The solvent was removed under reduced pressure and the residue was purified by chromatography on the Companion (4 g column, 2-5% MeOH/DCM) to afford the title compound (9 mg) as a cream solid.

$^1$H NMR (400 MHz, DMSO-d6) δ 9.48 (s, 1H), 9.28 (s, 1H), 8.93 (s, 1H), 8.46 (d, 1H), 8.31 (d, 1H), 8.17 (d, 1H), 8.11 (d, 1H), 8.10 (t, 1H), 7.87 (d, 1H), 7.78-7.67 (m, 3H), 7.62 (ddd, 1H), 7.61-7.55 (m, 2H), 7.41 (d, 1H), 7.23 (dd, 1H), 7.22 (d, 1H), 6.66 (dd, 1H), 6.16 (d, 1H), 3.85 (s, 3H), 3.83 (s, 3H), 3.57-3.48 (m, 8H), 3.47-3.37 (m, 4H), 3.22 (s, 3H), 1.27 (s, 9H).

LCMS m/z 795 (M+H)$^+$ (ES$^+$); 793 (M-H)$^-$ (ES$^-$)

Example 7

4-((4-((4-(3-(5-(tert-Butyl)-2-methoxy-3-(methylsulfonamido)phenyl)ureido)naphthalen-1-yl)oxy)pyridin-2-yl)amino)-2-methoxy-N-(2-(1-oxidothiomorpholino)ethyl)benzamide

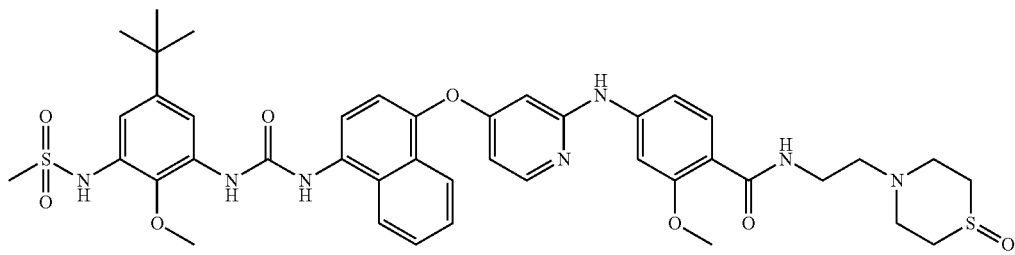 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCS(=O)CC1]

HATU (80 mg, 0.210 mmol) was added to a solution of 4-((4-((4-(3-(5-(tert-butyl)-2-methoxy-3-(methylsulfonamido)phenyl)ureido)naphthalen-1-yl)oxy)pyridin-2-yl)amino)-2-methoxybenzoic acid (see Example 1 above; 100 mg, 0.143 mmol), 4-(2-aminoethyl)thiomorpholine 1-oxide (30 mg, 0.185 mmol) and Hünig's Base (75 µL, 0.429 mmol) in N,N-dimethylformamide (2 mL) and stirred at rt for 2 h. The mixture was diluted with water (10 mL) then the precipitate was collected by filtration and washed with water (2×3 mL). The filter cake was purified by chromatography on silica gel (12 g column, 2% MeOH:DCM to 10%) and then by preparative HPLC (Waters, Acidic (0.1% Formic acid), Acidic, Waters X-Select Prep-C18, 5 µm, 19×50 mm column, 20-50% MeCN in Water) to afford the title compound (18 mg) as a colourless solid.

¹H NMR (400 MHz, DMSO-d6) δ 9.41 (s, 1H), 9.26 (s, 1H), 9.14 (s, 1H), 8.92 (s, 1H), 8.31 (d, 1H), 8.24-8.07 (m, 4H), 7.87 (d, 1H), 7.76 (d, 1H), 7.74-7.67 (m, 1H), 7.66-7.59 (m, 1H), 7.57 (d, 1H), 7.40 (d, 1H), 7.23 (d, 1H), 7.03 (d, 1H), 6.66 (dd, 1H), 6.16 (d, 1H), 3.86 (s, 3H), 3.81 (s, 3H), 3.46-3.35 (m, 2H), 3.10 (s, 3H), 3.01-2.81 (m, 4H), 2.81-2.63 (m, 4H), 2.55 (t, 2H), 1.27 (s, 9H).

LCMS m/z 845 (M+H)⁺ (ES⁺)

Example 8

N-(5-(tert-Butyl)-3-(3-(4-((2-((3-cyano-4-(2-(2-(2-methoxyethoxy)ethoxy)ethoxy)phenyl) amino)pyridin-4-yl)oxy)naphthalen-1-yl)ureido)-2-methoxyphenyl)methanesulfonamide

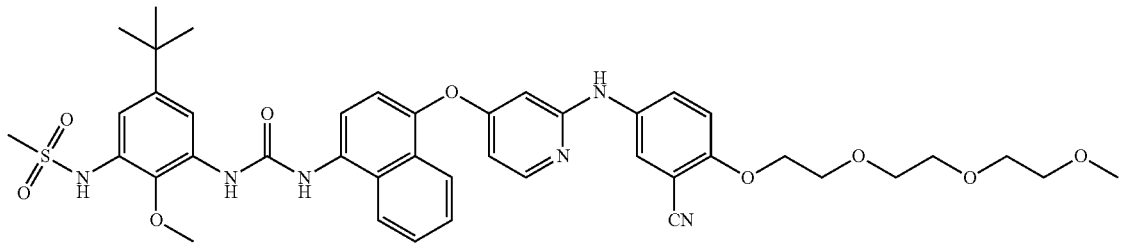

(i) N-(5-(tert-Butyl)-3-(3-(4-((2-chloropyridin-4-yl) oxy)naphthalen-1-yl)ureido)-2-methoxyphenyl) methanesulfonamide 4-((2-Chloropyridin-4-yl)oxy)naphthalen-1-amine (see, for example, Ito, K. et al., WO 2010/112936, 7 Oct. 2010; 3 g, 11.08 mmol) was added to a solution of phenyl (5-(tert-butyl)-2-methoxy-3-(methylsulfonamido)phenyl) carbamate (see Example 1 (iv) above; 4.78 g, 12.19 mmol) and TEA (320 µL, 2.296 mmol) in 2-Me-THF (40 mL) and heated at 65° C. (block temperature) for 20 h. Further portions of phenyl (5-(tert-butyl)-2-methoxy-3-(methylsulfonamido)phenyl)carbamate (1 g) and TEA (0.1 mL) were added and heating continued for a further 5 h. The resultant solid was filtered off, washed with iPrOAc then ether to afford the sub-title compound (5.711 g).

¹H NMR (400 MHz, DMSO-d6) δ 9.42 (s, 1H), 9.16 (s, 1H), 8.96 (s, 1H), 8.32 (d, 1H), 8.28 (d, 1H), 8.18 (d, 1H), 8.14 (d, 1H), 7.84 (d, 1H), 7.74-7.70 (m, 1H), 7.64-7.60 (m, 1H), 7.43 (d, 1H), 7.04-7.02 (m, 2H), 6.94 (dd, 1H), 3.80 (s, 3H), 3.10 (s, 3H), 1.27 (s, 9H).

LCMS m/z 569/571 (M+H)⁺ (ES⁺); 567/569 (M−H)⁻ (ES⁻)

(ii) 2-(2-(2-(2-Methoxyethoxy)ethoxy)ethoxy)-5-nitrobenzonitrile 2-(2-(2-Methoxyethoxy)ethoxy)ethanol (172 µL, 1.505 mmol) was added to a solution of NaH (60.2 mg, 1.505 mmol) in NMP (5 mL). After stirring for 30 min, 2-fluoro-5-nitrobenzonitrile (300 mg, 1.806 mmol) was added to the reaction mixture. The reaction mixture was stirred at rt for 3 days. The reaction was quenched with a saturated aqueous solution of NH₄Cl (10 mL) and extracted with ethyl acetate (10 mL). The organic layer was washed with brine, dried over MgSO₄, filtered and concentrated in vacuo. The crude product was purified by chromatography on the Companion (12 g column, 0-10% MeOH in DCM) to afford the sub-title compound (392 mg) as a pale yellow oil.

LCMS m/z 311 (M+H)⁺ (ES⁺)

(iii) 5-Amino-2-(2-(2-(2-methoxyethoxy)ethoxy) ethoxy)benzonitrile

To a solution of the product from step (ii) above (390 mg, 1.194 mmol) in EtOH (6 mL) was added Fe powder (667 mg, 11.94 mmol) followed by a solution of NH₄Cl (89 mg, 1.672 mmol) in water (2 mL). The reaction mixture was heated at 80° C. for 1 h. The reaction mixture was cooled to rt, filtered through Celite and concentrated in vacuo. The residue was dissolved in DCM (3 mL), sonicated, filtered, and concentrated in vacuo to afford the sub-title compound (214 mg) as a brown oil.

LCMS m/z 281 (M+H)⁺ (ES⁺). 87% purity (iv) N-(5-(tert-Butyl)-3-(3-(4-((2-((3-cyano-4-(2-(2-(2-methoxyethoxy)ethoxy)ethoxy)phenyl) amino) pyridin-4-yl)oxy)naphthalen-1-yl)ureido)-2-methoxyphenyl)methanesulfonamide A mixture of the product from step (iii) above (47 mg, 0.151 mmol), the product from step (i) above (100 mg, 0.149 mmol), K₂CO₃ (60 mg, 0.434 mmol), and BrettPhos G1 precatalyst (5 mg, 6.26 µmol) were degassed under vacuum back-filling with nitrogen 3 times. DMF (1 mL) was added and the suspension degassed under vacuum back-filling with nitrogen 3 times. The reaction was then heated under nitrogen at 85° C. (block temperature) for 2 h. The reaction was cooled and diluted with water to give a fine suspension. The product was extracted with 10% MeOH:DCM (5×10 mL). The organics were separated, bulked, dried (MgSO₄), filtered and solvent evaporated to give a brown glass. The crude product was purified by chromatography on the Companion (12 g column, 0-5% MeOH in DCM) to afford a white solid which was purified by preparative HPLC (Varian, Acidic (0.1% Formic acid), Acidic, Waters X-Select Prep-C18, 5 µm, 19×50 mm column, 35-65% MeCN in Water) to afford a colourless solid. The residue was diluted in DCM (3 mL), washed with a saturated solution of NaHCO₃ (3 mL), separated via a hydrophobic phase separator, and concentrated in vacuo to afford the title compound (18 mg).

¹H NMR (400 MHz, DMSO-d6) δ 9.39 (s, 1H), 9.15 (s, 1H), 9.03 (s, 1H), 8.90 (s, 1H), 8.29 (d, 1H), 8.12-8.09 (m, 4H), 7.85 (d, 1H), 7.69 (dd, 1H), 7.62-7.59 (m, 2H), 7.39 (d, 1H), 7.15 (d, 1H), 7.01 (d, 1H), 6.60 (dd, 1H), 5.99 (d, 1H), 4.18 (t, 2H), 3.80 (s, 3H), 3.75 (t, 2H), 3.61-3.59 (m, 2H), 3.53-3.49 (m, 4H), 3.41-3.39 (m, 2H), 3.21 (s, 3H), 3.07 (s, 3H), 1.26 (s, 9H).

LCMS m/z 813 (M+H)⁺ (ES⁺); 811 (M−H)⁻ (ES⁻)

Example 9

N-(5-(tert-Butyl)-3-(3-(4-((2-((3-cyano-4-(2-morpholinoethoxy)phenyl)amino)pyridin-4-yl)oxy)naphthalen-1-yl)ureido)-2-methoxyphenyl)methanesulfonamide

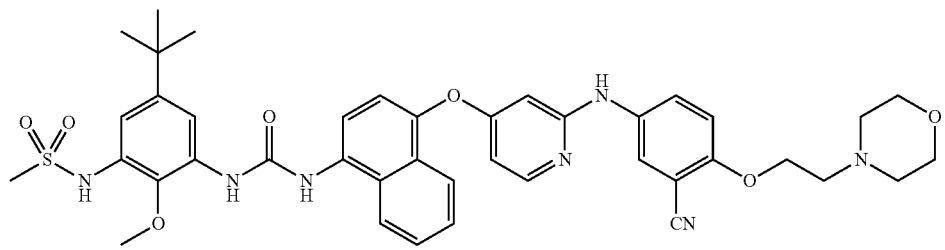 [SMILES: COc1c(NC(=O)Nc2ccc(Oc3ccnc(Nc4ccc(OCCN5CCOCC5)c(C#N)c4)c3)c3ccccc23)cc(C(C)(C)C)cc1NS(C)(=O)=O]

(i) 2-(2-Morpholinoethoxy)-5-nitrobenzonitrile

2-Morpholinoethanol (182 µL, 1.505 mmol) was added to a solution of NaH (60 mg, 1.500 mmol) in NMP (5 mL). After stirring 30 min, 2-fluoro-5-nitrobenzonitrile (300 mg, 1.806 mmol) was added to the reaction mixture. The reaction was stirred at rt for 3 days. The reaction was quenched with a saturated aqueous solution of NH$_4$Cl (10 mL), extracted with ethyl acetate (10 mL). The organic layer was washed with brine, dried over MgSO$_4$, filtered and concentrated in vacuo. The crude product was purified by chromatography on the Companion (12 g column, 0-8% MeOH in DCM) to afford the sub-title compound (285 mg) as an iridescent red crystalline solid.

LCMS m/z 278 (M+H)$^+$ (ES$^+$)

(ii) 5-Amino-2-(2-morpholinoethoxy)benzonitrile

To a solution of the product from step (i) above (280 mg, 1.010 mmol) in EtOH (6 mL) was added Fe powder (564 mg, 10.10 mmol) followed by a solution of NH$_4$Cl (76 mg, 1.414 mmol) in water (2 mL). The reaction mixture was heated at 80° C. for 1 h. The reaction mixture was cooled to rt, filtered through Celite and concentrated in vacuo to afford the sub-title compound (179 mg) as a yellow solid.

LCMS m/z 248 (M+H)$^+$ (ES$^+$)

(iii) tert-Butyl (4-((2-((3-cyano-4-(2-morpholinoethoxy)phenyl)amino)pyridin-4-yl)oxy)-naphthalen-1-yl)carbamate A mixture of the product from step (ii) above (179 mg, 0.680 mmol), tert-butyl (4-((2-chloropyridin-4-yl)oxy)naphthalen-1-yl)carbamate (see Example 1(i) above; 255 mg, 0.689 mmol), K$_2$CO$_3$ (190 mg, 1.377 mmol) and BrettPhos G1 precatalyst (11 mg, 0.014 mmol) were degassed under vacuum, back-filling with nitrogen 3 times. tBuOH (3 mL) was added and the suspension degassed an additional 3 times. The reaction was heated under nitrogen at 85° C. for 16 hours. Another aliquot of BrettPhos G1 precatalyst (11 mg, 0.014 mmol) was added, and the reaction mixture was heated for further 16 hours at 85° C. The reaction mixture was diluted with DCM (20 mL), filtered through Celite and concentrated in vacuo. The crude product was purified by chromatography on the Companion (12 g column, 0-10% MeOH in DCM) to afford the sub-title compound (213 mg) as a flocculent brown powder.

LCMS m/z 291 (M+2H)$^{2+}$ (ES$^+$); 86% purity

(iv) 5-((4-((4-Aminonaphthalen-1-yl)oxy)pyridin-2-yl)amino)-2-(2-morpholinoethoxy)-benzonitrile TFA (2 mL, 26.0 mmol) was added to a solution of the product from step (iii) above (213 mg, 0.366 mmol) in DCM (20 mL) and stirred at rt for 1 h. The volatiles were removed under reduced pressure and the residue was redissolved in DCM (50 mL). The solution was washed with saturated NaHCO$_3$ solution (20 mL). The two layers were separated via a hydrophobic phase separator. The organic layer was concentrated in vacuo to afford the sub-title compound (179 mg) as a flocculent brown solid.

LCMS m/z 241 (M+2H)$^{2+}$ (ES$^+$)

(v) N-(5-(tert-Butyl)-3-(3-(4-((2-((3-cyano-4-(2-morpholinoethoxy)phenyl)amino)pyridin-4-yl)oxy)naphthalen-1-yl)ureido)-2-methoxyphenyl)methanesulfonamide Triethylamine (11 µL, 0.079 mmol) was added to a mixture of phenyl (5-(tert-butyl)-2-methoxy-3-(methylsulfonamido)phenyl)carbamate (see Example 1(iv) above; 146 mg, 0.372 mmol) and the product from step (iv) above (179 mg, 0.372 mmol) in isopropyl acetate (10 mL) and the mixture heated at 70° C. (block temperature) overnight (48 hours). The reaction mixture was concentrated in vacuo. The crude product was purified by chromatography on the Companion (12 g column, 0.5-2% MeOH in DCM, flushed with 20% MeOH in DCM) to afford a tan powder. The crude product was purified by preparative HPLC (Varian, Acidic (0.1% Formic acid), Acidic, Waters X-Select Prep-C18, 5 µm, 19×50 mm column, 20-50% MeCN in Water) to afford a pink oil. The residue was diluted in DCM (3 mL), washed with a saturated solution of NaHCO$_3$ (3 mL), separated via a hydrophobic phase separator, and concentrated in vacuo to afford the title compound (80 mg).

$^1$H NMR (400 MHz, DMSO-d6) δ 9.39 (s, 1H), 9.15 (s, 1H), 9.03 (s, 1H), 8.90 (s, 1H), 8.29 (d, 1H), 8.15 (s, 1H), 8.11-8.09 (m, 3H), 7.85 (d, 1H), 7.70 (dd, 1H), 7.64-7.59 (m, 2H), 7.39 (d, 1H), 7.15 (d, 1H), 7.01 (d, 1H), 6.60 (dd, 1H), 5.99 (d, 1H), 4.17 (t, 2H), 3.80 (s, 3H), 3.55 (t, 4H), 3.08 (s, 3H), 2.69 (t, 2H), 1.26 (s, 9H). (4 protons under DMSO and water peak)

LCMS m/z 390 (M+2H)$^{2+}$ (ES$^+$)

Example 10

N-(5-(tert-Butyl)-3-(3-(4-((2-((3-cyano-4-(3-morpholinopropoxy)phenyl)amino)pyridin-4-yl)oxy)naphthalen-1-yl)ureido)-2-methoxyphenyl)methanesulfonamide

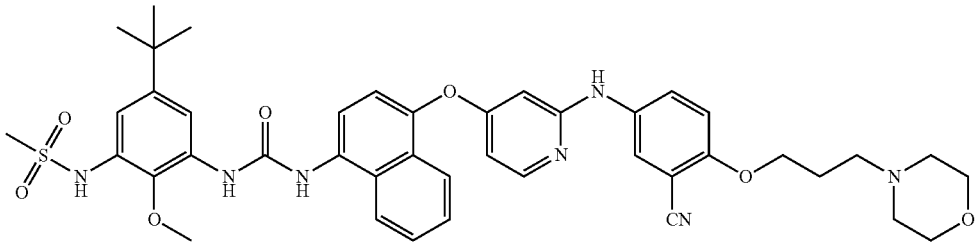 [SMILES: COc1c(NC(=O)Nc2ccc(Oc3ccnc(Nc4ccc(OCCCN5CCOCC5)c(C#N)c4)c3)c3ccccc23)cc(C(C)(C)C)cc1NS(C)(=O)=O]

(i) 2-(3-Morpholinopropoxy)-5-nitrobenzonitrile

3-Morpholinopropan-1-ol (417 µL, 3.01 mmol) was added to a solution of NaH (120 mg, 3.01 mmol) in NMP (8 mL). After stirring 30 min, 2-fluoro-5-nitrobenzonitrile (600 mg, 3.61 mmol) was added to the reaction mixture. The reaction was stirred at rt for 3 days. The reaction was quenched with a saturated aqueous solution of $NH_4Cl$ (10 mL), extracted with ethyl acetate (10 mL). The organic layer was washed with brine, dried over $MgSO_4$, filtered and concentrated in vacuo. The crude product was purified by chromatography on the Companion (12 g column, 0-5% Methanol in DCM) to afford the sub-title compound (765 mg) as an iridescent red gum.

LCMS m/z 292 $(M+H)^+$ $(ES^+)$

(ii) 5-Amino-2-(3-morpholinopropoxy)benzonitrile

To a solution of the product from step (i) above (760 mg, 2.61 mmol) in EtOH (9 mL) was added Fe powder (1457 mg, 26.1 mmol) followed by a solution of $NH_4Cl$ (195 mg, 3.65 mmol) in water (3 mL). The reaction mixture was heated at 80° C. for 1 h. The reaction mixture was cooled to rt, filtered through Celite and concentrated in vacuo. The resulting residue was dissolved in 10% MeOH in DCM (3 mL), sonicated and filtered. The solvents were evaporated to afford the sub-title compound (544 mg) as a sticky yellow gum.

LCMS m/z 262 $(M+H)^+$ $(ES^+)$; 260 $(M-H)^-$ $(ES^-)$

(iii) N-(5-(tert-Butyl)-3-(3-(4-((2-((3-cyano-4-(3-morpholinopropoxy)phenyl)amino)pyridin-4-yl)oxy)naphthalen-1-yl)ureido)-2-methoxyphenyl)methanesulfonamide A mixture of the product from step (ii) above (72 mg, 0.276 mmol), N-(5-(tert-butyl)-3-(3-(4-((2-chloropyridin-4-yl)oxy)naphthalen-1-yl)ureido)-2-methoxyphenyl)methanesulfonamide (see Example 8(i) above; 200 mg, 0.299 mmol), $K_2CO_3$ (120 mg, 0.868 mmol), and BrettPhos G1 precatalyst (10 mg, 0.013 mmol) were degassed under vacuum back-filling with nitrogen 3 times. DMF (2 mL) was added and the suspension degassed under vacuum back-filling with nitrogen 3 times. The reaction was then heated under nitrogen at 85° C. (block temperature) for 17 h. The reaction was cooled and diluted with water to give a fine suspension. The product was extracted with 10% MeOH: DCM (5×10 mL). The organics were separated, bulked, dried ($MgSO_4$), filtered and solvent evaporated to give a brown glass. The crude product was purified by chromatography on the Companion (4 g column, 0-10% MeOH in DCM) then purified by preparative HPLC (Gilson, Basic (0.1% Ammonium Bicarbonate), Basic, Waters X-Bridge Prep-C18, 5 µm, 19×50 mm column, 40-60% MeCN in Water) to afford the title compound (8 mg) as an off-white solid.

$^1$H NMR (400 MHz, DMSO-d6) δ 9.40 (s, 1H), 9.17 (bs, 1H), 9.03 (s, 1H), 8.90 (s, 1H), 8.29 (d, 1H), 8.13-8.09 (m, 4H), 7.85 (d, 1H), 7.70 (dd, 1H), 7.64-7.58 (m, 2H), 7.38 (d, 1H), 7.14 (d, 1H), 7.01 (d, 1H), 6.60 (dd, 1H), 5.99 (d, 1H), 4.09 (t, 2H), 3.80 (s, 3H), 3.55 (t, 4H), 3.05 (s, 3H), 2.42 (t, 2H), 2.34 (bs, 4H), 1.86 (tt, 2H), 1.25 (s, 9H).

LCMS m/z 397 $(M+2H)2+$ $(ES^+)$, 794 $(M+H)^+$ $(ES^+)$

Example 11

N-(5-(tert-Butyl)-2-methoxy-3-(3-(4-((2-((3-methoxy-4-((2-(2-(2-methoxyethoxy)ethoxy)ethyl)sulfinyl)phenyl)amino)pyridin-4-yl)oxy)naphthalen-1-yl)ureido)phenyl)methanesulfonamide

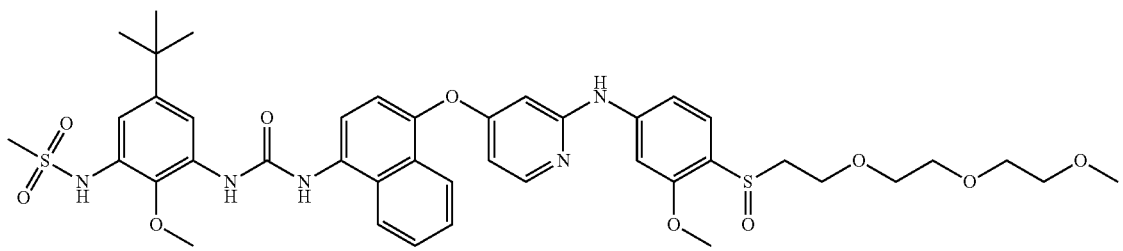

(i) (2-Methoxy-4-nitrophenyl)(2-(2-(2-methoxyethoxy)ethoxy)ethyl)sulfane

1-Bromo-2-(2-(2-methoxyethoxy)ethoxy)ethane (562 µl, 3.24 mmol) was added to a solution of 2-methoxy-4-nitrobenzenethiol (500 mg, 2.70 mmol) and K$_2$CO$_3$ (410 mg, 2.97 mmol) in acetone 5 mL. The reaction mixture was stirred at rt for 17 h. The reaction mixture was concentrated in vacuo, diluted with EtOAc (40 mL), washed with 5 wt % aq NaOH (40 mL). The organic layer was dried over MgSO$_4$, filtered and concentrated in vacuo to afford the sub-title compound (1.044 g) as a yellow oil.

$^1$H NMR (400 MHz, CDCl$_3$) δ 7.82 (dd, 1H), 7.62 (d, 1H), 7.27 (d, 1H), 3.96 (s, 3H), 3.74 (t, 2H), 3.66-3.61 (m, 6H), 3.53-3.51 (m, 2H), 3.36 (s, 3H), 3.18 (t, 2H).

LCMS m/z 354 (M+Na)$^+$ (ES$^+$); 71% purity

(ii) 2-Methoxy-1-((2-(2-(2-methoxyethoxy)ethoxy)ethyl)sulfinyl)-4-nitrobenzene mCPBA (218 mg, 0.974 mmol) was added slowly to an ice cold solution of the product from step (i) above (500 mg, 1.071 mmol) in DCM (5 mL). The reaction was stirred at 0° C. for 1 h then mCPBA (35 mg, 0.156 mmol) added and stirring at 0° C. continued for a further 10 minutes. The reaction mixture was filtered cold and the filtrate immediately partitioned with sodium bisulphite soln. 20% w/w (5 mL). The organic layer was separated, washed with sat. NaHCO$_3$ soln. (5 mL), dried (MgSO$_4$), filtered and the solvent evaporated to a yellow oil. The crude product was purified by chromatography on silica gel (12 g column, 0% MeOH:EtOAc to 5%) to afford the sub-title compound (380 mg) as a yellow oil.

LCMS m/z 348 (M+H)$^+$ (ES$^+$)

(iii) 3-Methoxy-4-((2-(2-(2-methoxyethoxy)ethoxy)ethyl)sulfinyl)aniline

A suspension of the product from step (ii) above (380 mg, 1.094 mmol) and 5% Pd/C (75 mg, 50% paste with water) in ethanol (5 mL) was stirred under hydrogen (5 bar) for 2 h. Another aliquot of 5% Pd/C (75 mg) was added, and the mixture was stirred under hydrogen atmosphere (5 bar) for 17 hours. The catalyst was removed by filtration and the filtrate was concentrated under reduced pressure to yield a pale yellow oil. The crude product was purified by chromatography on the Companion (12 g column, 0-5% MeOH in DCM) to afford the sub-title compound (110 mg) as a sticky orange oil.

LCMS m/z 318 (M+H)$^+$ (ES$^+$); 93% purity

(iv) N-(5-(tert-Butyl)-2-methoxy-3-(3-(4-((2-((3-methoxy-4-((2-(2-(2-methoxyethoxy)ethoxy)-ethyl)sulfinyl)phenyl)amino)pyridin-4-yl)oxy)naphthalen-1-yl)ureido)phenyl)-methanesulfonamide A mixture of the product from step (iii) above (50 mg, 0.158 mmol), N-(5-(tert-butyl)-3-(3-(4-((2-chloropyridin-4-yl)oxy)naphthalen-1-yl)ureido)-2-methoxyphenyl)methanesulfonamide (see Example 8(i) above; 81 mg, 0.143 mmol), K$_2$CO$_3$ (60 mg, 0.434 mmol), and BrettPhos G1 precatalyst (4 mg, 5.01 µmol) were degassed under vacuum back-filling with nitrogen 3 times. DMF (1 mL) was added and the suspension degassed under vacuum back-filling with nitrogen 3 times. The reaction was then heated under nitrogen at 85° C. (block temperature) for 2 h. The reaction was cooled and diluted with water to give a fine suspension. The suspension was filtered to afford a dark red thick gum, which was diluted with DCM, washed with NaHCO$_3$ (10 mL). The organic layer was separated via a hydrophobic phase separator then concentrated in vacuo. The crude product was purified by chromatography on the Companion (4 g column, 0-5% MeOH in DCM) then purified by preparative HPLC (Waters, Basic (0.1% Ammonium Bicarbonate), Basic, Waters X-Bridge Prep-C18, 5 µm, 19×50 mm column, 50-80% MeCN in Water) to afford the title compound (31 mg) as a pale brown powder.

$^1$H NMR (400 MHz, DMSO-d6) δ 9.38 (s, 1H), 9.25 (s, 1H), 9.13 (s, 1H), 8.90 (s, 1H), 8.30 (d, 1H), 8.17 (d, 1H), 8.12 (dd, 2H), 7.86 (d, 1H), 7.70 (dd, 1H), 7.61 (dd, 1H), 7.53 (s, 1H), 7.41-7.38 (m, 3H), 7.02 (d, 1H), 6.63 (dd, 1H), 6.14 (d, 1H), 3.80 (s, 3H), 3.77 (s, 3H), 3.76-3.73 (m, 1H), 3.65-3.61 (m, 1H), 3.50-3.46 (m, 6H), 3.42-3.39 (m, 2H), 3.22 (s, 3H), 3.19-3.13 (m, 1H), 3.08 (s, 3H), 2.78-2.72 (m, 1H), 1.26 (s, 9H).

LCMS m/z 850 (M+H)$^+$ (ES$^+$); 848 (M−H)$^-$ (ES$^-$)

Example 12

1-[5-tert-Butyl-3-(methanesulfonamido)-2-methoxyphenyl]-3-[4-[[2-[3-methoxy-4-[2-(2-methoxyethoxy)ethoxy]ethylsulfonyl]anilino]-4-pyridyl]oxy]-1-naphthyl]urea

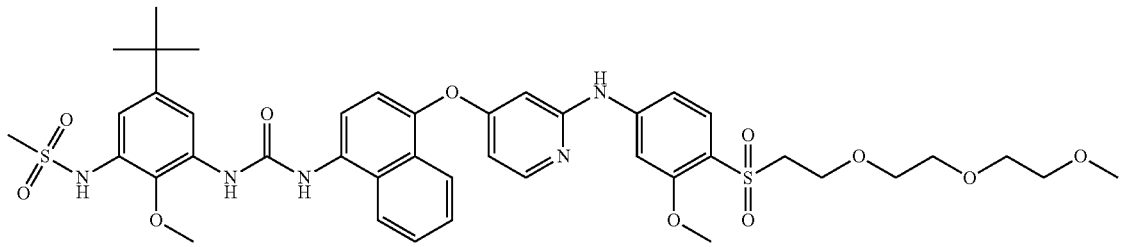

(i) (2-Methoxy-4-nitrophenyl) (2-(2-(2-methoxyethoxy)ethoxy)ethyl)sulfane

1-Bromo-2-(2-(2-methoxyethoxy)ethoxy)ethane (303 µL, 1.749 mmol) was added to a solution of 2-methoxy-4-nitrobenzenethiol (270 mg, 1.458 mmol) and K$_2$CO$_3$ (222 mg, 1.604 mmol) in acetone 5 mL. The reaction mixture was stirred at rt for 17 hours. The reaction mixture was concentrated in vacuo, diluted with EtOAc (40 mL), washed with 5 wt % aq NaOH (40 mL). The organic layer was dried over MgSO$_4$, filtered and concentrated in vacuo to afford a yellow oil. The crude product was purified by chromatography on the Companion (12 g column, 0-100% ethyl acetate in iso-hexane) to afford the sub-title compound (222 mg) as a thick brown oil.

LCMS m/z 354 (M+Na)+ (ES+)

(ii) 2-Methoxy-1-((2-(2-(2-methoxyethoxy)ethoxy)ethyl)sulfonyl)-4-nitrobenzene mCPBA (336 mg, 1.501 mmol) was added slowly to an ice cold solution of the product from step (i) above (222 mg, 0.670 mmol) in DCM (5 mL). The reaction was stirred at 0° C. for 30 min. then allowed to warm to rt and stirred for 1 h. The reaction mixture was filtered and the filtrate immediately partitioned with sodium bisulphite solution 20% w/w (5 mL). The organic layer was separated, washed with sat. NaHCO$_3$ soln. (5 mL), dried (MgSO$_4$), filtered and the solvent evaporated to afford the sub-title compound as a yellow oil.

LCMS m/z 364 (M+H)+ (ES+)

(iii) 3-Methoxy-4-((2-(2-(2-methoxyethoxy)ethoxy)ethyl)sulfonyl)aniline

A suspension of the product from step (ii) above (114 mg, 0.314 mmol) and 5% Pd/C (50% paste with water, 40 mg) in ethanol (5 mL) was stirred under hydrogen (5 bar) for 2 h. The mixture was filtered, and recharged with 5% Pd/C (50% paste with water, 40 mg), stirred under hydrogen (5 bar) for 17 h. The catalyst was removed by filtration and the filtrate was concentrated under reduced pressure to yield the sub-title compound (103 mg) as a colourless oil.

LCMS m/z 334 (M+H)+ (ES+)

(iv) N-(5-(tert-Butyl)-2-methoxy-3-(3-(4-((2-((3-methoxy-4-((2-(2-(2-methoxyethoxy)ethoxy)- ethyl)sulfonyl)phenyl)amino)pyridin-4-yl)oxy)naphthalen-1-yl)ureido)phenyl)methanesulfonamide A mixture of the product from step (iii) above (103 mg, 0.309 mmol), N-(5-(tert-butyl)-3-(3-(4-((2-chloropyridin-4-yl)oxy)naphthalen-1-yl)ureido)-2-methoxyphenyl)methanesulfonamide (see Example 8(i) above; 160 mg, 0.281 mmol), K$_2$CO$_3$ (90 mg, 0.651 mmol), and BrettPhos G1 precatalyst (6 mg, 7.51 μmol) were degassed under vacuum back-filling with nitrogen 3 times. DMF (1 mL) was added and the suspension degassed under vacuum back-filling with nitrogen 3 times. The reaction was then heated under nitrogen at 85° C. (block temperature) for 2 h. The reaction mixture was diluted with water (10 mL) forming a white precipitate. The precipitate was filtered, diluted with DCM (10 mL), washed with NaHCO$_3$ (10 mL), dried over MgSO$_4$, filtered and concentrated in vacuo. The crude product was purified by chromatography on the Companion (4 g column, 1-4% MeOH in DCM) then purified by preparative HPLC (Gilson, Basic (0.1% Ammonium Bicarbonate), Basic, Waters X-Bridge Prep-C18, 5 μm, 19×50 mm column, 25-75% MeCN in Water) to afford the title compound (6 mg) as an off-white solid.

$^1$H NMR (400 MHz, DMSO-d6) δ 9.47 (s, 1H), 9.39 (s, 1H), 9.14 (bs, 1H), 8.90 (s, 1H), 8.30 (d, 1H), 8.19 (d, 1H), 8.15 (d, 1H), 8.12 (d, 1H), 7.85 (d, 1H), 7.73-7.68 (m, 1H), 7.66 (d, 1H), 7.62-7.59 (m, 1H), 7.54 (d, 1H), 7.40 (d, 1H), 7.29 (dd, 1H), 7.02 (d, 1H), 6.70 (dd, 1H), 6.18 (d, 1H), 3.85 (s, 3H), 3.80 (s, 3H), 3.61-3.60 (m, 2H), 3.54-3.52 (m, 2H), 3.36-3.34 (m, 4H), 3.28-3.24 (m, 4H), 3.16 (s, 3H), 3.07 (s, 3H), 1.26 (s, 9H).

LCMS m/z 866 (M+H)+ (ES+); 864 (M−H)− (ES−)

Example 13

1-[5-tert-Butyl-3-(methanesulfonamido)-2-methoxyphenyl]-3-[4-[[2-[3-methoxy-4-[methyl(3-morpholinopropyl)sulfamoyl]anilino]-4-pyridyl]oxy]-1-naphthyl]urea

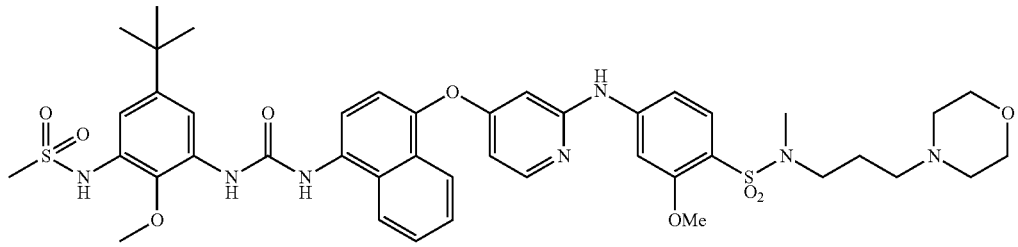 [SMILES: COc1cc(Nc2cc(Oc3ccc(NC(=O)Nc4cc(C(C)(C)C)cc(NS(C)(=O)=O)c4OC)c4ccccc34)ccn2)ccc1S(=O)(=O)N(C)CCCN1CCOCC1]

(i) 2-Methoxy-N-methyl-N-(3-morpholinopropyl)-4-nitrobenzenesulfonamide

2-Methoxy-4-nitrobenzene-1-sulfonyl chloride (239 mg, 0.948 mmol) in MeCN (3 mL) was added dropwise to an ice-cold solution of N-methyl-3-morpholinopropan-1-amine (150 mg, 0.948 mmol) and Et$_3$N (396 μL, 2.84 mmol) in MeCN (3 mL). The reaction mixture was allowed to warm to rt and stirred for 1 h. The reaction was concentrated in vacuo, the residue was diluted with EtOAc (5 mL), filtered and concentrated in vacuo to a brown-yellow oil. The crude product was purified by chromatography on the Companion (12 g column, 0-5% MeOH in DCM) to afford the sub-title compound (171 mg) as a sticky yellow oil.

LCMS m/z 374 (M+H)+ (ES+)

(ii) 4-Amino-2-methoxy-N-methyl-N-(3-morpholinopropyl)benzenesulfonamide

A suspension of the product from step (i) above (171 mg, 0.458 mmol) and 5% Pd/C (50% paste with water, 50 mg) in ethanol (5 mL) was stirred under hydrogen (balloon) for 17 h. The reaction mixture was filtered through Celite, concentrated in vacuo to afford the sub-title compound (146 mg) as a pale yellow oil.

LCMS m/z 344 (M+H)+ (ES+); 342 (M−H)− (ES−)

(iii) tert-Butyl (4-((2-((3-methoxy-4-(N-methyl-N-(3-morpholinopropyl)sulfamoyl)phenyl)-amino)pyridin-4-yl)oxy)naphthalen-1-yl)carbamate A mixture of tert-butyl (4-((2-chloropyridin-4-yl)oxy)naphthalen-1-yl)carbamate (see Example 1(i) above; 158 mg, 0.425 mmol), the product from step (ii) above (146 mg, 0.425 mmol), K$_2$CO$_3$ (176 mg, 1.275 mmol), and BrettPhos G1 precatalyst (8 mg, 10.01 mol) were degassed under vacuum back-filling with nitrogen 3 times. DMF (1 mL) was added and the suspension degassed under vacuum back-filling with nitrogen 3 times. The reaction was then heated under nitrogen at 85° C. (block temperature) for 2 h. The reaction mixture was diluted with water (10 mL), filtered. The brown solid was purified by chromatography on the Companion (12 g column, 0.5-5% MeOH in DCM) to afford the sub-title compound (50 mg) as a pale purple solid.

LCMS m/z 678 (M+H)$^+$ (ES$^+$); 676 (M−H)$^−$ (ES$^−$), 80% purity (iv) 4-((4-((4-Aminonaphthalen-1-yl)oxy)pyridin-2-yl)amino)-2-methoxy-N-methyl-N-(3-morpholinopropyl)benzenesulfonamide TFA (0.1 mL, 1.298 mmol) was added to the product from step (iii) above (50 mg, 0.059 mmol) in DCM (1 mL). The reaction mixture was stirred for one hour at rt. The crude mixture was concentrated and loaded onto a column of SCX (10 g) in MeOH. The column was washed with MeOH and then the product was eluted with 0.7 M ammonia in MeOH. The resultant mixture was concentrated in vacuo to afford the sub-title compound (41 mg) as a pale tan foam.

LCMS m/z 578 (M+H)$^+$ (ES$^+$), 289 (M+2H)$^{2+}$ (ES$^+$); 576 (M−H)$^−$ (ES$^−$), 89% purity (v) 4-((4-((4-(3-(5-(tert-Butyl)-2-methoxy-3-(methylsulfonamido)phenyl)ureido)naphthalen-1-yl)oxy)pyridin-2-yl)amino)-2-methoxy-N-methyl-N-(3-morpholinopropyl)benzenesulfonamide Triethylamine (2 μL, 0.014 mmol) was added to a mixture of phenyl (5-(tert-butyl)-2-methoxy-3-(methylsulfonamido)phenyl)carbamate (see Example 1(iv) above; 28 mg, 0.071 mmol) and the product from step (iv) above (41 mg, 0.071 mmol) in isopropyl acetate (5 mL) and the mixture heated at 70° C. (block temperature) overnight (7 hours). The reaction mixture was concentrated in vacuo. then purified by preparative HPLC (Gilson, Basic (0.1% Ammonium Bicarbonate), Basic, Waters X-Bridge Prep-C18, 5 μm, 19×50 mm column, 25-75% MeCN in Water) to afford the title compound (16 mg) as an off-white powder.

$^1$H NMR (400 MHz, DMSO-d6) δ 9.40 (bs, 2H), 9.13 (bs, 1H), 8.91 (s, 1H), 8.30 (d, 1H), 8.18-8.17 (m, 2H), 8.12 (d, 1H), 7.86 (d, 1H), 7.73-7.68 (m, 1H), 7.63-7.59 (m, 2H), 7.53 (d, 1H), 7.40 (d, 1H), 7.23 (dd, 1H), 7.02 (d, 1H), 6.68 (dd, 1H), 6.16 (s, 1H), 3.80 (s, 3H), 3.79 (s, 3H), 3.52-3.50 (m, 4H), 3.09 (s, 3H), 3.04-3.00 (m, 2H), 2.70 (s, 3H), 2.26-2.18 (m, 6H), 1.56 (tt, 2H), 1.26 (s, 9H).

LCMS m/z 876 (M+H)$^+$ (ES$^+$); 874 (M−H)$^−$ (ES$^−$)

Example 14

4-[[4-[[4-[[5-tert-Butyl-3-(methanesulfonamido)-2-methoxy-phenyl]carbamoylamino]-1-naphthyl]oxy]-2-pyridyl]amino]-2-methoxy-N-[2-(1-methyl-4-piperidyl)ethyl]benzamide

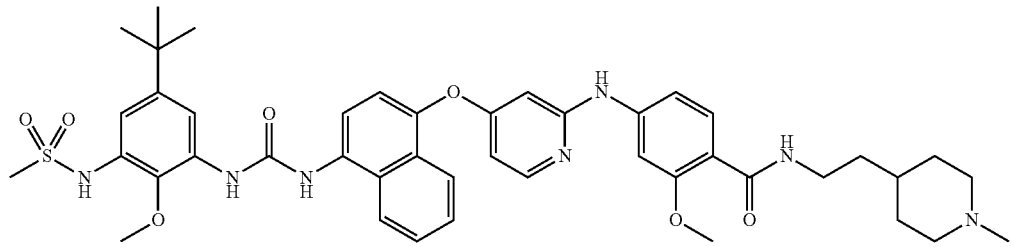

HATU (80 mg, 0.210 mmol) was added to a stirred solution of 4-((4-((4-(3-(5-(tert-butyl)-2-methoxy-3-(methylsulfonamido)phenyl)ureido)naphthalen-1-yl)oxy)pyridin-2-yl)amino)-2-methoxybenzoic acid, hydrochloride (see Example 1 above; 100 mg, 0.136 mmol), 2-(1-methylpiperidin-4-yl)ethanamine (27 mg, 0.190 mmol) and Hünig's Base (100 μL, 0.573 mmol) in DMF (2 mL) at rt. The mixture was stirred for 2 h then poured into water (10 mL) and partitioned with EtOAc (10 mL). The organic phase was concentrated in vacuo. The crude product was purified by preparative HPLC (Waters, Acidic (0.1% Formic acid), Acidic, Waters X-Select Prep-C18, 5 μm, 19×50 mm column, 20-50% MeCN in Water) to afford a white solid. The solid was partitioned between NaHCO$_3$ solution and 10% MeOH in DCM. The organic phase was dried via hydrophobic frit and concentrated in vacuo. The residue was re-concentrated from MeCN and the residue dried in vacuo at 45° C. to afford the title compound (53 mg) as an off-white solid.

$^1$H NMR (400 MHz, DMSO-d6) δ: 9.40 (s, 1H), 9.25 (s, 1H), 9.14 (s, 1H), 8.92 (s, 1H), 8.30 (d, 1H), 8.11-8.19 (m, 3H), 7.93 (t, 1H), 7.87 (d, 1H), 7.68-7.73 (m, 2H), 7.62 (t, 1H), 7.55 (d, 1H), 7.40 (d, 1H), 7.22 (dd, 1H), 7.03 (d, 1H), 6.66 (dd, 1H), 6.15 (d, 1H), 3.83 (s, 3H), 3.81 (s, 3H), 3.28 (q, 2H), 3.10 (s, 3H), 2.73 (d, 2H), 2.12 (s, 3H), 1.80 (t, 2H), 1.64 (d, 2H), 1.42 (q, 2H), 1.27 (s, 9H), 1.10-1.22 (m, 3H)

LCMS m/z 824 (M+H)$^+$ (ES$^+$)

Example 15

4-[[4-[[4-[[5-tert-Butyl-3-(methanesulfonamido)-2-methoxy-phenyl]carbamoylamino]-1-naphthyl]oxy]-2-pyridyl]amino]-2-ethynyl-N-(2-morpholinoethyl)benzamide

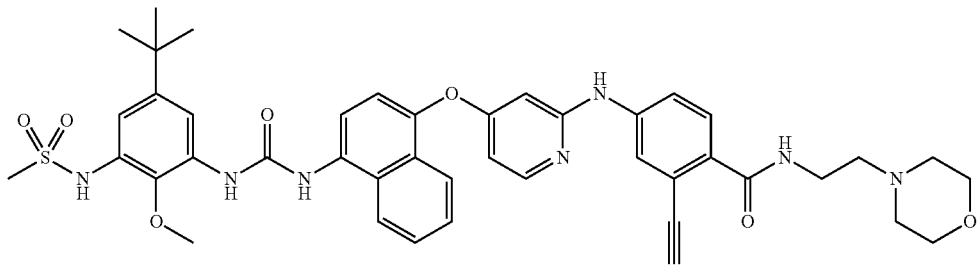 [SMILES: C#Cc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCOCC1]

(i) 2-Bromo-N-(2-morpholinoethyl)-4-nitrobenzamide

HATU (4.25 g, 11.18 mmol) was added to a mixture of 2-bromo-4-nitrobenzoic acid (2.5 g, 10.16 mmol), 2-morpholinoethanamine (1.600 mL, 12.19 mmol) and Hünig's Base (5 mL, 28.6 mmol) in DMF (30 mL). The mixture was stirred at rt for 2 h, a further portion of HATU (1 g) added and stirred for 2 h. The mixture was partitioned between EtOAc (200 mL) and water (200 mL), the organic layer washed with sat $Na_2CO_3$ soln (100 mL), brine (100 mL), dried ($MgSO_4$), filtered and evaporated under reduced pressure. The residue was purified by chromatography on silica gel (80 g column, 0-5% MeOH/DCM) to afford the sub-title compound (2.36 g) as a solid.

$^1$H NMR (400 MHz, $CDCl_3$) δ 8.50 (d, 1H), 8.25 (dd, 1H), 7.76 (d, 1H), 6.82 (s, 1H), 3.77-3.62 (m, 6H), 2.72 (t, 2H), 2.61 (brs, 4H).

LCMS m/z 358/360 (M+H)$^+$ (ES$^+$); 356/358 (M−H)$^−$ (ES$^−$)

(ii) N-(2-morpholinoethyl)-4-nitro-2-((triisopropylsilyl)ethynyl)benzamide

Pd(PPh$_3$)$_4$ (0.379 g, 0.328 mmol) was added to a mixture of the product from step (i) above (2.35 g, 6.56 mmol), ethynyltriisopropylsilane (2.2 mL, 9.81 mmol) and CuI (0.062 g, 0.328 mmol) in Et$_3$N (10 mL) and DMF (25 mL) and heated at 85° C. for 4 h. The mixture was partitioned between ether (200 mL) and water (200 mL), the organic layer washed with brine (100 mL), dried ($MgSO_4$), filtered and evaporated under reduced pressure. The residue was purified by chromatography on silica gel (80 g column, 0-100% EtOAc/isohexane) then purified further on silica gel (80 g column, 0-3% MeOH/DCM) to afford the sub-title compound (1.737 g) as a solid.

LCMS m/z 460 (M+H)$^+$ (ES$^+$) at 2.04 min, 90% purity

(iii) 4-Amino-N-(2-morpholinoethyl)-2-((triisopropylsilyl)ethynyl)benzamide

A mixture of the product from step (ii) above (1.72 g, 3.74 mmol), Fe powder (2 g, 35.8 mmol) and NH$_4$Cl (100 mg, 1.869 mmol) in EtOH (20 mL) and water (5 mL) was heated at 80° C. for 3 h then filtered through Celite. The filtrate was evaporated under reduced pressure and the residue partitioned between DCM (100 mL) and aq sat NaHCO$_3$ soln (50 mL). The organic layer was washed with brine (50 mL), dried (MgSO$_4$), filtered and evaporated under reduced pressure. The crude product was purified by chromatography on silica gel (80 g column, 0-5% MeOH/DCM) to afford the sub-title compound (1.23 g) as a solid.

$^1$H NMR (400 MHz, CDCl$_3$) δ 7.98 (d, 1H), 7.87 (brs, 1H), 6.80 (d, 1H), 6.71 (dd, 1H), 3.97 (s, 2H), 3.74 (brs 4H), 3.63-3.58 (m, 2H), 2.65-2.52 (brm, 6H), 1.19-1.15 (m, 21H).

LCMS m/z 430 (M+H)$^+$ (ES$^+$)

(iv) tert-Butyl (4-((2-((4-((2-morpholinoethyl)carbamoyl)-3-((triisopropylsilyl)ethynyl)phenyl)amino)pyridin-4-yl)oxy)naphthalen-1-yl)carbamate BrettPhos G1 Precatalyst (68 mg, 0.085 mmol) was added to a mixture of tert-butyl (4-((2-chloropyridin-4-yl)oxy)naphthalen-1-yl)carbamate (see Example 1(i) above; 785 mg, 2.118 mmol), the product from step (iii) above (910 mg, 2.118 mmol) and K$_2$CO$_3$ (600 mg, 4.34 mmol) in DMF (5 mL) and heated at 80° C. for 4 h. A further portion of BrettPhos G1 Precatalyst (68 mg, 0.085 mmol) was added, stirred for 20 h at 80° C. then partitioned between EtOAc (100 mL) and water (50 mL). The organic layer was washed with brine (50 mL), dried (MgSO$_4$), filtered and evaporated under reduced pressure. The crude product was purified by chromatography on silica gel (80 g column, EtOAc) to afford the sub-title compound (580 mg) as a yellow foam.

$^1$H NMR (400 MHz, CDCl$_3$) δ 8.11 (d, 1H), 8.00-7.95 (m, 3H), 7.88-7.81 (m, 2H), 7.63-7.51 (m, 3H), 7.46 (dd, 1H), 7.22 (d, 1H), 6.90 (s, 1H), 6.70 (s, 1H), 6.50 (dd, 1H), 6.26 (d, 1H), 3.76-3.74 (m, 4H), 3.65-3.60 (m, 2H), 2.68-2.52 (m, 6H), 1.60 (s, 9H), 1.18-1.16 (m, 21H).

LCMS m/z 764 (M+H)$^+$ (ES$^+$)

(v) 4-((4-((4-Aminonaphthalen-1-yl)oxy)pyridin-2-yl)amino)-N-(2-morpholinoethyl)-2-((triisopropylsilyl)ethynyl)benzamide TFA (2 mL, 26.0 mmol) was added to a solution of the product from step (iv) above (570 mg, 0.746 mmol) in DCM (10 mL), the mixture stirred for 4 h then evaporated under reduced pressure. The residue was partitioned between DCM (50 mL) and sat aq NaHCO$_3$ soln (20 mL), the organic layer washed with brine (20 mL), dried (MgSO$_4$), filtered and evaporated under reduced pressure to afford the sub-title compound (474 mg) as a light brown foam.

LCMS m/z 664 (M+H)$^+$ (ES$^+$)

(vi) 4-((4-((4-(3-(5-(tert-Butyl)-2-methoxy-3-(methylsulfonamido)phenyl)ureido)naphthalen-1-yl)oxy)pyridin-2-yl)amino)-N-(2-morpholinoethyl)-2-((triisopropylsilyl)ethynyl)benzamide A mixture of phenyl (5-(tert-butyl)-2-methoxy-3-(methylsulfonamido)phenyl)carbamate (see Example 1(iv) above; 167 mg, 0.425 mmol), the product from step (v) above (235 mg, 0.354 mmol) and Et$_3$N (15 μL, 0.108 mmol) in iPrOAc (5 mL) was heated at 60° C. for 6 h then evaporated under reduced pressure. The crude product was purified by chromatography on silica gel (40 g column, 0-5% MeOH/DCM) to afford the sub-title compound (254 mg) as a foam.

LCMS m/z 962.5 (M+H)$^+$ (ES$^+$), 80% purity (vii) 4-((4-((4-(3-(5-(tert-Butyl)-2-methoxy-3-(methylsulfonamido)phenyl)ureido)naphthalen-1-yl)oxy)pyridin-2-yl)amino)-2-ethynyl-N-(2-morpholinoethyl)benzamide TBAF (300 μL, 0.300 mmol, 1 M in THF) was added to a stirred solution of the product from step (vi) above (250 mg, 0.208 mmol) in THF (2 mL). The mixture was stirred at rt for 3 h then partitioned between EtOAc (50 mL) and sat aq NaHCO$_3$ (30 mL). The organic layer was dried (MgSO$_4$), filtered and evaporated under reduced pressure. The residue was purified by chromatography on silica gel (40 g column, 0-5% MeOH/DCM) then by preparative HPLC (Gilson, Basic (0.1% Ammonium Bicarbonate), Basic, Waters X-Bridge Prep-C18, 5 μm, 19×50 mm column, 20-70% MeCN in Water) to afford a foam that was slurried in ether, filtered then dried to afford the title compound (91 mg) as a solid.

$^1$H NMR (400 MHz, DMSO-d6) δ 9.40 (s, 1H), 9.24 (s, 1H), 9.15 (s, 1H), 8.91 (s, 1H), 8.30 (s, 1H), 8.19-8.17 (m, 2H), 8.12 (d, 1H), 8.05-8.02 (dd, 1H), 7.96 (d, 1H), 7.87 (d, 1H), 7.72 (dd, 1H), 7.64-7.57 (m, 2H), 7.48 (d, 1H), 7.41 (d, 1H), 7.03 (d, 1H), 6.66 (dd, 1H), 6.12 (d, 1H), 4.35 (s, 1H), 3.81 (s, 3H), 3.60-3.56 (m, 4H), 3.10 (s, 3H), 2.47-2.37 (m, 6H), 1.27 (s, 9H). 2H under water peak at 3.33

LCMS m/z 806 (M+H)$^+$ (ES$^+$); 804 (M−H)$^−$ (ES$^−$)

Example 16

4-[[4-[[4-[[5-tert-Butyl-3-(methanesulfonamido)-2-methoxy-phenyl]carbamoylamino]-1-naphthyl]oxy]-2-pyridyl]amino]-N-[2-[2-(2-hydroxyethoxy)ethoxy]ethyl]-2-methoxy-benzamide HATU (80 mg, 0.210 mmol) was added to a stirred solution of 4-((4-((4-(3-(5-(tert-butyl)-2-methoxy-3-(methylsulfonamido)phenyl)ureido)naphthalen-1-yl)oxy)pyridin-2-yl)amino)-2-methoxybenzoic acid, hydrochloride salt (see Example 1 above; 100 mg, 0.136 mmol), 2-(2-(2-aminoethoxy)ethoxy)ethanol (28 mg, 0.188 mmol) and Hünig's Base (100 μL, 0.573 mmol) in DMF (2 mL) at rt. The mixture was stirred for overnight then poured into water (10 mL) and partitioned with EtOAc (10 mL). The organic phase was concentrated in vacuo. The residue was purified by preparative HPLC (Waters, Acidic (0.1% Formic acid), Acidic, Waters X-Select Prep-C18, 5 μm, 19×50 mm column, 35-65% MeCN in Water) to afford a pale pink solid. The solid was partitioned between NaHCO$_3$ solution and 10% MeOH in DCM. The organic phase was dried via hydrophobic frit and concentrated in vacuo. The residue was re-concentrated from MeCN and the residue dried in vacuo at 45° C. to afford the title compound (58 mg) as a white solid.

$^1$H NMR (400 MHz, DMSO-d6) δ: 9.39 (s, 1H), 9.27 (s, 1H), 9.14 (s, 1H), 8.91 (s, 1H), 8.30 (d, 1H), 8.09-8.19 (m, 4H), 7.87 (d, 1H), 7.76 (d, 1H), 7.69-7.73 (m, 1H), 7.59-7.64 (m, 2H), 7.40 (d, 1H), 7.23 (dd, 1H), 7.03 (d, 1H), 6.66 (dd, 1H), 6.16 (d, 1H), 4.57 (t, 1H), 3.86 (s, 3H), 3.81 (s, 3H), 3.43-3.55 (m, 12H), 3.10 (s, 3H), 1.27 (s, 9H).

LCMS m/z 831 (M+H)$^+$ (ES$^+$)

Example 17

The following compounds were prepared by methods analogous to those described above. Where chemical shifts from $^1$H NMR spectra are reported, these were obtained at 400 MHz and ambient temperature, unless otherwise specified.

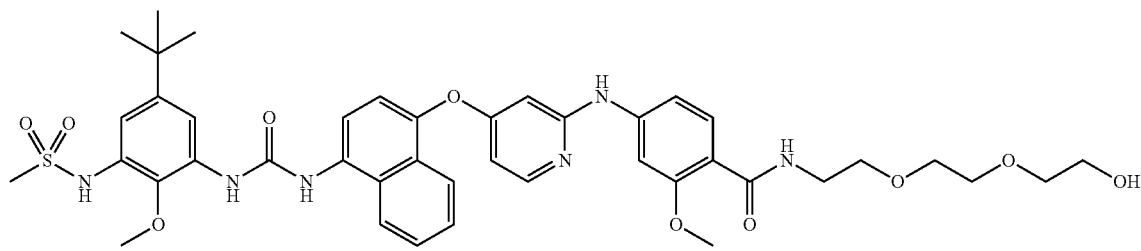 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCOCCOCCO]

(a) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[2-(4-methyl-piperazin-1-yl)ethyl]benzamide

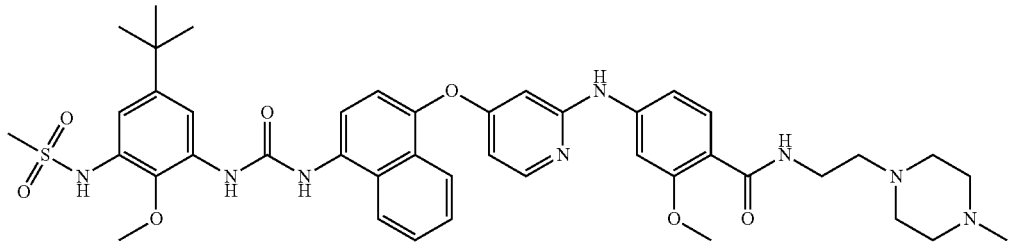

¹H NMR (400 MHz, DMSO-d6) δ: 9.39 (s, 1H), 9.27 (s, 1H), 9.15 (s, 1H), 8.84 (s, 1H), 8.31 (d, 1H), 8.20 (t, 1H), 8.17 (d, 1H), 8.12 (d, 1H), 8.03 (s, 1H), 7.86 (d, 1H), 7.77 (d, 1H), 7.71 (t, 1H), 7.61 (t, 1H), 7.56 (s, 1H), 7.40 (d, 1H), 7.24 (dd, 1H), 7.03 (d, 1H), 6.67 (dd, 1H), 6.16 (d, 1H), 3.87 (s, 3H), 3.81 (s, 3H), 3.37 (q, 2H), 2.97 (s, 3H), 2.25-2.46 (m, 10H), 2.17 (s, 3H), 1.26 (s, 9H).
LCMS m/z 413 (M+2H)$^{2+}$ (ES$^+$)

(b) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(3-morpholino-propyl)benzamide

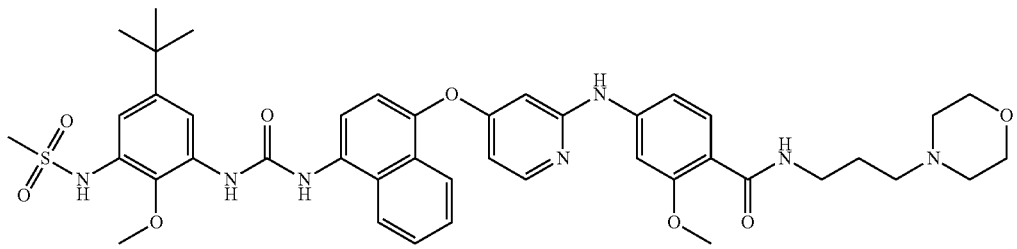 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCCN1CCOCC1]

¹H NMR (400 MHz, DMSO-d6) δ: 9.39 (s, 1H), 9.24 (s, 1H), 9.14 (s, 1H), 8.89 (s, 1H), 8.30 (d, 1H), 8.11-8.17 (m, 3H), 7.98 (t, 1H), 7.87 (d, 1H), 7.69-7.73 (m, 2H), 7.61 (t, 1H), 7.56 (d, 1H), 7.40 (d, 1H), 7.22 (dd, 1H), 7.03 (d, 1H), 6.66 (dd, 1H), 6.15 (d, 1H), 3.83 (s, 3H), 3.81 (s, 3H), 3.55-3.57 (m, 4H), 3.29 (q, 2H), 3.05 (s, 3H), 2.29-2.34 (m, 6H), 1.65 (quint, 2H), 1.27 (s, 9H).
LCMS m/z 826 (M+H)$^+$ (ES$^+$)

(c) 4-[[4-[[4-[[5-tert-butyl-3-(methanesulfonamido)-2-methoxy-phenyl]carbamoylamino]-1-naphthyl]oxy]-2-pyridyl]amino]-N-[2-[(2S,6R)-2,6-dimethyl-morpholin-4-yl]ethyl]-2-methoxy-benzamide

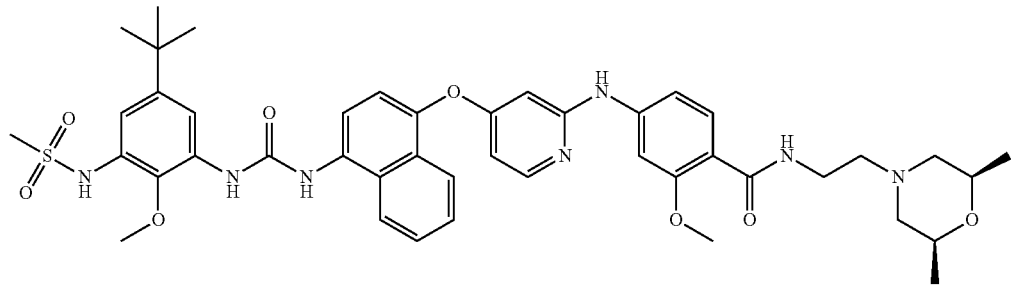

¹H NMR (400 MHz, DMSO-d6) δ: 9.39 (s, 1H), 9.26 (s, 1H), 9.13 (s, 1H), 8.91 (s, 1H), 8.30 (d, 1H), 8.11-8.21 (m, 4H), 7.87 (d, 1H), 7.77 (d, 1H), 7.71 (t, 1H), 7.62 (t, 1H), 7.57 (d, 1H), 7.40 (d, 1H), 7.24 (dd, 1H), 7.03 (d, 1H), 6.66 (dd, 1H), 6.16 (d, 1H), 3.86 (s, 3H), 3.81 (s, 3H), 3.55-3.62 (m, 2H), 3.39 (q, 2H), 3.10 (s, 3H), 2.79 (d, 2H), 2.44 (t, 2H), 1.66 (t, 2H), 1.27 (s, 9H), 1.07 (d, 6H).
LCMS m/z 840 (M+H)⁺ (ES⁺)

(d) 4-[[4-[[4-[[5-tert-butyl-3-(methanesulfonamido)-2-methoxy-phenyl]carbamoylamino]-1-naphthyl]oxy]-2-pyridyl]amino]-N-[2-(2,2-dimethylmorpholin-4-yl)ethyl]-2-methoxy-benzamide

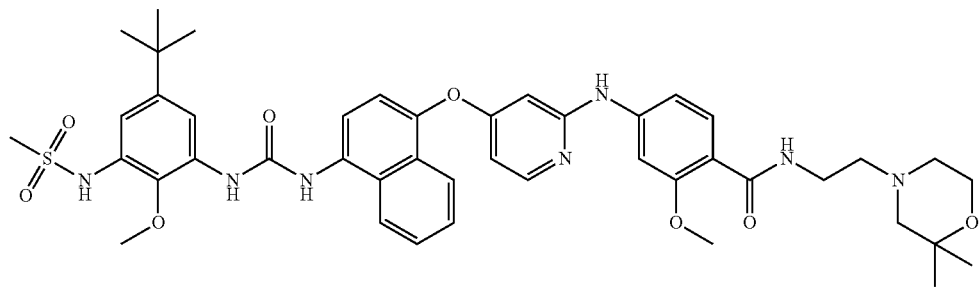

¹H NMR (400 MHz, DMSO-d6) δ: 9.39 (s, 1H), 9.26 (s, 1H), 9.13 (s, 1H), 8.91 (s, 1H), 8.30 (d, 1H), 8.08-8.19 (m, 4H), 8.87 (d, 1H), 7.78 (d, 1H), 7.69-7.73 (m, 1H), 7.60-7.63 (m, 1H), 7.58 (d, 1H), 7.40 (d, 1H), 7.23 (dd, 1H), 7.03 (d, 1H), 6.66 (dd, 1H), 6.16 (d, 1H), 3.86 (s, 3H), 3.81 (s, 3H), 3.61-3.64 (m, 2H), 3.39 (q, 2H), 3.10 (s, 3H), 2.41 (t, 2H), 2.34 (bs, 2H), 2.20 (s, 2H), 1.27 (s, 9H), 1.17 (s, 6H).
LCMS m/z 840 (M+H)⁺ (ES⁺)

(e) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(2-morpholino-2-oxo-ethyl)benzamide

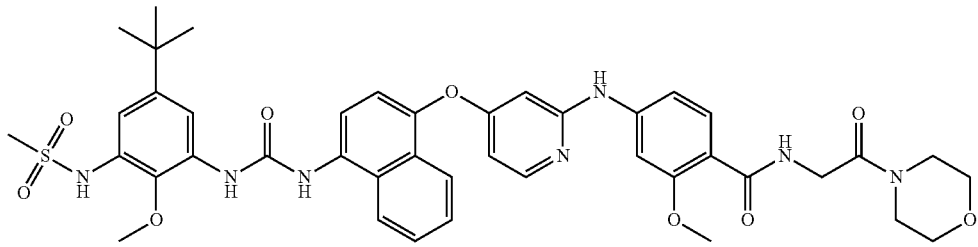 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCC(=O)N1CCOCC1]

¹H NMR (400 MHz, DMSO-d6) δ: 9.41 (s, 1H), 9.31 (s, 1H), 9.17 (s, 1H), 8.93 (s, 1H), 8.58 (t, 1H), 8.31 (d, 1H), 8.20 (d, 1H), 8.18 (d, 1H), 8.13 (d, 1H), 7.87 (d, 1H), 7.81 (d, 1H), 7.72 (t, 1H), 7.60-7.64 (m, 2H), 7.41 (d, 1H), 7.25 (dd, 1H), 7.03 (d, 1H), 6.67 (dd, 1H), 6.16 (d, 1H), 4.18 (d, 2H), 3.88 (s, 3H), 3.81 (s, 3H), 3.57-3.61 (m, 4H), 3.43-3.49 (m, 4H), 3.10 (s, 3H), 1.27 (s, 9H).

LCMS m/z 826 (M+H)⁺ (ES⁺)

(f) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[2-(4-methyl-1,4-diazepan-1-yl)ethyl]benzamide

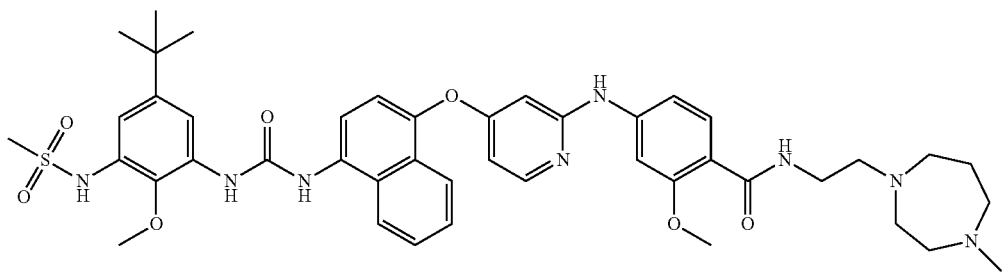

¹H NMR (400 MHz, DMSO-d6) δ: 9.39 (s, 1H), 9.26 (s, 1H), 9.13 (s, 1H), 8.90 (s, 1H), 8.30 (d, 1H), 8.11-8.17 (m, 4H), 7.87 (d, 1H), 7.78 (d, 1H), 7.71 (t, 1H), 7.62 (t, 1H), 7.58 (d, 1H), 7.40 (d, 1H), 7.23 (dd, 1H), 7.03 (d, 1H), 6.66 (dd, 1H), 6.16 (d, 1H), 3.87 (s, 3H), 3.81 (s, 3H), 2H under water, 3.09 (s, 3H), 2.65-2.70 (m, 4H), 2.51-2.59 (m, 6H), 2.25 (s, 3H), 1.73 (quint, 2H), 1.27 (s, 9H).

LCMS m/z 420 (M+2H)²⁺ (ES⁺)

(g) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[(1R)-2-[2-(2-methoxyethoxy)ethoxy]-1-methyl-ethyl]benzamide

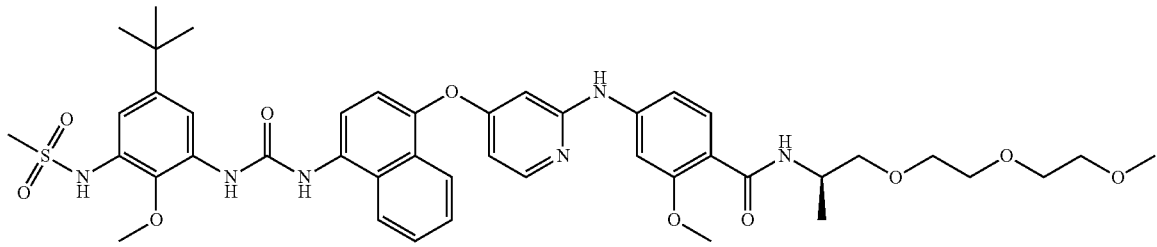

$^1$H NMR (400 MHz, DMSO-d6) δ: 9.40 (s, 1H), 9.28 (s, 1H), 9.17 (s, 1H), 8.93 (s, 1H), 8.30 (d, 1H), 8.20 (d, 1H), 8.17 (d, 1H), 8.13 (d, 1H), 7.96 (d, 1H), 7.87 (d, 1H), 7.75 (d, 1H), 7.71 (d, 1H), 7.63 (d, 1H), 7.59 (d, 1H), 7.41 (d, 1H), 7.23 (dd, 1H), 7.03 (d, 1H), 6.67 (dd, 1H), 6.15 (d, 1H), 4.06-4.15 (m, 1H), 3.85 (s, 3H), 3.81 (s, 3H), 3.51-3.55 (m, 6H), 3.45-3.49 (m, 1H), 3.39-3.43 (m, 3H), 3.22 (s, 3H), 3.10 (s, 3H), 1.27 (s, 9H), 1.15 (d, 3H).

LCMS m/z 859 (M+H)$^+$ (ES$^+$)

(h) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[(1S)-2-[2-(2-methoxyethoxy)ethoxy]-1-methyl-ethyl]benzamide

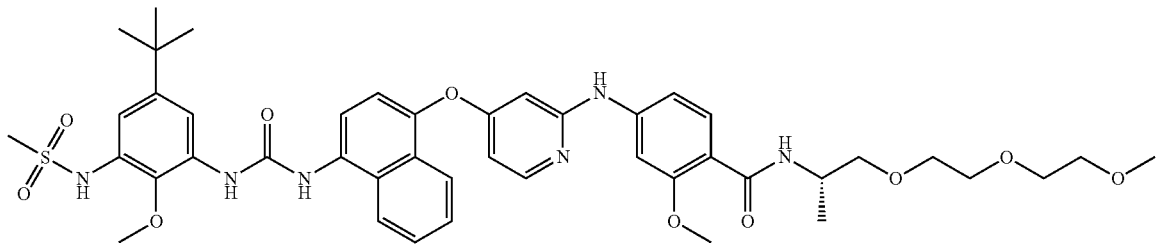

$^1$H NMR (400 MHz, DMSO-d6) δ: 9.40 (s, 1H), 9.28 (s, 1H), 9.17 (s, 1H), 8.93 (s, 1H), 8.30 (d, 1H), 8.20 (d, 1H), 8.17 (d, 1H), 8.13 (d, 1H), 7.96 (d, 1H), 7.87 (d, 1H), 7.75 (d, 1H), 7.71 (d, 1H), 7.63 (d, 1H), 7.59 (d, 1H), 7.41 (d, 1H), 7.23 (dd, 1H), 7.03 (d, 1H), 6.67 (dd, 1H), 6.15 (d, 1H), 4.06-4.15 (m, 1H), 3.85 (s, 3H), 3.81 (s, 3H), 3.51-3.55 (m, 6H), 3.45-3.49 (m, 1H), 3.39-3.43 (m, 3H), 3.22 (s, 3H), 3.10 (s, 3H), 1.27 (s, 9H), 1.15 (d, 3H).

LCMS m/z 859 (M+H)$^+$ (ES$^+$)

(i) 4-[[4-[[4-[[5-tert-butyl-3-(methanesulfonamido)-2-methoxy-phenyl]carbamoylamino]-1-naphthyl]oxy]pyrimidin-2-yl]amino]-2-methoxy-N-(2-morpholinoethyl)benzamide

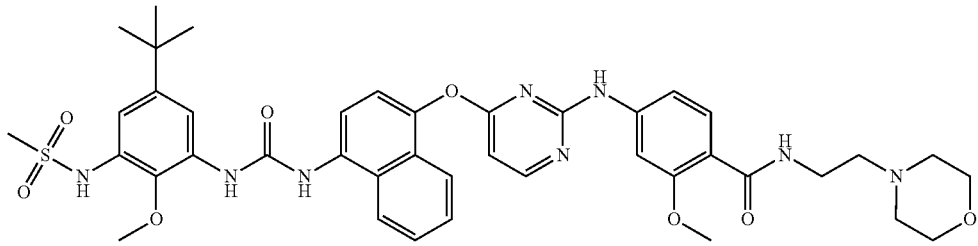 [SMILES: COc1cc(Nc2nccc(Oc3ccc(NC(=O)Nc4cc(C(C)(C)C)cc(NS(C)(=O)=O)c4OC)c4ccccc34)n2)ccc1C(=O)NCCN1CCOCC1]

$^1$H NMR (400 MHz, DMSO-d6) δ 9.81 (s, 1H), 9.42 (s, 1H), 9.16 (s, 1H), 8.95 (s, 1H), 8.48 (d, 1H), 8.31 (d, 1H), 8.20 (d, 1H), 8.16-8.12 (m, 2H), 7.85 (d, 1H), 7.72-7.68 (m, 1H), 7.62-7.55 (m, 2H), 7.43 (d, 1H), 7.35 (s, 1H), 7.08 (brd, 1H), 7.02 (d, 1H), 6.68 (d, 1H), 3.82 (s, 3H), 3.60-3.52 (m, 7H), 3.10 (s, 3H), 2.43-2.33 (m, 6H), 1.27 (s, 9H). 2H underwater
LCMS m/z 813 (M+H)$^+$ (ES$^+$); 811 (M−H)$^-$ (ES$^-$)

(j) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(1-methyl-4-piperidyl)benzamide

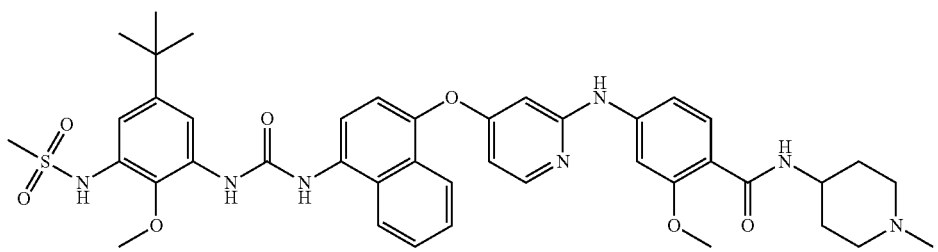

$^1$H NMR (400 MHz, DMSO-d6) δ: 9.43 (s, 1H), 9.27 (s, 1H), 9.19 (bs, 1H), 8.91 (s, 1H), 8.31 (d, 1H), 8.11-8.17 (m, 3H), 7.86 (d, 1H), 7.80 (d, 1H), 7.68-7.78 (m, 2H), 7.58-7.63 (m, 2H), 7.40 (d, 1H), 7.22 (d, 1H), 7.03 (d, 1H), 6.66 (dd, 1H), 6.14 (d, 1H), 3.85 (s, 3H), 3.81 (s, 3H), 3.70-3.77 (m, 1H), 3.07 (s, 3H), 2.61-2.63 (m, 2H), 2.16 (s, 3H), 2.04 (t, 2H), 1.78-1.81 (m, 2H), 1.52 (q, 2H), 1.26 (s, 9H).
LCMS m/z 796 (M+H)$^+$ (ES$^+$)

(k) 4-[[4-[[4-[[5-tert-butyl-3-(methanesulfonamido)-2-methoxy-phenyl]carbamoylamino]-1-naphthyl]oxy]-2-pyridyl]amino]-N-[2-(3,3-dimethylmorpholin-4-yl)ethyl]-2-methoxy-benzamide

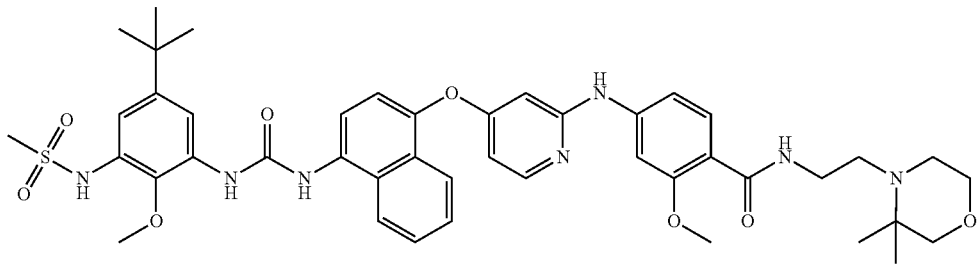 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCOCC1(C)C]

$^1$H NMR (400 MHz, DMSO-d6) δ: 9.40 (s, 1H), 9.28 (s, 1H), 9.16 (s, 1H), 8.93 (s, 1H), 8.30 (d, 1H), 8.12-8.20 (m, 4H), 7.87 (d, 1H), 7.79 (d, 1H), 7.71 (t, 1H), 7.62 (t, 1H), 7.58 (d, 1H), 7.41 (d, 1H), 7.23 (dd, 1H), 7.03 (d, 1H), 6.67 (dd, 1H), 6.15 (d, 1H), 3.88 (s, 3H), 3.81 (s, 3H), 3.60-3.63 (m, 2H), 3.31 (q, 2H), 3.25 (s, 2H), 3.10 (s, 3H), 4H under DMSO, 1.27 (s, 9H), 0.94 (s, 6H).

LCMS m/z 840 (M+H)$^+$ (ES$^+$)

(l) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(2-thiomorpholinoethyl)benzamide

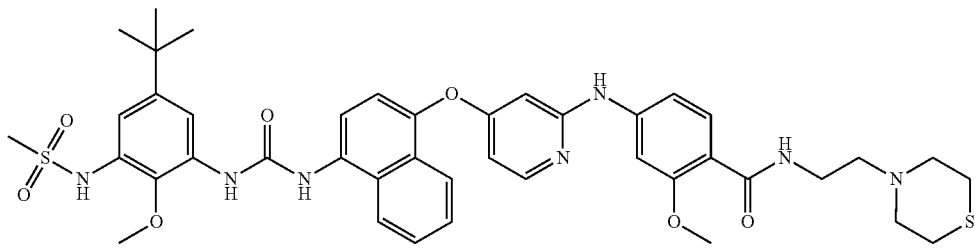 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCSCC1]

$^1$H NMR (400 MHz, DMSO-d6) δ: 9.40 (s, 1H), 9.27 (s, 1H), 9.16 (s, 1H), 8.93 (s, 1H), 8.30 (d, 1H), 8.12-8.19 (m, 4H), 7.87 (d, 1H), 7.77 (d, 1H), 7.71 (t, 1H), 7.62 (t, 1H), 7.57 (d, 1H), 7.41 (d, 1H), 7.23 (dd, 1H), 7.03 (d, 1H), 6.66 (dd, 1H), 6.15 (d, 1H), 3.87 (s, 3H), 3.81 (s, 3H), 3.37 (q, 2H), 3.10 (s, 3H), 2.68-2.69 (m, 4H), 2.63-2.64 (m, 4H), 2H under DMSO, 1.27 (s, 9H).

LCMS m/z 828 (M+H)$^+$ (ES$^+$)

(m) 4-[[4-[[4-[[5-tert-butyl-3-(methanesulfonamido)-2-methoxy-phenyl]carbamoylamino]-1-naphthyl]oxy]-2-pyridyl]amino]-N-[2-(4-hydroxy-1-piperidyl)ethyl]-2-methoxy-benzamide

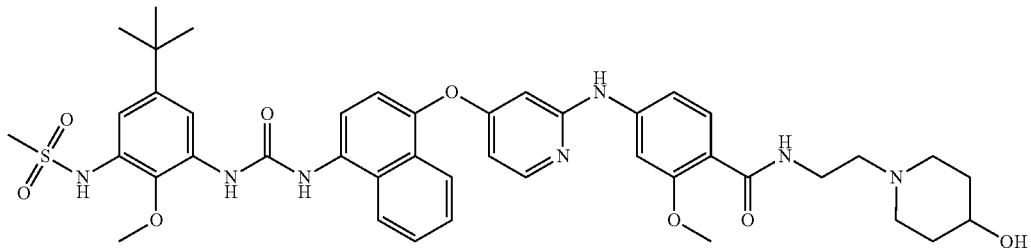 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCC(O)CC1]

¹H NMR (400 MHz, DMSO-d6) δ: 9.40 (s, 1H), 9.27 (s, 1H), 9.16 (s, 1H), 8.93 (s, 1H), 8.30 (d, 1H), 8.23 (t, 1H), 8.11-8.19 (m, 3H), 7.87 (d, 1H), 7.77 (d, 1H), 7.71 (t, 1H), 7.62 (t, 1H), 7.57 (d, 1H), 7.40 (d, 1H), 7.25 (dd, 1H), 7.03 (d, 1H), 6.66 (dd, 1H), 6.15 (d, 1H), 4.59 (d, 1H), 3.87 (s, 3H), 3.81 (s, 3H), 3.43-3.48 (m, 1H), 2H under H$_2$O, 3.10 (s, 3H), 2.68-2.75 (m, 2H), 2.42 (t, 2H), 2.05 (t, 2H), 1.73-1.76 (m, 2H), 1.40 (q, 2H), 1.27 (s, 9H).

LCMS m/z 826 (M+H)⁺ (ES⁺)

(n) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(2-methyl-2-morpholino-propyl)benzamide

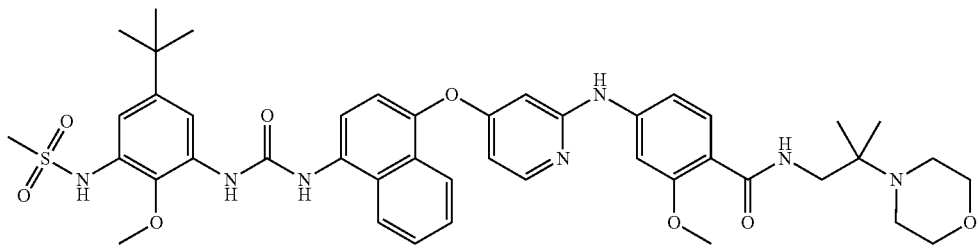 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCC(C)(C)N1CCOCC1]

¹H NMR (400 MHz, DMSO-d6) δ: 9.40 (s, 1H), 9.29 (s, 1H), 9.16 (s, 1H), 8.93 (s, 1H), 8.30 (d, 1H), 8.25 (t, 1H), 8.12-8.19 (m, 3H), 7.87 (d, 1H), 7.81 (d, 1H), 7.71 (t, 1H), 7.60-7.64 (m, 2H), 7.41 (d, 1H), 7.24 (dd, 1H), 7.03 (d, 1H), 6.67 (dd, 1H), 6.16 (d, 1H), 3.93 (s, 3H), 3.81 (s, 3H), 3.61 (bs 4H), 3.26 (d, 2H), 3.10 (s, 3H), 4H under DMSO, 1.27 (s, 9H), 1.00 (s, 6H)

LCMS m/z 840 (M+H)⁺ (ES⁺)

(o) 1-[5-tert-butyl-3-(methanesulfonamido)-2-methoxy-phenyl]-3-[4-[[2-[3-methoxy-4-[methyl(2-morpholinoethyl)sulfamoyl]anilino]-4-pyridyl]oxy]-1-naphthyl]urea

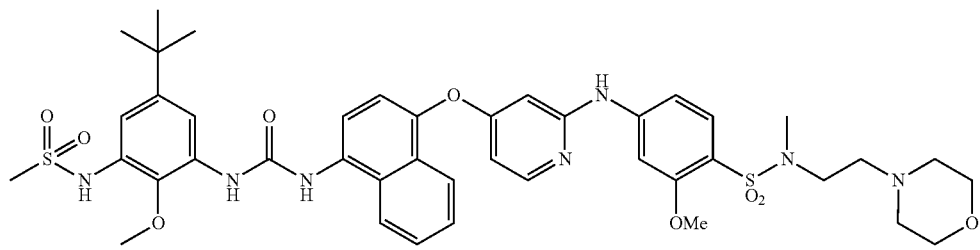 [SMILES: COc1cc(Nc2cc(Oc3ccc(NC(=O)Nc4cc(C(C)(C)C)cc(NS(C)(=O)=O)c4OC)c4ccccc34)ccn2)ccc1S(=O)(=O)N(C)CCN1CCOCC1]

¹H NMR (400 MHz, DMSO-d6) δ 9.40 (s, 1H), 9.39 (s, 1H), 9.13 (s, 1H), 8.90 (s, 1H), 8.30 (d, 1H), 8.18-8.17 (m, 2H), 8.12 (d, 1H), 7.86 (d, 1H), 7.73-7.68 (m, 1H), 7.63-7.60 (m, 2H), 7.54 (d, 1H), 7.40 (d, 1H), 7.24 (dd, 1H), 7.02 (d, 1H), 6.68 (dd, 1H), 6.16 (d, 1H), 3.80 (s, 3H), 3.79 (s, 3H), 3.52-3.50 (m, 4H), 3.15-3.11 (m, 2H), 3.09 (s, 3H), 2.73 (s, 3H), 2.38 (t, 2H), 2.33-2.31 (m, 4H), 1.26 (s, 9H).
LCMS m/z 862 (M+H)⁺ (ES⁺); 860 (M−H)⁻ (ES⁻)

(p) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[2-(1-piperidyl)ethyl]benzamide

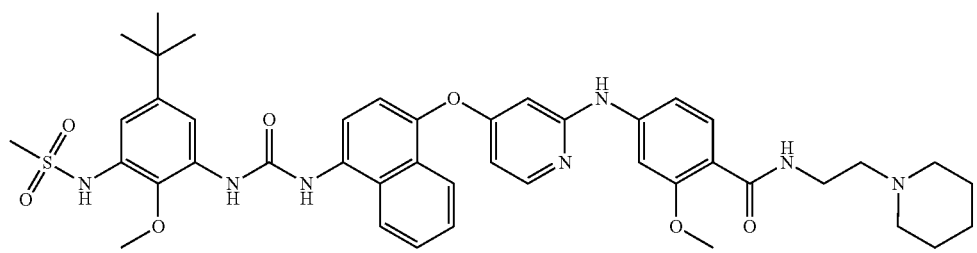 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCCCC1]

¹H NMR (400 MHz, DMSO-d6) δ: 9.40 (s, 1H), 9.27 (s, 1H), 9.16 (s, 1H), 8.93 (s, 1H), 8.30 (d, 1H), 8.23 (t, 1H), 8.12-8.19 (m, 3H), 7.87 (d, 1H), 7.78 (d, 1H), 7.71 (t, 1H), 7.62 (t, 1H), 7.57 (s, 1H), 7.41 (d, 1H), 7.23 (d, 1H), 7.03 (d, 1H), 6.66 (dd, 1H), 6.15 (d, 1H), 3.86 (s, 3H), 8.31 (s, 3H), 2H under H₂O, 3.10 (s, 3H), 2.30-2.43 (m, 6H), 1.47-1.58 (m, 4H), 1.35-1.46 (m, 2H), 1.27 (s, 9H)
LCMS m/z 810 (M+H)⁺ (ES⁺)

(q) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(2-pyrrolidin-1-ylethyl)benzamide

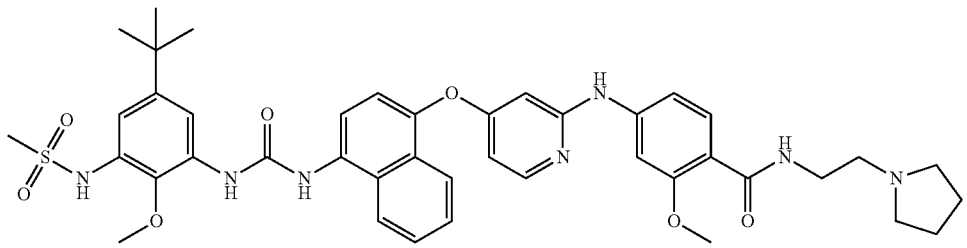 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCCC1]

$^1$H NMR (400 MHz, DMSO-d6) δ: 9.40 (s, 1H), 9.27 (s, 1H), 9.16 (s, 1H), 8.93 (s, 1H), 8.30 (d, 1H), 8.22 (t, 1H), 8.12-8.19 (m, 3H), 7.87 (d, 1H), 7.76 (d, 1H), 7.71 (t, 1H), 7.62 (t, 1H), 7.56 (d, 1H), 7.40 (d, 1H), 7.22 (dd, 1H), 7.03 (d, 1H), 6.66 (dd, 1H), 6.15 (d, 1H), 3.83 (s, 3H), 3.81 (s, 3H), 2H under H$_2$O, 3.10 (s, 3H), 2.56 (t, 2H), 4H under DMSO, 1.71 (bs, 4H), 1.27 (s, 9H)

LCMS m/z 796 (M+H)$^+$ (ES$^+$)

(r) 4-[[4-[[4-[[5-tert-butyl-3-(methanesulfonamido)-2-methoxy-phenyl]carbamoylamino]-1-naphthyl]oxy]-2-pyridyl]amino]-N-[2-(1,1-dioxo-1,4-thiazinan-4-yl)ethyl]-2-methoxy-benzamide

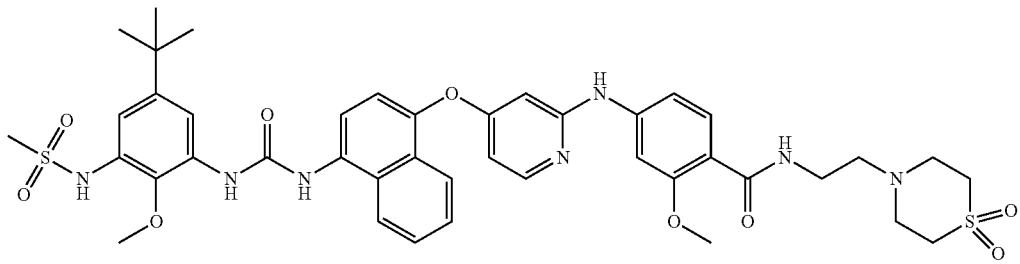 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCS(=O)(=O)CC1]

$^1$H NMR (400 MHz, DMSO-d6) δ: 9.40 (s, 1H), 9.27 (s, 1H), 9.16 (s, 1H), 8.93 (s, 1H), 8.30 (d, 1H), 8.10-8.19 (m, 4H), 7.87 (d, 1H), 7.70-7.76 (m, 2H), 7.62 (t, 1H), 7.57 (s, 1H), 7.40 (d, 1H), 7.23 (dd, 1H), 7.03 (d, 1H), 6.66 (dd, 1H), 6.15 (d, 1H), 3.85 (s, 3H), 3.81 (s, 3H), 2H under H$_2$O, 3.10 (s, 3H), 3.05-3.14 (m, 4H), 2.93-3.01 (m, 4H), 2.65 (t, 2H), 1.27 (s, 9H)

LCMS m/z 860 (M+H)$^+$ (ES$^+$)-

(s) 5-[[4-[[4-[[4-[[5-tert-butyl-3-(methanesulfona-mido)-2-methoxy-phenyl]carbamoylamino]-1-naph-thyl]oxy]-2-pyridyl]amino]-2-methoxy-benzoyl]amino]pentanoic acid

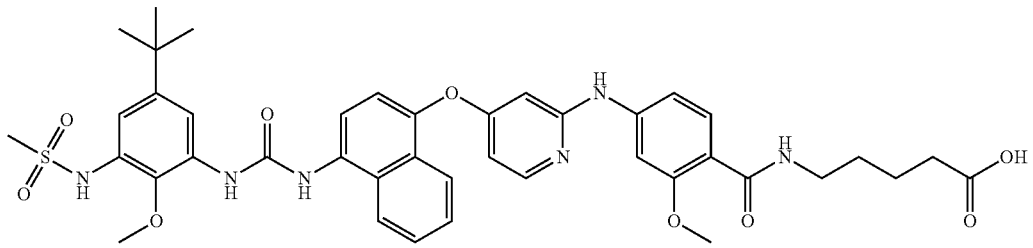 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCCCC(=O)O]

$^1$H NMR (of hydrochloride salt; 400 MHz, DMSO-d6) δ: 9.67 (bs, 1H), 9.52 (s, 1H), 9.14 (s, 1H), 8.98 (s, 1H), 8.35 (d, 1H), 8.18 (d, 1H), 8.12-8.15 (m, 2H), 8.02 (t, 1H), 7.87 (d, 1H), 7.70-7.74 (m, 2H), 7.62-7.65 (m, 1H), 7.41-7.44 (m, 2H), 7.12 (d, 1H), 7.03 (d, 1H), 6.75 (d, 1H), 6.23 (d, 1H), 3.84 (s, 3H), 3.81 (s, 3H), 3.26 (q, 2H), 3.10 (s, 3H), 2.25 (t, 2H), 1.47-1.55 (m, 4H), 1.27 (s, 9H).

LCMS (of hydrochloride salt) m/z 799 (M+H)$^+$ (ES$^+$); 797 (M−H)$^−$ (ES$^−$)

(t) 4-[[4-[[4-[[5-tert-butyl-3-(methanesulfonamido)-2-methoxy-phenyl]carbamoylamino]-1-naphthyl]oxy]-2-pyridyl]amino]benzoic acid

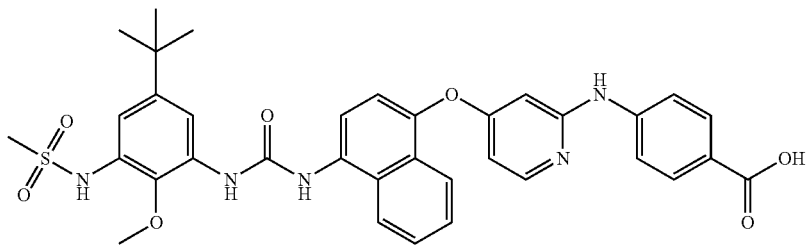 [SMILES: COc1c(NC(=O)Nc2ccc(Oc3ccnc(Nc4ccc(C(=O)O)cc4)c3)c3ccccc23)cc(C(C)(C)C)cc1NS(C)(=O)=O]

$^1$H NMR (400 MHz, DMSO-d6) δ 12.39 (s, 1H), 9.40 (s, 1H), 9.33 (s, 1H), 9.14 (s, 1H), 8.92 (s, 1H), 8.30 (d, 1H), 8.20-8.15 (m, 2H), 8.12 (d, 1H), 7.91-7.85 (m, 1H), 7.79 (d, 2H), 7.75-7.67 (m, 3H), 7.62 (ddd, 1H), 7.41 (d, 1H), 7.03 (d, 1H), 6.67 (dd, 1H), 6.17 (d, 1H), 3.81 (s, 3H), 3.10 (s, 3H), 1.27 (s, 9H).

LCMS m/z 670 (M+H)$^+$ (ES$^+$); 668 (M−H)$^−$ (ES$^−$)

(u) 4-[[4-[[4-[[5-tert-butyl-3-(methanesulfonamido)-2-methoxy-phenyl]carbamoylamino]-1-naphthyl]oxy]-2-pyridyl]amino]-N-(2-morpholinoethyl)benzamide

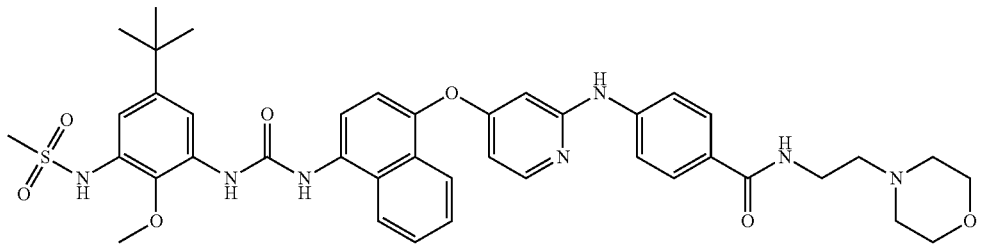 [SMILES: COc1c(NC(=O)Nc2ccc(Oc3ccnc(Nc4ccc(C(=O)NCCN5CCOCC5)cc4)c3)c3ccccc23)cc(C(C)(C)C)cc1NS(C)(=O)=O]

$^1$H NMR (400 MHz, DMSO-d6) δ 9.39 (s, 1H), 9.20 (s, 1H), 9.13 (s, 1H), 8.90 (s, 1H), 8.30 (d, 1H), 8.19-8.08 (m, 4H), 7.87 (d, 1H), 7.75-7.58 (m, 6H), 7.40 (d, 1H), 7.03 (d, 1H), 6.64 (dd, 1H), 6.15 (d, 1H), 3.81 (s, 3H), 3.57 (t, 4H), 3.35 (d, 2H), 3.08 (s, 3H), 2.43 (dd, 6H), 1.27 (s, 9H).
LCMS 782 (M+H)$^+$ (ES$^+$); 780 (M–H)$^-$ (ES$^-$)

(v) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[(1S)-1-methyl-2-morpholino-ethyl]benzamide

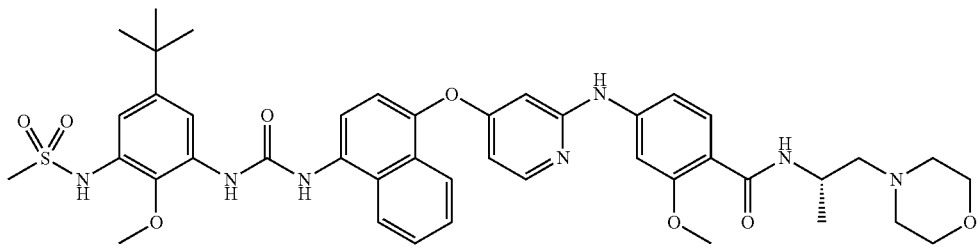 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)N[C@@H](C)CN1CCOCC1]

$^1$H NMR (400 MHz, DMSO-d6) δ: 9.39 (s, 1H), 9.25 (s, 1H), 9.14 (s, 1H), 8.91 (s, 1H), 8.30 (d, 1H), 8.19 (d, 1H), 8.17 (d, 1H), 8.12 (d, 1H), 7.98 (d, 1H), 7.87 (d, 1H), 7.69-7.74 (m, 2H), 7.60-7.64 (m, 1H), 7.58 (d, 1H), 7.40 (d, 1H), 7.23 (dd, 1H), 7.03 (d, 1H), 6.66 (dd, 1H), 6.15 (d, 1H), 4.01-4.08 (m, 1H), 3.86 (s, 3H), 3.82 (s, 3H), 3.54-3.60 (m, 4H), 3.10 (s, 3H), 2.39-2.43 (m, 5H), 2.31 (dd, 1H), 1.27 (s, 9H), 1.16 (d, 3H).
LCMS m/z 826 (M+H)$^+$ (ES$^+$)

(w) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(2-piperazin-1-ylethyl)benzamide

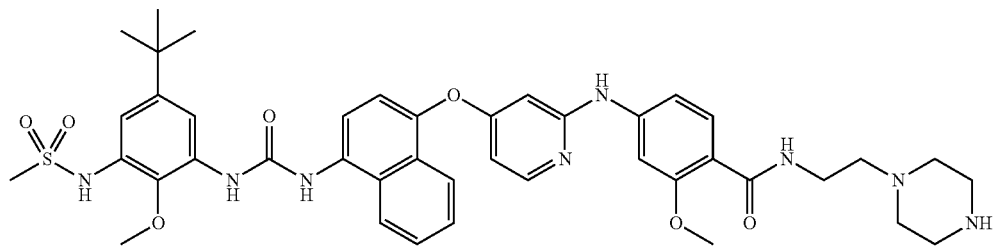 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCNCC1]

$^1$H NMR (400 MHz, DMSO-d6) δ: 9.40 (s, 1H), 9.26 (s, 1H), 8.91 (s, 1H), 8.31 (d, 1H), 8.22 (t, 1H), 8.11-8.18 (m, 3H), 7.87 (d, 1H), 7.78 (d, 1H), 7.71 (t, 1H), 7.58-7.63 (m, 2H), 7.40 (d, 1H), 7.23 (dd, 1H), 7.03 (d, 1H), 6.66 (dd, 1H), 6.16 (d, 1H), 3.88 (s, 3H), 3.81 (s, 3H), 5H under water, 3.09 (s, 3H), 2.72-2.74 (m, 3H), 2.42 (t, 2H), 2.35 (bs, 4H), 1.27 (s, 9H)

LCMS m/z 811 (M+H)$^+$ (ES$^+$)

(x) 3-[2-[2-[[4-[[4-[[4-[[5-tert-butyl-3-(methanesulfonamido)-2-methoxyphenyl]carbamoyl-amino]-1-naphthyl]oxy]-2-pyridyl]amino]-2-methoxy-benzoyl]amino]ethoxy]ethoxy]propanoic acid

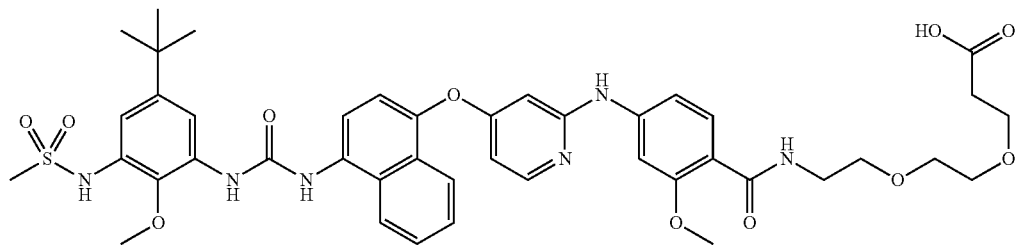 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCOCCOCCC(=O)O]

$^1$H NMR (400 MHz, DMSO-d6) δ: 9.45 (s, 1H), 9.27 (s, 1H), 8.95 (s, 1H), 8.31 (d, 1H), 8.08-8.18 (m, 4H), 7.87 (d, 1H), 7.76 (d, 1H), 7.71 (t, 1H), 7.62 (t, 1H), 7.57 (d, 1H), 7.40 (d, 1H), 7.22 (dd, 1H), 7.03 (d, 1H), 6.67 (dd, 1H), 6.17 (d, 1H), 3.84 (s, 3H), 3.81 (s, 3H), 3.60-3.64 (m, 2H), 3.50-3.53 (m, 6H), 3.43 (q, 2H), 3.10 (s, 3H), 2.42-2.45 (m, 2H), 1.27 (s, 9H).

LCMS m/z 859 (M+H)$^+$ (ES$^+$)

(y) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(4-morpholinobutyl)benzamide

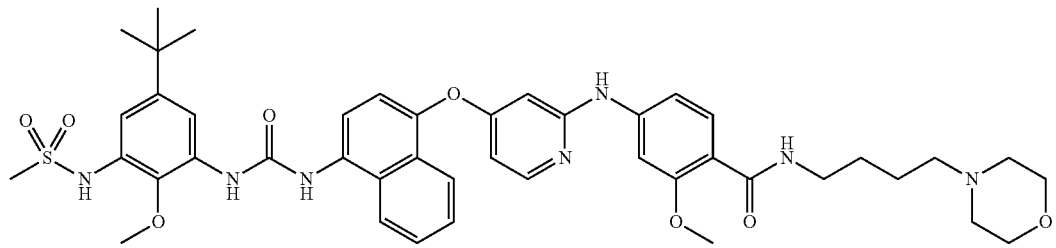 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCCCN1CCOCC1]

¹H NMR (400 MHz, DMSO-d6) δ: 9.39 (s, 1H), 9.24 (s, 1H), 9.14 (s, 1H), 8.91 (s, 1H), 8.30 (d, 1H), 8.19 (d, 1H), 8.16 (d, 1H), 8.12 (d, 1H), 7.95 (t, 1H), 7.87 (d, 1H), 7.68-7.73 (m, 2H), 7.60-7.63 (m, 1H), 7.56 (d, 1H), 7.40 (d, 1H), 7.22 (dd, 1H), 7.03 (d, 1H), 6.66 (dd, 1H), 6.16 (d, 1H), 3.83 (s, 3H), 3.81 (s, 3H), 3.54-3.56 (m, 4H), 3.26 (q, 2H), 3.10 (s, 3H), 2.25-2.32 (m, 6H), 1.43-1.53 (m, 4H), 1.27 (s, 9H).

LCMS m/z 840 (M+H)⁺ (ES⁺)

(z) 4-[[4-[[4-[[5-tert-butyl-3-(methanesulfonamido)-2-methoxy-phenyl]carbamoylamino]-1-naphthyl]oxy]-2-pyridyl]amino]-N-[2-[4-(2-hydroxyethyl)piperazin-1-yl]ethyl]-2-methoxy-benzamide

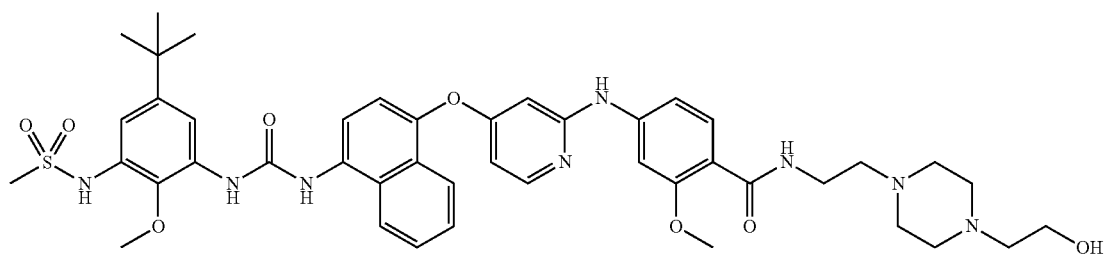 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCN(CCO)CC1]

¹H NMR (400 MHz, DMSO-d6) δ: 9.39 (s, 1H), 9.26 (s, 1H), 9.14 (s, 1H), 8.91 (s, 1H), 8.30 (d, 1H), 8.11-8.22 (m, 4H), 7.87 (d, 1H), 7.77 (d, 1H), 7.71 (t, 1H), 7.62 (t, 1H), 7.57 (s, 1H), 7.40 (d, 1H), 7.24 (d, 1H), 7.03 (s, 1H), 6.66 (d, 1H), 6.16 (s, 1H), 4.37 (t, 1H), 3.88 (s, 3H), 3.81 (s, 3H), 3.50 (q, 2H), 2H under H₂O, 3.10 (s, 3H), 2.37-2.44 (m, 12H), 1.27 (s, 9H)

LCMS m/z 855 (M+H)⁺ (ES⁺)

(aa) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[3-(4-methylpiperazin-1-yl)propyl]benzamide

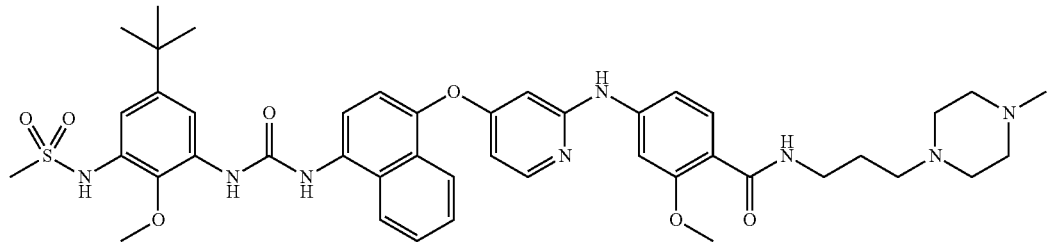

$^1$H NMR (400 MHz, DMSO-d6) δ: 9.39 (s, 1H), 9.24 (s, 1H), 9.14 (s, 1H), 8.91 (s, 1H), 8.30 (d, 1H), 8.19 (d, 1H), 8.17 (d, 1H), 8.12 (d, 1H), 7.97 (t, 1H), 7.87 (d, 1H), 7.69-7.73 (m, 2H), 7.60-7.64 (m, 1H), 7.55 (s, 1H), 7.40 (d, 1H), 7.22 (d, 1H), 7.03 (d, 1H), 6.65 (dd, 1H), 6.15 (d, 1H), 3.83 (s, 3H), 3.81 (s, 3H), 2H under water, 3.10 (s, 3H), 2.22-2.40 (m, 10H), 2.14 (s, 3H), 1.64 (quint, 2H), 1.27 (s, 9H)

LCMS m/z 839 (M+H)$^+$ (ES$^+$)

(ab) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-methyl-N-(2-morpholinoethyl)benzamide

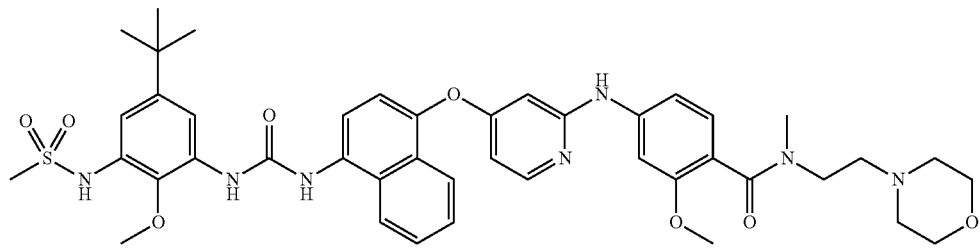 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)N(C)CCN1CCOCC1]

$^1$H NMR (400 MHz, DMSO-d6) δ: 9.39 (s, 1H), 9.14 (s, 1H), 9.07 (s, 1H), 8.91 (s, 1H), 8.30 (d, 1H), 8.19 (d, 1H), 8.11-8.14 (m, 2H), 7.87 (d, 1H), 7.71 (t, 1H), 7.62 (t, 1H), 7.38-7.40 (m, 2H), 7.21 (d, 1H), 7.03 (d, 1H), 6.97 (t, 1H), 6.62 (dd, 1H), 6.12 (s, 1H), 3.81 (s, 3H), 3.70 (s, 3H, rotamer 1), 3.69 (s, 3H, rotamer 2), 3.56-3.59 (m, 2H), 3.44-3.54 (m, 3H), 3.10-3.23 (bs, 1H), 3.10 (s, 3H), 2.93 (s, 3H, rotamer 1), 2.76 (s, 3H, rotamer 2), 2.38-2.48 (m, 3H), 2.26-2.38 (bs, 1H), 2.10-2.19 (m, 2H), 1.27 (s, 9H).

LCMS m/z 826 (M+H)$^+$ (ES$^+$)

(ac) 4-[[4-[[4-[[5-tert-butyl-3-(methanesulfona-mido)-2-methoxy-phenyl]carbamoylamino]-1-naph-thyl]oxy]-2-pyridyl]amino]-N-[2-[2-hydroxyethyl(methyl)amino]ethyl]-2-methoxy-benzamide

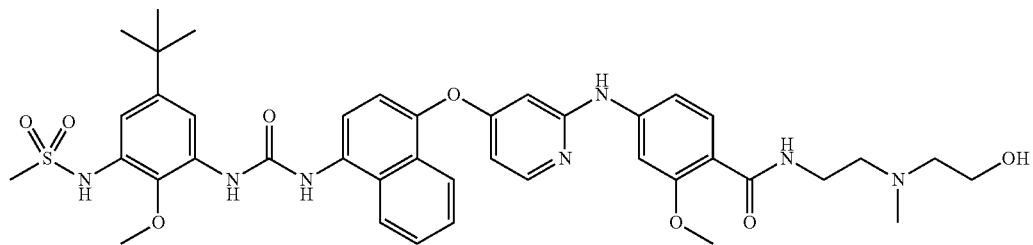 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN(C)CCO]

$^1$H NMR (400 MHz, DMSO-d6) δ: 9.39 (s, 1H), 9.26 (s, 1H), 9.14 (s, 1H), 8.92 (s, 1H), 8.31 (d, 1H), 8.11-8.19 (m, 4H), 7.87 (d, 1H), 7.76 (d, 1H), 7.71 (t, 1H), 7.62 (t, 1H), 7.58 (d, 1H), 7.40 (d, 1H), 7.23 (dd, 1H), 7.03 (d, 1H), 6.66 (dd, 1H), 6.16 (d, 1H), 4.38 (t, 1H), 3.85 (s, 3H), 3.81 (s, 3H), 3.51 (q, 2H), 2H under water, 3.10 (s, 3H), 4H under DMSO, 2.24 (s, 3H), 1.27 (s, 9H).
LCMS m/z 800 (M+H)$^+$ (ES$^+$)

(ad) 4-[[4-[[4-[[5-tert-butyl-3-(methanesulfona-mido)-2-methoxy-phenyl]carbamoylamino]-1-naph-thyl]oxy]-2-pyridyl]amino]-2-methoxy-N-[2-[2-methoxyethyl(methyl)amino]ethyl]-benzamide

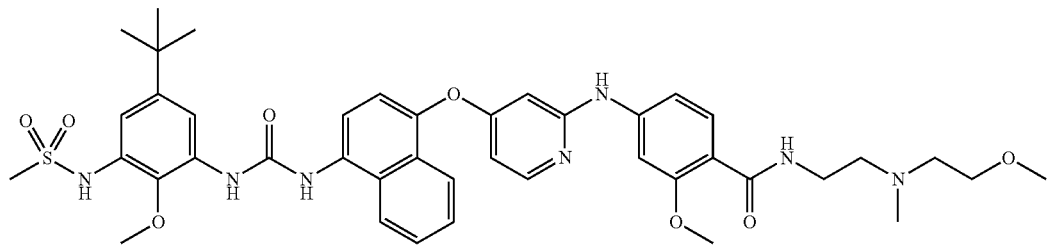

$^1$H NMR (400 MHz, DMSO-d6) δ: 9.39 (s, 1H), 9.26 (s, 1H), 9.14 (s, 1H), 8.92 (s, 1H), 8.31 (d, 1H), 8.11-8.19 (m, 4H), 7.87 (d, 1H), 7.77 (d, 1H), 7.71 (t, 1H), 7.62 (t, 1H), 7.58 (d, 1H), 7.40 (d, 1H), 7.22 (dd, 1H), 7.03 (d, 1H), 6.66 (dd, 1H), 6.16 (d, 1H), 3.85 (s, 3H), 3.81 (s, 3H), 3.44 (t, 2H), 2H under water, 3.23 (s, 3H), 3.10 (s, 3H), 2.54-2.57 (m, 2H), 2H under DMSO, 2.24 (s, 3H), 1.27 (s, 9H).
LCMS m/z 814 (M+H)$^+$ (ES$^+$)

(ae) 4-[[4-[[4-[[5-tert-butyl-3-(methanesulfonamido)-2-methoxy-phenyl]carbamoylamino]-1-naphthyl]oxy]-2-pyridyl]amino]-2,6-dimethoxy-N-(2-morpholinoethyl)benzamide

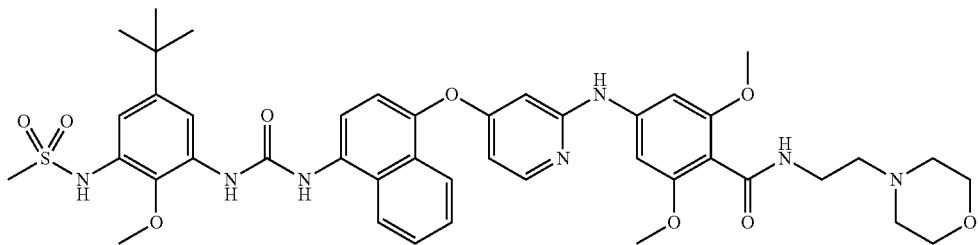 [SMILES: COc1cc(Nc2cc(Oc3ccc(NC(=O)Nc4cc(C(C)(C)C)cc(NS(C)(=O)=O)c4OC)c4ccccc34)ccn2)cc(OC)c1C(=O)NCCN1CCOCC1]

$^1$H NMR (400 MHz, DMSO-d6) δ: 9.39 (s, 1H), 9.14 (s, 1H), 9.02 (s, 1H), 8.91 (s, 1H), 8.30 (d, 1H), 8.19 (d, 1H), 8.11-8.14 (m, 2H), 7.87 (d, 1H), 7.69-7.73 (m, 2H), 7.60-7.63 (m, 1H), 7.39 (d, 1H), 7.03 (d, 1H), 6.93 (s, 2H), 6.62 (dd, 1H), 6.12 (d, 1H), 3.81 (s, 3H), 3.61 (s, 6H), 3.55-3.57 (m, 4H), 3.23 (q, 2H), 3.10 (s, 3H), 2.34-2.40 (m, 6H), 1.27 (s, 9H).
LCMS m/z 842 (M+H)$^+$ (ES$^+$)

(af) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-methyl-N-(3-morpholinopropyl)benzamide

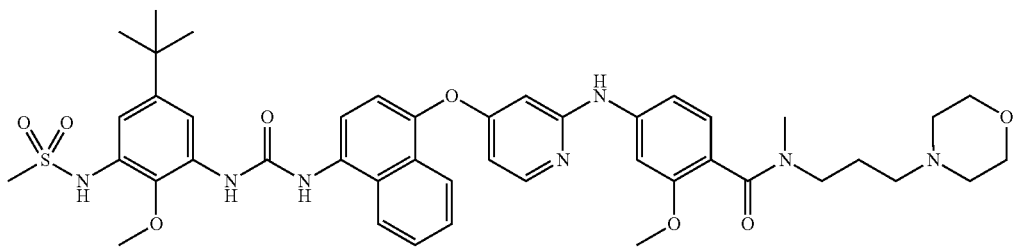 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)N(C)CCCN1CCOCC1]

$^1$H NMR (400 MHz, DMSO-d6, 90° C.) δ: 9.17 (s, 1H), 8.83 (s, 1H), 8.63-8.69 (m, 2H), 8.29 (d, 1H), 8.12-8.13 (m, 2H), 8.04 (d, 1H), 7.93 (d, 1H), 7.66-7.70 (m, 1H), 7.58-7.62 (m, 1H), 7.40 (d, 1H), 7.34 (d, 1H), 7.18 (dd, 1H), 7.08 (d, 1H), 6.96 (d, 1H), 6.56 (dd, 1H), 6.27 (d, 1H), 3.86 (s, 3H), 3.72 (s, 3H), 3.41-3.61 (bm, 4H), 3.10 (s, 3H), 2.85 (bs, 3H), 2.00-2.46 (bm, 8H), 1.55-1.75 (bm, 2H), 1.30 (s, 9H).
LCMS m/z 840 (M+H)$^+$ (ES$^+$)

(ag) 4-[[4-[[4-[[5-tert-butyl-3-(methanesulfonamido)-2-methoxy-phenyl]carbamoylamino]-1-naphthyl]oxy]-pyridyl]amino]-2-methoxy-N-[3-(1-oxo-1,4-thiazan-4-yl)propyl]benzamide

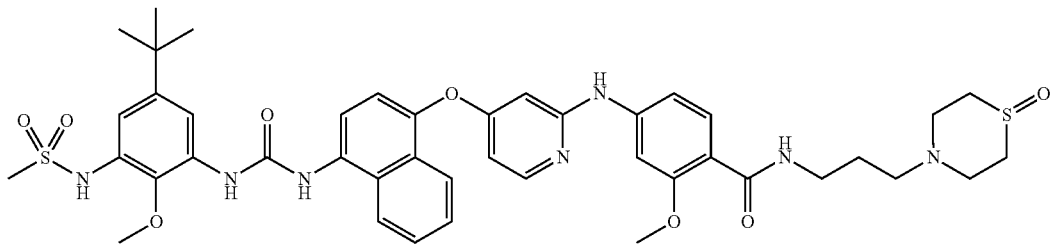 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCCN1CCS(=O)CC1]

¹H NMR (400 MHz, DMSO-d6) δ: 9.39 (s, 1H), 9.24 (s, 1H), 9.14 (s, 1H), 8.91 (s, 1H), 8.30 (d, 1H), 8.11-8.18 (m, 3H), 7.98 (t, 1H), 7.87 (d, 1H), 7.69-7.73 (m, 2H), 7.60-7.63 (m, 1H), 7.56 (d, 1H), 7.40 (d, 1H), 7.22 (dd, 1H), 7.03 (d, 1H), 6.66 (dd, 1H), 6.15 (d, 1H), 3.84 (s, 3H), 3.81 (s, 3H), 2H underwater, 3.10 (s, 3H), 2.81-2.90 (m, 4H), 2.62-2.73 (m, 4H), 2.40 (t, 2H), 1.67 (quint, 2H), 1.27 (s, 9H).
LCMS m/z 858 (M+H)⁺ (ES⁺)

(ah) 4-[[4-[[4-[[5-tert-butyl-3-(methanesulfonamido)-2-methoxy-phenyl]carbamoylamino]-1-naphthyl]oxy]-2-pyridyl]amino]-N-[3-(1,1-dioxo-1,4-thiazinan-4-yl)propyl]-2-methoxy-benzamide

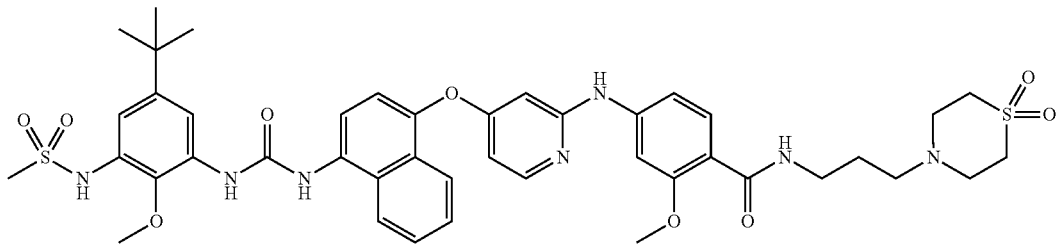 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCCN1CCS(=O)(=O)CC1]

¹H NMR (400 MHz, DMSO-d6) δ: 9.39 (s, 1H), 9.24 (s, 1H), 9.14 (s, 1H), 8.91 (s, 1H), 8.30 (d, 1H), 8.11-8.19 (m, 3H), 7.98 (t, 1H), 7.87 (d, 1H), 7.69-7.73 (m, 2H), 7.60-7.64 (m, 1H), 7.56 (d, 1H), 7.40 (d, 1H), 7.22 (dd, 1H), 7.03 (d, 1H), 6.66 (dd, 1H), 6.15 (d, 1H), 3.84 (s, 3H), 3.81 (s, 3H), 2H under water, 3.10 (s, 3H), 3.06-3.08 (m, 4H), 2.83-2.92 (m, 4H), 2H under DMSO, 1.66 (quint, 2H), 1.27 (s, 9H).
LCMS m/z 874 (M+H)⁺ (ES⁺)

(ai) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[2-(1,4-oxazepan-4-yl)ethyl]benzamide

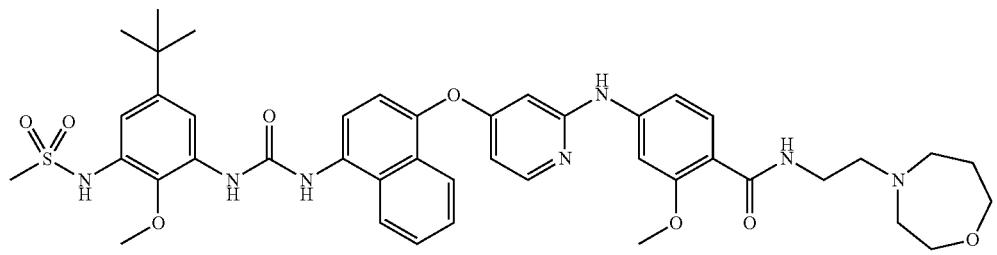 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCCOCC1]

$^1$H NMR (400 MHz, DMSO-d6) δ: 9.36 (s, 1H), 9.26 (s, 1H), 9.14 (s, 1H), 8.91 (s, 1H), 8.30 (d, 1H), 8.11-8.21 (m, 4H), 7.87 (d, 1H), 7.78 (d, 1H), 7.71 (t, 1H), 7.62 (t, 1H), 7.57 (d, 1H), 7.40 (d, 1H), 7.23 (dd, 1H), 7.03 (d, 1H), 6.66 (dd, 1H), 6.16 (d, 1H), 3.87 (s, 3H), 3.81 (s, 3H), 3.69 (t, 2H), 3.62-3.64 (m, 2H), 2H underwater, 3.10 (s, 3H), 2.67-2.70 (m, 4H), 2.62 (t, 2H), 1.81 (quint, 2H), 1.27 (s, 9H).

LCMS 826 (M+H)$^+$ (ES$^+$)

(aj) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[3-(1,4-oxazepan-4-yl)propyl]benzamide

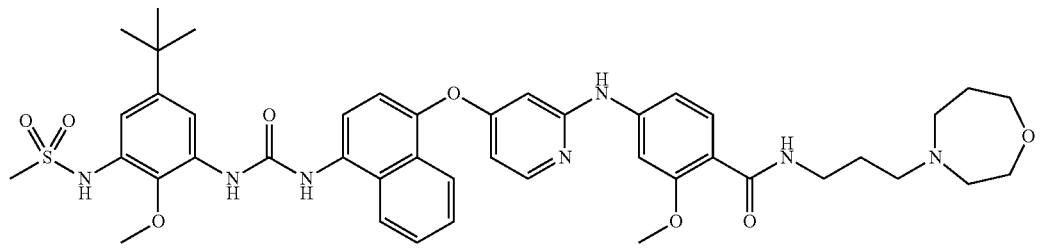 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCCN1CCCOCC1]

$^1$H NMR (400 MHz, DMSO-d6) δ: 9.39 (s, 1H), 9.24 (s, 1H), 9.14 (s, 1H), 8.91 (s, 1H), 8.30 (d, 1H), 8.11-8.19 (m, 3H), 7.98 (t, 1H), 7.87 (d, 1H), 7.69-7.73 (m, 2H), 7.60-7.64 (m, 1H), 7.56 (d, 1H), 7.40 (d, 1H), 7.22 (dd, 1H), 7.03 (d, 1H), 6.66 (dd, 1H), 6.15 (d, 1H), 3.84 (s, 3H), 3.81 (s, 3H), 3.66 (t, 2H), 3.58-3.60 (m, 2H), 2H underwater, 3.10 (s, 3H), 2.59-2.63 (m, 4H), 2H under DMSO, 1.78 (quint, 2H), 1.64 (quint, 2H), 1.27 (s, 9H).

LCMS 840 (M+H)$^+$ (ES$^+$)

(ak) 4-[[4-[[4-[[5-tert-butyl-3-(methanesulfona-mido)-2-methoxy-phenyl]carbamoylamino]-1-naphthyl]oxy]-2-pyridyl]amino]-2-methoxy-N-[(1-methyl-4-piperidyl)methyl]benzamide

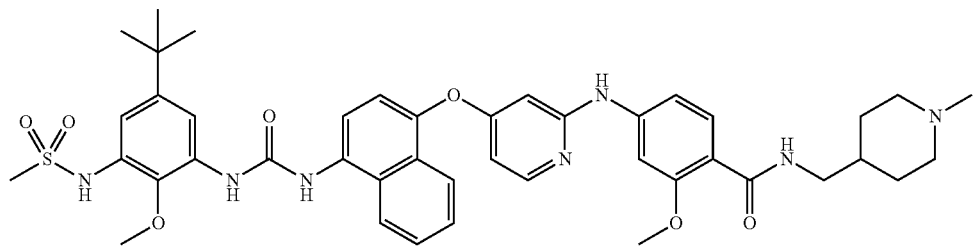

$^1$H NMR (400 MHz, DMSO-d6) δ: 9.40 (s, 1H), 9.24 (s, 1H), 9.11 (s, 1H), 8.91 (s, 1H), 8.31 (d, 1H), 8.11-8.19 (m, 3H), 7.96 (t, 1H), 7.87 (d, 1H), 7.69-7.73 (m, 2H), 7.60-7.63 (m, 1H), 7.57 (d, 1H), 7.40 (d, 1H), 7.21 (dd, 1H), 7.03 (d, 1H), 6.66 (dd, 1H), 6.16 (d, 1H), 3.84 (s, 3H), 3.81 (s, 3H), 3.16 (t, 2H), 3.10 (s, 3H), 2.74 (bd, 2H), 2.13 (s, 3H), 1.77-1.82 (m, 2H), 1.60 (bd, 2H), 1.42-1.47 (bm, 1H), 1.27 (s, 9H), 1.15-1.22 (m, 2H).
LCMS m/z 810 (M+H)$^+$ (ES$^+$)

(al) 4-[[4-[[4-[[5-tert-butyl-3-(methanesulfonamido)-2-methoxy-phenyl]carbamoylamino]-1-naphthyl]oxy]-2-pyridyl]amino]-N-[2-(4,4-difluoro-1-piperidyl)ethyl]-2-methoxy-benzamide

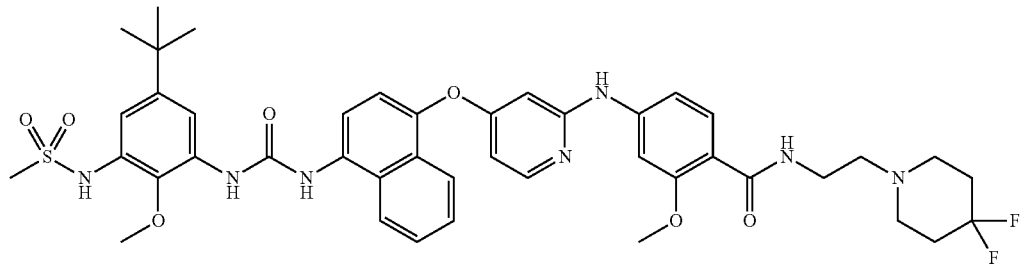 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCC(F)(F)CC1]

$^1$H NMR (400 MHz, DMSO-d6) δ: 9.39 (s, 1H), 9.26 (s, 1H), 9.14 (s, 1H), 8.91 (s, 1H), 8.30 (d, 1H), 8.11-8.19 (m, 4H), 7.87 (d, 1H), 7.76 (d, 1H), 7.69-7.73 (m, 1H), 7.60-7.64 (m, 1H), 7.57 (d, 1H), 7.40 (d, 1H), 7.24 (dd, 1H), 7.03 (d, 1H), 6.66 (dd, 1H), 6.16 (d, 1H), 3.85 (s, 3H), 3.81 (s, 3H), 3.39 (q, 2H), 3.10 (s, 3H), 2.54-2.64 (m, 6H), 1.92-2.01 (m, 4H), 1.27 (s, 9H).
LCMS m/z 846 (M+H)$^+$ (ES$^+$)

(am) 4-[[4-[[4-[[5-tert-butyl-3-(methanesulfonamido)-2-methoxy-phenyl]carbamoylamino]-1-naphthyl]oxy]-2-pyridyl]amino]-2-(dimethylamino)benzoic acid

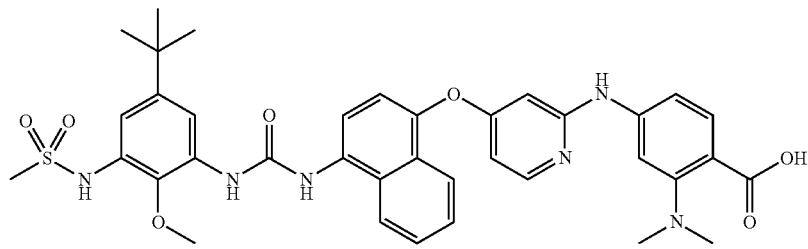 [SMILES: COc1c(NC(=O)Nc2ccc(Oc3ccnc(Nc4ccc(C(=O)O)c(N(C)C)c4)c3)c3ccccc23)cc(C(C)(C)C)cc1NS(C)(=O)=O]

¹H NMR (400 MHz, DMSO-d6) δ: 9.44 (s, 1H), 9.41 (s, 1H), 9.16 (s, 1H), 8.93 (s, 1H), 8.31 (d, 1H), 8.19-8.21 (m, 2H), 8.13 (d, 1H), 7.95 (d, 1H), 7.86 (d, 1H), 7.83 (d, 1H), 7.72 (t, 1H), 7.62 (t, 1H), 7.52 (dd, 1H), 7.41 (d, 1H), 7.03 (d, 1H), 6.70 (dd, 1H), 6.17 (d, 1H), 3.81 (s, 3H), 3.10 (s, 3H), 2.71 (s, 6H), 1.27 (s, 9H).

LCMS m/z 713 (M+H)⁺ (ES⁺)

(an) 4-((4-((4-(3-(5-(tert-butyl)-2-methoxy-3-(methylsulfonamido)phenyl)ureido)naphthalen-1-yl)oxy)pyrimidin-2-yl)amino)-2-methoxy-N-(2-(1-methylpiperidin-4-yl)ethyl)benzamide

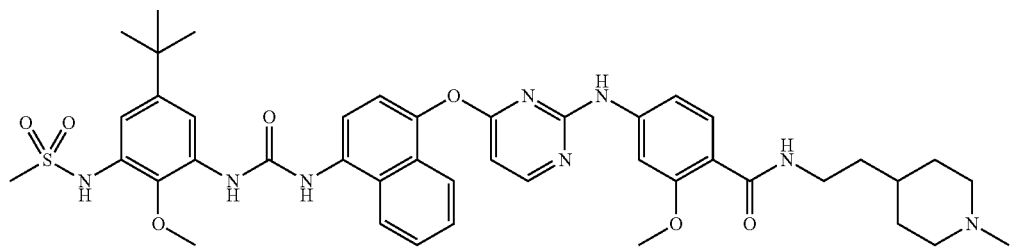

¹H NMR (400 MHz, DMSO-d6) δ: 9.77 (s, 1H), 9.41 (s, 1H), 9.16 (bs, 1H), 8.93 (s, 1H), 8.48 (d, 1H), 8.30 (d, 1H), 8.19 (d, 1H), 8.12 (d, 1H), 7.84-7.88 (m, 2H), 7.67-7.71 (m, 1H), 7.58-7.62 (m, 1H), 7.47 (d, 1H), 7.42 (d, 1H), 7.33 (s, 1H), 7.06 (d, 1H), 7.03 (d, 1H), 6.68 (d, 1H), 3.82 (s, 3H), 3.51 (s, 3H), 3.23 (q, 2H), 3.09 (s, 3H), 2.70 (bd, 2H), 2.10 (s, 3H), 1.77 (t, 2H), 1.61 (d, 2H), 1.38 (q, 2H), 1.27 (s, 9H), 1.06-1.17 (m, 3H).

LCMS m/z 825 (M+H)⁺ (ES⁺)

(ao) 4-((4-((4-(3-(5-(tert-Butyl)-2-methoxy-3-(methylsulfonamido)phenyl)ureido)naphthalen-1-yl)oxy)pyrimidin-2-yl)amino)-2-methoxy-N-(3-morpholinopropyl)benzamide

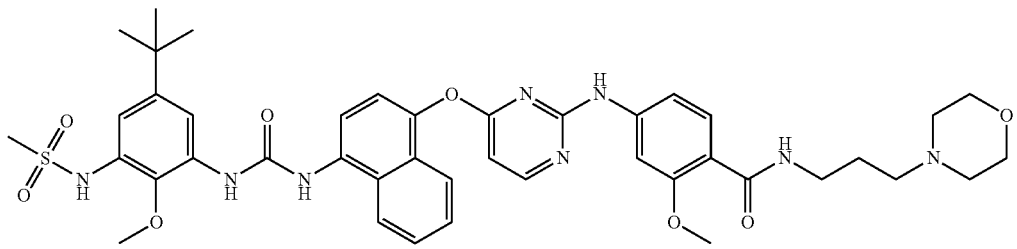 [SMILES: COc1cc(Nc2nccc(Oc3ccc(NC(=O)Nc4cc(C(C)(C)C)cc(NS(C)(=O)=O)c4OC)c4ccccc34)n2)ccc1C(=O)NCCCN1CCOCC1]

$^1$H NMR (400 MHz, DMSO-d6) δ 9.79 (s, 1H), 9.42 (s, 1H), 9.16 (s, 1H), 8.95 (s, 1H), 8.49 (d, 1H), 8.31 (d, 1H), 8.21 (d, 1H), 8.13 (d, 1H), 7.98-7.91 (br m, 1H), 7.86 (d, 1H), 7.72-7.68 (m, 1H), 7.63-7.59 (m, 1H), 7.50 (d, 1H), 7.44 (d, 1H), 7.35 (s, 1H), 7.11-7.05 (br m, 1H), 7.04 (d, 1H), 6.69 (d, 1H), 3.83 (s, 3H), 3.59-3.49 (m, 7H), 3.28-3.22 (m, 2H), 3.02 (s, 3H), 2.37-2.24 (m, 6H), 1.66-1.58 (m, 2H), 1.28 (s, 9H).

LCMS m/z 827 (M+H)$^+$ (ES$^+$); 825 (M−H)$^−$ (ES$^−$)

(ap) 4-((4-((4-(3-(5-(tert-Butyl)-2-methoxy-3-(methylsulfonamido)phenyl)ureido)naphthalen-1-yl)oxy)pyrimidin-2-yl)amino)-2-methoxy-N-(3-(4-methylpiperazin-1-yl)propyl)benzamide

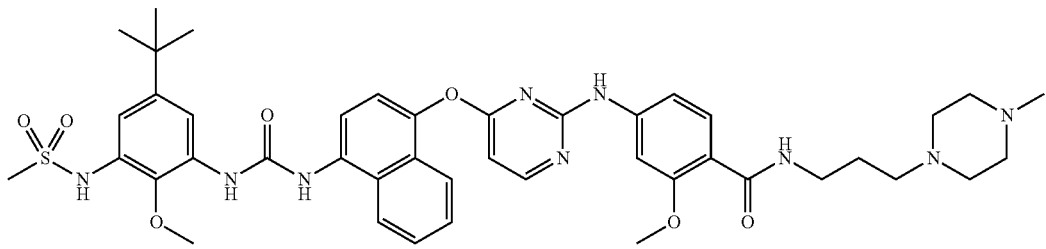

$^1$H NMR (400 MHz, DMSO-d6) δ: 9.77 (s, 1H), 9.40 (s, 1H), 9.15 (bs, 1H), 8.92 (s, 1H), 8.48 (d, 1H), 8.30 (d, 1H), 8.19 (d, 1H), 8.12 (d, 1H), 7.91 (t, 1H), 7.85 (d, 1H), 7.67-7.71 (m, 1H), 7.58-7.62 (m, 1H), 7.49 (d, 1H), 7.42 (d, 1H), 7.33 (s, 1H), 7.07 (bd, 1H), 7.03 (d, 1H), 6.68 (d, 1H), 3.82 (s, 3H), 3.50 (s, 3H), 3.23 (q, 2H), 3.10 (s, 3H), 2.18-2.44 (bm, 10H), 2.11 (s, 3H), 1.59 (quint, 2H), 1.27 (s, 9H).

LCMS m/z 840 (M+H)$^+$ (ES$^+$); 421 (M+2H)$^{2+}$ (ES$^+$)

(aq) 4-((4-((4-(3-(5-(tert-Butyl)-2-methoxy-3-(methylsulfonamido)phenyl)ureido)naphthalen-1-yl)oxy)pyrimidin-2-yl)amino)-2-methoxy-N-(2-(4-methylpiperazin-1-yl)ethyl)benzamide

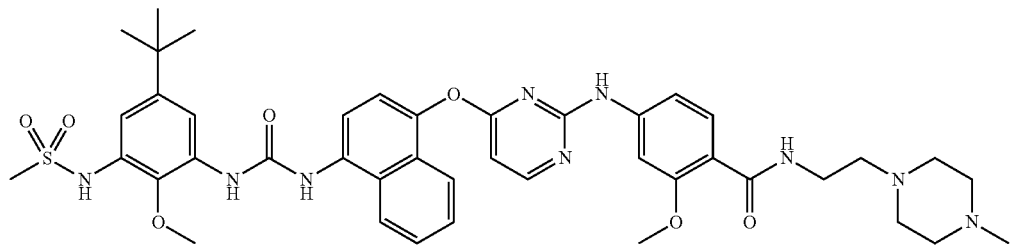

¹H NMR (400 MHz, DMSO-d6) δ: 9.80 (s, 1H), 9.41 (s, 1H), 9.14 (s, 1H), 8.92 (s, 1H), 8.48 (d, 1H), 8.30 (d, 1H), 8.20 (d, 1H), 8.11-8.15 (m, 2H), 7.86 (d, 1H), 7.67-7.71 (m, 1H), 7.57-7.62 (m, 2H), 7.43 (d, 1H), 7.36 (s, 1H), 7.08 (d, 1H), 7.03 (d, 1H), 6.69 (d, 1H), 3.82 (s, 3H), 3.52 (s, 3H), 2H under water, 3.10 (s, 3H), 2.24-2.42 (m, 10H), 2.14 (s, 3H), 1.27 (s, 9H).

LCMS m/z 826 (M+H)⁺ (ES⁺)

(ar) 2-(4-((4-((4-(3-(5-(tert-Butyl)-2-methoxy-3-(methylsulfonamido)phenyl)ureido)naphthalen-1-yl)oxy)pyridin-2-yl)amino)-2-methoxybenzamido)acetic acid

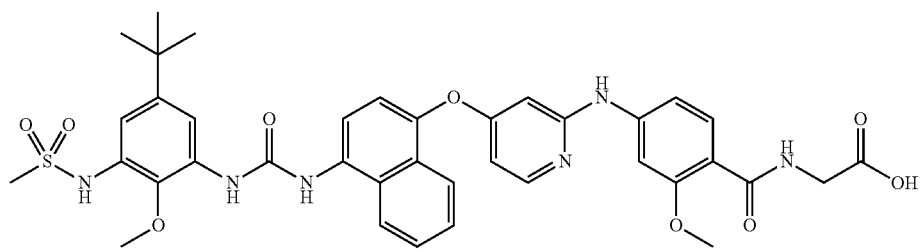 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCC(=O)O]

¹H NMR (of hydrochloride salt; 400 MHz, DMSO-d6) δ: 9.61 (s, 1H), 9.49 (s, 1H), 9.14 (s, 1H), 8.97 (s, 1H), 8.33-8.39 (m, 2H), 8.13-8.19 (m, 3H), 7.87 (d, 1H), 7.82 (d, 1H), 7.72 (t, 1H), 7.63 (t, 1H), 7.50 (s, 1H), 7.43 (d, 1H), 7.16 (d, 1H), 7.03 (d, 1H), 6.74 (dd, 1H), 6.23 (dd, 1H), 3.97 (d, 2H), 3.87 (s, 3H), 3.81 (s, 3H), 3.10 (s, 3H), 1.27 (s, 9H).

LCMS (of hydrochloride salt) m/z 757 (M+H)⁺ (ES⁺)

(as) 4-(4-((4-((4-(3-(5-(tert-Butyl)-2-methoxy-3-(methylsulfonamido)phenyl)ureido)-naphthalen-1-yl)oxy)pyridin-2-yl)amino)-2-methoxybenzamido)butanoic acid

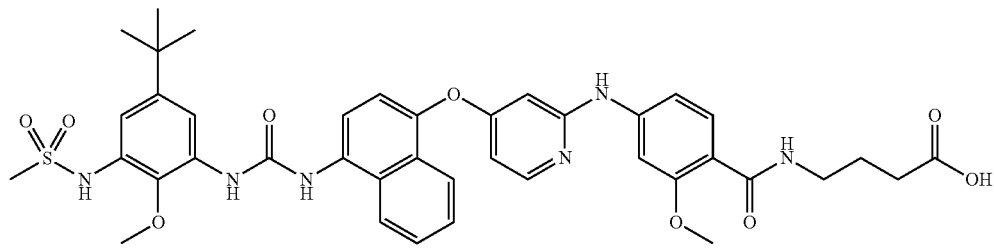 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCCC(=O)O]

$^1$H NMR (of hydrochloride salt; 400 MHz, DMSO-d6) δ: 9.57 (s, 1H), 9.49 (s, 1H), 9.14 (s, 1H), 8.96 (s, 1H), 8.34 (d, 1H), 8.18 (d, 1H), 8.15 (d, 1H), 8.13 (s, 1H), 8.04 (t, 1H), 7.87 (d, 1H), 7.70-7.74 (m, 2H), 7.61-7.65 (m, 1H), 7.42-7.44 (m, 2H), 7.13 (d, 1H), 7.03 (d, 1H), 6.74 (dd, 1H), 6.22 (d, 1H), 3.84 (s, 3H), 3.81 (s, 3H), 3.28 (q, 2H), 3.10 (s, 3H), 2.25 (t, 2H), 1.73 (quint, 2H), 1.27 (s, 9H).

LCMS (of hydrochloride salt) m/z 785 (M+H)$^+$ (ES$^+$)

(at) 4-((4-((4-(3-(5-(tert-Butyl)-2-methoxy-3-(methylsulfonamido)phenyl)ureido)naphthalen-1-yl)oxy)pyridin-2-yl)amino)-2,6-dimethoxy-N-(2-(1-methylpiperidin-4-yl)ethyl)benzamide

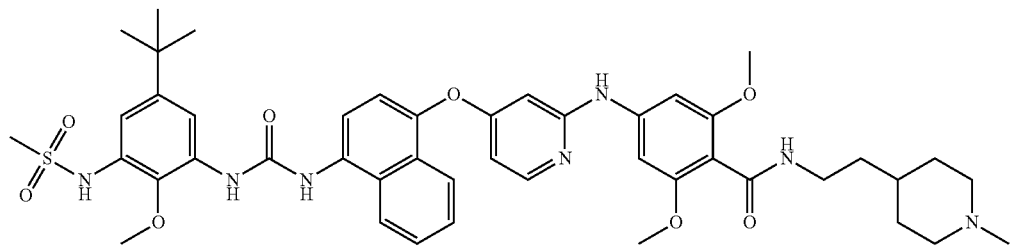

$^1$H NMR (400 MHz, DMSO-d6) δ 9.39 (s, 1H), 9.01 (s, 1H), 8.91 (s, 1H), 8.30 (d, 1H), 8.17 (d, 1H), 8.13 (d, 1H), 8.11 (d, 1H), 7.87 (d, 1H), 7.76 (t, 1H), 7.73-7.67 (m, 1H), 7.65-7.55 (m, 1H), 7.39 (d, 1H), 7.03 (d, 1H), 6.92 (s, 2H), 6.61 (dd, 1H), 6.11 (d, 1H), 3.81 (s, 3H), 3.61 (s, 6H), 3.14 (q, 2H), 3.09 (s, 3H), 2.79-2.66 (m, 2H), 2.12 (s, 3H), 1.86-1.69 (m, 2H), 1.70-1.57 (m, 2H), 1.41-1.29 (m, 3H), 1.27 (s, 9H), 1.17-0.98 (m, 2H).

LCMS m/z 854 (M+H)$^+$ (ES$^+$)

(au) 4-((4-((4-(3-(5-(tert-Butyl)-2-methoxy-3-(methylsulfonamido)phenyl)ureido)naphthalen-1-yl)oxy)pyridin-2-yl)amino)-2,6-dimethoxy-N-(3-(4-methylpiperazin-1-yl)propyl)benzamide

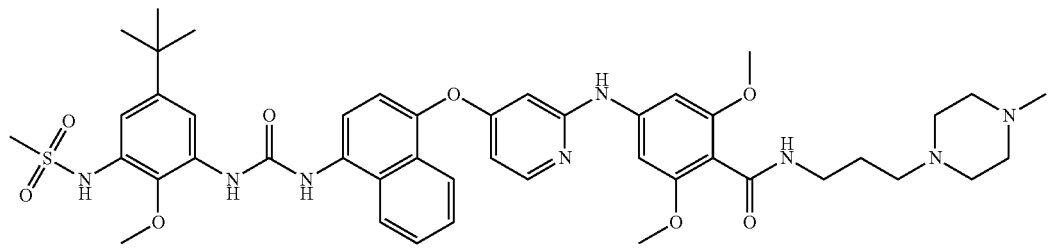

¹H NMR (400 MHz, DMSO-d6) δ 9.39 (s, 1H), 9.12 (s, 1H), 9.01 (s, 1H), 8.91 (s, 1H), 8.30 (d, 1H), 8.18 (d, 1H), 8.13 (d, 1H), 8.12 (d, 1H), 7.87 (d, 1H), 7.83 (t, 1H), 7.75-7.66 (m, 1H), 7.65-7.52 (m, 1H), 7.39 (d, 1H), 7.03 (d, 1H), 6.92 (s, 2H), 6.61 (dd, 1H), 6.12 (d, 1H), 3.81 (s, 3H), 3.61 (s, 6H), 3.13 (q, 2H), 3.09 (s, 3H), 2.48-2.14 (m, 10H), 2.11 (s, 3H), 1.56 (p, 2H), 1.27 (s, 9H).
LCMS m/z 869 (M+H)⁺ (ES⁺)

(av) (S)-2-(4-((4-((4-(3-(5-(tert-Butyl)-2-methoxy-3-(methylsulfonamido)phenyl)ureido)-naphthalen-1-yl)oxy)pyridin-2-yl)amino)-2-methoxybenzamido)-3-(1H-imidazol-4-yl)propanoic acid

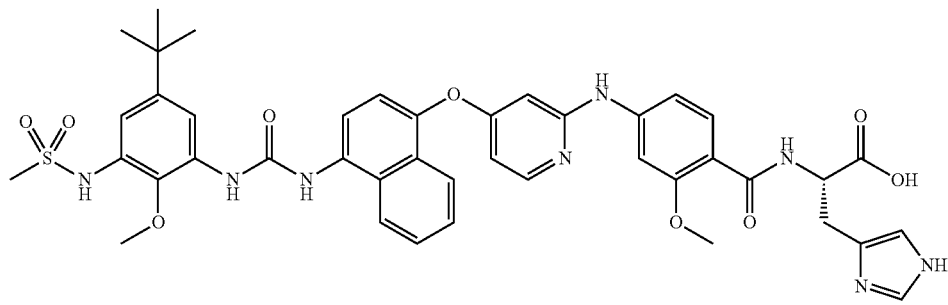 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)N[C@@H](Cc1c[nH]cn1)C(=O)O]

¹H NMR (of dihydrochloride salt; 400 MHz, DMSO-d6) δ: 14.48 (s, 1H), 14.29 (s, 1H), 9.98 (bs, 1H), 9.76 (s, 1H), 9.13 (s, 1H), 9.10 (s, 1H), 9.02 (s, 1H), 8.43 (d, 1H), 8.37 (d, 1H), 8.12-8.16 (m, 3H), 7.86 (d, 1H), 7.69-7.73 (m, 2H), 7.61-7.65 (m, 1H), 7.40-7.44 (m, 3H), 7.10 (d, 1H), 7.03 (d, 1H), 6.79 (d, 1H), 6.31 (s, 1H), 4.80 (q, 1H), 3.83 (s, 3H), 3.82 (s, 3H), 3.18-3.31 (m, 2H), 3.10 (s, 3H), 1.27 (s, 9H).
LCMS (of dihydrochloride salt) m/z 837 (M+H)⁺ (ES⁺)

(aw) (S)-1-(4-((4-((4-(3-(5-(tert-Butyl)-2-methoxy-3-(methylsulfonamido)phenyl)ureido)-naphthalen-1-yl)oxy)pyridin-2-yl)amino)-2-methoxybenzoyl)pyrrolidine-2-carboxylic acid

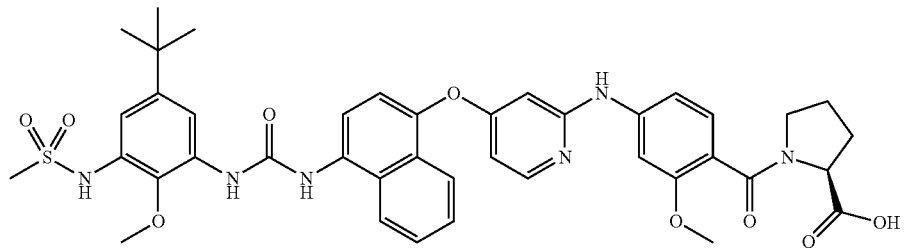 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)N1CCC[C@H]1C(=O)O]

2:1 mixture of rotamers. $^1$H NMR (of hydrochloride salt; 400 MHz, DMSO-d6) δ: 10.00 (bs, 1H), 9.61 (s, 1H), 9.14 (s, 1H), 9.03 (s, 1H), 8.38 (d, 1H), 8.15-8.17 (m, 2H), 8.08 (d, 1H, major rotamer), 8.07 (d, 1H, minor rotamer), 7.86 (d, 1H), 7.71-7.75 (m, 1H), 7.63-7.67 (m, 1H), 7.46 (d, 1H, major rotamer), 7.45 (d, 1H, minor rotamer), 7.18 (s, 1H), 7.12 (d, 1H), 7.96-7.05 (m, 2H), 6.84 (d, 1H, major rotamer), 6.79 (d, 1H, minor rotamer), 6.26 (d, 1H), 4.33 (dd, 1H, major rotamer), 4.04 (dd, 1H, minor rotamer), 3.81 (s, 3H), 3.72 (s, 3H, major rotamer), 3.71 (s, 3H, minor rotamer), 3.49-3.56 (m, 2H, minor rotamer), 3.23 (t, 2H, major rotamer), 3.10 (s, 3H), 2.12-2.26 (m, 1H), 1.76-1.95 (m, 3H), 1.27 (s, 9H).

LCMS (of hydrochloride salt) m/z 797 (M+H)$^+$ (ES$^+$)

(ax) 4-((4-((4-(3-(5-(tert-Butyl)-2-methoxy-3-(methylsulfonamido)phenyl)ureido)naphthalen-1-yl)oxy)pyrimidin-2-yl)amino)-2-methoxybenzoic acid

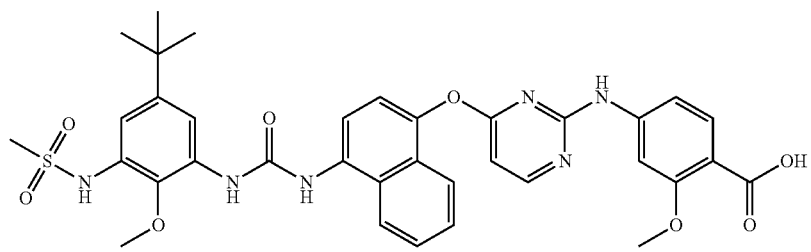 [SMILES: COc1cc(Nc2nccc(Oc3ccc(NC(=O)Nc4cc(C(C)(C)C)cc(NS(C)(=O)=O)c4OC)c4ccccc34)n2)ccc1C(=O)O]

$^1$H NMR (of sodium salt; 400 MHz, DMSO-d6) δ 9.54 (s, 1H), 9.41 (s, 1H), 8.69 (s, 1H), 8.40 (d, 1H), 8.32 (d, 1H), 8.06 (d, 1H), 7.82 (d, 1H), 7.67-7.59 (m, 1H), 7.59-7.49 (m, 2H), 7.37 (d, 1H), 7.21-7.05 (m, 2H), 7.03 (d, 1H), 6.90 (s, 1H), 6.54 (d, 1H), 3.78 (s, 3H), 2.57 (s, 3H), 1.22 (s, 9H). -Me obscured by water peak 3.33 ppm LCMS (of sodium salt) m/z 701 (M+H)$^+$ 723 (M+Na)$^+$ (ES$^+$)

(ay) 3-(4-((4-((4-(3-(5-(tert-Butyl)-2-methoxy-3-(methylsulfonamido)phenyl)ureido)-naphthalen-1-yl)oxy)pyridin-2-yl)amino)-2-methoxybenzamido)propanoic acid

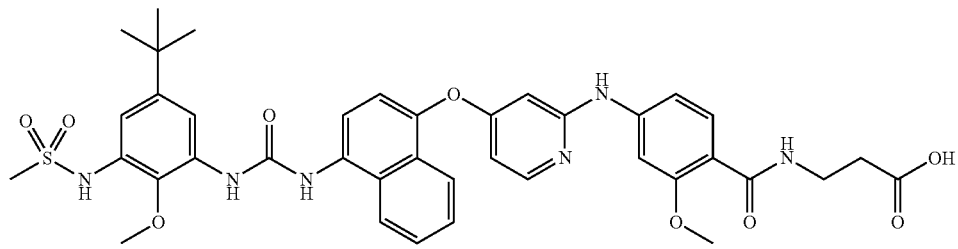 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCC(=O)O]

¹H NMR (of hydrochloride salt; 400 MHz, DMSO-d6) δ: 9.76 (bs, 1H), 9.55 (s, 1H), 9.13 (s, 1H), 8.99 (s, 1H), 8.36 (d, 1H), 8.27 (t, 1H), 8.18 (d, 1H), 8.12-8.15 (m, 2H), 7.86 (d, 1H), 7.79 (d, 1H), 7.70-7.74 (m, 1H), 7.62-7.65 (m, 1H), 7.43 (d, 1H), 7.40 (s, 1H), 7.11 (d, 1H), 7.03 (d, 1H), 6.77 (dd, 1H), 6.25 (d, 1H), 3.84 (s, 3H), 3.81 (s, 3H), 3.48 (q, 2H), 3.10 (s, 3H), 2H under H2O, 1.27 (s, 9H).
LCMS (of hydrochloride salt) m/z 771 (M+H)⁺ (ES⁺)

(az) 4-((4-((4-(3-(5-(tert-Butyl)-2-methoxy-3-(methylsulfonamido)phenyl)ureido)naphthalen-1-yl)oxy)pyrimidin-2-yl)amino)-2,6-dimethoxy-N-(2-(4-methylpiperazin-1-yl)ethyl)benzamide

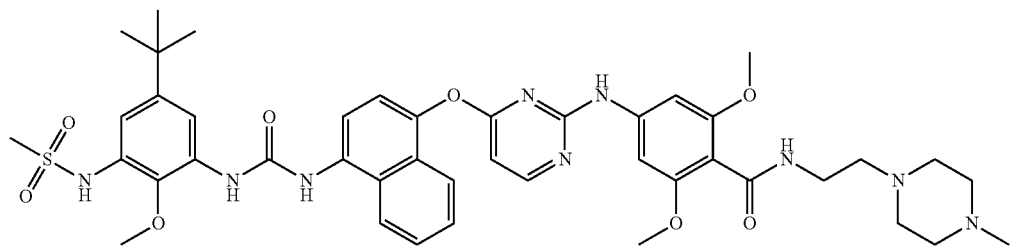

¹H NMR (400 MHz, DMSO-d6) δ 9.54 (s, 1H), 9.38 (s, 1H), 9.14 (s, 1H), 8.91 (s, 1H), 8.46 (d, 1H), 8.27 (d, 1H), 8.19 (d, 1H), 8.08 (d, 1H), 7.84 (d, 1H), 7.76-7.53 (m, 3H), 7.41 (d, 1H), 7.03 (d, 1H), 6.88 (s, 2H), 6.65 (d, 1H), 3.81 (s, 3H), 3.17 (q, 2H), 3.10 (s, 3H), 2.47-2.20 (m, 10H), 2.16 (s, 3H), 1.27 (s, 9H). 2×—OMe obscured by water peak.
LCMS m/z 856 (M+H)⁺ (ES⁺)

(ba) 4-((4-((4-(3-(5-(tert-Butyl)-2-methoxy-3-(methylsulfonamido)phenyl)ureido)naphthalen-1-yl)oxy)pyridin-2-yl)amino)-2-methoxy-N-methyl-N-(2-(1-methylpiperidin-4-yl)ethyl) benzenesulfonamide

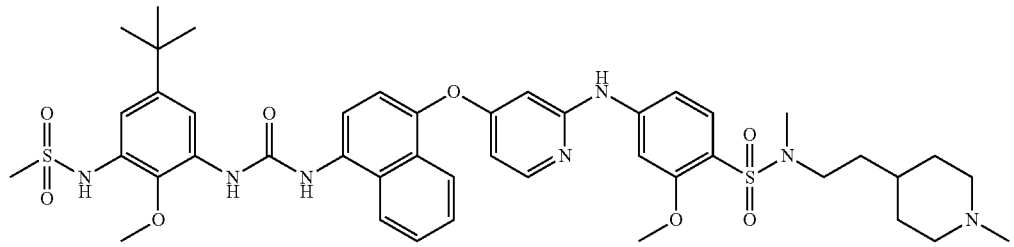

$^1$H NMR (400 MHz, DMSO-d6) δ 9.39 (s, 2H), 9.14 (bs, 1H), 8.90 (s, 1H), 8.30 (d, 1H), 8.17-8.10 (m, 3H), 7.86 (d, 1H), 7.70 (dd, 1H), 7.62-7.59 (m, 2H), 7.53 (d, 1H), 7.40 (d, 1H), 7.23 (dd, 1H), 7.02 (d, 1H), 6.68 (dd, 1H), 6.16 (d, 1H), 3.80 (s, 3H), 3.78 (s, 3H), 3.07 (s, 3H), 3.01 (t, 2H), 2.66-2.64 (m, 5H), 2.08 (s, 3H), 1.73 (t, 2H), 1.56-1.53 (m, 2H), 1.32 (q, 2H), 1.26 (s, 9H), 1.12-1.03 (m, 3H).
LCMS m/z 874 (M+H)$^+$ (ES$^+$)

(bb) 4-((4-((4-(3-(5-(tert-Butyl)-2-methoxy-3-(methylsulfonamido)phenyl)ureido)naphthalen-1-yl)oxy)pyridin-2-yl)amino)-2-methoxy-N-methyl-N-(2-(4-methylpiperazin-1-yl)ethyl)benzenesulfonamide

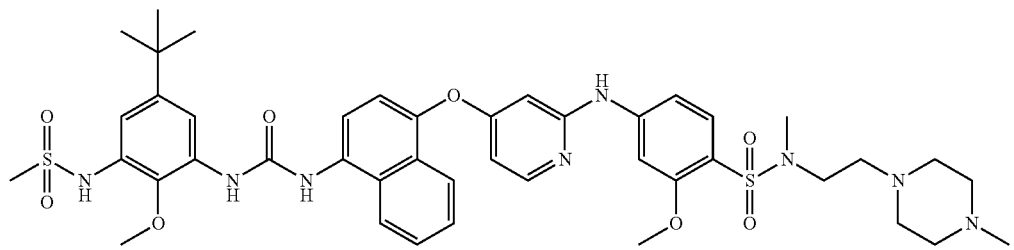

$^1$H NMR (400 MHz, DMSO-d6) 9.39 (bs, 2H), 9.13 (bs, 1H), 8.90 (s, 1H), 8.30 (d, 1H), 8.18-8.16 (m, 2H), 8.11 (d, 1H), 7.86 (d, 1H), 7.72-7.69 (m, 1H), 7.63-7.59 (m, 2H), 7.54 (d, 1H), 7.40 (d, 1H), 7.23 (dd, 1H), 7.02 (d, 1H), 6.68 (dd, 1H), 6.16 (d, 1H), 3.80 (s, 3H), 3.79 (s, 3H), 3.11 (t, 2H), 3.08 (s, 3H), 2.73 (s, 3H), 2.37 (t, 2H), 2.33-2.25 (m, 8H), 2.10 (s, 3H), 1.26 (s, 9H).
LCMS m/z 875.4 (M+H)$^+$ (ES$^+$)

(bc) 4-((4-((4-(3-(5-(tert-Butyl)-2-methoxy-3-(methylsulfonamido)phenyl)ureido)naphthalen-1-yl)oxy)pyrimidin-2-yl)amino)-2-(dimethylamino)benzoic acid

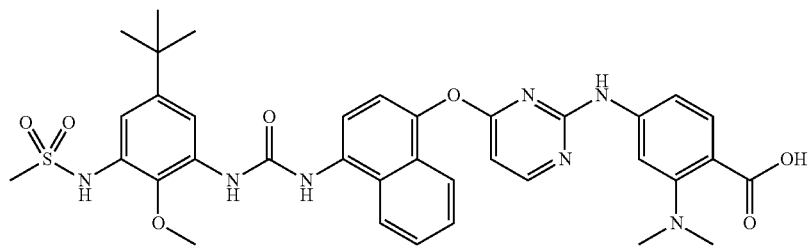 [SMILES: COc1c(NC(=O)Nc2ccc(Oc3ccnc(Nc4ccc(C(=O)O)c(N(C)C)c4)n3)c3ccccc23)cc(C(C)(C)C)cc1NS(C)(=O)=O]

$^1$H NMR (400 MHz, DMSO-d6) δ 9.97 (s, 1H), 9.40 (s, 1H), 8.92 (s, 1H), 8.50 (d, 1H), 8.30 (d, 1H), 8.15 (d, 1H), 8.12 (d, 1H), 7.85 (d, 1H), 7.70-7.66 (m, 2H), 7.63-7.57 (m, 2H), 7.43 (d, 1H), 7.30 (d, 1H), 7.02 (d, 1H), 6.74 (d, 1H), 3.81 (s, 3H), 3.08 (s, 3H), 2.42 (s, 6H), 1.26 (s, 9H).
LCMS m/z 714 (M+H)$^+$ (ES$^+$)

(bd) 4-((4-((4-(3-(5-(tert-Butyl)-2-methoxy-3-(methylsulfonamido)phenyl)ureido)naphthalen-1-yl)oxy)pyridin-2-yl)amino)-N-(5-(dimethylamino)pentyl)-2-methoxybenzamide

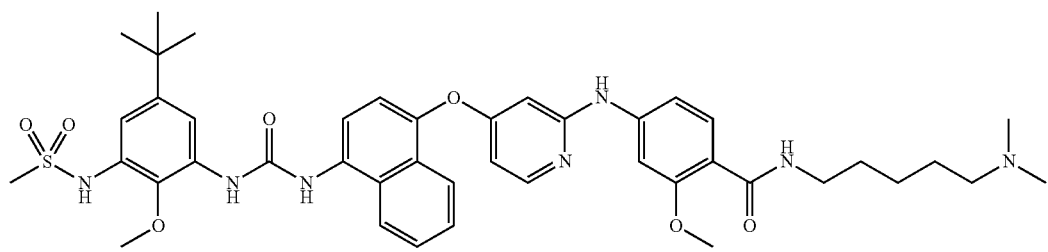

$^1$H NMR (400 MHz, DMSO-d6) δ: 9.40 (s, 1H), 9.24 (s, 1H), 9.13 (bs 1H), 8.91 (s, 1H), 8.31 (d, 1H), 8.11-8.18 (m, 3H), 7.94 (t, 1H), 7.87 (d, 1H), 7.69-7.73 (m, 2H), 7.59-7.63 (m, 1H), 7.56 (d, 1H), 7.40 (d, 1H), 7.22 (dd, 1H), 7.03 (d, 1H), 6.65 (dd, 1H), 6.15 (d, 1H), 3.84 (s, 3H), 3.81 (s, 3H), 3.25 (q, 2H), 3.09 (s, 3H), 2.17 (t, 2H), 2.10 (s, 6H), 1.46-1.54 (m, 2H), 1.37-1.45 (m, 2H), 1.24-1.33 (m, 2H), 1.27 (s, 9H).
LCMS m/z 812 (M+H)$^+$ (ES$^+$)

(be) 4-((4-((4-(3-(5-(tert-Butyl)-2-methoxy-3-(methylsulfonamido)phenyl)ureido)naphthalen-1-yl)oxy)pyridin-2-yl)amino)-N-(2-(4-ethylpiperazin-1-yl)ethyl)-2-methoxybenzamide

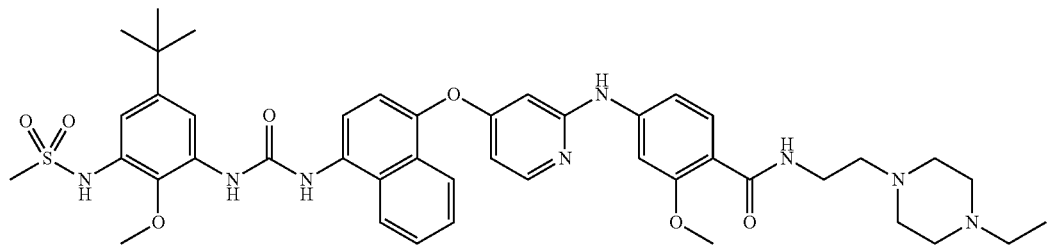 [SMILES: CCN1CCN(CCNC(=O)c2ccc(Nc3cc(Oc4ccc(NC(=O)Nc5cc(C(C)(C)C)cc(NS(C)(=O)=O)c5OC)c5ccccc45)ccn3)cc2OC)CC1]

$^1$H NMR (400 MHz, DMSO-d6) δ: 9.39 (s, 1H), 9.26 (s, 1H), 9.14 (bs, 1H), 8.91 (s, 1H), 8.30 (d, 1H), 8.11-8.22 (m, 4H), 7.87 (d, 1H), 7.77 (d, 1H), 7.71 (t, 1H), 7.60-7.63 (m, 1H), 7.57 (d, 1H), 7.40 (d, 1H), 7.24 (dd, 1H), 7.03 (d, 1H), 6.66 (dd, 1H), 6.16 (d, 1H), 3.87 (s, 3H), 3.81 (s, 3H), 3.37 (q, 2H), 3.10 (s, 3H), 2.29-2.50 (m, 12H), 1.27 (s, 9H), 0.99 (t, 3H).

LCMS m/z 839 (M+H)$^+$ (ES$^+$)

(bf) 4-((4-((4-(3-(5-(tert-Butyl)-2-methoxy-3-(methylsulfonamido)phenyl)ureido)naphthalen-1-yl)oxy)pyridin-2-yl)amino)-N-(2-(4-isopropylpiperazin-1-yl)ethyl)-2-methoxybenzamide

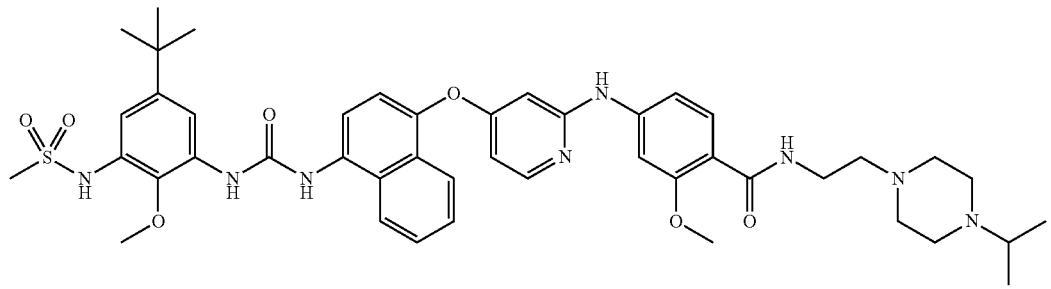 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCN(C(C)C)CC1]

$^1$H NMR (400 MHz, DMSO-d6) δ: 9.39 (s, 1H), 9.26 (s, 1H), 9.14 (s, 1H), 8.91 (s, 1H), 8.30 (d, 1H), 8.11-8.23 (m, 4H), 7.87 (d, 1H), 7.78 (d, 1H), 7.71 (t, 1H), 7.58-7.63 (m, 2H), 7.40 (d, 1H), 7.23 (d, 1H), 7.03 (s, 1H), 6.66 (d, 1H), 6.16 (s, 1H), 3.88 (s, 3H), 3.81 (s, 3H), 3.37 (q, 2H), 3.10 (s, 3H), 2.58-2.64 (m, 2H), 2.34-2.51 (m, 9H), 1.27 (s, 9H), 0.97 (d, 6H).

LCMS m/z 853 (M+H)$^+$ (ES$^+$)

(bg) 4-((4-((4-(3-(5-(tert-Butyl)-2-methoxy-3-(methylsulfonamido)phenyl)ureido)naphthalen-1-yl)oxy)pyridin-2-yl)amino)-N-(2-(4-hydroxy-1-methylpiperidin-4-yl)ethyl)-2-methoxy benzamide

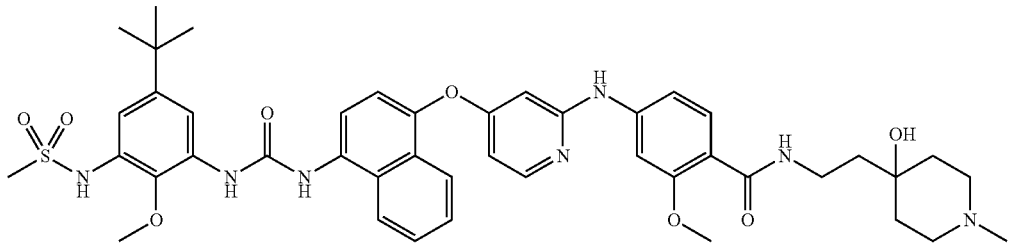

$^1$H NMR (400 MHz, DMSO-d6) δ: 9.39 (s, 1H), 9.23 (s, 1H), 9.13 (bs, 1H), 8.91 (s, 1H), 8.30 (d, 1H), 8.21 (t, 1H), 8.11-8.17 (m, 3H), 7.87 (d, 1H), 7.69-7.75 (m, 2H), 7.60-7.63 (m, 1H), 7.56 (d, 1H), 7.40 (d, 1H), 7.21 (dd, 1H), 7.03 (d, 1H), 6.65 (dd, 1H), 6.16 (d, 1H), 4.22 (s, 1H), 3.83 (s, 3H), 3.81 (s, 3H), 3.37 (q, 2H), 3.09 (s, 3H), 2.24-2.37 (m, 4H), 2.14 (s, 3H), 1.61 (t, 2H), 1.45-1.54 (m, 4H), 1.27 (s, 9H).

LCMS m/z 840 (M+H)$^+$ (ES$^+$)

(bh) 4-((4-((4-(3-(5-(tert-Butyl)-2-methoxy-3-(methylsulfonamido)phenyl)ureido)naphthalen-1-yl)oxy)pyridin-2-yl)amino)-2-methoxy-N-methyl-N-(2-(4-methylpiperazin-1-yl)ethyl)benzamide

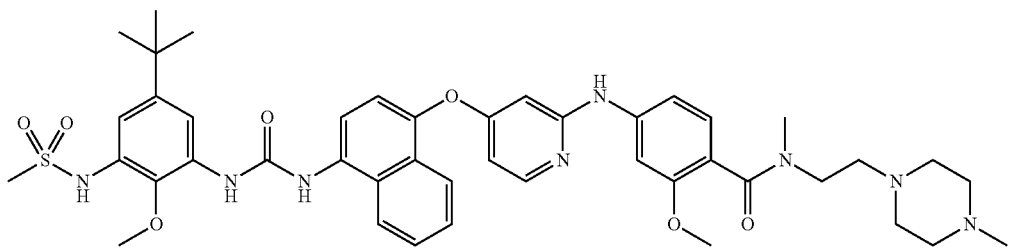

1:1 mixture of rotamers. $^1$H NMR (400 MHz, DMSO-d6) δ: 9.38 (s, 1H), 9.14 (s, 1H), 9.07 (s, 1H), 8.91 (s, 1H), 8.30 (d, 1H), 8.19 (d, 1H), 8.11-8.13 (m, 2H), 7.87 (d, 1H), 7.69-7.73 (m, 1H), 7.60-7.63 (m, 1H), 7.38-7.40 (m, 2H), 7.19-7.22 (m, 1H), 7.03 (d, 1H), 6.96 (dd, 1H), 6.61 (dd, 1H), 6.12 (d, 1H), 3.81 (s, 3H), 3.70 (s, 3H, 1st rotamer), 3.69 (s, 3H, 2nd rotamer), 3.48 (t, 1H), 3.10-3.21 (bm, 1H), 3.10 (s, 3H), 2.92 (s, 3H, 1st rotamer), 2.76 (s, 3H, 2nd rotamer), 2.15-2.48 (bm, 10H), 2.15 (s, 3H, 1st rotamer), 2.08 (s, 3H, 2nd rotamer), 1.27 (s, 9H).

LCMS m/z 839 (M+H)$^+$ (ES$^+$)

(bi) 4-((4-((4-(3-(5-(tert-Butyl)-2-methoxy-3-(methylsulfonamido)phenyl)ureido)naphthalen-1-yl)oxy)pyridin-2-yl)amino)-2-methoxy-N-(2-(2,2,4-trimethylpiperazin-1-yl)ethyl)benzamide

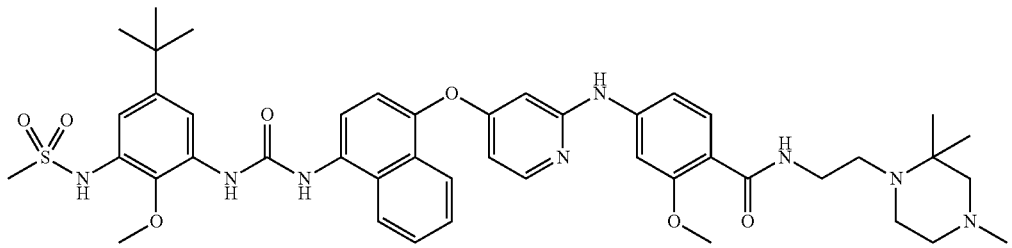

$^1$H NMR (400 MHz, DMSO-d6) δ: 9.39 (s, 1H), 9.26 (s, 1H), 9.13 (s, 1H), 8.91 (s, 1H), 8.30 (d, 1H), 8.11-8.19 (m, 4H), 7.87 (d, 1H), 7.80 (d, 1H), 7.69-7.73 (m, 1H), 7.60-7.63 (m, 1H), 7.57 (d, 1H), 7.40 (d, 1H), 7.23 (dd, 1H), 7.03 (d, 1H), 6.66 (dd, 1H), 6.16 (d, 1H), 3.89 (s, 3H), 3.81 (s, 3H), 2H under water, 3.10 (s, 3H), 2.19-2.58 (bm, 6H), 2.01-2.16 (m, 2H), 2.12 (s, 3H), 1.27 (s, 9H), 0.97 (s, 6H).

LCMS m/z 853 (M+H)$^+$ (ES$^+$)

(bj) (S)-2-(4-((4-((4-(3-(5-(tert-Butyl)-2-methoxy-3-(methylsulfonamido)phenyl)ureido)-naphthalen-1-yl)oxy)pyridin-2-yl)amino)-2-methoxybenzamido)-3-hydroxypropanoic acid

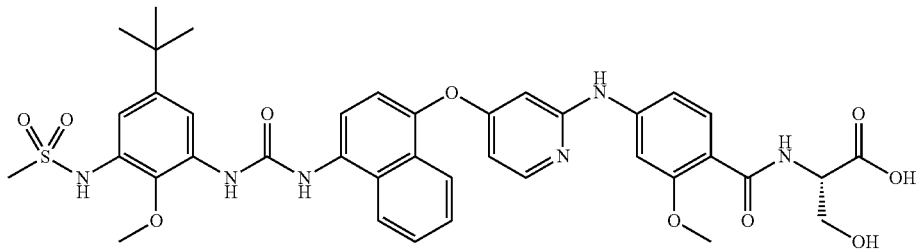 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)N[C@@H](CO)C(=O)O]

$^1$H NMR (400 MHz, DMSO-d6) δ: 9.43 (s, 1H), 9.30 (s, 1H), 8.93 (s, 1H), 8.59 (d, 1H), 8.31 (d, 1H), 8.12 (d, 1H), 8.05-8.38 (bm, 3H), 7.87 (d, 1H), 7.81 (d, 1H), 7.69-7.73 (m, 1H), 7.60-63 (m, 2H), 7.40 (d, 1H), 7.25 (dd, 1H), 7.03 (d, 1H), 6.67 (dd, 1H), 6.17 (d, 1H), 4.22-4.30 (m, 1H), 3.87 (s, 3H), 3.81 (s, 3H), 3.78-3.81 (m, 1H), 3.58-3.61 (m, 1H), 3.10 (s, 3H), 1.27 (s, 9H).

LCMS m/z 787 (M+H)$^+$ (ES$^+$)

$^1$H NMR (of sodium salt; 400 MHz, DMSO-d6) δ: 9.39 (s, 1H), 9.27 (s, 1H), 8.82 (d, 1H), 8.69 (s, 1H), 8.33 (d, 1H), 8.17 (d, 1H), 8.11 (d, 1H), 7.84 (d, 1H), 7.79 (d, 1H), 7.74-7.63 (m, 2H), 7.63-7.50 (m, 2H), 7.38 (d, 1H), 7.25 (dd, 1H), 7.03 (d, 1H), 6.66 (dd, 1H), 6.14 (d, 1H), 5.99 (s, 1H), 3.95-3.80 (m, 4H), 3.79 (s, 3H), 3.70 (s, 1H), 3.33-3.21 (m, 2H), 2.66 (s, 3H), 1.23 (s, 9H).

LCMS (of sodium salt) m/z 787 (M+H)$^+$ (ES$^+$)

(bk) N-((4-((4-((4-(3-(5-(tert-Butyl)-2-methoxy-3-(methylsulfonamido)phenyl)ureido)-naphthalen-1-yl)oxy)pyrimidin-2-yl)amino)-2-methoxyphenyl)sulfonyl)propionamide

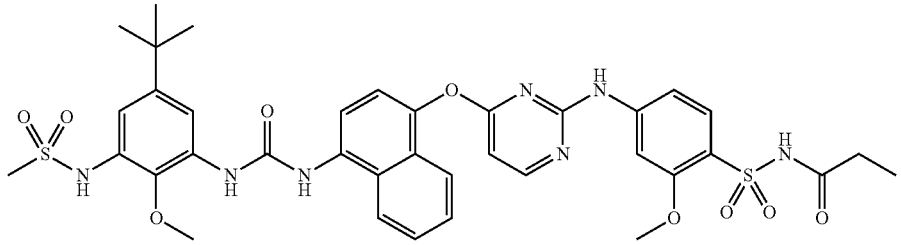 [SMILES: CCC(=O)NS(=O)(=O)c1ccc(Nc2nccc(Oc3ccc(NC(=O)Nc4cc(C(C)(C)C)cc(NS(C)(=O)=O)c4OC)c4ccccc34)n2)cc1OC]

¹H NMR (400 MHz, DMSO-d6) δ 11.63 (s, 1H), 9.98 (s, 1H), 9.41 (s, 1H), 9.13 (s, 1H), 8.92 (s, 1H), 8.51 (d, 1H), 8.30 (d, 1H), 8.20 (d, 1H), 8.12 (d, 1H), 7.85 (d, 1H), 7.71-7.67 (m, 1H), 7.62-7.58 (m, 1H), 7.49-7.41 (m, 3H), 7.15-7.11 (m, 1H), 7.03 (d, 1H), 6.73 (d, 1H), 3.82 (s, 3H), 3.50 (s, 3H), 3.10 (s, 3H), 2.14 (q, 2H), 1.27 (s, 9H), 0.84 (t, 3H).

LCMS m/z 792 (M+H)⁺ (ES⁺); 790 (M−H)⁻ (ES⁻)

¹H NMR (of sodium salt; 400 MHz, DMSO-d6) δ: 9.60 (s, 1H), 9.43 (s, 1H), 9.17 (s, 1H), 8.84 (s, 1H), 8.44 (d, 1H), 8.28 (d, 1H), 8.19-7.91 (m, 2H), 7.84 (dd, 1H), 7.71-7.63 (m, 1H), 7.63-7.52 (m, 1H), 7.41 (d, 1H), 7.33 (d, 1H), 7.18 (s, 1H), 7.03 (d, 1H), 6.94 (s, 1H), 6.61 (d, 1H), 3.81 (s, 3H), 3.37 (s, 3H), 2.98 (s, 3H), 1.89 (q, 2H), 1.26 (s, 9H), 0.84 (t, 3H).

LCMS (of sodium salt) m/z 792 (M+H)⁺ (ES⁺)

(bl) 4-((4-((4-(3-(5-(tert-Butyl)-2-methoxy-3-(methylsulfonamido)phenyl)ureido)naphthalen-1-yl)oxy)pyridin-2-yl)amino)-2-methoxy-N-(1-(4-methylpiperazin-1-yl)propan-2-yl)benzamide

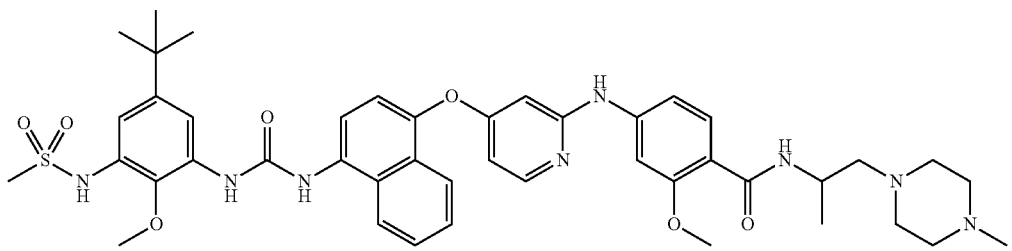

¹H NMR (400 MHz, DMSO-d6) δ: 9.39 (s, 1H), 9.25 (s, 1H), 9.14 (s, 1H), 8.91 (s, 1H), 8.31 (d, 1H), 8.16-8.19 (m, 2H), 8.12 (d, 1H), 7.98 (d, 1H), 7.87 (d, 1H), 7.69-7.75 (m, 2H), 7.60-7.63 (m, 1H), 7.58 (d, 1H), 7.40 (d, 1H), 7.23 (d, 1H), 7.03 (d, 1H), 6.66 (dd, 1H), 6.16 (d, 1H), 3.97-4.03 (m, 1H), 3.86 (s, 3H), 3.81 (s, 3H), 3.10 (s, 3H), 2.21-2.43 (m, 10H), 2.14 (s, 3H), 1.27 (s, 9H), 1.15 (d, 3H).

LCMS m/z 839 (M+H)⁺ (ES⁺)

(bm) 4-((4-((4-(3-(5-(tert-Butyl)-2-methoxy-3-(methylsulfonamido)phenyl)ureido)naphthalen-1-yl)oxy)pyridin-2-yl)amino)-N-(2-(2-hydroxyethoxy)ethyl)-2-methoxybenzamide

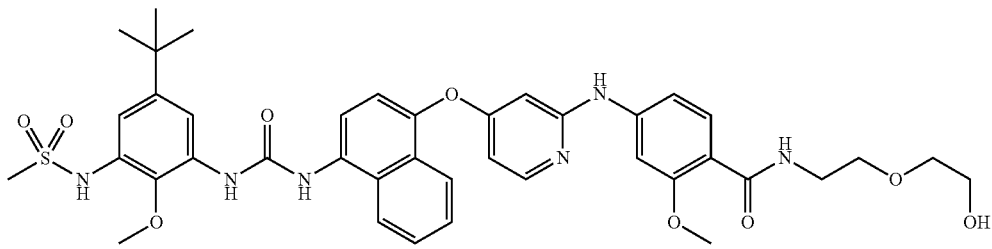 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCOCCO]

¹H NMR (400 MHz, DMSO-d6) δ: 9.39 (s, 1H), 9.27 (s, 1H), 9.14 (s, 1H), 8.91 (s, 1H), 8.30 (d, 1H), 8.16-8.19 (m, 2H), 8.10-8.13 (m, 2H), 7.87 (d, 1H), 7.76 (d, 1H), 7.69-7.73 (m, 1H), 7.58-7.64 (m, 2H), 7.40 (d, 1H), 7.23 (dd, 1H), 7.02 (d, 1H), 6.66 (dd, 1H), 6.16 (d, 1H), 4.62 (t, 1H), 3.85 (s, 3H), 3.81 (s, 3H), 3.51-3.55 (m, 4H), 3.42-3.47 (m, 4H), 3.10 (s, 3H), 1.27 (s, 9H).
LCMS m/z 787 (M+H)⁺ (ES⁺)

(bn) 4-((4-((4-(3-(5-(tert-Butyl)-2-methoxy-3-(methylsulfonamido)phenyl)ureido)naphthalen-1-yl)oxy)pyridin-2-yl)amino)-N-(2-hydroxyethyl)-2-methoxybenzamide

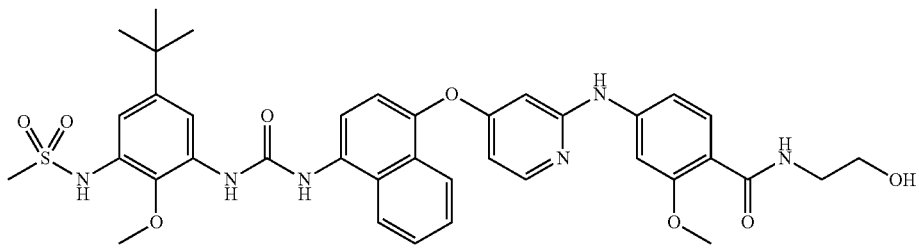 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCO]

¹H NMR (400 MHz, DMSO-d6) δ: 9.39 (s, 1H), 9.26 (s, 1H), 9.14 (s, 1H), 8.92 (s, 1H), 8.30 (d, 1H), 8.16-8.19 (m, 2H), 8.08-8.13 (m, 2H), 7.87 (d, 1H), 7.77 (d, 1H), 7.69-7.73 (m, 1H), 7.59-7.64 (m, 2H), 7.40 (d, 1H), 7.23 (dd, 1H), 7.03 (d, 1H), 6.66 (dd, 1H), 6.16 (d, 1H), 4.77 (t, 1H), 3.85 (s, 3H), 3.81 (s, 3H), 3.50 (q, 2H), 2H under water, 3.10 (s, 3H), 1.27 (s, 9H).
LCMS m/z 743 (M+H)⁺ (ES⁺)

(bo) 4-((4-((4-(3-(3-(tert-Butyl)-5-(methylsulfona-mido)phenyl)ureido)naphthalen-1-yl)oxy)pyridin-2-yl)amino)-2-methoxy-N-(2-(4-methylpiperazin-1-yl)ethyl)benzamide

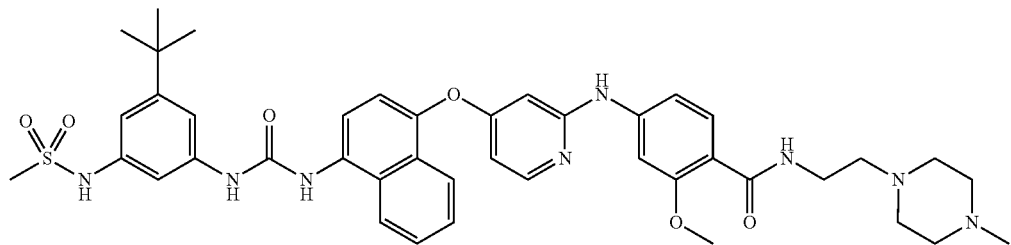

$^1$H NMR (400 MHz, DMSO-d6) δ: 9.68 (s, 1H), 9.28 (s, 1H), 9.21 (s, 1H), 8.85 (s, 1H), 8.20-8.23 (m, 2H), 8.17 (d, 1H), 8.08 (d, 1H), 7.86 (d, 1H), 7.77 (d, 1H), 7.68-7.72 (m, 1H), 7.59-7.63 (m, 1H), 7.57 (d, 1H), 7.40 (d, 1H), 7.36 (s, 1H), 7.30 (s, 1H), 7.24 (dd, 1H), 6.89 (s, 1H), 6.67 (dd, 1H), 6.15 (d, 1H), 3.87 (s, 3H), 2H under water, 3.01 (s, 3H), 2.22-2.50 (m, 10H), 2.17 (s, 3H), 1.28 (s, 9H).

LCMS m/z 795 (M+H)$^+$ (ES$^+$)

(bp) 4-((4-((4-(3-(3-(tert-Butyl)-5-(methylsulfona-mido)phenyl)ureido)naphthalen-1-yl)oxy)pyridin-2-yl)amino)-2-methoxy-N-(3-(4-methylpiperazin-1-yl)propyl)benzamide

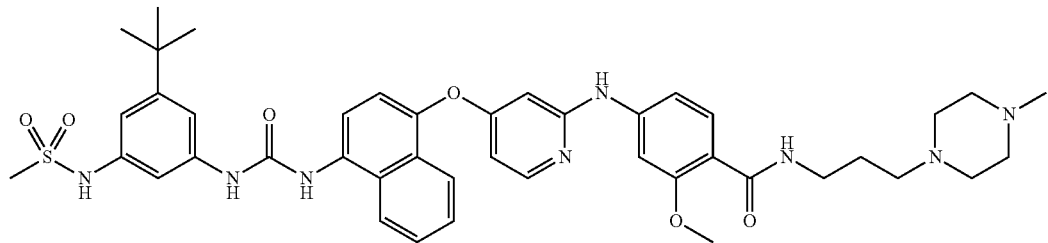

$^1$H NMR (400 MHz, DMSO-d6) δ: 9.68 (s, 1H), 9.25 (s, 1H), 9.19 (s, 1H), 8.83 (s, 1H), 8.22 (d, 1H), 8.16 (d, 1H), 8.08 (d, 1H), 7.98 (t, 1H), 7.86 (d, 1H), 7.69-7.72 (m, 2H), 7.59-7.63 (m, 1H), 7.55 (d, 1H), 7.40 (d, 1H), 7.36 (s, 1H), 7.30 (s, 1H), 7.22 (dd, 1H), 6.89 (s, 1H), 6.66 (dd, 1H), 6.14 (d, 1H), 3.83 (s, 3H), 3.27 (q, 2H), 3.01 (s, 3H), 2.19-2.46 (m, 10H), 2.13 (s, 3H), 1.63 (quint, 2H), 1.28 (s, 9H).

LCMS m/z 809 (M+H)$^+$ (ES$^+$)

(bq) 4-((4-((4-(3-(5-(tert-Butyl)-2-methoxy-3-(methylsulfonamido)phenyl)ureido)naphthalen-1-yl)oxy)pyridin-2-yl)amino)-2-(dimethylamino)-N-(2-(4-methylpiperazin-1-yl)ethyl)benzamide

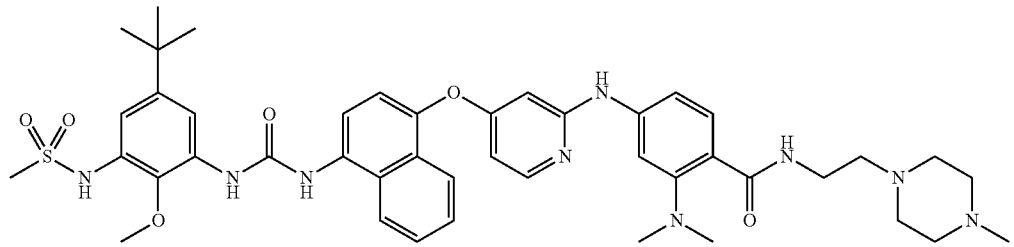

¹H NMR (400 MHz, DMSO-d6) δ: 9.49 (t, 1H), 9.40 (s, 1H), 9.10-9.17 (m, 2H), 8.92 (s, 1H), 8.30 (d, 1H), 8.19 (d, 1H), 8.11-8.16 (m, 2H), 7.87 (d, 1H), 7.68-7.73 (m, 2H), 7.60-7.63 (m, 1H), 7.47 (d, 1H), 7.39-7.43 (m, 2H), 7.03 (d, 1H), 6.64 (dd, 1H), 6.14 (d, 1H), 3.81 (s, 3H), 3.38 (q, 2H), 3.10 (s, 3H), 2.62 (s, 6H), 2.20-2.48 (m, 10H), 2.15 (s, 3H), 1.27 (s, 9H).
LCMS m/z 838 (M+H)⁺ (ES⁺)

(br) 4-((4-((4-(3-(5-(tert-Butyl)-2-methoxy-3-(methylsulfonamido)phenyl)ureido)naphthalen-1-yl)oxy)pyridin-2-yl)amino)-2-methoxy-N-((3R,4R,5S,6R)-2,4,5-trihydroxy-6-(hydroxymethyl)tetrahydro-2H-pyran-3-yl)benzamide

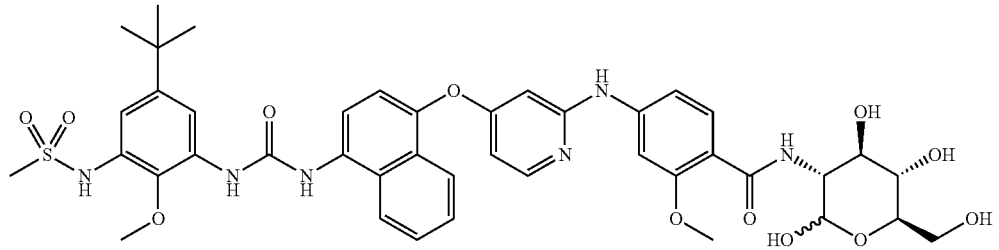 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)N[C@H]1C(O)O[C@H](CO)[C@@H](O)[C@@H]1O]

¹H NMR (400 MHz, DMSO-d6) δ: 9.46 (s, 1H), 9.42 (s, 1H), 9.16 (s, 1H), 8.94 (s, 1H), 8.31 (d, 1H), 8.13-8.19 (m, 3H), 7.98 (d, 1H), 7.79-7.88 (m, 2H), 7.70-7.74 (m, 1H), 7.61-7.65 (m, 1H), 7.55 (s, 1H), 7.42 (d, 1H), 7.21 (d, 1H), 7.03 (d, 1H), 6.72 (d, 1H), 6.59 (bs, 1H), 6.19 (s, 1H), 5.08 (d, 1H—Major anomer), 4.64 (s, 1H—Minor anomer), 3.87 (s, 3H), 3.81 (s, 3H), 3.81-3.87 (m, 1H), 3.60-3.71 (m, 2H), 3.44-3.54 (m, 2H), 3.13-3.21 (m, 1H), 3.10 (s, 3H), 1.27 (s, 9H).
LCMS m/z 861 (M+H)⁺ (ES⁺)

(bs) 4-((4-((4-(3-(3-(tert-Butyl)-5-(methylsulfona-mido)phenyl)ureido)naphthalen-1-yl)oxy)pyridin-2-yl)amino)-2-methoxy-N-(2-(1-methylpiperidin-4-yl)ethyl)benzamide

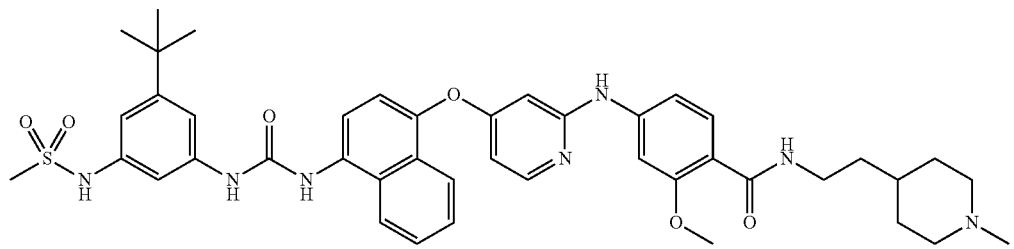

$^1$H NMR (400 MHz, DMSO-d6) δ: 9.63 (s, 1H), 9.25 (s, 1H), 9.19 (s, 1H), 8.83 (s, 1H), 8.22 (d, 1H), 8.16 (d, 1H), 8.08 (d, 1H), 7.93 (t, 1H), 7.86 (d, 1H), 7.68-7.72 (m, 2H), 7.59-7.63 (m, 1H), 7.55 (d, 1H), 7.40 (d, 1H), 7.36 (s, 1H), 7.29 (s, 1H), 7.22 (dd, 1H), 6.88 (s, 1H), 6.66 (dd, 1H), 6.14 (d, 1H), 3.83 (s, 3H), 3.28 (q, 2H), 3.01 (s, 3H), 2.71 (d, 2H), 2.12 (s, 3H), 1.79 (t, 2H), 1.64 (d, 2H), 1.42 (q, 2H), 1.28 (s, 9H), 1.09-1.22 (m, 3H).
LCMS m/z 794 (M+H)$^+$ (ES$^+$)

(bt) 4-((4-((4-(3-(5-(tert-Butyl)-2-methoxy-3-(meth-ylsulfonamido)phenyl)ureido)naphthalen-1-yl)oxy)pyridin-2-yl)amino)-2-(dimethylamino)-N-(2-(2-(2-hydroxyethoxy)ethoxy)ethyl) benzamide

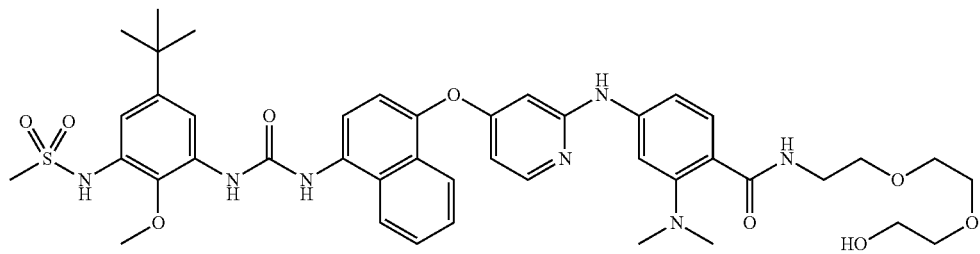 [SMILES: COc1c(NC(=O)Nc2ccc(Oc3ccnc(Nc4ccc(C(=O)NCCOCCOCCO)c(N(C)C)c4)c3)c3ccccc23)cc(C(C)(C)C)cc1NS(C)(=O)=O]

$^1$H NMR (400 MHz, DMSO-d6) δ: 9.44 (t, 1H), 9.39 (s, 1H), 9.16 (s, 1H), 9.14 (s, 1H), 8.92 (s, 1H), 8.30 (d, 1H), 8.19 (d, 1H), 8.11-8.16 (m, 2H), 7.87 (d, 1H), 7.67-7.73 (m, 2H), 7.60-7.63 (m, 1H), 7.49 (d, 1H), 7.39-7.42 (m, 2H), 7.03 (d, 1H), 6.64 (m, 1H), 6.14 (d, 1H), 4.57 (t, 1H), 3.81 (s, 3H), 3.41-3.55 (m, 12H), 3.10 (s, 3H), 2.62 (s, 6H), 1.27 (s, 9H).
LCMS m/z 844 (M+H)$^+$ (ES$^+$)

(bu) (S)-2-Amino-6-(4-((4-((4-(3-(5-(tert-butyl)-2-methoxy-3-(methylsulfonamido)phenyl)-ureido)naphthalen-1-yl)oxy)pyridin-2-yl)amino)-2-methoxybenzamido)hexanoic acid

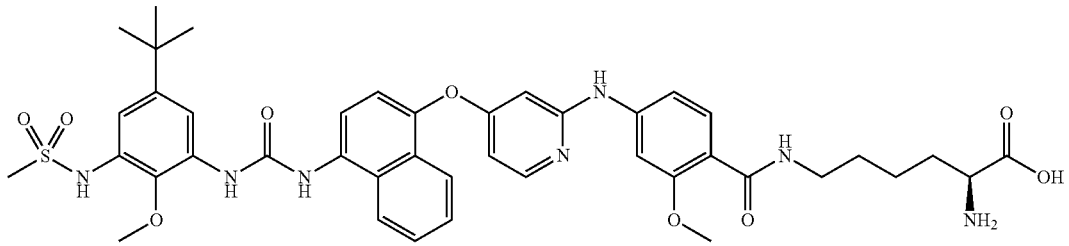 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCCC[C@H](N)C(=O)O]

$^1$H NMR (of dihydrochloride salt; 400 MHz, DMSO-d6) δ: 10.23 (bs, 1H), 9.88 (s, 1H), 9.17 (s, 1H), 9.13 (s, 1H), 8.47 (d, 1H), 8.39-8.40 (m, 3H), 8.11-8.16 (m, 3H), 8.07 (t, 1H), 8.07-8.48 (bm, 1H), 7.85 (d, 1H), 7.69-7.76 (m, 2H), 7.62-7.66 (m, 1H), 7.45 (d, 1H), 7.28 (s, 1H), 7.03-7.05 (m, 2H), 6.82 (dd, 1H), 6.35 (s, 1H), 3.83-3.91 (m, 1H), 3.91 (s, 3H), 3.82 (s, 3H), 3.26 (q, 2H), 3.10 (s, 3H), 1.77-1.88 (m, 2H), 1.35-1.58 (m, 4H), 1.27 (s, 9H).
LCMS (of dihydrochloride salt) m/z 414 (M+2H)$^{2+}$ (ES$^+$)

(bv) 4-((4-((4-(3-(5-(tert-Butyl)-2-methoxy-3-(methylsulfonamido)phenyl)ureido)naphthalen-1-yl)oxy)pyridin-2-yl)amino)-2-methoxy-N-(2-(2-(2-(((3R,4S,5R,6R)-3,4,5-trihydroxy-6-(hydroxymethyl)tetrahydro-2H-pyran-2-yl)oxy)ethoxy)ethoxy)ethyl)benzamide

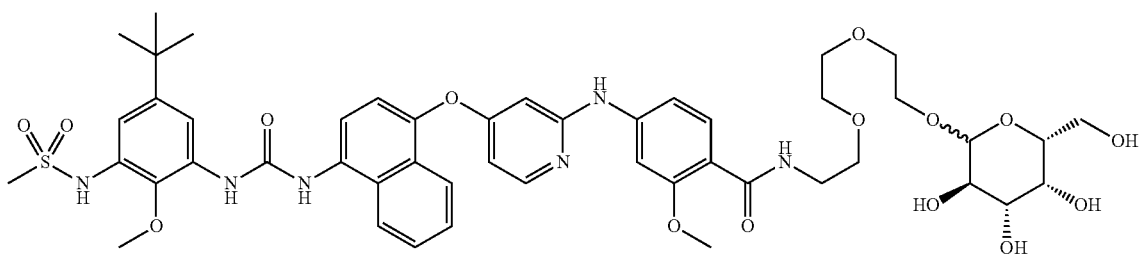 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCOCCOCCOC1O[C@H](CO)[C@H](O)[C@H](O)[C@H]1O]

$^1$H NMR (400 MHz, DMSO-d6) δ: 9.40 (s, 1H), 9.27 (s, 1H), 9.15 (s, 1H), 8.91 (s, 1H), 8.31 (d, 1H), 8.07-8.20 (m, 4H), 7.87 (d, 1H), 7.69-7.78 (m, 2H), 7.60-7.64 (m, 2H), 7.40 (d, 1H), 7.23 (d, 1H), 7.03 (s, 1H), 6.66 (d, 1H), 6.16 (s, 1H), 4.82 (d, 1H), 4.68 (d, 1H), 4.51-4.56 (m, 1H), 4.34 (d, 1H), 4.10 (d, 1H), 3.86 (s, 3H), 3.81 (s, 3H), 3.49-3.62 (m, 12H), 3.38-3.46 (m, 2H), 3.20-3.29 (m, 3H), 3.09 (s, 3H), 1.27 (s, 9H).
LCMS m/z 993 (M+H)$^+$ (ES$^+$)

(bw) 4-((4-((4-(3-(5-(tert-Butyl)-2-methoxy-3-(methylsulfonamido)phenyl)ureido)naphthalen-1-yl)oxy)pyridin-2-yl)amino)-2-methoxy-N-((2S,3R,4R,5R)-2,3,4,5,6-pentahydroxyhexyl) benzamide

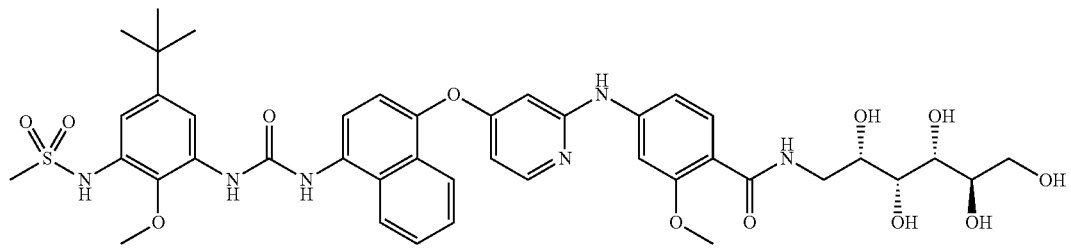 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NC[C@H](O)[C@@H](O)[C@H](O)[C@H](O)CO]

$^1$H NMR (400 MHz, DMSO-d6) δ: 9.40 (s, 1H), 9.27 (s, 1H), 9.08 (s, 1H), 8.91 (s, 1H), 8.30 (d, 1H), 8.11-8.19 (m, 4H), 7.87 (d, 1H), 7.78 (d, 1H), 7.69-7.73 (m, 1H), 7.60-7.64 (m, 2H), 7.40 (d, 1H), 7.23 (dd, 1H), 7.03 (d, 1H), 6.66 (dd, 1H), 6.16 (d, 1H), 4.92 (d, 1H), 4.47 (d, 1H), 4.40 (t, 2H), 4.33 (t, 1H), 3.86 (s, 3H), 3.81 (s, 3H), 3.67-3.72 (m, 1H), 3.47-3.67 (m, 4H), 3.37-3.45 (m, 2H), 3.17-3.23 (m, 1H), 3.10 (s, 3H), 1.27 (s, 9H).
LCMS m/z 863 (M+H)$^+$ (ES$^+$)

(bx) 6-(4-((4-((4-(3-(5-(tert-Butyl)-2-methoxy-3-(methylsulfonamido)phenyl)ureido)-naphthalen-1-yl)oxy)pyridin-2-yl)amino)-2-methoxybenzamido) hexanoic acid

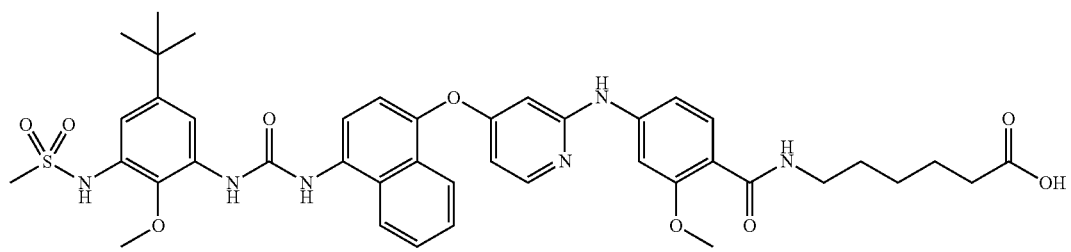 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCCCCC(=O)O]

$^1$H NMR (of hydrochloride salt; 400 MHz, DMSO-d6) δ: 9.96 (s, 1H), 9.65 (s, 1H), 9.14 (s, 1H), 9.05 (s, 1H), 8.40 (d, 1H), 8.10-8.17 (m, 3H), 8.02 (t, 1H), 7.86 (d, 1H), 7.70-7.75 (m, 2H), 7.62-7.66 (m, 1H), 7.45 (d, 1H), 7.32 (s, 1H), 7.06 (d, 1H), 7.03 (d, 1H), 6.81 (d, 1H), 6.29 (s, 1H), 3.83 (s, 3H), 3.82 (s, 3H), 3.25 (q, 2H), 3.10 (s, 3H), 2.21 (t, 2H), 1.46-1.56 (m, 4H), 1.24-1.34 (m, 11H).
LCMS (of hydrochloride salt) m/z 813 (M+H)$^+$ (ES$^+$)

(by) 4-((4-((4-(3-(5-(tert-Butyl)-2-methoxy-3-(methylsulfonamido)phenyl)ureido)naphthalen-1-yl)oxy)pyrimidin-2-yl)amino)-N-(2-(2-(2-hydroxyethoxy)ethoxy)ethyl)-2-methoxybenzamide

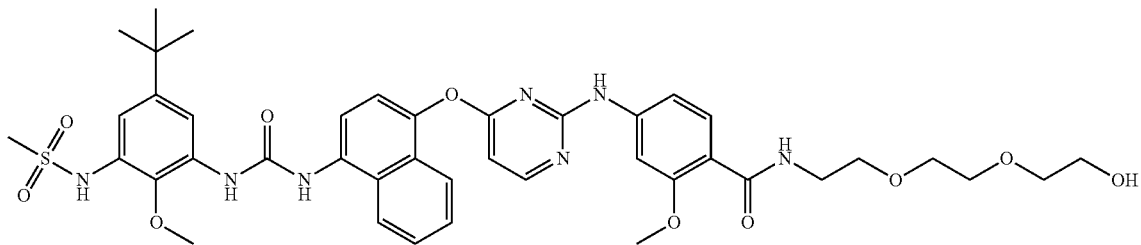 [SMILES: COc1cc(Nc2nccc(Oc3ccc(NC(=O)Nc4cc(C(C)(C)C)cc(NS(C)(=O)=O)c4OC)c4ccccc34)n2)ccc1C(=O)NCCOCCOCCO]

$^{1}$H NMR (400 MHz, DMSO-d6) δ 9.79 (s, 1H), 9.41 (s, 1H), 9.13 (s, 1H), 8.92 (s, 1H), 8.48 (d, 1H), 8.30 (d, 1H), 8.20 (d, 1H), 8.12 (d, 1H), 8.04 (dd, 1H), 7.85 (d, 1H), 7.71-7.67 (d, 1H), 7.62-7.55 (m, 2H), 7.43 (d, 1H), 7.36 (s, 1H), 7.10 (br d, 1H), 7.03 (d, 1H), 6.68 (d, 1H), 4.56 (t, 1H), 3.82 (s, 3H), 3.60-3.45 (m, 11H), 3.42-3.36 (m, 4H), 3.10 (s, 3H), 1.27 (s, 9H).

LCMS m/z 832 (M+H)$^{+}$ (ES$^{+}$); 830 (M−H)$^{−}$ (ES$^{−}$)

(bz) 4-((4-((4-(3-(5-(tert-Butyl)-2-methoxy-3-(methylsulfonamido)phenyl)ureido)naphthalen-1-yl)oxy)pyridin-2-yl)amino)-2,6-dimethoxy-N-(1-methylpiperidin-4-yl)benzamide

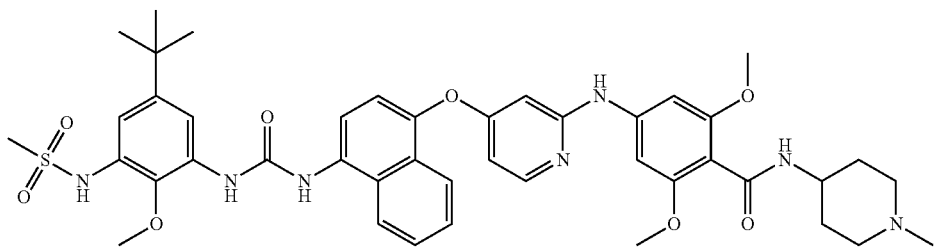

$^{1}$H NMR (400 MHz, DMSO-d6) δ 9.39 (s, 1H), 9.14 (s, br, 1H), 9.01 (s, 1H), 8.91 (s, 1H), 8.30 (d, 1H), 8.17 (d, 1H), 8.13 (d, 1H), 8.11 (d, 1H), 7.87 (d, 1H), 7.78-7.66 (m, 2H), 7.66-7.57 (m, 1H), 7.39 (d, 1H), 7.03 (d, 1H), 6.92 (s, 2H), 6.61 (dd, 1H), 6.11 (d, 1H), 3.81 (s, 3H), 3.61 (s, 6H), 3.59-3.51 (m, 1H), 3.08 (s, 3H), 2.75-2.61 (m, 2H), 2.13 (s, 3H), 1.98-1.83 (m, 2H), 1.77-1.64 (m, 2H), 1.52-1.35 (m, 2H), 1.27 (s, 9H).

LCMS m/z 826 (M+H)$^{+}$ (ES$^{+}$)

(ca) 4-((4-((4-(3-(5-(tert-Butyl)-2-methoxy-3-(methylsulfonamido)phenyl)ureido)naphthalen-1-yl)oxy)pyridin-2-yl)amino)-2,6-dimethoxy-N-((1-methylpiperidin-4-yl)methyl)benzamide

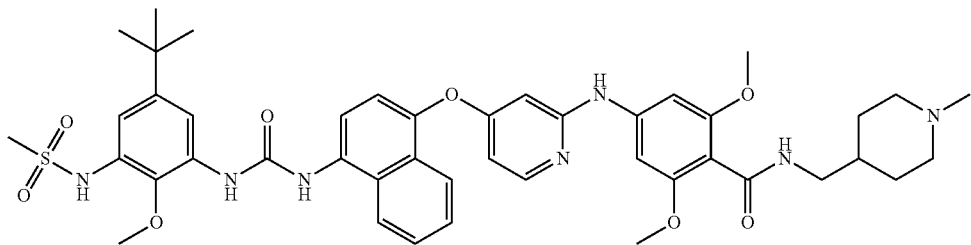

$^1$H NMR (400 MHz, DMSO-d6) δ 9.39 (s, 1H), 9.13 (s, 1H), 9.01 (s, 1H), 8.89 (s, 1H), 8.30 (d, 1H), 8.21-8.04 (m, 3H), 7.87 (d, 1H), 7.83 (t, 1H), 7.75-7.66 (m, 1H), 7.65-7.57 (m, 1H), 7.39 (d, 1H), 7.03 (d, 1H), 6.93 (s, 2H), 6.61 (dd, 1H), 6.11 (d, 1H), 3.81 (s, 3H), 3.60 (s, 6H), 3.06 (s, 3H), 2.98 (t, 2H), 2.79-2.68 (m, 2H), 2.12 (s, 3H), 1.85-1.72 (m, 2H), 1.71-1.59 (m, 2H), 1.47-1.32 (m, 1H), 1.27 (s, 9H), 1.19-1.04 (m, 2H).
LCMS m/z 840 (M+H)$^+$ (ES$^+$)

(cb) 3-(3-(4-((4-(4-(3-(5-(tert-Butyl)-2-methoxy-3-(methylsulfonamido)phenyl)ureido)-naphthalen-1-yl)oxy)pyridin-2-yl)amino)-2-methoxybenzamido)propoxy)propanoic acid

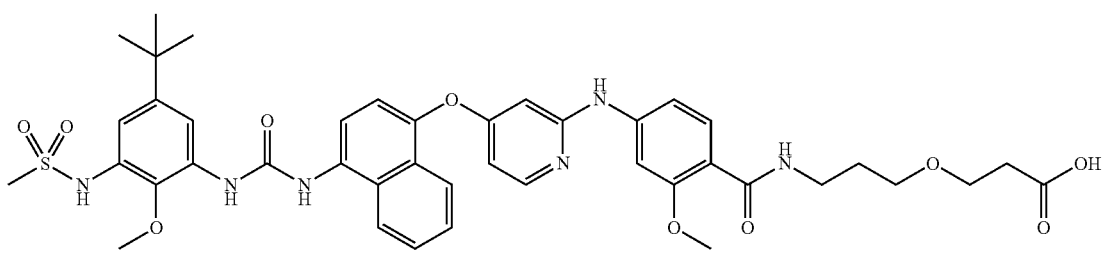 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCCOCCC(=O)O]

$^1$H NMR (400 MHz, DMSO-d6) δ: 9.08-10.01 (bs, 1H), 9.47 (s, 1H), 9.24 (s, 1H), 8.96 (s, 1H), 8.31 (d, 1H), 8.16-8.18 (m, 2H), 8.12 (d, 1H), 8.00 (t, 1H), 7.87 (d, 1H), 7.69-7.72 (m, 2H), 7.59-7.63 (m, 1H), 7.53 (d, 1H), 7.40 (d, 1H), 7.21 (dd, 1H), 7.03 (d, 1H), 6.66 (dd, 1H), 6.16 (d, 1H), 3.82 (s, 3H), 3.81 (s, 3H), 3.59 (t, 2H), 3.43 (t, 2H), 3.30 (q, 2H), 3.10 (s, 3H), 2.44 (d, 2H), 1.71 (quint, 2H), 1.27 (s, 9H).
LCMS m/z 829 (M+H)$^+$ (ES$^+$)

(cc) 2-(2-(4-((4-((4-(3-(5-(tert-Butyl)-2-methoxy-3-(methylsulfonamido)phenyl)ureido)-naphthalen-1-yl)oxy)pyridin-2-yl)amino)-2-methoxybenzamido)ethoxy)ethyl dihydrogen phosphate

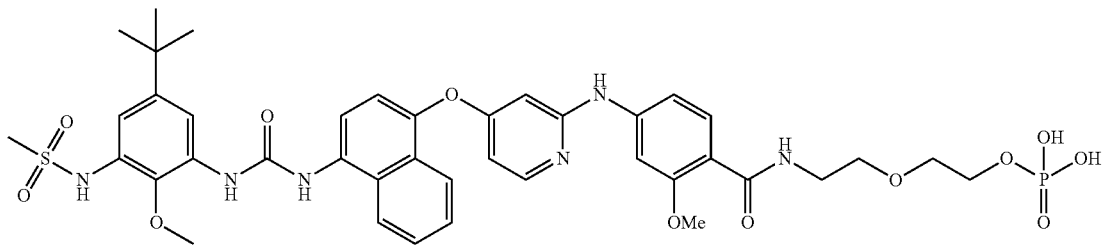 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCOCCOP(=O)(O)O]

$^1$H NMR (of sodium salt; 400 MHz, DMSO-d6) δ 9.99 (bs, 1H), 9.30 (s, 1H), 9.25 (s, 1H), 8.45 (d, 1H), 8.17 (d, 1H), 8.13-8.08 (m, 3H), 7.83 (dd, 1H), 7.74 (d, 1H), 7.65 (dd, 1H), 7.59 (dd, 1H), 7.37 (d, 1H), 7.15 (bs, 1H), 7.07 (d, 1H), 7.01 (d, 1H), 6.71 (dd, 1H), 6.17 (d, 1H), 3.86-3.80 (m, 5H), 3.56-3.39 (m, 9H), 3.08 (s, 3H), 1.25 (s, 9H).
LCMS (of sodium salt) m/z 867 (M+H)$^+$ (ES$^+$)

(cd) 4-((2-(4-((4-((4-(3-(5-(tert-Butyl)-2-methoxy-3-(methylsulfonamido)phenyl)ureido)-naphthalen-1-yl)oxy)pyridin-2-yl)amino)-2-methoxybenzamido)ethyl)amino)-4-oxobutanoic acid

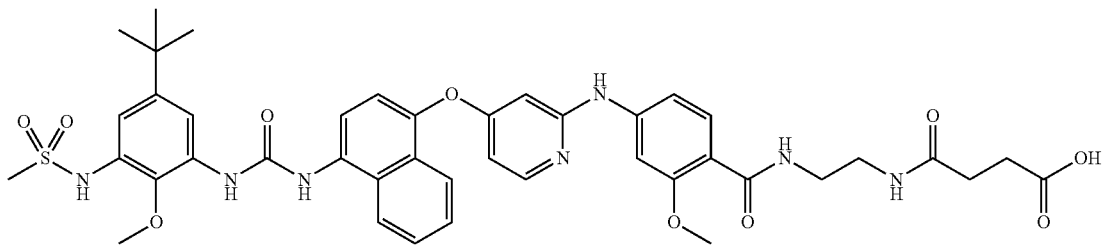 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCNC(=O)CCC(=O)O]

$^1$H NMR (of hydrochloride salt; 400 MHz, DMSO-d6) δ: 9.81 (bs, 1H), 9.57 (s, 1H), 9.14 (s, 1H), 9.01 (s, 1H), 8.37 (d, 1H), 8.11-8.17 (m, 4H), 8.01 (t, 1H), 7.86 (d, 1H), 7.78 (d, 1H), 7.70-7.74 (m, 1H), 7.62-7.66 (m, 1H), 7.44 (d, 1H), 7.37 (s, 1H), 7.10 (d, 1H), 7.03 (s, 1H), 6.78 (d, 1H), 6.26 (s, 1H), 3.85 (s, 3H), 3.81 (s, 3H), 3.30-3.37 (m, 2H), 3.16-3.25 (m, 2H), 3.10 (s, 3H), 2.44 (t, 2H), 2.33 (t, 2H), 1.27 (s, 9H).
LCMS (of hydrochloride salt) m/z 842 (M+H)$^+$ (ES$^+$)

(ce) 3-(3-(4-((4-((4-(3-(5-(tert-Butyl)-2-methoxy-3-(methylsulfonamido)phenyl)ureido)-naphthalen-1-yl)oxy)pyridin-2-yl)amino)-2-methoxybenzamido)propanamido)propanoic acid

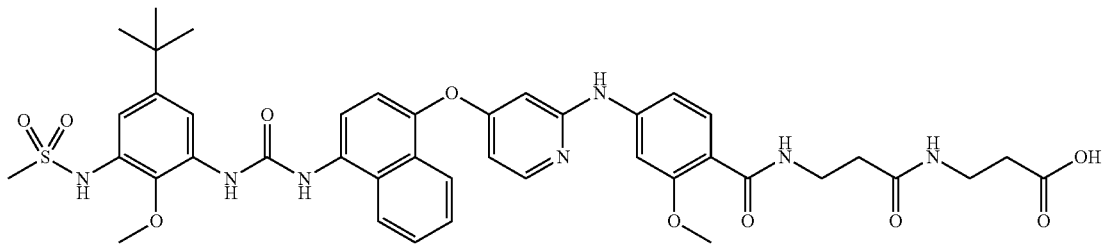 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCC(=O)NCCC(=O)O]

$^1$H NMR (400 MHz, DMSO-d6) δ: 9.64 (s, 1H), 9.28 (s, 1H), 9.08 (s, 1H), 8.33 (d, 1H), 8.23 (t, 1H), 8.16-8.18 (m, 2H), 8.12 (d, 1H), 8.02 (t, 1H), 7.86 (d, 1H), 7.74 (d, 1H), 7.68-7.72 (m, 1H), 7.59-7.63 (m, 1H), 7.45 (s, 1H), 7.40 (d, 1H), 7.18 (d, 1H), 7.02 (d, 1H), 6.68 (dd, 1H), 6.15 (d, 1H), 3.81 (s, 3H), 3.74 (s, 3H), 3.44 (q, 2H), 3.25 (q, 2H), 3.09 (s, 3H), 2.29-2.35 (m, 4H), 1.26 (s, 9H).
LCMS m/z 842 (M+H)$^+$ (ES$^+$)

(cf) 4-((4-((4-(3-(5-(tert-Butyl)-2-methoxy-3-(methylsulfonamido)phenyl)ureido)naphthalen-1-yl)oxy)pyridin-2-yl)amino)-2-methoxy-N-(3-oxo-3-((2R,3R,4R,5S)-3,4,5-trihydroxy-2-(hydroxymethyl)piperidin-1-yl)propyl)benzamide

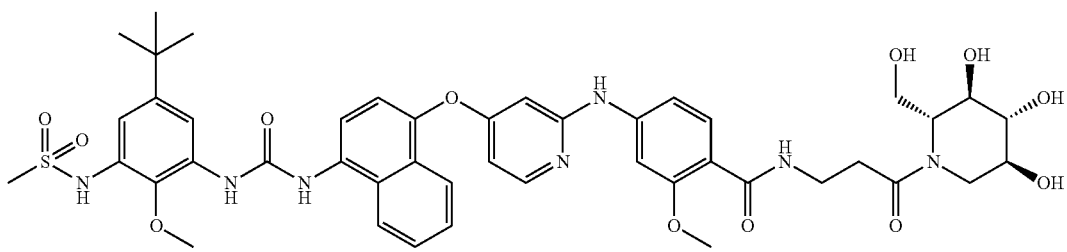 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCC(=O)N1C[C@H](O)[C@@H](O)[C@H](O)[C@H]1CO]

$^1$H NMR (400 MHz, DMSO-d6, 333K) δ 9.27 (s, 1H), 9.11 (s, 1H), 8.88 (s, 1H), 8.75 (s, 1H), 8.29 (d, 1H), 8.24 (t, 1H), 8.16-8.14 (m, 2H), 8.07 (d, 1H), 7.90 (dd, 1H), 7.76 (d, 1H), 7.71-7.67 (m, 1H), 7.62-7.58 (m, 1H), 7.55 (d, 1H), 7.36 (d, 1H), 7.21 (dd, 1H), 7.05 (d, 1H), 6.61 (dd, 1H), 6.22 (d, 1H), 5.00 (bs, 1H), 4.79 (bs, 2H), 4.53 (bs, 1H), 3.84 (s, 3H), 3.83 (s, 3H), 3.65-3.49 (m, 7H), 3.09 (s, 3H), 3.68-3.65 (m, 2H), 1.28 (s, 9H).
LCMS m/z 916.4 (M+H)$^+$ (ES$^+$); 914.2 (M–H)$^-$ (ES$^-$)

(cg) N-(5-(tert-Butyl)-3-(3-(4-((2-((4-(4-(2-(dimethylamino)ethyl)piperazine-1-carbonyl)-3,5-dimethoxyphenyl)amino)pyridin-4-yl)oxy)naphthalen-1-yl)ureido)-2-methoxyphenyl)methane sulfonamide

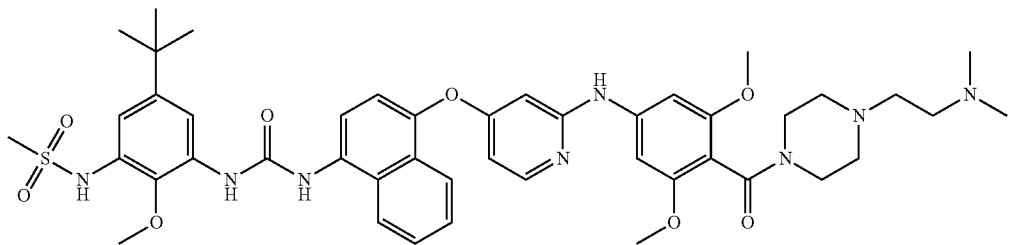

$^1$H NMR (400 MHz, DMSO-d6) δ 9.41 (s, 1H), 9.18 (br, s, 1H), 9.08 (s, 1H), 8.93 (s, 1H), 8.30 (d, 1H), 8.18 (d, 1H), 8.14 (s, 1H), 8.12 (d, 1H), 7.86 (d, 1H), 7.76-7.66 (m, 1H), 7.66-7.56 (m, 1H), 7.40 (d, 1H), 7.02 (d, 1H), 6.98 (s, 2H), 6.61 (dd, 1H), 6.11 (d, 1H), 3.81 (s, 3H), 3.63 (s, 6H), 3.58-3.47 (br, m, 2H), 3.09 (s, 3H), 3.08-3.04 (br, m, 2H), 2.41-2.21 (m, 8H), 2.11 (s, 6H), 1.27 (s, 9H).
LCMS m/z 869 (M+H)$^+$ (ES$^+$)

(ch) N-(5-(tert-Butyl)-2-methoxy-3-(3-(4-((2-((3-methoxy-4-((3-(4-methylpiperazin-1-yl)propyl)sulfonyl)phenyl)amino)pyridin-4-yl)oxy)naphthalen-1-yl)ureido)phenyl)methanesulfonamide

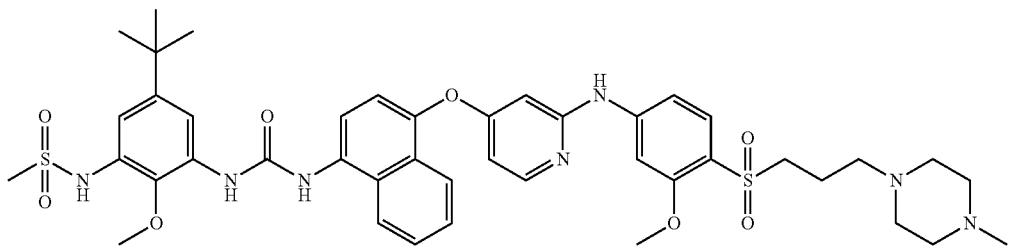

$^1$H NMR (400 MHz, DMSO-d6) δ 9.50 (s, 1H), 9.42 (s, 1H), 9.15 (bs, 1H), 8.94 (s, 1H), 8.30 (d, 1H), 8.20-8.18 (m, 2H), 8.13 (d, 1H), 7.85 (d, 1H), 7.71 (dd, 1H), 7.65-7.55 (m, 3H), 7.41 (d, 1H), 7.30 (d, 1H), 7.01 (d, 1H), 6.70 (dd, 1H), 6.17 (d, 1H), 3.84 (s, 3H), 3.80 (s, 3H), 3.30-3.26 (m, 2H), 3.09 (s, 3H), 2.34-2.13 (m, 10H), 2.10 (s, 3H), 1.58 (quint, 2H), 1.26 (s, 9H).
LCMS m/z 860 (M+H)$^+$ (ES$^+$); 858 (M−H)$^-$ (ES$^-$)

(ci) N-(5-(tert-Butyl)-2-methoxy-3-(3-(4-((2-((3-methoxy-4-((2R,3R,4R,5S)-3,4,5-trihydroxy-2-(hydroxymethyl)piperidine-1-carbonyl)phenyl)amino)pyridin-4-yl)oxy) naphthalen-1-yl)ureido)phenyl) methanesulfonamide

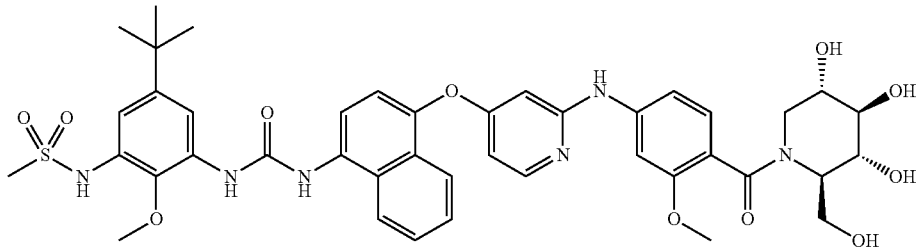 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)N1C[C@H](O)[C@@H](O)[C@H](O)[C@H]1CO]

Mixture of rotamers. $^1$H NMR (400 MHz, DMSO-d6, 100° C.) δ: 9.13 (s, 1H), 8.65-8.88 (m, 2H), 8.58 (s, 1H), 8.29 (d, 1H), 8.12 (d, 1H), 8.08 (d, 1H), 8.02 (d, 1H), 7.94 (d, 1H), 7.65-7.69 (m, 1H), 7.58-7.62 (m, 1H), 7.39 (d, 1H), 7.33 (d, 1H), 7.17 (dd, 1H), 7.09 (d, 1H), 7.02 (d, 1H), 6.55 (dd, 1H), 6.29 (d, 1H), 4.83 (bs, 1H), 4.56 (bs, 1H), 4.49 (bs, 1H), 3.98-4.28 (m, 2H), 3.86 (s, 3H), 3.53-3.76 (m, 6H), 3.72 (s, 3H), 3.32 (d, 1H), 3.07 (s, 3H), 1.30 (s, 9H).
LCMS m/z 845 (M+H)$^+$ (ES$^+$)

(cj) 4-((4-((4-(3-(5-(tert-Butyl)-2-methoxy-3-(methylsulfonamido)phenyl)ureido)naphthalen-1-yl)oxy) pyridin-2-yl)amino)-N-(2-(4-(2-(dimethylamino)acetyl)piperazin-1-yl)ethyl)-2-methoxybenzamide

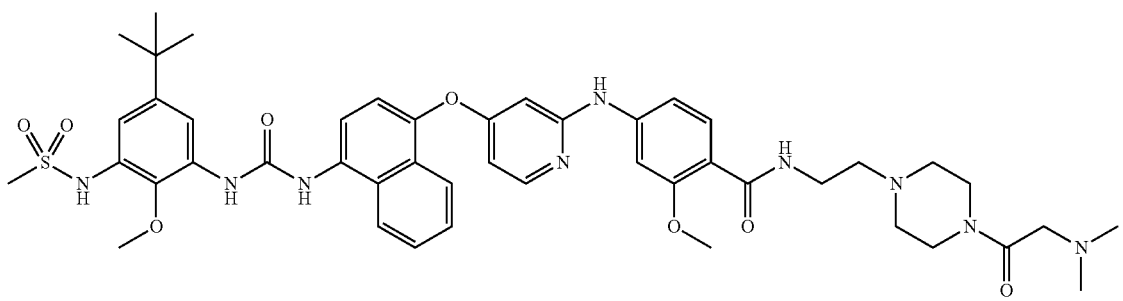

$^1$H NMR (400 MHz, DMSO-d6) δ: 9.41 (s, 1H), 9.27 (s, 1H), 9.20 (bs, 1H), 8.92 (s, 1H), 8.31 (d, 1H), 8.21 (t, 1H), 8.16-8.17 (m, 2H), 8.12 (d, 1H), 7.86 (d, 1H), 7.77 (d, 1H), 7.6-7.73 (m, 1H), 7.58-7.63 (m, 2H), 7.40 (d, 1H), 7.24 (d, 1H), 7.02 (s, 1H), 6.66 (d, 1H), 6.15 (s, 1H), 3.87 (s, 3H), 3.81 (s, 3H), 3.55 (bs, 2H), 3.46 (bs, 2H), 3.40 (q, 2H), 3.08 (s, 3H), 3.05 (s, 2H), 2.48 (t, 2H), 2.42 (bs, 2H), 2.38 (bs, 2H), 2.17 (s, 6H), 1.27 (s, 9H).
LCMS m/z 897 (M+H)$^+$ (ES$^+$)

(ck) 4-(4-(2-(4-((4-((4-(3-(5-(tert-Butyl)-2-methoxy-3-(methylsulfonamido)phenyl)ureido)-naphthalen-1-yl)oxy)pyridin-2-yl)amino)-2-methoxybenzamido)ethyl)piperazin-1-yl)-4-oxobutanoic acid

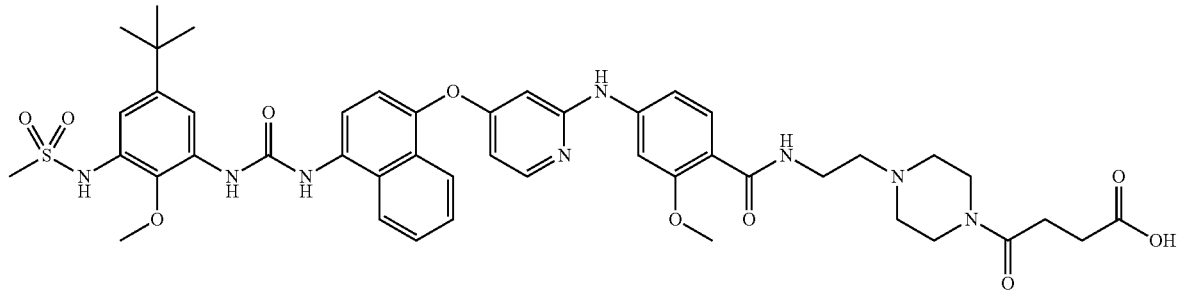 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCN(C(=O)CCC(=O)O)CC1]

¹H NMR (400 MHz, DMSO-d6) δ: 9.50 (s, 1H), 9.27 (s, 1H), 8.97 (s, 1H), 8.32 (d, 1H), 8.21 (t, 1H), 8.11-8.17 (m, 3H), 7.86 (d, 1H), 7.77 (d, 1H), 7.68-7.72 (m, 1H), 7.59-7.63 (m, 1H), 7.53 (s, 1H), 7.40 (d, 1H), 7.22 (d, 1H), 7.03 (d, 1H), 6.67 (dd, 1H), 6.15 (d, 1H), 3.83 (s, 3H), 3.80 (s, 3H), 3.43-3.52 (m, 6H), 2H under water, 3.06 (s, 3H), 2.33-2.47 (m, 8H), 1.26 (s, 9H).

LCMS m/z 911 (M+H)⁺ (ES⁺)

(cl) (S)-2-Amino-5-(4-(2-(4-((4-((4-(3-(5-(tert-butyl)-2-methoxy-3-(methylsulfonamido)-phenyl)ureido)naphthalen-1-yl)oxy)pyridin-2-yl)amino)-2-methoxybenzamido)ethyl)piperazin-1-yl)-5-oxopentanoic acid

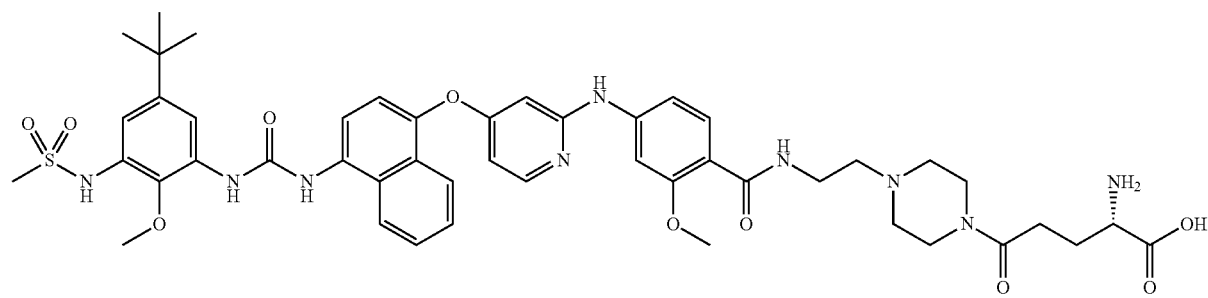

¹H NMR (400 MHz, DMSO-d6) δ: 9.51 (s, 1H), 9.29 (s, 1H), 8.99 (s, 1H), 8.32 (d, 1H), 8.11-8.21 (m, 4H), 7.86 (d, 1H), 7.77 (d, 1H), 7.68-7.72 (m, 1H), 7.59-7.63 (m, 1H), 7.54 (s, 1H), 7.40 (d, 1H), 7.29 (bs, 1H), 7.22 (d, 1H), 7.03 (d, 1H), 6.67 (dd, 1H), 6.16 (d, 1H), 3.83 (s, 3H), 3.81 (s, 3H), 8H under water, 3.10 (s, 3H), 2.33-2.55 (m, 7H), 1.82-1.95 (m, 2H), 1.27 (s, 9H).

LCMS m/z 940 (M+H)⁺ (ES⁺), 471 (M+2H)²⁺ (ES⁺)

(cm) 4-((4-((4-(3-(5-(tert-Butyl)-2-methoxy-3-(methylsulfonamido)phenyl)ureido)naphthalen-1-yl)oxy)pyridin-2-yl)amino)-N-(1,3-dihydroxy-2-(hydroxymethyl)propan-2-yl)-2-methoxybenzamide

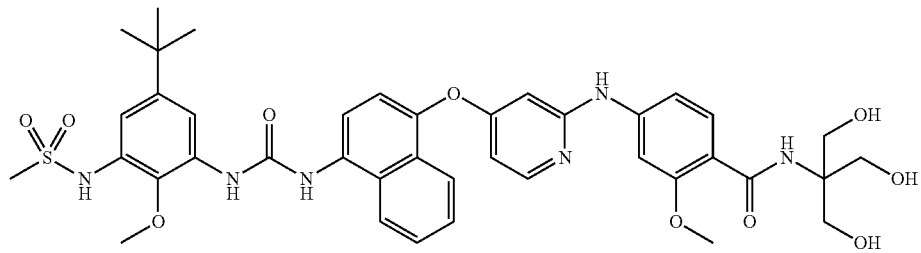 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NC(CO)(CO)CO]

$^1$H NMR (400 MHz, DMSO-d6) δ: 9.41 (s, 1H), 9.32 (s, 1H), 9.16 (s, 1H), 8.92 (s, 1H), 8.58 (s, 1H), 8.31 (d, 1H), 8.17-8.19 (m, 2H), 8.13 (d, 1H), 7.81-7.87 (m, 2H), 7.69-7.73 (m, 1H), 7.60-7.63 (m, 2H), 7.41 (d, 1H), 7.24-7.25 (dd, 1H), 7.03 (d, 1H), 6.68 (dd, 1H), 6.16 (d, 1H), 5.05 (t, 3H), 3.85 (s, 3H), 3.81 (s, 3H), 3.58 (d, 6H), 3.09 (s, 3H), 1.27 (s, 9H).
LCMS m/z 803 (M+H)$^+$ (ES$^+$)

(cn) 4-((4-((4-(3-(5-(tert-Butyl)-2-methoxy-3-(methylsulfonamido)phenyl)ureido)naphthalen-1-yl)oxy)pyridin-2-yl)amino)-N-(3-hydroxy-2,2-bis(hydroxymethyl)propyl)-2,6-dimethoxybenzamide

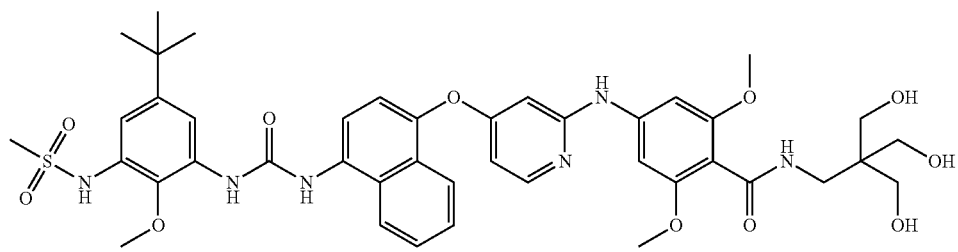 [SMILES: COc1cc(Nc2cc(Oc3ccc(NC(=O)Nc4cc(C(C)(C)C)cc(NS(C)(=O)=O)c4OC)c4ccccc34)ccn2)cc(OC)c1C(=O)NCC(CO)(CO)CO]

$^1$H NMR (400 MHz, DMSO-d6) δ 9.41 (s, 1H), 9.11 (br, s, 1H), 9.07 (s, 1H), 8.91 (s, 1H), 8.31 (d, 1H), 8.23-8.06 (m, 3H), 7.91 (t, 1H), 7.87 (d, 1H), 7.75-7.67 (m, 1H), 7.65-7.58 (m, 1H), 7.39 (d, 1H), 7.03 (d, 1H), 6.98 (s, 2H), 6.62 (dd, 1H), 6.11 (d, 1H), 4.29 (t, 3H), 3.81 (s, 3H), 3.64 (s, 6H), 3.30 (d, 6H), 3.13-2.95 (m, 5H), 1.27 (s, 9H).
LCMS m/z 847 (M+H)$^+$ (ES$^+$)

(co) 4-((4-((4-(3-(5-(tert-Butyl)-2-methoxy-3-(methylsulfonamido)phenyl)ureido)naphthalen-1-yl)oxy)pyridin-2-yl)amino)-2-methoxy-N-(((2S,3R,4R,5S,6R)-3,4,5-trihydroxy-6-(hydroxymethyl)tetrahydro-2H-pyran-2-yl)methyl)benzamide

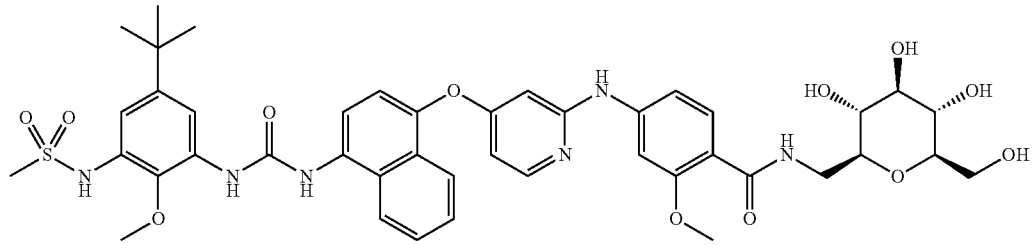 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NC[C@@H]1O[C@H](CO)[C@@H](O)[C@H](O)[C@H]1O]

$^1$H NMR (400 MHz, DMSO-d6) δ: 9.41 (s, 1H), 9.28 (s, 1H), 9.17 (s, 1H), 8.92 (s, 1H), 8.31 (d, 1H), 8.24 (t, 1H), 8.16-8.18 (m, 2H), 8.12 (d, 1H), 7.87 (d, 1H), 7.79 (d, 1H), 7.69-7.73 (m, 1H), 7.59-7.63 (m, 2H), 7.40 (d, 1H), 7.25 (dd, 1H), 7.03 (d, 1H), 6.66 (dd, 1H), 6.15 (d, 1H), 5.14 (d, 1H), 4.96 (d, 1H), 4.92 (d, 1H), 4.53 (t, 1H), 3.87 (s, 3H), 3.81 (s, 3H), 3.67-3.77 (m, 2H), 3.41-3.47 (m, 1H), 3.24-3.30 (m, 1H), 3.12-3.20 (m, 3H), 3.08 (s, 3H), 2.97-3.06 (m, 2H), 1.27 (s, 9H).

LCMS m/z 875 (M+H)$^+$ (ES$^+$)

(cp) 2-((5-(tert-Butyl)-2-methoxy-3-(3-(4-((2-((3-methoxy-4-((2-(1-oxidothiomorpholino)-ethyl)carbamoyl)phenyl)amino)pyridin-4-yl)oxy)naphthalen-1-yl)ureido)phenyl)amino)-2-oxoethyl dihydrogen phosphate

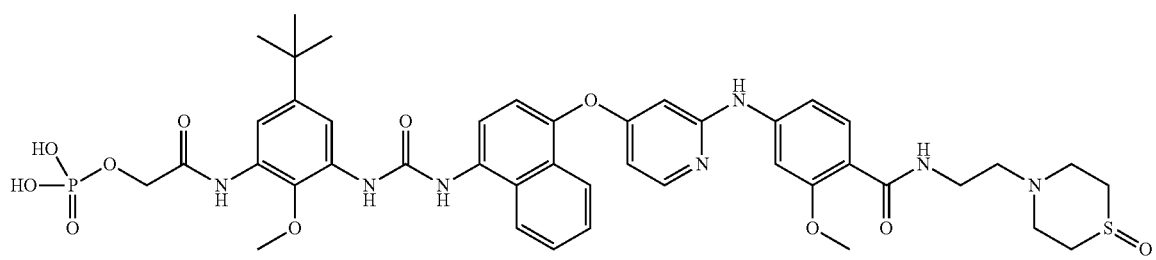 [SMILES: COc1cc(Nc2cc(Oc3ccc(NC(=O)Nc4cc(C(C)(C)C)cc(NC(=O)COP(=O)(O)O)c4OC)c4ccccc34)ccn2)ccc1C(=O)NCCN1CCS(=O)CC1]

$^1$H NMR (of ammonium salt; 400 MHz, DMSO-d6) δ 9.51 (s, 1H), 9.27 (s, 1H), 8.91 (s, 1H), 8.37-8.30 (m, 1H), 8.20-8.08 (m, 4H), 7.86 (d, 2H), 7.73 (dd, 2H), 7.65-7.53 (m, 2H), 7.40 (d, 1H), 7.24 (dd, 1H), 6.67 (dd, 1H), 6.14 (d, 1H), 4.37-4.29 (m, 2H), 3.85 (s, 3H), 3.82 (s, 3H), 3.39 (d, 2H), 3.00-2.84 (m, 4H), 2.78-2.68 (m, 4H), 2.60-2.54 (m, 2H), 1.27 (s, 9H).

LCMS (of ammonium salt) m/z 904 (M+H)$^+$ (ES$^+$)

(cq) (R)-4-((4-((4-(3-(5-(tert-Butyl)-2-methoxy-3-(methylsulfonamido)phenyl)ureido)-naphthalen-1-yl)oxy)pyridin-2-yl)amino)-2-methoxy-N-(1-methyl-pyrrolidin-3-yl)benzamide

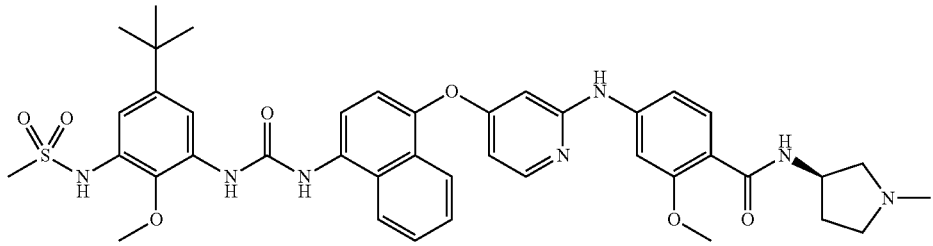

$^1$H NMR (400 MHz, DMSO-d6) δ: 9.40 (s, 1H), 9.26 (s, 1H), 9.16 (s, 1H), 8.92 (s, 1H), 8.31 (d, 1H), 8.16-8.19 (m, 2H), 8.12 (d, 1H), 7.96 (d, 1H), 7.87 (d, 1H), 7.70-7.73 (m, 2H), 7.59-7.63 (m, 2H), 7.40 (d, 1H), 7.22 (dd, 1H), 7.03 (d, 1H), 6.66 (dd, 1H), 6.15 (d, 1H), 4.31-4.39 (m, 1H), 3.85 (s, 3H), 3.81 (s, 3H), 3.10 (s, 3H), 2.59-2.67 (m, 2H), 2.41 (dd, 1H), 2.31 (q, 1H), 2.25 (s, 3H), 2.41-2.23 (m, 1H), 1.57-1.65 (m, 1H), 1.27 (s, 9H).
LCMS m/z 782 (M+H)$^+$ (ES$^+$)

(cr) (R)-4-((4-((4-(3-(5-(tert-Butyl)-2-methoxy-3-(methylsulfonamido)phenyl)ureido)-naphthalen-1-yl)oxy)pyridin-2-yl)amino)-N-(2-(3-hydroxypyrrolidin-1-yl)ethyl)-2-methoxybenzamide

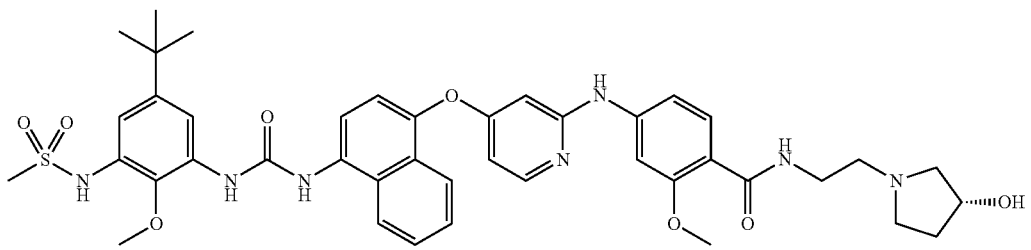 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CC[C@@H](O)C1]

$^1$H NMR (400 MHz, DMSO-d6) δ: 9.40 (s, 1H), 9.26 (s, 1H), 9.15 (s, 1H), 8.92 (s, 1H), 8.31 (d, 1H), 8.11-8.22 (m, 4H), 7.87 (d, 1H), 7.69-7.77 (m, 2H), 7.60-7.63 (m, 1H), 7.56 (s, 1H), 7.40 (d, 1H), 7.23 (d, 1H), 7.03 (s, 1H), 6.65-6.66 (m, 1H), 6.15 (s, 1H), 4.70 (s, 1H), 4.21 (s, 1H), 3.85 (s, 3H), 3.81 (s, 3H), 2H underwater, 3.10 (s, 3H), 2.71-2.74 (m, 1H), 2.63 (q, 1H), 2H under DMSO, 2.42-2.46 (m, 1H), 2.37 (d, 1H), 1.96-2.04 (m, 1H), 1.51-1.62 (m, 1H), 1.27 (s, 9H).
LCMS m/z 812 (M+H)$^+$ (ES$^+$)

(cs) 4-[[4-[[4-[[5-tert-Butyl-3-(methanesulfona-mido)-2-methoxy-phenyl]carbamoylamino]-1-naphthyl]oxy]-2-pyridyl]amino]-2-chloro-benzoic acid

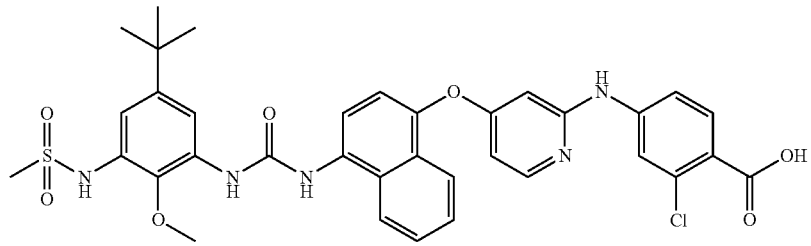 [SMILES: COc1c(NC(=O)Nc2ccc(Oc3ccnc(Nc4ccc(C(=O)O)c(Cl)c4)c3)c3ccccc23)cc(C(C)(C)C)cc1NS(C)(=O)=O]

$^1$H NMR (400 MHz, DMSO-d6) δ: 9.48 (s, 1H), 9.41 (s, 1H), 8.97 (s, 1H), 8.31 (d, 1H), 8.23-8.15 (m, 2H), 8.12 (d, 1H), 8.00 (d, 1H), 7.86 (d, 1H), 7.76-7.66 (m, 2H), 7.66-7.56 (m, 1H), 7.45 (dd, 1H), 7.41 (d, 1H), 7.02 (d, 1H), 6.71 (dd, 1H), 6.13 (d, 1H), 3.81 (s, 3H), 3.10 (s, 3H), 1.27 (s, 9H).
LCMS m/z 704/706 (M+H)$^+$ (ES$^+$)

(ct) 4-[[4-[[4-[[5-tert-Butyl-3-(methanesulfona-mido)-2-methoxy-phenyl]carbamoylamino]-1-naphthyl]oxy]-2-pyridyl]amino]-2-ethyl-benzoic acid

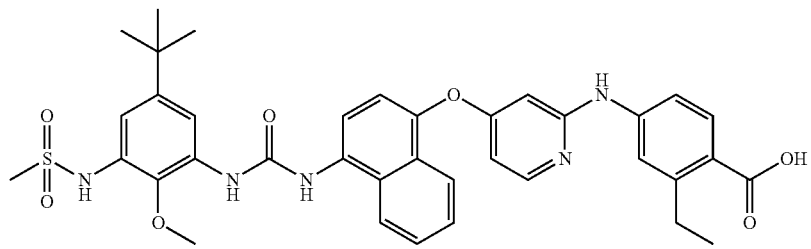 [SMILES: CCc1cc(Nc2cc(Oc3ccc(NC(=O)Nc4cc(C(C)(C)C)cc(NS(C)(=O)=O)c4OC)c4ccccc34)ccn2)ccc1C(=O)O]

$^1$H NMR (400 MHz, DMSO-d6) δ: 12.26 (s, 1H), 9.44 (s, 1H), 9.24 (s, 1H), 9.16 (s, 1H), 8.95 (s, 1H), 8.31 (d, 1H), 8.11-8.19 (m, 3H), 7.87 (d, 1H), 7.69-7.75 (m, 2H), 7.60-7.63 (m, 2H), 7.39-7.43 (m, 2H), 7.03 (s, 1H), 6.65 (d, 1H), 6.16 (s, 1H), 3.81 (s, 3H), 3.10 (s, 3H), 2.89 (q, 2H), 1.27 (s, 9H), 1.11 (t, 3H).
LCMS m/z 698 (M+H)$^+$ (ES$^+$)

(cu) 4-[[4-[[4-[[5-tert-Butyl-3-(methanesulfona-mido)-2-methoxy-phenyl]carbamoylamino]-1-naphthyl]oxy]-2-pyridyl]amino]-2-(difluoromethoxy)benzoic acid

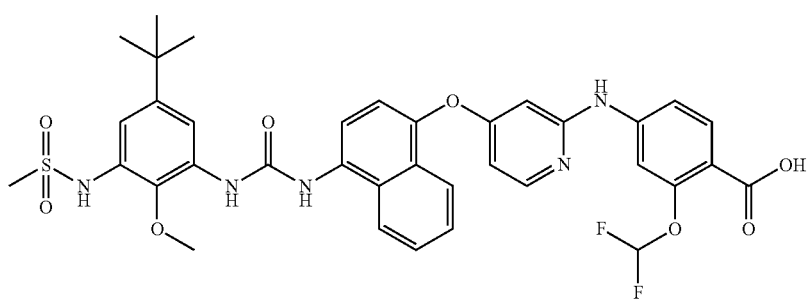 [SMILES: COc1c(NC(=O)Nc2ccc(Oc3ccnc(Nc4ccc(C(=O)O)c(OC(F)F)c4)c3)c3ccccc23)cc(C(C)(C)C)cc1NS(C)(=O)=O]

¹H NMR (400 MHz, DMSO-d6) δ: 9.47 (s, 1H), 9.37 (s, 1H), 9.14 (bs, 1H), 8.96 (s, 1H), 8.31 (d, 1H), 8.17-8.18 (m, 2H), 8.12 (d, 1H), 7.86 (d, 1H), 7.68-7.72 (m, 2H), 7.59-7.65 (m, 2H), 7.47 (d, 1H), 7.40 (d, 1H), 7.09 (t, J=76.2 Hz, 1H), 7.03 (d, 1H), 6.68 (dd, 1H), 6.14 (d, 1H), 3.81 (s, 3H), 3.10 (s, 3H), 1.27 (s, 9H).

LCMS m/z 736 (M+H)$^+$ (ES$^+$)

(cv) 6-[[4-[[4-[[5-tert-Butyl-3-(methanesulfonamido)-2-methoxy-phenyl]carbamoylamino]-1-naphthyl]oxy]-2-pyridyl]amino]-4-methoxy-pyridine-3-carboxylic acid

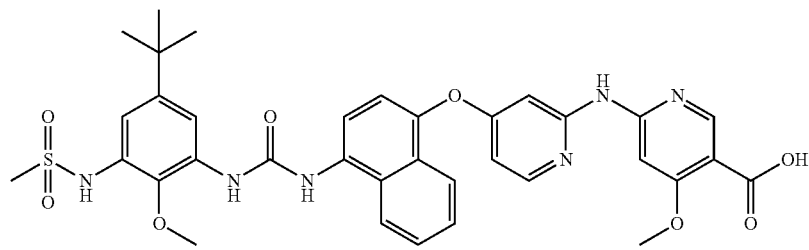 [SMILES: COc1cc(Nc2cc(Oc3ccc(NC(=O)Nc4cc(C(C)(C)C)cc(NS(C)(=O)=O)c4OC)c4ccccc34)ccn2)ncc1C(=O)O]

¹H NMR (400 MHz, DMSO-d6) δ: 12.29 (s, 1H), 9.96 (s, 1H), 9.40 (s, 1H), 8.93 (s, 1H), 8.42 (s, 1H), 8.30 (d, 1H), 8.19 (d, 1H), 8.16 (d, 1H), 8.11 (d, 1H), 7.88 (d, 1H), 7.75-7.64 (m, 1H), 7.64-7.52 (m, 2H), 7.37 (d, 1H), 7.33 (d, 1H), 7.02 (d, 1H), 6.50 (dd, 1H), 3.85 (s, 3H), 3.81 (s, 3H), 3.10 (s, 3H), 1.27 (s, 9H).

LCMS m/z 701 (M+H)$^+$ (ES$^+$)

(cw) 4-[[4-[[4-[[5-tert-Butyl-3-(methanesulfonamido)-2-methoxy-phenyl]carbamoylamino]-1-naphthyl]oxy]-2-pyridyl]amino]-2-hydroxy-benzoic acid

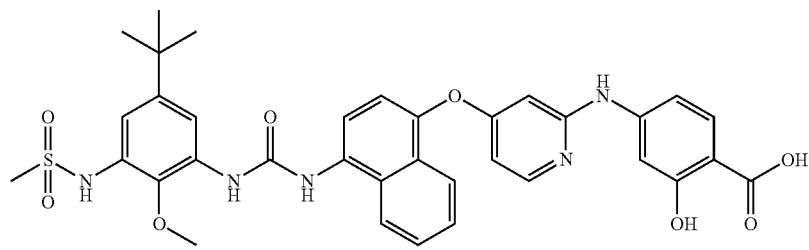 [SMILES: COc1c(NC(=O)Nc2ccc(Oc3ccnc(Nc4ccc(C(=O)O)c(O)c4)c3)c3ccccc23)cc(C(C)(C)C)cc1NS(C)(=O)=O]

¹H NMR (400 MHz, DMSO-d6) δ: 9.43 (s, 1H), 9.04 (s, 1H), 8.94 (s, 1H), 8.30 (d, 1H), 8.19 (d, 1H), 8.14 (d, 1H), 8.11 (d, 1H), 7.87 (dd, 1H), 7.68-7.72 (m, 1H), 7.59-7.63 (m, 1H), 7.51 (d, 1H), 7.40 (d, 1H), 7.30 (s, 1H), 7.03 (d, 1H), 6.82 (dd, 1H), 6.62 (dd, 1H), 6.14 (d, 1H), 3.81 (s, 3H), 3.10 (s, 3H), 1.27 (s, 9H).

LCMS m/z 686 (M+H)$^+$ (ES$^+$)

(cx) 4-[[4-[[4-[[5-tert-Butyl-3-(methanesulfonamido)-2-methoxy-phenyl]carbamoylamino]-1-naphthyl]oxy]-2-pyridyl]amino]-2-fluoro-benzoic acid

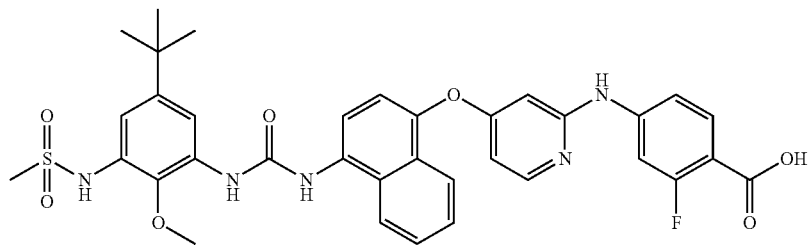

$^1$H NMR (of hydrochloride salt; 400 MHz, DMSO-d6) δ: 9.60 (s, 1H), 9.45 (s, 1H), 9.15 (s, 1H), 8.95 (s, 1H), 8.32 (d, 1H), 8.21 (d, 1H), 8.19 (d, 1H), 8.12 (d, 1H), 7.85-7.91 (m, 2H), 7.69-7.75 (m, 2H), 7.60-7.64 (m, 1H), 7.42 (d, 1H), 7.23 (dd, 1H), 7.03 (d, 1H), 6.75 (dd, 1H), 6.18 (d, 1H), 3.81 (s, 3H), 3.10 (s, 3H), 1.27 (s, 9H).

LCMS (of hydrochloride salt) m/z 688 (M+H)$^+$ (ES$^+$)

(cy) (2S)-2-Amino-3-[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]phenyl]-propanoic acid

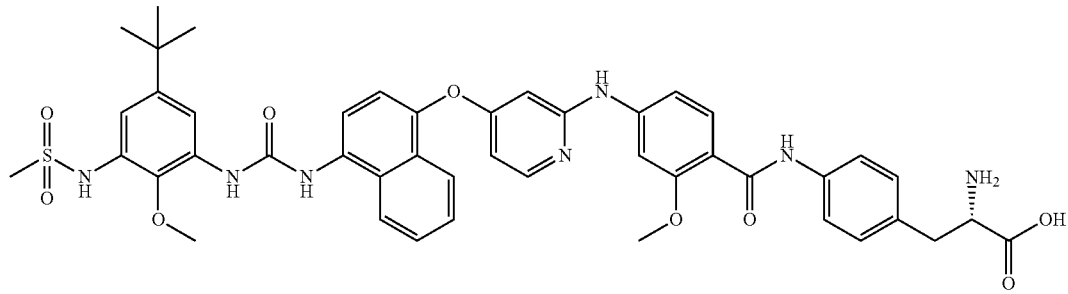 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)Nc1ccc(C[C@H](N)C(=O)O)cc1]

$^1$H NMR (of dihydrochloride salt; 400 MHz, DMSO-d6) δ: 9.89 (s, 1H), 9.54 (s, 1H), 9.36 (s, 1H), 9.15 (s, 1H), 9.00 (s, 1H), 7.97-8.44 (bm, 2H), 8.35 (d, 1H), 8.15-8.21 (m, 2H), 8.12 (d, 1H), 7.87 (d, 1H), 7.60-7.73 (m, 6H), 7.41 (d, 1H), 7.29 (d, 1H), 7.22 (d, 2H), 7.03 (s, 1H), 6.68 (d, 1H), 6.17 (s, 1H), 4.06-4.14 (m, 1H), 3.91 (s, 3H), 3.81 (s, 3H), 3.02-3.14 (m, 2H), 3.10 (s, 3H), 1.27 (s, 9H).

LCMS (of dihydrochloride salt) m/z 862 (M+H)$^+$ (ES$^+$)

Example 18

The following compounds are prepared by methods analogous to those described above.

(a) 4-[[4-[[4-[[5-tert-butyl-3-(methanesulfonamido)-
2-methoxy-phenyl]carbamoylamino]-1-naphthyl]
oxy]-2-pyridyl]amino]-2-methoxy-N-[(1R)-1-
methyl-2-morpholino-ethyl]benzamide

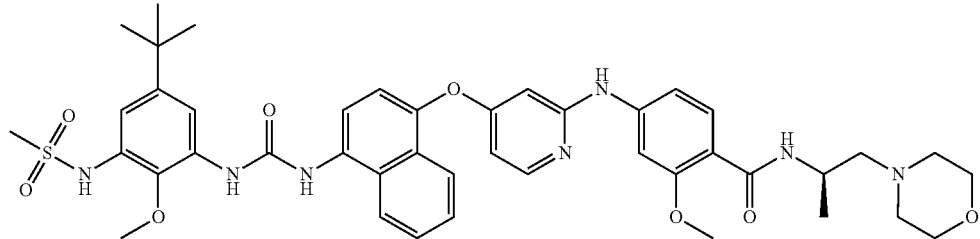 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)N[C@H](C)CN1CCOCC1]

(b) 4-[[4-[[4-[[5-tert-butyl-3-(methanesulfonamido)-
2-methoxy-phenyl]carbamoylamino]-1-naphthyl]
oxy]-2-pyridyl]amino]-2-hydroxy-N-(2-morpholino-
ethyl)benzamide

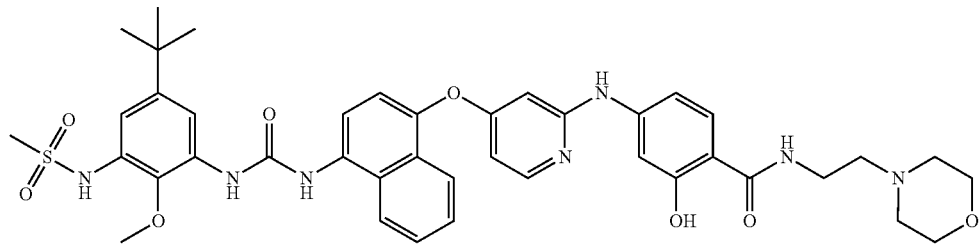 [SMILES: COc1c(NC(=O)Nc2ccc(Oc3ccnc(Nc4ccc(C(=O)NCCN5CCOCC5)c(O)c4)c3)c3ccccc23)cc(C(C)(C)C)cc1NS(C)(=O)=O]

(c) 4-[[4-[[4-[[5-tert-butyl-3-(methanesulfonamido)-
2-methoxy-phenyl]carbamoylamino]-1-naphthyl]
oxy]-2-pyridyl]amino]-N-[2-[2-(2-methoxyethoxy)
ethoxy]ethyl]benzamide

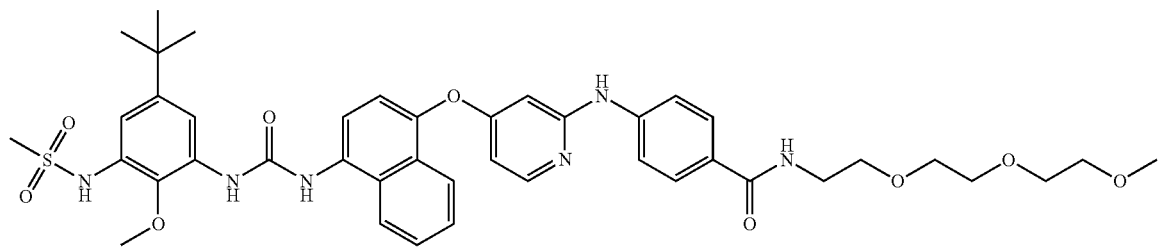

(d) 4-[[4-[[4-[[5-tert-butyl-3-(methanesulfonamido)-
2-methoxy-phenyl]carbamoylamino]-1-naphthyl]
oxy]-2-pyridyl]amino]-N-[2-(4-fluoro-1-piperidyl)
ethyl]-2-methoxy-benzamide

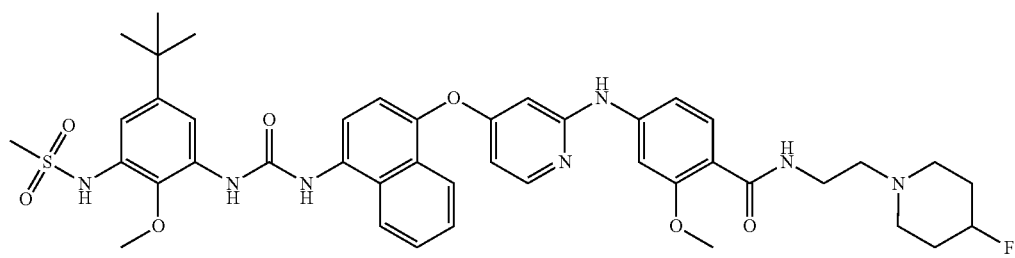 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCC(F)CC1]

(e) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-quinuclidin-4-yl-benzamide

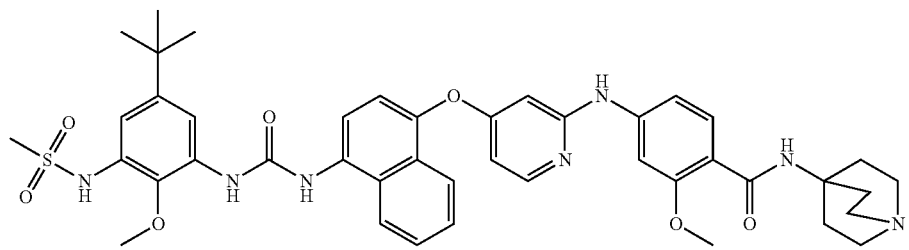 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NC12CCN(CC1)CC2]

(f) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(quinuclidin-4-ylmethyl)benzamide

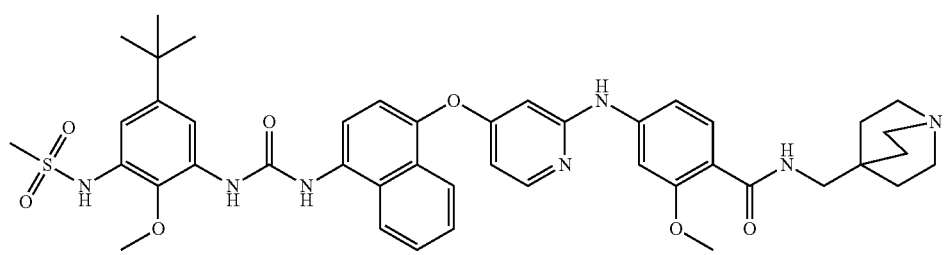 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCC12CCN(CC1)CC2]

(g) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-(2-quinuclidin-4-ylethyl)benzamide

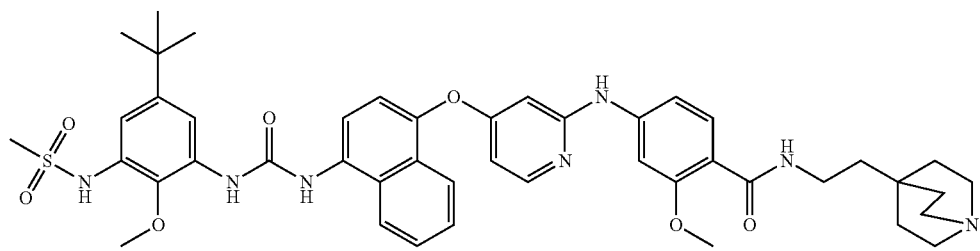 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCC12CCN(CC1)CC2]

(h) 1-[5-tert-butyl-3-(methanesulfonamido)-2-methoxy-phenyl]-3-[4-[[2-(3-methoxy-4-methylsulfonyl-anilino)-4-pyridyl]oxy]-1-naphthyl]urea
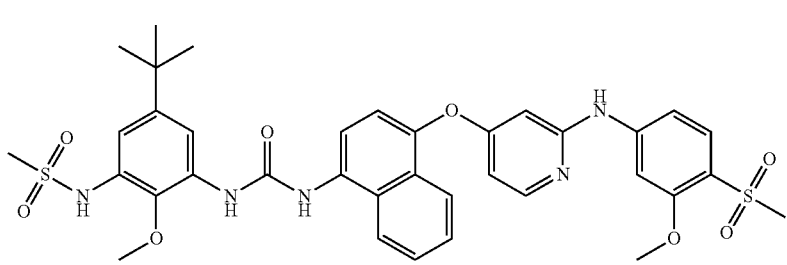
(i) 1-[5-tert-butyl-3-(methanesulfonamido)-2-methoxy-phenyl]-3-[4-[[2-(3-methoxy-4-methylsulfinyl-anilino)-4-pyridyl]oxy]-1-naphthyl]urea
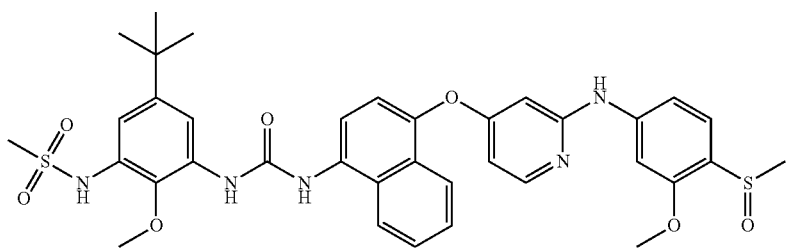
(j) 1-[5-tert-butyl-3-(methanesulfonamido)-2-methoxy-phenyl]-3-[4-[[2-[3-methoxy-4-(2-morpholinoethylsulfonyl)anilino]-4-pyridyl]oxy]-1-naphthyl]urea
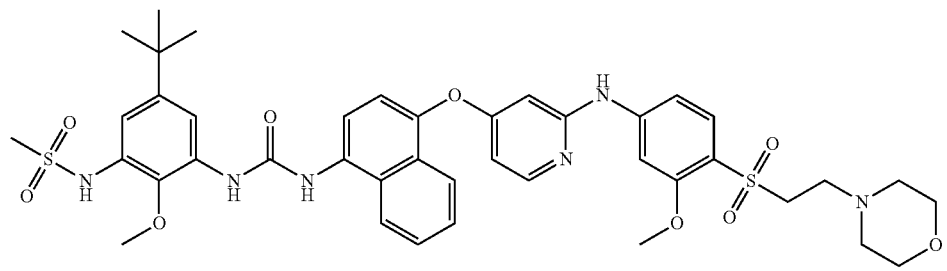 [SMILES: COc1cc(Nc2cc(Oc3ccc(NC(=O)Nc4cc(C(C)(C)C)cc(NS(C)(=O)=O)c4OC)c4ccccc34)ccn2)ccc1S(=O)(=O)CCN1CCOCC1]

(k) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[3-(1-methyl-4-piperidyl)propyl]benzamide

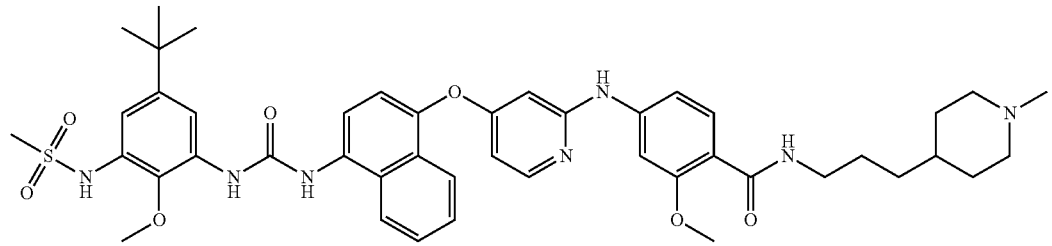

(l) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[2-(4-piperidyl)ethyl]benzamide

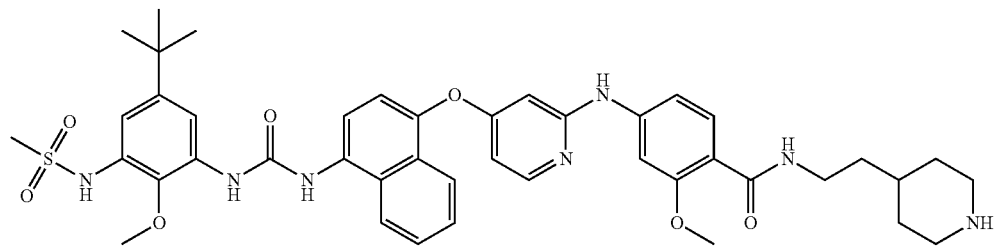 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCC1CCNCC1]

(m) 4-[[4-[[4-[[5-tert-butyl-3-(methanesulfonamido)-2-methoxy-phenyl]carbamoylamino]-1-naphthyl]oxy]-2-pyridyl]amino]-2,6-dimethoxy-N-(4-morpholinobutyl)benzamide

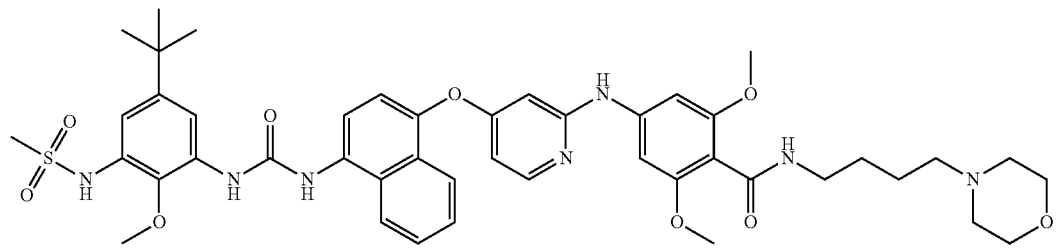 [SMILES: COc1cc(Nc2cc(Oc3ccc(NC(=O)Nc4cc(C(C)(C)C)cc(NS(C)(=O)=O)c4OC)c4ccccc34)ccn2)cc(OC)c1C(=O)NCCCCN1CCOCC1]

(n) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[(1R)-1-methyl-3-morpholino-propyl]benzamide

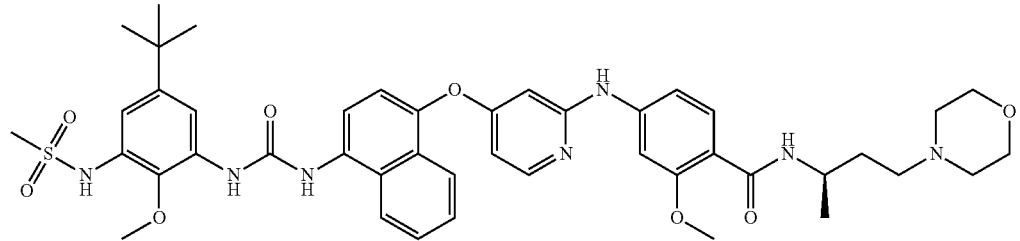 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)N[C@H](C)CCN1CCOCC1]

(o) 4-[[4-[[4-[[5-tert-butyl-3-(methanesulfonamido)-2-methoxy-phenyl]carbamoylamino]-1-naphthyl]oxy]-2-pyridyl]amino]-2-methoxy-N-[(1S)-1-methyl-3-morpholino-propyl]benzamide

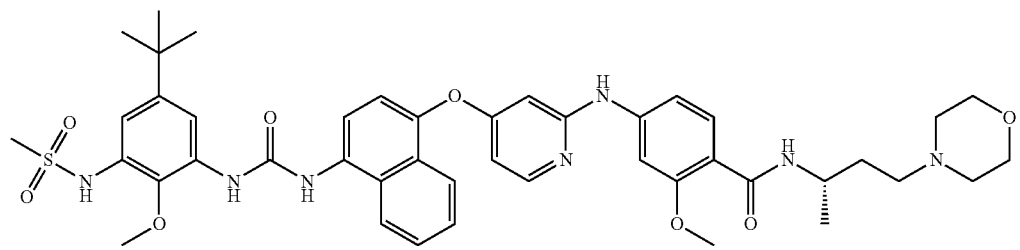

(p) 2-[5-tert-butyl-2-methoxy-3-[[4-[[2-[3-methoxy-4-[2-(1-oxo-1,4-thiazinan-4-yl)ethylcarbamoyl]anilino]-4-pyridyl]oxy]-1-naphthyl]carbamoylamino]-N-methylsulfonyl-anilino]ethyl dihydrogen phosphate

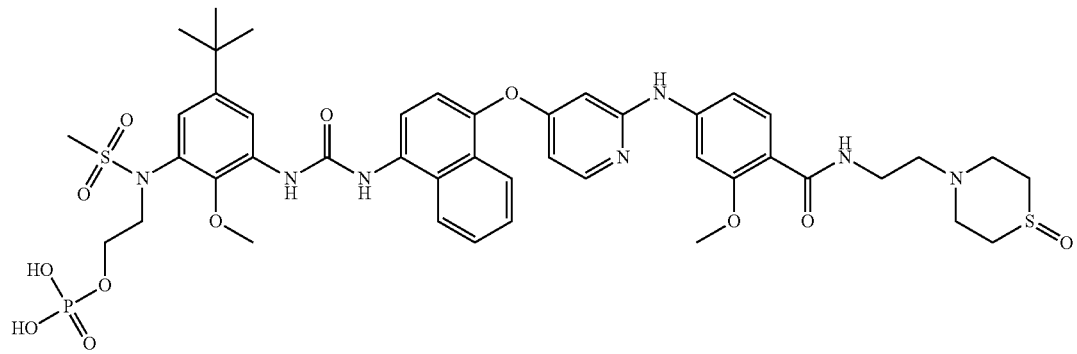 [SMILES: COc1cc(Nc2cc(Oc3ccc(NC(=O)Nc4cc(C(C)(C)C)cc(N(CCOP(=O)(O)O)S(C)(=O)=O)c4OC)c4ccccc34)ccn2)ccc1C(=O)NCCN1CCS(=O)CC1]

(q) [4-[[4-[[4-[[5-tert-butyl-3-(methanesulfonamido)-2-methoxy-phenyl]carbamoylamino]-1-naphthyl]oxy]-2-pyridyl]amino]-2-methoxy-phenyl]phosphinic acid

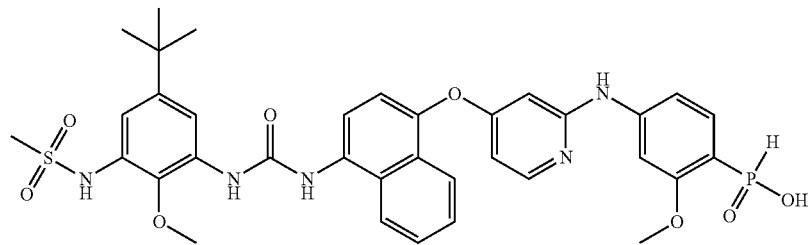 [SMILES: COc1cc(Nc2cc(Oc3ccc(NC(=O)Nc4cc(C(C)(C)C)cc(NS(C)(=O)=O)c4OC)c4ccccc34)ccn2)ccc1[PH](=O)O]

(r) [4-[[4-[[4-[[5-tert-butyl-3-(methanesulfonamido)-2-methoxy-phenyl]carbamoylamino]-1-naphthyl]oxy]-2-pyridyl]amino]-2-methoxy-phenyl]phosphonic acid

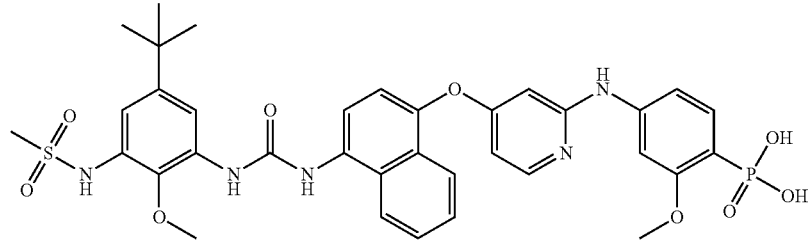 [SMILES: COc1cc(Nc2cc(Oc3ccc(NC(=O)Nc4cc(C(C)(C)C)cc(NS(C)(=O)=O)c4OC)c4ccccc34)ccn2)ccc1P(=O)(O)O]

(s) [4-[[4-[[4-[[5-tert-butyl-3-(methanesulfonamido)-2-methoxy-phenyl]carbamoylamino]-1-naphthyl]oxy]-2-pyridyl]amino]-2,6-dimethoxy-phenyl]-methyl-phosphinic acid

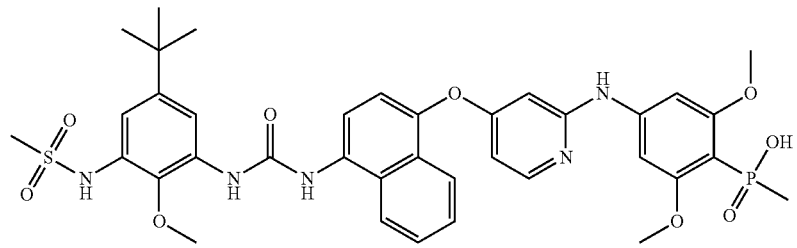

(t) 4-[[4-[[4-[[5-tert-butyl-3-(methanesulfonamido)-2-methoxy-phenyl]carbamoylamino]-1-naphthyl]oxy]-2-pyridyl]amino]-2-methoxy-benzenesulfinic acid

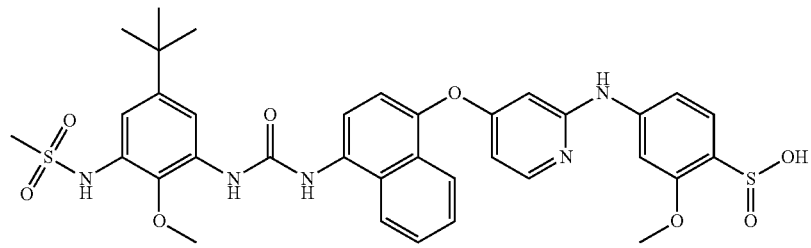 [SMILES: COc1cc(Nc2cc(Oc3ccc(NC(=O)Nc4cc(C(C)(C)C)cc(NS(C)(=O)=O)c4OC)c4ccccc34)ccn2)ccc1S(=O)O]

(u) 4-[[4-[[4-[[5-tert-butyl-3-(methanesulfonamido)-2-methoxy-phenyl]carbamoylamino]-1-naphthyl]oxy]-2-pyridyl]amino]-2-(trifluoromethoxy)benzoic acid

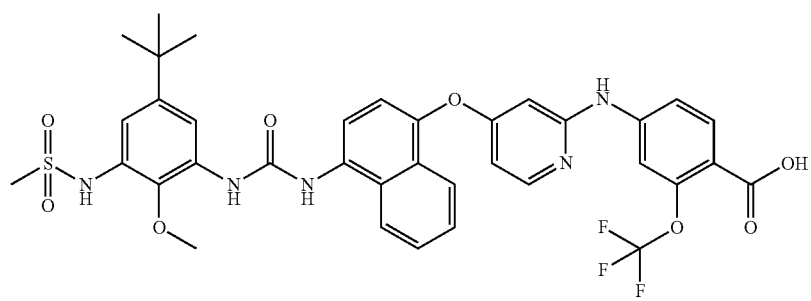 [SMILES: COc1c(NC(=O)Nc2ccc(Oc3ccnc(Nc4ccc(C(=O)O)c(OC(F)(F)F)c4)c3)c3ccccc23)cc(C(C)(C)C)cc1NS(C)(=O)=O]

(v) 6-[[4-[[4-[[5-tert-butyl-3-(methanesulfonamido)-2-methoxy-phenyl]carbamoylamino]-1-naphthyl]oxy]-2-pyridyl]amino]-2-methoxy-pyridine-3-carboxylic acid

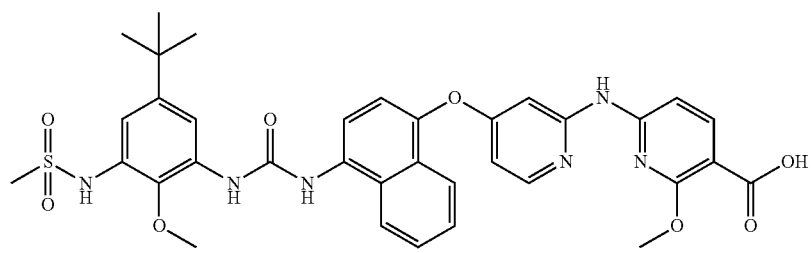 [SMILES: COc1nc(Nc2cc(Oc3ccc(NC(=O)Nc4cc(C(C)(C)C)cc(NS(C)(=O)=O)c4OC)c4ccccc34)ccn2)ccc1C(=O)O]

(w) 4-[[4-[[4-[[5-tert-butyl-3-(methanesulfonamido)-2-methoxy-phenyl]carbamoylamino]-1-naphthyl]oxy]-2-pyridyl]amino]-2,6-dimethyl-benzoic acid

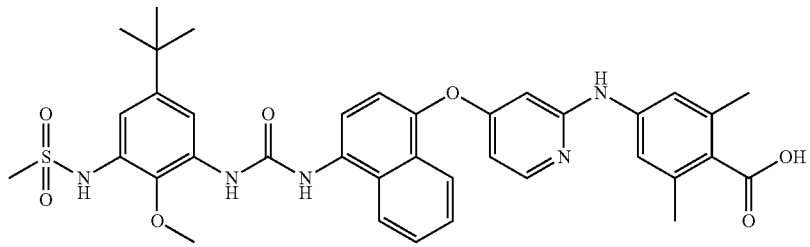 [SMILES: COc1c(NC(=O)Nc2ccc(Oc3ccnc(Nc4cc(C)c(C(=O)O)c(C)c4)c3)c3ccccc23)cc(C(C)(C)C)cc1NS(C)(=O)=O]

Example 19

2-(2-(2-(4-((4-((4-(3-(5-(tert-Butyl)-2-methoxy-3-(methylsulfonamido)phenyl)ureido)-naphthalen-1-yl)oxy)pyridin-2-yl)amino)-2-methoxybenzamido)ethoxy)ethoxy)ethyl dihydrogen phosphate

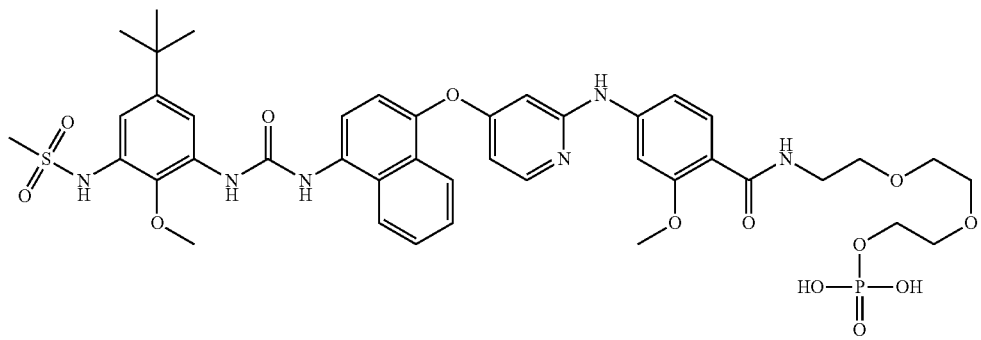 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCOCCOCCOP(=O)(O)O]

(i) Benzyl (2-(2-(2-((di-tert-butoxyphosphoryl)oxy)ethoxy)ethoxy)ethyl)carbamate Di-tert-butyl diethylphosphoramidite (1.6 mL, 5.75 mmol) was added to a solution of benzyl (2-(2-(2-hydroxyethoxy)ethoxy)ethyl)carbamate (1.1 g, 3.88 mmol) and 5-methyl-1H-tetrazole (700 mg, 8.33 mmol) in THF (10 mL) and the mixture stirred at rt for 3 hours. The reaction mixture was cooled to 0° C. and $H_2O_2$ (1.6 mL, 15.66 mmol) was added. After 10 min, the cooling bath was removed and the mixture was stirred for a further 3 hours. $Na_2SO_3$ (20 mL of a 10% w/w solution in water) was added and the reaction mixture stirred for 30 min. The resulting mixture was partitioned between ethyl acetate (25 mL) and water (20 mL). The organics were separated, dried over $MgSO_4$, filtered and concentrated in vacuo. The crude product was purified by chromatography on the Companion (40 g column, 0-100% ethyl acetate in iso-hexane) to afford the sub-title compound (1.2 g) as a clear colourless oil.

$^1$H NMR (400 MHz, $CDCl_3$) δ 7.45-7.29 (m, 5H), 5.37 (s, 1H), 5.12 (s, 2H), 4.12-4.03 (m, 2H), 3.71 (ddd, 2H), 3.68-3.60 (m, 4H), 3.58 (t, 2H), 3.41 (q, 2H), 1.49 (s, 18H).

(ii) 2-(2-(2-Aminoethoxy)ethoxy)ethyl di-tert-butyl phosphate

5% Pd—C, J&M type 39, 50% w/w paste with water (0.3 g) was added to a solution of the product from step (i) above (1.2 g, 2.52 mmol) in EtOH (10 mL) and the mixture stirred under hydrogen (5 bar) for 3 h. The reaction mixture was filtered (Whatmans GF/F) and the filtrate evaporated to afford the sub-title compound (0.8 g) as a colourless oil.

1H NMR (400 MHz, $CDCl_3$) δ 4.22-3.98 (m, 2H), 3.79-3.60 (m, 6H), 3.60-3.42 (m, 2H), 2.92 (t, 2H), 1.50 (s, 18H).
LCMS m/z 342 (M+H)$^+$ (ES$^+$); no chromophore (iii) Di-tert-butyl (2-(2-(2-(4-((4-((4-(3-(5-(tert-butyl)-2-methoxy-3-(methylsulfonamido)phenyl)-ureido)naphthalen-1-yl)oxy)pyridin-2-yl)amino)-2-methoxybenzamido)ethoxy)ethoxy)ethyl)-phosphate HATU (450 mg, 1.183 mmol) was added to a solution of 4-((4-((4-(3-(5-(tert-butyl)-2-methoxy-3-(methylsulfonamido)phenyl)ureido)naphthalen-1-yl)oxy)pyridin-2-yl)amino)-2-methoxybenzoic acid, hydrochloride salt (see Example 1 above; 600 mg, 0.815 mmol), the product from step (ii) above (380 mg, 1.113 mmol) and Hünig's base (500 µL, 2.86 mmol) in DMF (7 mL). The reaction mixture was stirred at rt for 16 h. The mixture was poured into water (100 mL) and partitioned repeatedly with 10% MeOH:DCM (6×100 mL). The organics were separated, bulked, dried (MgSO$_4$), filtered and evaporated to a brown gum. The crude product was purified by chromatography on silica gel (40 g column, 2% MeOH:DCM to 10%) to afford the sub-title compound (510 mg) as a colourless foam.

¹H NMR (400 MHz, DMSO-d6) δ 9.39 (s, 1H), 9.27 (s, 1H), 9.14 (s, 1H), 8.92 (s, 1H), 8.30 (d, 1H), 8.24-8.04 (m, 4H), 7.87 (d, 1H), 7.77 (d, 1H), 7.71 (t, 1H), 7.66-7.56 (m, 2H), 7.41 (d, 1H), 7.22 (d, 1H), 7.03 (s, 1H), 6.66 (dd, 1H), 6.16 (s, 1H), 3.99-3.89 (m, 2H), 3.86 (s, 3H), 3.82 (s, 3H), 3.67-3.47 (m, 8H), 3.47-3.38 (m, 2H), 3.10 (s, 3H), 1.39 (s, 18H), 1.27 (s, 9H).
LCMS m/z 967 (M+H-tBu)⁺ (ES⁺)

(iv) 2-(2-(2-(4-((4-((4-(3-(5-(tert-Butyl)-2-methoxy-3-(methylsulfonamido)phenyl)ureido)-naphthalen-1-yl)oxy)pyridin-2-yl)amino)-2-methoxybenzamido)ethoxy)ethoxy)ethyl dihydrogen phosphate TFA (1 mL, 12.98 mmol) was added to a solution of the product from step (iii) above (510 mg, 0.439 mmol) in DCM (3 mL) and the reaction left stirring for 16 h. The solvents were evaporated and the residue azeotroped with toluene. The crude product was loaded onto a column of SCX (10 g) in MeOH. The column was washed with MeOH and then the product was eluted with 0.7 M ammonia in MeOH. Product-rich fractions were concentrated in vacuo to afford the product as the ammonium salt (380 mg). [¹H NMR (400 MHz, DMSO-d₆) δ 9.66 (s, 1H), 9.45 (s, 1H), 9.09 (s, 1H), 8.37 (d, 1H), 8.24-8.03 (m, 4H), 7.85 (d, 1H), 7.75 (d, 1H), 7.72-7.64 (m, 1H), 7.63-7.56 (m, 1H), 7.48-7.34 (m, 2H), 7.26 (dd, 1H), 7.02 (d, 1H), 6.64 (dd, 1H), 6.20 (d, 1H), 3.82 (s, 3H), 3.80-3.69 (m, 4H), 3.53 (s, 3H), 3.52-3.46 (m, 6H), 3.46-3.38 (m, 2H), 3.09 (s, 3H), 1.26 (s, 9H); LCMS m/z 911 (M+H)⁺ (ES⁺)]. The ammonium salt (260 mg) was loaded onto a column of Dowex 50WX2 N⁺ form (20 g) in water (200 µL). The column was washed with water (100 mL) to elute the sodium salt. The product-rich fractions were freeze-dried to afford the sodium salt of the title compound (245 mg) as a colourless solid.
¹H NMR (of sodium salt; 400 MHz, DMSO-d6) δ 9.76 (s, 1H), 9.49 (s, 1H), 9.14 (s, 1H), 8.40 (d, 1H), 8.27-8.01 (m, 4H), 7.85 (d, 1H), 7.75 (d, 1H), 7.71-7.63 (m, 1H), 7.63-7.53 (m, 1H), 7.48-7.33 (m, 2H), 7.28 (d, 1H), 7.03 (d, 1H), 6.63 (dd, 1H), 6.22 (d, 1H), 3.82 (s, 3H), 3.81-3.73 (m, 5H), 3.57-3.46 (m, 8H), 3.46-3.37 (m, 2H), 3.09 (s, 3H), 1.27 (s, 9H).
LCMS (of sodium salt) m/z 911 (M+H)⁺ (ES⁺)

Example 20

N-(5-(tert-Butyl)-2-methoxy-3-(3-(4-((2-((3-methoxy-4-((3-morpholinopropyl)sulfonyl)phenyl)-amino)pyridin-4-yl)oxy)naphthalen-1-yl)ureido)phenyl)methanesulfonamide (i) 3-((2-Methoxy-4-nitrophenyl)thio)propan-1-ol 3-Bromopropan-1-ol (352 µL, 3.89 mmol) was added to a solution of 2-methoxy-4-nitrobenzenethiol (600 mg, 3.24 mmol) and K₂CO₃ (493 mg, 3.56 mmol) in acetone (5 mL). The reaction mixture was stirred at rt for 17 hours, concentrated in vacuo, diluted with EtOAc (10 mL) and washed with 5 wt % aq NaOH (10 mL). The organic layer was dried over MgSO₄, filtered and concentrated in vacuo to afford a yellow oil. The crude product was purified by chromatography on the Companion (40 g column, 0-100% ethyl acetate in iso-hexane) to afford the sub-title compound (489 mg) as a sticky yellow-brown oil.
LCMS m/z 244 (M+H)⁺ (ES⁺)

(ii) 3-((2-Methoxy-4-nitrophenyl)sulfonyl)propan-1-ol

To a solution of the product from step (i) above (489 mg, 2.010 mmol) in AcOH (2 mL) and H₂O (2 mL) in an ice bath was added H₂O₂ solution (30 wt. % in H2O, 616 µL, 6.03 mmol) dropwise. The mixture was then refluxed for 20 min and cooled. Another aliquot of H₂O₂ solution (30 wt. % in H₂O, 616 µL, 6.03 mmol) was added dropwise in an ice bath. The mixture was then refluxed for 20 min and cooled. NaHCO₃ was added to neutralise the solution, followed by ethyl acetate. The organic layer was separated, washed with brine, dried over MgSO₄, filtered and concentrated in vacuo to afford a yellow solid. The crude product was purified by chromatography on the Companion (12 g column, 0-100% ethyl acetate in iso-hexane) to afford the sub-title compound (259 mg) as a yellow solid.
LCMS m/z 276 (M+H)⁺ (ES⁺)

(iii) 3-((2-Methoxy-4-nitrophenyl)sulfonyl)propyl methanesulfonate

The product from step (ii) above (259 mg, 0.941 mmol) was dissolved in pyridine (1 mL) and treated with methanesulfonyl chloride (95 µL, 1.223 mmol) and DMAP (3.45 mg, 0.028 mmol). The reaction mixture was stirred at rt for 1 hour, concentrated to afford an oil that was partitioned between DCM (2 mL) and HCl (1 M, 2 mL). The phases were separated via a hydrophobic phase separator, the organic layer was concentrated to afford the sub-title compound (300 mg) as an oil. The product was used without further purification.

(iv) 4-(3-((2-Methoxy-4-nitrophenyl)sulfonyl)propyl)morpholine

To a solution of the crude product from step (iii) above (300 mg) in DMF (5 mL) was added morpholine (148 µL, 1.698 mmol) and K₂CO₃ (106 mg, 0.764 mmol). The reac-

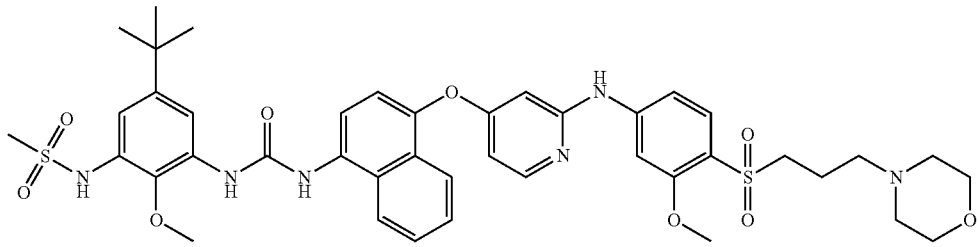 [SMILES: COc1cc(Nc2cc(Oc3ccc(NC(=O)Nc4cc(C(C)(C)C)cc(NS(C)(=O)=O)c4OC)c4ccccc34)ccn2)ccc1S(=O)(=O)CCCN1CCOCC1]

tion mixture was stirred at 100° C. for 2 hours then over the weekend at rt. Another aliquot of morpholine (148 μL, 1.698 mmol) was added. The reaction mixture was stirred at 100° C. for 1 hour, then another aliquot of K₂CO₃ (106 mg, 0.764 mmol) was added. The reaction mixture was stirred at 1000° C. for 1 hour then concentrated in vacuo. The crude product was purified by chromatography on the Companion (12 g column, 0-10% MeOH in DCM) to afford a thick yellow oil. The product was diluted in ethyl acetate (5 mL), washed with water (5 mL) then brine (5 mL), dried via a phase separator and concentrated in vacuo to afford the sub-title compound (61 mg) as a thick yellow film.

¹H NMR (400 MHz, DMSO-d6) δ 8.17 (d, 1H), 7.96 (dd, 1H), 7.89 (d, 1H), 4.13 (s, 3H), 3.71-3.69 (m, 4H), 3.53-3.49 (m, 2H), 2.46-2.41 (m, 6H), 1.96-1.88 (m, 2H).

LCMS m/z 345 (M+H)⁺ (ES⁺)

(v)
3-Methoxy-4-((3-morpholinopropyl)sulfonyl)aniline

A suspension of the product from step (iv) above (60 mg, 0.174 mmol) and 5% Pd/C (50% paste with water, 20 mg) in ethanol (2 mL) was stirred under hydrogen (5 bar) for 2 h at rt. The reaction mixture was filtered through Celite, concentrated in vacuo. The residue was suspended in ethanol (2 mL) and fresh 5% Pd/C (50% paste with water, 20 mg) was added. The reaction mixture was stirred under hydrogen (5 bar) for another hour at rt. The reaction mixture was filtered through Celite, concentrated in vacuo to afford the sub-title compound (44 mg) as a yellow oil.

LCMS m/z 315 (M+H)⁺ (ES⁺); 313 (M−H)⁻ (ES⁻)

(vi) N-(5-(tert-Butyl)-2-methoxy-3-(3-(4-((2-((3-methoxy-4-((3-morpholinopropyl)sulfonyl) phenyl) amino)pyridin-4-yl)oxy)naphthalen-1-yl)ureido) phenyl)methanesulfonamide A mixture of the product from step (v) above (44 mg, 0.133 mmol), N-(5-(tert-butyl)-3-(3-(4-((2-chloropyridin-4-yl)oxy)naphthalen-1-yl)ureido)-2-methoxyphenyl)methanesulfonamide (see Example 8(i) above; 76 mg, 0.133 mmol), K₂CO₃ (37 mg, 0.268 mmol), and Brett Phos G3 catalyst (3 mg, 3.31 μmol) were degassed under vacuum back-filling with nitrogen 3 times. tBuOH (2 mL) was added and the suspension degassed under vacuum back-filling with nitrogen 3 times. The reaction was then heated under nitrogen at 85° C. (block temperature) for 24 h. The reaction was cooled and diluted with DCM. The solution was filtered through Celite, washed with DCM and concentrated in vacuo. The crude product was purified by chromatography on the Companion (4 g column, 1-8% MeOH in DCM) to afford a pale orange oil which was purified by preparative HPLC (Varian, Basic (0.1% Ammonium Bicarbonate), Basic, Waters X-Bridge Prep-C18, 5 μm, 19×50 mm column, 35-65% MeCN in Water) to afford the title compound (23 mg) as a colourless solid.

¹H NMR (400 MHz, DMSO-d6) δ 9.48 (s, 1H), 9.39 (s, 1H), 9.14 (s, 1H), 8.90 (s, 1H), 8.30 (d, 1H), 8.19 (d, 1H), 8.16 (d, 1H), 8.12 (d, 1H), 7.85 (d, 1H), 7.71 (dd, 1H), 7.65 (d, 1H), 7.61 (dd, 1H), 7.56 (d, 1H), 7.40 (d, 1H), 7.31 (dd, 1H), 7.02 (d, 1H), 6.70 (dd, 1H), 6.18 (d, 1H), 3.84 (s, 3H), 3.80 (s, 3H), 3.50 (t, 4H), 3.07 (s, 3H), 2.25 (t, 2H), 2.20-2.18 (m, 4H), 1.61 (quint, 2H), 1.26 (s, 9H). (2H under the water signal)

LCMS m/z 847 (M+H)⁺ (ES⁺); 424 (M+2H)²⁺ (ES⁺)

Example 21

4-((4-((4-(3-(5-(tert-Butyl)-2-methoxy-3-(methylsulfonamido)phenyl)ureido)naphthalen-1-yloxy)pyridin-2-yl)amino)-2-(dimethylamino)-N-(2-morpholinoethyl)benzamide

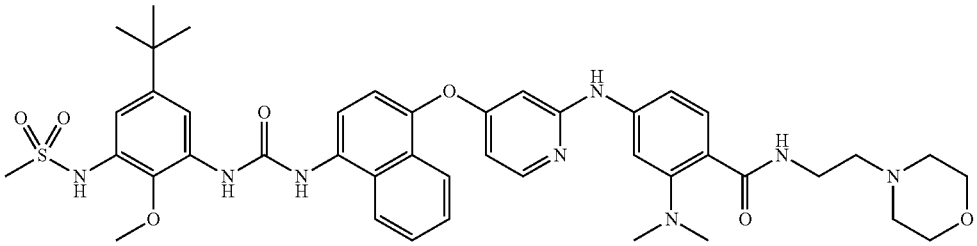 [SMILES: COc1c(NC(=O)Nc2ccc(Oc3ccnc(Nc4ccc(C(=O)NCCN5CCOCC5)c(N(C)C)c4)c3)c3ccccc23)cc(C(C)(C)C)cc1NS(C)(=O)=O]

(i) 2-(Dimethylamino)-N-(2-morpholinoethyl)-4-nitrobenzamide

HATU (662 mg, 1.741 mmol) was added to a stirred solution of 2-(dimethylamino)-4-nitrobenzoic acid (244 mg, 1.161 mmol), 2-morpholinoethanamine (181 mg, 1.393 mmol) and Hünig's base (912 μL, 5.22 mmol) in DMF (5 mL) at rt. The mixture was stirred overnight. The reaction was diluted with water (25 mL) and the aqueous phase extracted with EtOAc (2×10 mL). The combined organic phase was washed with water (2×5 mL) and reduced to around half its initial volume in vacuo. The resulting solution was loaded onto a pre-conditioned cartridge of SCX resin. The resin was washed with MeOH then the product release in 1% NH₃ in MeOH. The ammonia solution was concentrated in vacuo affording the sub-title compound (292 mg) as a dark orange oil.

¹H NMR (400 MHz, DMSO-d6) δ: 8.71 (t, 1H), 7.69-7.71 (m, 2H), 7.59-7.61 (m, 1H), 3.57-3.59 (m, 4H), 3.39 (q, 2H), 3.34 (s, 6H), 2.47 (t, 2H), 2.41 (bs, 4H).

(ii) 4-Amino-2-(dimethylamino)-N-(2-morpholinoethyl)benzamide

5% Pd/C (50% paste with water, 200 mg) was added to a degassed solution of the product from step (i) above (292 mg, 0.906 mmol) in MeOH (10 mL). The reaction was degassed with H₂ and stirred under a H₂ atmosphere for 2 h. The reaction mixture was degassed with N₂ then filtered through celite and the filtrate concentrated in vacuo affording the sub-title compound (250 mg) as a colourless oil which solidified on standing.

LCMS m/z 293 (M+H)⁺ (ES⁺)

(iii) 4-((4-((4-(3-(5-(tert-Butyl)-2-methoxy-3-(methylsulfonamido)phenyl)ureido)naphthalen-1-yl)oxy)pyridin-2-yl)amino)-2-(dimethylamino)-N-(2-morpholinoethyl)benzamide A suspension of the product from step (ii) above (100 mg, 0.342 mmol), N-(5-(tert-butyl)-3-(3-(4-((2-chloropyridin-4-yl)oxy)naphthalen-1-yl)ureido)-2-methoxyphenyl)methanesulfonamide (see Example 8(i) above; 195 mg, 0.342 mmol), $K_2CO_3$ (120 mg, 0.868 mmol), and BrettPhos G1 precatalyst (10 mg, 0.013 mmol) in DMF (4 mL) was degassed with nitrogen for 10 mins. The reaction was then heated under nitrogen at 85° C. (block temperature) for 2 h. The reaction was cooled and partitioned between EtOAc (20 mL) and water (20 mL). The organic phase was dried ($MgSO_4$), filtered and concentrated in vacuo affording a dark yellow oil. The crude product was purified by preparative HPLC (Waters, Basic (0.1% Ammonium Bicarbonate), Basic, Waters X-Bridge Prep-C18, 5 μm, 19×50 mm column, 35-65% MeCN in Water) to afford a beige solid. The crude product was re-purified by preparative HPLC (Waters, Acidic (0.1% Formic acid), Acidic, Waters X-Select Prep-C18, 5 μm, 19×50 mm column, 20-50% MeCN in Water) to afford a white solid. The solid was partitioned between 10% MeOH in DCM and sat. aq. $NaHCO_3$ solution. The organic phase was dried via hydrophobic frit and concentrated in vacuo then re-concentrated from MeCN to afford the title compound (103 mg) as a white solid.

$^1$H NMR (400 MHz, DMSO-d6) δ: 9.48 (t, 1H), 9.39 (s, 1H), 9.14-9.16 (m, 2H), 8.91 (s, 1H), 8.30 (d, 1H), 8.19 (d, 1H), 8.11-8.16 (m, 2H), 7.87 (d, 1H), 7.68-7.73 (m, 2H), 7.60-7.63 (m, 1H), 7.48 (d, 1H), 7.39-7.42 (m, 2H), 7.03 (d, 1H), 6.64 (dd, 1H), 6.14 (d, 1H), 3.81 (s, 3H), 3.58-3.60 (m, 4H), 3.39 (q, 2H), 310 (s, 3H), 2.63 (s, 6H), 2.46 (t, 2H), 2.41 (bs, 4H), 1.27 (s, 9H).

LCMS m/z 825 (M+H)$^+$ (ES$^+$); 413 (M+2H)$^{2+}$ (ES$^+$)

Example 22

4-((4-((4-(3-(5-(tert-Butyl)-2-methoxy-3-(methylsulfonamido)phenyl)ureido)naphthalen-1-yl)oxy)pyridin-2-yl)amino)-2,6-dimethoxy-N-(2-(4-methylpiperazin-1-yl)ethyl)benzamide

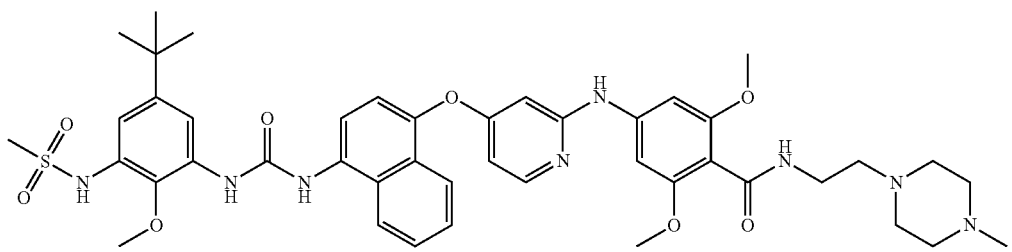

(i) Sodium 4-amino-2,6-dimethoxybenzoate

NaOH solution 50% w/w (4 mL, 76 mmol) was added to a solution of methyl 4-amino-2,6-dimethoxybenzoate (2 g, 9.47 mmol) in MeOH (40 mL). The reaction was heated at 60° C. (block temperature) for 16 h. The reaction mixture was cooled in an ice bath filtered and washed with ice cold methanol (1 mL) then dried to constant weight to afford the sub-title compound (1.75 g) as a tan crystalline solid.

LCMS m/z 198 (M+H)$^+$ (ES$^+$)

(ii) 4-((tert-Butoxycarbonyl)amino)-2,6-dimethoxybenzoic acid

TEA (900 μL, 6.46 mmol) was added to a solution of the product from step (i) above (0.68 g, 3.09 mmol) in 1,4-dioxane (7 mL) and water (3 mL). The mixture was stirred for 5 minutes then di-tert-butyl dicarbonate (1.4 g, 6.41 mmol) was added in one portion and the reaction mixture left stirring for 16 h. The organics were evaporated and the aqueous residue acidified to pH 1 with 1N HCl. The resulting solid was filtered off, washed with water (5 mL), isohexane (5 mL) and dried to constant weight to afford the sub-title compound (550 mg) as a tan solid.

$^1$H NMR (400 MHz, CDCl$_3$) δ 6.74 (s, 2H), 6.66 (s, 1H), 3.91 (s, 6H), 1.53 (s, 9H).

(iii) tert-Butyl (3,5-dimethoxy-4-((2-(4-methylpiperazin-1-yl)ethyl)carbamoyl)phenyl) carbamate HATU (700 mg, 1.841 mmol) was added to a solution of the product from step (ii) above (400 mg, 1.345 mmol), 2-(4-methylpiperazin-1-yl)ethanamine (300 mg, 2.095 mmol) and Hünig's base (700 μL, 4.01 mmol) in DCM (5 mL). The reaction mixture was stirred at rt for 16 h. The mixture was partitioned between DCM (15 mL) and water (15 mL). The organics were separated, dried (MgSO$_4$) filtered and evaporated to give a yellow gum which was pre-absorbed onto silica (4 g) and purified by chromatography on silica gel (12 g column, 2% MeOH:DCM to 10%) to afford the sub-title compound (410 mg) as a pale yellow glass.

$^1$H NMR (400 MHz, DMSO-d6) δ 9.37 (s, 1H), 7.72 (t, 1H), 6.83 (s, 2H), 3.66 (s, 6H), 3.28-3.15 (m, 2H), 2.48-2.25 (m, 10H), 2.17 (s, 3H), 1.48 (s, 9H).

LCMS m/z 423 (M+H)$^+$ (ES$^+$)

(iv) 4-Amino-2,6-dimethoxy-N-(2-(4-methylpiperazin-1-yl)ethyl)benzamide

TFA (2 mL, 26.0 mmol) was added to a solution of the product from step (iii) above (400 mg, 0.947 mmol) in DCM (10 mL) and the reaction stirred overnight. The solvents were evaporated and the residue was loaded onto a column of SCX (10 g) in MeOH. The column was washed with MeOH and then the product was eluted with 0.7 M ammonia in MeOH. The filtrate was concentrated in vacuo to afford the sub-title compound (295 mg) as a pale yellow crystalline solid.

LCMS m/z 323 (M+H)$^+$ (ES$^+$)

(v) 4-((4-((4-(3-(5-(tert-Butyl)-2-methoxy-3-(methylsulfonamido)phenyl)ureido)naphthalen-1-yl)oxy)pyridin-2-yl)amino)-2,6-dimethoxy-N-(2-(4-methylpiperazin-1-yl)ethyl)benzamide A mixture of N-(5-(tert-butyl)-3-(3-(4-((2-chloropyridin-4-yl)oxy)naphthalen-1-yl)ureido)-2-methoxyphenyl)methanesulfonamide (see Example 8(i) above; 150 mg, 0.264 mmol), the product from step (iv) above (120 mg, 0.372 mmol), K₂CO₃ (100 mg, 0.724 mmol), and BrettPhos G1 Precatalyst (5 mg, 5.64 μmol) were degassed under vacuum back-filling with nitrogen 3 times. DMF (2 mL) was added and the stirred suspension was degassed under vacuum back-filling with nitrogen 3 times. The reaction was then heated under nitrogen at 85° C. (block temperature) for 1 h. The mixture was cooled to rt and partitioned between water (25 mL) and 10% MeOH:DCM (2×20 mL). The organics were bulked and washed with 20% w/w NaCl solution, separated, dried (MgSO₄), filtered and the solvent evaporated to a dark oil. The crude product was purified by preparative HPLC (Varian, Basic (0.1% Ammonium Bicarbonate), Basic, Waters X-Bridge Prep-C18, 5 μm, 19×50 mm column, 20-50% MeCN in Water) to afford the title compound (115 mg) as a colourless solid.

¹H NMR (400 MHz, DMSO-d6) δ 9.39 (s, 1H), 9.14 (s, br, 1H), 9.02 (s, 1H), 8.91 (s, 1H), 8.30 (d, 1H), 8.18 (d, 1H), 8.15-8.05 (m, 2H), 7.87 (dt, 1H), 7.78-7.54 (m, 3H), 7.39 (d, 1H), 7.03 (d, 1H), 6.93 (s, 2H), 6.61 (dd, 1H), 6.11 (d, 1H), 3.81 (s, 3H), 3.61 (s, 6H), 3.21 (q, 2H), 3.10 (s, 3H), 2.48-2.17 (m, 10H), 2.14 (s, 3H), 1.27 (s, 9H).

LCMS m/z 855 (M+H)⁺ (ES⁺)

Example 23

4-((4-((4-(3-(5-(tert-Butyl)-2-methoxy-3-(methylsulfonamido)phenyl)ureido)naphthalen-1-yl)oxy)pyridin-2-yl)amino)-2,6-dimethoxy-N-(3-morpholinopropyl)benzamide ¹H NMR (400 MHz, DMSO-d6) δ 9.39 (s, 1H), 7.68-7.49 (m, 1H), 6.85 (s, 2H), 3.67 (s, 6H), 3.63-3.46 (m, br, 2H), 3.26-3.09 (m, br, 4H), 2.90 (s, 4H), 2.47-2.18 (m, br, 2H), 1.87-1.59 (m, br, 2H), 1.48 (s, 9H).

LCMS m/z 424 (M+H)⁺ (ES⁺)

(ii) 4-Amino-2,6-dimethoxy-N-(3-morpholinopropyl)benzamide

TFA (1 mL, 12.98 mmol) was added to a solution of the product from step (i) above (295 mg, 0.697 mmol) in DCM (5 mL) and the reaction stirred overnight. The solvents were evaporated and the residue was loaded onto a column of SCX (5 g) in MeOH. The column was washed with MeOH and then the product was eluted with 0.7 M ammonia in MeOH. The resultant mixture was concentrated in vacuo to afford the sub-title compound (190 mg) as a pale yellow solid.

LCMS m/z 324 (M+H)⁺ (ES⁺)

(iii) 4-((4-((4-(3-(5-(tert-Butyl)-2-methoxy-3-(methylsulfonamido)phenyl)ureido)naphthalen-1-yl)oxy)pyridin-2-yl)amino)-2,6-dimethoxy-N-(3-morpholinopropyl)benzamide A mixture of N-(5-(tert-butyl)-3-(3-(4-((2-chloropyridin-4-yl)oxy)naphthalen-1-yl)ureido)-2-methoxyphenyl)methanesulfonamide (see Example 8(i) above; 140 mg, 0.246 mmol), the product from step (ii) above (100 mg, 0.309 mmol), K₂CO₃ (150 mg, 1.085 mmol), and BrettPhos G1 Precatalyst (5 mg, 5.64 μmol) were degassed under vacuum back-filling with nitrogen 3 times. DMF (2 mL) was added and the stirred suspension was degassed under vacuum back-filling with nitrogen 3 times. The reaction was then heated under nitrogen at 85° C. (block temperature) for 1 h. The mixture was cooled to rt and partitioned between water (25 mL) and 10% MeOH:DCM (2×50 mL). The organics were bulked and washed with 20% w/w NaCl solution, separated, dried (MgSO₄), filtered and the solvent evaporated to a dark oil. The crude product was purified by preparative HPLC (Varian, Basic (0.1% Ammonium Bicarbonate), Basic, Waters X-Bridge Prep-C18, 5 μm, 19×50 mm column, 20-50% MeCN in Water) to afford the title compound (90 mg) as a colourless solid.

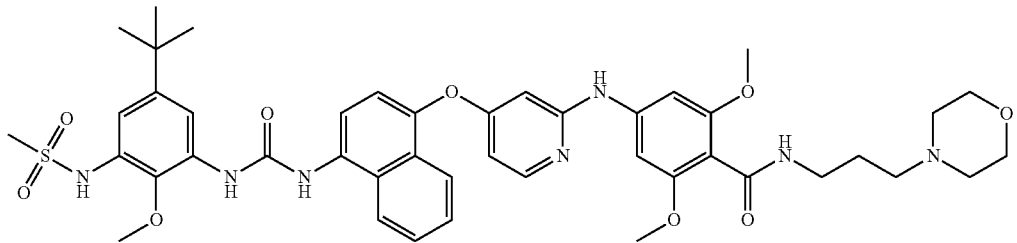 [SMILES: COc1cc(Nc2cc(Oc3ccc(NC(=O)Nc4cc(C(C)(C)C)cc(NS(C)(=O)=O)c4OC)c4ccccc34)ccn2)cc(OC)c1C(=O)NCCCN1CCOCC1]

(i) tert-Butyl (3,5-dimethoxy-4-((3-morpholinopropyl)carbamoyl)phenyl)carbamate

HATU (350 mg, 0.920 mmol) was added to a solution of 4-((tert-butoxycarbonyl)amino)-2,6-dimethoxybenzoic acid (see Example 22(ii) above; 200 mg, 0.673 mmol), 3-morpholinopropan-1-amine (152 μL, 1.040 mmol) and Hünig's base (350 μL, 2.004 mmol) in DCM (2 mL). The reaction mixture was stirred at rt for 16 h. The mixture was partitioned between DCM (15 mL) and water (15 mL). The organics were separated, dried (MgSO₄), filtered and evaporated to give a yellow gum which was purified by chromatography on silica gel (12 g column, 2% MeOH:DCM to 10%) to afford the sub-title compound (275 mg) as a pale yellow glass.

¹H NMR (400 MHz, DMSO-d6) δ 9.39 (s, 1H), 9.13 (s, 1H), 9.01 (s, 1H), 8.91 (s, 1H), 8.30 (d, 1H), 8.18 (d, 1H), 8.13 (d, 1H), 8.12 (d, 1H), 7.87 (d, 1H), 7.82 (t, 1H), 7.75-7.68 (m, 1H), 7.65-7.58 (m, 1H), 7.39 (d, 1H), 7.03 (d, 1H), 6.93 (s, 2H), 6.61 (dd, 1H), 6.11 (d, 1H), 3.81 (s, 3H), 3.61 (s, 6H), 3.54 (t, 4H), 3.14 (q, 2H), 3.10 (s, 3H), 2.46-2.21 (m, 6H), 1.58 (p, 2H), 1.27 (s, 9H).

LCMS m/z 856 (M+H)⁺ (ES⁺)

Example 24

N-(5-(tert-Butyl)-2-methoxy-3-(3-(4-((2-((3-methoxy-4-(2H-tetrazol-5-yl)phenyl)amino)pyridin-4-yl)oxy)naphthalen-1-yl)ureido)phenyl)methanesulfonamide

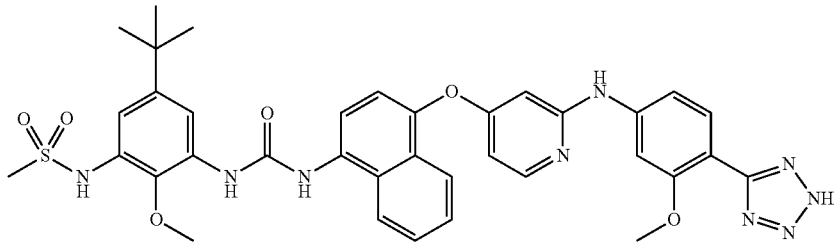 [SMILES: COc1cc(Nc2cc(Oc3ccc(NC(=O)Nc4cc(C(C)(C)C)cc(NS(C)(=O)=O)c4OC)c4ccccc34)ccn2)ccc1-c1nn[nH]n1]

(i) tert-Butyl (4-((2-((4-cyano-3-methoxyphenyl)amino)pyridin-4-yl)oxy)naphthalen-1-yl)carbamate tert-Butyl (4-((2-chloropyridin-4-yl)oxy)naphthalen-1-yl)carbamate (see Example 1(i) above; 2.5 g, 6.74 mmol), 4-amino-2-methoxybenzonitrile (1 g, 6.75 mmol), BrettPhos G1 precatalyst (100 mg, 0.125 mmol), NaOtBu (1.3 g, 13.53 mmol) were degassed for 3 min. The tBuOH (20 mL) was added, and the mixture was degassed for 3 min. The reaction mixture was stirred at 75° C. for 2 h and evaporated under reduced pressure. The residue was purified by chromatography on silica gel (80 g column, 0-5% MeOH/DCM) then purified further by chromatography on silica gel (80 g column, 0-50% EtOAc/isohexane) to afford the sub-title compound (1.087 g) as a foam $^1$H NMR (400 MHz, DMSO-d6) δ 9.53 (s, 1H), 9.41 (s, 1H), 8.20 (d, 1H), 8.14 (d, 1H), 7.82 (d, 1H), 7.65-7.55 (m, 4H), 7.49 (d, 1H), 7.38 (d, 1H), 7.26 (dd, 1H), 6.73 (dd, 1H), 6.14 (d, 1H), 3.82 (s, 3H), 1.53 (s, 9H).

LCMS m/z 483 (M+H)$^+$ (ES$^+$); 481 (M−H)$^−$ (ES$^−$)

(ii) tert-Butyl (4-((2-((3-methoxy-4-(2H-tetrazol-5-yl)phenyl)amino)pyridin-4-yl)oxy)-naphthalen-1-yl)carbamate A mixture of the product from step (i) above (500 mg, 1.036 mmol) and azidotributylstannane (1.2 g, 3.61 mmol) in glyme (10 mL) were heated under reflux for 5 days (solvent evaporated off over the weekend). The residue was purified by chromatography on silica gel (80 g column, 0-100% EtOAc/isohexane) to afford the sub-title compound (344 mg) as a white solid.

$^1$H NMR (400 MHz, DMSO-d6) δ 15.59 (brs, 1H), 9.40 (s, 1H), 9.39 (s, 1H), 8.20 (d, 1H), 8.15 (d, 1H), 7.94 (d, 1H), 7.84 (d, 1H), 7.73 (d, 1H), 7.66-7.56 (m, 3H), 7.38 (d, 1H), 7.32 (dd, 1H), 6.68 (dd, 1H), 6.15 (d, 1H), 3.90 (s, 3H), 1.53 (s, 9H).

LCMS m/z 526 (M+H)+ (ES+); 524 (M−H)− (ES−)

(iii) 4-((4-Aminonaphthalen-1-yl)oxy)-N-(3-methoxy-4-(2H-tetrazol-5-yl)phenyl)pyridin-2-amine TFA (1 mL, 12.98 mmol) was added to a solution of the product from step (ii) above (339 mg, 0.645 mmol) in DCM (5 mL) and stirred at rt for 5 h. The mixture was evaporated under reduced pressure and the crude product was loaded onto a column of SCX in MeOH. The column was washed with MeOH and then the product was eluted with 0.7 M ammonia in MeOH. The resultant mixture was concentrated in vacuo and the residue purified by chromatography on silica gel (40 g column, 0-100% EtOAc/isohexane) to afford the sub-title compound (196 mg) as brown solid.

$^1$H NMR (400 MHz, DMSO-d6) δ 15.58 (brs, 1H), 9.30 (s, 1H), 8.19-8.16 (m, 1H), 8.14 (d, 1H), 7.93 (d, 1H), 7.70 (d, 1H), 7.66-7.62 (m, 1H), 7.48-7.44 (m, 2H), 7.31 (dd, 1H), 7.12 (d, 1H), 6.73 (d, 1H), 6.62 (dd, 1H), 6.12 (d, 1H), 5.84 (s, 2H), 3.89 (s, 3H).

LCMS m/z 426 (M+H)$^+$ (ES$^+$); 424 (M−H)$^−$ (ES$^−$)

(iv) N-(5-(tert-Butyl)-2-methoxy-3-(3-(4-((2-((3-methoxy-4-(2H-tetrazol-5-yl)phenyl)amino) pyridin-4-yl)oxy)naphthalen-1-yl)ureido)phenyl)methanesulfonamide A mixture of phenyl (5-(tert-butyl)-2-methoxy-3-(methylsulfonamido)phenyl)carbamate (see Example 1(iv) above; 210 mg, 0.536 mmol), the product from step (iii) above (190 mg, 0.447 mmol) and Et$_3$N (81 μL, 0.581 mmol) in THF (3 mL) was heated at 60° C. for 24 h. The mixture was evaporated under reduced pressure and the residue triturated with MeOH. The solid was filtered off (symmetrical urea) and the filtrate loaded onto a column of SCX. The column was washed with MeOH and then the product was eluted with 0.7 M ammonia in MeOH. The resultant mixture was concentrated in vacuo and the residue purified by chromatography on silica gel (40 g column, 0-10% MeOH/DCM) then purified by preparative HPLC (Varian, Basic (0.1% Ammonium Bicarbonate), Basic, Waters X-Bridge Prep-C18, 5 m, 19×50 mm column, 20-50% MeCN in Water) to afford the title compound (104 mg) as a white solid.

$^1$H NMR (400 MHz, DMSO-d6) δ 15.59 (s, 1H), 9.40 (s, 1H), 9.37 (s, 1H), 9.14 (s, 1H), 8.92 (s, 1H), 8.31 (d, 1H), 8.20-8.19 (m, 2H), 8.13 (d, 1H), 7.88 (d, 1H), 7.74-7.70 (m, 2H), 7.64-7.60 (m, 1H), 7.41 (d, 1H), 7.33 (dd, 1H), 7.03 (d, 1H), 6.68 (dd, 1H), 6.18 (d, 1H), 3.90 (s, 3H), 3.82 (s, 3H), 3.10 (s, 3H), 1.27 (s, 9H).

LCMS m/z 724 (M+H)$^+$ (ES$^+$); 722 (M−H)$^−$ (ES$^−$)

Example 25

4-((4-((4-(3-(5-(tert-Butyl)-2-methoxy-3-(methylsulfonamido)phenyl)ureido)naphthalen-1-yl)oxy)pyridin-2-yl)amino)-2-methoxy-N-methyl-N-(3-(4-methylpiperazin-1-yl)propyl)benzenesulfonamide

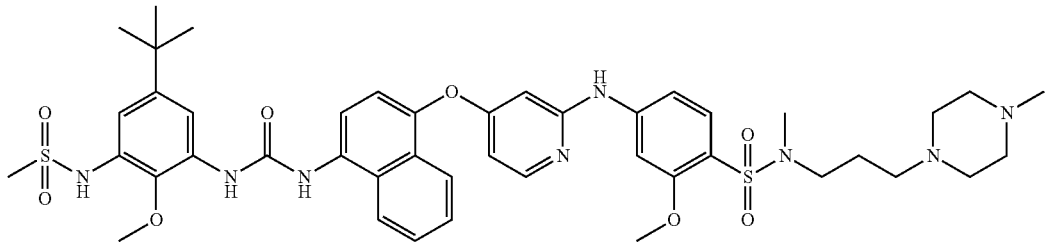

(i) 2-Methoxy-N-methyl-N-(3-(4-methylpiperazin-1-yl)propyl)-4-nitrobenzenesulfonamide 2-Methoxy-4-nitrobenzene-1-sulfonyl chloride (250 mg, 0.993 mmol) in MeCN (3 mL) was added dropwise to an ice-cold solution of N-methyl-3-(4-methylpiperazin-1-yl)propan-1-amine (170 mg, 0.993 mmol) and Et₃N (415 µL, 2.98 mmol) in MeCN (3 mL). The reaction mixture was allowed to warm to rt and stirred for one hour. The reaction was concentrated in vacuo, the residue diluted with EtOAc (5 mL), filtered and concentrated in vacuo to give a brown yellow oil. The crude product was purified by chromatography on the Companion (12 g column, 0-10% MeOH in DCM) to afford the sub-title compound (227 mg) as a sticky yellow oil.
LCMS m/z 387 (M+H)⁺ (ES⁺)

(ii) 4-Amino-2-methoxy-N-methyl-N-(3-(4-methylpiperazin-1-yl)propyl)benzenesulfonamide A suspension of the product from step (i) above (227 mg, 0.587 mmol) and 5% Pd/C (50% paste with water, 150 mg) in ethanol (5 mL) was stirred under hydrogen (5 bar) for 2 h. The reaction mixture was filtered through celite, washed with methanol and concentrated in vacuo to afford the sub-title compound (162 mg) as a pale yellow oil.
¹H NMR (400 MHz, DMSO-d6) δ 7.33 (d, 1H), 6.24 (d, 1H), 6.13 (dd, 1H), 5.96 (s, 2H), 3.74 (s, 3H), 2.97 (t, 2H), 2.66 (s, 3H), 2.28-2.18 (m, 10H), 2.12 (s, 3H), 1.54 (quint., 2H).
LCMS m/z 357 (M+H)⁺ (ES⁺); 355 (M–H)⁻ (ES⁻)

(iii) 4-((4-((4-(3-(5-(tert-Butyl)-2-methoxy-3-(methylsulfonamido)phenyl)ureido)naphthalen-1-yl)oxy)pyridin-2-yl)amino)-2-methoxy-N-methyl-N-(3-(4-methylpiperazin-1-yl)propyl)benzene sulfonamide A suspension of the product from step (ii) above (68 mg, 0.179 mmol), N-(5-(tert-butyl)-3-(3-(4-((2-chloropyridin-4-yl)oxy)naphthalen-1-yl)ureido)-2-methoxyphenyl)methanesulfonamide (see Example 8(i) above; 102 mg, 0.179 mmol), K₂CO₃ (74 mg, 0.535 mmol), and BrettPhos G3 precatalyst (5 mg, 5.52 µmol) in DMF (7 mL) was degassed with nitrogen for 10 mins. The reaction was then heated under nitrogen at 85° C. (block temperature) for 2 h, cooled to rt and added to water (20 mL). The organic layer was extracted with DCM (20 mL), dried over MgSO₄, filtered and concentrated in vacuo. The crude product was purified by chromatography on the Companion (4 g column, 0-20% MeOH in DCM) then purified by preparative HPLC (Varian, Basic (0.1% Ammonium Bicarbonate), Basic, Waters X-Bridge Prep-C18, 5 µm, 19×50 mm column, 20-50% MeCN in Water) to afford the title compound (6 mg) as a colourless solid.
¹H NMR (400 MHz, DMSO-d6) δ 9.39 (s, 2H), 9.14 (bs, 1H), 8.88 (s, 1H), 8.30 (d, 1H), 8.18 (d, 1H), 8.12-8.10 (m, 2H), 7.85 (d, 1H), 7.68 (dd, 1H), 7.59-7.52 (m, 3H), 7.39 (d, 1H), 7.24 (dd, 1H), 7.02 (d, 1H), 6.68 (dd, 1H), 6.16 (d, 1H), 3.80 (s, 3H), 3.78 (s, 3H), 3.04 (s, 3H), 3.00 (t, 2H), 2.69 (s, 3H), 2.25 (bs, 6H), 2.17 (t, 2H), 2.10 (s, 3H), 1.54 (quint, 2H), 1.26 (s, 9H).
LCMS m/z 889 (M+H)⁺ (ES⁺)

Example 26

4-((4-((4-(3-(5-(tert-Butyl)-2-methoxy-3-(methylsulfonamido)phenyl)ureido)naphthalen-1-yl)oxy)pyridin-2-yl)amino)-N-(2-(4-cyclopropylpiperazin-1-yl)ethyl)-2-methoxybenzamide

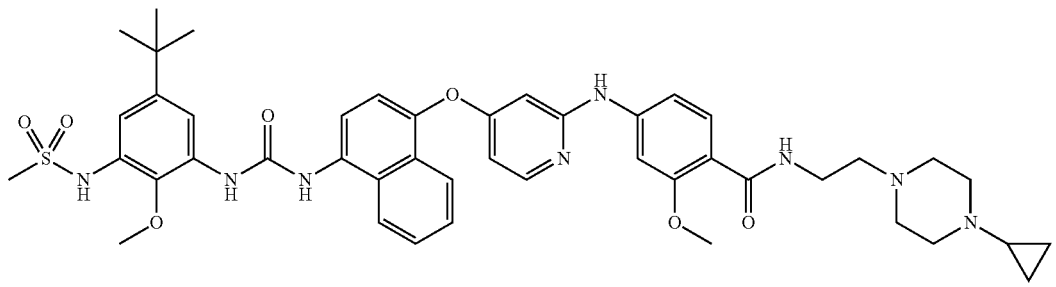 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCN(C2CC2)CC1]

HATU (80 mg, 0.210 mmol) was added to a stirred solution of 4-((4-((4-(3-(5-(tert-butyl)-2-methoxy-3-(methylsulfonamido)phenyl)ureido)naphthalen-1-yl)oxy)pyridin-2-yl)amino)-2-methoxybenzoic acid, hydrochloride salt (see Example 1 above; 100 mg, 0.136 mmol), 2-(4-cyclopropylpiperazin-1-yl)ethanamine (33 mg, 0.166 mmol) and Hünig's base (100 µL, 0.573 mmol) in DMF (2 mL) at rt. The mixture was stirred overnight then poured into water (10 mL) and partitioned with EtOAc (10 mL). The organic phase was concentrated in vacuo. The residue was dissolved in DMSO (2 mL) and transferred to a 96 well plate. The crude product was purified by preparative HPLC (Waters, Acidic (0.1% Formic acid), Acidic, Waters X-Select Prep-C18, 5 µm, 19×50 mm column, 20-50% MeCN in Water) to afford a pale yellow solid. The solid was partitioned between NaHCO$_3$ solution and 10% MeOH in DCM. The organic phase was dried via hydrophobic frit and concentrated in vacuo. The residue was re-concentrated from MeCN and the residue dried in vacuo at 45° C. to afford the title compound (48 mg) as an off-white solid.

$^1$H NMR (400 MHz, DMSO-d6) δ: 9.39 (s, 1H), 9.26 (s, 1H), 9.13 (s, 1H), 8.91 (s, 1H), 8.30 (d, 1H), 8.11-8.22 (m, 4H), 7.87 (d, 1H), 7.78 (d, 1H), 7.69-7.73 (m, 1H), 7.60-7.63 (m, 1H), 7.58 (d, 1H), 7.40 (d, 1H), 7.24 (dd, 1H), 7.03 (d, 1H), 6.66 (dd, 1H), 6.16 (d, 1H), 3.89 (s, 3H), 3.81 (s, 3H), 3.36 (q, 2H), 3.10 (s, 3H), 2.55-2.64 (m, 4H), 2.30-2.45 (m, 6H), 1.58-1.63 (m, 1H), 1.27 (s, 9H), 0.38-0.42 (m, 2H), 0.27-0.30 (m, 2H).

LCMS m/z 851 (M+H)$^+$ (ES$^+$)

Example 27

4-((4-((4-(3-(5-(tert-Butyl)-2-methoxy-3-(methylsulfonamido)phenyl)ureido)naphthalen-1-yl)oxy)pyridin-2-yl)amino)-2-methoxy-N-(2-(piperidin-4-yl)ethyl)benzamide (i) tert-Butyl 4-(2-(4-((4-((4-(3-(5-(tert-butyl)-2-methoxy-3-(methylsulfonamido)phenyl) ureido) naphthalen-1-yl)oxy)pyridin-2-yl)amino)-2-methoxybenzamido)ethyl)piperidine-1-carboxylate HATU (120 mg, 0.316 mmol) was added to a stirred solution of 4-((4-((4-(3-(5-(tert-butyl)-2-methoxy-3-(methylsulfonamido)phenyl)ureido)naphthalen-1-yl)oxy)pyridin-2-yl)amino)-2-methoxybenzoic acid, hydrochloride salt (see Example 1 above; 150 mg, 0.204 mmol), tert-butyl 4-(2-aminoethyl)piperidine-1-carboxylate (60 mg, 0.263 mmol) and Hünig's base (150 µL, 0.859 mmol) in DMF (2 mL) at rt. The mixture was stirred overnight then poured into water (10 mL) resulting in the precipitation of a white solid. The solid was isolated by filtration, washing with additional water, then the solid dried at 50° C. in vacuo. The crude product was purified by chromatography on the Companion (12 g column, 1-5% MeOH in DCM) to afford the sub-title compound (135 mg) as a white solid.

LCMS m/z 910 (M+H)$^+$ (ES$^+$)

(ii) 4-((4-((4-(3-(5-(tert-Butyl)-2-methoxy-3-(methylsulfonamido)phenyl)ureido)naphthalen-1-yl)oxy)pyridin-2-yl)amino)-2-methoxy-N-(2-(piperidin-4-yl)ethyl)benzamide TFA (229 µL, 2.97 mmol) was added to a solution of the product from step (i) above (135 mg, 0.148 mmol) in DCM (2 mL) and the reaction left stirring overnight. The reaction was concentrated in vacuo affording a pale yellow oil. The oil was dissolved in DCM and partitioned with NaHCO$_3$ solution resulting in a gelatinous precipitate. The aqueous phase was decanted off and the organic phase washed with water. The organic phase was diluted with MeOH affording a homogeneous mixture which was concentrated in vacuo affording a white solid. The solid was dissolved in DMSO (2 mL) and transferred to a 96 well plate. The crude product was purified by preparative HPLC (Waters, Basic (0.1% Ammonium Bicarbonate), Basic, Waters X-Bridge Prep-C18, 5 µm, 19×50 mm column, 35-65% MeCN in Water) to afford the title compound (68 mg) as an off-white solid.

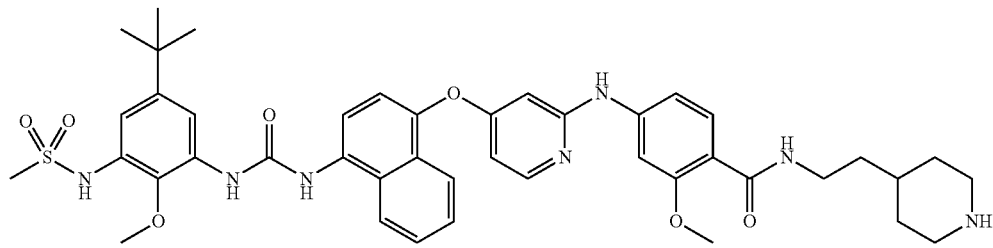 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCC1CCNCC1]

$^1$H NMR (400 MHz, DMSO-d6) δ: 9.41 (s, 1H), 9.24 (s, 1H), 8.90 (s, 1H), 8.31 (d, 1H), 8.11-8.17 (m, 3H), 7.92 (t, 1H), 7.87 (d, 1H), 7.68-7.73 (m, 2H), 7.59-7.63 (m, 1H), 7.55 (d, 1H), 7.40 (d, 1H), 7.22 (dd, 1H), 7.03 (d, 1H), 6.66 (dd, 1H), 6.15 (d, 1H), 3.83 (s, 3H), 3.81 (s, 3H), 3.29 (q, 2H), 3.06 (s, 3H), 2.97 (d, 2H), 2H under DMSO, 1.65 (d, 2H), 1.35-1.48 (m, 3H), 1.27 (s, 9H), 1.01-1.11 (m, 2H).

LCMS m/z 810 (M+H)$^+$ (ES$^+$)

Example 28

4-((4-((4-(3-(5-(tert-Butyl)-2-methoxy-3-(methylsulfonamido)phenyl)ureido)naphthalen-1-yl)oxy)pyrimidin-2-yl)amino)-2-methoxybenzenesulfonamide

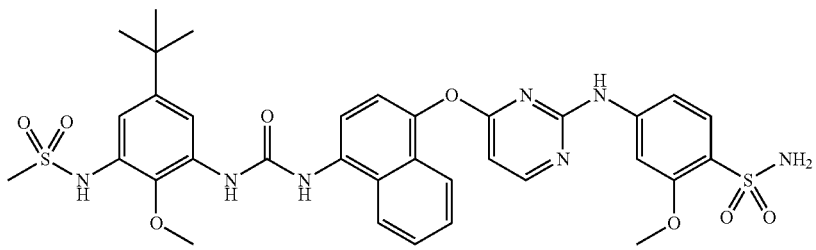 [SMILES: COc1cc(Nc2nccc(Oc3ccc(NC(=O)Nc4cc(C(C)(C)C)cc(NS(C)(=O)=O)c4OC)c4ccccc34)n2)ccc1S(N)(=O)=O]

A mixture of N-(5-(tert-butyl)-3-(3-(4-((2-chloropyrimidin-4-yl)oxy)naphthalen-1-yl)ureido)-2-methoxyphenyl)methanesulfonamide (see, for example, Baker, T. et al., WO 2014/162126, 9 Oct. 2014; 200 mg, 0.351 mmol), 4-amino-2-methoxybenzene sulfonamide (120 mg, 0.593 mmol) and pTsOH monohydrate (22 mg, 0.116 mmol) in dioxane (2 mL) was heated at 65° C. for 1 h. DMF (0.5 mL) was added and the mixture heated for a further 24 h. The mixture was partitioned between EtOAc (40 mL) and sat aq NaHCO$_3$ (20 mL), the organic layer separated, washed with brine (20 mL), dried (MgSO$_4$) and evaporated under reduced pressure. The crude product was purified by chromatography on silica gel (40 g column, 0-60% MeOH/DCM) to afford the product (180 mg, 95% purity) as a solid. Of that product, 75 mg was purified by preparative HPLC (Varian, Basic (0.1% Ammonium Bicarbonate), Basic, Waters X-Bridge Prep-C18, 5 μm, 19×50 mm column, 20-50% MeCN in Water) to afford the title compound (31 mg).

$^1$H NMR (400 MHz, DMSO-d6) δ 9.85 (s, 1H), 9.41 (s, 1H), 9.14 (s, 1H), 8.93 (s, 1H), 8.50 (d, 1H), 8.31 (d, 1H), 8.18 (d, 1H), 8.13 (d, 1H), 7.85 (d, 1H), 7.71-7.67 (m, 1H), 7.62-7.58 (m, 1H), 7.43 (d, 1H), 7.37 (s, 1H), 7.34 (d, 1H), 7.07 (brd, 1H), 7.03 (d, 1H), 6.78 (s, 2H), 6.70 (d, 1H), 3.82 (s, 3H), 3.50 (s, 3H), 3.10 (s, 3H), 1.27 (s, 9H).

LCMS m/z 736 (M+H)$^+$ (ES$^+$)

Example 29

4-((4-((4-(3-(5-(tert-Butyl)-2-methoxy-3-(methylsulfonamido)phenyl)ureido)naphthalen-1-yl)oxy)pyridin-2-yl)amino)-2-hydroxy-N-(3-morpholinopropyl)benzamide (i) Methyl 2-(benzyloxy)-4-((4-((4-(3-(5-(tert-butyl)-2-methoxy-3-(methylsulfonamido)phenyl)-ureido)naphthalen-1-yl)oxy)pyridin-2-yl)amino)benzoate A mixture of methyl 4-amino-2-(benzyloxy)benzoate (149 mg, 0.580 mmol; Azzarito, V. et al., *Org. Biomol. Chem.* 2012, 10, 6469-6472), N-(5-(tert-butyl)-3-(3-(4-((2-chloropyridin-4-yl)oxy)naphthalen-1-yl)ureido)-2-methoxyphenyl)methane sulfonamide (see Example 8(i) above; 300 mg, 0.527 mmol), K$_2$CO$_3$ (182 mg, 1.318 mmol), and Brett Phos G3 catalyst (25 mg, 0.028 mmol) in DMF (6 mL) were degassed under nitrogen for 5 min. The reaction was then heated at 85° C. (block temperature) for 4 h. The mixture was cooled then partitioned between EtOAc (50 mL) and water (50 mL). The organic layer was washed with water (50 mL), dried (MgSO$_4$), filtered and evaporated under reduced pressure. The residue was purified by chromatography on silica gel (40 g column, 0-80% EtOAc/isohexane) to afford the sub-title compound (342 mg) as a foam.

$^1$H NMR (400 MHz, DMSO-d6) δ 9.39 (s, 1H), 9.33 (s, 1H), 9.14 (s, 1H), 8.91 (s, 1H), 8.30 (d, 1H), 8.20-8.18 (m, 2H), 8.12 (d, 1H), 7.87 (d, 1H), 7.78-7.60 (m, 4H), 7.52 (d, 2H), 7.41-7.37 (m, 3H), 7.33-7.29 (m, 1H), 7.19 (dd, 1H), 7.03 (d, 1H), 6.68 (dd, 1H), 6.16 (d, 1H), 5.13 (s, 2H), 3.81 (s, 3H), 3.74 (s, 3H), 3.10 (s, 3H), 1.27 (s, 9H).

(ii) 2-(Benzyloxy)-4-((4-((4-(3-(5-(tert-butyl)-2-methoxy-3-(methylsulfonamido)phenyl)ureido)-naphthalen-1-yl)oxy)pyridin-2-yl)amino)benzoic acid, hydrochloride salt Aqueous 1 M NaOH (1.5 mL, 1.500 mmol) was added to a solution of the product from step (i) above (335 mg, 0.424

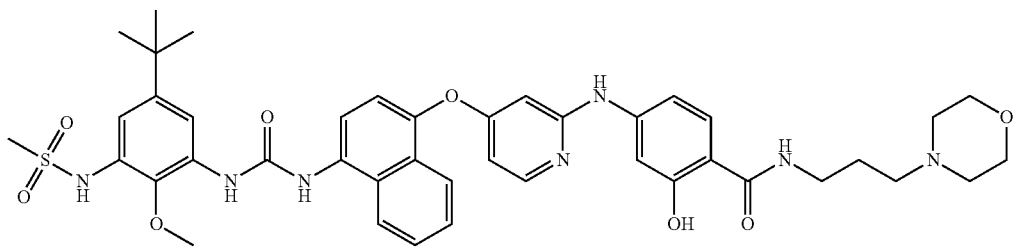 [SMILES: COc1c(NC(=O)Nc2ccc(Oc3ccnc(Nc4ccc(C(=O)NCCCN5CCOCC5)c(O)c4)c3)c3ccccc23)cc(C(C)(C)C)cc1NS(C)(=O)=O]

mmol) in THF (4 mL) and MeOH (2 mL) and stirred for 48 h. The solvent was evaporated, the residue dissolved in water (5 mL) then acidified to pH 1 with aqueous 1 M HCl (10 mL). The precipitate was filtered, washed with water then ether and dried under vacuum to afford the sub-title compound (288 mg) as an off white solid.

$^1$H NMR (400 MHz, DMSO-d6) δ 9.90 (s, 1H), 9.67 (s, 1H), 9.13 (s, 1H), 9.05 (s, 1H), 8.39 (d, 1H), 8.17 (s, 1H), 8.13 (d, 2H), 7.86 (d, 1H), 7.73-7.61 (m, 3H), 7.52-7.29 (m, 7H), 7.06 (d, 1H), 7.03 (s, 1H), 6.78 (d, 1H), 6.28 (s, 1H), 5.14 (s, 2H), 3.82 (s, 3H), 3.10 (s, 3H), 1.27 (s, 9H).

LCMS m/z 776 (M+H)$^+$ (ES$^+$)

(d, 1H), 3.81 (s, 3H), 3.57-3.55 (m, 4H), 3.30-3.26 (m, 2H), 3.10 (s, 3H), 2.35-2.30 (m, 6H), 1.71-1.64 (m, 2H), 1.27 (s, 9H).

LCMS m/z 812 (M+H)$^+$ (ES$^+$); 810 (M−H)$^−$ (ES$^−$)

Example 30

4-((4-((4-(3-(3-(tert-Butyl)-5-(methylsulfonamido)phenyl)ureido)naphthalen-1-yl)oxy)pyridin-2-yl)amino)-2-methoxybenzoic acid

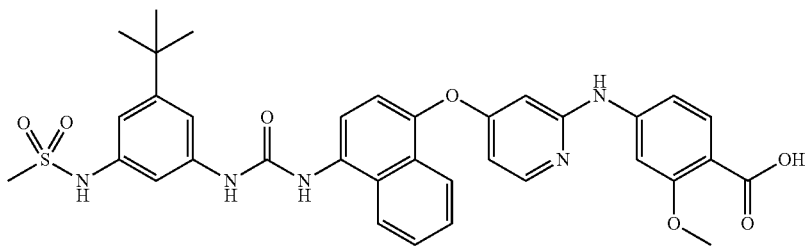 [SMILES: COc1cc(Nc2cc(Oc3ccc(NC(=O)Nc4cc(NS(C)(=O)=O)cc(C(C)(C)C)c4)c4ccccc34)ccn2)ccc1C(=O)O]

(iii) 2-(Benzyloxy)-4-((4-((4-(3-(5-(tert-butyl)-2-methoxy-3-(methylsulfonamido)phenyl)-ureido)naphthalen-1-yl)oxy)pyridin-2-yl)amino)-N-(3-morpholinopropyl)benzamide HATU (103 mg, 0.272 mmol) was added to a mixture of the product from step (ii) above (184 mg, 0.227 mmol), Hünig's base (100 µL, 0.573 mmol) and 3-morpholinopropan-1-amine (40 mg, 0.277 mmol) in DMF (3 mL) and stirred for 6 h. The mixture was partitioned between EtOAc (30 mL) and water (20 mL), the organic layer separated, washed with sat aq NaHCO$_3$ soln (20 mL), dried (MgSO$_4$), filtered and evaporated under reduced pressure. The residue was purified by chromatography on silica gel (24 g column, 0-8% MeOH/DCM) to afford the sub-title compound (154 mg) as a foam.

LCMS m/z 902 (M+H)$^+$ (ES$^+$); 900 (M−H)$^−$ (ES$^−$)

(iv) 4-((4-((4-(3-(5-(tert-Butyl)-2-methoxy-3-(methylsulfonamido)phenyl)ureido)naphthalen-1-yl)oxy)pyridin-2-yl)amino)-2-hydroxy-N-(3-morpholinopropyl)benzamide A mixture of the product from step (iii) above (152 mg, 0.169 mmol) and 5% Pd/C (30 mg) in EtOH (2 mL) and THF (3 mL) was hydrogenated under a balloon of hydrogen for 24 h then filtered through Celite. The solvent was evaporated and the residue triturated with ether, filtered and dried to afford a solid that was loaded onto a column of SCX in MeOH. The column was washed with MeOH and then the product was eluted with 0.7 M ammonia in MeOH. The resultant mixture was concentrated in vacuo and the product was purified by chromatography on silica gel (24 g column, 0-10% MeOH/DCM) to afford the title compound (77 mg) as a white foam.

$^1$H NMR (400 MHz, DMSO-d6) δ 12.88 (s, 1H), 9.39 (s, 1H), 9.17 (s, 1H), 9.13 (s, 1H), 8.91 (s, 1H), 8.53 (brs, 1H), 8.30 (d, 1H), 8.18 (d, 1H), 8.16 (d, 1H), 8.12 (d, 1H), 7.87 (d, 1H), 7.73-7.69 (m, 1H), 7.64-7.59 (m, 2H), 7.45 (d, 1H), 7.40 (d, 1H), 7.02 (d, 1H), 6.92 (dd, 1H), 6.66 (dd, 1H), 6.14

(i) Methyl 4-((4-((4-(3-(3-(tert-butyl)-5-(methylsulfonamido)phenyl)ureido)naphthalen-1-yl)oxy)pyridin-2-yl)amino)-2-methoxybenzoate Triethylamine (25 µL, 0.179 mmol) was added to a solution of phenyl (3-(tert-butyl)-5-(methylsulfonamido)phenyl)carbamate (see, for example, Baker, T. et al., WO 2014/162126, 9 Oct. 2014; 319 mg, 0.880 mmol) and methyl 4-((4-((4-aminonaphthalen-1-yl)oxy)pyridin-2-yl)amino)-2-methoxybenzoate (see Example 1(iii) above; 332 mg, 0.800 mmol) in iPrOAc (15 mL) at 65° C. (block temperature) and the mixture stirred for 24 h. Additional triethylamine (25 µL, 0.179 mmol) was added and the temperature increased to 75° C. and stirring continued overnight. The reaction was cooled to rt and concentrated in vacuo onto silica gel. The crude product was purified by chromatography on the Companion (40 g column, 1-5% MeOH in DCM) to afford the sub-title compound (332 mg) as a pale pink gummy solid.

$^1$H NMR (400 MHz, DMSO-d6) δ: 9.66 (s, 1H), 9.34 (s, 1H), 9.14 (s, 1H), 8.79 (s, 1H), 8.22 (d, 1H), 8.18 (d, 1H), 8.08 (d, 1H), 7.86 (d, 1H), 7.69-7.72 (m, 1H), 7.59-7.63 (m, 2H), 7.53 (d, 1H), 7.40 (d, 1H), 7.36 (s, 1H), 7.29 (t, 1H), 7.23 (dd, 1H), 6.89 (t, 1H), 6.69 (dd, 1H), 6.17 (d, 1H), 3.74 (s, 3H), 3.71 (s, 3H), 3.01 (s, 3H), 1.28 (s, 9H).

LCMS m/z 684 (M+H)$^+$ (ES$^+$)

(ii) 4-((4-((4-(3-(3-(tert-Butyl)-5-(methylsulfonamido)phenyl) ureido)naphthalen-1-yl)oxy)-pyridin-2-yl)amino)-2-methoxybenzoic acid To a stirred solution of the product from step (i) above (332 mg, 0.486 mmol) in THF (15 mL) was added NaOH (2 M aq.) (5.0 mL, 10.00 mmol). MeOH (5 mL) was added and stirring continued overnight. The reaction was concentrated in vacuo affording a pale pink solid. The material was acidified with 1M HCl causing a white solid to precipitate. The solid was collected by filtration, washing with water. The resulting solid was dried at 40° C. under vacuum affording 4-((4-((4-(3-(3-(tert-butyl)-5-(methylsulfonamido)phenyl)ureido)naphthalen-1-yl)oxy)pyridin-2-yl)amino)-2-methoxybenzoic acid, hydrochloride (314 mg) as a white solid.

LCMS m/z 670 (M+H)$^+$ (ES$^+$)

100 mg of the hydrochloride salt was purified by preparative HPLC (Varian, Basic (0.1% Ammonium Bicarbonate), Basic, Waters X-Bridge Prep-C18, 5 μm, 19×50 mm column, 20-50% MeCN in Water) to afford the title compound (36 mg) as a white solid.

$^1$H NMR (400 MHz, DMSO-d6) δ: 10.50 (bs, 1H), 9.33 (s, 1H), 9.28 (s, 1H), 8.98 (s, 1H), 8.24 (d, 1H), 8.17 (d, 1H), 8.07 (d, 1H), 7.86 (d, 1H), 7.67-7.71 (m, 1H), 7.59-7.62 (m, 2H), 7.49 (s, 1H), 7.40 (d, 1H), 7.37 (s, 1H), 7.32 (s, 1H), 7.21 (dd, 1H), 6.89 (s, 1H), 6.68 (dd, 1H), 6.16 (d, 1H), 3.74 (s, 3H), 3.01 (s, 3H), 1.28 (s, 9H).

LCMS m/z 670 (M+H)$^+$ (ES$^+$)

Example 31

N-(5-(tert-Butyl)-2-methoxy-3-(3-(4-((2-((3-methoxy-4-(2-oxopyridin-1 (2H)-yl)phenyl)amino)-pyridin-4-yl)oxy)naphthalen-1-yl)ureido)phenyl)methanesulfonamide

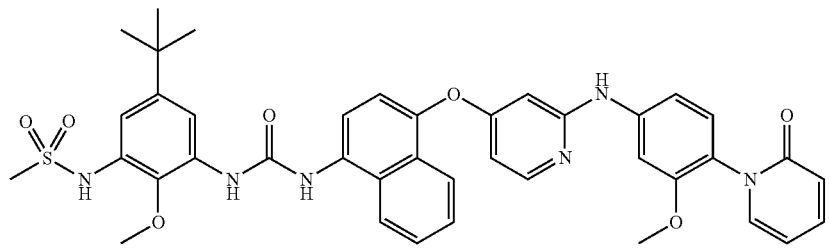 [SMILES: COc1cc(Nc2cc(Oc3ccc(NC(=O)Nc4cc(C(C)(C)C)cc(NS(C)(=O)=O)c4OC)c4ccccc34)ccn2)ccc1-n1ccccc1=O]

(i) 1-(2-Methoxy-4-nitrophenyl)pyridin-2(1H)-one

To a stirred solution of 1-fluoro-2-methoxy-4-nitrobenzene (250 mg, 1.461 mmol) and 2-hydroxypyridine (140 mg, 1.472 mmol) in DMF (4 mL) was added cesium carbonate (625 mg, 1.918 mmol). The mixture was heated to 120° C. and stirred overnight. The reaction was cooled to rt and quenched with water (15 mL). On standing, a solid slowly precipitated from the mixture and was removed by filtration, washing with additional water. The filtrate was extracted with DCM and the organic phase dried via hydrophobic frit and concentrated in vacuo affording a yellow oil. The oil was purified by chromatography on the Companion (24 g column, 0.5-3% MeOH in DCM) to afford the sub-title compound (92 mg) as a yellow solid.

LCMS m/z 247 (M+H)$^+$ (ES$^+$)

(ii) 1-(4-Amino-2-methoxyphenyl)pyridin-2(1H)-one

The product from step (i) above (120 mg, 0.487 mmol) was dissolved in ethanol (4 mL) and Fe powder (250 mg, 4.48 mmol) was added followed by a solution of NH$_4$Cl (30 mg, 0.561 mmol) in water (1 mL). The resulting suspension was heated at 80° C. for 2 h. The reaction was cooled to rt and filtered through Celite. The filtrate was concentrated in vacuo affording a green solid. The material was sonicated in EtOAc (5 mL) and DCM (20 mL) for 5 mins, then filtered and the filtrate concentrated in vacuo affording the sub-title compound (110 mg) as a yellow solid.

LCMS m/z 217 (M+H)$^+$ (ES$^+$)

(iii) N-(5-(tert-Butyl)-2-methoxy-3-(3-(4-((2-((3-methoxy-4-(2-oxopyridin-1 (2H)-yl)phenyl)-amino)pyridin-4-yl)oxy)naphthalen-1-yl)ureido)phenyl)methanesulfonamide A suspension of the product from step (ii) above (36 mg, 0.166 mmol), N-(5-(tert-butyl)-3-(3-(4-((2-chloropyridin-4-yl)oxy)naphthalen-1-yl)ureido)-2-methoxyphenyl)methanesulfonamide (see Example 8(i) above; 100 mg, 0.162 mmol), K$_2$CO$_3$ (70 mg, 0.506 mmol), and BrettPhos G3 precatalyst (5 mg, 5.52 μmol) in DMF (3 mL) was degassed with nitrogen for 10 mins. The reaction was then heated under nitrogen at 85° C. (block temperature) for 2 h. The reaction was cooled and partitioned between EtOAc (10 mL) and water (10 mL). The aqueous phase was extracted with EtOAc (5 mL). The combined organic phase was washed with brine (5 mL) then dried (MgSO$_4$), filtered and concentrated in vacuo affording a dark yellow oil. The crude product was purified by chromatography on the Companion (12 g column, 1-6% MeOH in DCM) to afford the title compound (94 mg) as a pale beige foam.

$^1$H NMR (400 MHz, DMSO-d6) δ: 9.39 (s, 1H), 9.14 (s, 2H), 8.91 (s, 1H), 8.31 (d, 1H), 8.20 (d, 1H), 8.11-8.14 (m, 2H), 7.89 (d, 1H), 7.70-7.73 (m, 1H), 7.61-7.64 (m, 1H), 7.51 (d, 1H), 7.40-7.47 (m, 3H), 7.27 (dd, 1H), 7.03-7.06 (m, 2H), 6.62 (dd, 1H), 6.41 (d, 1H), 6.21 (t, 1H), 6.14 (d, 1H), 3.81 (s, 3H), 3.66 (s, 3H), 3.10 (s, 3H), 1.27 (s, 9H).

LCMS m/z 749 (M+H)$^+$ (ES$^+$)

Example 32

5-(tert-Butyl)-N-(2-hydroxyethyl)-2-methoxy-3-(3-(4-((2-((3-methoxy-4-((2-(1-oxidothiomorpholino)ethyl)carbamoyl)phenyl)amino)pyridin-4-yl)oxy)naphthalen-1-yl)ureido)benzamide

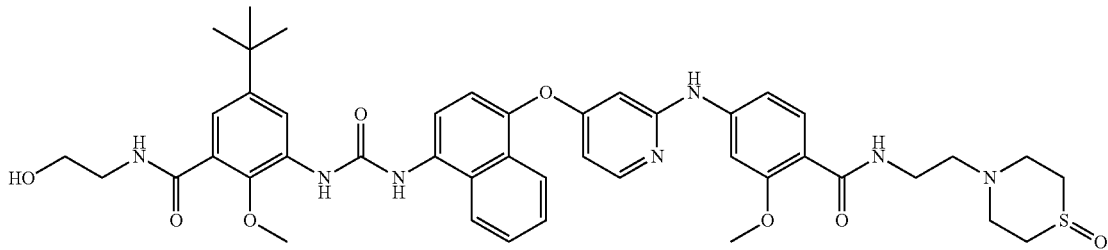 [SMILES: COc1cc(Nc2cc(Oc3ccc(NC(=O)Nc4cc(C(C)(C)C)cc(C(=O)NCCO)c4OC)c4ccccc34)ccn2)ccc1C(=O)NCCN1CCS(=O)CC1]

$^1$H NMR (400 MHz, DMSO-d6) δ 9.37 (s, 1H), 9.28 (s, 1H), 8.34-8.01 (m, 3H), 7.84 (d, 1H), 7.76 (d, 1H), 7.70-7.53 (m, 4H), 7.37 (d, 1H), 7.22 (dd, 1H), 6.66 (dd, 1H), 6.13 (d, 1H), 3.86 (s, 3H), 3.39 (q, 2H), 3.05-2.82 (m, 4H), 2.82-2.65 (m, 4H), 2.55 (t, 2H), 1.53 (s, 9H).

LCMS m/z 646 (M+H)$^+$ (ES$^+$)

(i) 4-((4-((4-(((tert-Butoxycarbonyl)amino)naphthalen-1-yl)oxy)pyridin-2-yl)amino)-2-methoxybenzoic acid, hydrochloride salt To a stirred solution of methyl 4-((4-((4-(((tert-butoxycarbonyl)amino)naphthalen-1-yl)oxy)pyridin-2-yl)amino)-2-methoxybenzoate (see Example 1(ii) above; 1 g, 1.940 mmol) in THF (5 mL) and MeOH (2 mL) was added LiOH (0.065 g, 2.72 mmol) and water (2 mL) and the reaction left stirring overnight at 40° C. The reaction was concentrated in vacuo affording a pale brown foam. The foam was suspended in water (5 mL) and acidified with 1M HCl (6 mL) resulting in the formation of a pale suspension. The solid was recovered by filtration washing with water until the filtrate was pH 2. The cake was washed with isohexane to remove excess water and dried to afford the sub-title compound (1 g).

$^1$H NMR (400 MHz, DMSO-d6) δ 9.71 (s, 1H), 9.40 (s, 1H), 8.38-8.04 (m, 2H), 7.91-7.75 (m, 1H), 7.73-7.54 (m, 4H), 7.45-7.31 (m, 2H), 7.11 (dd, 1H), 6.75 (dd, 1H), 6.22 (d, 1H), 3.74 (s, 3H), 1.52 (s, 9H).

LCMS m/z 502 (M+H)$^+$ (ES$^+$)

(ii) tert-Butyl (4-((2-((3-methoxy-4-((2-(1-oxidothiomorpholino)ethyl)carbamoyl)phenyl)-amino)pyridin-4-yl)oxy)naphthalen-1-yl)carbamate HATU (1 g, 2.63 mmol) was added to a solution of the product from step (i) above (1 g, 1.859 mmol), 4-(2-aminoethyl)thiomorpholine 1-oxide, hydrochloride salt (500 mg, 2.52 mmol) and Hünig's base (1.5 mL, 8.59 mmol) in DMF (7.5 mL). The reaction mixture was stirred at rt for 16 h. The mixture was poured into water (100 mL) and partitioned with DCM 2× (50 mL). The organics were separated, bulked, dried (MgSO$_4$), filtered and evaporated to a brown gum. The crude product was purified by chromatography on silica gel (12 g column, 2% MeOH:DCM to 10%) to afford the sub-title compound (800 mg) as a tan solid.

(iii) 4-((4-((4-Aminonaphthalen-1-yl)oxy)pyridin-2-yl)amino)-2-methoxy-N-(2-(1-oxidothiomorpholino)ethyl)benzamide TFA (1 mL, 12.98 mmol) was added to a solution of the product from step (ii) above (800 mg, 1.239 mmol) in DCM (10 mL) and the reaction stirred overnight. The solvents were evaporated and the residue was loaded onto a column of SCX (10 g) in MeOH. The column was washed with MeOH and then the product was eluted with 0.7 M ammonia in MeOH. The resultant mixture was concentrated in vacuo to afford the sub-title compound (650 mg) as a tan solid.

$^1$H NMR (400 MHz, DMSO-d6) δ 9.19 (s, 1H), 8.35-7.98 (m, 3H), 7.75 (d, 1H), 7.68-7.59 (m, 1H), 7.59-7.50 (m, 1H), 7.50-7.36 (m, 2H), 7.20 (dd, 1H), 7.11 (dd, 1H), 6.72 (dd, 1H), 6.60 (dd, 1H), 6.08 (d, 1H), 5.84 (s, 2H), 3.84 (d, 3H), 3.39 (q, 2H), 3.04-2.82 (m, 4H), 2.78-2.62 (m, 4H), 2.55 (t, 2H).

LCMS m/z 546 (M+H)$^+$ (ES$^+$)

(iv) Methyl 5-(tert-butyl)-2-methoxy-3-(3-(4-((2-((3-methoxy-4-((2-(1-oxidothiomorpholino)-ethyl)carbamoyl)phenyl)amino)pyridin-4-yl)oxy)naphthalen-1-yl)ureido)benzoate A solution of methyl 5-(tert-butyl)-2-methoxy-3-((phenoxycarbonyl)amino)benzoate (see, for example, Baker, T. et al., WO 2014/162126, 9 Oct. 2014; 500 mg, 1.399 mmol) and the product from step (iii) above (650 mg, 1.191 mmol) and TEA (40 µL, 0.287 mmol) in THF (10 mL) was heated at 60° C. (block temperature) for 16 h. The solvent was evaporated and the crude product was purified by chromatography on silica gel (40 g column, 2% MeOH:DCM to 10%) to afford the sub-title compound (625 mg).

$^1$H NMR (400 MHz, DMSO-d6) δ 9.50 (s, 1H), 9.27 (s, 1H), 8.97 (s, 1H), 8.61 (d, 1H), 8.31 (d, 1H), 8.20-8.06 (m, 3H), 7.88 (d, 1H), 7.78-7.68 (m, 2H), 7.62 (t, 1H), 7.58 (d, 1H), 7.41 (d, 1H), 7.35 (d, 1H), 7.23 (dd, 1H), 6.66 (dd, 1H), 6.16 (d, 1H), 3.88 (s, 3H), 3.86 (s, 3H), 3.85 (s, 3H), 3.39 (q, 2H), 3.03-2.81 (m, 4H), 2.80-2.64 (m, 4H), 2.55 (t, 2H), 1.29 (s, 9H).

LCMS m/z 809 (M+H)+ (ES+)

(v) 5-(tert-Butyl)-2-methoxy-3-(3-(4-((2-((3-methoxy-4-((2-(1-oxidothiomorpholino)ethyl)-carbamoyl)phenyl)amino)pyridin-4-yl)oxy)naphthalen-1-yl)ureido)benzoic acid, hydrochloride salt To a stirred solution of the product from step (iv) above (620 mg, 0.766 mmol) in THF (5 mL) and MeOH (2 mL) was added LiOH (25 mg, 1.044 mmol) and water (2 mL) and the reaction left stirring overnight at 40° C. The reaction was concentrated in vacuo affording a pale brown foam. The foam was suspended in water (5 mL) and acidified with HCl (100 µL, 1.170 mmol), the resulting solution was pH 1-2. The desired compound was recovered by freeze drying to afford the sub-title compound (650 mg).

LCMS m/z 795 (M+H)+ (ES+)

(vi) 5-(tert-Butyl)-N-(2-hydroxyethyl)-2-methoxy-3-(3-(4-((2-((3-methoxy-4-((2-(1-oxidothiomorpholino)ethyl)carbamoyl)phenyl)amino)pyridin-4-yl)oxy)naphthalen-1-yl)ureido)benzamide HATU (75 mg, 0.197 mmol) was added to a solution of the product from step (v) above (110 mg, 0.119 mmol), 2-aminoethanol (20 µL, 0.331 mmol) and Hünig's base (80 µL, 0.458 mmol) in DMF (2 mL). The reaction mixture was stirred at rt for 1 h. The mixture was poured into water (10 mL) and partitioned repeatedly with 10% MeOH:DCM (6×10 mL). The organics were separated, bulked, dried (MgSO4), filtered and evaporated to a brown gum. The crude product was purified by chromatography on silica gel (12 g column, 2% MeOH:DCM to 20%) to afford the title compound (80 mg).

1H NMR (400 MHz, DMSO-d6) δ 9.51 (s, 1H), 9.28 (s, 1H), 8.95 (s, 1H), 8.46 (d, 1H), 8.32 (d, 1H), 8.26 (t, 1H), 8.21-8.04 (m, 3H), 7.87 (d, 1H), 7.76 (d, 1H), 7.72 (t, 1H), 7.62 (t, 1H), 7.58 (s, 1H), 7.41 (d, 1H), 7.30-7.15 (m, 2H), 6.66 (dd, 1H), 6.16 (d, 1H), 4.80 (t, 1H), 3.86 (s, 3H), 3.82 (s, 3H), 3.57 (q, 2H), 3.39 (q, 4H), 3.04-2.81 (m, 4H), 2.80-2.63 (m, 4H), 2.55 (s, 2H), 1.29 (s, 9H).

LCMS m/z 838 (M+H)+ (ES+)

Example 33

4-(2-(4-((4-(3-(5-(tert-Butyl)-2-methoxy-3-(methylsulfonamido)phenyl)ureido)naphthalen-1-yl)oxy)pyridin-2-yl)amino)-2-methoxybenzamido)ethyl)morpholine 4-oxide

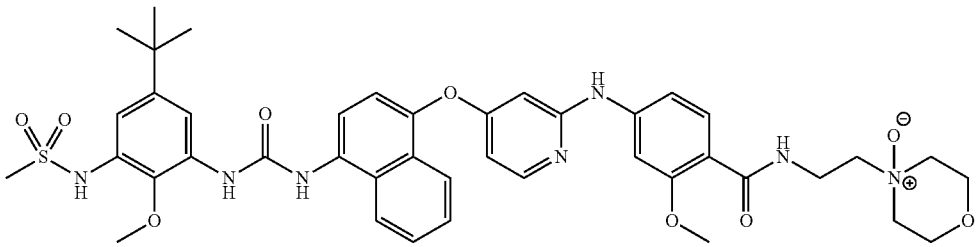 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCC[N+]1(O)CCOCC1]

HATU (120 mg, 0.316 mmol) was added to a stirred solution of 4-((4-((4-(3-(5-(tert-butyl)-2-methoxy-3-(methylsulfonamido)phenyl)ureido)naphthalen-1-yl)oxy)pyridin-2-yl)amino)-2-methoxybenzoic acid, hydrochloride salt (see Example 1 above; 150 mg, 0.204 mmol), 4-(2-aminoethyl) morpholine 4-oxide (John, V. and Maillard, M., WO 2003/103653; 40 mg, 0.246 mmol) and Hünig's base (150 µL, 0.859 mmol) in DMF (2 mL) at rt. The mixture was stirred for 2 h then concentrated in vacuo affording a brown oil. 100 mg of the crude material was purified by preparative HPLC (Varian, Basic (0.1% Ammonium Bicarbonate), Basic, Waters X-Bridge Prep-C18, 5 µm, 19×50 mm column, 20-50% MeCN in Water) to afford the title compound (10 mg) as a white solid.

1H NMR (400 MHz, DMSO-d6) δ: 9.62 (s, 1H), 9.41 (s, 1H), 9.23 (s, 1H), 9.13 (s, 1H), 8.95 (s, 1H), 8.30 (d, 1H), 8.09-8.18 (m, 3H), 7.86 (d, 1H), 7.74-7.68 (m, 2H), 7.59-7.68 (m, 1H), 7.52 (s, 1H), 7.37-7.40 (m, 1H), 7.18 (d, 1H), 7.02 (d, 1H), 6.63-6.64 (m, 1H), 6.14 (s, 1H), 4.15 (t, 2H), 3.80 (s, 3H), 3.78 (s, 3H), 3.65-3.74 (m, 4H), 4H under H2O, 3.09 (s, 3H), 3.01 (d, 2H), 1.26 (s, 9H).

LCMS m/z 828 (M+H)+ (ES+)

Example 34

7-(4-((4-((4-(3-(5-(tert-Butyl)-2-methoxy-3-(methyl-sulfonamido)phenyl)ureido)naphthalen-1-yl)oxy) pyridin-2-yl)amino)-2-methoxybenzamido)heptanoic acid

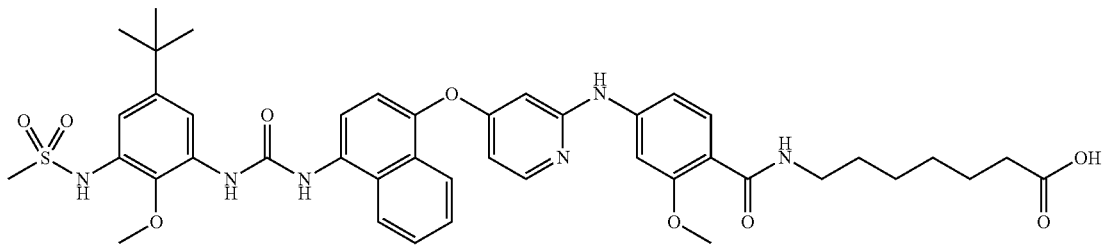 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCCCCCC(=O)O]

(i) Methyl 7-(4-((4-((4-(3-(5-(tert-butyl)-2-methoxy-3-(methylsulfonamido)phenyl)ureido)-naphthalen-1-yl)oxy)pyridin-2-yl)amino)-2-methoxybenzamido) heptanoate HATU (120 mg, 0.316 mmol) was added to a stirred solution of 4-((4-((4-(3-(5-(tert-butyl)-2-methoxy-3-(methylsulfonamido)phenyl)ureido)naphthalen-1-yl)oxy)pyridin-2-yl)amino)-2-methoxybenzoic acid, hydrochloride salt (see Example 1 above; 150 mg, 0.204 mmol), methyl 7-aminoheptanoate, hydrochloride salt (50 mg, 0.256 mmol) and Hünig's base (150 µL, 0.859 mmol) in DMF (2 mL) at rt. The mixture was stirred overnight. The mixture was poured into water (10 mL) resulting in the precipitation of a white solid. The solid was isolated by filtration, washing with additional water, then the solid dried at 50° C. The crude product was purified by chromatography on the Companion (12 g column, 1-5% MeOH in DCM) to afford the sub-title compound (120 mg) as a white solid.

LCMS m/z 841 (M+H)+ (ES+)

(ii) 7-(4-((4-((4-(3-(5-(tert-Butyl)-2-methoxy-3-(methylsulfonamido)phenyl)ureido)naphthalen-1-yl) oxy)pyridin-2-yl)amino)-2-methoxybenzamido)heptanoic acid, hydrochloride salt To a stirred solution of the product from step (i) above (120 mg, 0.143 mmol) in THF (5 mL) was added NaOH (2M aq.) (1.5 mL, 3.00 mmol). MeOH (1 mL) was added and stirring continued overnight. The reaction was concentrated in vacuo affording a yellow solid. The material was acidified with 1M HCl causing a pink solid to precipitate. The solid was collected by filtration, washing with water. The resulting solid was dried at 40° C. under vacuum to afford the title compound (115 mg) as a white solid.

$^1$H NMR (400 MHz, DMSO-d6) δ: 9.74 (s, 1H), 9.54 (s, 1H), 9.14 (s, 1H), 8.99 (s, 1H), 8.36 (d, 1H), 8.11-8.18 (m, 3H), 8.00 (t, 1H), 7.86 (d, 1H), 7.70-7.74 (m, 2H), 7.62-7.66 (m, 1H), 7.44 (d, 1H), 7.37 (s, 1H), 7.10 (d, 1H), 7.03 (d, 1H), 6.77 (d, 1H), 6.24 (s, 1H), 3.83 (s, 3H), 3.81 (s, 3H), 3.24 (q, 2H), 3.10 (s, 3H), 2.20 (s, 2H), 1.42-1.56 (m, 4H), 1.27 (s, 9H), 1.22-1.36 (m, 4H).

LCMS m/z 827 (M+H)+ (ES+)

Example 35

2-(4-((4-((4-(3-(5-(tert-Butyl)-2-methoxy-3-(methyl-sulfonamido)phenyl)ureido)naphthalen-1-yl)oxy) pyridin-2-yl)amino)-2-methoxybenzamido)ethyl dihydrogen phosphate

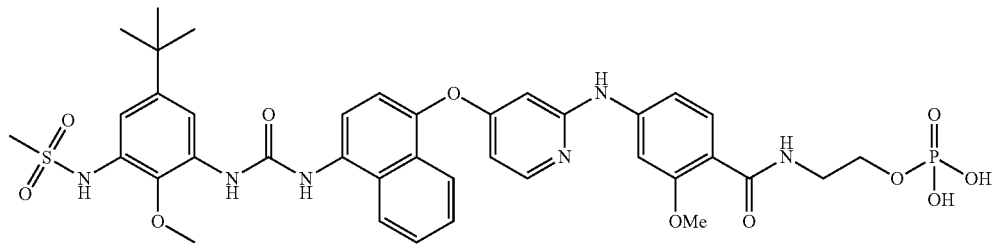 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCOP(=O)(O)O]

(i) Di-tert-butyl (2-(4-((4-((4-(3-(5-(tert-butyl)-2-methoxy-3-(methylsulfonamido)phenyl)-ureido) naphthalen-1-yl)oxy)pyridin-2-yl)amino)-2-methoxybenzamido)ethyl) phosphate HATU (108 mg, 0.285 mmol) was added to a solution of 4-((4-((4-(3-(5-(tert-butyl)-2-methoxy-3-(methylsulfonamido)phenyl)ureido)naphthalen-1-yl)oxy)pyridin-2-yl) amino)-2-methoxybenzoic acid, hydrochloride salt (see Example 1 above; 150 mg, 0.204 mmol), 2-aminoethyl di-tert-butyl phosphate (100 mg, 0.395 mmol) and Hünig's base (107 µL, 0.611 mmol) in DMF (1 mL). The reaction mixture was stirred at rt for 16 h. HATU (20 mg) was added to the reaction mixture, and the mixture was stirred for a further 4 hours. The mixture was poured into water (20 mL) and partitioned repeatedly with 10% MeOH:DCM (5×10 mL). The organics were separated, bulked, dried (MgSO$_4$), filtered and evaporated to a yellow oil. The crude product was purified by chromatography on the Companion (4 g column, 0-10% MeOH in iso-hexane) to afford the sub-title compound (205 mg) as a thick tan oil.

LCMS m/z 935 (M+H)+ (ES+)

(ii) 2-(4-((4-((4-(3-(5-(tert-Butyl)-2-methoxy-3-(methylsulfonamido)phenyl)ureido)naphthalen-1-yl)oxy)pyridin-2-yl)amino)-2-methoxybenzamido)ethyl dihydrogen phosphate TFA (0.2 mL, 2.60 mmol) was added to a solution of the product from step (i) above (200 mg, 0.214 mmol) in DCM (2 mL). The reaction mixture was stirred at rt for one hour then concentrated in vacuo. The crude product was loaded onto a column of SCX (3 g) in MeOH. The column was washed with MeOH and then the product was eluted with 0.7 M ammonia in MeOH. The resultant mixture was concentrated in vacuo and the residue triturated with acetonitrile (2 mL). The resultant solid was filtered and dried in vacuo to afford the ammonium salt of the title compound (77 mg) as an off-white solid.

$^1$H NMR (of ammonium salt; 400 MHz, DMSO-d6) δ 9.63 (s, 1H), 9.26 (s, 1H), 9.04 (s, 1H), 8.33 (d, 1H), 8.24 (t, 1H), 8.16-8.14 (m, 2H), 8.08 (d, 1H), 7.85 (d, 1H), 7.73 (d, 1H), 7.67 (dd, 1H), 7.58 (dd, 1H), 7.42 (s, 1H), 7.38 (d, 1H), 7.16 (d, 1H), 7.01 (d, 1H), 6.65 (dd, 1H), 6.14 (d, 1H), 3.82 (s, 3H), 3.81-3.76 (m, 2H), 3.74 (s, 3H), 3.41 (q, 2H), 3.08 (s, 3H), 1.26 (s, 9H).

LCMS (of ammonium salt) m/z 823 (M+H)$^+$ (ES$^+$); 821 (M−H)$^−$ (ES$^−$)

The ammonium salt (77 mg, 0.092 mmol) was loaded onto a column of Dowex 50WX2 Na$^+$ form (4 g) in water (2 mL). The column was eluted with water (10 mL) to get the sodium salt. The product-rich fractions were freeze dried to afford the sodium salt of the title compound (40 mg) as a colourless solid.

$^1$H NMR (of sodium salt; 400 MHz, DMSO-d6) δ 9.70 (s, 1H), 9.25 (s, 1H), 9.08 (bs, 2H), 8.34 (d, 1H), 8.24 (t, 1H), 8.16-8.15 (m, 2H), 8.05 (d, 1H), 7.84 (d, 1H), 7.73 (d, 1H), 7.66 (dd, 1H), 7.57 (dd, 1H), 7.38-7.36 (m, 2H), 7.15 (d, 1H), 7.01 (d, 1H), 6.66 (dd, 1H), 6.14 (d, 1H), 3.83 (s, 3H), 3.82-3.80 (m, 2H), 3.71 (s, 3H), 3.44-3.41 (m, 2H), 3.08 (s, 3H), 1.26 (s, 9H).

LCMS (of sodium salt) m/z 823 (M+H)$^+$ (ES$^+$)

Example 36

4-((4-((4-(3-(5-(tert-Butyl)-2-methoxy-3-(methylsulfonamido)phenyl)ureido)naphthalen-1-yl)oxy)pyridin-2-yl)amino)-N-(2-(2-(2-hydroxyethoxy)ethoxy)ethyl)-2,6-dimethoxybenzamide

(i) tert-Butyl (4-((2-(2-(2-hydroxyethoxy)ethoxy)ethyl)carbamoyl)-3,5-dimethoxyphenyl)carbamate HATU (300 mg, 0.789 mmol) was added to a solution of 4-((tert-butoxycarbonyl)amino)-2,6-dimethoxybenzoic acid (see Example 22(ii) above; 200 mg, 0.673 mmol), 2-(2-(2-aminoethoxy)ethoxy)ethanol (150 mg, 1.005 mmol) and Hünig's base (400 μL, 2.290 mmol) in DCM (5 mL) and DMF (1 mL). The reaction mixture was stirred at rt for 16 h. The mixture was partitioned between DCM (15 mL) and water (15 mL). The organics were separated, dried (MgSO$_4$) filtered and evaporated to give a yellow gum which was pre-absorbed onto silica (4 g) and purified by chromatography on silica gel (12 g column, 2% MeOH:DCM to 10%) to afford the sub-title compound (190 mg).

$^1$H NMR (400 MHz, DMSO-d6) δ 9.37 (s, 1H), 7.87 (t, 1H), 6.83 (s, 2H), 4.58 (t, 1H), 3.66 (s, 6H), 3.59-3.37 (m, 10H), 3.27 (q, 2H), 1.48 (s, 9H).

LCMS m/z 429 (M+H)$^+$ (ES$^+$)

(ii) 4-Amino-N-(2-(2-(2-hydroxyethoxy)ethoxy)ethyl)-2,6-dimethoxybenzamide

TFA (350 μL, 4.54 mmol) was added to a solution of the product from step (i) above (180 mg, 0.420 mmol) in DCM (2 mL) and the reaction left stirring for 72 h. The reaction was found to contain a mixture of starting material and trifluoroacetic ester. The mixture was redissolved in DCM (2 mL) and TFA (1 mL) added. The reaction was stirred for 3 h and solvents evaporated. The residue was refluxed in MeOH and K$_2$CO$_3$ (200 mg, 1.447 mmol) for 1 h, cooled and filtered. The filtrate was evaporated to afford the sub-title compound (150 mg) as a yellow gum.

LCMS m/z 329 (M+H)$^+$ (ES$^+$); 85% purity @ 254 nm.

(iii) 4-((4-((4-(3-(5-(tert-Butyl)-2-methoxy-3-(methylsulfonamido)phenyl)ureido)naphthalen-1-yl)oxy)pyridin-2-yl)amino)-N-(2-(2-(2-hydroxyethoxy)ethoxy)ethyl)-2,6-dimethoxybenzamide Method 1

A mixture of N-(5-(tert-butyl)-3-(3-(4-((2-chloropyridin-4-yl)oxy)naphthalen-1-yl)ureido)-2-methoxyphenyl)methanesulfonamide (see Example 8(i) above; 150 mg, 0.264 mmol), the product from step (ii) above (150 mg, 0.388 mmol), K$_2$CO$_3$ (100 mg, 0.724 mmol), and BrettPhos G1 Precatalyst (5 mg, 5.64 μmol) were degassed under vacuum back-filling with nitrogen 3 times. DMF (2 mL) was added

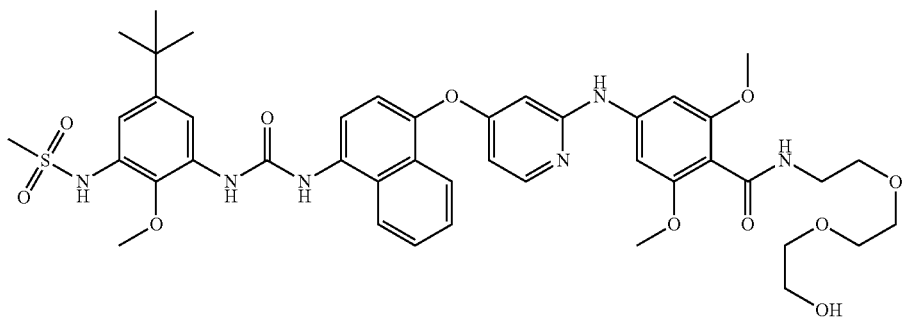 [SMILES: COc1cc(Nc2cc(Oc3ccc(NC(=O)Nc4cc(C(C)(C)C)cc(NS(C)(=O)=O)c4OC)c4ccccc34)ccn2)cc(OC)c1C(=O)NCCOCCOCCO]

and the stirred suspension was degassed under vacuum back-filling with nitrogen 3 times. The reaction was then heated under nitrogen at 85° C. (block temperature) for 1 h. The mixture was cooled to rt and filtered. The crude product was purified by preparative HPLC (Varian, Basic (0.1% Ammonium Bicarbonate), Basic, Waters X-Bridge Prep-C18, 5 μm, 19×50 mm column, 20-50% MeCN in Water) to afford the title compound (95 mg) as a colourless solid.

batches were combined in DCM and re-concentrated affording the title compound (11.46 g) as an off-white foam.
LCMS m/z 861 (M+H)$^+$ (ES$^+$)

Example 37

4-((4-((4-(3-(5-(tert-Butyl)-2-methoxy-3-(methylsulfonamido)phenyl)ureido)naphthalen-1-yl)oxy)pyridin-2-yl)amino)-N-(2-(4-(2-hydroxyethyl)piperazin-1-yl)ethyl)-2,6-dimethoxybenzamide

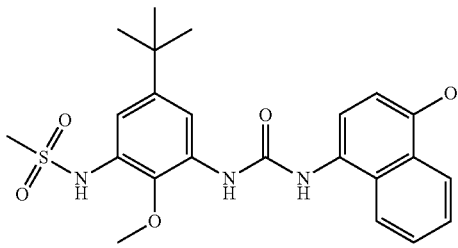
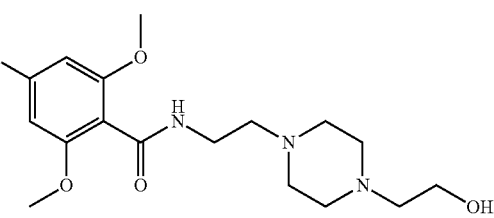

$^1$H NMR (400 MHz, DMSO-d6) δ 9.40 (s, 1H), 9.07 (s, br, 1H), 9.02 (s, 1H), 8.92 (s, 1H), 8.30 (d, 1H), 8.19 (d, 1H), 8.14-8.05 (m, 2H), 7.92-7.85 (m, 1H), 7.82 (t, 1H), 7.76-7.66 (m, 1H), 7.66-7.57 (m, 1H), 7.39 (d, 1H), 7.03 (d, 1H), 6.94 (s, 2H), 6.61 (dd, 1H), 6.11 (d, 1H), 4.57 (t, 1H), 3.81 (s, 3H), 3.61 (s, 6H), 3.56-3.36 (m, 10H), 3.26 (q, 2H), 3.10 (s, 3H), 1.27 (s, 9H).

LCMS m/z 861 (M+H)$^+$ (ES$^+$)

Method 2

A solution of 4-[[4-[[4-[[5-tert-butyl-3-(methanesulfonamido)-2-methoxyphenyl]carbamoyl-amino]-1-naphthyl]oxy]-2-pyridyl]amino]-2,6-dimethoxy-benzoic acid (see Example 46 below; 15 g, 18.91 mmol), Hünig's base (14 mL, 80 mmol) and HATU (7.2 g, 18.94 mmol) in NMP (200 mL) was stirred at rt for 30 mins. Additional HATU (3.0 g) was added and stirring continued for 10 mins. 2-(2-(2-aminoethoxy)ethoxy)ethanol (3.7 g, 24.80 mmol) was added and the reaction stirred for 10 mins. The reaction was then heated to 40° C. for 2 h then cooled to rt and stirred overnight. The reaction was partitioned between EtOAc (300 mL) and water (400 mL). The aqueous phase was extracted with EtOAc (100 mL) and the combined organics washed with water (2×300 mL) then dried (MgSO$_4$), filtered and concentrated in vacuo affording a yellow foam. The crude product was purified by chromatography on the Companion (220 g column, 1-10% MeOH in DCM) to afford the sub-title compound as an off-white foam. On standing, a large amount of a dark coloured oil precipitated from the combined aqueous layer. LCMS analysis showed this to be predominantly the product. Most of the aqueous material was decanted off and the oil diluted with EtOAc. Only some of the oil was solubilised so MeOH (~1/10 the volume of EtOAc) was added. The resulting solution was washed with water (10 mL). The combined aqueous phase was re-extracted with 10% MeOH in EtOAc and the organics combined, washed with water (100 mL), dried (MgSO$_4$), filtered and concentrated in vacuo affording a beige foam. The crude product was purified by chromatography on the Companion (220 g column, 1-10% MeOH in DCM) affording the sub title compound as an off-white foam. The two (i) tert-Butyl (4-((2-(4-(2-hydroxyethyl)piperazin-1-yl)ethyl)carbamoyl)-3,5-dimethoxyphenyl)carbamate HATU (300 mg, 0.789 mmol) was added to a solution of 4-((tert-butoxycarbonyl)amino)-2,6-dimethoxybenzoic acid (see Example 22(ii) above; 200 mg, 0.673 mmol), 2-(4-(2-aminoethyl)piperazin-1-yl)ethanol (150 mg, 0.866 mmol) and Hünig's base (400 μL, 2.290 mmol) in DCM (5 mL) and DMF (1 mL). The reaction mixture was stirred at rt for 16 h. The mixture was partitioned between DCM (15 mL) and water (15 mL). The organics were separated, dried (MgSO$_4$) filtered and evaporated to give a yellow gum which was pre-absorbed onto silica (4 g) and purified by chromatography on silica gel (12 g column, 2% MeOH:DCM to 10% then 10% 7N NH$_3$ MeOH:DCM) to afford the sub-title compound (110 mg).

$^1$H NMR (400 MHz, DMSO-d6) δ 9.37 (s, 1H), 7.74 (t, 1H), 6.83 (s, 2H), 4.48 (s, 1H), 3.66 (s, 6H), 3.60-3.45 (m, 2H), 3.24 (q, 2H), 2.49-2.34 (m, 12H), 1.48 (s, 9H).

LCMS m/z 453 (M+H)$^+$ (ES$^+$)

(ii) 4-Amino-N-(2-(4-(2-hydroxyethyl)piperazin-1-yl)ethyl)-2,6-dimethoxybenzamide, 2TFA TFA (200 μL, 2.60 mmol) was added to a solution of the product from step (i) above (110 mg, 0.243 mmol) in DCM (1 mL) and the reaction left stirring for 72 h. The solvents were evaporated and the residue azeotroped with toluene to afford the sub-title compound (120 mg) as a pale brown gum.

LCMS m/z 353 (M+H)$^+$ (ES$^+$); 85% purity @ 254 nm.

(iii) 4-((4-((4-(3-(5-(tert-Butyl)-2-methoxy-3-(methylsulfonamido)phenyl)ureido)naphthalen-1-yl)oxy)pyridin-2-yl)amino)-N-(2-(4-(2-hydroxyethyl)piperazin-1-yl)ethyl)-2,6-dimethoxybenzamide A mixture of N-(5-(tert-butyl)-3-(3-(4-((2-chloropyridin-4-yl)oxy)naphthalen-1-yl)ureido)-2-methoxyphenyl)methanesulfonamide (see Example 8(i) above; 110 mg, 0.193 mmol), the product from step (ii) above (110 mg, 0.190 mmol), K$_2$CO$_3$ (150 mg, 1.085 mmol) and BrettPhos G1 Precatalyst (5 mg, 5.64 μmol) were degassed under vacuum back-filling with nitrogen 3 times. DMF (2 mL) was added and the stirred suspension was degassed under vacuum back-filling with nitrogen 3 times. The reaction was then heated under nitrogen at 85° C. (block temperature) for 16 h. The mixture was cooled to rt and filtered. The crude product was purified by preparative HPLC (Varian, Basic (0.1% Ammonium Bicarbonate), Basic, Waters X-Bridge Prep-C18, 5 μm, 19×50 mm column, 20-50% MeCN in Water) to afford the title compound (35 mg) as a pale tan solid.

$^1$H NMR (400 MHz, DMSO-d6) δ 9.40 (s, 1H), 9.14 (s, 1H), 9.02 (s, 1H), 8.92 (s, 1H), 8.30 (d, 1H), 8.19 (d, 1H), 8.12 (t, 2H), 7.87 (d, 1H), 7.77-7.53 (m, 3H), 7.39 (d, 1H), 7.03 (d, 1H), 6.94 (s, 2H), 6.61 (dd, 1H), 6.11 (d, 1H), 4.40 (s, br, 1H), 3.81 (s, 3H), 3.61 (s, 6H), 3.55-3.42 (m, 2H), 3.22 (q, 2H), 3.10 (s, 3H), 2.48-2.21 (m, 8H), 1.27 (s, 9H). 4H under water peak at 3.32 ppm.

LCMS m/z 885 (M+H)$^+$ (ES$^+$)

X-Bridge Prep-C18, 5 μm, 19×50 mm column, 35-65% MeCN in Water) to afford the title compound (45 mg) as a white solid.

$^1$H NMR (400 MHz, DMSO-d6) δ: 9.40 (s, 1H), 9.27 (s, 1H), 9.7 (s, 1H), 8.91 (s, 1H), 8.48 (t, 1H), 8.31 (d, 1H), 8.16-8.18 (m, 2H), 8.12 (d, 1H), 7.87 (d, 1H), 7.77 (d, 1H), 7.69-7.73 (m, 1H), 7.60-7.63 (m, 2H), 7.40 (d, 1H), 7.22 (dd, 1H), 7.03 (d, 1H), 6.66 (dd, 1H), 6.16 (d, 1H), 4.49 (t, 3H), 3.84 (s, 3H), 3.81 (s, 3H), 8H under H$_2$O, 3.08 (s, 3H), 1.27 (s, 9H).

LCMS m/z 817 (M+H)$^+$ (ES$^+$)

Example 38

4-((4-((4-(3-(5-(tert-Butyl)-2-methoxy-3-(methylsulfonamido)phenyl)ureido)naphthalen-1-yl)oxy)pyridin-2-yl)amino)-N-(3-hydroxy-2,2-bis(hydroxymethyl)propyl)-2-methoxybenzamide Example 39

4-((4-((4-(3-(5-(tert-Butyl)-2-methoxy-3-(methylsulfonamido)phenyl)ureido)naphthalen-1-yl)oxy)pyridin-2-yl)amino)-N-(2-(dimethylamino)ethyl)-2,6-dimethoxybenzamide

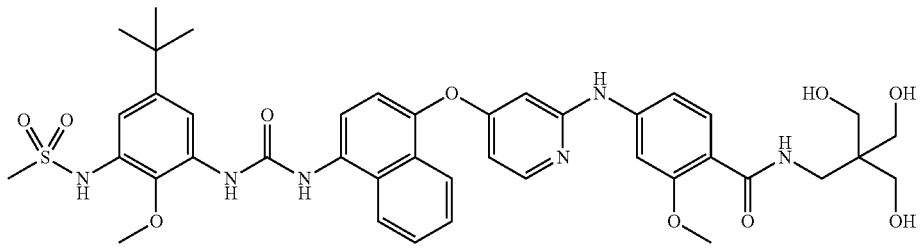 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCC(CO)(CO)CO]

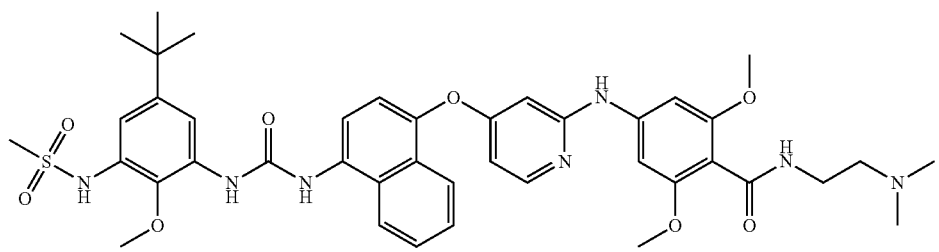

HATU (80 mg, 0.210 mmol) was added to a stirred solution of 4-((4-((4-(3-(5-(tert-butyl)-2-methoxy-3-(methylsulfonamido)phenyl)ureido)naphthalen-1-yl)oxy)pyridin-2-yl)amino)-2-methoxybenzoic acid, hydrochloride salt (see Example 1 above; 100 mg, 0.136 mmol), 2-(aminomethyl)-2-(hydroxymethyl)propane-1,3-diol (22 mg, 0.163 mmol) and Hünig's base (120 μL, 0.687 mmol) in DMF (2 mL) at rt. The mixture was stirred overnight then poured into water (10 mL) and partitioned with EtOAc (10 mL). The organic phase was concentrated in vacuo affording a pale yellow oil. The crude product was purified by preparative HPLC (Waters, Basic (0.1% Ammonium Bicarbonate), Basic, Waters (i) tert-Butyl (4-((2-(dimethylamino)ethyl)carbamoyl)-3,5-dimethoxyphenyl)carbamate HATU (1 g, 2.63 mmol) was added to a solution of 4-((tert-butoxycarbonyl)amino)-2,6-dimethoxybenzoic acid (see Example 22(ii) above; 300 mg, 1.009 mmol), N1,N1-dimethylethane-1,2-diamine (400 μL, 3.66 mmol) and Hünig's base (500 μL, 2.86 mmol) in DMF (5 mL). The reaction mixture was stirred at rt for 1 h. The mixture was partitioned between DCM (15 mL) and water (15 mL). The organics were separated, dried (MgSO$_4$) filtered and evaporated to give a yellow gum which was pre-absorbed onto silica (4 g) and purified by chromatography on silica gel (12 g column, 2% MeOH:DCM to 20%) to give a yellow gum.

This material was redissolved in EtOAc (20 mL) and washed with water (20 mL). The organics were separated, dried (MgSO₄) filtered and the solvent evaporated to afford the sub-title compound (220 mg) as a tan glass.

¹H NMR (400 MHz, DMSO-d6) δ 9.39 (s, 1H), 7.98 (t, 1H), 6.85 (s, 2H), 3.67 (s, 6H), 3.03-2.83 (m, 2H), 2.83-2.66 (m, 2H), 1.48 (s, 9H). —N(CH3)2 obscured by water peak 3.32 ppm.

LCMS m/z 368 (M+H)⁺ (ES⁺)

(ii) 4-Amino-N-(2-(dimethylamino)ethyl)-2,6-dimethoxybenzamide, bis(trifluoroacetate) salt TFA (1 mL, 12.98 mmol) was added to a solution of the product from step (i) above (220 mg, 0.599 mmol) in DCM (2 mL) and the reaction left stirring for 16 h. The solvents were evaporated to afford the sub-title compound (200 mg)

LCMS m/z 268 (M+H)⁺ (ES⁺)

(iii) 4-((4-((4-(3-(5-(tert-Butyl)-2-methoxy-3-(methylsulfonamido)phenyl)ureido)naphthalen-1-yl)oxy) pyridin-2-yl)amino)-N-(2-(dimethylamino)ethyl)-2, 6-dimethoxybenzamide A mixture of N-(5-(tert-butyl)-3-(3-(4-((2-chloropyridin-4-yl)oxy)naphthalen-1-yl)ureido)-2-methoxyphenyl)methanesulfonamide (see Example 8(i) above; 150 mg, 0.264 mmol), the product from step (ii) above (200 mg, 0.404 mmol), K₂CO₃ (200 mg, 1.447 mmol), and BrettPhos G1 precatalyst (10 mg, 0.011 mmol) were degassed under vacuum back-filling with nitrogen 3 times. DMF (2 mL) was added and the stirred suspension was degassed under vacuum back-filling with nitrogen 3 times. The reaction was then heated under nitrogen at 85° C. (block temperature) for 16 h. BrettPhos G1 Precatalyst (100 mg, 0.113 mmol) was added and stirring at 80° C. was continued for a further 4 h. The mixture was cooled to rt and filtered. The crude product was purified by preparative HPLC (Varian, Basic (0.1% Ammonium Bicarbonate), Basic, Waters X-Bridge Prep-C18, 5 am, 19×50 mm column, 20-50% MeCN in Water) to afford the title compound (30 mg) as a tan solid.

¹H NMR (400 MHz, DMSO-d6) δ 9.39 (s, 1H), 9.11 (s, 1H), 9.02 (s, 1H), 8.88 (s, 1H), 8.30 (d, 1H), 8.25-8.00 (m, 3H), 7.96-7.79 (m, 1H), 7.78-7.51 (m, 3H), 7.39 (d, 1H), 7.03 (d, 1H), 6.93 (s, 2H), 6.61 (dd, 1H), 6.11 (d, 1H), 3.81 (s, 3H), 3.61 (s, 6H), 3.19 (q, 2H), 3.04 (s, 3H), 2.31 (t, 2H), 2.15 (s, 6H), 1.26 (s, 9H).

LCMS m/z 800 (M+H)⁺ (ES⁺)

Example 40

N-(5-(tert-Butyl)-3-(3-(4-((2-((4-((2-(2-(2-hydroxyethoxy)ethoxy)ethyl)sulfonyl)-3-methoxyphenyl) amino)pyridin-4-yl)oxy)naphthalen-1-yl)ureido)-2-methoxyphenyl)-methanesulfonamide

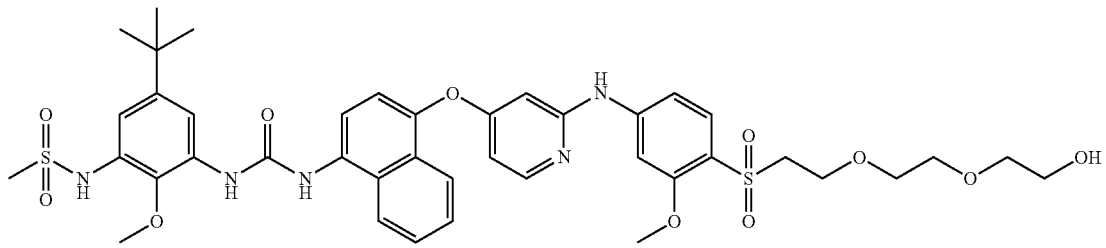 [SMILES: COc1cc(Nc2cc(Oc3ccc(NC(=O)Nc4cc(C(C)(C)C)cc(NS(C)(=O)=O)c4OC)c4ccccc34)ccn2)ccc1S(=O)(=O)CCOCCOCCO]

(i) (2-(2-(2-(Benzyloxy)ethoxy)ethoxy)ethyl)(2-methoxy-4-nitrophenyl)sulfane ((2-(2-(2-Bromoethoxy)ethoxy)methyl)benzene (1310 mg, 3.89 mmol) was added to a solution of 2-methoxy-4-nitrobenzenethiol (600 mg, 3.24 mmol) and K₂CO₃ (493 mg, 3.56 mmol) in acetone (10 mL). The reaction mixture was stirred at rt for 17 hours. The reaction mixture was concentrated in vacuo, diluted with EtOAc (10 mL), washed with 5 wt % aq NaOH (10 mL). The organic layer was dried over MgSO₄, filtered and concentrated in vacuo to afford a yellow oil. The crude product was purified by chromatography on the Companion (40 g column, 0-100% ethyl acetate in iso-hexane) to afford the sub-title compound (1.055 g) as a sticky yellow-brown oil.

¹H NMR (400 MHz, DMSO-d6) δ 7.83 (dd, 1H), 7.69 (d, 1H), 7.45 (d, 1H), 7.35-7.25 (m, 5H), 4.47 (s, 2H), 3.94 (s, 3H), 3.68 (t, 2H), 3.58-3.52 (m, 8H), 3.23 (t, 2H).

(ii) 1-((2-(2-(2-(Benzyloxy)ethoxy)ethoxy)ethyl) sulfonyl)-2-methoxy-4-nitrobenzene mCPBA (616 mg, 2.75 mmol) was added slowly to an ice cold solution of the product from step (i) above (500 mg, 1.227 mmol) in DCM (5 mL). The reaction was stirred at 0° C. for 30 min. then allowed to warm to rt and stirred for 1 h. The reaction mixture was filtered and the filtrate immediately partitioned with sodium bisulphite solution 20% w/w (5 mL). The organic layer was separated, washed with sat. NaHCO₃ soln. (5 mL), dried (MgSO₄), filtered and the solvent evaporated to a yellow oil. The crude product was purified by chromatography on silica gel (12 g column, 0-70% EtOAc in iso-hexane) to afford the sub-title compound (456 mg) as a pale yellow oil.

¹H NMR (400 MHz, DMSO-d6) δ 8.03-7.94 (m, 3H), 7.37-7.28 (m, 5H), 4.45 (s, 2H), 4.04 (s, 3H), 3.76-3.73 (m, 2H), 3.70-3.67 (m, 2H), 3.47-3.45 (m, 2H), 3.38-3.36 (m, 2H), 3.28-3.26 (m, 2H), 3.18-3.16 (m, 2H).

LCMS m/z 440 (M+H)⁺ (ES⁺)

(iii) 2-(2-(2-((4-Amino-2-methoxyphenyl)sulfonyl) ethoxy)ethoxy)ethanol

A suspension of the product from step (ii) above (456 mg, 1.038 mmol) and 5% Pd/C (50% paste with water, 120 mg) in ethanol (5 mL) was stirred under hydrogen (5 bar) for 2 h. The reaction mixture was filtered (Whatmans GF/F) and the filtrate evaporated to give partially reduced product. A suspension of the crude product and 5% Pd/C (50% paste with water, 120 mg) in ethanol (5 mL) was stirred under hydrogen (5 bar) for 2 h. The reaction mixture was filtered (Whatmans GF/F) and the filtrate evaporated to afford the sub-title compound (312 mg) as a thick orange oil.

$^1$H NMR (400 MHz, DMSO-d6) δ 7.36 (d, 1H), 6.27 (s, 1H), 6.19 (d, 1H), 6.11 (bs, 2H), 3.80 (s, 3H), 3.59 (t, 2H), 3.47-3.43 (m, 6H), 3.38-3.34 (m, 4H).

LCMS m/z 320 (M+H)$^+$ (ES$^+$)

(iv) N-(5-(tert-Butyl)-3-(3-(4-((2-((4-((2-(2-(2-hydroxyethoxy)ethoxy)ethyl)sulfonyl)-3-methoxyphenyl)amino)pyridin-4-yl)oxy)naphthalen-1-yl)ureido)-2-methoxyphenyl)-methanesulfonamide A suspension of the product from step (iii) above (67.3 mg, 0.211 mmol), N-(5-(tert-butyl)-3-(3-(4-((2-chloropyridin-4-yl)oxy)naphthalen-1-yl)ureido)-2-methoxyphenyl) methanesulfonamide (see Example 8(i) above; 100 mg, 0.176 mmol), K$_2$CO$_3$ (68.0 mg, 0.492 mmol), and BrettPhos G3 precatalyst (5 mg, 5.52 mol) in DMF (7 mL) was degassed with nitrogen for 10 mins. The reaction was then heated under nitrogen at 85° C. (block temperature) for 2 h. The reaction mixture was concentrated in vacuo and the crude product was purified by preparative HPLC (Varian, Basic (0.1% Ammonium Bicarbonate), Basic, Waters X-Bridge Prep-C18, 5 μm, 19×50 mm column, 20-50% MeCN in Water) to afford the title compound (44 mg) as an off-white solid.

$^1$H NMR (400 MHz, DMSO-d6) δ 9.49 (s, 1H), 9.41 (s, 1H), 9.17 (s, 1H), 8.94 (s, 1H), 8.30 (d, 1H), 8.20-8.18 (m, 2H), 8.13 (d, 1H), 7.85 (dd, 1H), 7.71 (dd, 1H), 7.65-7.59 (m, 2H), 7.54 (d, 1H), 7.41 (d, 1H), 7.30 (dd, 1H), 7.01 (d, 1H), 6.71 (dd, 1H), 6.17 (d, 1H), 4.54 (t, 1H), 3.84 (s, 3H), 3.80 (s, 3H), 3.62-3.59 (m, 2H), 3.54-3.51 (m, 2H), 3.42-3.38 (m, 2H), 3.32-3.27 (m, 6H), 3.09 (s, 3H), 1.26 (s, 9H).

LCMS m/z 852 (M+H)$^+$ (ES$^+$); 850 (M−H)$^-$ (ES$^-$)

Example 41

4-((4-((4-(3-(5-(tert-Butyl)-3-(2-hydroxyacetamido)-2-methoxyphenyl)ureido)naphthalen-1-yl)oxy)pyridin-2-yl)amino)-2-methoxy-N-(2-(1-oxidothiomorpholino)ethyl)benzamide

(i) 2-(Benzyloxy)-N-(5-(tert-butyl)-2-methoxy-3-nitrophenyl)acetamide

HATU (2.80 g, 7.36 mmol) was added to a mixture of 5-(tert-butyl)-2-methoxy-3-nitroaniline (1.5 g, 6.69 mmol), 2-(benzyloxy)acetic acid (1.3 g, 7.82 mmol) and Hünig's base (3.50 mL, 20.07 mmol) in DMF (20 mL) and stirred at rt for 72 h. The mixture was partitioned between ether (100 mL) and water (100 mL), the organic layer washed with sat. aq NaHCO$_3$ (50 mL), brine (50 mL), dried (MgSO$_4$), filtered and evaporated under reduced pressure. The residue was purified by chromatography on silica gel (80 g column, 0-20% EtOAc/isohexane) to afford the sub-title compound (1.99 g) as a yellow oil.

$^1$H NMR (400 MHz, CDCl$_3$) δ 9.14 (s, 1H), 8.81 (s, 1H), 7.62 (s, 1H), 7.45-7.36 (m, 5H), 4.72 (s, 2H), 4.19 (s, 2H), 3.86 (s, 3H), 1.36 (s, 9H).

LCMS m/z 373 (M+H)$^+$ (ES$^+$); 371 (M−H)$^-$ (ES$^-$)

(ii) N-(3-Amino-5-(tert-butyl)-2-methoxyphenyl)-2-(benzyloxy)acetamide

A mixture of the product from step (i) above (1.9 g, 5.10 mmol), Fe powder (2.5 g, 44.8 mmol) and NH$_4$Cl (0.082 g, 1.531 mmol) in EtOH (25 mL) and water (7 mL) was heated at 80° C. for 2 h. The mixture was filtered through celite and evaporated under reduced pressure. The residue was partitioned between EtOAc (80 mL) and sat aq NaHCO$_3$ (50 mL), the organic layer washed with brine (50 mL), dried (MgSO$_4$), filtered and evaporated to afford the sub-title compound (1.75 g) as an oil.

LCMS m/z 343 (M+H)$^+$ (ES$^+$); 341 (M−H)$^-$ (ES$^-$)

(iii) Phenyl (3-(2-(benzyloxy)acetamido)-5-(tert-butyl)-2-methoxyphenyl)carbamate Phenyl chloroformate (200 μL, 1.594 mmol) was added to a mixture of the product from step (ii) above (500 mg, 1.460 mmol) and NaHCO$_3$ (370 mg, 4.40 mmol) in DCM (6 mL) and THF (3 mL). The mixture was stirred for 3 h then partitioned between DCM (50 mL) and water (40 mL), the organic layer was washed with brine (20 ml), dried (MgSO$_4$), filtered and evaporated under reduced pressure. Used crude in next step.

$^1$H NMR (400 MHz, CDCl$_3$) δ 8.86 (s, 1H), 8.16 (d, 1H), 7.96 (s, 1H), 7.44-7.34 (m, 8H), 7.29-7.20 (m, 3H), 4.71 (s, 2H), 4.17 (s, 2H), 3.76 (s, 3H), 1.31 (s, 9H).

LCMS m/z 463 (M+H)$^+$ (ES$^+$)

(iv) Phenyl (5-(tert-butyl)-3-(2-hydroxyacetamido)-2-methoxyphenyl)carbamate A mixture of the product from step (iii) above (430 mg, 0.930 mmol) and 5% Pd—C (100 mg) in THF (8 mL) was

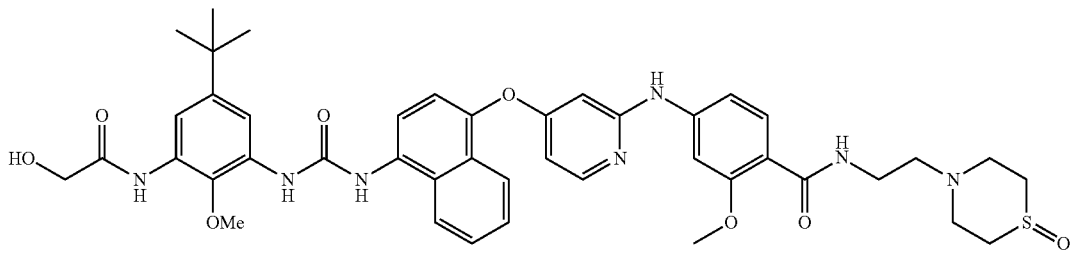 [SMILES: COc1cc(Nc2cc(Oc3ccc(NC(=O)Nc4cc(C(C)(C)C)cc(NC(=O)CO)c4OC)c4ccccc34)ccn2)ccc1C(=O)NCCN1CCS(=O)CC1]

hydrogenated at 4 bar (4×10⁵ Pa) for 3 h. The solution was filtered to afford the sub-title compound as a solution in THF (8 mL) which was used crude in the next step.

LCMS m/z 373 (M+H)⁺ (ES⁺); 371 (M−H)⁻ (ES⁻)

(v) 4-((4-((4-(3-(5-(tert-Butyl)-3-(2-hydroxyacetamido)-2-methoxyphenyl)ureido)naphthalen-1-yl)oxy)pyridin-2-yl)amino)-2-methoxy-N-(2-(1-oxidothiomorpholino)ethyl)benzamide Et₃N (25 μL, 0.179 mmol) and 4-((4-((4-aminonaphthalen-1-yl)oxy)pyridin-2-yl)amino)-2-methoxy-N-(2-(1-oxidothiomorpholino)ethyl)benzamide (see Example 32(iii) above; 254 mg, 0.465 mmol) were added to a solution of the product from step (iv) above (0.465 mmol) in THF (4 mL). The mixture was heated at 60° C. for 24 h then evaporated under reduced pressure. The residue was purified by chromatography on silica gel (40 g column, 0-15% MeOH/DCM) to afford a solid that was triturated with MeCN, filtered and dried to afford the title compound (50 mg) as a white solid.

¹H NMR (400 MHz, DMSO-d6) δ 9.45 (s, 1H), 9.28 (s, 1H), 9.19 (s, 1H), 8.89 (s, 1H), 8.31 (d, 1H), 8.18-8.11 (m, 4H), 7.96 (d, 1H), 7.87 (d, 1H), 7.76 (d, 1H), 7.74-7.70 (m, 1H), 7.64-7.60 (m, 1H), 7.57 (d, 1H), 7.43 (d, 1H), 7.22 (dd, 1H), 6.66 (dd, 1H), 6.20-6.15 (m, 2H), 4.04 (d, 2H), 3.86 (s, 3H), 3.81 (s, 3H), 3.41-3.36 (m, 2H), 2.96-2.84 (m, 4H), 2.75-2.68 (m, 4H), 2.55 (t, 2H), 1.27 (s, 9H).

LCMS m/z 824 (M+H)⁺ (ES⁺); 822 (M−H)⁻ (ES⁻)

Example 42

4-((4-((4-(3-(5-(tert-Butyl)-2-methoxy-3-(methylsulfonamido)phenyl)ureido)naphthalen-1-yl)oxy)pyridin-2-yl)amino)-2-methoxy-N-((2S,3S4R)-2,3,4,5-tetrahydroxypentyl)benzamide

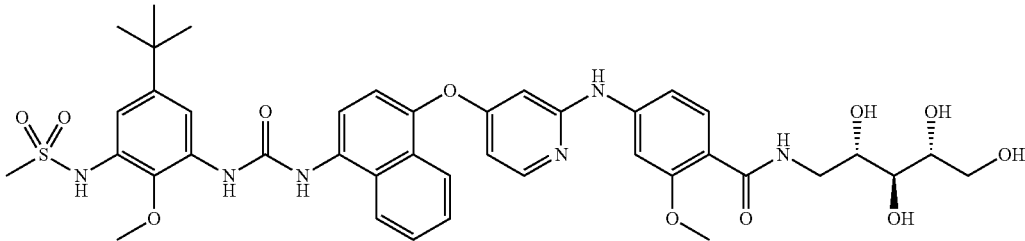 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NC[C@H](O)[C@H](O)[C@H](O)CO]

HATU (80 mg, 0.210 mmol) was added to a stirred solution of 4-((4-((4-(3-(5-(tert-butyl)-2-methoxy-3-(methylsulfonamido)phenyl)ureido)naphthalen-1-yl)oxy)pyridin-2-yl)amino)-2-methoxybenzoic acid, hydrochloride salt (see Example 1 above; 100 mg, 0.136 mmol), (2R,3S,4S)-5-aminopentane-1,2,3,4-tetraol (30 mg, 0.198 mmol) and Hünig's base (120 μL, 0.687 mmol) in NMP (2 mL) at rt. The mixture was stirred for 2 h. The reaction was repeated on a 50 mg scale, combined and diluted with MeOH (2 mL). The mixture was loaded onto a pre-conditioned cartridge of SCX resin. The resin was washed with MeOH then the product released with 1% NH₃ in MeOH. The ammonia solution was concentrated in vacuo affording a pale yellow oil. The crude product was purified by preparative HPLC (Varian, Basic (0.1% Ammonium Bicarbonate), Basic, Waters X-Bridge Prep-C18, 5 μm, 19×50 mm column, 20-50% MeCN in Water) to afford the title compound (42 mg) as a white solid.

¹H NMR (400 MHz, DMSO-d6) δ: 9.41 (s, 1H), 9.28 (s, 1H), 9.16 (s, 1H), 8.93 (s, 1H), 8.26-8.32 (m, 2H), 8.16-8.19 (m, 2H), 8.13 (d, 1H), 7.87 (d, 1H), 7.80 (d, 1H), 7.69-7.73 (m, 1H), 7.57-7.64 (m, 2H), 7.41 (d, 1H), 7.23 (dd, 1H), 7.03 (d, 1H), 6.67 (dd, 1H), 6.16 (d, 1H), 4.96 (d, 1H), 4.86 (d, 1H), 4.70 (d, 1H), 4.40 (t, 1H), 3.85 (s, 3H), 3.81 (s, 3H), 3.65-3.70 (m, 1H), 3.51-3.62 (m, 3H), 3.37-3.43 (m, 2H), 3.26-3.32 (m, 1H), 3.10 (s, 3H), 1.27 (s, 9H).

LCMS m/z 833 (M+H)⁺ (ES⁺)

Example 43

Ethyl (4-((4-((4-(3-(5-(tert-butyl)-2-methoxy-3-(methylsulfonamido)phenyl)ureido)naphthalen-1-yl)oxy)pyridin-2-yl)amino)-2-methoxyphenyl)(methyl)phosphinate

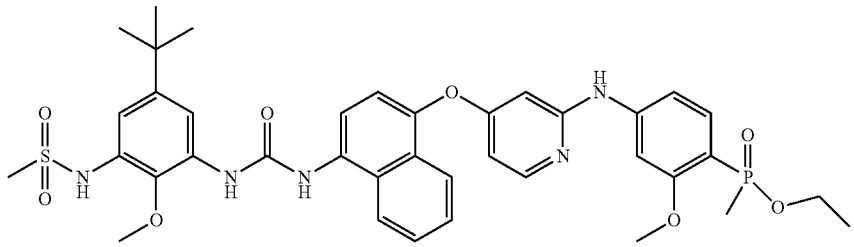 [SMILES: CCOP(C)(=O)c1ccc(Nc2cc(Oc3ccc(NC(=O)Nc4cc(C(C)(C)C)cc(NS(C)(=O)=O)c4OC)c4ccccc34)ccn2)cc1OC]

(i) Ethyl (2-methoxy-4-nitrophenyl)(methyl)phosphinate

Method 1

A mixture of 1-iodo-2-methoxy-4-nitrobenzene (1 g, 3.58 mmol), Et$_3$N (1 mL, 7.17 mmol), Pd(Ph$_3$P)$_4$ (0.166 g, 0.143 mmol) and ethyl methylphosphinate (see, for example, Chebib, M. et al., WO 2006/000043, 5 Jan. 2006; 450 μL, 4.38 mmol) in toluene (15 mL) was degassed with N$_2$ for 5 min the heated at 100° C. for 6 h. The mixture was partitioned between EtOAc (60 mL) and aq 1M HCl (60 mL), the organic layer washed with water (50 mL), dried (MgSO$_4$), filtered and evaporated under reduced pressure. The crude product was purified by chromatography on silica gel (80 g column, 50-100% EtOAc/isohexane) to afford the sub-title compound (224 mg) as a brown solid.

$^1$H NMR (400 MHz, CDCl$_3$) δ 8.18 (dd, 1H), 7.94 (dt, 1H), 7.80 (dd, 1H), 4.14-4.05 (m, 1H), 4.04 (s, 3H), 3.89-3.79 (m, 1H), 1.80 (d, 3H), 1.29 (t, 3H).

LCMS m/z 260 (M+H)$^+$ (ES$^+$)

Method 2

A solution of 1-iodo-2-methoxy-4-nitrobenzene (15 g, 53.8 mmol), DIPEA (30 mL, 172 mmol) and ethyl methylphosphinate (9.51 mL, 64.8 mmol) in toluene (100 mL) was vacuum degassed and back filled with N$_2$ three times. The reaction mixture was warmed to 50° C. XantPhos G3 precatalyst (1 g, 1.056 mmol) was added and the reaction heated under N$_2$ at 85° C. (internal temperature, 100° C. block temperature) for 1 h. The reaction mixture was cooled, preabsorbed onto silica (9.9 g) and purified by chromatography on silica gel (40 g column, 50% EtOAc:isohexane to 100%) to afford the sub-title compound (10 g) as a pale tan solid.

$^1$H NMR (400 MHz, DMSO-d6) δ 8.02 (dd, 1H), 7.94 (dt, 1H), 7.88 (dd, 1H), 4.01 (s, 3H), 3.98-3.85 (m, 1H), 3.81-3.68 (m, 1H), 1.71 (d, 3H), 1.16 (t, 3H).

LCMS m/z 260 (M+H)$^+$ (ES$^+$)

(ii) Ethyl (4-amino-2-methoxyphenyl)(methyl)phosphinate

A mixture of the product from step (i) above (2.6 g, 10.03 mmol) and 5% Pd—C (50 mg) in EtOH (20 mL) was hydrogenated at 5 Bar (5×10$^5$ Pa) for 2 h. The mixture was filtered and the filtrate evaporated under reduced pressure to afford the sub title compound as a pale yellow gum (2.2 g).

$^1$H NMR (400 MHz, DMSO-d6) δ 7.35 (dd, 1H), 6.23-6.18 (m, 2H), 5.79 (s, 2H), 3.81-3.56 (m, 2H), 3.73 (s, 3H), 1.51 (d, 3H), 1.11 (t, 3H).

LCMS m/z 230 (M+H)$^+$ (ES$^+$)

(iii) tert-Butyl (4-((2-((4-(ethoxy(methyl)phosphoryl)-3-methoxyphenyl)amino)pyridin-4-yl)oxy)naphthalen-1-yl)carbamate A mixture of tert-butyl (4-((2-chloropyridin-4-yl)oxy)naphthalen-1-yl)carbamate (see Example 1(i) above; 5 g, 13.48 mmol), the product from step (ii) above (2.6 g, 11.34 mmol), potassium carbonate (6 g, 43.4 mmol), and BrettPhos G3 precatalyst (0.3 g, 0.331 mmol) were degassed under vacuum, back-filling with N$_2$ 3 times. DMF (50 mL) was added and the stirred suspension was degassed under vacuum, back-filling with N$_2$ 3 times. The reaction was then heated under N$_2$ at 85° C. (internal temperature) for 1 h. The mixture was cooled to room temperature and filtered and the solvent evaporated to give a dark oil. The crude product was preabsorbed onto silica (20 g) and purified by chromatography on silica gel 120 g column, 2% MeOH:DCM to 5%) to afford the sub-title compound (6.35 g) as a pale tan glass.

$^1$H NMR (400 MHz, DMSO-d6) δ 9.39 (s, 1H), 9.33 (s, 1H), 8.27-8.11 (m, 2H), 7.84 (d, 1H), 7.65 (d, 1H), 7.63-7.49 (m, 4H), 7.38 (d, 1H), 7.27 (dt, 1H), 6.67 (dd, 1H), 6.15 (d, 1H), 3.87-3.72 (m, 4H), 3.71-3.57 (m, 1H), 1.57 (d, 3H), 1.53 (s, 9H), 1.12 (t, 3H).

LCMS m/z 564 (M+H)$^+$ (ES$^+$)

(iv) Ethyl (4-((4-((4-aminonaphthalen-1-yl)oxy)pyridin-2-yl)amino)-2-methoxyphenyl)(methyl)phosphinate The product from step (iii) above (6.35 g, 10.93 mmol) was dissolved in DCM (50 mL) and TFA (5 mL, 64.9 mmol) added. The reaction mixture was stirred at room temperature for 16 h. The solvents were evaporated and the residue azeotroped with toluene. The crude product was loaded onto a column of SCX (60 g) in MeOH. The column was washed with MeOH and then the product was eluted with 0.7 M ammonia in MeOH. The resultant mixture was concentrated in vacuo to afford the sub-title compound (5 g) as a dark brown glass.

$^1$H NMR (400 MHz, DMSO-d6) δ 9.23 (s, 1H), 8.24-8.13 (m, 1H), 8.11 (d, 1H), 7.71-7.60 (m, 1H), 7.57-7.39 (m, 4H), 7.26 (dt, 1H), 7.11 (d, 1H), 6.72 (d, 1H), 6.61 (dd, 1H), 6.10 (d, 1H), 5.85 (s, 2H), 3.84-3.77 (m, 1H), 3.76 (s, 3H), 3.70-3.56 (m, 1H), 1.56 (d, 3H), 1.11 (t, 3H).

LCMS m/z 464 (M+H)$^+$ (ES$^+$)

257

(v) Ethyl (4-((4-((4-(3-(5-(tert-butyl)-2-methoxy-3-(methylsulfonamido)phenyl)ureido)-naphthalen-1-yl)oxy)pyridin-2-yl)amino)-2-methoxyphenyl)(methyl)phosphinate

Method 1

A suspension of the product from step (ii) above (97 mg, 0.422 mmol), N-(5-(tert-butyl)-3-(3-(4-((2-chloropyridin-4-yl)oxy)naphthalen-1-yl)ureido)-2-methoxyphenyl)methanesulfonamide (see Example 8(i) above; 200 mg, 0.351 mmol), $K_2CO_3$ (136 mg, 0.984 mmol), and BrettPhos G3 precatalyst (10 mg, 0.011 mmol) in DMF (7 mL) was degassed with nitrogen for 10 mins. The reaction was then heated under nitrogen at 85° C. (block temperature) for 2 h. The reaction was cooled to rt and added to water (10 mL). The organic layer was extracted with DCM (10 mL), dried via a hydrophobic phase separator and concentrated in vacuo. The crude product was purified by chromatography on the Companion (4 g column, 1-8% MeOH in DCM) to afford a tan thin film (54 mg). The aqueous layer was further extracted with 10% MeOH in DCM (10 mL), dried via a hydrophobic phase separator and concentrated in vacuo. Both fractions (column and second extraction) were combined to afford the title compound (94 mg) as a tan thin film.

LCMS m/z 762 (M+H)$^+$ (ES$^+$); 76% purity @ 254 nm.

258

Method 2

Triethylamine (300 µL, 2.152 mmol) was added to a warm solution of phenyl (5-(tert-butyl)-2-methoxy-3-(methylsulfonamido)phenyl)carbamate (see Example 1(iv) above; 5 g, 12.74 mmol) and the product from step (iv) above (5 g, 10.25 mmol) in THF (50 mL) at 75° C. (block temperature) and the mixture stirred for 16 h. The solvents were evaporated and the crude product was purified by chromatography on silica gel (120 g column, 2% MeOH:DCM to 5%) to afford a pale tan glass. This material was stirred in THF (100 mL) for 16 h. The resulting solid was filtered off and washed with ice cold THF (5 mL) to yield the title compound (4.88 g).

$^1$H NMR (400 MHz, DMSO-d6) δ 9.40 (s, 1H), 9.30 (s, 1H), 9.14 (s, 1H), 8.92 (s, 1H), 8.30 (d, 1H), 8.24-8.03 (m, 3H), 7.87 (d, 1H), 7.71 (t, 1H), 7.62 (t, 1H), 7.57-7.45 (m, 2H), 7.40 (d, 1H), 7.27 (dt, 1H), 7.03 (d, 1H), 6.66 (dd, 1H), 6.17 (d, 1H), 3.90-3.71 (m, 7H), 3.71-3.56 (m, 1H), 3.10 (s, 3H), 1.56 (d, 3H), 1.27 (s, 9H), 1.11 (t, 3H).

LCMS m/z 762 (M+H)$^+$ (ES$^+$)

Example 44

(4-((4-((4-(3-(5-(tert-Butyl)-2-methoxy-3-(methylsulfonamido)phenyl)ureido)naphthalen-1-yl)oxy)pyridin-2-yl)amino)-2-methoxyphenyl)(methyl)phosphinic acid

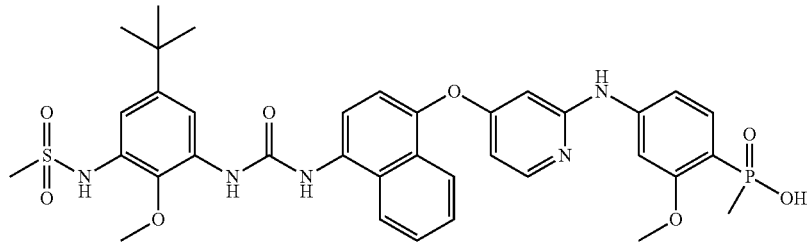 [SMILES: COc1cc(Nc2cc(Oc3ccc(NC(=O)Nc4cc(C(C)(C)C)cc(NS(C)(=O)=O)c4OC)c4ccccc34)ccn2)ccc1P(C)(=O)O]

Method 1

A solution of ethyl (4-((4-((4-(3-(5-(tert-butyl)-2-methoxy-3-(methylsulfonamido)phenyl)-ureido)naphthalen-1-yl)oxy)pyridin-2-yl)amino)-2-methoxyphenyl)(methyl)phosphinate (see Example 43 above; 94 mg, 0.091 mmol) in 1,4-dioxane (0.5 mL) was stirred with aq. 1M NaOH (913 µL, 0.091 mmol) at rt. After 4 hours, another aliquot of NaOH was added (250 µL, 1M), and stirred overnight (18 hours) at rt. The reaction mixture was heated at 45° C. for 48 hours then concentrated in vacuo. The crude product was purified by preparative HPLC (Varian, Basic (0.1% Ammonium Bicarbonate), Basic, Waters X-Bridge Prep-C18, 5 µm, 19×50 mm column, 20-50% MeCN in Water) to afford the title compound (13 mg) as a colourless powder.

$^1$H NMR (of ammonium salt; 400 MHz, DMSO-d6) δ 9.78 (bs, 1H), 9.15 (s, 1H), 9.09 (s, 1H), 8.33 (d, 1H), 8.16-8.08 (m, 3H), 7.82 (d, 1H), 7.63-7.47 (m, 3H), 7.37 (d, 1H), 7.25 (d, 1H), 7.11 (d, 1H), 7.00 (d, 1H), 6.60 (dd, 1H), 6.08 (d, 1H), 3.79 (s, 3H), 3.63 (s, 3H), 3.07 (s, 3H), 1.33 (d, 3H), 1.25 (s, 9H).

LCMS (of ammonium salt) m/z 734 (M+H)$^+$ (ES$^+$); 732 (M−H)$^-$ (ES$^-$)

Method 2

A suspension of ethyl (4-((4-((4-(3-(5-(tert-butyl)-2-methoxy-3-(methylsulfonamido)phenyl)-ureido)naphthalen-1-yl)oxy)pyridin-2-yl)amino)-2-methoxyphenyl)(methyl)phosphinate (4.88 g, 6.28 mmol) in 1,4-dioxane (75 mL) and water (8 mL) was stirred with sodium hydroxide 50% w/w (0.5 mL, 9.47 mmol) at 45° C. for 16 h. Analysis by LCMS showed 30% conversion. More sodium hydroxide 50% w/w (0.25 mL, 4.74 mmol) was added and heating continued to 48 h. The reaction was cooled and acetic acid (0.75 mL, 13.10 mmol) was added. The solvents were evaporated and the residue purified by chromatography on reverse phase C18 (88 g column, 15%-75% MeCN: 10 mmol ammonium bicarbonate soln.) to afford the title compound as the free acid (4 g).

$^1$H NMR (of free acid; 400 MHz, DMSO-d6) δ 9.44 (s, 1H), 9.22 (s, 1H), 9.13 (s, 2H), 8.94 (s, 1H), 8.31 (d, 1H), 8.19 (d, 1H), 8.16 (d, 1H), 8.12 (d, 1H), 7.87 (d, 1H), 7.76-7.65 (m, 1H), 7.65-7.57 (m, 1H), 7.51 (dd, 1H), 7.45-7.33 (m, 2H), 7.23 (dt, 1H), 7.03 (d, 1H), 6.64 (dd, 1H), 6.15 (d, 1H), 3.81 (s, 3H), 3.74 (s, 3H), 3.10 (s, 3H), 1.47 (d, 3H), 1.27 (s, 9H).

LCMS (of free acid) m/z 734 (M+H)$^+$ (ES$^+$)

The title compound (505 mg, 0.688 mmol) was suspended in water (5 mL). Sodium hydroxide 0.1 N (6 mL, 0.614 mmol) was added but an homogeneous solution was not obtained. 0.7N NH$_3$ in MeOH (10 mL) was added and the resulting solution evaporated to a volume of circa 5 mL. This solution was loaded onto a column of Dowex 50WX2 Na$^+$ form (50 g) and the column was washed with water (100 mL) to elute the title compound as the sodium salt.

$^1$H NMR (of sodium salt; 400 MHz, DMSO-d6) δ 10.61 (s, 1H), 9.75 (s, 1H), 9.16 (s, 1H), 8.95 (s, 1H), 8.49 (d, 1H), 8.20-7.97 (m, 3H), 7.75 (d, 1H), 7.58 (dd, 1H), 7.52-7.38 (m, 2H), 7.33 (d, 1H), 7.16-6.87 (m, 3H), 6.59 (dd, 1H), 5.99 (d, 1H), 3.80 (s, 3H), 3.44 (s, 3H), 3.00 (s, 3H), 1.45-1.03 (m, 12H).

LCMS (of sodium salt) m/z 734 (M+H)$^+$ (ES$^+$)

Example 45

N-(5-(tert-Butyl)-3-(3-(4-((2-((4-((3-hydroxy-2,2-bis(hydroxymethyl)propyl)sulfonyl)-3-methoxyphenyl)amino)pyridin-4-yl)oxy)naphthalen-1-yl)ureido)-2-methoxyphenyl)-methanesulfonamide

(i) 2-(Hydroxymethyl)-2-(((2-methoxy-4-nitrophenyl)thio)methyl)propane-1,3-diol A mixture of 2-methoxy-4-nitrobenzenethiol (950 mg, 5.13 mmol), K$_2$CO$_3$ (850 mg, 6.15 mmol) and 2-(bromomethyl)-2-(hydroxymethyl)propane-1,3-diol (1225 mg, 6.16 mmol) in DMF (10 mL) was heated at 90° C. for 12 h. The mixture was cooled and partitioned between EtOAc (80 mL) and water (80 mL), the organic layer separated, dried (MgSO$_4$) and filtered. The MgSO$_4$ cake was washed with DCM (100 mL) and the combined filtrate evaporated under reduced pressure. The residue was triturated with ether (40 mL) and filtered to afford the sub-title compound (810 mg) as a yellow solid.

$^1$H NMR (400 MHz, DMSO-d6) δ 7.90 (dd, 1H), 7.70 (d, 1H), 7.48 (d, 1H), 4.57 (t, 3H), 3.99 (s, 3H), 3.44 (d, 6H), 2.99 (s, 2H).

LCMS m/z 326 (M+Na)$^+$ (ES$^+$)

(ii) 2-(Hydroxymethyl)-2-(((2-methoxy-4-nitrophenyl)sulfonyl)methyl)propane-1,3-diol mCPBA (1625 mg, 6.59 mmol) was added portionwise to a suspension of the product from step (i) above (800 mg, 2.64 mmol) in DCM (20 mL). The resulting solution was stirred at rt for 4 h, evaporated to ~10 mL then purified by chromatography on silica gel (80 g column, 0-10% MeOH/DCM) to afford the sub-title compound (638 mg) as a white solid.

LCMS m/z 336 (M+H)$^+$ (ES$^+$)

(iii) 2-(((4-Amino-2-methoxyphenyl)sulfonyl)methyl)-2-(hydroxymethyl)propane-1,3-diol A mixture of the product from step (ii) above (630 mg, 1.879 mmol) and 5% Pd—C (100 mg) in THF (4 mL) and EtOH (4 mL) was hydrogenated at 2 bar (2×10$^5$ Pa) for 3 days. The mixture was filtered and the solvent evaporated to afford the sub-title compound (540 mg) as a sticky solid.

LCMS m/z 306 (M+H)$^+$ (ES$^+$)

(iv) N-(5-(tert-Butyl)-3-(3-(4-((2-((4-((3-hydroxy-2,2-bis(hydroxymethyl)propyl)sulfonyl)-3-methoxyphenyl)amino)pyridin-4-yl)oxy)naphthalen-1-yl)ureido)-2-methoxyphenyl)-methanesulfonamide A suspension of the product from step (iii) above (107 mg, 0.351 mmol), N-(5-(tert-butyl)-3-(3-(4-((2-chloropyridin-4-yl)oxy)naphthalen-1-yl)ureido)-2-methoxyphenyl)methanesulfonamide (see Example 8(i) above; 200 mg, 0.351 mmol), K$_2$CO$_3$ (136 mg, 0.984 mmol), and BrettPhos G3 precatalyst (10 mg, 0.011 mmol) in DMF (7 mL) was degassed with nitrogen for 10 mins. The reaction was then heated under nitrogen at 85° C. (block temperature) for 2 h.

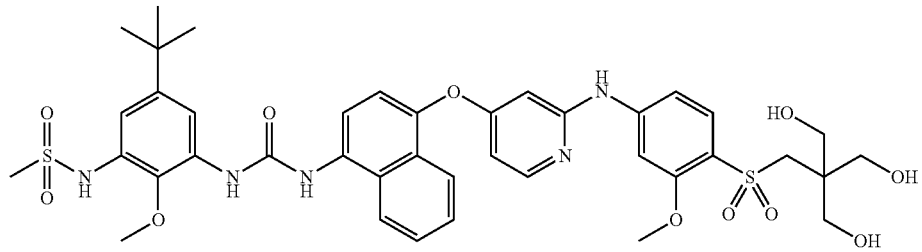 [SMILES: COc1cc(Nc2cc(Oc3ccc(NC(=O)Nc4cc(C(C)(C)C)cc(NS(C)(=O)=O)c4OC)c4ccccc34)ccn2)ccc1S(=O)(=O)CC(CO)(CO)CO]

The reaction mixture was concentrated in vacuo and the crude product was purified by preparative HPLC (Varian, Basic (0.1% Ammonium Bicarbonate), Basic, Waters X-Bridge Prep-C18, 5 μm, 19×50 mm column, 20-50% MeCN in Water) to afford a pale tan foam. The product was purified by chromatography on the Companion (4 g column, 1-10% MeOH in DCM, product elutes at 8%) to afford the title compound (103 mg) as a colourless powder.

$^1$H NMR (400 MHz, DMSO-d6) δ 9.47 (s, 1H), 9.40 (s, 1H), 9.14 (s, 1H), 8.92 (s, 1H), 8.30 (d, 1H), 8.20-8.18 (m, 2H), 8.12 (d, 1H), 7.86 (d, 1H), 7.71 (dd, 1H), 7.64-7.59 (m, 2H), 7.56 (d, 1H), 7.40 (d, 1H), 7.31 (dd, 1H), 7.02 (d, 1H), 6.70 (dd, 1H), 6.18 (d, 1H), 4.34 (t, 3H), 3.84 (s, 3H), 3.81 (s, 3H), 3.44-3.43 (m, 8H), 3.09 (s, 3H), 1.26 (s, 9H).

LCMS m/z 838 (M+H)$^+$ (ES$^+$); 836 (M−H)$^−$ (ES$^−$)

Example 46

4-[[4-[[4-[[5-tert-Butyl-3-(methanesulfonamido)-2-methoxyphenyl]carbamoylamino]-1-naphthyl]oxy]-2-pyridyl]amino]-2,6-dimethoxybenzoic acid

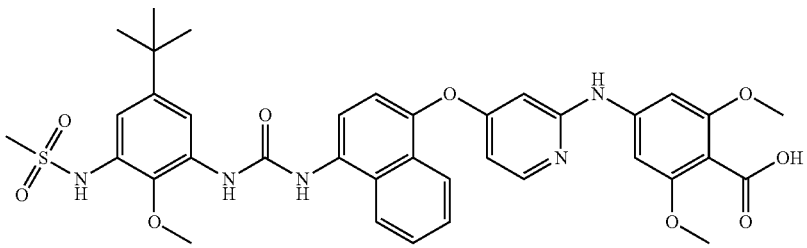

(i) Benzyl 3-bromo-2,6-dimethoxybenzoate

Benzyl bromide (5 mL, 42.0 mmol) was added to a thick suspension of 3-bromo-2,6-dimethoxybenzoic acid (9.4 g, 36.0 mmol) and K$_2$CO$_3$ (20 g, 145 mmol) in DMF (300 mL). The mixture was heated at 70° C. (block temperature 55° C. internal) for 2 h. The reaction mixture was concentrated in vacuo to circa 20 mL then partitioned between diethyl ether (500 mL) and 20% w/w NaCl soln. (250 mL). The organics were separated, and washed successively with a 10% vol/vol solution of 880 ammonia in water (250 mL) 1 N HCl (250 mL) and sat. NaHCO$_3$ (250 mL). The organics were separated, dried (MgSO$_4$), filtered and evaporated to afford the sub-title compound (12 g).

$^1$H NMR (400 MHz, DMSO-d6) δ 7.68 (d, 1H), 7.52-7.28 (m, 5H), 6.90 (d, 1H), 5.35 (s, 2H), 3.79 (s, 3H), 3.70 (s, 3H).

LCMS m/z 351/353 (M+H)$^+$ (ES$^+$); BP 373/375 (M+Na)$^+$ (ES$^+$)

(ii) Benzyl 4-amino-2,6-dimethoxybenzoate

Sodium (4.5 g, 196 mmol) was added portionwise to a solution of iron(III) chloride (50 mg, 0.308 mmol) in liquid ammonia (150 mL) over circa 20 min. The dark grey suspension was stirred at reflux for 10 minutes then cooled to −70° C. before dropwise addition of the product from step (i) above (16 g, 45.6 mmol) in THF (50 mL) over 5 min. The reaction mixture was then allowed to reflux (circa −30° C.) for 90 minutes before cooling to −50° C. and addition of NH$_4$Cl (12 g, 224 mmol). The condenser was removed and the reaction allowed to evaporate overnight. The residue was partitioned between 1 N HCl (200 mL) and Et$_2$O (250 mL). The desired product as the hydrochloride salt was found in both layers. The aqueous was separated and basified with NaOH (10 mL, 189 mmol) to pH 8 then partitioned with Et$_2$O (300 mL). The organics were separated and bulked with the first Et$_2$O extract and washed with sat. NaHCO$_3$. The organics were separated, dried (MgSO$_4$), filtered and evaporate to a brown oil. The crude product was purified by chromatography on silica gel (120 g column, 10% EtOAc: isohexane to 50%) to afford the sub-title compound (8 g) as a tan solid.

$^1$H NMR (400 MHz, DMSO-d6) δ 7.44-7.28 (m, 5H), 5.86 (s, 2H), 5.55 (s, 2H), 5.18 (s, 2H), 3.65 (s, 6H).

LCMS m/z 288 (M+H)$^+$ (ES$^+$)

(iii) Benzyl 4-((4-((4-((tert-butoxycarbonyl)amino)naphthalen-1-yl)oxy)pyridin-2-yl)amino)-2,6-dimethoxybenzoate BrettPhos G3 Precatalyst (1.5 g, 1.655 mmol) was added to a degassed mixture of tert-butyl (4-((2-chloropyridin-4-yl)oxy)naphthalen-1-yl)carbamate (see Example 1(i) above; 11.82 g, 31.9 mmol), the product from step (ii) above (9.16 g, 31.9 mmol) and K$_2$CO$_3$ (8.81 g, 63.8 mmol) in DMF (150 mL). The mixture was heated at 85° C. for 3 h. The reaction was cooled and partitioned between EtOAc (400 mL) and water (400 mL). The organic layer was washed with water (2×400 mL) and brine (400 mL), then dried (MgSO$_4$), filtered and concentrated in vacuo, affording a brown foam. The crude product was purified by chromatography on silica gel (220 g column, 20-50% EtOAc/isohexane) to afford the sub-title compound (17.7 g) as an orange foam.

LCMS m/z 622 (M+H)$^+$ (ES$^+$)

(iv) Benzyl 4-((4-((4-aminonaphthalen-1-yl)oxy)pyridin-2-yl)amino)-2,6-dimethoxybenzoate TFA (22 mL, 286 mmol) was added to a solution of the product from step (iv) above (17.7 g, 28.5 mmol) in DCM (250 mL) and the reaction stirred overnight. The reaction was concentrated in vacuo affording a dark red oil. The oil was dissolved in DCM (300 mL) and washed with sat. aq. NaHCO$_3$ solution. The aqueous phase was extracted with DCM (100 mL) and the combined organics were dried via hydrophobic frit and concentrated in vacuo, affording the sub-title compound (14.5 g) as a brown foam.

1H NMR (400 MHz, DMSO-d6) δ: 9.10 (s, 1H), 8.15-8.17 (m, 1H), 8.10 (d, 1H), 7.62-7.64 (m, 1H), 7.44-7.46 (m, 2H), 7.36-7.40 (m, 4H), 7.31-7.33 (m, 1H), 7.11 (d, 1H), 7.00 (s, 2H), 6.72 (d, 1H), 6.59 (dd, 1H), 6.07 (d, 1H), 5.87 (s, 2H), 5.23 (s, 2H), 3.65 (s, 6H).

LCMS m/z 522 (M+H)$^+$ (ES$^+$)

(v) Benzyl 4-((4-((4-(3-(5-(tert-butyl)-2-methoxy-3-(methylsulfonamido)phenyl)ureido)-naphthalen-1-yl)oxy)pyridin-2-yl)amino)-2,6-dimethoxybenzoate Method 1

BrettPhos G3 Precatalyst (200 mg, 0.221 mmol) was added to a degassed mixture of N-(5-(tert-butyl)-3-(3-(4-

((2-chloropyridin-4-yl)oxy)naphthalen-1-yl)ureido)-2-methoxyphenyl)-methanesulfonamide (see Example 8(i) above; 2.15 g, 3.78 mmol), the product from step (ii) above (1.3 g, 4.52 mmol) and K$_2$CO$_3$ (1.05 g, 7.60 mmol) in DMF (30 mL). The mixture was heated at 85° C. for 2 h then partitioned between EtOAc (300 mL) and 10% brine solution (300 mL). The organic layer was separated, washed with water (200 mL), dried (MgSO$_4$), filtered and evaporated under reduced pressure. The crude product was purified by chromatography on silica gel (120 g column, 0-100% EtOAc/isohexane) to afford the sub-title compound (1.495 g) as a foam.

$^1$H NMR (400 MHz, DMSO-d6) δ 9.40 (s, 1H), 9.17 (s, 1H), 9.15 (s, 1H), 8.92 (s, 1H), 8.30 (d, 1H), 8.19 (d, 1H), 8.15 (d, 1H), 8.13 (d, 1H), 7.86 (d, 1H), 7.73-7.69 (m, 1H), 7.63-7.59 (m, 1H), 7.41-7.29 (m, 6H), 7.03-7.01 (m, 3H), 6.64 (dd, 1H), 6.14 (d, 1H), 5.22 (s, 2H), 3.81 (s, 3H), 3.67 (s, 6H), 3.10 (s, 3H), 1.27 (s, 9H).

LCMS m/z 820 (M+H)$^+$ (ES$^+$)

Method 2

Triethylamine (1 mL, 7.17 mmol) was added to a solution of phenyl (5-(tert-butyl)-2-methoxy-3-(methylsulfonamido)phenyl)carbamate (see Example 1(iv) above; 11.2 g, 28.5 mmol) and the product from step (iv) above (14.5 g, 26.7 mmol) in 2-Me-THF (300 mL) at 80° C. and the mixture stirred for 24 h. The reaction was cooled to rt and concentrated in vacuo. The crude product was purified by chromatography on the Companion (220 g column, 30-80% EtOAc in hexane) to afford the sub-title compound (18.9 g) as a pink foam.

$^1$H NMR (400 MHz, DMSO-d6) δ: 9.40 (s, 1H), 9.17 (s, 1H), 9.15 (s, 1H), 8.92 (s, 1H), 8.30 (d, 1H), 8.20 (d, 1H), 8.12-8.16 (m, 2H), 7.87 (d, 1H), 7.69-7.73 (m, 1H), 7.59-7.63 (m, 1H), 7.36-7.41 (m, 5H), 7.29-7.33 (m, 1H), 7.02-7.03 (m, 3H), 6.64 (dd, 1H), 6.14 (d, 1H), 5.23 (s, 2H), 3.81 (s, 3H), 3.67 (s, 6H), 3.10 (s, 3H), 1.27 (s, 9H).

LCMS m/z 820 (M+H)$^+$ (ES$^+$)

(vii) 4-[[4-[[4-[[5-tert-Butyl-3-(methanesulfonamido)-2-methoxyphenyl]carbamoylamino]-1-naphthyl]oxy]-2-pyridyl]amino]-2,6-dimethoxybenzoic acid Method 1

A mixture of the product from step (iii) above (1.485 g, 1.811 mmol) and 5% Pd/C (200 mg) in THF (10 mL) and EtOH (10 mL) was hydrogenated at 4 bar (4×10$^5$ Pa) for 20 h. A further portion of 5% Pd/C (200 mg) was added and the mixture hydrogenated at 5 bar (5×10$^5$ Pa) for a further 8 h then at 2 bar (2×10$^5$ Pa) for 72 h. The mixture was diluted with 1% NH$_3$/MeOH (20 mL) and filtered through Celite. The filtrate was evaporated under reduced pressure and the solid triturated with ether, filtered and dried to afford the title compound (1.27 g) as a solid.

$^1$H NMR (400 MHz, DMSO-d6) δ: 9.42 (s, 1H), 9.06 (s, 1H), 8.92 (s, 1H), 8.30 (d, 1H), 8.10-8.18 (m, 3H), 7.87 (d, 1H), 7.71 (t, 1H), 7.61 (t, 1H), 7.38-7.41 (m, 1H), 6.97-7.03 (m, 3H), 6.61-6.62 (m, 1H), 6.12 (s, 1H), 3.81 (s, 3H), 3.65 (s, 6H), 3.10 (s, 3H), 1.27 (s, 9H).

LCMS m/z 730 (M+H)$^+$ (ES$^+$)

Method 2

A mixture of the product from step (vi) above (18.9 g, 21.21 mmol) and Pd/C (5 wt %, 5.0 g, 2.349 mmol) in THF (100 mL) and EtOH (100 mL) was hydrogenated at 5 Bar (5×10$^5$ Pa) for 20 h. The reaction was filtered through Celite, washing with MeOH, and the filtrate concentrated in vacuo, affording the title compound (15 g) as a grey solid.

LCMS m/z 730 (M+H)$^+$ (ES$^+$)

Example 47

2-(2-(2-(4-((4-((4-(3-(5-(tert-butyl)-2-methoxy-3-(methylsulfonamido)phenyl)ureido)-naphthalen-1-yl)oxy)pyridin-2-yl)amino)-2,6-dimethoxybenzamido)ethoxy)ethoxy)ethyl dihydrogen phosphate

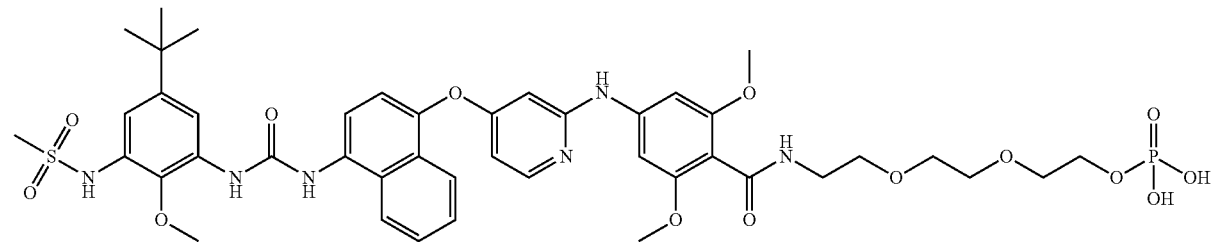 [SMILES: COc1cc(Nc2cc(Oc3ccc(NC(=O)Nc4cc(C(C)(C)C)cc(NS(C)(=O)=O)c4OC)c4ccccc34)ccn2)cc(OC)c1C(=O)NCCOCCOCCOP(=O)(O)O]

Route 1

(i) Di-tert-butyl (2-(2-(2-(4-((4-((4-(3-(5-(tert-butyl)-2-methoxy-3-(methylsulfonamido)phenyl)ureido)naphthalen-1-yl)oxy)pyridin-2-yl)amino)-2,6-dimethoxybenzamido)ethoxy)ethoxy)-ethyl) phosphate HATU (0.788 g, 2.072 mmol) was added to a stirred solution of 4-[[4-[[4-[[5-tert-butyl-3-(methanesulfonamido)-2-methoxyphenyl]carbamoylamino]-1-naphthyl]oxy]-2-pyridyl]amino]-2,6-dimethoxybenzoic acid (see Example 46 above; 1.26 g, 1.727 mmol), 2-(2-(2-aminoethoxy)ethoxy)ethyl di-tert-butyl phosphate (see Example 19(ii) above; 2.68 mmol) and Hünig's base (0.8 mL, 4.58 mmol) in DMF (20 mL). The mixture was stirred for 3 h then a further portion of Hünig's base (0.8 mL, 4.58 mmol) and HATU (0.788 g, 2.072 mmol) were added, stirred for 2 h then partitioned between EtOAc (200 mL) and water (150 mL). The organic layer was separated, washed with sat aq NaHCO$_3$ soln (100 mL), brine (100 mL), dried (MgSO$_4$), filtered and evaporated under reduced pressure. The crude product was purified by chromatography on silica gel (80 g column, 0-10% MeOH/DCM) to afford the sub-title compound (240 mg) as a foam.

$^1$H NMR (400 MHz, DMSO-d6) δ 9.40 (s, 1H), 9.15 (s, 1H), 9.03 (s, 1H), 8.92 (s, 1H), 8.30 (d, 1H), 8.19 (d, 1H), 8.14 (d, 1H), 8.12 (d, 1H), 7.87 (d, 1H), 7.83 (t, 1H), 7.71 (t, 1H), 7.61 (t, 1H), 7.39 (d, 1H), 7.02 (d, 1H), 6.94 (s, 2H), 6.61 (dd, 1H), 6.10 (d, 1H), 3.95-3.91 (m, 2H), 3.81 (s, 3H), 3.61 (s, 6H), 3.60-3.57 (m, 2H), 3.54 (s, 4H), 3.44 (t, 2H), 3.28-3.23 (m, 2H), 3.10 (s, 3H), 1.40 (s, 18H), 1.27 (s, 9H).

LCMS m/z 1053 (M+H)$^+$ (ES$^+$); 75% purity @ 254 nm.

(ii) 2-(2-(2-(4-((4-((4-(3-(5-(tert-Butyl)-2-methoxy-3-(methylsulfonamido)phenyl)ureido)-naphthalen-1-yl)oxy)pyridin-2-yl)amino)-2,6-dimethoxybenzamido)ethoxy)ethoxy)ethyl dihydrogen phosphate TFA (500 µL, 6.49 mmol) was added to a solution of the product from step (i) above (230 mg, 0.164 mmol) in DCM (5 mL) and the mixture stirred for 1 h. The solvent was evaporated and the residue loaded onto a column of SCX in MeCN. The column was washed with MeOH and then the product was eluted with 0.7 M ammonia in MeOH. The filtrate was concentrated in vacuo to afford a foam that was triturated with MeCN, filtered and dried to give a solid. The solid was purified by preparative HPLC (Varian, Basic (0.1% Ammonium Bicarbonate), Basic, Waters X-Bridge Prep-C18, 5 µm, 19×50 mm column, 20-50% MeCN in Water) to afford the title compound as the ammonium salt (72 mg) as a colourless solid.

$^1$H NMR (of ammonium salt; 400 MHz, DMSO-d6) δ 9.58 (s, 1H), 9.05 (s, 2H), 8.36 (d, 1H), 8.17 (d, 1H), 8.16-8.10 (m, 2H), 7.91-7.82 (m, 2H), 7.73-7.65 (m, 1H), 7.64-7.56 (m, 1H), 7.38 (d, 1H), 7.02 (d, 1H), 6.86 (s, 2H), 6.62 (dd, 1H), 6.12 (d, 1H), 3.87-3.73 (m, 5H), 3.57 (s, 6H), 3.55-3.49 (m, 6H), 3.44 (t, 2H), 3.25 (q, 2H), 3.09 (s, 3H), 1.27 (s, 9H).

LCMS (of ammonium salt) m/z 941 (M+H)$^+$ (ES$^+$)

Route 2

(A) Dibenzyl (2-(2-(2-(4-((4-((4-(3-(5-(tert-butyl)-2-methoxy-3-(methylsulfonamido)phenyl)-ureido)naphthalen-1-yl)oxy)pyridin-2-yl)amino)-2,6-dimethoxybenzamido)ethoxy)ethoxy)-ethyl) phosphate Dibenzyl diisopropylphosphoramidite (4.00 mL, 11.93 mmol) was added dropwise to a solution of 4-((4-((4-(3-(5-(tert-butyl)-2-methoxy-3-(methylsulfonamido)phenyl)ureido)naphthalen-1-yl)oxy)pyridin-2-yl)amino)-N-(2-(2-(2-hydroxyethoxy)ethoxy)ethyl)-2,6-dimethoxybenzamide (see Example 36 above; 5.44 g, 5.94 mmol) and 5-methyl-1H-tetrazole (1.75 g, 20.81 mmol) in a mixture of THF (15 mL) and DMF (45 mL) and the mixture stirred at rt for 22 h. The reaction was cooled to 0° C. and H$_2$O$_2$ (3.00 mL, 26.4 mmol) added. The reaction was warmed to rt and stirring continued for 1 h. The reaction was partitioned between EtOAc (300 mL) and water (300 mL). The organic phase was washed with saturated sodium bisulfite solution (150 mL), sat aq. NaHCO$_3$ solution (150 mL) and brine (150 mL), then dried (MgSO$_4$), filtered and concentrated in vacuo, affording a pale yellow foam. The crude product was purified by chromatography on the Companion (220 g column, 1-8% MeOH in DCM) to afford the sub-title compound (5.69 g) as an off-white foam.

$^1$H NMR (400 MHz, DMSO-d6) δ: 9.39 (s, 1H), 9.14 (s, 1H), 9.02 (s, 1H), 8.92 (s, 1H), 8.30 (d, 1H), 8.20 (d, 1H), 8.11-8.14 (m, 2H), 7.87 (d, 1H), 7.81 (t, 1H), 7.69-7.73 (m, 1H), 7.59-7.63 (m, 1H), 7.33-7.40 (m, 11H), 7.03 (d, 1H), 6.94 (s, 2H), 6.61 (dd, 1H), 6.12 (d, 1H), 5.04 (d, 4H), 4.05-4.09 (m, 2H), 3.81 (s, 3H), 3.57-3.63 (m, 8H), 3.52 (s, 4H), 3.42 (t, 2H), 3.24 (q, 2H), 3.10 (s, 3H), 1.27 (s, 9H).

LCMS m/z 1121 (M+H)$^+$ (ES$^+$); 561 (M+2H)$^{2+}$ (ES$^+$)

(B) 2-(2-(2-(4-((4-((4-(3-(5-(tert-Butyl)-2-methoxy-3-(methylsulfonamido)phenyl)ureido)-naphthalen-1-yl)oxy)pyridin-2-yl)amino)-2,6-dimethoxybenzamido)ethoxy)ethoxy)ethyl dihydrogen phosphate

Method 1

A solution of sodium bicarbonate (837 mg, 9.96 mmol) in water (30 mL) was added to a mixture of the product from step (A) above (5.69 g, 4.97 mmol) and Pd/C (5 wt %, 2.3 g, 1.081 mmol) in MeOH (150 mL) and THF (50 mL). The mixture was hydrogenated at 5 Bar (5×10$^5$ Pa) over the weekend. Additional Pd/C (500 mg) was added and stirring continued under H$_2$ overnight. Additional Pd/C (700 mg) was added and stirring continued under H$_2$ for 48 h. The reaction was filtered through celite, washing with MeOH and the filtrate concentrated in vacuo. When most of the organic solvent had been removed, the remaining aqueous solution was azeotroped with MeCN. The resulting solid was further dried at 50° C. in a dessicator overnight, affording the title compound, di-sodium salt (4.65 g) as a beige solid.

$^1$H NMR (of disodium salt; 400 MHz, DMSO-d6) δ: 9.69 (s, 1H), 9.08 (s, 1H), 8.92 (s, 1H), 8.43 (d, 1H), 8.13 (d, 2H), 7.88 (t, 1H), 7.83 (d, 1H), 7.64-7.70 (m, 2H), 7.56-7.60 (m, 1H), 7.35 (d, 1H), 7.03 (d, 1H), 6.82 (s, 2H), 6.63 (d, 1H), 6.13 (d, 1H), 3.79 (s, 3H), 3.73 (m, 2H), 3.54 (s, 6H), 3.42-3.50 (m, 8H), 3.25 (q, 2H), 2.70 (s, 3H), 1.23 (s, 9H).

LCMS (of disodium salt) m/z 941 (M+H)$^+$ (ES$^+$)

Method 2

To a mixture of the product from step (A) above (410 mg, 0.366 mmol) and Pd/C (5 wt %, 50 mg, 0.023 mmol) in EtOH (6 mL) and THF (3 mL) was added NaOH (30 mg, 0.750 mmol) in water (3 mL) and the resulting mixture hydrogenated at 5 Bar (5×10$^5$ Pa) overnight. The reaction was filtered through Celite, washing with MeOH. The filtrate was concentrated in vacuo affording an off-white foam. The solid was dissolved in water (1 mL) and loaded onto a column of Dowex resin (Na$^+$ form, 15 g). The product was eluted with water (25 mL) and the aqueous material lyophilised affording the title compound, mono-sodium salt (300 mg) as a low density white solid.

$^1$H NMR (of mono-sodium salt; 400 MHz, DMSO-d6) δ: 9.44 (s, 1H), 9.15 (s, 1H), 9.04 (s, 1H), 8.95 (s, 1H), 8.31 (d, 1H), 8.19 (d, 1H), 8.11-8.14 (m, 2H), 7.84-7.87 (m, 2H), 7.68-7.72 (m, 1H), 7.59-7.63 (m, 1H), 7.39 (d, 1H), 7.03 (d, 1H), 6.92 (s, 2H), 6.61 (dd, 1H), 6.12 (d, 1H), 3.87 (q, 2H), 3.81 (s, 3H), 3.60 (s, 6H), 3.53-3.57 (m, 6H), 3.45 (t, 2H), 3.26 (q, 2H), 3.10 (s, 3H), 1.27 (s, 9H).

LCMS (of mono-sodium salt) m/z 941 (M+H)$^+$ (ES$^+$)

Example 48

4-((4-((4-(3-(5-(tert-Butyl)-3-(N-(2-hydroxyethyl)methylsulfonamido)-2-methoxyphenyl)-ureido)naphthalen-1-yl)oxy)pyridin-2-yl)amino)-2-methoxy-N-(2-(1-oxidothiomorpholino)-ethyl)benzamide

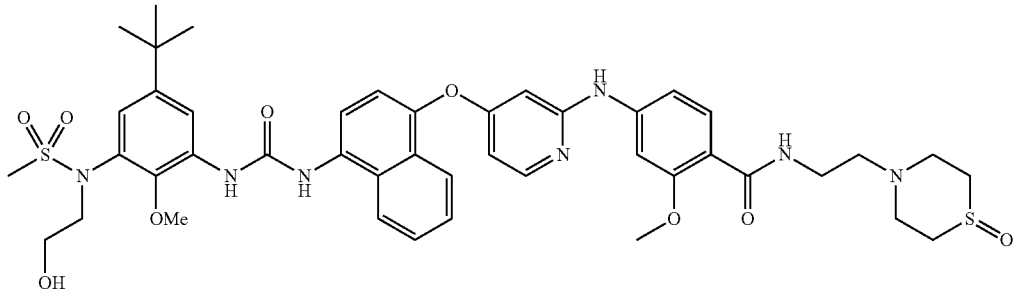 [SMILES: COc1cc(Nc2cc(Oc3ccc(NC(=O)Nc4cc(C(C)(C)C)cc(N(CCO)S(C)(=O)=O)c4OC)c4ccccc34)ccn2)ccc1C(=O)NCCN1CCS(=O)CC1]

(i) N-(2-(Benzyloxy)ethyl)-N-(5-(tert-butyl)-2-methoxy-3-nitrophenyl)methanesulfonamide A mixture of N-(5-(tert-butyl)-2-methoxy-3-nitrophenyl)methanesulfonamide (0.5 g, 1.654 mmol), ((2-bromoethoxy)methyl)benzene (400 mg, 1.860 mmol) and $K_2CO_3$ (0.457 g, 3.31 mmol) in DMF (8 mL) was stirred at rt for 24 h then heated at 50° C. for 48 h. The mixture was partitioned between ether (70 mL) and water (60 mL), the organic layer washed with brine (50 mL), dried ($MgSO_4$), filtered and evaporated under reduced pressure. The residue was purified by chromatography on silica gel (40 g column, 0-30% EtOAc/isohexane) to afford the sub-title compound (618 mg) as a yellow oil.

$^1$H NMR (400 MHz, $CDCl_3$) δ 7.82 (s, 1H), 7.54 (s, 1H), 7.38-7.26 (m, 5H), 4.48 (s, 2H), 3.99 (s, 3H), 3.93 (brs, 2H), 3.52 (t, 2H), 3.14 (s, 3H), 1.32 (s, 9H)

(ii) N-(3-Amino-5-(tert-butyl)-2-methoxyphenyl)-N-(2-(benzyloxy)ethyl)methanesulfonamide A mixture of the product from step (i) above (600 mg, 1.375 mmol), Fe powder (800 mg, 14.33 mmol) and $NH_4Cl$ (30 mg, 0.561 mmol) in THF (15 mL) and water (5 mL) was heated at 70° C. for 2 h. The mixture was filtered through celite and the residue partioned between EtOAc (50 mL) and sat aq $NaHCO_3$ soln (40 mL). The organic layer was washed with brine (40 mL), dried ($MgSO_4$), filtered and evaporated under reduced pressure. The residue was purified by chromatography on silica gel (40 g column, 0-35% EtOAc/isohexane) to afford the sub-title compound (425 mg) as a white solid.

$^1$H NMR (400 MHz, $CDCl_3$) δ 7.38-7.29 (m, 5H), 7.03 (s, 1H), 6.81 (s, 1H), 4.51 (s, 2H), 3.98 (s, 3H), 3.98-3.87 (br m, 2H), 3.49 (t, 2H), 3.16 (s, 3H), 1.28 (s, 9H).

LCMS m/z 407 (M+H)$^+$ (ES$^+$)

(iii) Phenyl (3-(N-(2-(benzyloxy)ethyl)methylsulfonamido)-5-(tert-butyl)-2-methoxyphenyl)-carbamate Phenyl chloroformate (141 μL, 1.123 mmol) was added to a mixture of the product from step (ii) above (415 mg, 1.021 mmol) and $NaHCO_3$ (257 mg, 3.06 mmol) in DCM (10 mL) and THF (5 mL). The mixture was stirred for 18 h then partitioned between DCM (50 mL) and water (50 mL), the organic layer dried ($MgSO_4$) and evaporated under reduced pressure to afford the sub-title compound which was used crude in the next step.

(iv) Phenyl (5-(tert-butyl)-3-(N-(2-hydroxyethyl)methylsulfonamido)-2-methoxyphenyl)-carbamate A mixture of the product from step (iii) above (537 mg, 1.02 mmol) and 5% Pd—C (60 mg) in THF (10 mL) was hydrogenated at 2 Bar for 3 days. The mixture was filtered and the filtrate used crude as a solution in the next step.

LCMS m/z 437 (M+H)$^+$ (ES$^+$); 435 (M−H)$^-$ (ES$^-$)

(v) 4-((4-((4-(3-(5-(tert-Butyl)-3-(N-(2-hydroxyethyl)methylsulfonamido)-2-methoxyphenyl)ureido)naphthalen-1-yl)oxy)pyridin-2-yl)amino)-2-methoxy-N-(2-(1-oxidothiomorpholino)ethyl) benzamide To a stirred solution of the product from step (iv) above (218 mg, 0.499 mmol) in THF (5 mL) was added 4-((4-((4-aminonaphthalen-1-yl)oxy)pyridin-2-yl)amino)-2-methoxy-N-(2-(1-oxidothiomorpholino)ethyl)benzamide (see Example 32(iii) above; 273 mg, 0.499 mmol) and triethylamine (25 μL, 0.179 mmol). The resulting mixture was heated to 60° C. overnight. The mixture was heated at 60° C. for 24 h then evaporated under reduced pressure. The crude product was purified by preparative HPLC (Varian, Basic (0.1% Ammonium Bicarbonate), Basic, Waters X-Bridge Prep-C18, 5 μm, 19×50 mm column, 20-50% MeCN in Water) to afford a beige solid. The crude product was purified by chromatography on the Companion (12 g column, 1-10% MeOH in DCM) to afford the title compound (61 mg) as a white solid.

$^1$H NMR (400 MHz, DMSO-d6) δ: 9.40 (s, 1H), 9.26 (s, 1H), 8.92 (s, 1H), 8.29-8.32 (m, 2H), 8.12-8.17 (m, 3H), 7.87 (d, 1H), 7.76 (d, 1H), 7.69-7.73 (m, 1H), 7.63-7.60 (m, 1H), 7.58 (d, 1H), 7.41 (d, 1H), 7.23 (dd, 1H), 7.03 (d, 1H), 6.67 (dd, 1H), 6.15 (d, 1H), 4.90 (t, 1H), 3.91 (s, 3H), 3.86 (s, 3H), 3.68 (bs, 2H), 3.47 (q, 2H), 3.39 (q, 2H), 3.23 (s, 3H), 2.84-2.97 (m, 4H), 2.68-2.75 (m, 4H), 2.55 (t, 2H), 1.29 (s, 9H).

LCMS m/z 888 (M+H)$^+$ (ES$^+$)

Example 49

Diethyl (4-((4-((4-(3-(5-(tert-butyl)-2-methoxy-3-(methylsulfonamido)phenyl)ureido)-naphthalen-1-yl)oxy)pyridin-2-yl)amino)-2-methoxyphenyl)phosphonate

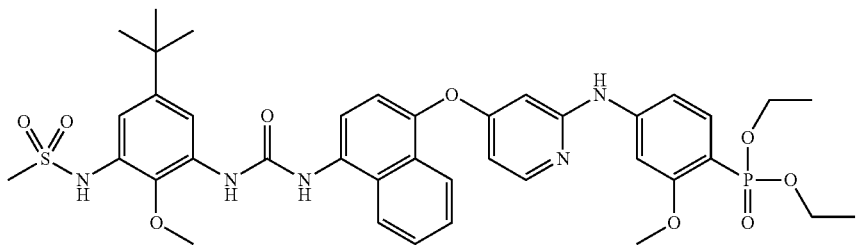 [SMILES: CCOP(=O)(OCC)c1ccc(Nc2cc(Oc3ccc(NC(=O)Nc4cc(C(C)(C)C)cc(NS(C)(=O)=O)c4OC)c4ccccc34)ccn2)cc1OC]

(i) Diethyl (2-methoxy-4-nitrophenyl)phosphonate

1-Iodo-2-methoxy-4-nitrobenzene (1.00 g, 3.58 mmol) was azeotroped with toluene (12 mL) then dissolved in fresh toluene (12 mL) before addition of DIPEA (1.878 mL, 10.75 mmol) and diethyl phosphonate (0.600 mL, 4.66 mmol). The mixture was degassed under vacuum and back filled with nitrogen three times. XantPhos G3 precatalyst (0.102 g, 0.108 mmol) was added and the reaction heated at 100° C. (block temperature), 90° C. (internal temperature), under nitrogen for 2 h. The reaction was cooled and the solvent evaporated to give a brown gum. The crude material was purified by chromatography on silica gel (12 g column, dry load, 50-100% EtOAc/isohexane, product eluted at 70%) to afford the sub-title compound (549 mg) as a waxy brown solid.

$^1$H NMR (400 MHz, CDCl$_3$) δ: 8.02 (dd, 1H), 7.88 (ddd, 1H), 7.79 (dd, 1H), 4.23 (m, 4H), 4.04 (s, 3H), 1.38 (td, 6H).

LCMS m/z 290 (M+H)$^+$ (ES$^+$)

(ii) Diethyl (4-amino-2-methoxyphenyl)phosphonate

A mixture of the product from step (i) above (0.55 g, 1.902 mmol) and 5% Pd/C (50 mg) in EtOH (5 mL) was hydrogenated at 5 Bar (5×10$^5$ Pa) for 16 h. The mixture was filtered, washed with EtOH (2×2 mL) and the filtrate was evaporated under reduced pressure to afford a green solid. The mixture was re-dissolved in EtOH (10 mL), and 5% Pd/C (50 mg) was added followed by conc. HCl (1 drop) and the mixture was hydrogenated at 5 Bar (5×10$^5$ Pa) for 16 h. The mixture was filtered, washed with EtOH (2×2 mL) and the filtrate evaporated under reduced pressure to afford a pale brown gum. The mixture was re-dissolved in EtOH (10 mL), and 5% Pd/C (50 mg) was added followed by conc. HCl (1 drop) and the mixture was hydrogenated at 5 Bar (5×10$^5$ Pa) for 16 h. The mixture was filtered, washed with EtOH (2×2 mL) and the filtrate evaporated under reduced pressure to afford a pale brown solid. The crude product was purified by chromatography on silica gel (loaded in DCM, EtOAc/MeOH, 0-20%) to furnish the sub-title compound (397 mg) as a beige solid. 35 $^1$H NMR (400 MHz, DMSO-d6) δ: 7.27 (dd, 1H), 6.21 (dd, 1H), 6.16 (ddd, 1H), 5.84 (s, 2H), 3.89 (dqt, 4H), 3.71 (s, 3H), 1.19 (t, 6H).

LCMS m/z 260 (M+H)$^+$ (ES$^+$)

(iii) tert-Butyl (4-((2-((4-(diethoxyphosphoryl)-3-methoxyphenyl)amino)pyridin-4-yl)oxy)-naphthalen-1-yl)carbamate A mixture of tert-butyl (4-((2-chloropyridin-4-yl)oxy) naphthalen-1-yl)carbamate (see Example 1(i) above; 298 mg, 0.804 mmol), the product from step (ii) above (250 mg, 0.964 mmol), potassium carbonate (222 mg, 1.607 mmol), and BrettPhos G3 precatalyst (7 mg, 7.89 μmol) were degassed under vacuum, back filling with nitrogen 3 times. DMF (3 mL) was added and the stirred suspension was degassed under vacuum, back filling with nitrogen 3 times. The reaction was then heated under nitrogen at 85° C. (block temperature) for 16 h. The mixture was filtered, washed with DCM (2 mL) and concentrated under reduced pressure. The crude product was purified by chromatography on silica (12 g column, dry load, DCM/MeOH 0-10%, product eluted at 6%) to furnish the sub-title compound (340 mg) as a pale brown solid.

$^1$H NMR (400 MHz, DMSO-d6) δ: 9.35 (d, 2H), 8.17 (d, 1H), 8.14 (m, 1H), 7.83 (m, 1H), 7.61 (m, 3H), 7.51 (dd, 1H), 7.46 (dd, 1H), 7.37 (d, 1H), 7.23 (ddd, 1H), 6.67 (dd, 1H), 6.14 (d, 1H), 3.94 (m, 4H), 3.75 (s, 3H), 1.53 (s, 9H), 1.20 (t, 6H).

(iv) Diethyl (4-((4-((4-aminonaphthalen-1-yl)oxy) pyridin-2-yl)amino)-2-methoxyphenyl)-phosphonate TFA (221 μL, 2.86 mmol) was added to a solution of the product from step (iii) above (340 mg, 0.573 mmol) in DCM (12 mL) and the mixture stirred at rt for 3 h. Additional TFA (221 μL, 2.86 mmol) was added and the mixture was stirred for a further 18 h. The mixture was diluted with DCM (30 mL) and 2M NaOH (20 mL) was added. The phases were separated on a phase separation cartridge and the organics concentrated under reduced pressure to furnish the sub-title compound (330 mg) as a brown oil.

$^1$H NMR (400 MHz, DMSO-d6) δ: 9.24 (s, 1H), 8.17 (m, 1H), 8.11 (d, 1H), 7.63 (m, 1H), 7.46 (m, 4H), 7.23 (m, 1H), 7.11 (d, 1H), 6.72 (d, 1H), 6.61 (dd, 1H), 6.09 (d, 1H), 5.84 (s, 2H), 3.94 (m, 4H), 3.73 (s, 3H), 1.19 (t, 6H).

(v) Diethyl (4-((4-((4-(3-(5-(tert-butyl)-2-methoxy-3-(methylsulfonamido)phenyl)ureido)-naphthalen-1-yl)oxy)pyridin-2-yl)amino)-2-methoxyphenyl)phosphonate Triethylamine (0.02 mL, 0.143 mmol) was added to a solution of phenyl (5-(tert-butyl)-2-methoxy-3-(methylsulfonamido)phenyl)carbamate (see Example 1(iv) above; 0.262 g, 0.669 mmol) and the product from step (iv) above (0.33 g, 0.669 mmol) in THF (10 mL) at 65° C. (block temperature). The mixture was stirred for 24 h then the solvent was removed under reduced pressure. The crude material was purified by chromatography on silica gel (12 g column, dry load, 0-10% MeOH/DCM, product eluted at 5%) to afford a brown solid. The product was further purified by chromatography on a C18 column (24 g column, loaded in DMSO, 25%-100% MeCN: 10 mmol ammonium bicarbonate soln.) to furnish the title compound (170 mg) as a white solid.

¹H NMR (400 MHz, DMSO-d6) δ: 9.40 (s, 1H), 9.31 (s, 1H), 9.15 (s, 1H), 8.92 (s, 1H), 8.30 (d, 1H), 8.19 (d, 1H), 8.17 (d, 1H), 8.13 (d, 1H), 7.92-7.79 (m, 1H), 7.76-7.67 (m, 1H), 7.62 (ddd, 1H), 7.52-7.42 (m, 2H), 7.41 (d, 1H), 7.25 (dt, 1H), 7.02 (d, 1H), 6.67 (dd, 1H), 6.16 (d, 1H), 3.94 (dqd, 4H), 3.81 (s, 3H), 3.75 (s, 3H), 3.10 (s, 3H), 1.27 (s, 9H), 1.20 (t, 6H).

LCMS m/z 793 (M+H)⁺ (ES⁺)

Example 50

[4-[[4-[[4-[[5-tert-Butyl-3-(methanesulfonamido)-2-methoxy-phenyl]carbamoylamino]-1-naphthyl]oxy]-2-pyridyl]amino]-2-methoxy-phenyl]-ethoxy-phosphinic acid

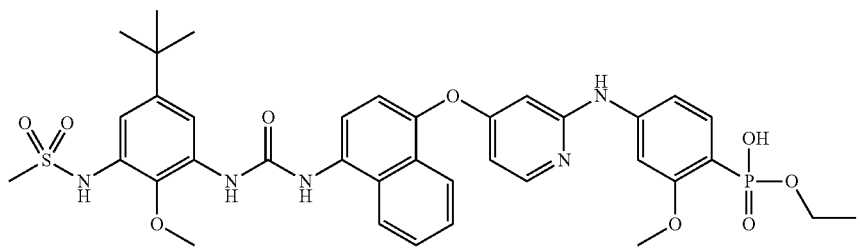 [SMILES: CCOP(=O)(O)c1ccc(Nc2cc(Oc3ccc(NC(=O)Nc4cc(C(C)(C)C)cc(NS(C)(=O)=O)c4OC)c4ccccc34)ccn2)cc1OC]

To a solution of diethyl (4-((4-((4-(3-(5-(tert-butyl)-2-methoxy-3-(methylsulfonamido)phenyl)-ureido)naphthalen-1-yl)oxy)pyridin-2-yl)amino)-2-methoxyphenyl)phosphonate (see Example 49 above; 75 mg, 0.095 mmol) in 1,4-dioxane (1 mL) and water (0.1 mL) was added sodium hydroxide 50 wt % (15 μL, 0.284 mmol) and the solution was stirred at 50° C. (block temperature) for 24 h. Additional sodium hydroxide 50 wt % (15 μL, 0.284 mmol) was added and the mixture was stirred for a further 2 days. More sodium hydroxide 50 wt % (54 μL) was added and the mixture was stirred for a further 24 h. EtOH (0.5 mL) was added and the mixture was stirred for a further 3 days. Acetic acid (27 μL, 0.472 mmol) was added and the mixture was concentrated under reduced pressure. The crude product was purified by preparative HPLC (Waters, Basic (0.1% Ammonium Bicarbonate), Basic, Waters X-Bridge Prep-C18, 5 μm, 19×50 mm column, 35-65% MeCN in Water) to afford the title compound (15 mg) as a white solid.

¹H NMR (400 MHz, DMSO-d6) δ: 9.57 (s, 1H), 9.03 (d, 2H), 8.32 (d, 1H), 8.17 (d, 1H), 8.11 (dd, 2H), 7.91-7.78 (m, 1H), 7.63 (dt, 2H), 7.46 (s, 1H), 7.38 (d, 1H), 7.25 (s, 1H), 7.11 (s, 1H), 7.02 (d, 1H), 6.65-6.54 (m, 1H), 6.11 (s, 1H), 3.81 (s, 3H), 3.69 (m, 5H), 3.09 (s, 3H), 1.27 (s, 9H), 1.06 (t, 3H).

LCMS m/z 765 (M+H)⁺ (ES⁺)

Example 51

Ethyl (4-((4-((4-(3-(5-(tert-butyl)-2-methoxy-3-(methylsulfonamido)phenyl)ureido)naphthalen-1-yl)oxy)pyridin-2-yl)amino)-2-methoxyphenyl)(ethyl)phosphinate

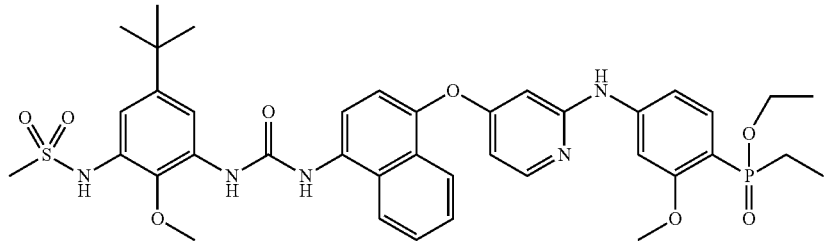 [SMILES: CCOP(=O)(CC)c1ccc(Nc2cc(Oc3ccc(NC(=O)Nc4cc(C(C)(C)C)cc(NS(C)(=O)=O)c4OC)c4ccccc34)ccn2)cc1OC]

(i) Ethyl ethyl(2-methoxy-4-nitrophenyl)phosphinate

1-Iodo-2-methoxy-4-nitrobenzene (1 g, 3.58 mmol), was azeotroped with toluene (12 mL) then dissolved in fresh toluene (12 mL) before addition of DIPEA (1.878 mL, 10.75 mmol) and ethyl ethylphosphinate (see, for example, Petnehazy, I. et al., Synth. Commun. 2003, 33, 1665-1674; 0.569 g, 4.66 mmol). The mixture was degassed under vacuum and back filled with nitrogen three times. XantPhos G3 precatalyst (0.102 g, 0.108 mmol) was added and the reaction heated at 100° C. (block temperature), 90° C. (internal temperature), under nitrogen for 2.5 h. The reaction was cooled and the solvent evaporated to give a brown gum. The crude material was purified by chromatography on silica gel (12 g column, dry load, 50-100% EtOAc/isohexane, product eluted at 98%) to afford the sub-title compound (0.92 g) as a pale brown solid.

$^1$H NMR (400 MHz, CDCl$_3$) δ: 8.17 (dd, 1H), 7.94 (dt, 1H), 7.79 (dd, 1H), 4.03 (s, 3H), 3.96 (dddq, 2H), 2.09 (m, 2H), 1.29 (t, 3H), 1.12 (dt, 3H).

LCMS m/z 274 (M+H)$^+$ (ES$^+$)

(ii) Ethyl (4-amino-2-methoxyphenyl)(ethyl)phosphinate

A mixture of the product from step (i) above (0.92 g, 3.37 mmol) and 5% Pd/C (50 mg) in EtOH (10 mL) was hydrogenated at 5 Bar (5×10$^5$ Pa) for 16 h. The mixture was filtered, washed with EtOH (2×2 mL) and the filtrate evaporated under reduced pressure to afford a pale brown gum. The mixture was re-dissolved in EtOH (10 mL), and 5% Pd/C (50 mg) was added followed by conc. HCl (1 drop) and the mixture was hydrogenated at 5 Bar (5×10$^5$ Pa) for 16 h. The mixture was filtered, washed with EtOH (2×2 mL) and the filtrate evaporated under reduced pressure to afford a pale brown gum. The mixture was re-dissolved in EtOH (10 mL), and 5% Pd/C (50 mg) was added followed by conc. HCl (1 drop) and the mixture was hydrogenated at 5 Bar (5×10$^5$ Pa) for 16 h. The mixture was filtered, washed with EtOH (2×2 mL) and the filtrate evaporated under reduced pressure to afford a pale brown solid. The crude product was purified by chromatography on silica gel (loaded in DCM, EtOAc/MeOH, 0-20%) to furnish the sub-title compound (459 mg) as a cream solid.

LCMS m/z 244 (M+H)$^+$ (ES$^+$)

(iii) tert-Butyl (4-((2-((4-(ethoxy(ethyl)phosphoryl)-3-methoxyphenyl)amino)pyridin-4-yl)oxy)naphthalen-1-yl)carbamate A mixture of tert-butyl (4-((2-chloropyridin-4-yl)oxy) naphthalen-1-yl)carbamate (see Example 1(i) above; 368 mg, 0.994 mmol), the product from step (ii) above (290 mg, 1.192 mmol), potassium carbonate (275 mg, 1.987 mmol), and BrettPhos G3 precatalyst (8.8 mg, 9.92 µmol) were degassed under vacuum, back filling with nitrogen 3 times. DMF (3 mL) was added and the stirred suspension was degassed under vacuum, back filling with nitrogen 3 times. The reaction was then heated under nitrogen at 85° C. (block temperature) for 16 h. The mixture was diluted with DCM (20 mL) then water (20 mL) was added and the phases separated on a phase separation cartridge. The crude product was purified by chromatography on silica (24 g column, dry load, DCM/MeOH, 0-10%) to give a white solid. The product was further purified by chromatography on silica (24 g column, dry load, PhMe/iPrOH 0-30%, product eluted at 15%) to furnish the sub-title compound (304 mg) as a white solid.

$^1$H NMR (400 MHz, DMSO-d6) δ: 9.35 (d, 2H), 8.27-8.06 (m, 2H), 7.90-7.78 (m, 1H), 7.68-7.49 (m, 5H), 7.37 (d, 1H), 7.26 (dt, 1H), 6.66 (dd, 1H), 6.14 (d, 1H), 3.87-3.72 (m, 4H), 3.65 (ddq, 1H), 1.94-1.78 (m, 2H), 1.53 (s, 9H), 1.12 (t, 3H), 0.91 (dt, 3H).

LCMS m/z 578 (M+H)$^+$ (ES$^+$)

(iv) Ethyl (4-((4-((4-aminonaphthalen-1-yl)oxy) pyridin-2-yl)amino)-2-methoxyphenyl)(ethyl)phosphinate TFA (203 µL, 2.64 mmol) was added to a solution of the product from step (iii) above (305 mg, 0.528 mmol) in DCM (4 mL) and the mixture stirred at rt for 3 h. Additional TFA (203 µL, 2.64 mmol) was added and the mixture was stirred for a further 16 h. The solvent was removed under reduced pressure and the residue azeotroped with toluene (5 mL) to furnish a brown oil. The residue was dissolved in DCM (20 mL) and washed with 1M NaOH (20 mL). The aqueous was extracted with DCM (20 mL) and the combined organics were washed with brine (20 mL), dried (MgSO$_4$) and concentrated under reduced pressure to furnish the sub-title compound (310 mg) as a white solid.

$^1$H NMR (400 MHz, DMSO-d6) δ: 9.13 (s, 1H), 8.11-8.04 (m, 1H), 8.02 (d, 1H), 7.56-7.51 (m, 1H), 7.49-7.41 (m, 1H), 7.41-7.33 (m, 3H), 7.21-7.13 (m, 2H), 7.12-7.05 (m, 1H), 7.02 (d, 1H), 6.63 (d, 1H), 6.51 (dd, 1H), 6.01 (d, 1H), 3.76-3.67 (m, 1H), 3.65 (s, 3H), 3.60-3.50 (m, 1H), 1.82-1.70 (m, 2H), 1.02 (td, 3H), 0.81 (dtd, 3H).

LCMS m/z 478 (M+H)$^+$ (ES$^+$)

(v) Ethyl (4-((4-((4-(3-(5-(tert-butyl)-2-methoxy-3-(methylsulfonamido)phenyl)ureido)-naphthalen-1-yl)oxy)pyridin-2-yl)amino)-2-methoxyphenyl)(ethyl) phosphinate Triethylamine (0.018 mL, 0.130 mmol) was added to a solution of phenyl (5-(tert-butyl)-2-methoxy-3-(methylsulfonamido)phenyl)carbamate (see Example 1(iv) above; 0.255 g, 0.649 mmol) and the product from step (iv) above (0.31 g, 0.649 mmol) in THF (10 mL) at 65° C. (block temperature). The mixture was stirred for 24 h then the solvent was removed under reduced pressure. The crude material was purified by chromatography on silica gel (12 g column, dry load, 0-10% MeOH/DCM, product eluted at 5%) to afford a beige solid. The product was further purified by chromatography on a C18 column (24 g column, loaded in DMSO, 25%-100% MeCN: 10 mmol ammonium bicarbonate soln.) to furnish the title compound (233 mg) as a white solid.

$^1$H NMR (400 MHz, DMSO-d6) δ: 9.44 (s, 1H), 9.30 (s, 1H), 8.94 (s, 1H), 8.31 (m, 2H), 8.20-8.09 (m, 3H), 7.86 (d, 1H), 7.71 (ddd, 1H), 7.61 (ddd, 1H), 7.57-7.47 (m, 2H), 7.40 (d, 1H), 7.27 (dt, 1H), 7.03 (d, 1H), 6.66 (dd, 1H), 6.17 (d, 1H), 3.85-3.76 (m, 1H), 3.81 (s, 3H), 3.76 (s, 3H), 3.65 (dddd, 1H), 3.10 (s, 3H), 1.92-1.79 (m, 2H), 1.27 (s, 9H), 1.11 (t, 3H), 0.90 (dt, 3H).

LCMS m/z 777 (M+H)$^+$ (ES$^+$)

Example 52

[4-[[4-[[4-[[5-tert-Butyl-3-(methanesulfonamido)-2-methoxy-phenyl]carbamoylamino]-naphthyl]oxy]-2-pyridyl]amino]-2-methoxy-phenyl]-ethyl-phosphinic acid

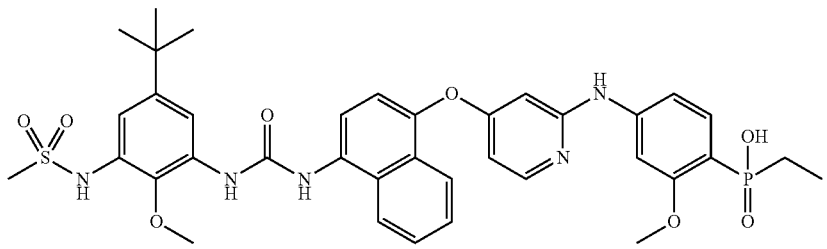 [SMILES: CCP(=O)(O)c1ccc(Nc2cc(Oc3ccc(NC(=O)Nc4cc(C(C)(C)C)cc(NS(C)(=O)=O)c4OC)c4ccccc34)ccn2)cc1OC]

To a solution of ethyl (4-((4-((4-(3-(5-(tert-butyl)-2-methoxy-3-(methylsulfonamido)phenyl)-ureido)naphthalen-1-yl)oxy)pyridin-2-yl)amino)-2-methoxyphenyl)(ethyl) phosphinate (see Example 51 above; 100 mg, 0.129 mmol) in 1,4-dioxane (1.0 mL) and water (0.1 mL) was added sodium hydroxide 50 wt % (10 µL, 0.189 mmol) and the mixture was stirred at 50° C. (hotplate temperature) for 24 h. Additional sodium hydroxide 50 wt % (9.61 µL, 0.182 mmol) was added and the mixture was stirred for a further 24 h before more sodium hydroxide 50 wt % (74 µL) was added. After a further 24 h, EtOH (0.5 mL) was added and the mixture was stirred for a further 3 days. Acetic acid (37 µL, 0.646 mmol) was added and the mixture was concentrated under reduced pressure. The crude product was purified by preparative HPLC (Waters, Basic (0.1% Ammonium Bicarbonate), Basic, Waters X-Bridge Prep-C18, 5 µm, 19×50 mm column, 35-65% MeCN in Water) to afford the title compound (23 mg) as a white solid.

$^1$H NMR (400 MHz, DMSO-d6) δ: 9.53 (s, 1H), 9.17 (s, 1H), 8.99 (s, 1H), 8.31 (d, 1H), 8.23-8.06 (m, 3H), 7.90-7.81 (m, 1H), 7.74-7.56 (m, 2H), 7.50 (dd, 1H), 7.39 (d, 2H), 7.18 (d, 1H), 7.02 (d, 1H), 6.63 (dd, 1H), 6.14 (d, 1H), 3.81 (s, 3H), 3.69 (s, 3H), 3.09 (s, 3H), 1.72 (dq, 2H), 1.27 (s, 9H), 0.86 (dt, 3H).

LCMS m/z 749 (M+H)$^+$ (ES$^+$)

Example 53

Ethyl (4-((4-((4-(3-(5-(tert-butyl)-2-methoxy-3-(methylsulfonamido)phenyl)ureido)-naphthalen-1-yl)oxy)pyridin-2-yl)amino)-2-methoxyphenyl)(phenyl)phosphinate

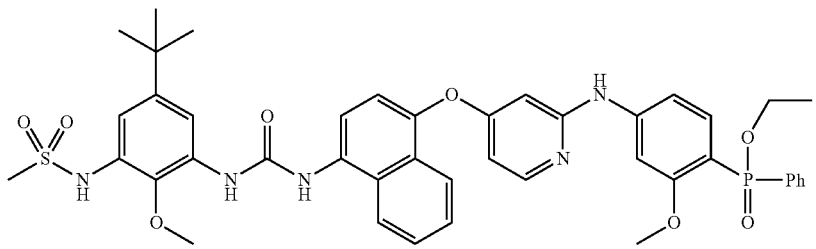 [SMILES: CCOP(=O)(c1ccccc1)c1ccc(Nc2cc(Oc3ccc(NC(=O)Nc4cc(C(C)(C)C)cc(NS(C)(=O)=O)c4OC)c4ccccc34)ccn2)cc1OC]

(i) Ethyl (2-methoxy-4-nitrophenyl)(phenyl)phosphinate

1-Iodo-2-methoxy-4-nitrobenzene (1.00 g, 3.58 mmol), was azeotroped with toluene (12 mL) then dissolved in fresh toluene (12 mL) before addition of DIPEA (1.9 mL, 10.88 mmol) and ethyl phenylphosphinate (0.79 g, 4.64 mmol). The mixture was degassed under vacuum and back filled with nitrogen three times. XantPhos G3 precatalyst (0.10 g, 0.106 mmol) was added and the reaction heated at 100° C. (block temperature), 90° C. (internal temperature), under nitrogen for 2.5 h. The reaction was cooled and the solvent evaporated to give a brown gum. The crude material was purified by chromatography on silica gel (12 g column, dry load, 50-100% EtOAc/isohexane, product eluted at 70%) to afford the sub-title compound (0.95 g) as a brown, waxy solid.

$^1$H NMR (400 MHz, CDCl$_3$) δ: 8.19 (dd, 1H), 7.91 (dt, 1H), 7.85 (m, 2H), 7.69 (dd, 1H), 7.55 (m, 1H), 7.46 (m, 2H), 4.14 (dq, 2H), 3.82 (s, 3H), 1.39 (t, 3H).

LCMS m/z 322 (M+H)$^+$ (ES$^+$)

(ii) Ethyl (4-amino-2-methoxyphenyl)(phenyl)phosphinate

A mixture of the product from step (i) above (0.95 g, 2.96 mmol) and 5% Pd/C (50 mg) in EtOH (10 mL) was hydrogenated at 5 Bar (5×10$^5$ Pa) for 16 h. The mixture was filtered, washed with EtOH (2×2 mL) and the filtrate evaporated under reduced pressure to afford a pale brown gum. The mixture was re-dissolved in EtOH (10 mL) and 5% Pd/C (50 mg) was added followed by conc. HCl (1 drop) and the mixture was hydrogenated at 5 Bar (5×10$^5$ Pa) for 16 h. The mixture was filtered, washed with EtOH (2×2 mL) and the filtrate evaporated under reduced pressure to afford a pale brown gum. The mixture was re-dissolved in EtOH (10 mL), and 5% Pd/C (50 mg) was added followed by conc. HCl (1 drop) and the mixture was hydrogenated at 5 Bar (5×10$^5$ Pa) for 16 h. The mixture was filtered, washed with EtOH (2×2 mL) and the filtrate evaporated under reduced pressure to afford a pale brown solid. The crude product was purified by chromatography on silica gel (loaded in DCM, EtOAc/MeOH, 0-20%) to furnish the sub-title compound (446 mg) as an orange solid.

$^1$H NMR (400 MHz, DMSO-d6) δ: 7.70 (m, 2H), 7.52-7.41 (m, 4H), 6.22 (dt, 1H), 6.15 (dd, 1H), 5.85 (s, 2H), 3.86 (m, 2H), 3.59 (s, 3H), 1.22 (t, 3H).

LCMS m/z 292 (M+H)$^+$ (ES$^+$)

(iii) tert-Butyl (4-((2-((4-(ethoxy(phenyl)phosphoryl)-3-methoxyphenyl)amino)pyridin-4-yl)oxy)naphthalen-1-yl)carbamate A mixture of tert-butyl (4-((2-chloropyridin-4-yl)oxy)naphthalen-1-yl)carbamate (see Example 1(i) above; 279 mg, 0.752 mmol), the product from step (ii) above (263 mg, 0.903 mmol), potassium carbonate (208 mg, 1.505 mmol), and BrettPhos G3 precatalyst (6.7 mg, 7.55 µmol) were degassed under vacuum, back filling with nitrogen 3 times. DMF (3 mL) was added and the stirred suspension was degassed under vacuum, back filling with nitrogen 3 times. The reaction was then heated under nitrogen at 85° C. (block temperature) for 16 h. The mixture was filtered, washed with DCM (2 mL) and concentrated under reduced pressure. The crude product was purified by chromatography on silica (12 g column, dry load, DCM/MeOH 0-10%, product eluted at 6%) to give a beige solid. The product was further purified by chromatography on silica (24 g column, dry load, PhMe/iPrOH 0-30%, product eluted at 11%) to furnish the sub-title compound (324 mg) as a white solid.

$^1$H NMR (400 MHz, DMSO-d6) δ: 9.36 (d, 2H), 8.23-8.02 (m, 2H), 7.91-7.78 (m, 1H), 7.75-7.67 (m, 2H), 7.67-7.61 (m, 3H), 7.61-7.56 (m, 1H), 7.56-7.50 (m, 1H), 7.48-7.43 (m, 3H), 7.37 (d, 1H), 7.27 (dt, 1H), 6.65 (dd, 1H), 6.13 (d, 1H), 3.97-3.81 (m, 2H), 3.62 (s, 3H), 1.52 (s, 9H), 1.23 (t, 3H).

LCMS m/z 627 (M+H)$^+$ (ES$^+$)

(iv) Ethyl (4-((4-((4-aminonaphthalen-1-yl)oxy)pyridin-2-yl)amino)-2-methoxyphenyl)(phenyl)phosphinate TFA (200 µL, 2.60 mmol) was added to a solution of the product from step (iii) above (325 mg, 0.519 mmol) in DCM (4 mL) and the mixture stirred at rt for 3 h. Additional TFA (200 µL, 2.60 mmol) was added and the mixture was stirred for a further 16 h. The mixture was diluted with DCM (20 mL) and washed with 1M NaOH (20 mL). The aqueous was extracted with DCM (20 mL) and the combined organics were washed with brine (20 mL), dried (MgSO$_4$) and concentrated under reduced pressure to furnish the sub-title compound (270 mg) as a white solid.

$^1$H NMR (400 MHz, DMSO-d6) δ: 9.15 (s, 1H), 8.13-8.03 (m, 1H), 8.00 (d, 1H), 7.70-7.57 (m, 2H), 7.57-7.47 (m, 2H), 7.47-7.40 (m, 1H), 7.40-7.26 (m, 5H), 7.17 (dt, 1H), 7.01 (d, 1H), 6.62 (d, 1H), 6.51 (dd, 1H), 6.00 (d, 1H), 5.76 (s, 1H), 5.67 (s, 1H), 3.92-3.70 (m, 2H), 3.51 (s, 3H), 1.14 (t, 3H).

LCMS m/z 526 (M+H)$^+$ (ES$^+$)

(v) Ethyl (4-((4-((4-(3-(5-(tert-butyl)-2-methoxy-3-(methylsulfonamido)phenyl)ureido)-naphthalen-1-yl)oxy)pyridin-2-yl)amino)-2-methoxyphenyl)(phenyl)phosphinate Triethylamine (0.014 mL, 0.103 mmol) was added to a solution of phenyl (5-(tert-butyl)-2-methoxy-3-(methylsulfonamido)phenyl)carbamate (see Example 1(iv) above; 0.202 g, 0.514 mmol) and the product from step (iv) above (0.27 g, 0.514 mmol) in THF (10 mL) at 65° C. (block temperature). The mixture was stirred for 24 h then the solvent was removed under reduced pressure. The crude material was purified by chromatography on silica gel (12 g column, dry load, 0-10% MeOH/DCM, product eluted at 5%) to afford a beige solid. The product was further purified by chromatography on a C18 column (24 g column, loaded in DMSO, 25%-100% MeCN: 10 mmol ammonium bicarbonate soln.) to furnish the title compound (181 mg) as a white solid.

LCMS m/z 825 (M+H)$^+$ (ES$^+$)

Example 54

[4-[[4-[[4-[[5-tert-Butyl-3-(methanesulfonamido)-2-methoxy-phenyl]carbamoylamino]-1-naphthyl]oxy]-2-pyridyl]amino]-2-methoxy-phenyl]-phenyl-phosphinic acid

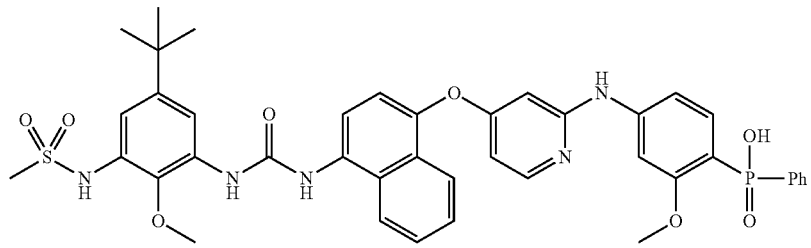 [SMILES: COc1cc(Nc2cc(Oc3ccc(NC(=O)Nc4cc(C(C)(C)C)cc(NS(C)(=O)=O)c4OC)c4ccccc34)ccn2)ccc1P(=O)(O)c1ccccc1]

To a solution of ethyl (4-((4-((4-(3-(5-(tert-butyl)-2-methoxy-3-(methylsulfonamido)phenyl)-ureido)naphthalen-1-yl)oxy)pyridin-2-yl)amino)-2-methoxyphenyl)(phenyl)phosphinate (see Example 53 above; 100 mg, 0.121 mmol) in 1,4-dioxane (1.0 mL) and water (0.1 mL) was added sodium hydroxide 50 wt % (10 µL, 0.189 mmol) and the mixture was stirred at 50° C. (hotplate temperature) for 24 h. Additional sodium hydroxide 50 wt % (10 µL, 0.189 mmol) was added and the mixture was stirred for a further 24 h before more sodium hydroxide 50 wt % (74 µL) was added. After a further 24 h, EtOH (0.5 mL) was added and the mixture was stirred for a further 3 days. Acetic acid (100 µL, 1.747 mmol) was added and the mixture was concentrated under reduced pressure. The crude product was purified by preparative HPLC (Waters, Basic (0.1% Ammonium Bicarbonate), Waters X-Bridge Prep-C18, 5 µm, 19×50 mm column, 35-65% MeCN in Water) to afford the title compound (31 mg) as a white solid.

¹H NMR (400 MHz, DMSO-d6) δ: 9.70 (s, 1H), 9.09 (d, 2H), 8.37-8.27 (m, 1H), 8.15 (d, 1H), 8.10 (d, 1H), 8.07 (d, 1H), 7.83 (dd, 1H), 7.72-7.53 (m, 5H), 7.36 (d, 1H), 7.29 (d, 3H), 7.22-7.08 (m, 2H), 7.02 (d, 1H), 6.58 (dd, 1H), 6.11 (d, 1H), 3.79 (s, 3H), 3.44 (s, 3H), 3.08 (s, 3H), 1.26 (s, 9H).

LCMS m/z 797 (M+H)⁺ (ES⁺)

Example 55

Ethyl (4-((4-((4-(3-(5-(tert-butyl)-2-methoxy-3-(N-methylmethylsulfonamido)phenyl)-ureido)naphthalen-1-yl)oxy)pyridin-2-yl)amino)-2-methoxyphenyl)(methyl)phosphinate

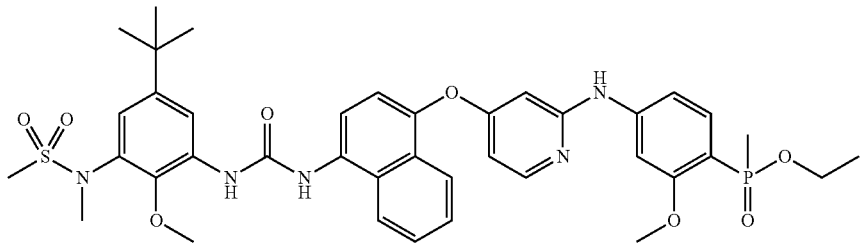 [SMILES: CCOP(C)(=O)c1ccc(Nc2cc(Oc3ccc(NC(=O)Nc4cc(C(C)(C)C)cc(N(C)S(C)(=O)=O)c4OC)c4ccccc34)ccn2)cc1OC]

(i) N-(5-(tert-Butyl)-2-methoxy-3-nitrophenyl)-N-methylmethanesulfonamide

To a solution of N-(5-(tert-butyl)-2-methoxy-3-nitrophenyl)methanesulfonamide (see, for example, Cirillo, P. F. et al., WO 2002/083628, 24 Oct. 2002; 1.51 g, 4.99 mmol) in DMF (10 mL) was added potassium carbonate (1.035 g, 7.49 mmol) followed by iodomethane (0.468 mL, 7.49 mmol), and the mixture was stirred at rt for 20 h. The mixture was poured into water (50 mL) and extracted with Et₂O (2×50 mL). The combined organics were washed with water (50 mL) and brine (50 mL), dried (MgSO₄) and concentrated under reduced pressure. The crude product was purified by chromatography on silica (24 g column, dry load, isohexane/EtOAc 0-100%, to furnish the sub-title compound (1.51 g) as a white solid.

¹H NMR (400 MHz, DMSO) δ: 7.83 (d, 1H), 7.73 (d, 1H), 3.88 (s, 3H), 3.25 (s, 3H), 3.17 (s, 3H), 1.31 (s, 9H).

LCMS m/z 317 (M+H)⁺ (ES⁺)

(ii) N-(3-Amino-5-(tert-butyl)-2-methoxyphenyl)-N-methylmethanesulfonamide

A mixture of the product from step (i) above (1.5 g, 4.74 mmol) and 5% Pd/C (5 g, Type 39, 58% w/w paste with water) in EtOAc (10 mL) and EtOH (5 mL) was hydrogenated at 5 bar (5×10⁵ Pa) for 16 h. The mixture was filtered through celite washing with EtOAc (3×25 mL) then evaporated under reduced pressure to give a beige solid. The residue was slurried in ether/isohexane (1:1, 300 mL), filtered and washed with isohexane (50 mL) to afford the sub-title compound (1.25 g) as a white solid.

¹H NMR (400 MHz, DMSO-d6) δ: 6.73 (d, 1H), 6.51 (d, 1H), 4.96 (s, 2H), 3.69 (s, 3H), 3.15 (s, 3H), 3.07 (s, 3H), 1.22 (s, 9H).

LCMS m/z 287 (M+H)⁺ (ES⁺)

(iii) Phenyl (5-(tert-butyl)-2-methoxy-3-(N-methylmethylsulfonamido)phenyl)carbamate Phenyl chloroformate (0.55 mL, 4.38 mmol) was added dropwise over 10 min to a stirred solution of the product from step (ii) above (1.25 g, 4.36 mmol) and NaHCO₃ (0.733 g, 8.73 mmol) in THF (5 mL) and DCM (15 mL) at rt. The mixture was stirred overnight, then diluted with DCM (50 mL), washed with water (50 mL) and brine (50 mL), then dried (MgSO₄) and evaporated to give a solid. The product was slurried with cyclohexane/ether (1:1, 10 mL), filtered, washed with isohexane (3×5 mL) and dried at 40° C. under vacuum to give the sub-title compound (1.65 g) as a white solid.

¹H NMR (400 MHz, DMSO-d6) δ: 9.51 (s, 1H), 7.83-7.61 (m, 1H), 7.44 (dd, 2H), 7.31-7.20 (m, 3H), 7.17 (d, 1H), 3.85 (s, 3H), 3.22 (s, 3H), 3.12 (s, 3H), 1.27 (s, 9H).

LCMS m/z 429 (M+Na)⁺ (ES⁺)

(iv) Ethyl (4-((4-((4-(3-(5-(tert-butyl)-2-methoxy-3-(N-methylmethylsulfonamido)phenyl)-ureido)naphthalen-1-yl)oxy)pyridin-2-yl)amino)-2-methoxyphenyl)(methyl)phosphinate Triethylamine (10 μL, 0.072 mmol) was added to a solution of the product from step (iii) above (152 mg, 0.373 mmol) and ethyl (4-((4-((4-aminonaphthalen-1-yl)oxy)pyridin-2-yl)amino)-2-methoxyphenyl)(methyl)phosphinate (see Example 43(iv) above; 160 mg, 0.345 mmol) in THF (10 mL) at 65° C. (block temperature), and the mixture was stirred for 24 h. The solvent was removed under reduced pressure and the product was purified by chromatography on a 018 column (40 g column, loaded in DMSO, 25%-100% MeCN: 10 mmol ammonium bicarbonate soln.) to furnish the title compound (107 mg) as a white solid.

LCMS m/z 777 (M+H)⁺ (ES⁺)

Example 56

[4-[[4-[[4-[[5-tert-Butyl-2-methoxy-3-[methyl(methylsulfonyl)amino]phenyl]carbamoyl-amino]-1-naphthyl]oxy]-2-pyridyl]amino]-2-methoxy-phenyl]-methyl-phosphinic acid

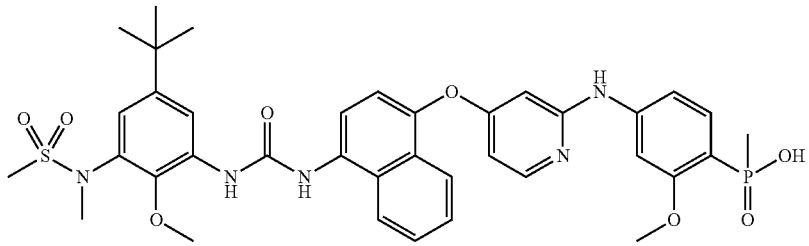 [SMILES: COc1cc(Nc2cc(Oc3ccc(NC(=O)Nc4cc(C(C)(C)C)cc(N(C)S(C)(=O)=O)c4OC)c4ccccc34)ccn2)ccc1P(C)(=O)O]

To a solution of ethyl (4-((4-((4-(3-(5-(tert-butyl)-2-methoxy-3-(N-methylmethylsulfonamido)-phenyl)ureido)naphthalen-1-yl)oxy)pyridin-2-yl)amino)-2-methoxyphenyl)(methyl)phosphinate (see Example 55 above; 85 mg, 0.110 mmol) in 1,4-dioxane (1.0 mL) and water (0.1 mL) was added sodium hydroxide 50 wt % (10 µL, 0.193 mmol) and the mixture was stirred at 50° C. (hotplate temperature) for 24 h. Further sodium hydroxide 50 wt % (10 µL, 0.189 mmol) was added and the mixture was stirred for 2 days. The mixture was cooled to rt, acetic acid (18 µL, 0.314 mmol) was added, the solvent was removed under reduced pressure and the residue azeotroped with toluene (2 mL). The crude product was purified by preparative HPLC (Waters, Basic (0.1% Ammonium Bicarbonate), Waters X-Bridge Prep-C18, 5 µm, 19×50 mm column, 35-65% MeCN in Water) to afford the title compound (13 mg) as a white solid.

$^1$H NMR (400 MHz, DMSO-d6) δ: 9.81 (s, 1H), 9.19 (s, 1H), 9.09 (s, 1H), 8.35 (d, 1H), 8.30 (d, 1H), 8.11 (dd, 2H), 7.83 (dd, 1H), 7.66-7.55 (m, 2H), 7.51 (t, 1H), 7.37 (d, 1H), 7.27 (s, 1H), 7.12 (d, 1H), 7.01 (d, 1H), 6.61 (dd, 1H), 6.10 (d, 1H), 3.88 (s, 3H), 3.64 (s, 3H), 3.24 (s, 3H), 3.13 (s, 3H), 1.34 (d, 3H), 1.28 (s, 9H).

LCMS m/z 749 (M+H)$^+$ (ES$^+$)

Example 57

Ethyl (4-((4-((4-(3-(5-(tert-butyl)-2-methoxy-3-(methylcarbamoyl)phenyl)ureido)-naphthalen-1-yl)oxy)pyridin-2-yl)amino)-2-methoxyphenyl)(methyl)phosphinate

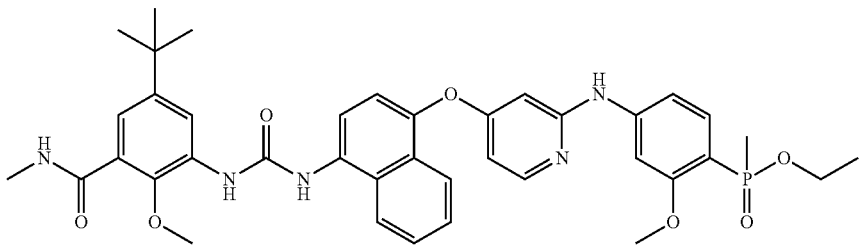 [SMILES: CCOP(C)(=O)c1ccc(Nc2cc(Oc3ccc(NC(=O)Nc4cc(C(C)(C)C)cc(C(=O)NC)c4OC)c4ccccc34)ccn2)cc1OC]

Triethylamine (5 µL, 0.036 mmol) was added to a warm solution of phenyl (5-(tert-butyl)-2-methoxy-3-(methylcarbamoyl)phenyl)carbamate (see, for example, Fyfe, M. C. T. et. al., WO 2014/162126, 9 Oct. 2014; 60 mg, 0.168 mmol) and ethyl (4-((4-((4-aminonaphthalen-1-yl)oxy)pyridin-2-yl)amino)-2-methoxyphenyl)(methyl)phosphinate (see Example 43(iv) above; 82 mg, 0.168 mmol) in THF (2 mL) at 75° C. (block temperature, internal temp. 60-65° C.), and the mixture stirred for 16 h. The solvent was evaporated and the residue purified by chromatography on silica gel (12 g column, 2-8% MeOH/DCM) to afford the title compound (90 mg) as a colourless solid.

$^1$H NMR (400 MHz, DMSO-d6) δ: 9.48 (s, 1H), 9.30 (s, 1H), 8.89 (s, 1H), 8.44 (d, 1H), 8.31 (d, 1H), 8.24-8.13 (m, 2H), 8.10 (d, 1H), 7.87 (d, 1H), 7.77-7.67 (m, 1H), 7.66-7.58 (m, 1H), 7.58-7.47 (m, 2H), 7.41 (d, 1H), 7.27 (dt, 1H), 7.12 (d, 1H), 6.66 (dd, 1H), 6.18 (d, 1H), 3.88-3.72 (m, 7H), 3.72-3.55 (m, 1H), 2.82 (d, 3H), 1.56 (d, 3H), 1.28 (s, 9H), 1.12 (t, 3H).

LCMS m/z 726 (M+H)$^+$ (ES$^+$)

Example 58

[4-[[4-[[4-[[5-tert-Butyl-2-methoxy-3-(methylcarbamoyl)phenyl]carbamoylamino]-1-naphthyl]oxy]-2-pyridyl]amino]-2-methoxy-phenyl]-methyl-phosphinic acid

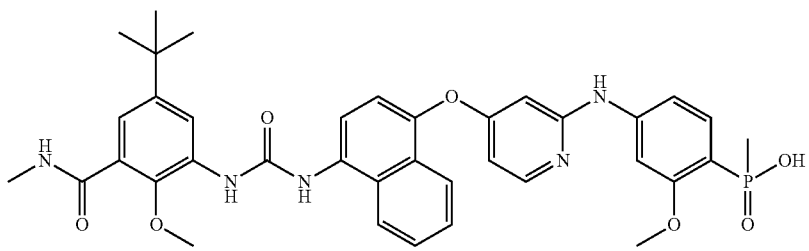 [SMILES: CNC(=O)c1cc(C(C)(C)C)cc(NC(=O)Nc2ccc(Oc3ccnc(Nc4ccc(P(C)(=O)O)c(OC)c4)c3)c3ccccc23)c1OC]

To a solution of ethyl (4-((4-((4-(3-(5-(tert-butyl)-2-methoxy-3-(methylcarbamoyl)phenyl)-ureido)naphthalen-1-yl)oxy)pyridin-2-yl)amino)-2-methoxyphenyl)(methyl) phosphinate (see Example 57 above; 90 mg, 0.124 mmol) in 1,4-dioxane (1 mL), water (0.1 mL) and EtOH (0.1 mL) was added sodium hydroxide 50 wt % (19.64 μL, 0.372 mmol) and the mixture was heated at 50° C. for 20 h. The mixture was diluted with EtOH (0.5 mL) and stirred for a further 24 h. After cooling to rt, acetic acid (35.5 μL, 0.620 mmol) was added then the mixture was concentrated under reduced pressure and azeotroped with toluene (2 mL). The crude product was purified by preparative HPLC (Waters, Basic (0.1% Ammonium Bicarbonate), Basic, Waters X-Bridge Prep-C18, 5 μm, 19×50 mm column, 35-65% MeCN in Water) to afford the title compound (53 mg) as a white solid.

$^1$H NMR (400 MHz, DMSO-d6) δ: 9.84 (s, 1H), 9.11 (s, 2H), 8.42 (d, 1H), 8.35 (d, 1H), 8.16 (d, 1H), 8.14-8.03 (m, 2H), 7.71-7.55 (m, 2H), 7.50 (dd, 1H), 7.38 (d, 1H), 7.28 (d, 1H), 7.17-7.06 (m, 2H), 6.61 (dd, 1H), 6.12 (d, 1H), 3.79 (s, 3H), 3.65 (s, 3H), 2.81 (d, 3H), 1.35 (d, 3H), 1.28 (s, 9H).

LCMS m/z 699 (M+H)$^+$ (ES$^+$)

Example 59

Ethyl (4-((4-((4-(3-(5-(tert-butyl)-2-methoxy-3-(methylsulfonamido)phenyl)ureido)naphthalen-1-yl)oxy)pyridin-2-yl)amino)-2-methylphenyl)(methyl) phosphinate (i) Ethyl methyl(2-methyl-4-nitrophenyl)phosphinate To a solution of ethyl methylphosphinate (see, for example, Chebib, M. et al., WO 2006/000043, 5 Jan. 2006; 504 mg, 4.66 mmol) in toluene (6 mL) were added 1-iodo-2-methyl-4-nitrobenzene (944 mg, 3.59 mmol) and DIPEA (1.9 mL, 10.88 mmol). The mixture was degassed under vacuum and back filled with nitrogen three times. XantPhos G3 precatalyst (102 mg, 0.108 mmol) was added, and the mixture was degassed three more times, then heated at 100° C. (block temperature) under nitrogen for 90 min. The reaction was cooled and the solvent evaporated to give a brown gum. The crude material was purified by chromatography on silica gel (12 g column, dry load, 50-100% EtOAc/isohexane, product eluted at 98%) to afford a pale brown solid. The residue was taken up in DCM (10 mL), washed with 1M HCl (10 mL) and concentrated to give a brown oil. The crude material was re-purified by chromatography on silica gel (12 g column, dry load, 0-10% DCM/MeOH) to afford the sub-title compound (578 mg) as a yellow oil.

$^1$H NMR (400 MHz, DMSO-d6) δ: 8.19 (m, 2H), 8.05 (dd, 1H), 4.01 (ddq, 1H), 3.87 (ddq, 1H), 2.68 (m, 3H), 1.75 (d, 3H), 1.25 (t, 3H).

LCMS m/z 244 (M+H)$^+$ (ES$^+$)

(ii) Ethyl (4-amino-2-methylphenyl)(methyl)phosphinate

A mixture of the product from step (i) above (575 mg, 2.364 mmol) and Pd/C (252 mg, 0.118 mmol) (Type 87L) in EtOH (6 mL, 103 mmol) and HCl (1 drop) was hydrogenated at 5 Bar (5×10$^5$ Pa) for 16 h. The mixture was filtered, washed with EtOH (2×5 mL) and water (5 mL), then the

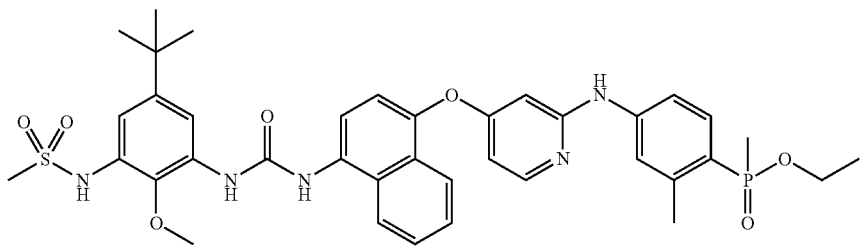 [SMILES: CCOP(C)(=O)c1ccc(Nc2cc(Oc3ccc(NC(=O)Nc4cc(C(C)(C)C)cc(NS(C)(=O)=O)c4OC)c4ccccc34)ccn2)cc1C]

solvent was removed under reduced pressure to furnish the sub-title compound (490 mg) as a yellow oil.

$^1$H NMR (400 MHz, DMSO-d6) δ: 7.62-7.28 (m, 1H), 6.56-6.39 (m, 2H), 3.86 (dp, 1H), 3.79-3.65 (m, 1H), 2.36 (s, 3H), 1.54 (d, 3H), 1.20 (t, 3H).

LCMS m/z 214 (M+H)$^+$ (ES$^+$)

(iii) tert-Butyl (4-((2-((4-(ethoxy(methyl)phosphoryl)-3-methylphenyl)amino)pyridin-4-yl)oxy)naphthalen-1-yl)carbamate A mixture of tert-butyl (4-((2-chloropyridin-4-yl)oxy)naphthalen-1-yl)carbamate (see Example 1(i) above; 937 mg, 2.53 mmol), the product from step (ii) above (490 mg, 2.298 mmol), potassium carbonate (635 mg, 4.60 mmol) and BrettPhos G3 precatalyst (20 mg, 0.023 mmol) were degassed under vacuum, back filling with nitrogen 3 times. DMF (5 mL) was added and the stirred suspension was degassed under vacuum, back filling with nitrogen 3 times. The reaction was then heated under nitrogen at 85° C. (block temperature) for 20 h. The mixture was diluted with water (50 mL) and extracted with DCM/IPA (10:1, 2×25 mL). The combined organics were washed with water (2×50 mL), dried (MgSO$_4$) and concentrated under reduced pressure to give a brown oil. The crude product was purified by chromatography on silica (24 g column, dry load, PhMe/IPA 0-30%, product eluted at 12%) to furnish the sub-title compound (0.79 g) as a pale pink solid.

$^1$H NMR (400 MHz, DMSO-d6) δ: 9.38 (s, 1H), 9.22 (s, 1H), 8.23-8.05 (m, 2H), 7.84 (dd, 1H), 7.68-7.54 (m, 3H), 7.52-7.43 (m, 1H), 7.37 (d, 1H), 7.31-7.10 (m, 2H), 6.65 (dd, 1H), 6.13 (d, 1H), 3.95-3.69 (m, 2H), 2.43 (d, 3H), 1.58 (d, 3H), 1.53 (s, 9H), 1.20 (t, 3H).

LCMS m/z 548 (M+H)$^+$ (ES$^+$)

(iv) Ethyl (4-((4-((4-aminonaphthalen-1-yl)oxy)pyridin-2-yl)amino)-2-methylphenyl)(methyl)phosphinate TFA (550 μL, 7.14 mmol) was added to a solution of the product from step (iii) above (790 mg, 1.443 mmol) in DCM (3.6 mL) and the mixture stirred at rt for 16 h. Additional TFA (550 μL, 7.14 mmol) was added and the mixture was stirred for a further 4 h. The mixture was diluted with DCM (20 mL) and washed with 2M NaOH (10 mL). The aqueous was extracted with DCM (20 mL) and the combined organics were washed with water (20 mL) and brine (20 mL), dried (MgSO$_4$) and concentrated under reduced pressure to furnish the sub-title compound (603 mg).

$^1$H NMR (400 MHz, DMSO-d6) δ: 9.22 (s, 1H), 8.11-8.03 (m, 1H), 8.00 (d, 1H), 7.61-7.46 (m, 2H), 7.46-7.37 (m, 3H), 7.35 (d, 1H), 7.06 (d, 1H), 6.70 (d, 1H), 6.55 (dd, 1H), 6.04 (d, 1H), 3.80 (dp, 1H), 3.73-3.60 (m, 1H), 2.34 (d, 3H), 1.50 (d, 3H), 1.12 (t, 3H).

LCMS m/z 448 (M+H)$^+$ (ES$^+$)

(v) Ethyl (4-((4-((4-(3-(5-(tert-butyl)-2-methoxy-3-(methylsulfonamido)phenyl)ureido)-naphthalen-1-yl)oxy)pyridin-2-yl)amino)-2-methylphenyl)(methyl)phosphinate Triethylamine (11 μL, 0.079 mmol) was added to a solution of phenyl (5-(tert-butyl)-2-methoxy-3-(methylsulfonamido)phenyl)carbamate (see Example 1(iv) above; 144 mg, 0.367 mmol) and the product from step (iv) above (150 mg, 0.335 mmol) in 2-Me-THF (2.5 mL) at 75° C. and the mixture stirred for 16 h. Additional triethylamine (11 μL, 0.079 mmol) was added and stirring continued overnight. The solution was cooled to rt and concentrated in vacuo onto silica gel. The crude product was purified by chromatography on the Companion (12 g column, 1-6% MeOH in DCM) to afford the title compound (187 mg) as a pale pink solid.

LCMS m/z 746 (M+H)$^+$ (ES$^+$)

Example 60

[4-[[4-[[4-[[5-tert-Butyl-3-(methanesulfonamido)-2-methoxy-phenyl]carbamoylamino]-naphthyl]oxy]-2-pyridyl]amino]-2-methyl-phenyl]-methyl-phosphinic acid

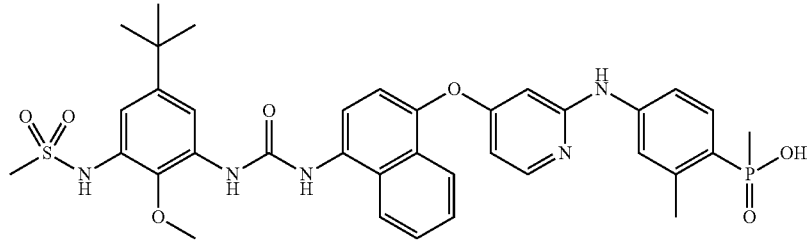 [SMILES: COc1c(NC(=O)Nc2ccc(Oc3ccnc(Nc4ccc(P(C)(=O)O)c(C)c4)c3)c3ccccc23)cc(C(C)(C)C)cc1NS(C)(=O)=O]

To a solution of ethyl (4-((4-((4-(3-(5-(tert-butyl)-2-methoxy-3-(methylsulfonamido)phenyl)-ureido)naphthalen-1-yl)oxy)pyridin-2-yl)amino)-2-methylphenyl)(methyl) phosphinate (see Example 59 above; 187 mg, 0.251 mmol) in 1,4-dioxane (2 mL), water (0.2 mL) and EtOH (0.2 mL) was added sodium hydroxide 50 wt % (40 μL, 0.758 mmol) and the mixture was heated at 50° C. for 20 h. The mixture was diluted with EtOH (1 mL), cooled to rt and acetic acid (72 μL, 1.258 mmol) was added. The mixture was concentrated under reduced pressure and azeotroped with toluene (2 mL) to give a white solid. The crude product was purified by preparative HPLC (Waters, Basic (0.1% Ammonium Bicarbonate), Basic, Waters X-Bridge Prep-C18, 5 μm, 19×50 mm column, 35-65% MeCN in Water) to afford an off-white solid. The resulting solid was slurried in hot MeCN (2 mL) and decanted to give the title compound (5 mg) as a pale pink solid.

$^1$H NMR (400 MHz, DMSO-d6) δ: 9.40 (s, 1H), 9.13 (d, 2H), 8.92 (s, 1H), 8.30 (d, 1H), 8.19 (d, 1H), 8.16-8.09 (m, 2H), 7.87 (dd, 1H), 7.71 (ddd, 1H), 7.64-7.50 (m, 3H), 7.44 (s, 1H), 7.39 (d, 1H), 7.03 (d, 1H), 6.62 (dd, 1H), 6.14 (d, 1H), 3.81 (s, 3H), 3.10 (s, 3H), 2.46 (s, 3H), 1.46 (d, 3H), 1.27 (s, 9H).

LCMS m/z 719 (M+H)$^+$ (ES$^+$)

Example 61

Ethyl (4-((4-((4-(3-(5-(tert-butyl)-2-methoxy-3-(methylsulfonamido)phenyl)ureido)-naphthalen-1-yl)oxy)pyridin-2-yl)amino)-2-ethoxyphenyl)(methyl)-phosphinate

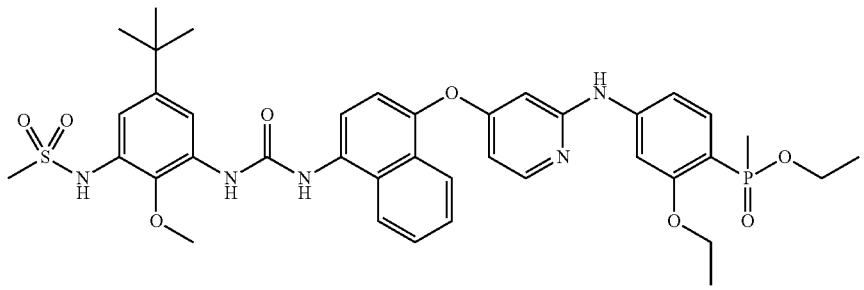 [SMILES: CCOc1cc(Nc2cc(Oc3ccc(NC(=O)Nc4cc(C(C)(C)C)cc(NS(C)(=O)=O)c4OC)c4ccccc34)ccn2)ccc1P(C)(=O)OCC]

(i) 2-Ethoxy-1-iodo-4-nitrobenzene

To a mixture of 2-iodo-5-nitrophenol (500 mg, 1.887 mmol) and potassium carbonate (1.3 g, 9.41 mmol) in DMF (6 mL) and water (0.6 mL) was added iodoethane (0.23 mL, 2.86 mmol) and the mixture was heated at 65° C. (block temperature) for 3 h. After cooling to rt, the mixture was diluted with water (50 mL) and extracted with EtOAc (2×25 mL). The combined organics were washed with water (3×25 mL) and brine (25 mL), dried (MgSO$_4$) and concentrated under reduced pressure to give a yellow solid (0.54 g). The crude product was purified by chromatography on silica gel (12 g column, loaded in DCM, iso-hexane/EtOAc, gradient 0-50%, product eluted at 12%) to furnish the sub-title compound (0.54 g) as a yellow solid.

$^1$H NMR (400 MHz, CDCl$_3$) δ: 7.96 (dd, 1H), 7.58 (m, 2H), 4.20 (q, 2H), 1.55 (t, 3H).

(ii) Ethyl (2-ethoxy-4-nitrophenyl)(methyl)phosphinate

To a solution of ethyl methylphosphinate (see, for example, Chebib, M. et al., WO 2006/000043, 5 Jan. 2006; 257 mg, 2.378 mmol) in toluene (3 mL) were added the product from step (i) above (540 mg, 1.843 mmol) and DIPEA (0.96 mL, 5.50 mmol). The mixture was degassed under vacuum and back filled with nitrogen three times. XantPhos G3 precatalyst (52 mg, 0.055 mmol) was added, and the mixture was degassed three more times. The reaction was heated at 100° C. (block temperature) under nitrogen for 2 h. The reaction was cooled and the solvent evaporated to give a brown gum. The resulting gum was dissolved in DCM (30 mL), 1M HCl (20 mL) was added and the phases were separated. The crude material was purified by chromatography on silica gel (12 g column, dry load, 50-100% EtOAc/isohexane, product eluted at 98%) to afford the sub-title compound (363 mg) as a yellow gum.

$^1$H NMR (400 MHz, DMSO-d6) δ: 8.02 (dd, 1H), 7.92 (dt, 1H), 7.84 (dd, 1H), 4.29 (qd, 2H), 3.92 (ddq, 1H), 3.72 (ddq, 1H), 1.73 (d, 3H), 1.40 (t, 3H), 1.17 (t, 3H).

LCMS m/z 274 (M+H)$^+$ (ES$^+$)

(iii) Ethyl (4-amino-2-ethoxyphenyl)(methyl)phosphinate

A mixture of the product from step (ii) above (0.36 g, 1.318 mmol) and Pd/C (0.140 g, 0.066 mmol) (Type 87L) in EtOH (6 mL, 103 mmol) was hydrogenated at 5 Bar (5×10$^5$ Pa) for 16 h. The mixture was filtered, washed with EtOH (2×5 mL) and water (5 mL), then the solvent was removed under reduced pressure to give the sub-title compound (326 mg) as a yellow oil.

$^1$H NMR (400 MHz, DMSO-d6) δ: 7.45-7.31 (m, 1H), 6.32-6.17 (m, 2H), 3.98 (dddd, 2H), 3.81-3.70 (m, 1H), 3.61 (ddq, 1H), 1.54 (d, 3H), 1.33 (t, 3H), 1.12 (t, 3H).

LCMS m/z 244 (M+H)$^+$ (ES$^+$)

(iv) tert-Butyl (4-((2-((3-ethoxy-4-(ethoxy(methyl)phosphoryl)phenyl)amino)pyridin-4-yl)oxy)naphthalen-1-yl)carbamate A mixture of tert-butyl (4-((2-chloropyridin-4-yl)oxy)naphthalen-1-yl)carbamate (see Example 1(i) above; 545 mg, 1.470 mmol), the product from step (iii) above (325 mg, 1.336 mmol), potassium carbonate (369 mg, 2.67 mmol), and BrettPhos G3 precatalyst (12 mg, 0.014 mmol) were degassed under vacuum, back filling with nitrogen 3 times. DMF (4 mL) was added and the stirred suspension was degassed under vacuum, back filling with nitrogen 3 times. The reaction was then heated under nitrogen at 85° C. (block temperature) for 20 h. The mixture was diluted with water (50 mL) and extracted with DCM/IPA (10:1, 2×25 mL). The combined organics were washed with water (2×50 mL), dried (MgSO$_4$) and concentrated under reduced pressure to give a brown oil. The crude product was purified by chromatography on silica (12 g column, dry load, DCM/MeOH 0-10%, product eluted at 6%) to furnish the sub-title compound (0.54 g) as a red solid.

$^1$H NMR (400 MHz, DMSO-d6) δ: 9.39 (s, 1H), 9.30 (s, 1H), 8.21-8.09 (m, 1H), 7.89-7.78 (m, 1H), 7.69-7.45 (m, 5H), 7.37 (d, 1H), 7.29-7.11 (m, 2H), 6.66 (dd, 1H), 6.13 (d, 1H), 4.09-3.92 (m, 2H), 3.90-3.50 (m, 2H), 1.58 (d, 3H), 1.53 (s, 9H), 1.35 (t, 3H), 1.12 (t, 3H).

LCMS m/z 578 (M+H)$^+$ (ES$^+$)

(v) Ethyl (4-((4-((4-aminonaphthalen-1-yl)oxy)pyridin-2-yl)amino)-2-ethoxyphenyl)(methyl)-phosphinate TFA (360 µL, 4.67 mmol) was added to a solution of the product from step (iv) above (540 mg, 0.935 mmol) in DCM (2.3 mL) and the mixture stirred at rt for 16 h. Additional TFA (360 µL, 4.67 mmol) was added and the mixture was stirred for a further 4 h. The mixture was diluted with DCM (20 mL) and washed with 2M NaOH (10 mL). The aqueous was extracted with DCM (20 mL) and the combined organics were washed with water (20 mL) and brine (20 mL), dried (MgSO$_4$) and concentrated under reduced pressure to furnish the sub-title compound (346 mg) as a white solid.

$^1$H NMR (400 MHz, DMSO-d6) δ: 9.11 (s, 1H), 8.12-8.04 (m, 1H), 8.01 (d, 1H), 7.54 (dt, 1H), 7.43 (dd, 1H), 7.40-7.33 (m, 3H), 7.12 (dt, 1H), 7.02 (d, 1H), 6.62 (d, 1H), 6.51 (dd, 1H), 6.00 (d, 1H), 3.91 (qd, 2H), 3.69 (ddt, 1H), 3.53 (ddq, 1H), 1.49 (d, 3H), 1.25 (t, 3H), 1.03 (t, 3H).

LCMS m/z 478 (M+H)$^+$ (ES$^+$)

(vi) Ethyl (4-((4-((4-(3-(5-(tert-butyl)-2-methoxy-3-(methylsulfonamido)phenyl)ureido)-naphthalen-1-yl)oxy)pyridin-2-yl)amino)-2-ethoxyphenyl)(methyl)-phosphinate Triethylamine (10 µL, 0.072 mmol) was added to a solution of phenyl (5-(tert-butyl)-2-methoxy-3-(methylsulfonamido)phenyl)carbamate (see Example 1(iv) above; 126 mg, 0.321 mmol) and the product from step (v) above (140 mg, 0.293 mmol) in 2-Me-THF (2.5 mL) at 75° C. and the mixture stirred for 16 h. The reaction was cooled to rt and concentrated in vacuo onto silica gel. The crude product was purified by chromatography on the Companion (12 g column, 1-7% MeOH in DCM) to afford the title compound (158 mg) as a pink solid.

LCMS m/z 776 (M+H)$^+$ (ES$^+$)

Example 62

[4-[[4-[[4-[[5-tert-Butyl-3-(methanesulfonamido)-2-methoxy-phenyl]carbamoylamino]-1-naphthyl]oxy]-2-pyridyl]amino]-2-ethoxy-phenyl]-methyl-phosphinic acid

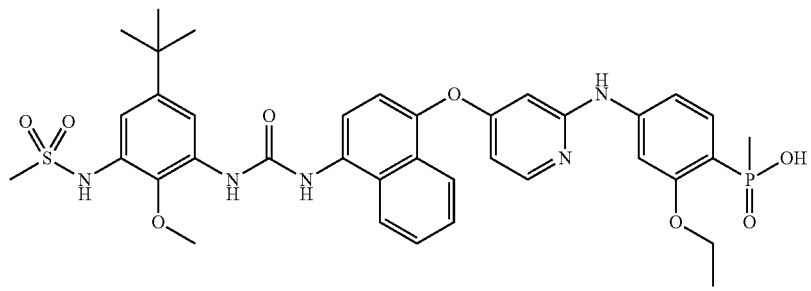 [SMILES: CCOc1cc(Nc2cc(Oc3ccc(NC(=O)Nc4cc(C(C)(C)C)cc(NS(C)(=O)=O)c4OC)c4ccccc34)ccn2)ccc1P(C)(=O)O]

To a solution of ethyl (4-((4-((4-(3-(5-(tert-Butyl)-2-methoxy-3-(methylsulfonamido)phenyl)-ureido)-naphthalen-1-yl)oxy)pyridin-2-yl)amino)-2-ethoxyphenyl)(methyl)-phosphinate (see Example 61 above; 158 mg, 0.204 mmol) in 1,4-dioxane (2 mL), water (0.2 mL) and EtOH (0.2 mL) was added sodium hydroxide 50 wt % (32.3 µL, 0.611 mmol) and the mixture was heated at 50° C. for 20 h. The mixture was diluted with EtOH (0.5 mL), cooled to rt and acetic acid (58.3 µL, 1.018 mmol) was added. The mixture was concentrated under reduced pressure and azeotroped with toluene (2 mL) to give an off white solid. The crude product was purified by preparative HPLC (Waters, Basic (0.1% Ammonium Bicarbonate), Basic, Waters X-Bridge Prep-C18, 5 µm, 19×50 mm column, 35-65% MeCN in Water) to afford a pale pink solid. The resulting solid was slurried in hot MeCN (2 mL) and decanted to give the title compound (5 mg) as a pale pink solid.

$^1$H NMR (400 MHz, DMSO-d6) δ: 9.49 (s, 1H), 9.17 (s, 2H), 8.97 (s, 1H), 8.31 (d, 1H), 8.18 (d, 1H), 8.16-8.07 (m, 2H), 7.69 (t, 1H), 7.61 (dd, 1H), 7.50 (dd, 1H), 7.39 (d, 2H), 7.17 (d, 1H), 7.02 (d, 1H), 6.64 (dd, 1H), 6.13 (d, 1H), 3.97 (q, 2H), 3.81 (s, 3H), 3.10 (s, 3H), 1.47 (d, 3H), 1.34 (t, 3H), 1.27 (s, 9H).

LCMS m/z 749 (M+H)$^+$ (ES$^+$)

Example 63

Ethyl (4-((4-((4-(3-(5-(tert-butyl)-2-methoxy-3-(methylsulfonamido)phenyl)ureido)-naphthalen-1-yl)oxy)pyrimidin-2-yl)amino)-2-methoxyphenyl)(methyl)phosphinate

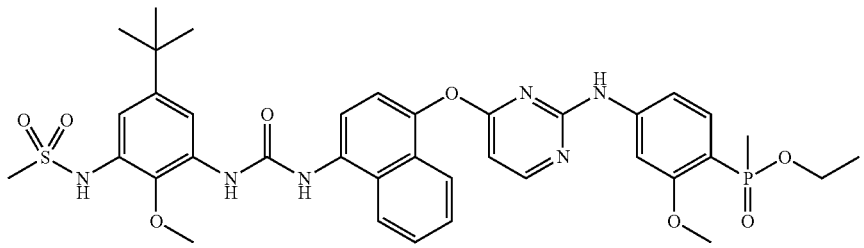 [SMILES: CCOP(C)(=O)c1ccc(Nc2nccc(Oc3ccc(NC(=O)Nc4cc(C(C)(C)C)cc(NS(C)(=O)=O)c4OC)c4ccccc34)n2)cc1OC]

(i) tert-Butyl (4-((2-((4-(ethoxy(methyl)phosphoryl)-3-methoxyphenyl)amino)pyrimidin-4-yl)oxy)naphthalen-1-yl)carbamate A mixture of tert-butyl (4-((2-chloropyrimidin-4-yl)oxy)naphthalen-1-yl)carbamate (see, for example, Ito, K. et. al, WO 2010/067130, 17 Jun. 2010; 372 mg, 1.000 mmol), ethyl (4-amino-2-methoxyphenyl)(methyl)phosphinate (see Example 43(ii) above; 275 mg, 1.201 mmol) and p-TSA monohydrate (38.1 mg, 0.200 mmol) in THF (5 mL) was heated at 50° C. (block temperature, 45° C. internal temperature) for 2 days. After 46 h, further p-TSA monohydrate (38.1 mg, 0.200 mmol) was added and the mixture was stirred for a further 5 days. The mixture was cooled then partitioned between EtOAc (50 mL) and 1M HCl (50 mL). The organic layer was washed with brine (50 mL), dried (MgSO$_4$), filtered and evaporated under reduced pressure to give a pale brown solid. The crude product was purified by chromatography on silica gel (12 g column, dry load PhMe/IPA 0-30%) to give a pale brown solid. The product was further purified by chromatography on silica gel (24 g column, dry load DCM/MeOH 0-10%, product eluted at 5%) to give the sub-title compound (382 mg) as a beige solid.

LCMS m/z 565 (M+H)$^+$ (ES$^+$)

(ii) Ethyl (4-((4-((4-aminonaphthalen-1-yl)oxy)pyrimidin-2-yl)amino)-2-methoxyphenyl)-(methyl)phosphinate TFA (259 μL, 3.37 mmol) was added to a solution of the product from step (i) above (380 mg, 0.673 mmol) in DCM (1.65 mL) and the mixture was stirred at rt for 3 h. Additional TFA (259 μL, 3.37 mmol) was added and the mixture was stirred for a further 16 h. More TFA (259 μL, 3.37 mmol) was added and the mixture was stirred for a further 4 h. The mixture was diluted with DCM (20 mL) and washed with 2M NaOH (10 mL). The aqueous was extracted with DCM (20 mL) and the combined organics were washed with water (20 mL) and brine (20 mL), dried (MgSO$_4$) and concentrated under reduced pressure to furnish the sub-title compound (254 mg) as a beige solid.

$^1$H NMR (400 MHz, DMSO-d6) δ: 9.71 (s, 1H), 8.32 (d, 1H), 8.16-7.97 (m, 1H), 7.62-7.47 (m, 1H), 7.41-7.19 (m, 4H), 7.08 (d, 1H), 7.04 (d, 1H), 6.61 (d, 1H), 6.44 (d, 1H), 5.72 (s, 2H), 3.68 (ddq, 1H), 3.51 (ddq, 1H), 3.24 (s, 3H), 1.44 (d, 3H), 1.01 (t, 3H).

LCMS m/z 465 (M+H)$^+$ (ES$^+$)

(iii) Ethyl (4-((4-((4-(3-(5-(tert-butyl)-2-methoxy-3-(methylsulfonamido)phenyl)ureido)-naphthalen-1-yl)oxy)pyrimidin-2-yl)amino)-2-methoxyphenyl)(methyl)phosphinate Triethylamine (7 μL, 0.050 mmol) was added to a solution of phenyl (5-(tert-butyl)-2-methoxy-3-(methylsulfonamido)phenyl)carbamate (see Example 1(iv) above; 93 mg, 0.237 mmol) and the product from step (ii) above (100 mg, 0.215 mmol) in 2-Me-THF (2.5 mL) at 75° C. and the mixture stirred for 16 h. Additional phenyl (5-(tert-butyl)-2-methoxy-3-(methylsulfonamido)phenyl)carbamate (25 mg) was added and heating continued for 24 h. Additional phenyl (5-(tert-butyl)-2-methoxy-3-(methylsulfonamido)phenyl)carbamate (40 mg) was added and heating continued overnight. The resulting solid was filtered off and washed with 2-Me-THF (50 mL). The filtrate was concentrated in vacuo onto silica gel. The crude product was purified by chromatography on the Companion (12 g column, 1-5% MeOH in DCM) to afford the title compound (97 mg) as a pink glass.

LCMS m/z 763 (M+H)$^+$ (ES$^+$)

Example 64

[4-[[4-[[4-[[5-tert-Butyl-3-(methanesulfonamido)-2-methoxy-phenyl]carbamoylamino]-1-naphthyl]oxy]pyrimidin-2-yl]amino]-2-methoxy-phenyl]-methyl-phosphinic acid

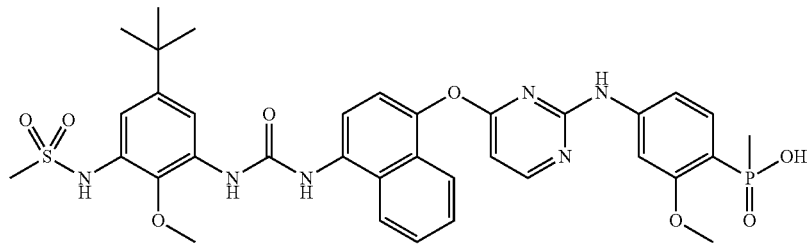 [SMILES: COc1cc(Nc2nccc(Oc3ccc(NC(=O)Nc4cc(C(C)(C)C)cc(NS(C)(=O)=O)c4OC)c4ccccc34)n2)ccc1P(C)(=O)O]

To a solution of ethyl (4-((4-((4-(3-(5-(tert-butyl)-2-methoxy-3-(methylsulfonamido)phenyl)-ureido)-naphthalen-1-yl)oxy)pyrimidin-2-yl)amino)-2-methoxyphenyl)(methyl)phosphinate (see Example 63 above; 97 mg, 0.127 mmol) in 1,4-dioxane (1 mL), water (0.1 mL) and EtOH (0.1 mL) was added sodium hydroxide 50 wt % (20 μL, 0.379 mmol) and the mixture was heated at 50° C. for 20 h. The mixture was diluted with EtOH (0.5 mL), cooled to rt and acetic acid (36 μL, 0.629 mmol) was added. The mixture was concentrated under reduced pressure and azeotroped with toluene (2 mL) to give a white solid. The crude product was purified by preparative HPLC (Waters, Basic (0.1% Ammonium Bicarbonate), Basic, Waters X-Bridge Prep-C18, 5 μm, 19×50 mm column, 35-65% MeCN in Water) to afford a white solid. The resulting solid was slurried in hot MeCN (2 mL) and decanted to give a pale yellow solid. The supernatant was concentrated to give a white solid. Both solids were found to be 94% pure by LCMS, and so were re-combined and purified by chromatography on reverse-phase flash C18 chromatography (12 g column, 25-100% MeCN/Water 0.1% Formic Acid) to afford the title compound (18 mg).

$^1$H NMR (400 MHz, DMSO-d6) δ: 9.73 (s, 1H), 9.54 (s, 1H), 9.13 (s, 1H), 9.02 (s, 1H), 8.47 (d, 1H), 8.30 (d, 1H), 8.18 (d, 1H), 8.09 (d, 1H), 7.83 (d, 1H), 7.58 (m, 2H), 7.40 (d, 1H), 7.25 (m, 2H), 7.02 (d, 2H), 6.68 (d, 1H), 3.81 (s, 3H), 3.45 (s, 3H), 3.09 (s, 3H), 1.42 (d, 3H), 1.26 (s, 9H).

LCMS m/z 736 (M+H)$^+$ (ES$^+$)

Example 65

Ethyl (4-((4-((4-(3-(5-(tert-butyl)-2-methoxy-3-(methylsulfonamido)phenyl)ureido)-naphthalen-1-yl)oxy)pyridin-2-yl)amino)-2-chlorophenyl)(methyl)phosphinate

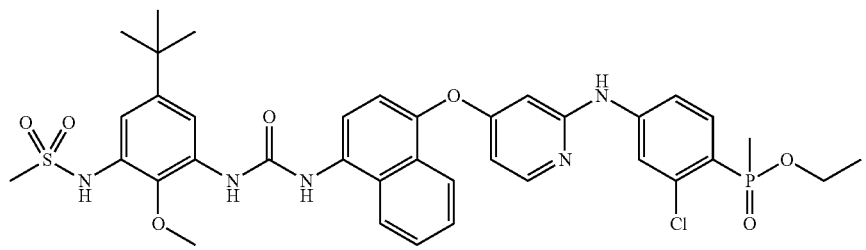 [SMILES: CCOP(C)(=O)c1ccc(Nc2cc(Oc3ccc(NC(=O)Nc4cc(C(C)(C)C)cc(NS(C)(=O)=O)c4OC)c4ccccc34)ccn2)cc1Cl]

(i) Ethyl (2-chloro-4-nitrophenyl)(methyl)phosphinate

To a solution of ethyl methylphosphinate (see, for example, Chebib, M. et al., WO 2006/000043, 5 Jan. 2006; 530 mg, 4.90 mmol) in toluene (5 mL) were added 2-chloro-1-iodo-4-nitrobenzene (835 mg, 2.95 mmol) and DIPEA (1.5 mL, 8.59 mmol). The mixture was degassed under vacuum and back filled with nitrogen three times. XantPhos G3 precatalyst (84 mg, 0.088 mmol) was added, and the mixture was degassed three more times. The reaction was heated at 100° C. (block temperature) under nitrogen for 1 h. The reaction was cooled and the solvent evaporated to give a brown gum. The resulting gum was dissolved in DCM (30 mL), 1M HCL (20 mL) was added and the phases were separated. The organic phase was dried (MgSO$_4$) and concentrated under reduced pressure. The crude material was purified by chromatography on silica gel (12 g column, dry load, 50-100% EtOAc/isohexane, product eluted at 98%) to afford the sub-title compound (519 mg) as a brown solid.

$^1$H NMR (400 MHz, DMSO-d6) δ: 8.40 (dd, 1H), 8.35 (ddd, 1H), 8.23 (dd, 1H), 4.00 (ddq, 1H), 3.83 (ddq, 1H), 1.85 (d, 3H), 1.23 (t, 3H).

LCMS m/z 264 (M+H)$^+$ (ES$^+$)

(ii) Ethyl (4-amino-2-chlorophenyl)(methyl)phosphinate

The product from step (i) above (200 mg, 0.759 mmol) was dissolved in EtOH (5 mL) and iron powder (425 mg, 7.61 mmol) was added followed by a solution of NH$_4$Cl (61 mg, 1.140 mmol) in water (1 mL). The resulting suspension was heated at 80° C. for 2 h. The reaction was cooled to rt and filtered through celite. The filtrate was concentrated in vacuo affording a dark brown solid. The material was partitioned between water (5 mL) and EtOAc (5 mL). The aqueous phase was extracted with EtOAc (2 mL) and the combined organic phases were washed with brine (5 mL), dried (MgSO$_4$), filtered and concentrated in vacuo affording the sub-title compound (148 mg) as a pale brown oil.

$^1$H NMR (400 Hz, DMSO-d6) δ: 7.57 (dd, 1H), 6.66 (dd, 1H), 6.57 (dt, 1H), 6.08 (s, 2H), 3.79-3.89 (m, 1H), 3.63-3.73 (m, 1H), 1.64 (d, 3H), 1.18 (t, 3H).

LCMS m/z 234 (M+H)$^+$ (ES$^+$)

(iii) tert-Butyl (4-((2-((3-chloro-4-(ethoxy(methyl)phosphoryl)phenyl)amino)pyridin-4-yl)oxy)naphthalen-1-yl)carbamate A mixture of tert-butyl (4-((2-chloropyridin-4-yl)oxy)naphthalen-1-yl)carbamate (see Example 1(i) above; 140 mg, 0.377 mmol) and the product from step (ii) above (80 mg, 0.342 mmol), were stirred in DMF (2 mL) at 45° C. until an homogeneous solution was obtained. Freshly ground potassium carbonate (142 mg, 1.027 mmol), was added and the mixture degassed under vacuum, back filling with nitrogen 3 times. BrettPhos G3 precatalyst (10 mg, 0.011 mmol) was added and the stirred suspension was heated under nitrogen at 75° C. (internal temperature) for 1 h. Additional BrettPhos G3 precatalyst was added (5 mg) and heating continued for 2 h. The reaction was cooled to rt and filtered. The filtrate was concentrated in vacuo onto silica gel. The crude product was purified by chromatography on the Companion (12 g column, 1-5% MeOH in DCM) to afford the sub-title compound (194 mg) as a beige glass.

LCMS m/z 568 (M+H)$^+$ (ES$^+$)

(iv) Ethyl (4-((4-((4-aminonaphthalen-1-yl)oxy)pyridin-2-yl)amino)-2-chlorophenyl)(methyl)-phosphinate TFA (250 μL, 3.24 mmol) was added to a solution of the product from step (iii) above (194 mg, 0.342 mmol) in DCM (2 mL) and the mixture stirred at rt for 16 h. The reaction was concentrated in vacuo affording a brown oil. The oil was re-dissolved in DCM (5 mL) and partitioned with sat. aq. NaHCO₃ solution (10 mL). The aqueous phase was extracted with DCM (2×1 mL) and the combined organics dried via hydrophobic frit then concentrated in vacuo affording the sub-title compound (158 mg) as a pale beige foam.

1H NMR (400 MHz, DMSO-d6) δ: 9.42 (s, 1H), 8.14-8.18 (m, 2H), 8.09 (dd, 1H), 7.75 (dd, 1H), 7.62-7.64 (m, 1H), 7.51 (d, 1H), 7.43-7.48 (m, 2H), 7.12 (d, 1H), 6.72 (d, 1H), 6.67 (dd, 1H), 6.09 (d, 1H), 5.86 (s, 2H), 3.83-3.92 (m, 1H), 3.66-3.76 (m, 1H), 1.69 (d, 3H), 1.19 (t, 3H).

LCMS m/z 468 (M+H)⁺ (ES⁺)

(v) Ethyl (4-((4-((4-(3-(5-(tert-butyl)-2-methoxy-3-(methylsulfonamido)phenyl)ureido)-naphthalen-1-yl)oxy)pyridin-2-yl)amino)-2-chlorophenyl)(methyl) phosphinate Triethylamine (10 μL, 0.072 mmol) was added to a solution of phenyl (5-(tert-butyl)-2-methoxy-3-(methylsulfonamido)phenyl)carbamate (see Example 1(iv) above; 128 mg, 0.326 mmol) and the product from step (iv) above (140 mg, 0.299 mmol) in 2-Me-THF (2.5 mL) at 75° C. and the mixture stirred for 16 h. The reaction was cooled to rt, filtered through celite and the filtrate concentrated in vacuo onto silica gel. The crude product was purified by chromatography on the Companion (12 g column, 1-7% MeOH in DCM) to afford the title compound (176 mg) as a pink solid.

LCMS m/z 766 (M+H)⁺ (ES⁺)

Example 66

[[4-[[4-[[4-[[5-tert-Butyl-3-(methanesulfonamido)-2-methoxy-phenyl]carbamoylamino]-1-naphthyl]oxy]-2-pyridyl]amino]-2-chloro-phenyl]-methyl-phosphinic acid

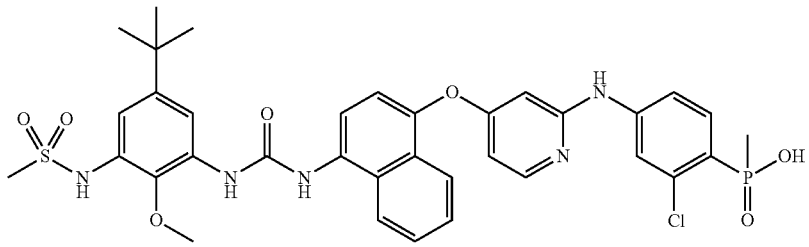 [SMILES: COc1c(NC(=O)Nc2ccc(Oc3ccnc(Nc4ccc(P(C)(=O)O)c(Cl)c4)c3)c3ccccc23)cc(C(C)(C)C)cc1NS(C)(=O)=O]

To a solution of ethyl (4-((4-((4-(3-(5-(tert-butyl)-2-methoxy-3-(methylsulfonamido)phenyl)-ureido)-naphthalen-1-yl)oxy)pyridin-2-yl)amino)-2-chlorophenyl)(methyl) phosphinate (see Example 65 above; 176 mg, 0.230 mmol) in 1,4-dioxane (2 mL), water (0.2 mL) and EtOH (0.2 mL) was added sodium hydroxide 50 wt % (36 μL, 0.682 mmol) and the mixture was heated at 50° C. for 20 h. The mixture was diluted with EtOH (1 mL), cooled to rt and acetic acid (66 μL, 1.153 mmol) was added. The mixture was concentrated under reduced pressure and azeotroped with toluene (2 mL) to give a white solid. The crude product was purified by preparative HPLC (Waters, Basic (0.1% Ammonium Bicarbonate), Basic, Waters X-Bridge Prep-C18, 5 μm, 19×50 mm column, 35-65% MeCN in Water) to afford the title compound (66 mg) as a white solid.

¹H NMR (400 MHz, DMSO-d6) δ: 9.73 (s, 1H), 9.23 (s, 1H), 9.14 (s, 1H), 8.35 (d, 1H), 8.20-8.07 (m, 3H), 7.90 (d, 1H), 7.83 (dd, 1H), 7.73 (dd, 1H), 7.65-7.54 (m, 2H), 7.37 (t, 2H), 7.02 (d, 1H), 6.65 (dd, 1H), 6.09 (d, 1H), 3.81 (s, 3H), 3.08 (s, 3H), 1.37 (d, 3H), 1.27 (s, 9H).

LCMS m/z 739 (M+H)⁺ (ES⁺)

Example 67

Ethyl (4-((4-((4-(3-(5-(tert-butyl)-2-methoxy-3-(methylsulfonamido)phenyl)ureido)-naphthalen-1-yl)oxy)pyridin-2-yl)amino)-2-(dimethylamino)phenyl)(methyl)phosphinate

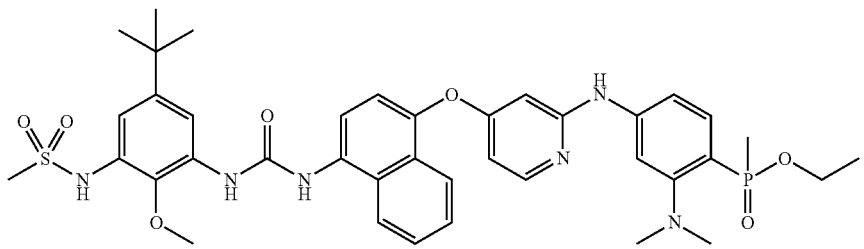 [SMILES: CCOP(C)(=O)c1ccc(Nc2cc(Oc3ccc(NC(=O)Nc4cc(C(C)(C)C)cc(NS(C)(=O)=O)c4OC)c4ccccc34)ccn2)cc1N(C)C]

(i) Ethyl (2-fluoro-4-nitrophenyl)(methyl)phosphinate

To a solution of ethyl methylphosphinate (see, for example, Chebib, M. et al., WO 2006/000043, 5 Jan. 2006; 356 mg, 3.30 mmol) in toluene (6 mL) were added 2-fluoro-1-iodo-4-nitrobenzene (880 mg, 3.30 mmol) and DIPEA (1.7 mL, 9.73 mmol). The mixture was degassed under vacuum and back filled with nitrogen three times. XantPhos G3 precatalyst (94 mg, 0.099 mmol) was added and the reaction heated at 100° C. (block temperature) under nitrogen for 90 min. The reaction was cooled and the solvent evaporated to give a brown gum. The crude material was purified by chromatography on silica gel (12 g column, dry load, 50-100% EtOAc/isohexane, product eluted at 98%) to afford a pale brown solid. The residue was taken up in DCM (10 mL), washed with 1M HCl (10 mL) and concentrated to give a brown oil. The crude material was purified by chromatography on silica gel (12 g column, dry load, 0-10% DCM/MeOH) to afford the sub-title compound (514 mg) as a yellow oil.

$^1$H NMR (400 MHz, DMSO-d6) δ: 8.25 (m, 2H), 8.08 (m, 1H), 4.02 (ddq, 1H), 3.85 (ddq, 1H), 1.80 (dd, 3H), 1.21 (t, 3H).

LCMS m/z 248 (M+H)$^+$ (ES$^+$)

(ii) Ethyl (2-(dimethylamino)-4-nitrophenyl)(methyl)phosphinate

To a stirred solution of the product from step (i) above (200 mg, 0.809 mmol) and dimethylamine hydrochloride (132 mg, 1.618 mmol) in DMF (1 mL), in a sealed tube, was added triethylamine (280 µL, 2.009 mmol) and the mixture heated to 70° C. for 2h. The reaction was cooled to rt, diluted with MeOH (5 mL) and concentrated in vacuo to dryness. The residue was re-dissolved in MeOH and loaded onto a pre-conditioned cartridge of SCX resin. The resin was washed with MeOH then the product released with 1% NH$_3$ in MeOH. The ammonia solution was concentrated in vacuo affording the sub-title compound (147 mg) as a yellow oil.

LCMS m/z 273 (M+H)$^+$ (ES$^+$)

(iii) Ethyl (4-amino-2-(dimethylamino)phenyl)(methyl)phosphinate

5% Pd/C (50 mg, 0.023 mmol) was added to a solution of the product from step (ii) above 147 mg, 0.491 mmol) in EtOH (5 mL). The reaction was stirred under hydrogen for 2 h. The catalyst was filtered off and the solvent evaporated to give the sub-title compound (117 mg) as a pale yellow solid $^1$H NMR (400 MHz, DMSO-d6) δ: 7.42 (dd, 1H), 6.52 (dd, 1H), 6.37 (d, 1H), 5.69 (bs, 2H), 3.86-3.96 (m, 1H), 3.72-3.81 (m, 1H), 2.58 (s, 6H), 1.61 (d, 3H), 1.21 (t, 3H).

LCMS m/z 243 (M+H)$^+$ (ES$^+$)

(iv) tert-Butyl (4-((2-((3-(dimethylamino)-4-(ethoxy(methyl)phosphoryl)phenyl)amino)pyridin-4-yl)oxy)naphthalen-1-yl)carbamate A mixture of tert-butyl (4-((2-chloropyridin-4-yl)oxy)naphthalen-1-yl)carbamate (see Example 1(i) above; 140 mg, 0.377 mmol) and the product from step (iii) above (100 mg, 0.343 mmol), were stirred in DMF (2 mL) at 45° C. until an homogeneous solution was obtained. Freshly ground potassium carbonate (142 mg, 1.028 mmol) was added and the mixture degassed under vacuum, back filling with nitrogen 3 times. BrettPhos G3 precatalyst (10 mg, 0.011 mmol) was added and the stirred suspension was heated under nitrogen at 75° C. (internal temperature) for 1 h. The mixture was cooled to room temperature, filtered and the solvent evaporated to give a dark oil. The residue was dissolved in DCM and pre-absorbed onto silica gel. The crude product was purified by chromatography on the Companion (12 g column, 1-5% MeOH in DCM) to afford the sub-title compound (196 mg) as a pale tan solid.

$^1$H NMR (400 MHz, DMSO-d6) δ: 9.39 (s, 1H), 9.26 (s, 1H), 8.13-8.187 (m, 2H), 7.83 (d, 1H), 7.55-7.66 (m, 5H), 7.50 (d, 1H), 7.39 (d, 1H), 6.65 (d, 1H), 6.12 (s, 1H), 3.88-3.99 (m, 1H), 3.74-3.85 (m, 1H), 2.58 (s, 6H), 1.66 (d, 3H), 1.53 (s, 9H), 1.22 (t, 3H)

LCMS m/z 577 (M+H)$^+$ (ES$^+$)

(v) Ethyl (4-((4-((4-aminonaphthalen-1-yl)oxy)pyridin-2-yl)amino)-2-(dimethylamino)phenyl)-(methyl)phosphinate TFA (250 µL, 3.24 mmol) was added to a solution of the product from step (iv) above (95 mg, 0.135 mmol) in DCM (2 mL) and the mixture stirred at rt for 16 h. The reaction was concentrated in vacuo affording a brown oil. The oil was re-dissolved in DCM (5 mL) and partitioned with sat. aq. NaHCO$_3$ solution (10 mL). The aqueous phase was extracted with DCM (2×1 mL) and the combined organics dried via hydrophobic frit then concentrated in vacuo affording the sub-title compound (74 mg) as a pale beige foam.

LCMS m/z 477 (M+H)$^+$ (ES$^+$)

(vi) Ethyl (4-((4-((4-(3-(5-(tert-butyl)-2-methoxy-3-(methylsulfonamido)phenyl)ureido)-naphthalen-1-yl)oxy)pyridin-2-yl)amino)-2-(dimethylamino)phenyl)(methyl)phosphinate Triethylamine (5 µL, 0.036 mmol) was added to a solution of phenyl (5-(tert-butyl)-2-methoxy-3-(methylsulfonamido)phenyl)carbamate (see Example 1(iv) above; 67 mg, 0.171 mmol) and the product from step (v) above (74 mg, 0.155 mmol) in 2-Me-THF (1.5 mL) at 75° C. and the mixture stirred for 16 h. The reaction was cooled to rt and concentrated in vacuo onto silica gel. The crude product was purified by chromatography on the Companion (12 g column, 1-7% MeOH in DCM) to afford the title compound (90 mg) as a pale yellow solid.

LCMS m/z 775 (M+H)⁺ (ES⁺)

Example 68

[4-[[4-[[4-[[5-tert-Butyl-3-(methanesulfonamido)-2-methoxy-phenyl]carbamoylamino]-1-naphthyl]oxy]-2-pyridyl]amino]-2-(dimethylamino)phenyl]-methyl-phosphinic acid

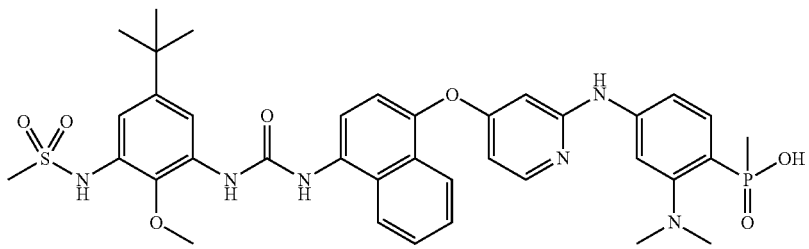 [SMILES: COc1c(NC(=O)Nc2ccc(Oc3ccnc(Nc4ccc(P(C)(=O)O)c(N(C)C)c4)c3)c3ccccc23)cc(C(C)(C)C)cc1NS(C)(=O)=O]

To a solution of ethyl (4-((4-((4-(3-(5-(tert-butyl)-2-methoxy-3-(methylsulfonamido)phenyl)-ureido)naphthalen-1-yl)oxy)pyridin-2-yl)amino)-2-(dimethylamino)phenyl)(methyl)phosphinate (see Example 67 above; 90 mg, 0.116 mmol) in 1,4-dioxane (1 mL), water (0.1 mL) and EtOH (0.1 mL) was added sodium hydroxide 50 wt % (18 µL, 0.341 mmol) and the mixture was heated at 50° C. for 20 h. The mixture was diluted with EtOH (0.5 mL), cooled to rt and acetic acid (33 µL, 0.576 mmol) was added. The mixture was concentrated under reduced pressure and azeotroped with toluene (2 mL) to give a white solid. The crude product was purified by preparative HPLC (Waters, Basic (0.1% Ammonium Bicarbonate), Basic, Waters X-Bridge Prep-C18, 5 µm, 19×50 mm column, 35-65% MeCN in Water) to afford the title compound (43 mg) as a white solid.

¹H NMR (400 MHz, DMSO-d6) δ: 9.46 (s, 1H), 9.26 (s, 1H), 8.95 (s, 1H), 8.31 (d, 1H), 8.21-8.14 (m, 2H), 8.12 (d, 1H), 7.86 (dd, 1H), 7.80 (dd, 1H), 7.69 (ddd, 1H), 7.64-7.45 (m, 3H), 7.40 (d, 1H), 7.03 (d, 1H), 6.65 (dd, 1H), 6.14 (d, 1H), 3.81 (s, 3H), 3.10 (s, 3H), 2.76 (s, 6H), 1.40 (d, 3H), 1.27 (s, 9H).

LCMS m/z 748 (M+H)⁺ (ES⁺)

¹H NMR (of sodium salt; 400 MHz, DMSO-d6) δ: 9.53 (s, 1H), 8.82 (s, 1H), 8.75 (s, 1H), 8.35 (d, 1H), 8.15-7.98 (m, 2H), 7.83 (dd, 1H), 7.74-7.47 (m, 4H), 7.35 (d, 1H), 7.19 (d, 1H), 7.13 (dd, 1H), 7.03 (d, 1H), 6.54 (dd, 1H), 6.07 (d, 1H), 3.78 (s, 3H), 2.68 (s, 6H), 2.60 (s, 3H), 1.22 (s, 9H), 1.18 (d, 3H).

LCMS (of sodium salt) m/z 747 (M+H)⁺ (ES⁺)

Example 69

Ethyl 4-((4-((4-(3-(5-(tert-butyl)-2-methoxy-3-(methylsulfonamido)phenyl)ureido)-naphthalen-1-yl)oxy)pyridin-2-yl)amino)-2-methoxybenzyl (methyl)phosphinate

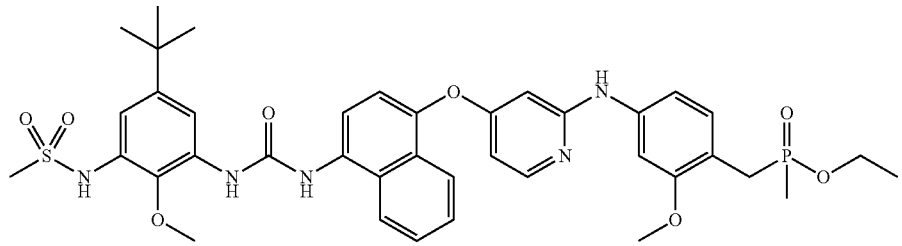 [SMILES: CCOP(C)(=O)Cc1ccc(Nc2cc(Oc3ccc(NC(=O)Nc4cc(C(C)(C)C)cc(NS(C)(=O)=O)c4OC)c4ccccc34)ccn2)cc1OC]

(i) Ethyl 2-methoxy-4-nitrobenzyl(methyl)phosphinate 1-(Bromomethyl)-2-methoxy-4-nitrobenzene (240 mg, 0.975 mmol) and diethyl methylphosphonite (200 mg, 1.469 mmol) were heated at 140° C. under a stream of nitrogen for 1 h. The reaction mixture was cooled to 50° C. and diluted with CHCl$_3$ (2 mL) then cooled further to 0° C. before addition of 5 N HCl (1 mL). The reaction mixture was stirred for 15 min then diluted with water (5 mL) and extracted with CHCl$_3$ (3×20 mL). The organics were bulked and partitioned with 2 N NaOH (10 mL). The organics were separated, dried (MgSO$_4$), filtered and the solvent evaporated to give the sub-title compound (270 mg) as a brown oil.

$^1$H NMR (400 MHz, DMSO-d6) δ: 7.90 (ddd, 1H), 7.83 (d, 1H), 7.58 (dd, 1H), 4.09-3.93 (m, 5H), 3.36 (d, 2H), 1.41 (d, 3H), 1.25 (t, 3H).

(ii) Ethyl 4-amino-2-methoxybenzyl(methyl)phosphinate

A mixture of the product from step (i) above (270 mg, 0.988 mmol) and 5% Pd/C J&M type 87L 50% w/w H$_2$O (100 mg, 0.023 mmol) in EtOH (2 mL) was hydrogenated at 5 Bar (5×10$^5$ Pa) for 16 h. The mixture was filtered and the filtrate evaporated under reduced pressure to afford a brown oil. The crude product was loaded onto a column of SCX (10 g) in MeOH. The column was washed with MeOH and then the product was eluted with 0.7 M ammonia in MeOH. The resultant mixture was concentrated in vacuo to afford the sub-title compound (190 mg) as a brown oil.

$^1$H NMR (400 MHz, DMSO-d6) δ: 6.83 (dd, 1H), 6.22 (dd, 1H), 6.11 (ddd, 1H), 5.03 (s, 2H), 3.91 (pd, 2H), 3.69 (s, 3H), 2.91 (dq, 2H), 1.25-1.15 (m, 6H).

LCMS m/z 244 (M+H)$^+$ (ES$^+$)

(iii) tert-Butyl (4-((2-((4-((ethoxy(methyl)phosphoryl)methyl)-3-methoxyphenyl)amino)pyridin-4-yl)oxy)naphthalen-1-yl)carbamate A mixture of tert-butyl (4-((2-chloropyridin-4-yl)oxy)naphthalen-1-yl)carbamate (see Example 1(i) above; 168 mg, 0.452 mmol) and the product from step (ii) above (100 mg, 0.411 mmol), were stirred in DMF (2 mL) at 45° C. until an homogeneous solution was obtained. Freshly ground potassium carbonate (170 mg, 1.233 mmol), was added and the mixture degassed under vacuum, back filling with nitrogen 3 times. BrettPhos G3 precatalyst (10 mg, 0.011 mmol) was added and the stirred suspension was heated under nitrogen at 75° C. (internal temperature) for 1 h. The mixture was cooled to rt and filtered and the solvent evaporated to give a dark oil. The residue was dissolved in DCM and pre-absorbed onto silica gel. The crude product was purified by chromatography on the Companion (12 g column, 1-5% MeOH in DCM) to afford the sub-title compound (229 mg) as a yellow oil.

LCMS m/z 578 (M+H)$^+$ (ES$^+$)

(iv) Ethyl 4-((4-((4-aminonaphthalen-1-yl)oxy)pyridin-2-yl)amino)-2-methoxybenzyl(methyl)-phosphinate TFA (500 μL, 6.49 mmol) was added to a solution of the product from step (iii) above (229 mg, 0.396 mmol) in DCM (2 mL) and the mixture stirred at rt for 2 h. The reaction was concentrated in vacuo affording a brown oil. The oil was re-dissolved in DCM (5 mL) and partitioned with sat. aq. NaHCO$_3$ solution (10 mL). The aqueous phase was extracted with DCM (2×1 mL) and the combined organics dried via hydrophobic frit then concentrated in vacuo affording the sub-title compound (172 mg) as a pale brown foam.

$^1$H NMR (400 MHz, DMSO-d6) δ: 9.31 (bs, 1H), 8.16-8.18 (m, 1H), 8.01 (d, 1H), 7.62-7.65 (m, 1H), 7.45-7.50 (m, 2H), 7.16 (s, 1H), 7.13 (d, 1H), 7.08 (d, 1H), 6.98 (d, 1H), 6.73 (d, 1H), 6.64 (d, 1H), 6.08 (s, 1H), 3.92 (quint, 2H), 3.68 (s, 3H), 2.96-3.10 (m, 2H), 1.24 (d, 3H), 1.18 (t, 3H).

LCMS m/z 478 (M+H)$^+$ (ES$^+$)

(v) Ethyl 4-((4-((4-(3-(5-(tert-butyl)-2-methoxy-3-(methylsulfonamido)phenyl)ureido)-naphthalen-1-yl)oxy)pyridin-2-yl)amino)-2-methoxybenzyl (methyl)phosphinate Triethylamine (7 μL, 0.050 mmol) was added to a solution of phenyl (5-(tert-butyl)-2-methoxy-3-(methylsulfonamido)phenyl)carbamate (see Example 1(iv) above; 90 mg, 0.229 mmol) and the product from step (iv) above (100 mg, 0.209 mmol) in 2-Me-THF (2 mL) at 75° C. and the mixture stirred for 24 h. Additional triethylamine (7 μL, 0.050 mmol) was added and heating continued overnight. The reaction was cooled to rt, filtered and the filtrate concentrated in vacuo onto silica gel. The crude product was purified by chromatography on the Companion (12 g column, 1-5% MeOH in DCM) to afford the title compound (85 mg) as a pale beige solid.

$^1$H NMR (400 MHz, DMSO-d6) δ: 9.38 (s, 1H), 9.14 (s, 1H), 8.91 (s, 2H), 8.30 (d, 1H), 8.19 (d, 1H), 8.09-8.12 (m, 2H), 7.87 (d, 1H), 7.69-7.72 (m, 1H), 7.63-7.59 (m, 1H), 7.39 (d, 1H), 7.31 (s, 1H), 7.10 (d, 1H), 7.00-7.03 (m, 2H), 6.57 (dd, 1H), 6.09 (d, 1H), 3.91 (quint, 2H), 3.81 (s, 3H), 3.70 (s, 3H), 3.10 (s, 3H), 3.00 (dd, 2H), 1.27 (s, 9H), 1.23 (d, 3H), 1.17 (s, 3H). LCMS m/z 776 (M+H)$^+$ (ES$^+$)

Example 70

(4-((4-((4-(3-(5-(tert-Butyl)-2-methoxy-3-(methylsulfonamido)phenyl)ureido)naphthalen-1-yl)oxy)pyridin-2-yl)amino)-2-methoxybenzyl)(methyl)phosphinic acid

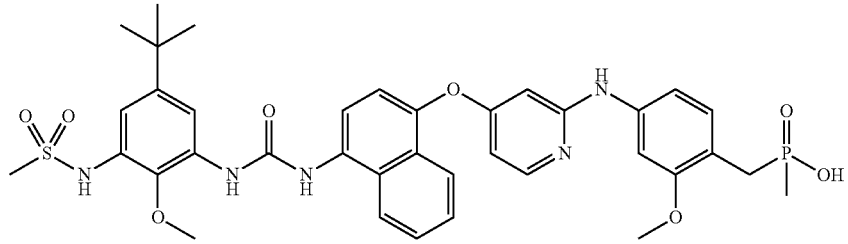 [SMILES: COc1cc(Nc2cc(Oc3ccc(NC(=O)Nc4cc(C(C)(C)C)cc(NS(C)(=O)=O)c4OC)c4ccccc34)ccn2)ccc1CP(C)(=O)O]

To a solution of ethyl 4-((4-((4-(3-(5-(tert-butyl)-2-methoxy-3-(methylsulfonamido)phenyl)-ureido)naphthalen-1-yl)oxy)pyridin-2-yl)amino)-2-methoxybenzyl (methyl)phosphinate (see Example 69 above; 85 mg, 0.110 mmol) in 1,4-dioxane (1 mL), water (0.1 mL) and EtOH (0.2 mL) was added sodium hydroxide 50 wt % (18 µL, 0.341 mmol) and the mixture was heated at 50° C. for 20 h. The mixture was diluted with EtOH (0.5 mL), cooled to rt and acetic acid (32 µL, 0.559 mmol) was added. The mixture was concentrated under reduced pressure and azeotroped with toluene (2 mL) affording a pale orange solid. The crude product was purified by preparative HPLC (Waters, Basic (0.1% Ammonium Bicarbonate), Basic, Waters X-Bridge Prep-C18, 5 µm, 19×50 mm column, 35-65% MeCN in Water) to afford the title compound (56 mg) as a tan solid.

$^1$H NMR (400 MHz, DMSO-d6) δ: 9.78 (s, 1H), 9.12 (s, 1H), 8.80 (s, 1H), 8.32 (d, 1H), 8.18 (d, 1H), 8.05-8.07 (m, 2H), 7.83 (d, 1H), 7.63-7.67 (m, 1H), 7.56-7.59 (m, 1H), 7.36 (d, 1H), 7.16 (s, 1H), 6.99-7.07 (m, 2H), 6.87 (d, 1H), 6.55 (dd, 1H), 5.99 (s, 1H), 3.82 (s, 3H), 3.63 (s, 3H), 3.08 (s, 3H), 2.77 (d, 2H), 1.26 (s, 9H), 0.97 (d, 3H).

LCMS m/z 748 (M+H)$^+$ (ES$^+$)

$^1$H NMR (of sodium salt; 400 MHz, DMSO-d6) δ: 9.99 (s, 1H), 9.03 (s, 1H), 8.74 (s, 1H), 8.34 (d, 1H), 8.05 (d, 1H), 8.03 (d, 1H), 7.80 (d, 1H), 7.73 (d, 1H), 7.64-7.48 (m, 2H), 7.32 (d, 1H), 7.12 (d, 1H), 7.06 (dd, 1H), 7.02 (d, 1H), 6.81 (d, 1H), 6.52 (dd, 1H), 5.95 (d, 1H), 3.80 (s, 3H), 3.62 (s, 3H), 2.71 (s, 3H), 2.58 (d, 2H), 1.23 (s, 9H), 0.76 (d, 3H).

LCMS (of sodium salt) m/z 748 (M+H)$^+$ (ES$^+$)

Example 71

Ethyl (4-((4-((4-(3-(3-(tert-butyl)-5-(methylsulfonamido)phenyl)ureido)naphthalen-1-yl)oxy)pyridin-2-yl)amino)-2-methoxyphenyl)(methyl)phosphinate

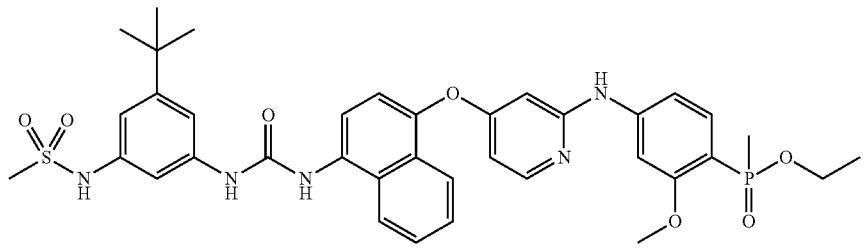 [SMILES: CCOP(C)(=O)c1ccc(Nc2cc(Oc3ccc(NC(=O)Nc4cc(NS(C)(=O)=O)cc(C(C)(C)C)c4)c4ccccc34)ccn2)cc1OC]

(i) Ethyl (4-((4-((4-(3-(3-(tert-butyl)-5-(methylsulfonamido)phenyl)ureido)naphthalen-1-yl)oxy)pyridin-2-yl)amino)-2-methoxyphenyl)(methyl)phosphinate To a solution of phenyl (3-(tert-butyl)-5-(methylsulfonamido)phenyl)carbamate (see, for example, Fyfe, M. C. T. et al., WO 2014/162126, 9 Oct. 2014; 118 mg, 0.326 mmol) and ethyl (4-((4-((4-aminonaphthalen-1-yl)oxy)pyridin-2-yl)amino)-2-methoxyphenyl)(methyl)phosphinate (see Example 43(iv) above; 150 mg, 0.324 mmol) in THF (10 mL) was added triethylamine (9 µL, 0.065 mmol) and the mixture was stirred at 65° C. (block temperature) for 40 h. The mixture was heated to reflux and stirred for a further 24 h. After cooling to rt, the mixture was concentrated under reduced pressure and purified by chromatography on silica gel (12 g column, dry load, 0-10% MeOH/DCM, product eluted at 6%) to afford a beige solid. The product was further purified by chromatography on a C18 column (24 g column, loaded in DMSO, 25%-100% MeCN: 10 mmol ammonium bicarbonate soln.) to furnish the title compound (43 mg) as a white solid.

LCMS m/z 733 (M+H)$^+$ (ES$^+$)

Example 72

[4-[[4-[[4-[[3-tert-Butyl-5-(methanesulfonamido)phenyl]carbamoylamino]-1-naphthyl]oxy]-2-pyridyl]amino]-2-methoxy-phenyl]-methyl-phosphinic acid

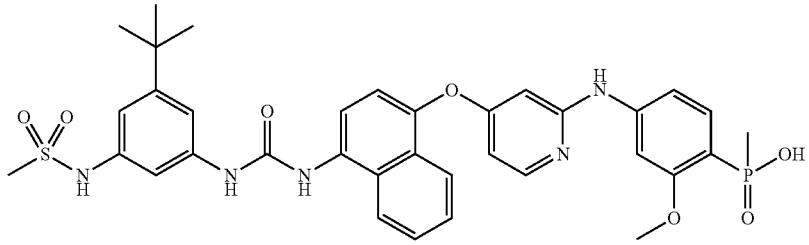 [SMILES: COc1cc(Nc2cc(Oc3ccc(NC(=O)Nc4cc(NS(C)(=O)=O)cc(C(C)(C)C)c4)c4ccccc34)ccn2)ccc1P(C)(=O)O]

To a solution of ethyl (4-((4-((4-(3-(3-(tert-butyl)-5-(methylsulfonamido)phenyl)ureido)-naphthalen-1-yl)oxy)pyridin-2-yl)amino)-2-methoxyphenyl)(methyl)phosphinate (see Example 71 above; 43.4 mg, 0.059 mmol) in 1,4-dioxane (0.7 mL), EtOH (0.2 mL) and water (0.1 mL) was added sodium hydroxide 50 wt % (9.4 μL, 0.178 mmol) and the solution was heated at 50° C. (block temperature) for 24 h. After cooling to rt, acetic acid (23.78 μL, 0.415 mmol) was added, the solvent was evaporated under reduced pressure and the resulting white solid was azeotroped with toluene (2 mL). The crude product was purified by preparative HPLC (Waters, Basic (0.1% Ammonium Bicarbonate), Basic, Waters X-Bridge Prep-C18, 5 μm, 19×50 mm column, 35-65% MeCN in Water) to afford a white solid. The resulting solid was slurried in hot MeCN (2 mL) and decanted to give the title compound (8 mg) as a white solid.

$^1$H NMR (400 MHz, DMSO-d6) δ: 9.63 (s, 1H), 9.14 (s, 1H), 8.28 (d, 1H), 8.14 (d, 1H), 8.08 (d, 1H), 7.81 (d, 1H), 7.69-7.46 (m, 3H), 7.45-7.28 (m, 4H), 7.13 (s, 1H), 6.87 (t, 1H), 6.65 (dd, 1H), 6.06 (s, 1H), 3.68 (s, 3H), 3.00 (s, 3H), 1.45 (d, 3H), 1.26 (s, 9H).

Example 73

The following compounds are prepared by methods analogous to those described above.

(a) 4-[[4-[[4-[[5-tert-butyl-3-(methanesulfonamido)-2-methoxy-phenyl]carbamoylamino]-1-naphthyl]oxy]-2-pyridyl]amino]-2-(trifluoromethyl)benzoic acid

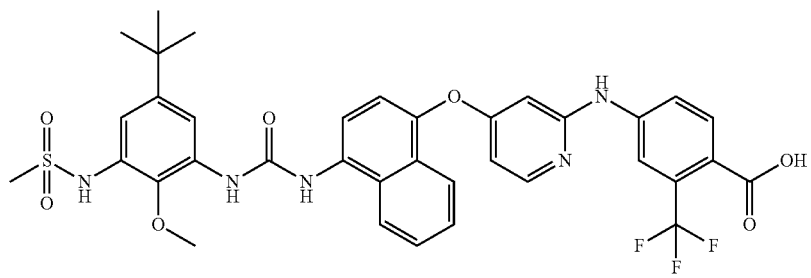 [SMILES: COc1c(NC(=O)Nc2ccc(Oc3ccnc(Nc4ccc(C(=O)O)c(C(F)(F)F)c4)c3)c3ccccc23)cc(C(C)(C)C)cc1NS(C)(=O)=O]

(b) (2R)-2-amino-3-[[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]propanoic acid

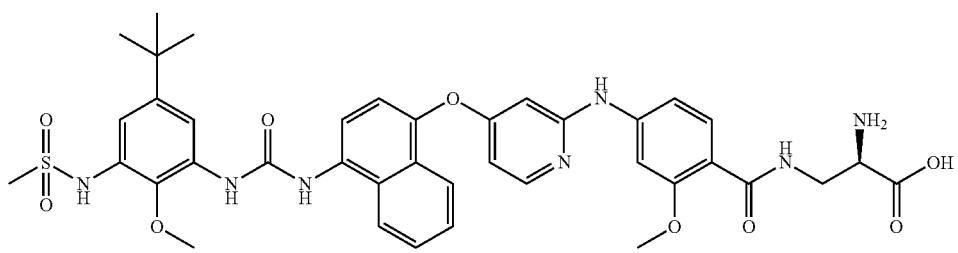 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NC[C@@H](N)C(=O)O]

(c) (2S)-2-amino-3-[[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]propanoic acid

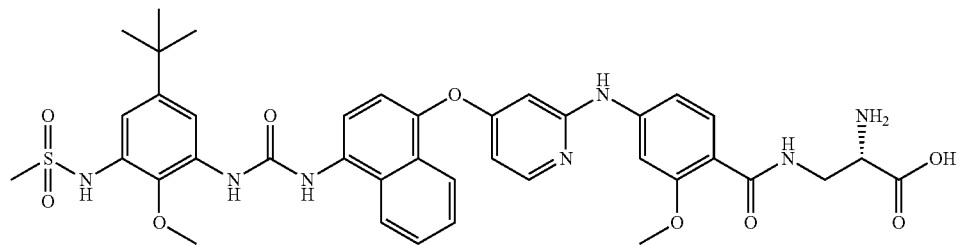 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NC[C@H](N)C(=O)O]

(d) (2R)-2-amino-4-[[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]butanoic acid

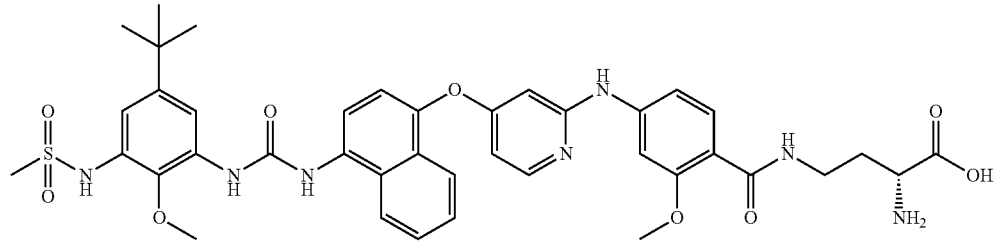 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCC[C@@H](N)C(=O)O]

(e) (2S)-2-amino-4-[[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]butanoic acid

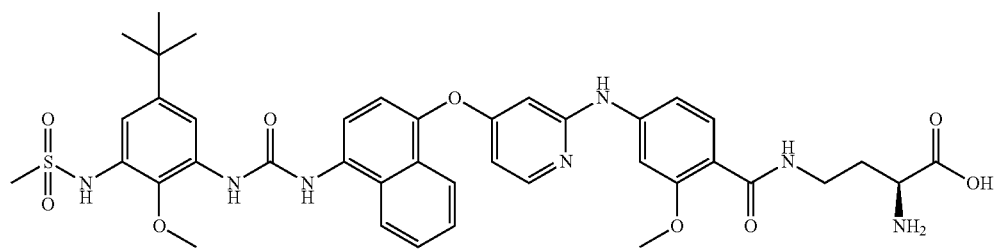 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCC[C@H](N)C(=O)O]

(f) (2R)-2-amino-5-[[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]pentanoic acid

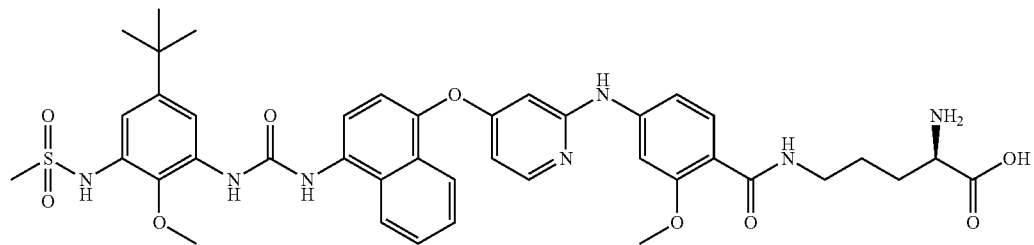 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCC[C@@H](N)C(=O)O]

(g) (2S)-2-amino-5-[[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]pentanoic acid

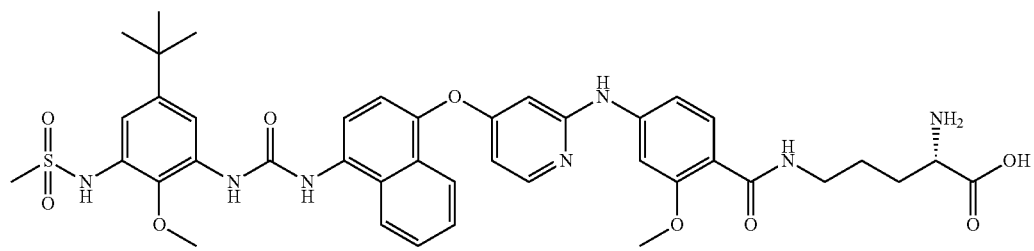 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCC[C@H](N)C(=O)O]

(h) (2R)-2-amino-6-[[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]hexanoic acid

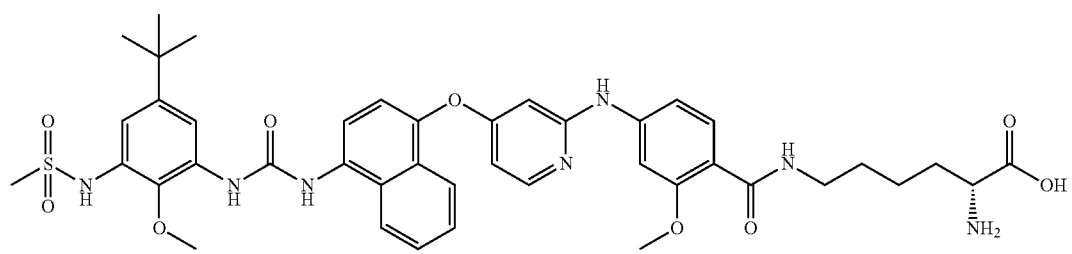 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCCC[C@@H](N)C(=O)O]

(i) (2R)-2-amino-7-[[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]heptanoic acid

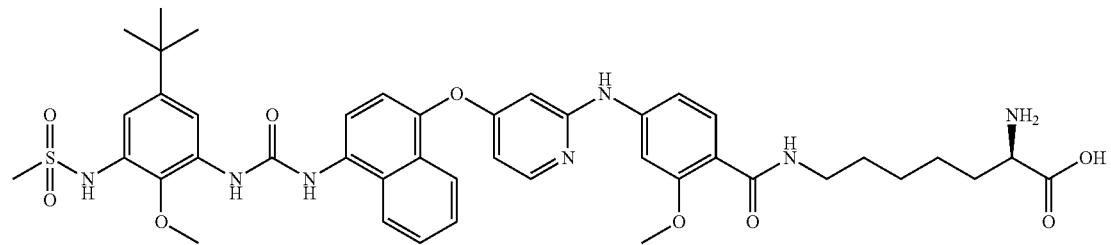 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCCCC[C@@H](N)C(=O)O]

(j) (2S)-2-amino-7-[[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]heptanoic acid

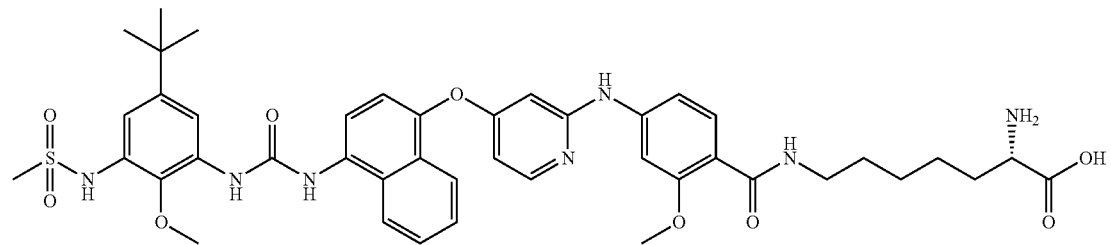 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCCCC[C@H](N)C(=O)O]

(k) (2S)-6-[[4-[[4-[[4-[[5-tert-butyl-3-(methanesulfonamido)-2-methoxy-phenyl]carbamoyl-amino]-1-naphthyl]oxy]-2-pyridyl]amino]-2-methoxy-benzoyl]amino]-2-(methylamino)hexanoic acid

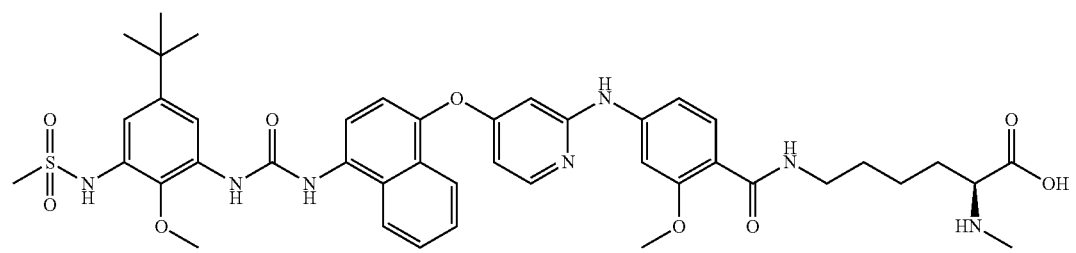 [SMILES: CN[C@@H](CCCCNC(=O)c1ccc(Nc2cc(Oc3ccc(NC(=O)Nc4cc(C(C)(C)C)cc(NS(C)(=O)=O)c4OC)c4ccccc34)ccn2)cc1OC)C(=O)O]

(l) (2S)-6-[[4-[[4-[[4-[[5-tert-butyl-3-(methanesulfonamido)-2-methoxy-phenyl]carbamoyl-amino]-1-naphthyl]oxy]-2-pyridyl]amino]-2-methoxy-benzoyl]amino]-2-(dimethylamino)-hexanoic acid

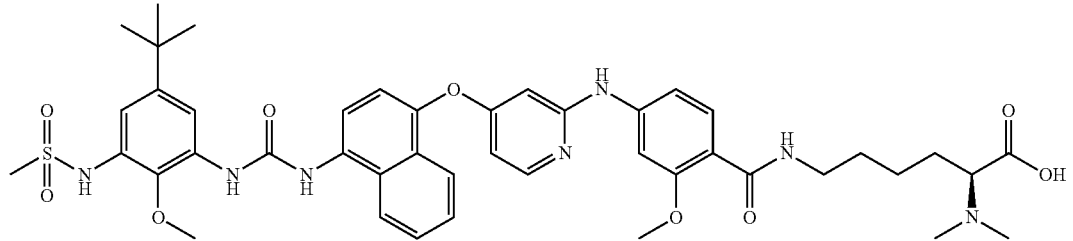 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCCC[C@@H](C(=O)O)N(C)C]

(m) (2R)-2-amino-5-[4-[2-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]ethyl]piperazin-1-yl]-5-oxo-pentanoic acid

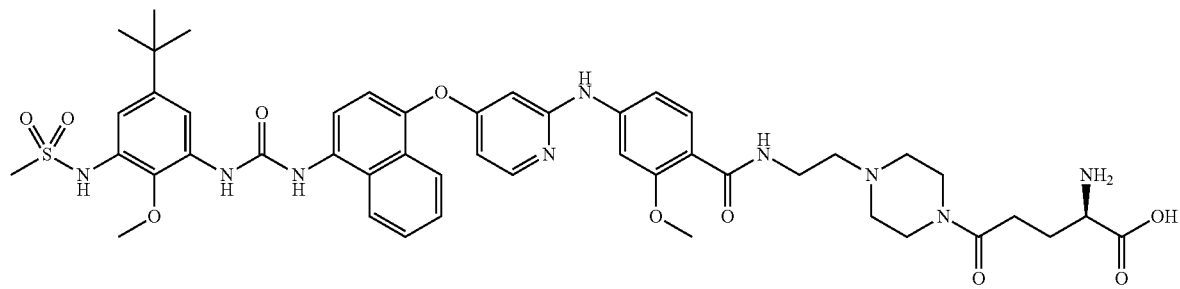 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCN(C(=O)CC[C@@H](N)C(=O)O)CC1]

(n) (2S)-2-amino-4-[4-[2-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]ethyl]piperazin-1-yl]-4-oxo-butanoic acid

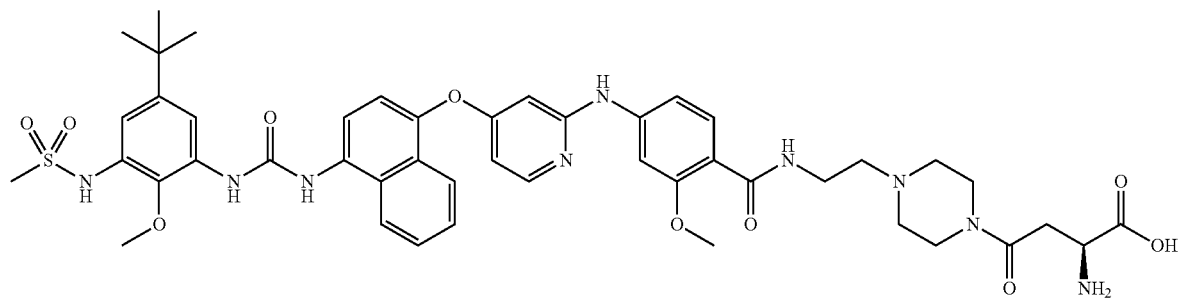 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCN(C(=O)C[C@H](N)C(=O)O)CC1]

(o) (2R)-2-amino-4-[4-[2-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]ethyl]piperazin-1-yl]-4-oxo-butanoic acid

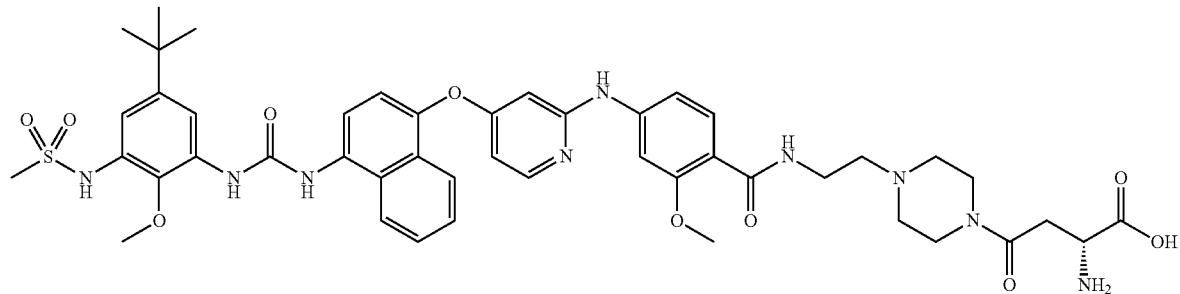 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCN(C(=O)C[C@@H](N)C(=O)O)CC1]

(p) 5-[[4-[[4-[[5-tert-butyl-3-(methanesulfonamido)-2-methoxy-phenyl]carbamoylamino]-1-naphthyl]oxy]-2-pyridyl]amino]-3-methoxy-pyridine-2-carboxylic acid

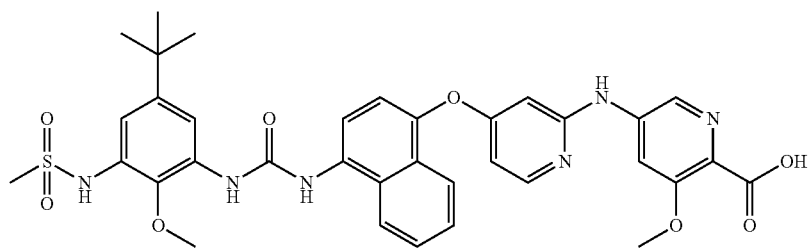 [SMILES: COc1cc(Nc2cc(Oc3ccc(NC(=O)Nc4cc(C(C)(C)C)cc(NS(C)(=O)=O)c4OC)c4ccccc34)ccn2)cnc1C(=O)O]

(q) 4-[[4-[[4-[[5-tert-butyl-3-(methanesulfonamido)-2-methoxy-phenyl]carbamoylamino]-1-naphthyl]oxy]-2-pyridyl]amino]-2-methylsulfanyl-benzoic acid

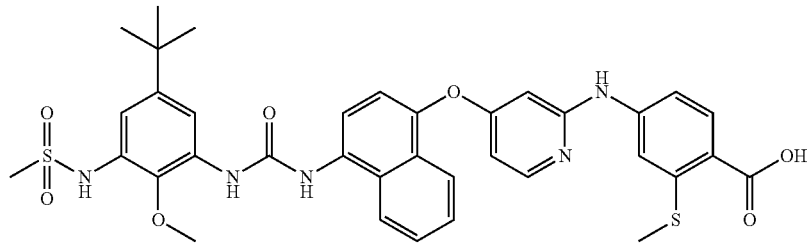

(r) 4-[[4-[[4-[[5-tert-butyl-3-(methanesulfonamido)-2-methoxy-phenyl]carbamoylamino]-1-naphthyl]oxy]-2-pyridyl]amino]-2-methylsulfinyl-benzoic acid

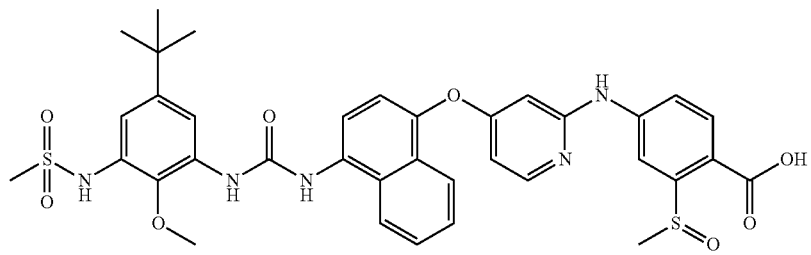 [SMILES: COc1c(NC(=O)Nc2ccc(Oc3ccnc(Nc4ccc(C(=O)O)c(S(C)=O)c4)c3)c3ccccc23)cc(C(C)(C)C)cc1NS(C)(=O)=O]

(s) 4-[[4-[[4-[[5-tert-butyl-3-(methanesulfonamido)-2-methoxy-phenyl]carbamoylamino]-1-naphthyl]oxy]-2-pyridyl]amino]-2-methylsulfonyl-benzoic acid

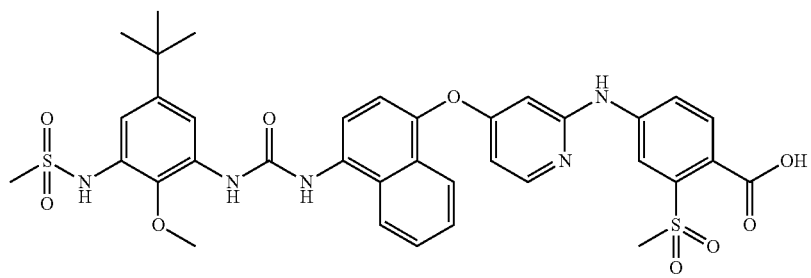 [SMILES: COc1c(NC(=O)Nc2ccc(Oc3ccnc(Nc4ccc(C(=O)O)c(S(C)(=O)=O)c4)c3)c3ccccc23)cc(C(C)(C)C)cc1NS(C)(=O)=O]

(t) 2-[4-[[4-[[4-[[5-tert-butyl-3-(methanesulfonamido)-2-methoxy-phenyl]carbamoylamino]-1-naphthyl]oxy]-2-pyridyl]amino]-2-methoxy-phenyl]acetic acid

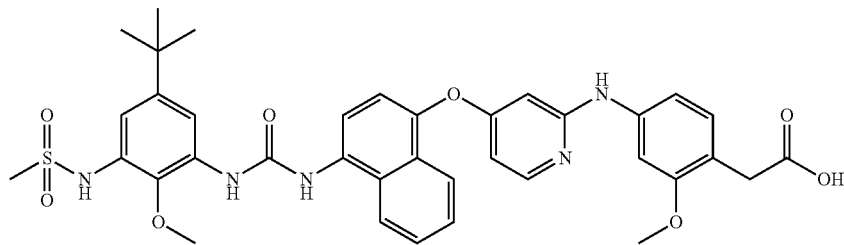 [SMILES: COc1cc(Nc2cc(Oc3ccc(NC(=O)Nc4cc(C(C)(C)C)cc(NS(C)(=O)=O)c4OC)c4ccccc34)ccn2)ccc1CC(=O)O]

(u) 2-[4-[[4-[[4-[[5-tert-butyl-3-(methanesulfonamido)-2-methoxy-phenyl]carbamoylamino]-1-naphthyl]oxy]-2-pyridyl]amino]-2-methoxy-benzoyl]amino]butoxy]acetic acid

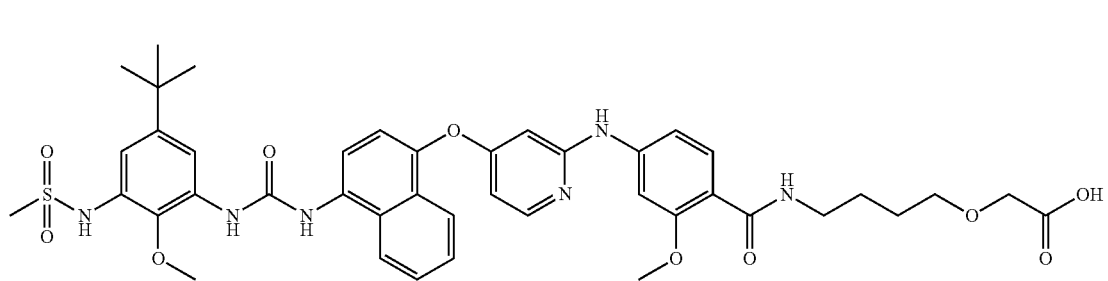 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCCCOCC(=O)O]

(v) 2-[4-[[4-[[4-[[5-tert-butyl-3-(methanesulfonamido)-2-methoxy-phenyl]carbamoylamino]-1-naphthyl]oxy]-2-pyridyl]amino]-2-methoxy-benzoyl]amino]butylamino]acetic acid

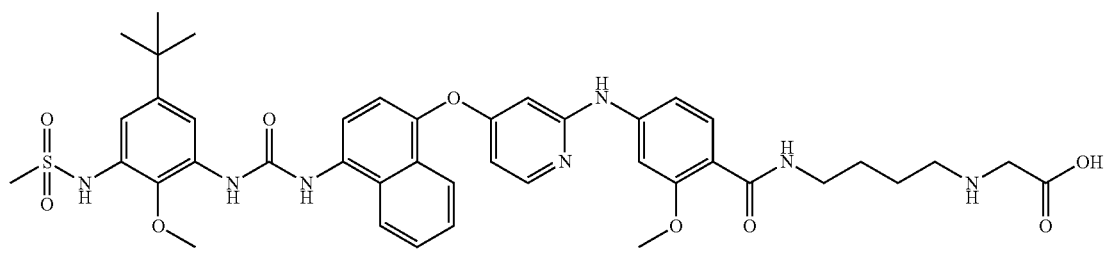 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCCCNCC(=O)O]

(w) 3-[3-[[4-[[4-[[5-tert-butyl-3-(methanesulfonamido)-2-methoxy-phenyl]carbamoylamino]-1-naphthyl]oxy]-2-pyridyl]amino]-2-methoxy-benzoyl]amino]propylamino]propanoic acid

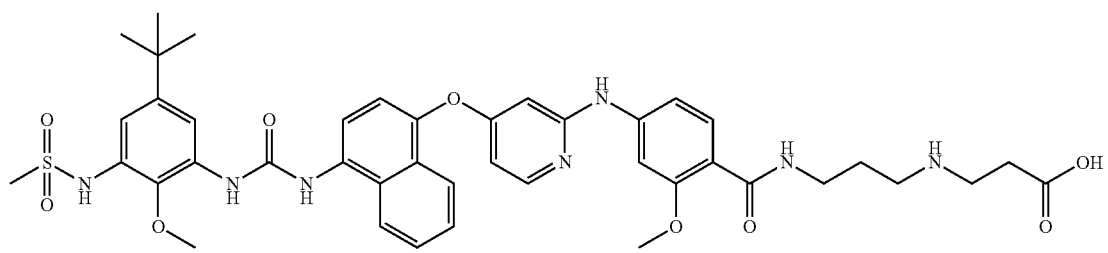 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCCNCCC(=O)O]

(x) 4-[2-[[4-[[4-[[4-[[5-tert-butyl-3-(methanesulfonamido)-2-methoxy-phenyl]carbamoylamino]-1-naphthyl]oxy]-2-pyridyl]amino]-2-methoxy-benzoyl]amino]ethylamino]butanoic acid

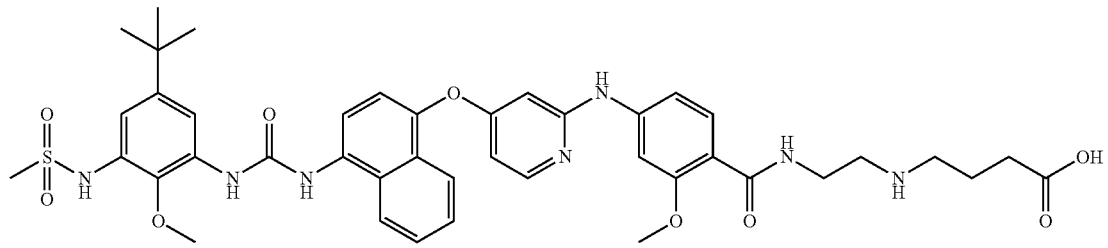 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCNCCCC(=O)O]

(y) (2S)-2-amino-3-[4-[[[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]methyl]phenyl]-propanoic acid

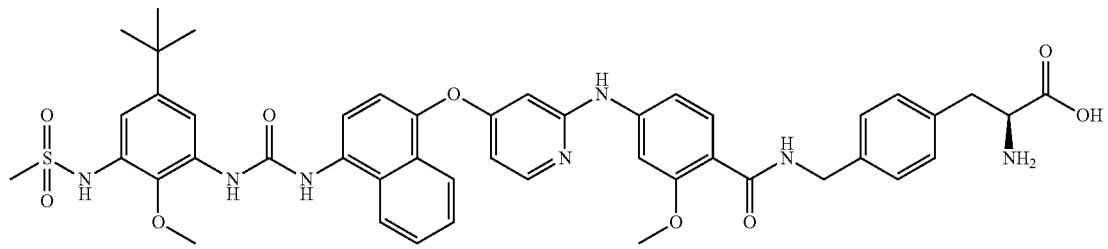 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCc1ccc(C[C@H](N)C(=O)O)cc1]

(z) (2R)-2-amino-3-[4-[[[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]methyl]phenyl]-propanoic acid

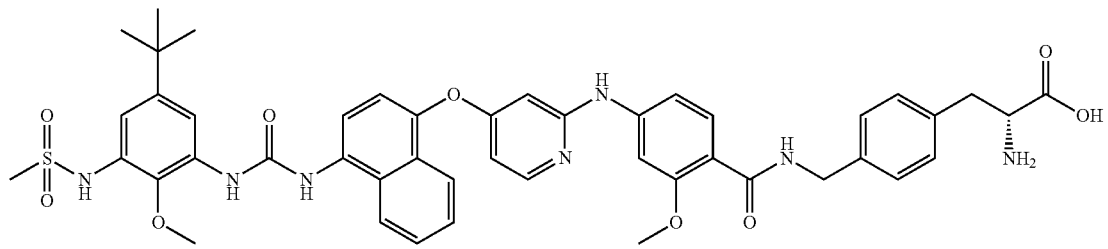 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCc1ccc(C[C@@H](N)C(=O)O)cc1]

(aa) (2R)-2-amino-3-[4-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]phenyl]-propanoic acid

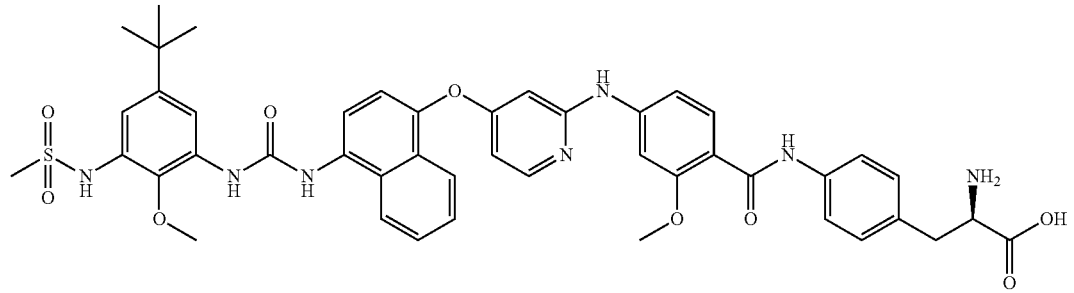 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)Nc1ccc(C[C@@H](N)C(=O)O)cc1]

(ab) (4S)-4-amino-5-[4-[2-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]ethyl]piperazin-1-yl]-5-oxo-pentanoic acid

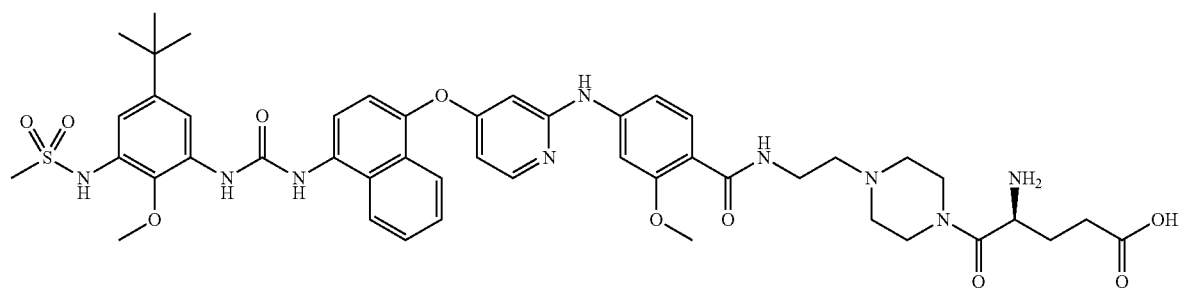 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCN(C(=O)[C@@H](N)CCC(=O)O)CC1]

(ac) (3S)-3-amino-4-[4-[2-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]ethyl]piperazin-1-yl]-4-oxo-butanoic acid

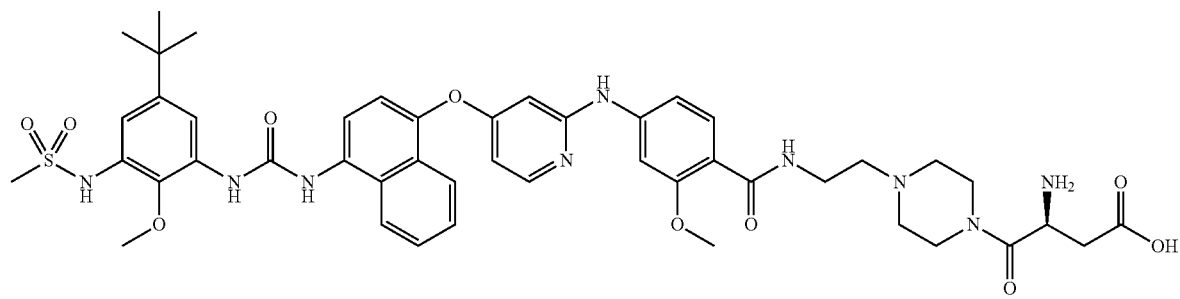 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCN(C(=O)[C@@H](N)CC(=O)O)CC1]

(ad) (2S)-2-amino-6-[4-[2-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]ethyl]piperazin-1-yl]-6-oxo-hexanoic acid

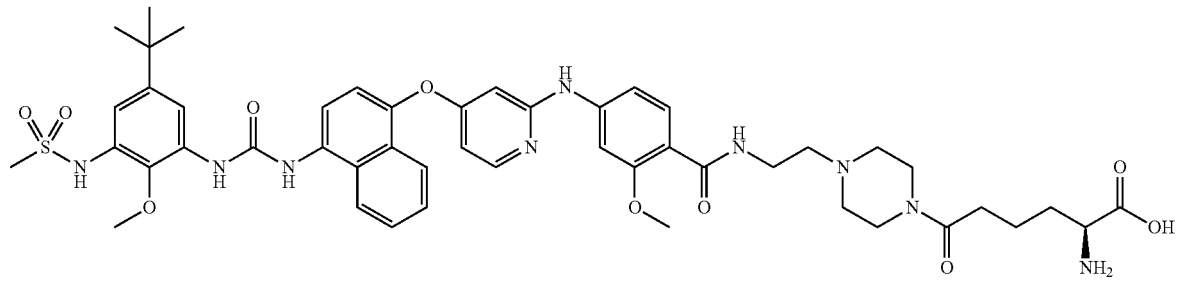 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCN(C(=O)CCC[C@H](N)C(=O)O)CC1]

(ae) (2R)-2-amino-6-[4-[2-[[4-[[4-[[5-tert-butyl-3-(methanesulfonamido)-2-methoxy-phenyl]carbamoylamino]-1-naphthyl]oxy]-2-pyridyl]amino]-2-methoxy-benzoyl]amino]ethyl]-piperazin-1-yl]-6-oxo-hexanoic acid

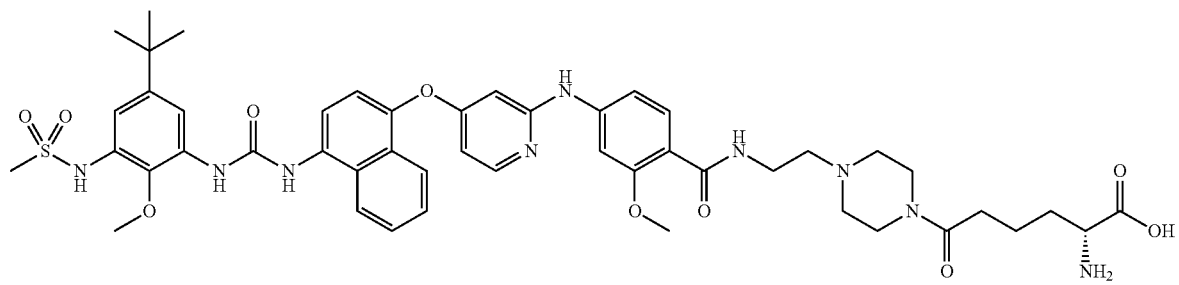 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCN(C(=O)CCC[C@@H](N)C(=O)O)CC1]

(af) (2S)-5-[4-[2-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]ethyl]piperazin-1-yl]-2-(methylamino)-5-oxo-pentanoic acid

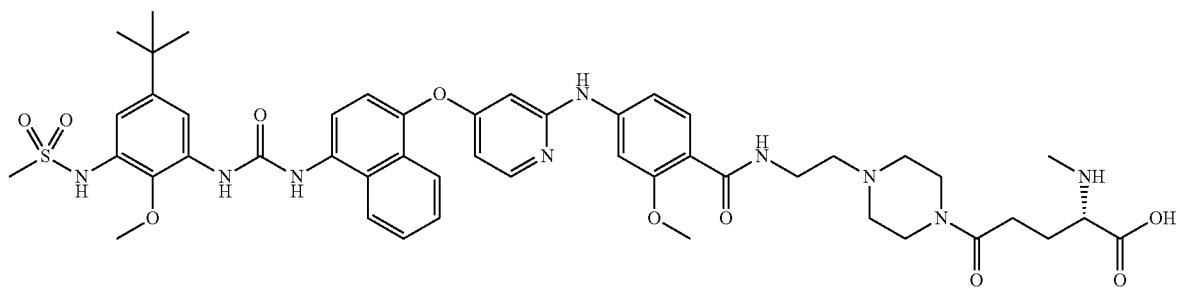 [SMILES: CN[C@@H](CCC(=O)N1CCN(CCNC(=O)c2ccc(Nc3cc(Oc4ccc(NC(=O)Nc5cc(C(C)(C)C)cc(NS(C)(=O)=O)c5OC)c5ccccc45)ccn3)cc2OC)CC1)C(=O)O]

(ag) (2S)-5-[4-[2-[[4-[[4-[[5-tert-butyl-3-(methanesulfonamido)-2-methoxy-phenyl]-carbamoylamino]-1-naphthyl]oxy]-2-pyridyl]amino]-2-methoxy-benzoyl]amino]ethyl]piperazin-1-yl]-2-(dimethylamino)-5-oxo-pentanoic acid

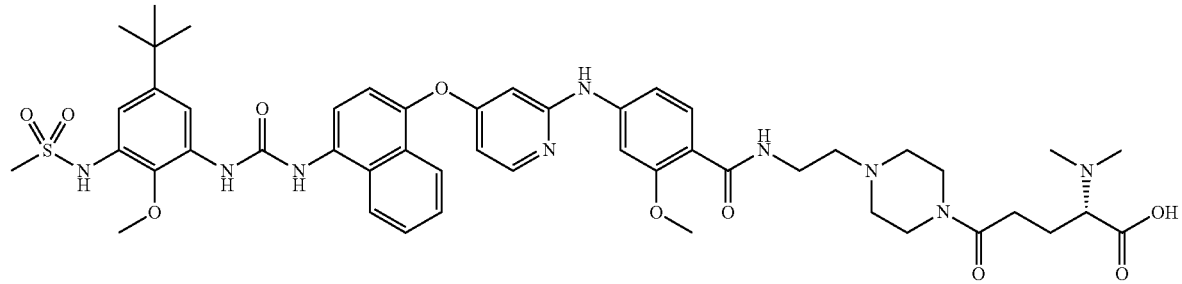 [SMILES: COc1cc(Nc2cc(Oc3ccc(NC(=O)Nc4cc(C(C)(C)C)cc(NS(C)(=O)=O)c4OC)c4ccccc34)ccn2)ccc1C(=O)NCCN1CCN(C(=O)CC[C@@H](C(=O)O)N(C)C)CC1]

Biological Testing: Experimental Methods
Enzyme Binding Assays (Kinomescan)

Kinase enzyme binding activities of compounds disclosed herein may be determined using a proprietary assay which measures active site-directed competition binding to an immobilized ligand (Fabian, M. A. et al., *Nature Biotechnol.*, 2005, 23:329-336). These assays may be conducted by DiscoverX (formerly Ambit; San Diego, Calif.). The percentage inhibition produced by incubation with a test compound may be calculated relative to the non-inhibited control.

Enzyme Inhibition Assays

The enzyme inhibitory activities of compounds disclosed herein are determined by FRET using synthetic peptides labelled with both donor and acceptor fluorophores (Z-LYTE, Invitrogen Ltd., Paisley, UK).

p38 MAPKα Enzyme Inhibition

The following two assay variants can be used for determination of p38 MAPKα inhibition.

Method 1

The inhibitory activities of test compounds against the p38 MAPKα isoform (MAPK14: Invitrogen) are evaluated indirectly by determining the level of activation/phosphorylation of the down-stream molecule, MAPKAP-K2. The p38 MAPKα protein (80 ng/mL, 2.5 µL) is mixed with the test compound (2.5 µL of either 4 µg/mL, 0.4 µg/mL, 0.04 µg/mL or 0.004 µg/mL) for 2 hr at RT. The mix solution (2.5 µL) of the p38α inactive target MAPKAP-K2 (Invitrogen, 600 ng/mL) and FRET peptide (8 µM; a phosphorylation target for MAPKAP-K2) is then added, then the kinase reaction is initiated by adding ATP (40 µM, 2.5 µL). The mixture is incubated for 1 hr at RT. Development reagent (protease, 5 µL) is added for 1 hr prior to detection in a fluorescence microplate reader (Varioskan® Flash, Thermo-Fisher Scientific).

Method 2

This method follows the same steps as Method 1 above, but utilises a higher concentration of the p38 MAPKα protein (2.5 µL of 200 ng/mL protein instead of 2.5 µL of 80 ng/mL protein) for mixing with the test compound (tested at either 1 µg/mL, 0.1 µg/mL, 0.01 µg/mL or 0.001 µg/mL).

p38 MAPKγ Enzyme Inhibition

The inhibitory activities of compounds of the invention against p38MAPKγ (MAPK12: Invitrogen), are evaluated in a similar fashion to that described hereinabove. The enzyme (800 ng/mL, 2.5 µL) is incubated with the test compound (2.5 µL of either 4 µg/mL, 0.4 µg/mL, 0.04 µg/mL, or 0.004 µg/mL) for 2 hr at RT. The FRET peptides (8 µM, 2.5 µL), and appropriate ATP solution (2.5 µL, 400 µM) are then added to the enzymes/compound mixtures and the whole is incubated for 1 hr. Development reagent (protease, 5 µL) is added for 1 hr prior to detection in a fluorescence microplate reader (Varioskan® Flash, Thermo Scientific).

c-Src and Syk Enzyme Inhibition

The inhibitory activities of compounds of the invention against c-Src and Syk enzymes (Invitrogen), are evaluated in a similar fashion to that described hereinabove. The relevant enzyme (3000 ng/mL or 2000 ng/mL respectively, 2.5 µL) is incubated with the test compound (either 1 µg/mL, 0.1 µg/mL, 0.01 µg/mL, or 0.001 µg/mL, 2.5 µL each) for 2 hr at RT. The FRET peptides (8 µM, 2.5 µL), and appropriate ATP solutions (2.5 µL, 800 µM for c-Src, and 60 µM ATP for Syk) are then added to the enzymes/compound mixtures and the mixture incubated for 1 hr. Development reagent (protease, 5 µL) is added for 1 hr prior to detection in a fluorescence microplate reader (Varioskan® Flash, Thermo-Fisher Scientific).

GSK 3α Enzyme Inhibition

The following two assay variants can be used for determination of GSK 3α inhibition.

Method 1

The inhibitory activities of compounds of the invention against the GSK 3α enzyme isoform (Invitrogen), are evaluated by determining the level of activation/phosphorylation of the target peptide. The GSK3-α protein (500 ng/mL, 2.5 µL) is mixed with the test compound (2.5 µL at either 4 µg/mL, 0.4 µg/mL, 0.04 µg/mL, or 0.004 µg/mL) for 2 hr at RT. The FRET peptide (8 µM, 2.5 µL), which is a phosphorylation target for GSK3α, and ATP (40 µM, 2.5 µL) are then added to the enzyme/compound mixture and the resulting mixture incubated for 1 hr. Development reagent (protease, 5 µL) is added for 1 hr prior to detection in a fluorescence microplate reader (Varioskan® Flash, ThermoFisher Scientific).

In all cases, the site-specific protease cleaves non-phosphorylated peptide only and eliminates the FRET signal.

Phosphorylation levels of each reaction are calculated using the ratio of coumarin emission (donor) over fluorescein emission (acceptor), for which high ratios indicate high phosphorylation and low ratios indicate low phosphorylation levels. The percentage inhibition of each reaction is calculated relative to non-inhibited control and the 50% inhibitory concentration ($IC_{50}$ value) is then calculated from the concentration-response curve.

Method 2

This method follows the same steps as Method 1 above, but utilises a shorter period of mixing of the test compound (105 minutes instead of 2 hours) with the GSK3-α protein. In addition, the concentrations of test compound employed are either 10 μg/mL, 1 μg/mL, 0.1 μg/mL, or 0.01 μg/mL Cellular Assays The compounds of the invention were studied using one or more of the following assays.

(a) Inhibition of p38 MAPKα and Lck in Jurkat Cells

Jurkat T cells were cultured in starve medium (RPMI 1640+5% FBS) for 24 h prior to the experiment. Cells were harvested and resuspended at $10 \times 10^6$ cells/mL in starve medium and then plated into round-bottomed 96 well plates at $1 \times 10^6$ cells/well. Serial dilutions of test compound were added (1% final DMSO concentration) for 2 h prior to stimulation. Following pre-incubation with compound, cells were stimulated with $H_2O_2$ (0.05% final) for 5 min. The reaction was stopped by centrifugation at 2000 rpm (3 min, 4° C.), then the supernatant was removed and 100 μL of cold fix/perm solution (BD Fix/Perm kit #554714) added. Plates were incubated for 20 min at 4° C. before centrifugation and washing with supplied ix wash medium (BD Fix/Perm kit #554714). Cells were stained for either phospho-p38α (T180/182), supplied by Cell Signalling Technology (9211s), or phospho-Lck (Y394), supplied by R&D (MAB7500). Antibodies were diluted to 5 μg/mL (R&D) or 1:200 (Cell Signalling Technology) in wash medium, before being incubated 1 h at 4° C. in the dark. Following 3 repeat washes with ice cold wash buffer, secondary antibody (anti-rabbit-FITC #F1362 or anti-mouse-FITC #F2883, both from Sigma) was added at a dilution of 1:1000 and incubated for 1 h at 4° C. in the dark. Cells were washed 3× times in cold wash buffer then, following a final wash in cold PBS, were resuspended in 150 μL cold PBS. Cells were analysed by flow cytometry using BD Accuri C6.

(aa) LPS-Induced TNFα/IL-8 Release in d-U937 Cells

U937 cells, a human monocytic cell line, are differentiated to macrophage-type cells by incubation with phorbol myristate acetate (PMA; 100 ng/mL) for 48 to 72 hr. Cells are pre-incubated with final concentrations of test compound for 2 hr and are then stimulated with 0.1 μg/mL of LPS (from E. Coli: 0111:B4, Sigma) for 4 hr. The supernatant is collected for determination of TNFα and IL-8 concentrations by sandwich ELISA (Duo-set, R&D systems). The inhibition of TNFα production is calculated as a percentage of that achieved by 10 μg/mL of BIRB796 at each concentration of test compound by comparison against vehicle control. The relative 50% effective concentration ($REC_{50}$) is determined from the resultant concentration-response curve. The inhibition of IL-8 production is calculated at each concentration of test compound by comparison with vehicle control. The 50% inhibitory concentration ($IC_{50}$) is determined from the resultant concentration-response curve.

(b) LPS-Induced TNFα/IL-8 Release in PBMC Cells

Peripheral blood mononuclear cells (PBMCs) from healthy subjects are separated from whole blood using a density gradient (Lymphoprep, Axis-Shield Healthcare). The PBMCs are seeded in 96 well plates and treated with compounds at the desired concentration for 2 hours before addition of 1 ng/mL LPS (Escherichia Coli 0111:B4 from Sigma Aldrich) for 24 hours under normal tissue culture conditions (37° C., 5% $CO_2$). The supernatant is harvested for determination of IL-8 and TNFα concentrations by sandwich ELISA (Duo-set, R&D systems) and read on the fluorescence microplate reader (Varioskan® Flash, Thermo-Fisher Scientific). The concentration at 50% inhibition ($IC_{50}$) of IL-8 and TNFα production is calculated from the dose response curve.

(c) IL-2 and IFN Gamma Release in CD3/CD28 Stimulated PBMC Cells

PBMCs from healthy subjects are separated from whole blood using a density gradient (Lymphoprep, Axis-Shield Healthcare). Cells are added to a 96 well plate pre-coated with a mixture of CD3/CD28 monoclonal antibodies (0.3 μg/mL eBioscience and 3 μg/mL BD Pharmingen respectively). Compound at the desired concentration is then added to the wells and the plate left for 3 days under normal tissue culture conditions. Supernatants are harvested and IL-2 and IFN gamma release determined by Sandwich ELISA (Duo-set, R&D System). The $IC_{50}$ is determined from the dose response curve.

(d) IL-1β-Induced IL-8 Release in HT29 Cells

HT29 cells, a human colon adenocarcinoma cell line, are plated in a 96 well plate (24 hr) and pre-treated with compounds at the desired concentration for 2 hours before addition of 5 ng/mL of IL-1β (Abcarn) for 24 hours. Supernatants are harvested for IL-8 quantification by Sandwich ELISA (Duo-set, R&D System). The $IC_{50}$ is determined from the dose response curve.

(e) LPS-Induced IL-8 and TNFα Release in Primary Macrophages

PBMCs from healthy subjects are separated from whole blood using a density gradient (Lymphoprep, Axis-Shield Healthcare). Cells are incubated for 2 hrs and non-adherent cells removed by washing. To differentiate the cells to macrophages, they are incubated with 5 ng/mL of GM-CSF (Peprotech) for 7 days under normal tissue culture conditions. Compounds are then added to the cells at the desired concentration for a 2 hour pre-treatment before stimulation with 10 ng/mL LPS for 24 hours. Supernatants are harvested and IL-8 and TNFα release determined by Sandwich ELISA (Duo-set, R&D System). The $IC_{50}$ is determined from the dose response curve.

(f) Poly I:C-Induced ICAM-1 Expression in BEAS2B Cells

Poly I:C is used in these studies as a simple, RNA virus mimic. Poly I:C-Oligofectamine mixture (1 μg/mL Poly I:C, ±2% Oligofectamine, 25 μL; Invivogen Ltd., San Diego, Calif., and Invitrogen, Carlsbad, Calif., respectively) is transfected into BEAS2B cells (human bronchial epithelial cells, ATCC). Cells are pre-incubated with final concentrations of test compounds for 2 hr and the level of ICAM1 expression on the cell surface is determined by cell-based ELISA. At a time point 18 hr after poly I:C transfection, cells are fixed with 4% formaldehyde in PBS and then endogenous peroxidase is quenched by the addition of washing buffer (100 μL, 0.05% Tween in PBS: PBS-Tween) containing 0.1% sodium azide and 1% hydrogen peroxide. Cells are washed with wash-buffer (3×200 μL) and after blocking the wells with 5% milk in PBS-Tween (100 μL) for 1 hr, the cells are incubated with anti-human ICAM-1 antibody (50 μL; Cell Signalling Technology, Danvers, Mass.) in 1% BSA PBS overnight at 4° C.

The cells are washed with PBS-Tween (3×200 μL) and incubated with the secondary antibody (100 μL; HRP-conjugated anti-rabbit IgG, Dako Ltd., Glostrup, Denmark). The cells are then incubated with substrate (50 μL) for 2-20 min, followed by the addition of stop solution (50 μL, 1N $H_2SO_4$). The ICAM-1 signal is detected by reading the absorbance at 450 nm against a reference wavelength of 655 nm using a spectrophotometer. The cells are then washed with PBS-Tween (3×200 μL) and total cell numbers in each well are determined by reading absorbance at 595 nm after Crystal Violet staining (50 μL of a 2% solution in PBS) and elution by 1% SDS solution (100 μL) in distilled water. The measured OD 450-655 readings are corrected for cell number by dividing with the OD595 reading in each well. The inhibition of ICAM-1 expression is calculated at each concentration of test compound by comparison with vehicle control. The 50% inhibitory concentration ($IC_{50}$) is determined from the resultant concentration-response curve.

(g) Cell Mitosis Assay

Peripheral blood mononucleocytes (PBMCs) from healthy subjects are separated from whole blood (Quintiles, London, UK) using a density gradient (Histopaque®-1077, Sigma-Aldrich, Poole, UK). The PBMCs (3 million cells per sample) are subsequently treated with 2% PHA (phytohaemagglutinin, Sigma-Aldrich, Poole, UK) for 48 hr, followed by a 20 hr exposure to varying concentrations of test compounds. At 2 hr before collection, PBMCs are treated with demecolcine (0.1 μg/mL; Invitrogen, Paisley, UK) to arrest cells in metaphase. To observe mitotic cells, PBMCs are permeabilized and fixed by adding Intraprep (50 μL; Beckman Coulter, France), and stained with anti-phospho-histone 3 (0.26 ng/L; #9701; Cell Signalling, Danvers, Mass.) and propidium iodide (1 mg/mL; Sigma-Aldrich, Poole, UK) as previously described (Muehlbauer P. A. and Schuler M. J., *Mutation Research*, 2003, 537:117-130). Fluorescence is observed using an ATTUNE flow cytometer (Invitrogen, Paisley, UK), gating for lymphocytes. The percentage inhibition of mitosis is calculated for each treatment relative to vehicle (0.5% DMSO) treatment.

(h) Rhinovirus-Induced IL-8 Release and ICAM-1 Expression

Human rhinovirus RV16 is obtained from the American Type Culture Collection (Manassas, Va.). Viral stocks are generated by infecting HeLa cells with HRV until 80% of the cells are cytopathic.

BEAS2B cells are infected with HRV at an MOI of 5 and incubated for 2 hr at 33° C. with gentle shaking to promote absorption. The cells are then washed with PBS, fresh media added and the cells are incubated for a further 72 hr. The supernatant is collected for assay of IL-8 concentrations using a Duoset ELISA development kit (R&D systems, Minneapolis, Minn.).

The level of ICAM-1 expressing cell surface is determined by cell-based ELISA. At 72 hr after infection, cells are fixed with 4% formaldehyde in PBS. After quenching endogenous peroxidase by adding 0.1% sodium azide and 1% hydrogen peroxide, wells are washed with wash-buffer (0.05% Tween in PBS: PBS-Tween). After blocking well with 5% milk in PBS-Tween for 1 hr, the cells are incubated with anti-human ICAM-1 antibody in 5% BSA PBS-Tween (1:500) overnight. Wells are washed with PBS-Tween and incubated with the secondary antibody (HRP-conjugated anti-rabbit IgG, Dako Ltd.). The ICAM-1 signal is detected by adding substrate and reading at 450 nm with a reference wavelength of 655 nm using a spectrophotometer. The wells are then washed with PBS-Tween and total cell numbers in each well are determined by reading absorbance at 595 nm after Crystal Violet staining and elution with 1% SDS solution. The measured $OD_{450-655}$ readings are corrected for cell number by dividing with the $OD_{595}$ reading in each well. Compounds are added 2 hr before HRV infection and 2 hr after infection when non-infected HRV is washed out.

(i) Assessment of HRV16 Induced Cytopathic Effect (CPE) in MRC5 Cells

MRC5 cells are infected with HRV16 at an MOI of 1 in DMEM containing 5% FCS and 1.5 mM $MgCl_2$, followed by incubation for 1 hr at 33° C. to promote adsorption. The supernatants are aspirated, and then fresh media added followed by incubation for 4 days. Where appropriate, cells are pre-incubated with compound or DMSO for 2 hr, and the compounds and DMSO added again after washout of the virus.

Supernatants are aspirated and incubated with methylene blue solution (100 μL, 2% formaldehyde, 10% methanol and 0.175% Methylene Blue) for 2 hr at RT. After washing, 1% SDS in distilled water (100 μL) is added to each well, and the plates are shaken lightly for 1-2 hr prior to reading the absorbance at 660 nm. The percentage inhibition for each well is calculated. The $IC_{50}$ value is calculated from the concentration-response curve generated by the serial dilutions of the test compounds.

(j) In Vitro RSV Virus Load in Primary Bronchial Epithelial Cells

Normal human bronchial epithelial cells (NHBEC) grown in 96 well plates are infected with RSV A2 (Strain A2, HPA, Salisbury, UK) at a MOI of 0.001 in the LHC8 Media: RPMI-1640 (50:50) containing 15 mM magnesium chloride and incubated for 1 hr at 37° C. for adsorption. The cells are washed with PBS (3×200 μL), then fresh media (200 μL) is added and incubation continued for 4 days. Where appropriate, cells are pre-incubated with the compound or DMSO for 2 hr, and then added again after washout of the virus.

The cells are fixed with 4% formaldehyde in PBS solution (50 μL) for 20 min, washed with WB (3×200 μL) (washing buffer, PBS including 0.5% BSA and 0.05% Tween-20) and incubated with blocking solution (5% condensed milk in PBS) for 1 hr. Cells are then washed with WB (3×200 μL) and incubated for 1 hr at RT with anti-RSV (2F7) F-fusion protein antibody (40 μL; mouse monoclonal, lot 798760, Cat. No. ab43812, Abcam) in 5% BSA in PBS-tween. After washing, cells are incubated with an HRP-conjugated secondary antibody solution (50 μL) in 5% BSA in PBS-Tween (lot 00053170, Cat. No. P0447, Dako) and then TMB substrate added (50 μL; substrate reagent pack, lot 269472, Cat. No. DY999, R&D Systems, Inc.). This reaction is stopped by the addition of 2N $H_2SO_4$ (50 μL) and the resultant signal is determined colourimetrically (OD: 450 nm with a reference wavelength of 655 nm) in a microplate reader (Varioskan® Flash, ThermoFisher Scientific).

Cells are then washed and a 2.5% crystal violet solution (50 μL; lot 8656, Cat. No. PL7000, Pro-Lab Diagnostics) is applied for 30 min. After washing with WB, 1% SDS in distilled water (100 μL) is added to each well, and plates are shaken lightly on the shaker for 1 hr prior to reading the absorbance at 595 nm. The measured $OD_{450-655}$ readings are corrected to the cell number by dividing the $OD_{450-655}$ by the $OD_{595}$ readings. The percentage inhibition for each well is calculated and the $IC_{50}$ value is calculated from the concentration-response curve generated from the serial dilutions of compound.

(k) Cell Viability Assay: MTT Assay

Differentiated U937 cells are pre-incubated with each test compound (final concentration 1 μg/mL or 10 μg/mL in 200 μL media indicated below) under two protocols: the first for 4 hr in 5% FCS RPM11640 media and the second in 10% FCS RPM11640 media for 24 h. The supernatant is replaced with new media (200 µL) and MTT stock solution (10 µL, 5 mg/mL) is added to each well. After incubation for 1 hr the media are removed, DMSO (200 µL) is added to each well and the plates are shaken lightly for 1 hr prior to reading the absorbance at 550 nm. The percentage loss of cell viability is calculated for each well relative to vehicle (0.5% DMSO) treatment. Consequently an apparent increase in cell viability for drug treatment relative to vehicle is tabulated as a negative percentage.

(l) Human Biopsy Assay

Intestinal mucosa biopsies are obtained from the inflamed regions of the colons of IBD patients. The biopsy material is cut into small pieces (2-3 mm) and placed on steel grids in an organ culture chamber at 37° C. in a 5% $CO_2$/95% $O_2$ atmosphere in serum-free media. DMSO control or test compounds at the desired concentration are added to the tissue and incubated for 24 hr in the organ culture chamber. The supernatant is harvested for determination of IL-6, IL-8, IL-1β and TNFα levels by R&D ELISA. Percentage inhibition of cytokine release by the test compounds is calculated relative to the cytokine release determined for the DMSO control (100%).

(m) Accumulation of β Catenin in d-U937 Cells

U937 cells, a human monocytic cell line, are differentiated into macrophage-type cells by incubation with PMA (100 ng/mL) for between 48 to 72 hr. The cells are then incubated with either final concentrations of test compound or vehicle for 18 hr. The induction of β-catenin by the test compounds is stopped by replacing the media with 4% formaldehyde solution. Endogenous peroxide activity is neutralised by incubating with quenching buffer (100 µL, 0.1% sodium azide, 1% $H_2O_2$ in PBS with 0.05% Tween-20) for 20 min. The cells are washed with washing buffer (200 µL; PBS containing 0.05% Tween-20) and incubated with blocking solution (200 µL; 5% milk in PBS) for 1 hr, re-washed with washing buffer (200 µL) and then incubated overnight with anti-β-catenin antibody solution (50 µL) in 1% BSA/PBS (BD, Oxford, UK).

After washing with washing buffer (3×200 µL; PBS containing 0.05% Tween-20), cells are incubated with a HRP-conjugated secondary antibody solution (100 µL) in 1% BSA/PBS (Dako, Cambridge, UK) and the resultant signal is determined colourimetrically (OD: 450 nm with a reference wavelength of 655 nm) using TMB substrate (50 µL; R&D Systems, Abingdon, UK). This reaction is stopped by addition of 1N $H_2SO_4$ solution (50 µL). Cells are then washed with washing buffer and 2% crystal violet solution (50 µL) is applied for 30 min. After washing with washing buffer (3×200 µL), 1% SDS (100 µL) is added to each well and the plates are shaken lightly for 1 hr prior to measuring the absorbance at 595 nm (Varioskan® Flash, Thermo-Fisher Scientific).

The measured $OD_{450-655}$ readings are corrected for cell number by dividing the $OD_{450-655}$ by the $OD_{595}$ readings. The percentage induction for each well is calculated relative to vehicle, and the ratio of induction normalised in comparison with the induction produced by a standard control comprising the Reference compound N-(4-(4-(3-(3-tert-butyl-1-p-tolyl-1H-pyrazol-5-yl)ureido)naphthalen-1-yloxy)pyridin-2-yl)-2-methoxyacetamide (1 µg/mL), which is defined as unity.

(n) T Cell Proliferation

PBMCs from healthy subjects are separated from whole blood using a density gradient (Lymphoprep, Axis-Shield Healthcare). The lymphocyte fraction is first enriched for CD4+ T cells by negative magnetic cell sorting as per the manufacturer's instructions (Miltenyi Biotec 130-091-155). Naïve CD4+ T cells are then separated using positive magnetic selection of CD45RA+ cells using microbeads as per the manufacturer's instructions (130-045-901). Cells are plated at $2 \times 10^5$ cells per well in 100 µL RPMI/10% FBS on 96 well flat bottomed plate (Corning Costar). 25 µL of test compound are diluted to the appropriate concentration (8× final concentration) in normal medium and added to duplicate wells on the plate to achieve a dose response range of 0.03 ng/mL-250 ng/mL. DMSO is added as a negative control. Plates are allowed to pre-incubate for 2 hours before stimulation with 1 µg/mL anti-CD3 (OKT3; eBioscience). After 72 h, the medium in each well is replaced with 150 µL of fresh medium containing 10 µM BrdU (Roche). After 16 h, the supernatant is removed, the plate is dried and the cells fixed by adding 100 µL of fix/denature solution to each well for 20 min as per the manufacturer's instructions (Roche). Plates are washed once with PBS before addition of the anti-BrdU detection antibody and incubated for 90 mins at room temperature. Plates are then washed gently 3× with the wash buffer supplied and developed by addition of 100 µL of substrate solution. The reaction is stopped by addition of 50 µL of 1 M $H_2SO_4$ and read for absorbance at 450 nm on a plate reader (Varioskan® Flash, ThermoFisher Scientific). The $IC_{50}$ is determined from the dose response curve.

(o) IL-2 and IFNγ release in CD3/CD28 stimulated LPMC cells from IBD patients

Lamina propria mononuclear cells (LPMCs) are isolated and purified from inflamed IBD mucosa of surgical specimens or from normal mucosa of surgical specimens as follows: The mucosa is removed from the deeper layers of the surgical specimens with a scalpel and cut in fragments of size 3-4 mm. The epithelium is removed by washing the tissue fragments three times with 1 mM EDTA (Sigma-Aldrich, Poole, UK) in HBSS (Sigma-Aldrich) with agitation using a magnetic stirrer, discarding the supernatant after each wash. The sample is subsequently treated with type 1A collagenase (1 mg/mL; Sigma-Aldrich) for 1 h with stirring at 37° C. The resulting cell suspension is then filtered using a 100 µm cell strainer, washed twice, resuspended in RPMI-1640 medium (Sigma-Aldrich) containing 10% fetal calf serum, 100 U/mL penicillin and 100 µg/mL streptomycin, and used for cell culture.

Freshly isolated LPMCs ($2 \times 10^5$ cells/well) are stimulated with 1 µg/mL α-CD3/α-CD28 for 48 h in the presence of either DMSO control or appropriate concentrations of compound. After 48 h, the supernatant is removed and assayed for the presence of TNFα and IFNγ by R&D ELISA. Percentage inhibition of cytokine release by the test compounds is calculated relative to the cytokine release determined for the DMSO control (100%).

(p) Inhibition of Cytokine Release from Myofibroblasts Isolated from IBD Patients Myofibroblasts from inflamed IBD mucosa are isolated as follows:

The mucosa is dissected and discarded and 1 mm-sized mucosal samples are cultured at 37° C. in a humidified $CO_2$ incubator in Dulbecco's modified Eagle's medium (DMEM, Sigma-Aldrich) supplemented with 20% FBS, 1% non-essential amino acids (Invitrogen, Paisley, UK), 100 U/mL penicillin, 100 µg/mL streptomycin, 50 µg/mL gentamycin, and 1 µg/mL amphotericin (Sigma-Aldrich). Established colonies of myofibroblasts are seeded into 25-$cm^2$ culture flasks and cultured in DMEM supplemented with 20% FBS and antibiotics to at least passage 4 to provide a sufficient quantity for use in stimulation experiments.

Subconfluent monolayers of myofibroblasts, seeded in 12-well plates at $3\times10^5$ cells per well, are starved in serum-free medium for 24 h at 37° C., 5% $CO_2$, before being cultured for 24 h in the presence of either DMSO control or appropriate concentrations of compound. After 24 h, the supernatant is removed and assayed for the presence of IL-8 and IL-6 by R&D ELISA. Percentage inhibition of cytokine release by the test compounds is calculated relative to the cytokine release determined for the DMSO control (100%).

(q) Human Neutrophil Degranulation

Neutrophils are isolated from human peripheral blood as follows:

Blood is collected by venepuncture and anti-coagulated by addition of 1:1 EDTA:sterile phosphate buffered saline (PBS, no Ca+/Mg+). Dextran (3% w/v) is added (1 part dextran solution to 4 parts blood) and the blood allowed to stand for approximately 20 minutes at rt. The supernatant is carefully layered on a density gradient (Lymphoprep, Axis-Shield Healthcare) and centrifuged (15 mins, 2000 rpm, no brake). The supernatant is aspirated off and the cell pellet is re-suspended in sterile saline (0.2%) for no longer than 60 seconds (to lyse contaminating red blood cells). 10 times volume of PBS is then added and the cells centrifuged (5 mins, 1200 rpm). Cells are re-suspended in HBSS+ (Hanks buffered salt solution (without phenol red) containing cytochalasin B (5 μg/mL) and 1 mM $CaCl_2$) to achieve $5\times10^6$ cells/mL.

$5\times10^4$ cells are added to each well of a V-bottom 96 well plate and are incubated (30 mins, 37° C.) with the appropriate concentration of test compound (0.3-1000 ng/mL) or vehicle (DMSO, 0.5% final conc). Degranulation is stimulated by addition of fMLP (final concentration 1 μM). After a further incubation (30 mins, 37° C.), the cells are removed by centrifugation (5 mins, 1500 rpm) and the supernatants transferred to a flat bottom 96 well plate. An equal volume of tetramethylbenzidine (TMB) is added and, after 10 mins, the reaction terminated by addition of an equal volume of sulphuric acid (0.5 M) and absorbance read at 450 nm (background at 655 nm subtracted). The 50% inhibitory concentration ($IC_{50}$) is determined from the resultant concentration-response curve.

(r) Cell Cytotoxicity Assay $1\times10^5$ Jurkat cells (immortalised human T lymphocytes) are added to the appropriate number of wells of a 96 well plate in 100 μL of media (RPMI supplemented with 10% foetal bovine serum). 1 μL of DMSO control (final concentration 1.0% v/v) or test compound (final concentration 20, 5 or 1 μg/mL) is added to the wells and incubated at 37° C., 5% $CO_2$. After 24 hours, the plate is centrifuged at 1200 rpm for 3 minutes and the supernatant discarded. Cells are then resuspended in 150 μL (final concentration 7.5 μg/mL) of propidium iodide (PI) in PBS and incubated at 37° C., 5% $CO_2$ for 15 minutes. After 15 minutes, cells are analysed by flow cytometry (BD accuri) using the FL3 window. The % viability is calculated as the % of cells that are PI negative in the test wells normalised to the DMSO control.

In Vivo Screening: Pharmacodynamics and Anti-Inflammatory Activity (i) LPS-Induced Neutrophil Accumulation in Mice Non-fasted Balb/c mice are dosed by the intra tracheal route with either vehicle, or the test substance at the indicated times (within the range 2-8 hr) before stimulation of the inflammatory response by application of an LPS challenge. At T=0, mice are placed into an exposure chamber and exposed to LPS (7.0 mL, 0.5 mg/mL solution in PBS) for 30 min. After a further 8 hr, the animals are anesthetized, their tracheas cannulated and BALF extracted by infusing and then withdrawing from their lungs 1.0 mL of PBS via the tracheal catheter. Total and differential white cell counts in the BALF samples are measured using a Neubauer haemocytometer. Cytospin smears of the BALF samples are prepared by centrifugation at 200 rpm for 5 min at RT and stained using a DiffQuik stain system (Dade Behring). Cells are counted using oil immersion microscopy. Data for neutrophil numbers in BAL are represented as mean±S.E.M. (standard error of the mean). The percentage inhibition of neutrophil accumulation is calculated for each treatment relative to vehicle treatment.

(ii) Cigarette Smoke Model

A/J mice (males, 5 weeks old) are exposed to cigarette smoke (4% cigarette smoke, diluted with air) for 30 min/day for 11 days using a Tobacco Smoke Inhalation Experiment System for small animals (Model SIS-CS; Sibata Scientific Technology, Tokyo, Japan). Test substances are administered intra-nasally (35 μL of solution in 50% DMSO/PBS) once daily for 3 days after the final cigarette smoke exposure. At 12 hr after the last dosing, each of the animals is anesthetized, the trachea cannulated and bronchioalveolar lavage fluid (BALF) is collected. The numbers of alveolar macrophages and neutrophils are determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil).

(iii) DSS-Induced Colitis in Mice

Non-fasted, 10-12 week old, male BDF1 mice are dosed by oral gavage twice daily with either vehicle, reference item (5-ASA) or test compound one day before (Day −1) stimulation of the inflammatory response by treatment with dextran sodium sulphate (DSS). On Day 0 of the study, DSS (5% w/v) is administered in the drinking water followed by BID dosing of the vehicle (5 mL/kg), reference (100 mg/kg) or test compound (5 mg/kg) for 7 days. The drinking water with DSS is replenished every 3 days. During the study, animals are weighed every day and stool observations are made and recorded as a score, based on stool consistency. At the time of sacrifice on Day +6, the large intestine is removed and the length and weight are recorded. Sections of the colon are taken for either MPO analysis, to determine neutrophil infiltration, or for histopathology scoring to determine disease severity.

(iv) TNBS-Induced Colitis in Mice

Non-fasted, 10-12 week old, male BDF1 mice are dosed by oral gavage twice daily with either vehicle (5 mL/kg), reference item (Budesonide 2.5 mg/kg) or test compound (1 or 5 mg/kg) one day before (Day −1) stimulation of the inflammatory response by treatment with 2,4,6-trinitrobenzenesulphonic acid (TNBS) (15 mg/mL in 50% ethanol/50% saline). On Day 0 of the study TNBS (200 μL) is administered intra-colonically via a plastic catheter with BID dosing of the vehicle, reference or test compound continuing for 2 or 4 days. During the study, animals are weighed every day and stool observations are made and recorded as a score, based on stool consistency. At the time of sacrifice on Day 2 (or Day 4), the large intestine is removed and the length and weight recorded. Sections of the colon are taken for histopathology scoring to determine disease severity.

(v) Adoptive Transfer in Mice

On Study day 0, female Balb/C mice are terminated and spleens obtained for CD45RB$^{high}$ cell isolation (Using SCID IBD cell Separation protocol). Approximately $4\times10^5$ cells/mL CD45RB$^{high}$ cells are then injected intraperitoneally (100 μL/mouse) into female SCID animals. On study day 14, mice are weighed and randomized into treatment groups based on body weight. On Day 14, compounds are administered BID, via oral gavage, in a dose volume of 5 mL/kg. Treatment continues until study day 42, at which point the animals are necropsied 4 hours after the morning administration. The colon length and weight are recorded and used as a secondary endpoint in the study as a measurement of colon oedema. The colon is then divided into six cross-sections, four of which are used for histopathology scoring (primary endpoint) and two are homogenised for cytokine analysis. Data shown is the % inhibition of the induction window between naïve animals and vehicle animals, where higher inhibition implies closer to the non-diseased, naïve, phenotype.

(vi) Endotoxin-Induced Uveitis in Rats

Male, Lewis rats (6-8 weeks old, Charles River UK Limited) are housed in cages of 3 at 19-21° C. with a 12 h light/dark cycle (07:00/19:00) and fed a standard diet of rodent chow and water ad libitum. Non-fasted rats are weighed, individually identified on the tail with a permanent marker, and receive a single intravitreal administration into the right vitreous humor (5 µL dose volume) of 100 ng/animal of LPS (*Escherichia coli* 0111:B4 prepared in PBS, Sigma Aldrich, UK) using a 32-gauge needle. Untreated rats are injected with PBS. Test compound or vehicle (4% polyoxyl 40 stearate, 4% mannitol in PBS (pH 74)) are administered by the topical route onto the right eye (10 µL) of animals 1 hour prior to LPS, at the time of LPS administration, and 1, 2 and 4 hours post LPS administration. Before administration, the solution to be administered is sonicated to ensure a clear solution. 6 hours after LPS dosing, animals are euthanized by overdose with pentobarbitone (via cardiac puncture). Immediately after euthanasia, 10 µL of aqueous humor is collected from the right eye of the rats by puncture of the anterior chamber using a 32 gauge needle under a surgical microscope. The aqueous humor is diluted in 20 µL of PBS and total cell counts are measured immediately using a Countess automated cell counter (Invitrogen). Following collection of the aqueous humour, the right eye of each animal is enucleated and dissected into front (anterior) and back (posterior) sections around the lens. Each section is weighed and homogenised in 500 µL of sterile phosphate buffered saline followed by 20 minutes centrifugation at 12000 rpm at 4° C. The resulting supernatant is divided into 3 aliquots and stored at −80° C. until subsequent cytokine analysis by R&D DuoSet ELISA.

Summary of In Vitro and In Vivo Screening Results

TABLE 1a

Dissociation constants for selected kinases determined by LeadHunter Discover Services (DiscoveRx Corporation, Fremont, CA), using the KINOMEscan ™ technology.

| Test Compound Example No. | Dissociation Constant (nM) | | |
|---|---|---|---|
| | Lck | p38 MAPKα | Syk |
| Example 1 | 4.2 | 2.8 | 7.1 |
| Example 2 | 5.8 | 23 | 18 |
| Example 44 | 5.3 | 1.9 | 6.6 |

Studies conducted by LeadHunter Discover Services (DiscoveRx Corporation, Fremont, Calif.) using the KINOMEscan™ technology determined that compounds of Example 1, 36, 44 and 47 did not have any significant effect on the binding of the kinases B-Raf and B-Raf (V600E) to their standard ligands. Moreover, these compounds showed improved selectivities compared to the Reference Compound N-(4-(4-(3-(3-tert-butyl-1-p-tolyl-1H-pyrazol-5-yl)ureido)naphthalen-1-yloxy)pyridin-2-yl)-2-methoxyacetamide (WO 2010/112936), as evidenced by lower selectivity scores (Table 1b).

TABLE 1b

KinomeScan Selectivity score data at 50 and 500 nM; S(35) = (number of non-mutant kinases with % Ctrl <35)/(number of non-mutant kinases tested); S(10) = (number of non-mutant kinases with % Ctrl <10)/(number of non-mutant kinases tested); S(1) = (number of non-mutant kinases with % Ctrl <1)/(number of non-mutant kinases tested)

| | KinomeScan Selectivity Scores/number of individual kinase hits | | | | | |
|---|---|---|---|---|---|---|
| | 50 nM | | | 500 nM | | |
| Compound | S(35) | S(10) | S(1) | S(35) | S(10) | S(1) |
| Reference Compound | 0.174/67 | 0.083/32 | 0.018/7 | 0.370/143 | 0.272/105 | 0.117/45 |
| Ex. 1 | 0.186/75 | 0.072/29 | 0.005/2 | 0.347/140 | 0.251/101 | 0.089/36 |
| Ex. 36 | 0.149/60 | 0.050/20 | 0.002/1 | 0.298/120 | 0.206/83 | 0.079/32 |
| Ex. 44 | 0.179/72 | 0.074/30 | 0.002/1 | 0.337/136 | 0.241/97 | 0.102/41 |
| Ex. 47 | 0.136/55 | 0.042/17 | 0.000/0 | 0.318/128 | 0.223/90 | 0.074/30 |

TABLE 1c

Results from in vitro p38 MAPKα (Method 2), c-Src, Syk and GSK3α (Method 2) inhibition assays

| Test Compound Example No. | IC50 Values for Enzyme Inhibition (nM) | | | |
|---|---|---|---|---|
| | p38 MAPKα | c-Src | Syk | GSK3α |
| 1 | 11 | 14 | 5 | 115 |
| 2 | 20 | 20 | 172 | 2295 |
| 3 | — | — | — | 139 |
| 4 | 121 | 37 | 277 | 2015 |
| 5 | 119 | 31 | 187 | 1344 |
| 6 | 137 | 36 | 315 | 1900 |
| 7 | 59 | 21 | 107 | 1104 |
| 8 | 214 | — | — | 3767 |
| 9 | 197 | 316 | >1282 | 4338 |
| 10 | — | — | — | 5559 |
| 11 | 35 | 76 | 318 | 1303 |
| 12 | 23 | 209 | 831 | 2144 |

TABLE 1c-continued

Results from in vitro p38 MAPKα (Method 2), c-Src, Syk and GSK3α (Method 2) inhibition assays

| Test Compound Example No. | IC50 Values for Enzyme Inhibition (nM) | | | |
|---|---|---|---|---|
| | p38 MAPKα | c-Src | Syk | GSK3α |
| 13 | — | 150 | 809 | 3634 |
| 14 | 10 | 19 | 92 | 2205 |
| 15 | 64 | 43 | 163 | 2789 |
| 16 | 34 | 22 | 107 | 3727 |
| 17(a) | — | 16 | — | 4003 |
| 17(b) | 52 | 20 | 98 | 4492 |
| 17(c) | — | — | — | >11905 |
| 17(d) | — | — | — | >11905 |
| 17(e) | — | — | — | 7421 |
| 17(f) | — | — | — | 1088 |
| 17(g) | — | — | — | 4096 |
| 17(h) | — | — | — | 4388 |
| 17(i) | — | — | — | 594 |
| 17(j) | 21 | 16 | 39 | 2000 |
| 17(k) | 156 | 74 | 336 | >11905 |
| 17(l) | 223 | 116 | 389 | >12077 |
| 17(m) | 25 | 19 | 192 | 2771 |
| 17(n) | — | — | — | >11905 |
| 17(o) | | 232 | 948 | 3321 |
| 17(p) | 20 | 21 | 172 | 4681 |
| 17(q) | — | — | — | 1979 |
| 17(r) | 119 | 37 | 102 | 4045 |
| 17(s) | — | — | — | 394 |
| 17(t) | — | — | — | 140 |
| 17(u) | 66 | 32 | 86 | 2247 |
| 17(v) | 116 | 43 | 232 | >12107 |
| 17(w) | — | — | — | 674 |
| 17(x) | — | — | — | 412 |
| 17(y) | — | — | — | 5575 |
| 17(z) | — | — | — | 2876 |
| 17(aa) | 20 | 24 | 61 | 2933 |
| 17(ab) | — | — | — | 596 |
| 17(ac) | — | — | — | 3024 |
| 17(ad) | — | — | — | 3062 |
| 17(ae) | 10 | 31 | 112 | 3003 |
| 17(af) | 5 | — | — | 680 |
| 17(ag) | — | 17 | 105 | 2745 |
| 17(ah) | — | 20 | 57 | 9187 |
| 17(ai) | — | 14 | 86 | 4476 |
| 17(aj) | — | 12 | 33 | 2644 |
| 17(ak) | — | 12 | 85 | 1818 |
| 17(al) | — | — | — | 11821 |
| 17(am) | 4 | 68 | 124 | — |
| 17(an) | — | — | — | — |
| 17(cm) | 47 | 29 | 82 | — |
| 17(cp) | — | 20 | 393 | — |
| 19 | 8 | 22 | 8 | — |
| 20 | — | 77 | 144 | — |
| 21 | — | 16 | 15 | — |
| 22 | 6 | 17 | 138 | — |
| 26 | 40 | — | — | — |
| 36 | 19 | 10 | 190 | — |
| 39 | 6 | 17 | 257 | — |
| 40 | 162 | 195 | 400 | — |
| 41 | 31 | 13 | 325 | — |
| 42 | 3 | 21 | 88 | — |
| 44 | 11 | 20 | 17 | — |
| 45 | 36 | 40 | 108 | — |
| 46 | — | — | — | 225 |
| 47 | 4 | 15 | 8 | — |
| 48 | 29 | 20 | 55 | — |

TABLE 2

Inhibition of cytokine release in stimulated cells (assays (b), (c) and (d) above).

| Test Compound Example No. | PBMCs | | |
|---|---|---|---|
| | IL-8 | IL-2 | IFNγ |
| 1 | 5.5 | 1125.5 | 9.5 |
| 2 | 0.6 | 101.8 | 6.2 |
| 3 | 23.7 | — | 16.7 |
| 4 | 2.3 | 137.5 | 11.8 |
| 5 | 1.5 | 358.2 | 10.1 |
| 6 | 2.6 | 420.2 | 12.8 |
| 7 | 1.3 | 220.9 | 5.8 |
| 8 | 2.9 | 397.8 | 10.3 |
| 9 | 3.0 | 268.1 | 20.6 |
| 10 | 6.9 | — | — |
| 11 | 1.4 | 425.8 | 2.7 |
| 12 | 1.7 | 860.1 | 9.9 |
| 13 | 4.7 | 1141.5 | 17.4 |
| 14 | 3.0 | 221.1 | 140.5 |
| 15 | 2.2 | 103.1 | 7.5 |
| 16 | 1.7 | 136.4 | 10.7 |
| 17(a) | 3.4 | — | 16.7 |
| 17(b) | 1.4 | 97.7 | 6.0 |
| 17(c) | 5.5 | — | — |
| 17(d) | 6.9 | — | — |
| 17(e) | 2.1 | — | — |
| 17(f) | 5.8 | — | — |
| 17(g) | 2.8 | — | — |
| 17(h) | 2.0 | — | — |
| 17(i) | 1.4 | — | — |
| 17(j) | 1.9 | 96.0 | 2.9 |
| 17(k) | 3.2 | 446.0 | 21.7 |
| 17(l) | 2.1 | 324.1 | 6.5 |
| 17(m) | 2.0 | 108.6 | 11.9 |
| 17(n) | 4.7 | — | — |
| 17(o) | 3.3 | 1096.6 | 3.6 |
| 17(p) | 3.1 | — | — |
| 17(q) | 4.8 | — | — |
| 17(r) | 1.7 | 153.6 | 7.0 |
| 17(s) | 12.0 | — | — |
| 17(t) | 13.1 | — | — |
| 17(u) | 1.7 | — | — |
| 17(v) | 3.9 | 227.2 | 14.3 |
| 17(w) | 7.2 | — | — |
| 17(x) | 25.9 | — | — |
| 17(y) | 2.6 | — | — |
| 17(z) | 2.7 | — | 15.3 |
| 17(aa) | 3.6 | 144.5 | 17.2 |
| 17(ab) | 2.7 | — | — |
| 17(ac) | 2.6 | — | — |
| 17(ad) | 2.8 | — | — |
| 17(ae) | 1.7 | 461.9 | 18.0 |
| 17(af) | 1.3 | 102.6 | 2.4 |
| 17(ag) | 1.3 | — | 5.9 |
| 17(ah) | 0.8 | 203.5 | 15.1 |
| 17(ai) | 1.8 | 122.0 | 13.5 |
| 17(aj) | 1.7 | — | — |
| 17(ak) | 1.7 | — | — |
| 17(al) | 6.4 | — | — |
| 17(am) | 2.0 | 471.6 | 7.1 |
| 17(an) | 2.5 | — | — |
| 17(ao) | 1.0 | — | — |
| 17(ap) | 2.6 | — | — |
| 17(aq) | 1.8 | — | — |
| 17(ar) | 88.7 | — | — |
| 17(as) | 15.8 | — | — |
| 17(at) | 14.8 | — | — |
| 17(au) | 5.7 | — | 26.4 |
| 17(av) | 112.6 | — | — |
| 17(aw) | 78.2 | — | — |
| 17(ax) | 18.2 | — | — |
| 17(ay) | 22.8 | — | 70.2 |
| 17(az) | 2.1 | — | — |
| 17(ba) | 5.0 | — | — |
| 17(bb) | 1.9 | — | — |
| 17(bc) | 2.9 | — | — |
| 17(bd) | 1.6 | — | — |
| 17(be) | 1.1 | — | — |

TABLE 2-continued

Inhibition of cytokine release in stimulated cells (assays (b), (c) and (d) above).

| Test Compound Example No. | PBMCs IL-8 | IL-2 | IFNγ |
|---|---|---|---|
| 17(bf) | 1.5 | — | — |
| 17(bg) | 2.2 | — | — |
| 17(bh) | 2.1 | — | — |
| 17(bi) | 3.1 | — | — |
| 17(bj) | 76.4 | — | 313.4 |
| 17(bk) | 11.3 | — | — |
| 17(bl) | 2.4 | — | — |
| 17(bm) | 0.6 | — | — |
| 17(bn) | 0.6 | — | — |
| 17(bo) | 2.2 | — | — |
| 17(bp) | 2.4 | — | — |
| 17(bq) | 1.2 | — | — |
| 17(br) | 14.3 | — | — |
| 17(bs) | 4.8 | — | — |
| 17(bt) | 1.4 | — | — |
| 17(bu) | 45.5 | — | >1,000 |
| 17(bv) | 74.5 | — | — |
| 17(bw) | 23.0 | — | 53.4 |
| 17(bx) | 7.9 | — | — |
| 17(by) | 0.7 | — | — |
| 17(bz) | 12.8 | — | — |
| 17(ca) | 10.3 | — | — |
| 17(cb) | 16.8 | — | — |
| 17(cc) | 211.4 | — | — |
| 17(cd) | 16.8 | — | — |
| 17(ce) | 309.4 | — | — |
| 17(cf) | 22.0 | — | — |
| 17(cg) | 16.2 | — | 237.1 |
| 17(ch) | 2.7 | — | — |
| 17(ci) | 38.6 | — | — |
| 17(cj) | 3.4 | — | — |
| 17(ck) | 31.7 | — | — |
| 17(cl) | 70.5 | — | 232.4 |
| 17(cm) | 1.8 | — | 2.6 |
| 17(cn) | 7.6 | — | — |
| 17(co) | 36.7 | — | — |
| 17(cp) | 395.0 | — | 1084.6 |
| 17(cq) | 2.3 | — | — |
| 17(cr) | 3.9 | — | — |
| 17(cs) | 23.6 | — | — |
| 17(ct) | 6.9 | — | — |
| 17(cu) | 23.1 | — | — |
| 17(cv) | 17.1 | — | — |
| 17(cw) | 53.0 | — | — |
| 19 | 149.0 | 1076.5 | 160.5 |
| 20 | 2.3 | — | — |
| 21 | 1.4 | — | — |
| 22 | 2.7 | — | 14.6 |
| 23 | 1.8 | — | — |
| 24 | 2.8 | — | — |
| 25 | 2.1 | — | — |
| 26 | 1.5 | — | — |
| 27 | 4.0 | — | — |
| 28 | 0.7 | — | — |
| 29 | 2.5 | — | — |
| 30 | 7.0 | — | — |
| 31 | 2.0 | — | — |
| 32 | 1.5 | — | — |
| 33 | 8.7 | — | — |
| 34 | 2.0 | — | — |
| 35 | 52.8 | — | — |
| 36 | 1.7 | — | 8.5 |
| 37 | 5.7 | — | 14.9 |
| 38 | 1.6 | — | — |
| 39 | 5.7 | — | 52.9 |
| 40 | 1.8 | — | 16.7 |
| 41 | 1.6 | — | 35.4 |
| 42 | 3.2 | — | 14.1 |
| 43 | 2.3 | — | — |
| 44 | 299.2 | — | >1,000 |
| 45 | 2.4 | — | — |
| 46 | 19.6 | — | — |
| 47 | 147.1 | — | 272.3 |
| 48 | 1.1 | — | 8.4 |
| 50 | 445.1 | — | — |
| 52 | 348.9 | — | — |
| 54 | 478.4 | — | — |
| 56 | >1,000 | — | — |
| 58 | >1,000 | — | — |
| 60 | >1,000 | — | — |
| 62 | >1,000 | — | — |
| 64 | >1,000 | — | — |
| 66 | >1,000 | — | — |
| 68 | 94.5 | — | 190.7 |
| 70 | 95.0 | — | — |
| 72 | 118.2 | — | — |

As illustrated in Table 3 below, compounds of the examples of the present invention are markedly less active than the Reference Compound (N-(4-(4-(3-(3-tert-butyl-1-p-tolyl-1H-pyrazol-5-yl)ureido)naphthalen-1-yloxy)pyridin-2-yl)-2-methoxyacetamide; WO 2010/112936) in assay (g) above, which measures impact on cell division (mitosis) in PBMCs. Similarly, compounds of the examples of the present invention are substantially less cytotoxic than the Reference Compound, displaying enhanced viabilities in cell cytotoxicity assay (r) above (Table 3).

TABLE 3

Effect of compounds of the examples on cell division in PBMCs (NT = not tested) and on Jurkat cell viability

| Test compound | % Inhibition of mitosis at 5 μg/mL | % Viability at 1 μg/mL | % Viability at 5 μg/mL | % Viability at 20 μg/mL |
|---|---|---|---|---|
| Reference compound | 87.8[a] | 23.5 | 18.9 | 17.3 |
| 1 | 2.4 | 94.4 | 95.9 | 95.7 |
| 2 | 48.0 | NT | NT | NT |
| 3 | NT | 93.4 | 95.9 | 91.9 |
| 4 | 46.2 | NT | NT | NT |
| 5 | 27.7 | NT | NT | NT |
| 6 | 28.8 | NT | NT | NT |
| 7 | 59.9 | NT | NT | NT |
| 9 | 29.8 | NT | NT | NT |
| 11 | 26.6 | NT | NT | NT |
| 12 | 22.1 | 74.5 | 81.8 | 82.9 |
| 14 | 60.1 | 101.9 | 98.8 | 0.7 |
| 15 | 62.3 | 99.5 | 75.0 | 74.5 |
| 16 | 50.1 | 90.1 | 52.5 | 19.1 |
| 17(a) | 75.6 | NT | NT | NT |
| 17(b) | 58.9 | 102.8 | 93.8 | 79.3 |
| 17(j) | 85.4 | NT | NT | NT |
| 17(k) | 24.0 | NT | NT | NT |
| 17(l) | 24.9 | 102.8 | 102.7 | 102.9 |
| 17(m) | 80.5 | NT | NT | NT |
| 17(p) | 92.0 | 102.1 | 49.9 | 1.5 |
| 17(r) | 36.6 | NT | NT | NT |
| 17(u) | 86.9 | NT | NT | NT |
| 17(v) | 34.4 | NT | NT | NT |
| 17(x) | NT | 95.4 | 94.2 | 38.9 |
| 17(y) | 70.8 | NT | NT | NT |
| 17(z) | 69.7 | 102.9 | 70.9 | 2.0 |
| 17(aa) | 77.7 | NT | NT | NT |
| 17(ab) | NT | 108.6 | 95.6 | 93.9 |
| 17(ac) | 85.8 | NT | NT | NT |
| 17(ad) | 93.4 | 101.4 | 6.3 | 0.4 |
| 17(ae) | 30.6 | 93.1 | 98.5 | 92.9 |
| 17(af) | NT | 96.7 | 76.2 | 54.1 |
| 17(ag) | 51.8 | NT | NT | NT |

TABLE 3-continued

Effect of compounds of the examples on cell division in
PBMCs (NT = not tested) and on Jurkat cell viability

| Test compound | % Inhibition of mitosis at 5 µg/mL | % Viability at 1 µg/mL | % Viability at 5 µg/mL | % Viability at 20 µg/mL |
|---|---|---|---|---|
| 17(ah) | 32.5 | NT | NT | NT |
| 17(ai) | 89.1 | NT | NT | NT |
| 17(aj) | 94.9 | NT | NT | NT |
| 17(ak) | 74.7 | 99.0 | 69.5 | 0.4 |
| 17(al) | 21.2 | NT | NT | NT |
| 17(am) | NT | 103.4 | 90.5 | 32.5 |
| 17(an) | NT | 97.9 | 37.9 | 1.1 |
| 17(ao) | NT | 89.2 | 16.5 | 1.6 |
| 17(ap) | NT | 97.8 | 40.1 | 0.6 |
| 17(aq) | NT | 95.1 | 0.2 | 1.3 |
| 17(ar) | NT | 96.1 | 96.2 | 95.3 |
| 17(at) | NT | 95.2 | 93.2 | 86.6 |
| 17(au) | NT | 94.0 | 91.8 | 80.6 |
| 17(ay) | NT | 95.3 | 94.6 | 90.1 |
| 17(az) | NT | 105.4 | 93.1 | 4.5 |
| 17(bb) | NT | 90.9 | 19.2 | 0.2 |
| 17(bc) | NT | 93.9 | 89.2 | 10.8 |
| 17(bd) | NT | 85.8 | 28.7 | 0.1 |
| 17(be) | NT | 92.4 | 0.7 | 0.5 |
| 17(bf) | NT | 90.7 | 1.5 | 0.6 |
| 17(bg) | NT | 86.5 | 60.0 | 0.3 |
| 17(bh) | NT | 99.5 | 67.8 | 0.6 |
| 17(bi) | NT | 97.4 | 0.8 | 0.6 |
| 17(bj) | NT | 96.2 | 96.6 | 94.8 |
| 17(bk) | NT | 93.0 | 71.8 | 65.6 |
| 17(bl) | NT | 103.6 | 0.2 | 0.5 |
| 17(bm) | NT | 103.6 | 0.2 | 0.5 |
| 17(bn) | NT | 102.8 | 65.6 | 19.5 |
| 17(bo) | NT | 98.5 | 45.3 | 14.0 |
| 17(bp) | NT | 93.2 | 41.0 | 2.0 |
| 17(bq) | NT | 87.2 | 55.3 | 2.0 |
| 17(br) | NT | 91.8 | 90.7 | 79.2 |
| 17(bs) | NT | 90.9 | 48.7 | 0.3 |
| 17(bt) | NT | 89.8 | 39.9 | 22.5 |
| 17(bu) | NT | 92.6 | 92.6 | 91.7 |
| 17(bw) | NT | 94.5 | 96.2 | 92.4 |
| 17(by) | NT | 102.4 | 81.5 | 1.6 |
| 17(bz) | NT | 93.6 | 92.7 | 64.1 |
| 17(ca) | NT | 92.6 | 94.0 | 75.8 |
| 17(cd) | NT | 96.4 | 96.5 | 91.4 |
| 17(cf) | NT | 96.7 | 96.7 | 96.8 |
| 17(cg) | NT | 96.1 | 95.3 | 92.3 |
| 17(ch) | NT | 82.0 | 10.2 | 0.7 |
| 17(ck) | NT | 96.1 | 96.1 | 95.5 |
| 17(cl) | NT | 93.6 | 94.0 | 93.7 |
| 17(cm) | NT | 95.9 | 77.0 | 14.5 |
| 17(co) | NT | 94.5 | 93.3 | 92.2 |
| 17(cp) | NT | 97.6 | 96.9 | 94.7 |
| 17(cq) | NT | 74.3 | 9.0 | 0.7 |
| 17(cr) | NT | 81.1 | 18.0 | 0.9 |
| 19 | NT | 105.0 | 106.0 | 100.9 |
| 20 | NT | 104.0 | 99.3 | 91.8 |
| 21 | NT | 101.2 | 82.4 | 77.1 |
| 22 | NT | 102.8 | 96.6 | 42.9 |
| 23 | NT | 92.4 | 88.9 | 89.8 |
| 24 | NT | 104.3 | 92.4 | 9.7 |
| 25 | NT | 91.8 | 78.9 | 0.7 |
| 26 | NT | 94.8 | 84.6 | 76.6 |
| 27 | NT | 101.2 | 94.9 | 1.7 |
| 28 | NT | 100.0 | 41.1 | 18.9 |
| 29 | NT | 101.2 | 46.6 | 2.0 |
| 31 | NT | 99.9 | 97.6 | 99.0 |
| 32 | NT | 95.4 | 43.1 | 2.5 |
| 33 | NT | 104.1 | 95.5 | 69.3 |
| 36 | NT | 93.3 | 89.3 | 84.9 |
| 37 | NT | 52.9 | 55.8 | 28.9 |
| 38 | NT | 90.0 | 63.7 | 6.0 |
| 39 | NT | 93.9 | 87.7 | 1.5 |
| 40 | NT | 89.6 | 73.6 | 67.1 |
| 41 | NT | 90.5 | 67.3 | 55.3 |
| 42 | NT | 96.6 | 91.7 | 21.3 |
| 44 | NT | 93.3 | 90.1 | 92.2 |
| 45 | NT | 97.7 | 93.7 | 9.8 |
| 47 | NT | 91.2 | 96.0 | 97.8 |
| 48 | NT | 89.0 | 63.8 | 54.2 |
| 68 | NT | 95.6 | 92.7 | 90.2 |
| 70 | NT | 95.3 | 91.9 | 63.8 |

[a]See, for example, the value reported in WO 2013/050757.

As illustrated in Table 4 below, the compound of Example 1 significantly and dose-dependently reduced cellular infiltration, as revealed by lowered cell counts, and cytokine IL-1β levels in both the anterior and posterior segments of the eyes of rats treated with intravitreal endotoxin LPS (see assay (vi) above).

TABLE 4

Dose-dependent effect of the compound of Example 1
on IL-1β levels and cell counts in the eyes of
LPS-stimulated rats. Data are reported as means ± SEM.

| Treatment | n | IL-1β (pg/mL) Anterior tissue | IL-1β (pg/mL) Posterior tissue | Cell counts ($\times 10^5$/mL) |
|---|---|---|---|---|
| Non-diseased | 5 | 14.1 ± 6.3 | 30.8 ± 11.3 | 1.8 ± 0.2 |
| Vehicle control | 8 | 1636.6 ± 145.1 | 877.3 ± 115.6 | 69.9 ± 5.4 |
| Example 1 (1 mg/mL) | 8 | 367.3 ± 100.4 | 188.1 ± 54.7 | 21.9 ± 5.0 |
| Example 1 (0.1 mg/mL) | 8 | 791.2 ± 131.9 | 327.4 ± 61.4 | 30.4 ± 6.7 |
| Example 1 (0.01 mg/mL) | 8 | 980.0 ± 110.8 | 740.5 ± 56.2 | 43.5 ± 6.3 |
| Example 1 (0.001 mg/mL) | 8 | 1558.1 ± 145.7 | 867.9 ± 120.8 | 63.6 ± 7.0 |

Summary of Additional Studies

Determination of Solubilities in Fasted-State Simulated Colonic Fluid (FaSSCoF)

The solubilities of compounds of the invention in FaSSCoF at pH 6.5 are determined using a modification of a previously-reported procedure (Vertzoni, M., et al. *Pharm. Res.* 2010, 27, 2187-2196). In place of the bile salt extract employed in the original procedure (which extract is no longer available), the modified procedure uses a mixture of sodium taurochlorate (0.15 g), glycocholic acid (0.15 g), ursodeoxycholic acid (0.05 g), cholic acid (0.05 g), and glycodeoxycholic acid (0.05 g). These five bile acids are ground together with a mortar and pestle to produce a fine white powder that is incorporated into the FaSSCoF, as outlined below.

FaSSCoF Medium:

Tris(hydroxymethyl)aminomethane (Tris; 0.275 g) and maleic acid (0.44 g) are dissolved in water (35 mL) to give a solution whose pH is adjusted to 6.5 by treatment with 0.5M NaOH (ca. 12 mL). The solution is then made up to 50 mL with water. A portion of this Tris/maleate buffer solution (ca. 25 mL) is added to a 0.5 L round-bottomed flask, before being treated with 0.00565 g of the bile acid mixture described above. Solutions of phosphatidylcholine (0.0111 g) in DCM (0.15 mL) and palmitic acid (0.0013 g) in DCM (0.15 mL) are added, then the organic solvent is evaporated off under reduced pressure at 40° C. until a clear solution, with no perceptible DCM odour, is achieved. The volume of the evaporated solution is adjusted to 50 mL by addition of the remainder of Tris/maleate buffer, then BSA (0.115 g) is added, before being dissolved by gentle agitation.

Solubility Determination:

Test compounds are suspended in the pH 6.5 FaSSCoF medium to give a maximum final concentration of 2-10 mg/mL. The suspensions are equilibrated at 25° C. for 24 h, before being filtered through a glass fibre C filter. The filtrates are then diluted as appropriate for injection and quantification by HPLC with reference to a standard. Different volumes of the standard, diluted and undiluted sample solutions are injected and the solubilities are calculated using the peak areas determined by integration of the peak found at the same retention time as the principal peak in the standard injection.

FaSSCoF solubilities are shown in Table 5 below, which reveals that many of the compounds of the Examples exhibited solubilities in the FaSSCoF medium at pH 6.5 of in excess of 0.01 mg/mL, while some displayed solubilities greater than 0.1 mg/mL. With few exceptions, pH 6.5 FaSSCoF solubilities were superior to those of Reference Compound A, 3-((4-((4-(3-(3-(tert-butyl)-1-(p-tolyl)-1H-pyrazol-5-yl)ureido)naphthalen-1-yl)oxy)pyrimidin-2-yl)amino)-5-ethynyl-N-(2-(2-(2-methoxyethoxy)ethoxy)ethyl)benzamide {Fyfe, M. C. T., WO 2014/140582}.

TABLE 5

Solubilities measured for certain compounds of the Examples of the present invention in FaSSCoF at pH 6.5.

| Test Compound | pH 6.5 FaSSCoF Solubility (mg/mL) | | | |
|---|---|---|---|---|
| Example No. | Run 1 | Run 2 | Run 3 | Run 4 |
| Reference Compound A | <0.001 | <0.001 | — | — |
| 1 | 0.016 | 0.018 | 0.010 | 0.011 |
| 1 (sodium salt) | 0.031 | 0.032 | 0.020 | 0.025 |
| 1 (hydrochloride salt) | 0.016 | 0.015 | — | — |
| 3 | 0.006 | 0.006 | — | — |
| 14 | 0.016 | 0.013 | — | — |
| 15 | 0.010 | 0.010 | — | — |
| 16 | 0.004 | 0.004 | — | — |
| 17(b) | 0.015 | 0.015 | — | — |
| 17(v) | 0.008 | 0.008 | — | — |
| 17(x) | 0.015 | 0.009 | — | — |
| 17(ae) | 0.011 | 0.012 | — | — |
| 17(af) | 0.010 | 0.010 | — | — |
| 17(am) | 0.010 | 0.012 | — | — |
| 17(an) | 0.047 | 0.049 | — | — |
| 17(ao) | 0.009 | 0.009 | — | — |
| 17(ap) | <0.001 | <0.001 | — | — |
| 17(aq) | <0.001 | <0.001 | — | — |
| 17(ar) (hydrochloride salt) | 0.204 | 0.198 | — | — |
| 17(at) | 0.009 | 0.009 | — | — |
| 17(au) | 0.032 | 0.023 | — | — |
| 17(ay) (hydrochloride salt) | 0.029 | 0.028 | — | — |
| 17(az) | 0.001 | 0.001 | — | — |
| 17(bb) | <0.001 | <0.001 | — | — |
| 17(bf) | 0.013 | 0.015 | — | — |
| 17(bg) | 0.016 | 0.019 | — | — |
| 17(bh) | 0.016 | 0.019 | — | — |
| 17(bj) (sodium salt) | 1.309 | — | — | — |
| 17(bk) (sodium salt) | 0.042 | 0.037 | — | — |
| 17(bl) | 0.016 | 0.017 | — | — |
| 17(bm) | 0.005 | 0.005 | — | — |
| 17(bn) | 0.008 | 0.006 | — | — |
| 17(bo) | 0.035 | 0.033 | — | — |
| 17(bp) | 0.023 | 0.024 | — | — |
| 17(bq) | 0.009 | 0.009 | — | — |
| 17(br) | 0.009 | 0.008 | — | — |

TABLE 5-continued

Solubilities measured for certain compounds of the Examples of the present invention in FaSSCoF at pH 6.5.

| Test Compound | pH 6.5 FaSSCoF Solubility (mg/mL) | | | |
|---|---|---|---|---|
| Example No. | Run 1 | Run 2 | Run 3 | Run 4 |
| 17(bu) (dihydrochloride salt) | 0.006 | 0.006 | — | — |
| 17(bw) | 0.002 | 0.003 | — | — |
| 17(bz) | 0.021 | 0.026 | 0.014 | 0.019 |
| 17(ca) | 0.002 | 0.002 | — | — |
| 17(cd) (hydrochloride salt) | 0.051 | 0.049 | — | — |
| 17(cf) | 0.003 | 0.001 | — | — |
| 17(cg) | 0.002 | — | — | — |
| 17(ci) | 0.006 | 0.006 | — | — |
| 17(cl) | 0.009 | 0.006 | — | — |
| 17(cm) | 0.008 | 0.009 | — | — |
| 17(cn) | 0.025 | 0.017 | — | — |
| 17(co) | 0.005 | 0.006 | — | — |
| 19 (ammonium salt) | 0.946 | 0.881 | — | — |
| 19 (sodium salt) | >4.7 | >4.7 | — | — |
| 20 | 0.004 | — | — | — |
| 21 | 0.010 | 0.010 | — | — |
| 22 | 0.017 | 0.025 | 0.013 | 0.009 |
| 23 | 0.008 | 0.008 | — | — |
| 24 | 0.012 | 0.010 | — | — |
| 26 | 0.011 | 0.011 | — | — |
| 28 | <0.001 | <0.001 | — | — |
| 29 | 0.011 | 0.009 | — | — |
| 31 | 0.003 | 0.003 | — | — |
| 33 | 0.005 | 0.005 | — | — |
| 34 (hydrochloride salt) | 0.001 | 0.001 | — | — |
| 35 (sodium salt) | >3.5 | >4.2 | — | — |
| 36 | 0.006 | 0.006 | — | — |
| 37 | 0.025 | 0.024 | 0.007 | 0.006 |
| 38 | 0.014 | 0.012 | — | — |
| 39 | 0.222 | 0.247 | 0.073 | 0.097 |
| 40 | 0.005 | 0.005 | — | — |
| 41 | 0.007 | 0.003 | — | — |
| 42 | 0.007 | 0.009 | — | — |
| 43 | 0.003 | 0.003 | — | — |
| 44 (ammonium salt) | >2.4 | >2.4 | — | — |
| 44 (sodium salt) | >7.6 | >5.5 | — | — |
| 45 | 0.005 | 0.005 | — | — |
| 47 (sodium salt) | >1.9 | >2.0 | — | — |
| 48 | 0.011 | 0.010 | — | — |
| 68 (sodium salt) | 0.020 | 0.020 | — | — |
| 70 (sodium salt) | >2.8 | >2.8 | — | — |

Determination of Pharmacokinetic Parameters

Studies were conducted by Sai Life Sciences (Hinjewadi, Pune, India) to investigate the systemic pharmacokinetics and total colon tissue distribution of compounds of the invention. In particular, pharmacokinetic studies were carried out in male C57BL/6 mice following a single oral administration of the compound.

The data catalogued in Table 6 reveal that the compounds of the invention achieve substantial colonic concentrations, while, in contrast, systemic plasma or blood exposures are very low or negligible.

TABLE 6

Mean plasma or blood concentrations (ng/mL) or total colon levels (ng/g) obtained following oral administration of compounds of the invention to mice at 5 mg/kg. Vehicle = 0.1% Tween 80 in 0.5% methylcellulose solution prepared in water.

| Cpd. Ex. No. | | | Time (h) | | | | | | | |
|---|---|---|---|---|---|---|---|---|---|---|
| D | M | Mx | 0.5 | 1 | 2 | 4 | 6 | 8 | 12 | 24 |
| 1 (Na salt) | 1 | Pl | 44.9 | 49.2 | 13.0 | 5.2 | 1.9 | 0.6 | 5.3 | 0.0 |
| | | TC | 4.3 | 9.3 | 52.4 | 10,403 | 4,049 | 12,898 | 535 | 41.4 |
| 19 (Na salt) | 19 | Bd | 0.0 | 0.0 | 0.0 | 0.0 | 0.0 | 0.0 | 0.0 | 0.0 |
| | | TC | 0.0 | 0.0 | 0.0 | 0.0 | 0.0 | 0.0 | 0.0 | 0.0 |
| | 16 | Bd | 1.3 | 1.4 | 0.6 | 0.0 | 0.0 | 0.2 | 0.0 | 0.0 |
| | | TC | 9.5 | 110 | 2,402 | 3,354 | 3,325 | 3,423 | 5,086 | 0.0 |
| 44 ($NH_4^+$ salt) | 44 | Pl | 0.0 | 0.0 | 0.0 | 0.0 | 0.0 | 0.0 | 0.0 | 0.0 |
| | | TC | 0.0 | 0.0 | 2,328 | 1,751 | 450 | 915 | 180 | 0.0 |
| 47 (Na salt) | 47 | Bd | 0.0 | 0.0 | 0.0 | 0.0 | 0.0 | 0.0 | 0.0 | 0.0 |
| | | TC | 0.0 | 0.0 | 0.0 | 0.0 | 0.0 | 0.0 | 0.0 | 0.0 |
| | 36 | Bd | 0.0 | 0.0 | 0.0 | 0.0 | 0.0 | 0.0 | 0.0 | 0.0 |
| | | TC | 37.8 | 95.1 | 643 | 798 | 380 | 1,068 | 139 | 0.0 |

Key to Table 6
D = compound administered (dosed)
M = compound measured
Mx = matrix
Pl = plasma
Bd = blood
TC = total colon hERG Inhibition Studies Compounds of the invention were tested for inhibition of the human ether a go-go (hERG) channel using IonWorks™ patch clamp electrophysiology at Essen Bioscience (Welwyn Garden City, England).

TABLE 7 hERG inhibition data for compounds of the invention

| Example | $IC_{50}$ (μM) | % Inhibition at Top Concentration | Top Concentration |
|---|---|---|---|
| 1 | >3.3 | −4 | 3 μM |
| 2 | >3.3 | −2 | 3 μM |
| 17(j) | >3.3 | 7 | 3 μM |
| 22 | >3.7 | 13 | 3.7 μM |
| 36 | >11.0 | 24 | 11 μM |
| 41 | >11.0 | 7 | 11 μM |
| 43 | >11.0 | 13 | 11 μM |
| 44 | >11.0 | 18 | 11 μM |
| 47 | >11.0 | 19 | 11 μM |
| 48 | >11.0 | −6 | 11 μM |

Acute Eye Irritation/Corrosion Study

The objective of the acute eye irritation/corrosion study was to assess the possible irritation or corrosion potential of the compound of Example 1 at two selected dose levels (0.1 and 1.0 mg/mL), in comparison to vehicle (4% w/v polyoxyethylene 40 stearate/4% w/v mannitol/phosphate buffer (pH 7.4) solution), after one treatment day (Phase 1) or three consecutive treatment days (Phase 2) with four daily administrations (4-hours apart) by the ocular route (bi-lateral instillations of 40 μL/eye/instillation) in the eyes of albino New Zealand White rabbits (13-15 weeks at initiation of dosing; 2 males and 2 females per dose group).

During the study, there were no unscheduled deaths, nor test item-related clinical signs. Furthermore, there were no effects on body weight, nor on food consumption.

In Phase 1, ocular reactions were limited mainly to conjunctival redness (grade 1 or 2) and occasionally to chemosis (grade 1) and discharge (grade 1), in all groups, after instillation of the vehicle or of the test item, Example 1, formulation at any dose levels. These scores were slight to moderate. There were no differences in the frequency, severity and incidence between the Example 1-treated animals and the vehicle controls. The conjunctival redness was the most frequent reaction, and was yet present (at grade 1) before the start of dosing. This local reaction is known to occur spontaneously in the albino rabbit during ocular studies and is related to the numerous ocular examinations undergone on the animals. Chemosis and discharge were sporadically observed in all groups after the first instillation and over the 3-day observation period thereafter. In addition, congestion of the iris was occasionally and unilaterally observed in the eyes of the two high dose group rabbits (1 mg/mL) and one vehicle group female. The Draize examination confirmed the integrity of the cornea after a single treatment day and the photomotor reflex was normal for all animals on all occasions. In summary, the local tolerability of the formulations was thus considered to be acceptable after a single dosing day. Similar local reactions were observed after instillation of the vehicle or formulations containing the compound of Example 1, indicative of a moderate vehicle-related effect on the ocular tolerance.

In Phase 2, the main ocular reactions were limited to conjunctival redness (grade 1) in all groups after instillation of the vehicle or of the test item formulations at any dose levels. This score was slight and was noted without any meaningful difference in the incidence and frequency between groups throughout the 3-day treatment period. The severity was occasionally higher (grade 2) in the vehicle group than in the test item-treated groups. This conjunctival redness was persistent and was still observed before the first instillation on the following day. In addition, congestion of the iris was occasionally observed in the eyes of the two high dose group rabbits and one vehicle group female. No discharge was observed in any animals at all occasions. The Draize examination confirmed the integrity of the cornea during the 3-day treatment period. The photomotor reflex was normal for all animals on all occasions. In summary, the local tolerability of the formulations was thus considered to be acceptable without any aggravation for the 3 treatment days. Similar local reactions were observed after instillation of the vehicle alone or formulations containing the compound of Example 1, indicative of the moderate vehicle-related effect on the ocular tolerance.

Mutagenicity Assessment (Bacterial Reverse Mutation Screen)

Studies were conducted by Sequani (Ledbury, Herefordshire, UK) to assess the compounds of Examples 1 and 44 in vitro for their ability to induce mutations in four histidine dependent auxotrophic mutants of *Salmonella typhimurium*, strains TA1535, TA1537, TA98 and TA100 and one tryptophan dependent auxotrophic mutant of *Escherichia coli*, WP2 uvrA.

The mutation screen was conducted using the plate incorporation method and was performed in both the presence and absence of S-9 mix (a liver post-mitochondrial fraction derived from the livers of Aroclor 1254 treated rats). The bacteria were exposed to the compound of Example 1 or Example 44 dissolved in dimethylsulphoxide, which solvent was also used as the negative control. The positive Control chemicals were Sodium Azide (TA1535 and TA100), 9-Aminoacridine (TA1537), 2-Nitrofluorene (TA98) and 4-Nitroquinoline-N-Oxide (WP2 uvrA) in the absence of S-9 mix and 2-Aminoanthracene (all strains) in the presence of S-9 mix.

The doses of the compound of Example 1 used in the mutation test under plate incorporation conditions were 15, 50, 150, 500 or 1500 µg/plate in all strains in the presence and absence of S-9 mix.

The doses of the compound of Example 44 used in the mutation test under plate incorporation conditions were 50, 150, 500, 1500 or 5000 µg/plate in all strains in the presence and absence of S-9 mix.

The compound of Example 1 was analysed up to the limit of solubility of 1500 µg/plate in all strains in the presence and absence of S-9 mix, under plate incorporation conditions. The compound of Example 44 was analysed up to the limit of solubility of 5000 µg/plate in all strains in the presence and absence of S-9 mix, under plate incorporation conditions.

Precipitation was observed:
  for the compound of Example 1, at 500 µg/plate in TA1537 and TA98 in the presence of S-9 mix, and at 1500 µg/plate in all strains in the presence and absence of S-9 mix; and
  for the compound of Example 44, at 5000 µg/plate in TA1535 in the presence and absence of S-9 mix, and in TA100 in the absence of S-9 mix There was also a reduction in the mean colony count:
  for the compound of Example 1, at 500 µg/plate and 1500 µg/plate in TA98 and at 1500 µg/plate in TA1535, in the presence of S-9 mix; and
  for the compound of Example 44, at 1500 µg/plate in TA98 and 5000 µg/plate in TA98 and WP2 uvrA, in the absence of S-9 mix, and at 5000 µg/plate in TA1535, TA1537, TA98 and TA100 in the presence of S-9 mix, indicating toxicity of the test items to the bacteria.

There were no dose-related or statistically significant increases in revertant numbers observed in any strain at any dose level of the compound of Example 1 or the compound of Example 44, in the presence or absence of S-9 mix, under plate incorporation conditions. This indicates the absence of any mutagenic effects for the compounds of Examples 1 and 44 under the conditions of the test.

Hydrolytic Stability Study

Chemical stability of compounds of the invention was assessed in a mixture of DMSO and water (3:1) at a test compound concentration of 1 mg/mL.

General HPLC Procedure

Agilent, Waters X-Select C18, 2.5 µm, 4.6×30 mm column, 4 min method, 5-95% MeCN/water (0.1% formic acid). Flow rate 2.5 mL/min. Column Oven Temperature 40° C. Detection 254 nm.

Sample Preparation

A 1.0 mg sample of test compound was dissolved in 750 µL of DMSO. Water (250 µL) was added slowly, ensuring no precipitation occurred.

Recording Stability

A 50 µL aliquot of the test solution was removed and analysed in duplicate by 5 µL HPLC injections. The peak area for the test compound was recorded following manual integration of the corresponding UV trace.

The test solution was heated to 60° C., with stirring, and 50 µL aliquots removed for HPLC analysis at 5 and 24 h timepoints. In all cases, 5 µL injections were used and the samples analysed in duplicate.

The peak areas for the test compounds were recorded at both subsequent timepoints and the % decomposition calculated from the % change in peak area over time.

Reference Compound B (3-ethynyl-5-((4-((4-(3-(3-isopropyl-1-(p-tolyl)-1H-pyrazol-5-yl)ureido)naphthalen-1-yl)oxy)pyrimidin-2-yl)amino)-N-(2-morpholinoethyl)benzamide; Cariou, C. A. M., et al, WO 2014/027209) was included in each stability study as a control to validate the study. In contrast to the compounds of the present invention, this Reference Compound underwent substantial decomposition under the conditions of the experiment.

The results of the study are reported in the table below.

| Test Compound | Time (min) | % Parent Remaining |
|---|---|---|
| Reference Compound B | 0 | 100 |
|  | 297 | 79 |
|  | 1429 | 18 |
| Example 44 | 0 | 100 |
|  | 307 | 102 |
|  | 1439 | 98 |
| Example 47 | 0 | 100 |
|  | 317 | 104 |
|  | 1450 | 89 |

Stability of Pharmaceutical Formulations 20 mL of 1 mg/mL stock solutions were prepared, in duplicate, of the sodium (Na) and hydrochloride (HCl) salts of the compound of Example 1 as follows: The appropriate quantities of each salt were mixed with 10 mM pH 7.2 phosphate buffer containing 4.5% mannitol and 3% polyoxyl 40 stearate. The samples were sonicated to achieve clear solutions having the following properties: Osmolality (mOsm/kg): 310 (Na), 314 (HCl); pH: 7.00 (Na), 7.05 (HCl). 0.5 mL of the stock solutions were diluted to 1 mL with 20% DMSO in water & injected for purity analysis by HPLC. The remaining stock solutions were then split into aliquots of 0.5 mL in HPLC vials, and stored at various conditions in duplicate. Samples were stored at 5 and 25° C., before being analysed by HPLC at 1, 2 and 4 weeks. Separate samples were stored at 40° C. and analysed at 4 weeks. The analysis shown in the Table below reveals that the Compound of Example 1 is stable in solution at 5° C.

| Test substance | Sample | Original Purity (%) | Temp (° C.) | Purity (%) at week n | | |
|---|---|---|---|---|---|---|
| | | | | n = 1 | n = 2 | n = 4 |
| Example 1, sodium salt | 1 | 98.6 | 5 | 98.2 | 98.4 | 98.3 |
| | | | 25 | 98.4 | 98.1 | 97.6 |
| | | | 40 | — | — | 76.0 |
| | 2 | 98.5 | 5 | 98.4 | 98.5 | 98.4 |
| | | | 25 | 98.5 | 98.1 | 97.6 |
| | | | 40 | — | — | 73.7 |
| Example 1, hydrochloride salt | 1 | 98.1 | 5 | 98.2 | 98.1 | 97.9 |
| | | | 25 | 98.0 | 97.7 | 97.2 |
| | | | 40 | — | — | 79.2 |
| | 2 | 98.1 | 5 | 98.2 | 98.0 | 98.0 |
| | | | 25 | 98.0 | 97.6 | 97.4 |
| | | | 40 | — | — | 80.4 |

ABBREVIATIONS

AcOH glacial acetic acid
aq aqueous
5-ASA 5-aminosalicylic acid
ATP adenosine-5'-triphosphate
BALF bronchoalveolar lavage fluid
BID bis in die (twice-daily)
BINAP 2,2'-bis(diphenylphosphino)-1,1'-binaphthyl
BOP (benzotriazol-1-yloxy)tris(dimethylamino)phosphonium hexafluorophosphate
br broad
BrdU 5-bromo-2'-deoxyuridine
BSA bovine serum albumin
CatCart® catalytic cartridge
CDI 1,1-carbonyl-diimidazole
COPD chronic obstructive pulmonary disease
d doublet
dba dibenzylideneacetone
DBU 1,8-diazabicyclo[5.4.0]undec-7-ene
DCC dicyclohexylcarbodiimide
DCM dichloromethane
DIAD diisopropyl azodicarboxylate
DIPEA diisopropylethylamine
DMAP 4-dimethylaminopyridine
DMEM Dulbecco's modified eagle medium
DMF N,N-dimethylformamide
DMSO dimethyl sulfoxide
DPPA diphenylphosphoryl azide
d-U937 cells PMA differentiated U-937 cells
EDTA ethylenediaminetetraacetic acid
ELISA enzyme-linked immunosorbent assay
(ES$^-$) electrospray ionization, negative mode
(ES$^+$) electrospray ionization, positive mode
Et ethyl
Et$_3$N triethylamine
EtOAc ethyl acetate
EtOH ethanol
FACS fluorescence-activated cell sorting
FBS foetal bovine serum
FCS foetal calf serum
fMLP formyl-methionyl-leucyl-phenylalanine
FRET fluorescence resonance energy transfer
GSK3α glycogen synthase kinase 3α
HBEC primary human bronchial epithelial cells
HBSS Hank's balanced salt solution
HPLC high performance liquid chromatography
HPMC hydroxypropylmethylcellulose
h or hr hour(s)
HATU 2-(1H-7-azabenzotriazol-1-yl)-1,1,3,3-tetramethyl uronium hexafluorophosphate
HOAt 1-hydroxy-7-azabenzotriazole
HOBt hydroxybenzotriazole
HRP horseradish peroxidise
HRV human rhinovirus
ICAM-1 inter-cellular adhesion molecule 1
IFNγ interferon-γ
IL interleukin
iPrOAc isopropyl acetate
JNK c-Jun N-terminal kinase
LC liquid chromatography
Lck lymphocyte-specific protein tyrosine kinase
LPS lipopolysaccharide
m multiplet
(M+H)$^+$ protonated molecular ion
MAPK mitogen-activated protein kinase
MAPKAP-K2 mitogen-activated protein kinase-activated protein kinase-2
mCPBA meta-chloroperbenzoic acid
Me methyl
MeCN acetonitrile
MeOH methanol
MHz megahertz
min or mins minute(s)
MMAD mass median aerodynamic diameter
MOI multiplicity of infection
MPO myeloperoxidase
MTT 3-(4,5-dimethylthiazol-2-yl)-2,5-diphenyltetrazolium bromide
MS mass spectrometry
m/z mass-to-charge ratio
NMP N-methyl pyrrolidinone
NMR nuclear magnetic resonance (spectroscopy)
OD optical density
PBMC peripheral blood mononuclear cell
PBS phosphate buffered saline
Ph phenyl
PHA phytohaemagglutinin
PMA phorbol myristate acetate
pTSA 4-methylbenzenesulfonic acid (para-toluenesulfonic acid)
PyBOP (benzotriazol-1-yloxy)tripyrrolidinophosphonium hexafluorophosphate
q quartet
rt or RT room temperature
RP HPLC reverse phase high performance liquid chromatography
rpm revolutions per minute
RPMI Roswell Park Memorial Institute
RSV respiratory syncytial virus
s singlet
sat or satd saturated
SCID severe combined immunodeficiency
SCX solid supported cation exchange (resin)
SDS sodium dodecyl sulfate
S$_N$Ar nucleophilic aromatic substitution
Syk Spleen tyrosine kinase
t triplet
T3P 1-propanephosphonic acid cyclic anhydride
TBAF tetrabutylammonium fluoride
TBDMS tert-butyldimethylsilyl
TCID$_{50}$ 50% tissue culture infectious dose
TEA triethylamine
THF tetrahydrofuran
TFA trifluoroacetic acid
TGFβ transforming growth factor beta TIPS triisopropylsilyl
TMB 3,3',5,5'-tetramethylbenzidine
TMS-Cl trimethylsilyl chloride
TNFα tumor necrosis factor alpha
Prefixes n-, s-, i-, t- and tert- have their usual meanings: normal, secondary, iso, and tertiary.

What is claimed is:
1. A compound of formula III,

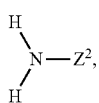

or a salt or protected derivative of said compound of formula III, wherein $Z^2$ represents a structural fragment of formula V:

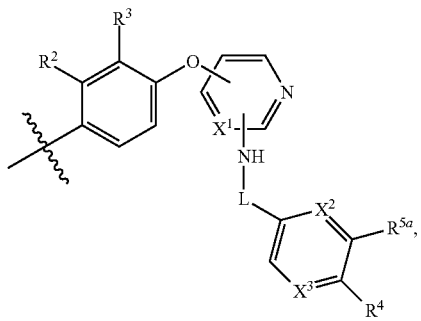

wherein
R$^2$ and R$^3$, together with the C-atoms to which they are attached, form a fused phenyl or pyridyl ring, which latter two rings are optionally substituted by one or more substituents selected from $C_{1-3}$ alkyl, $C_{1-3}$ haloalkyl, cyano and halo,
or one of R$^2$ and R$^3$ represents H, halo, cyano, $C_{1-3}$ alkyl or $C_{1-3}$ haloalkyl and the other independently represents halo, cyano, $C_{1-3}$ alkyl or $C_{1-3}$ haloalkyl,
or R$^2$ and R$^3$ together combine to form $C_{3-5}$ alkylene or $C_{3-5}$ alkenylene, which latter two groups are optionally substituted by one or more substituents selected from $C_{1-3}$ alkyl, $C_{1-3}$ haloalkyl, cyano and halo;
X$^1$ represents N or CH;
L represents a direct bond or $C_{1-2}$ alkylene;
X$^2$ represents CR$^Z$ or N;
X$^3$ represents CR$^{5b}$ or N;
R$^Z$ represents H, halo, cyano, hydroxy, $C_{1-3}$ alkyl or $C_{1-3}$ alkoxy, which latter two groups are optionally substituted by one or more halo atoms;
R$^4$ represents
-Q$^1$-[C(R$^{6c}$)(R$^{6d}$)—(CH$_2$)$_{0-1}$CH$_2$—Z]$_{1-12}$—CH$_2$(CH$_2$)$_{0-1}$CH$_2$—R$^{6a}$,
-Q$^2$-C(R$^{6c}$)(R$^{6d}$)—[C$_{1-5}$ alkylene]-R$^{6a}$, which $C_{1-5}$ alkylene group is optionally substituted by oxo and/or by one or more R$^{6e}$, -Q$^3$-[C$_{1-4}$ alkylene]$_{0-1}$-Het$^{x1}$, which $C_{1-4}$ alkylene group is optionally substituted by oxo and/or by one or more R$^{6e}$ and which Het$^{x1}$ group is optionally substituted by one or more substituents selected from halo, hydroxy, oxo, $C_{3-6}$ cycloalkyl, $C_{1-3}$ alkoxy and —[C(O)]$_{0-1}$—$C_{1-4}$ alkyl, the $C_{1-4}$ alkyl part of which latter group is optionally substituted by one or more R$^{6e}$,
-Q$^{22}$-[C$_{1-4}$ alkylene]$_{0-1}$-phenyl, which $C_{1-4}$ alkylene group is optionally substituted by oxo and/or by one or more R$^{6e}$, and which phenyl group is substituted by [C(O)]$_{0-1}$—$C_{1-4}$ alkyl, the $C_{1-4}$ alkyl part of which latter group is optionally substituted by one or more R$^{6e}$, and which phenyl group is optionally further substituted by one or more substituents selected from halo, hydroxy, oxo, $C_{3-6}$ cycloalkyl and $C_{1-3}$ alkoxy,
—S(O)$_p$R$^{6b}$,
—[C$_{1-4}$ alkylene]$_{0-1}$-CO$_2$H,
Het$^{x2}$ which Het$^{x2}$ group is optionally substituted by one or more substituents selected from halo, hydroxy, oxo, $C_{1-3}$ alkyl and $C_{1-3}$ alkoxy,
—COR$^{6b}$,
—CH$_2$OH,
—CH$_2$OP(O)(OH)$_2$ or
-Q$^4$-P(O)(OR$^9$)(R$^7$);
Z represents, independently upon each occurrence, O, C(O)N(R$^8$) or N(R$^8$)C(O);
R$^{5a}$ and R$^{5b}$ independently represent $C_{1-3}$ alkoxy or $C_{1-3}$ alkyl, which latter two groups are optionally substituted by one or more halo atoms, or R$^{5a}$ and R$^{5b}$ independently represent —N(R$^e$)(R$^f$), $C_{2-3}$ alkynyl, H, cyano, —C(O)NH$_2$, hydroxy, halo or —S(O)$_{0-2}$—$C_{1-3}$ alkyl;
R$^{6a}$ represents OR$^{7a}$, —S(O)$_{0-2}$R$^{7aa}$, N(R$^{7b}$)R$^{7c}$ or CO$_2$H;
R$^{6b}$ represents $C_{1-8}$ alkyl, $C_{3-8}$ cycloalkyl, phenyl, Het$^1$ or Het$^2$, which latter five groups are optionally substituted by one or more substituents selected from halo, hydroxy, —OP(O)(OH)$_2$, $C_{1-3}$ alkyl, $C_{1-3}$ alkoxy, —$C_{1-3}$ alkylene-R$^{6e}$ and CO$_2$H,
or R$^{6b}$ represents —$C_{1-4}$ alkylene-Het$^3$, which Het$^3$ group is optionally substituted by one or more substituents selected from halo, hydroxy, oxo, $C_{3-6}$ cycloalkyl, $C_{1-3}$ alkoxy and —[C(O)]$_{0-1}$—$C_{1-3}$ alkyl, which $C_{1-3}$ alkyl group is optionally substituted by one or more R$^{6e}$,
or, when p is 1 or 2, R$^{6b}$ may alternatively represent OH,
or, when p is 2, R$^{6b}$ may alternatively represent —N(R$^{7b}$)R$^{7c}$ or —N(R$^{7b}$)—C(O)—R$^{7c}$;
R$^{6e}$ represents, independently upon each occurrence, halo, hydroxy, —OP(O)(OH)$_2$, $C_{1-3}$ alkoxy, —N(R$^g$)(R$^h$) or —CO$_2$H;
R$^{7a}$ to R$^{7c}$ independently represent H or $C_{1-4}$ alkyl optionally substituted by one or more halo atoms or by —CO$_2$H,
or R$^{7a}$ represents P(O)(OH)$_2$ or Het$^3$, which latter group is optionally substituted by one or more substituents selected from halo, hydroxy, oxo, $C_{3-6}$ cycloalkyl, $C_{1-3}$ alkoxy and —[C(O)]$_{0-1}$—$C_{1-3}$ alkyl, which $C_{1-3}$ alkyl group is optionally substituted by one or more R$^{6e}$,
or R$^{7b}$ and/or R$^{7c}$ represents —[C$_a$ alkylene]-[C$_b$ alkylene]-OR$^{7d}$,
or R$^{7b}$ and R$^{7c}$ together with the N-atom to which they are attached, form a 4- to 7-membered heterocyclic group that is fully saturated, partially unsaturated or fully aromatic and which heterocyclic group contains one N atom (the atom to which $R^{7b}$ and $R^{7c}$ are attached) and, optionally, one or more further heteroatoms selected from O, S and N, and which heterocyclic group is optionally substituted by one or more substituents selected from halo, hydroxy, oxo, $C_{1-4}$ alkyl, $C_{1-4}$ alkoxy and $C_{1-4}$ hydroxyalkyl;

a and b independently represent an integer selected from 1, 2 and 3, wherein the sum of a and b is 2, 3 or 4;

$R^{7d}$ represents H or $C_{1-4}$ alkyl optionally substituted by one or more halo atoms;

$R^{7aa}$ represents —C($R^{7d}$)($R^{7e}$)—$C_{1-3}$ alkylene-OH or $C_{1-4}$ alkyl optionally substituted by one or more halo atoms or by —CO$_2$H;

$Q^1$, $Q^2$, $Q^{22}$ and $Q^3$ independently represent —C(O)N($R^8$)—, —O— or —S(O)$_2$N($R^8$)—, or $Q^1$, $Q^2$ and $Q^{22}$ independently represent S(O)$_q$;

$Q^4$ represents a direct bond or $C_{1-3}$ alkylene;

n, m, p and q independently represent 0, 1 or 2;

$R^{6c}$, $R^{6d}$, $R^e$, $R^f$, $R^g$, $R^h$ and $R^8$ independently represent H or methyl, or $R^{6c}$ and $R^{6d}$ independently represent hydroxymethyl;

$R^7$ represents H, hydroxy, $C_{1-4}$ alkyl, $C_{1-4}$ alkoxy, $C_{3-7}$ cycloalkyl or phenyl, which latter four groups are optionally substituted by one or more substituents selected from halo, OH, $C_{1-3}$ alkyl and $C_{1-3}$ alkoxy;

$R^9$ represents H or $C_{1-4}$ alkyl, which latter group is optionally substituted by one or more halo atoms or by phenyl, which phenyl group is optionally substituted by one or more substituents selected from halo, OH, $C_{1-3}$ alkyl and $C_{1-3}$ alkoxy;

Het$^{x1}$ and Het$^{x2}$ independently represent Het$^{1a}$ or Het$^3$;

Het$^1$ and Het$^{1a}$ represent, independently upon each occurrence, a 5- or 6-membered heterocyclic group that is fully aromatic, which group contains one or more heteroatoms selected from N, O and S; and Het$^2$ and Het$^3$ represent, independently upon each occurrence, a 4- to 9-membered heterocyclic group that is fully saturated or partially unsaturated, and is monocyclic or is fused or bridged bicyclic, which group contains one or more heteroatoms selected from N, O and S, wherein said protected derivative is a compound in which:

(a) a H-atom of the NH$_2$ group of formula III is replaced by:

R'—C(O)—, wherein R' is H, $C_{1-8}$ alkyl, phenyl or benzyl, which latter two groups are optionally substituted by one or more groups selected from halo, hydroxy, methyl and methoxy, or R"—O—C(O)—, wherein R" is tert-butyl, phenyl, benzyl or fluorenyl, which latter three groups are optionally substituted by one or more groups selected from halo, hydroxy, methyl and methoxy; and/or (b) when $R^4$ represents —CO$_2$H, said —CO$_2$H group is protected as a $C_{1-8}$ alkyl ester.

2. A compound of formula III, or a salt or protected derivative thereof, as claimed in claim 1, wherein said compound or protected derivative is methyl 4-((4-((4-aminonaphthalen-1-yl)oxy)pyridin-2-yl)amino)-2-methoxybenzoate or methyl 4-((4-((4-(((tert-butoxycarbonyl)amino)naphthalen-1-yl)oxy)pyridin-2-yl)amino)-2-methoxybenzoate.

3. A compound of formula VIIa,

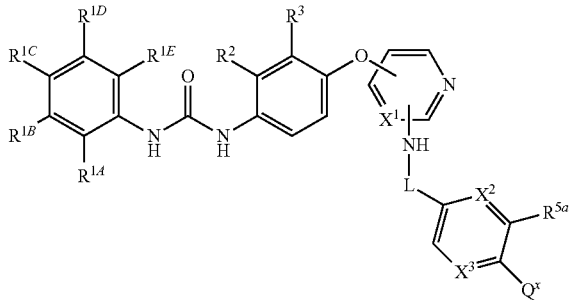

VIIa or a salt of said compound of formula VIIa, wherein $Q^X$ represents —[$C_{1-4}$ alkylene]$_{0-1}$—C(O)O—$C_{1-4}$ alkyl;

$R^{1A}$ represents:

$C_{1-6}$ alkoxy, $C_{1-6}$ alkyl, $C_{2-6}$ alkenyl, $C_{2-6}$ alkynyl, which latter four groups are optionally substituted by one or more substituents selected from $C_{1-2}$ alkyl, halo, hydroxy, —OP(O)(OH)$_2$ and $C_{1-2}$ alkoxy, H, halo, cyano, phenyl or Het$^1$, which latter two groups are optionally substituted with one or more substituents selected from $C_{1-2}$ alkyl and $C_{1-2}$ alkoxy, or $R^{1A}$ and $R^{1B}$ together represent a structural fragment selected from the following:

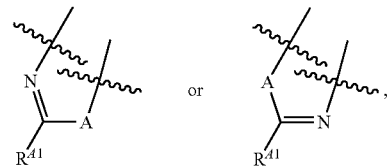

wherein the wavy lines represent the points of attachment to the phenyl ring;

A represents O, S or N($R^{42}$);

$R^{41}$ represents H, $C_{1-4}$ alkyl or hydroxy;

$R^{42}$ represents H or $C_{1-4}$ alkyl;

$R^{1B}$ is represents —NR$^X$S(O)$_2$R$^{Y1}$, —C(O)NR$^X$R$^Y$, H, halo, cyano, —$C_{1-4}$ alkylene-CN, —$C_{1-4}$ alkylene-OH, —NR$^X$R$^{X1}$, —C(O)OR$^X$, —S(O)$_2$NR$^X$R$^Y$, —NR$^X$C(O)R$^Y$, —NR$^{X2}$S(O)$_2$NR$^X$R$^Y$, —NR$^X$P(O)R$^{Y1}$R$^{Y2}$, —NR$^X$C(O)OR$^{Y1}$ or Het$^1$ optionally substituted with one or more substituents selected from halo, hydroxy, $C_{1-2}$ alkyl and $C_{1-2}$ alkoxy;

$R^X$ and $R^{X1}$ independently represent H or $C_{1-6}$ alkyl optionally substituted by one or more substituents selected from halo, hydroxy, —OP(O)(OH)$_2$ and $C_{1-2}$ alkoxy, or $R^X$ and $R^{X1}$ together represent $C_{3-6}$ n-alkylene or $C_{4-5}$ n-alkylene interrupted between C2 and C3 by —O— or —N($R^{X2}$)—, or $R^{X1}$ represents Het$^1$ optionally substituted with one or more substituents selected from halo, hydroxy, $C_{1-2}$ alkyl and $C_{1-2}$ alkoxy;

$R^Y$, $R^{Y1}$ and $R^{Y2}$ independently represent $C_{1-6}$ alkyl, $C_{3-7}$ cycloalkyl, phenyl, benzyl, Het$^1$ or Het$^2$, which latter six groups are optionally substituted by one or more substituents selected from $C_{1-2}$ alkyl, halo, hydroxy, —OP(O)(OH)$_2$, $C_{1-2}$ alkoxy, C(O)OH, C(O)O—($C_{1-4}$ alkyl) and —N($R^a$)($R^b$), and/or which $Het^2$ group is substituted with one or more oxo groups, or $R^Y$ represents H, or $R^X$ and $R^Y$ together represent $C_{3-6}$ n-alkylene or $C_{4-5}$ n-alkylene interrupted between C2 and C3 by —O—, —S(O)$_n$— or —N($R^{X2}$)—;

$R^a$ and $R^b$ independently represent H, methyl or —C($R^c$)($R^d$)—$C_{1-3}$ alkyl, the $C_{1-3}$ alkyl portion of which latter group is optionally substituted by one or more hydroxy substituents, or $R^a$ and $R^b$ together represent $C_{3-6}$ n-alkylene or $C_{4-5}$ n-alkylene interrupted between C2 and C3 by —O—, —S(O)$_m$— or —N($R^{X2}$)—;

$R^c$ and $R^d$ independently represent H or methyl;

each $R^{X2}$ independently represents H or $C_{1-4}$ alkyl;

$R^{1C}$ and $R^{1E}$ independently represent H, halo, cyano or methyl;

provided that at least one of $R^{1A}$, $R^{1B}$, $R^{1C}$ and $R^{1E}$ is other than H;

$R^{1D}$ represents trimethylsilyl, $C_{2-7}$ alkyl, $C_{2-7}$ alkenyl, $C_{2-7}$ alkynyl, $C_{3-7}$ cycloalkyl, phenyl, $Het^1$ or $Het^2$, which latter seven groups are optionally substituted by one or more substituents selected from $C_{1-2}$ alkyl, halo, cyano, hydroxy, —OP(O)(OH)$_2$ and $C_{1-2}$ alkoxy;

$R^2$ and $R^3$, together with the C-atoms to which they are attached, form a fused phenyl or pyridyl ring, which latter two rings are optionally substituted by one or more substituents selected from $C_{1-3}$ alkyl, $C_{1-3}$ haloalkyl, cyano and halo, or one of $R^2$ and $R^3$ represents H, halo, cyano, $C_{1-3}$ alkyl or $C_{1-3}$ haloalkyl and the other independently represents halo, cyano, $C_{1-3}$ alkyl or $C_{1-3}$ haloalkyl, or $R^2$ and $R^3$ together combine to form $C_{3-5}$ alkylene or $C_{3-5}$ alkenylene, which latter two groups are optionally substituted by one or more substituents selected from $C_{1-3}$ alkyl, $C_{1-3}$ haloalkyl, cyano and halo;

$X^1$ represents N or CH;

L represents a direct bond or $C_{1-2}$ alkylene;

$X^2$ represents $CR^Z$ or N;

$X^3$ represents $CR^{5b}$ or N;

$R^{5a}$ and $R^{5b}$ independently represent $C_{1-3}$ alkoxy or $C_{1-3}$ alkyl, which latter two groups are optionally substituted by one or more halo atoms, or $R^{5a}$ and $R^{5b}$ independently represent —N($R^e$)($R^f$), $C_{2-3}$ alkynyl, H, cyano, —C(O)NH$_2$, hydroxy, halo or —S(O)$_{0-2}$—$C_{1-3}$ alkyl;

$R^Z$ represents H, halo, cyano, hydroxy, $C_{1-3}$ alkyl or $C_{1-3}$ alkoxy, which latter two groups are optionally substituted by one or more halo atoms;

$R^e$ and $R^f$ independently represent H or methyl;

$Het^1$ represents, independently upon each occurrence, a 5- or 6-membered heterocyclic group that is fully aromatic, which group contains one or more heteroatoms selected from N, O and S; and $Het^2$ represents, independently upon each occurrence, a 4- to 9-membered heterocyclic group that is fully saturated or partially unsaturated, and is monocyclic or is fused or bridged bicyclic, which group contains one or more heteroatoms selected from N, O and S.

4. A compound of formula VIIa, or a salt thereof, as claimed in claim 3, wherein said compound is methyl 4-((4-((4-(3-(5-(tert-butyl)-2-methoxy-3-(methylsulfonamido)-phenyl)ureido)naphthalen-1-yl)oxy)pyridin-2-yl)amino)-2-methoxybenzoate.

* * * * *